United States Patent
Grice et al.

(10) Patent No.: US 11,161,856 B2
(45) Date of Patent: Nov. 2, 2021

(54) SPIROCYCLE COMPOUNDS AND METHODS OF MAKING AND USING SAME

(71) Applicant: H. Lundbeck A/S, Valby (DK)

(72) Inventors: Cheryl A. Grice, Encinitas, CA (US); Olivia D. Weber, San Diego, CA (US); Daniel J. Buzard, San Diego, CA (US); Michael B. Shaghafi, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 16/642,713

(22) PCT Filed: Aug. 28, 2018

(86) PCT No.: PCT/SU2018/048388
§ 371 (c)(1),
(2) Date: Feb. 27, 2020

(87) PCT Pub. No.: WO2019/046330
PCT Pub. Date: Mar. 7, 2019

(65) Prior Publication Data
US 2021/0214375 A1      Jul. 15, 2021

Related U.S. Application Data

(60) Provisional application No. 62/551,714, filed on Aug. 29, 2017.

(51) Int. Cl.
| C07D 519/00 | (2006.01) |
| C07D 401/12 | (2006.01) |
| C07D 211/58 | (2006.01) |
| C07D 471/10 | (2006.01) |

(52) U.S. Cl.
CPC .......... *C07D 519/00* (2013.01); *C07D 211/58* (2013.01); *C07D 401/12* (2013.01); *C07D 471/10* (2013.01)

(58) Field of Classification Search
CPC .. C07D 519/00; C07D 211/58; C07D 401/12; C07D 471/10
USPC .................................................... 514/210.16
See application file for complete search history.

(56) References Cited

U.S. PATENT DOCUMENTS

| 9,133,148 | B2 | 9/2015 | Cisar et al. |
| 9,487,495 | B2 | 11/2016 | Cisar et al. |
| 9,828,379 | B2 | 11/2017 | Jones et al. |
| 10,030,020 | B2 | 7/2018 | Cisar et al. |
| 2005/0234090 | A1 | 10/2005 | Colon-Cruz et al. |
| 2011/0071180 | A1 | 3/2011 | Akireddy et al. |
| 2012/0208812 | A1 | 8/2012 | Chai et al. |
| 2013/0165422 | A1 | 6/2013 | Bartsch et al. |
| 2016/0137649 | A1 | 5/2016 | Jones et al. |
| 2020/0022977 | A1 | 1/2020 | Cisar et al. |

FOREIGN PATENT DOCUMENTS

| WO | WO-2010141817 A1 | 12/2010 |
| WO | WO-2011109277 A1 | 9/2011 |
| WO | WO-2012052730 A1 | 4/2012 |
| WO | WO-2014048865 A1 | 4/2014 |
| WO | WO-2015003002 A1 | 1/2015 |
| WO | WO-2016149401 A2 | 9/2016 |
| WO | WO-2017021805 A1 | 2/2017 |
| WO | WO-2017197192 A1 | 11/2017 |
| WO | WO-2018093949 A1 | 5/2018 |
| WO | WO-2019046318 A1 | 3/2019 |
| WO | WO-2019046330 A1 | 3/2019 |

OTHER PUBLICATIONS

Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Brun et al. Drug sensitivity of Chinese Trypanosoma evansi and Trypanosoma equiperdum isolates. Vet. Parasitol. 52:37-46 (1994).
Chang et al. Highly Selective Inhibitors of Monoacylglycerol Lipase Bearing a Reactive Group that is Bioisosteric with Endocannabinoid Substrates. ChemBiol 19(5):579-588 (2012).
Changsen et al. Improved green fluorescent protein reporter gene-based microplate screening for antituberculosis compounds by utilizing an acctamidase promoter. Antimicrob AgentsChemother 47:3682-3687 (2003).
Chen et al. SAP102 mediates synaptic clearance of NMDA receptors. Cell Rep. 2(5):1120-1128 (2012).
Cho et al. Low-oxygen-recovery assay for high-throughput screening of compounds against nonreplicating Mycobacterium tuberculosis. Antimicrobl AgentsChemother 51:1380-1385 (2007).
Collins et al. Microplate alamar blue assay versus BACTEC 460 system for high-throughput screening of compounds against Mycobacterium tuberculosis and Mycobacterium avium. Antimicrobl Agents Chemother 41:1004-1009 (1997).
Fleisher et al. Improved oral drug delivery: solubility limitations overcome by the use of prodrugs. Advanced Drug Delivery Reviews 19:115-130 (1996).

(Continued)

*Primary Examiner* — Kahsay Habte
(74) *Attorney, Agent, or Firm* — Wilson Sonsini Goodrich & Rosati

(57) ABSTRACT

Provided herein are compounds of the formula:

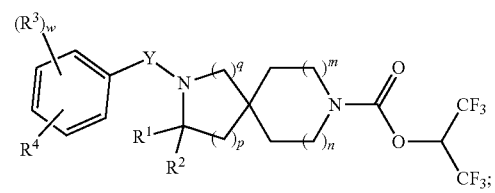

and compositions comprising the same, which are useful as modulators of MAGL. Furthermore, the subject compounds and compositions are useful for the treatment of pain.

15 Claims, No Drawings

(56) References Cited

OTHER PUBLICATIONS

Long et al. Selective blockade of 2-arachidonoylglycerol hydrolysis produces cannabinoid behavioral effects. Nat Chem Biol. 5(1):37-44 (2009).
Niphakis et al. Evaluation of NHS carbamates as a potent and selective class of endocannabinoid hydrolase inhibitors. ACS Chem Neurosci 4(9):1322-1332 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Activation of the endocannabinoid system by organophosphorus nerve agents. Nat Chem Biol. 4(6):373-378 (2008).
Nomura et al. Endocannabinoid hydrolysis generates brain prostaglandins that promote neuroinflammation. Science 334(6057):809-813 (2011).
Nomura et al. Monoacylglycerol lipase regulates 2-arachidonoylglycerol action and arachidonic acid levels. Bioorg Med Chem Lett. 18(22):5875-5878 (2008).
PCT/US2014/045145 International Search Report and Written Opinion dated Dec. 10, 2014.
PCT/US2017/032276 International Search Report and Written Opinion dated Sep. 26, 2017.
PCT/US2017/061870 International Search Report and Written Opinion dated Mar. 26, 2018.
PCT/US2017/061870 Invitation to Pay Additional Fees dated Jan. 22, 2018.
PCT/US2018/048372 International Search Report and Written Opinion dated Dec. 4, 2018.
PCT/US2018/048372 Invitation to Pay Additional Fees dated Oct. 4, 2018.
PCT/US2018/048388 International Search Report and Written Opinion dated Dec. 4, 2018.
PCT/US2018/048388 Invitation to Pay Additional Fees dated Oct. 4, 2018.
Piro et al. A dysregulated endocannabinoid-eicosanoid network supports pathogenesis in a mouse model of Alzheimer's disease. Cell Rep. 1(6):617-623 (2012).
Pubchem, Substance Database, SID 239803465. Retrieved from Internet:< URL: https://pubchem.ncbi.nlm.nih.gov/substance/239803465> ( 7pgs.) (Available Date Feb. 13, 2015) (retrieved Jun. 27, 2017).
Raz et al. The Alamar Blue® assay to determine drug sensitivity of African trypanosomes (T.b. rhodesiense and T.b. gambiense) in vitro. Acta Tropica 68:139-147 (1997).
Snewin et al. Assessment of immunity to mycobacterial infection with luciferase reporter constructs. Infection and Immunity 67:4586-4593 (1999).
U.S. Appl. No. 14/902,324 Office Action dated Dec. 30, 2016.

SPIROCYCLE COMPOUNDS AND METHODS OF MAKING AND USING SAME

CROSS-REFERENCE

This application is a U.S. National Stage entry of PCT application PCT/US2018/048388, filed Aug. 28, 2018, which claims the benefit of U.S. Provisional Application No. 62/551,714, filed on Aug. 29, 2017, which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound having the structure of Formula (I):

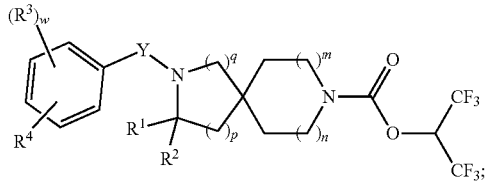

Formula (I)

wherein:
Y is —$CH_2$— or —C(O)—;
$R^1$ is H or $C_{1-6}$alkyl;
$R^2$ is H or $C_{1-6}$alkyl;
each $R^3$ is independently selected from $C_{1-6}$alkyl, halogen, —CN, $C_{1-6}$haloalkyl, —$SF_5$, and —$OR^7$;
$R^4$ is selected from —C≡C-$C_{1-6}$alkyl-$CO_2H$ and -$C_{3-8}$cycloalkyl-$CO_2H$;
each $R^7$ is independently selected from H, $C_{1-6}$alkyl, $C_{1-6}$haloalkyl, $C_{1-6}$aminoalkyl, $C_{3-8}$cycloalkyl, and -$C_{1-6}$alkyl-$C_{3-8}$cycloalkyl;
w is 0, 1, 2, 3, or 4;
n is 0 or 1;
m is 0 or 1;
p is 0, 1, or 2; and
q is 0, 1, or 2; provided that when q is 0, then p is 2;
or a solvate, hydrate, tautomer, N-oxide, stereoisomer, or pharmaceutically acceptable salt thereof.

In one embodiment is a compound of Formula (I) or a solvate, hydrate, tautomer, N-oxide, stereoisomer, or a pharmaceutically acceptable salt thereof, wherein $R^4$ is -$C_{3-8}$cycloalkyl-$CO_2H$. In another embodiment is a compound of Formula (I), or a solvate, hydrate, tautomer, N-oxide, stereoisomer, or a pharmaceutically acceptable salt thereof, wherein $R^4$ is

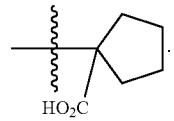

In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2H$. In another embodiment is a compound of Formula (I), or a solvate, hydrate, tautomer, N-oxide, stereoisomer, or a pharmaceutically acceptable salt thereof, wherein $R^4$ is

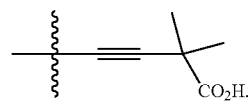

In another embodiment is a compound of Formula (I), or a solvate, hydrate, tautomer, N-oxide, stereoisomer, or a pharmaceutically acceptable salt thereof, wherein Y is —$CH_2$—. In another embodiment is a compound of Formula (I), or a solvate, hydrate, tautomer, N-oxide, stereoisomer, or a pharmaceutically acceptable salt thereof, wherein Y is —C(O)—.

In another aspect is a compound having the structure of Formula (I'):

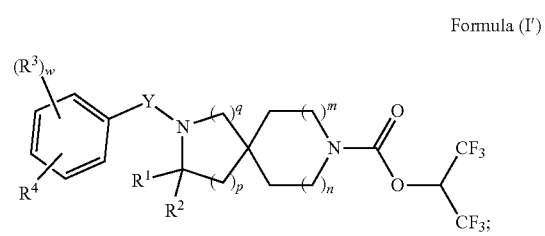

Formula (I')

wherein:
Y is —$CH_2$—;
$R^1$ is H or $C_{1-6}$alkyl;
$R^2$ is H or $C_{1-6}$alkyl;
each $R^3$ is independently selected from $C_{1-6}$alkyl, halogen, —CN, $C_{1-6}$haloalkyl, —$SF_5$, and —$OR^7$;
$R^4$ is selected from

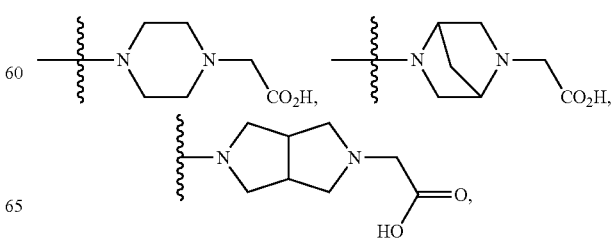

-continued

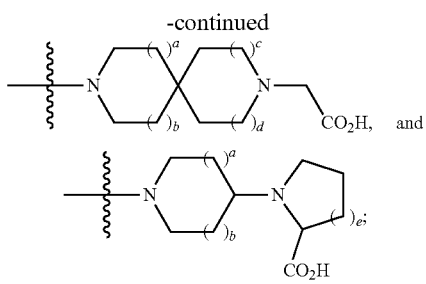

each $R^7$ is independently selected from H, $C_{1-6}$alkyl, $C_{1-6}$haloalkyl, $C_{3-8}$cycloalkyl, and -$C_{1-6}$alkyl-$C_{3-8}$cycloalkyl;
a, b, c, and d are independently 0 or 1;
e is 0, 1, or 2;
w is 0, 1, 2, 3, or 4;
n is 0 or 1;
m is 0 or 1;
p is 0, 1, or 2; and
q is 0, 1, or 2; provided that when q is 0, then p is 2;
or a solvate, hydrate, tautomer, N-oxide, stereoisomer, or pharmaceutically acceptable salt thereof.

In another embodiment is a compound of Formula (I'), or a solvate, hydrate, tautomer, N-oxide, stereoisomer, or a pharmaceutically acceptable salt thereof, wherein $R^4$ is

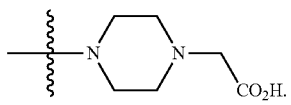

In another embodiment is a compound of Formula (I'), or a solvate, hydrate, tautomer, N-oxide, stereoisomer, or a pharmaceutically acceptable salt thereof, wherein $R^4$ is

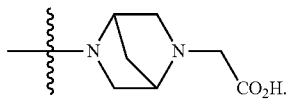

In another embodiment is a compound of Formula (I'), or a solvate, hydrate, tautomer, N-oxide, stereoisomer, or a pharmaceutically acceptable salt thereof, wherein $R^4$ is

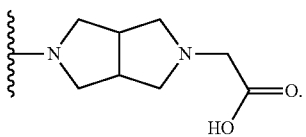 [SMILES: *N1CC2CN(CC(=O)O)CC2C1]

In another embodiment is a compound of Formula (I'), or a solvate, hydrate, tautomer, N-oxide, stereoisomer, or a pharmaceutically acceptable salt thereof, wherein $R^4$ is

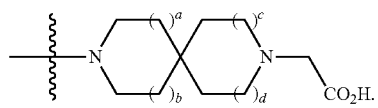

In another embodiment is a compound of Formula (I'), or a solvate, hydrate, tautomer, N-oxide, stereoisomer, or a pharmaceutically acceptable salt thereof, wherein $R^4$ is selected from

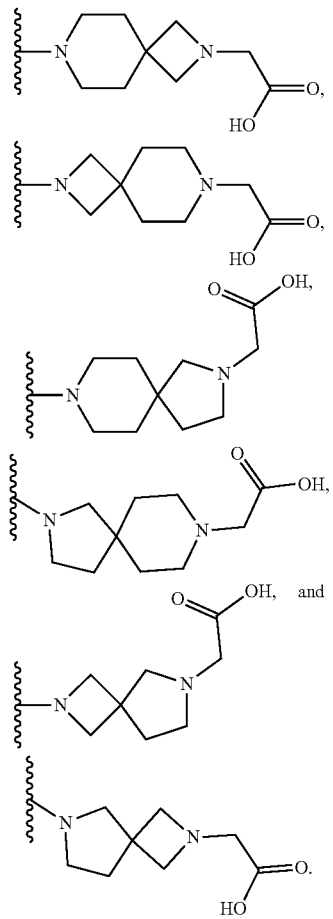

In another embodiment is a compound of Formula (I'), or a solvate, hydrate, tautomer, N-oxide, stereoisomer, or a pharmaceutically acceptable salt thereof, wherein $R^4$ is

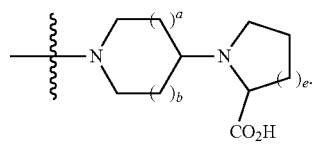

In another embodiment is a compound of Formula (I'), or a solvate, hydrate, tautomer, N-oxide, stereoisomer, or a pharmaceutically acceptable salt thereof, wherein $R^4$ is selected from

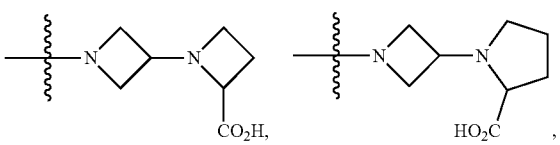

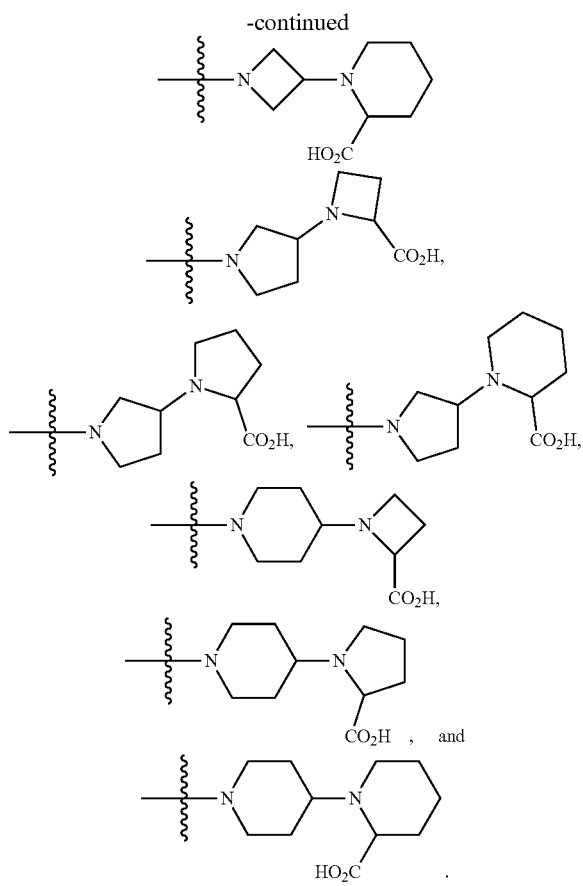

In another embodiment is a compound of Formula (I) or (I'), or a solvate, hydrate, tautomer, N-oxide, stereoisomer, or a pharmaceutically acceptable salt thereof, wherein $R^1$ is H. In another embodiment is a compound of Formula (I) or (I'), or a solvate, hydrate, tautomer, N-oxide, stereoisomer, or a pharmaceutically acceptable salt thereof, wherein $R^2$ is H. In another embodiment is a compound of Formula (I) or (I'), or a solvate, hydrate, tautomer, N-oxide, stereoisomer, or a pharmaceutically acceptable salt thereof, wherein $R^1$ and $R^2$ are both H. In another embodiment is a compound of Formula (I) or (I'), or a solvate, hydrate, tautomer, N-oxide, stereoisomer, or a pharmaceutically acceptable salt thereof, wherein each $R^3$ is independently selected from halogen and $C_{1-6}$haloalkyl. In another embodiment is a compound of Formula (I) or (I'), or a solvate, hydrate, tautomer, N-oxide, stereoisomer, or a pharmaceutically acceptable salt thereof, wherein each $R^3$ is independently selected from halogen. In another embodiment is a compound of Formula (I) or (I'), or a solvate, hydrate, tautomer, N-oxide, stereoisomer, or a pharmaceutically acceptable salt thereof, wherein each $R^3$ is —Cl. In another embodiment is a compound of Formula (I) or (I'), or a solvate, hydrate, tautomer, N-oxide, stereoisomer, or a pharmaceutically acceptable salt thereof, wherein each $R^3$ is independently selected from $C_{1-6}$haloalkyl. In another embodiment is a compound of Formula (I) or (I'), or a solvate, hydrate, tautomer, N-oxide, stereoisomer, or a pharmaceutically acceptable salt thereof, wherein each $R^3$ is —$CF_3$. In another embodiment is a compound of Formula (I) or (I'), or a solvate, hydrate, tautomer, N-oxide, stereoisomer, or a pharmaceutically acceptable salt thereof, wherein w is 2. In another embodiment is a compound of Formula (I) or (I'), or a solvate, hydrate, tautomer, N-oxide, stereoisomer, or a pharmaceutically acceptable salt thereof, wherein w is 1. In another embodiment is a compound of Formula (I) or (I'), or a solvate, hydrate, tautomer, N-oxide, stereoisomer, or a pharmaceutically acceptable salt thereof, wherein w is 0. In another embodiment is a compound of Formula (I) or (I'), or a solvate, hydrate, tautomer, N-oxide, stereoisomer, or a pharmaceutically acceptable salt thereof, wherein m is 1, n is 1, q is 1, and p is 1. In another embodiment is a compound of Formula (I) or (I'), or a solvate, hydrate, tautomer, N-oxide, stereoisomer, or a pharmaceutically acceptable salt thereof, wherein m is 1, n is 1, q is 0, and p is 2.

In another aspect is a compound having the structure of Formula (II):

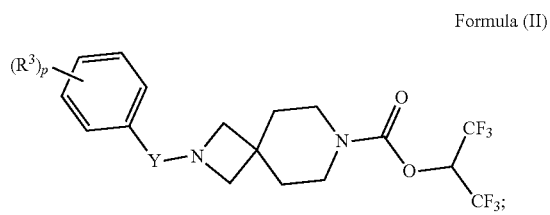

Formula (II)

wherein:
Y is —$CH_2$— or —C(O)—;
each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, -$C_{1-6}$alkyl($C_{2-9}$heterocycloalkyl), $C_{6-10}$aryl, $C_{1-9}$heteroaryl, —$SF_5$, —$NR^5R^6$, —$OR^7$, —$CO_2R^8$, and —C(O)$NR^8R^9$, wherein -$C_{1-6}$alkyl($C_{2-9}$heterocycloalkyl) and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
each $R^4$ is independently selected from $C_{1-6}$alkyl, $C_{1-6}$haloalkyl, $C_{3-8}$cycloalkyl, halogen, oxo, —CN, —$CO_2R^8$, -$C_{1-6}$alkyl-$CO_2R^8$, —C(O)$R^8$, —C(O)$NR^8R^9$, —$SO_2R^8$, —$NR^9$C(O)$R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-6}$heteroaryl are optionally substituted with one or two groups selected from oxo, $C_{1-6}$alkyl, $C_{1-6}$haloalkyl, $CO_2H$, and C(O)$NH_2$;
each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2H$, and C(O)$NH_2$;
each $R^{10}$ is independently selected from halogen, $C_{1-6}$alkyl, -$C_{1-6}$alkyl-$CO_2R^8$, $C_{1-6}$haloalkyl, $C_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$; and p is 0, 1, 2, 3, 4, or 5;

or a solvate, hydrate, tautomer, N-oxide, stereoisomer, or pharmaceutically acceptable salt thereof.

In another aspect is a compound having the structure of Formula (III):

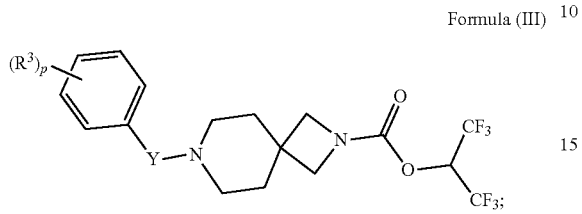

Formula (III)

wherein:
- Y is —CH$_2$— or —C(O)—;
- each R$^3$ is independently selected from C$_{1-6}$alkyl, C$_{1-6}$alkenyl, C$_{1-6}$alkynyl, halogen, —CN, C$_{1-6}$haloalkyl, C$_{1-6}$aminoalkyl, -C$_{1-6}$alkyl(C$_{2-9}$heterocycloalkyl), C$_{6-10}$aryl, C$_{1-9}$heteroaryl, —SF$_5$, —NR$^5$R$^6$, —OR$^7$, —CO$_2$R$^8$, and —C(O)NR$^8$R$^9$, wherein -C$_{1-6}$alkyl(C$_{2-9}$heterocycloalkyl) and C$_{1-9}$heteroaryl are optionally substituted with one or two R$^4$; or two adjacent R$^3$ form a C$_{2-9}$heterocycloalkyl ring, wherein the C$_{2-9}$heterocycloalkyl ring is optionally substituted with one, two, or three R$^4$;
- each R$^4$ is independently selected from C$_{1-6}$alkyl, C$_{1-6}$haloalkyl, C$_{3-8}$cycloalkyl, halogen, oxo, —CN, —CO$_2$R$^8$, -C$_{1-6}$alkyl-CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
- each R$^5$ and R$^6$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl; or R$^5$ and R$^6$, together with the nitrogen to which they are attached, form a C$_{2-9}$heterocycloalkyl ring optionally substituted with one, two, or three R$^{10}$;
- each R$^7$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one or two groups selected from oxo, C$_{1-6}$alkyl, C$_{1-6}$haloalkyl, CO$_2$H, and C(O)NH$_2$;
- each R$^8$ and R$^9$ is independently selected from H, C$_{1-6}$alkyl, C$_{1-6}$haloalkyl, C$_{3-8}$cycloalkyl, C$_{6-10}$aryl, and C$_{1-9}$heteroaryl; or R$^8$ and R$^9$, together with the nitrogen to which they are attached, form a C$_{2-9}$heterocycloalkyl ring optionally substituted with one or two groups selected from C$_{1-6}$alkyl, C$_{1-6}$haloalkyl, CO$_2$H, and C(O)NH$_2$;
- each R$^{10}$ is independently selected from halogen, C$_{1-6}$alkyl, -C$_{1-6}$alkyl-CO$_2$R$^8$, C$_{1-6}$haloalkyl, C$_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$; and
- p is 0, 1, 2, 3, 4, or 5;

or a solvate, hydrate, tautomer, N-oxide, stereoisomer, or pharmaceutically acceptable salt thereof.

In another embodiment is a compound of Formula (II) or (III), or a solvate, hydrate, tautomer, N-oxide, stereoisomer, or a pharmaceutically acceptable salt thereof, wherein Y is —CH$_2$—. In another embodiment is a compound of Formula (II) or (III), or a solvate, hydrate, tautomer, N-oxide, stereoisomer, or a pharmaceutically acceptable salt thereof, wherein Y is —C(O)—.

In another aspect is a compound having the structure of Formula (IV):

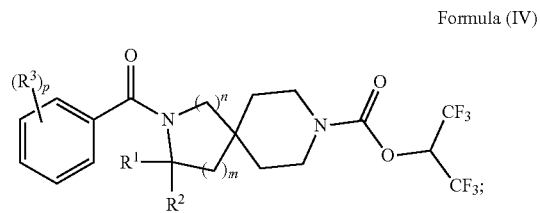

Formula (IV)

wherein:
- R$^1$ is H or C$_{1-6}$alkyl;
- R$^2$ is H or C$_{1-6}$alkyl;
- each R$^3$ is independently selected from C$_{1-6}$alkyl, C$_{1-6}$alkenyl, C$_{1-6}$alkynyl, halogen, —CN, C$_{1-6}$haloalkyl, C$_{1-6}$aminoalkyl, -C$_{1-6}$alkyl(C$_{2-9}$heterocycloalkyl), C$_{1-9}$heteroaryl, —SF$_5$, —NR$^5$R$^6$, —OR$^7$, —CO$_2$R$^8$, and —C(O)NR$^8$R$^9$, wherein -C$_{1-6}$alkyl(C$_{2-9}$heterocycloalkyl) and C$_{1-9}$heteroaryl are optionally substituted with one or two R$^4$; or two adjacent R$^3$ form a C$_{2-9}$heterocycloalkyl ring, wherein the C$_{2-9}$heterocycloalkyl ring is optionally substituted with one, two, or three R$^4$;
- each R$^4$ is independently selected from C$_{1-6}$alkyl, C$_{1-6}$haloalkyl, C$_{3-8}$cycloalkyl, halogen, oxo, —CN, —CO$_2$R$^8$, -C$_{1-6}$alkyl-CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
- each R$^5$ and R$^6$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl; or R$^5$ and R$^6$, together with the nitrogen to which they are attached, form a C$_{2-9}$heterocycloalkyl ring optionally substituted with one, two, or three R$^{10}$;
- each R$^7$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one or two groups selected from oxo, C$_{1-6}$alkyl, C$_{1-6}$haloalkyl, CO$_2$H, and C(O)NH$_2$;
- each R$^8$ and R$^9$ is independently selected from H, C$_{1-6}$alkyl, C$_{1-6}$haloalkyl, C$_{3-8}$cycloalkyl, C$_{6-10}$aryl, and C$_{1-9}$heteroaryl; or R$^8$ and R$^9$, together with the nitrogen to which they are attached, form a C$_{2-9}$heterocycloalkyl ring optionally substituted with one or two groups selected from C$_{1-6}$alkyl, C$_{1-6}$haloalkyl, CO$_2$H, and C(O)NH$_2$;
- each R$^{10}$ is independently selected from halogen, C$_{1-6}$alkyl, -C$_{1-6}$alkyl-CO$_2$R$^8$, C$_{1-6}$haloalkyl, C$_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$; and
- p is 0, 1, 2, 3, 4, or 5;
- n is 0 or 1; and
- m is 1 or 2; provided that when n is 0, then m is 2; and when n is 1, then m is 1;

or a solvate, hydrate, tautomer, N-oxide, stereoisomer, or pharmaceutically acceptable salt thereof.

In another embodiment is a compound of Formula (IV), or a solvate, hydrate, tautomer, N-oxide, stereoisomer, or a pharmaceutically acceptable salt thereof, wherein n is 0 and m is 2. In another embodiment is a compound of Formula (IV), or a solvate, hydrate, tautomer, N-oxide, stereoisomer, or a pharmaceutically acceptable salt thereof, wherein n is 1 and m is 1. In another embodiment is a compound of Formula (IV), or a solvate, hydrate, tautomer, N-oxide, stereoisomer, or a pharmaceutically acceptable salt thereof, wherein $R^1$ and $R^2$ are both H.

In another aspect is a compound having the structure of Formula (VI):

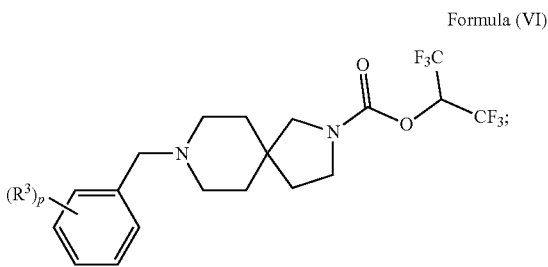

Formula (VI)

wherein:
- each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, -$C_{1-6}$alkyl($C_{2-9}$heterocycloalkyl), $C_{6-10}$aryl, $C_{1-9}$heteroaryl, —SF$_5$, —NR$^5$R$^6$, —OR$^7$, —CO$_2$R$^8$, and —C(O)NR$^8$R$^9$, wherein -$C_{1-6}$alkyl($C_{2-9}$heterocycloalkyl) and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
- each $R^4$ is independently selected from $C_{1-6}$alkyl, $C_{1-6}$haloalkyl, $C_{3-8}$cycloalkyl, halogen, oxo, —CN, —CO$_2$R$^8$, -$C_{1-6}$alkyl-CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
- each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
- each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, CO$_2$H, and C(O)NH$_2$;
- each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, CO$_2$H, and C(O)NH$_2$;
- each $R^{10}$ is independently selected from halogen, $C_{1-6}$alkyl, -$C_{1-6}$alkyl-CO$_2$R$^8$, $C_{1-6}$haloalkyl, $C_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$; and
- p is 0, 1, 2, 3, 4, or 5;

or a solvate, hydrate, tautomer, N-oxide, stereoisomer, or pharmaceutically acceptable salt thereof.

In another embodiment is a compound of Formula (II), (III), (IV), or (VI), or a solvate, hydrate, tautomer, N-oxide, stereoisomer, or a pharmaceutically acceptable salt thereof, wherein each $R^3$ is independently selected from halogen, $C_{1-6}$alkyl, $C_{1-6}$haloalkyl, -$C_{1-6}$alkyl($C_{2-9}$heterocycloalkyl), —NR$^5$R$^6$, —OR$^7$, —CO$_2$R$^8$, —C(O)NR$^8$R$^9$. In another embodiment is a compound of Formula (II), (III), (IV), or (VI), or a solvate, hydrate, tautomer, N-oxide, stereoisomer, or a pharmaceutically acceptable salt thereof, wherein each $R^3$ is independently selected from halogen, $C_{1-6}$haloalkyl, —NR$^5$R$^6$, and —OR$^7$. In another embodiment is a compound of Formula (II), (III), (IV), or (VI), or a solvate, hydrate, tautomer, N-oxide, stereoisomer, or a pharmaceutically acceptable salt thereof, wherein each $R^3$ is independently selected from halogen, $C_{1-6}$haloalkyl, and —NR$^5$R$^6$. In another embodiment is a compound of Formula (II), (III), (IV), or (VI), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (II), (III), (IV), or (VI), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring substituted with one or two $R^{10}$ independently selected from $C_{1-6}$alkyl, $C_{3-8}$cycloalkyl, $C_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (II), (III), (IV), or (VI), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring substituted with one or two $R^{10}$ independently selected from $C_{1-6}$alkyl and —CO$_2$H. In another embodiment is a compound of Formula (II), (III), (IV), or (VI), or a solvate, hydrate, tautomer, N-oxide, stereoisomer, or a pharmaceutically acceptable salt thereof, wherein $R^5$ and $R^6$, together with the nitrogen to which they are attached, form an unsubstituted $C_{2-9}$heterocycloalkyl ring. In another embodiment is a compound of Formula (II), (III), (IV), or (VI), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

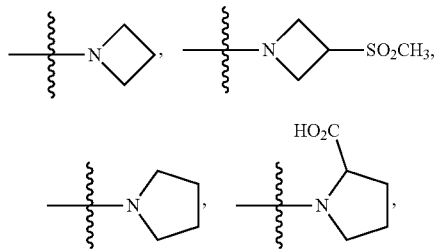

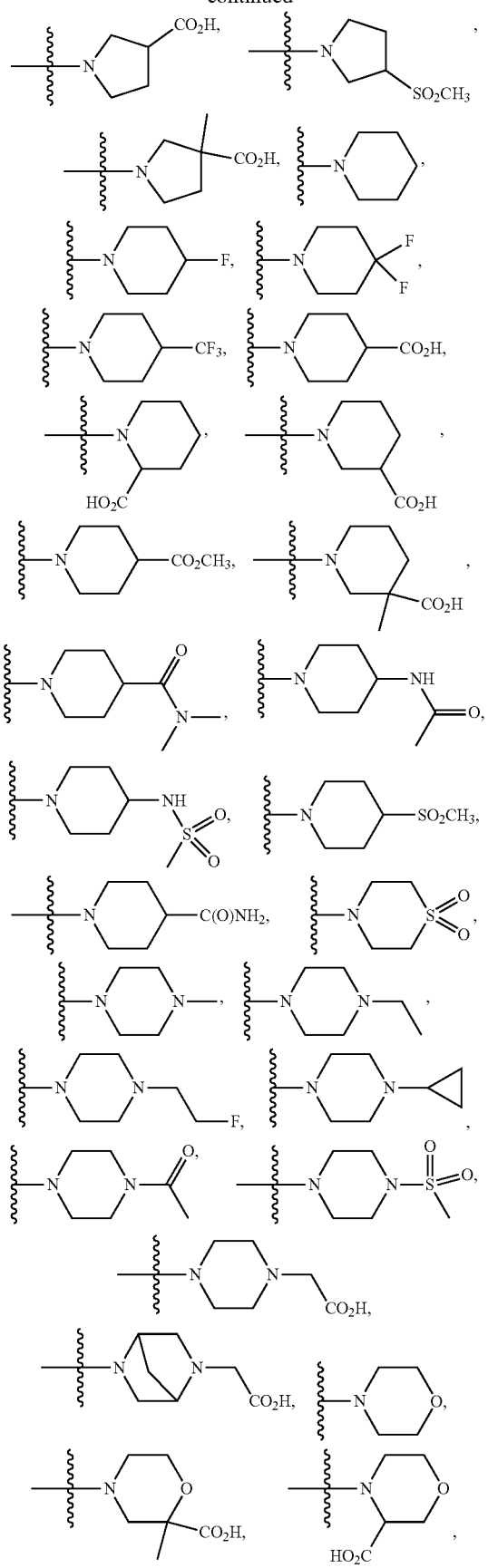
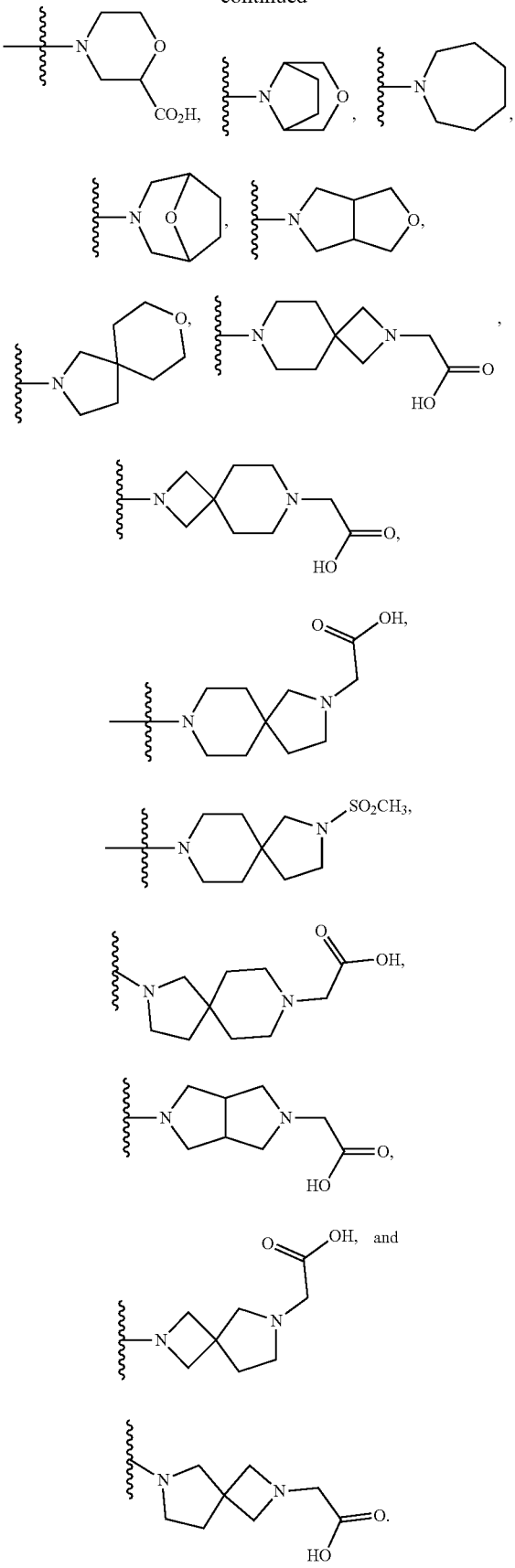

In another aspect is a compound having the structure of Formula (V):

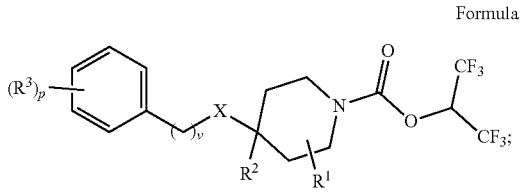

Formula (V)

wherein:
X is —O— or —N(R$^{11}$)—;
R$^1$ is H or C$_{1-6}$alkyl;
R$^2$ is C$_{1-6}$alkyl;
each R$^3$ is independently selected from C$_{1-6}$alkyl, C$_{2-6}$alkenyl, C$_{2-6}$alkynyl, —C≡C-C$_{1-6}$alkyl-CO$_2$H, halogen, —CN, C$_{1-6}$haloalkyl, C$_{1-6}$aminoalkyl, C$_{3-8}$cycloalkyl, -C$_{1-6}$alkyl(C$_{2-9}$heterocycloalkyl), C$_{1-9}$heteroaryl, —SF$_5$, —NR$^5$R$^6$, —OR$^7$, —CO$_2$R$^8$, and —C(O)NR$^8$R$^9$, wherein C$_{3-8}$cycloalkyl, -C$_{1-6}$alkyl(C$_{2-9}$heterocycloalkyl), and C$_{1-9}$heteroaryl are optionally substituted with one or two R$^4$; or two adjacent R$^3$ form a C$_{2-9}$heterocycloalkyl ring, wherein the C$_{2-9}$heterocycloalkyl ring is optionally substituted with one, two, or three R$^4$;
each R$^4$ is independently selected from C$_{1-6}$alkyl, C$_{3-8}$cycloalkyl, C$_{1-6}$haloalkyl, halogen, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
each R$^5$ and R$^6$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl; or R$^5$ and R$^6$, together with the nitrogen to which they are attached, form a C$_{2-9}$heterocycloalkyl ring optionally substituted with one, two, or three R$^{10}$;
each R$^7$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), -C$_{1-6}$alkyl-CO$_2$H, C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one or two groups selected from oxo, C$_{1-6}$alkyl, C$_{1-6}$haloalkyl, CO$_2$H, and CO$_2$NH$_2$;
each R$^8$ and R$^9$ is independently selected from H, C$_{1-6}$alkyl, C$_{1-6}$haloalkyl, C$_{3-8}$cycloalkyl, C$_{6-10}$aryl, and C$_{1-9}$heteroaryl; or R$^8$ and R$^9$, together with the nitrogen to which they are attached, form a C$_{2-9}$heterocycloalkyl ring optionally substituted with one or two groups selected from C$_{1-6}$alkyl, C$_{1-6}$haloalkyl, CO$_2$H, and CO$_2$NH$_2$;
each R$^{10}$ is independently selected from halogen, C$_{1-6}$alkyl, C$_{1-6}$haloalkyl, C$_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
R$^{11}$ is H, C$_{1-6}$alkyl, —C(O)-C$_{1-6}$alkyl, or —CH$_2$CO$_2$H;
p is 0, 1, 2, 3, 4, or 5; and
v is 0 or 1;
or a solvate, hydrate, tautomer, N-oxide, stereoisomer, or pharmaceutically acceptable salt thereof.

In another embodiment is a compound of Formula (V), or a solvate, hydrate, tautomer, N-oxide, stereoisomer, or a pharmaceutically acceptable salt thereof, wherein each R$^3$ is independently selected from halogen, C$_{1-6}$alkyl, C$_{1-6}$haloalkyl, -C$_{1-6}$alkyl(C$_{2-9}$heterocycloalkyl), —NR$^5$R$^6$, —OR$^7$, —CO$_2$R$^8$, —C(O)NR$^8$R$^9$, and C$_{3-8}$cycloalkyl substituted by —CO$_2$H. In another embodiment is a compound of Formula (V), or a each R$^3$ is independently selected from halogen, C$_{1-6}$haloalkyl, and C$_{3-8}$cycloalkyl substituted by —CO$_2$H. In another embodiment is a compound of Formula (V), or a solvate, hydrate, tautomer, N-oxide, stereoisomer, or a pharmaceutically acceptable salt thereof, wherein each R$^3$ is independently selected from halogen, C$_{1-6}$haloalkyl, —NR$^5$R$^6$, and —OR$^7$. In another embodiment is a compound of Formula (V), or a solvate, hydrate, tautomer, N-oxide, stereoisomer, or a pharmaceutically acceptable salt thereof, wherein R$^5$ and R$^6$, together with the nitrogen to which they are attached, form a C$_{2-9}$heterocycloalkyl ring optionally substituted with one, two, or three R$^{10}$. In another embodiment is a compound of Formula (V), or a solvate, hydrate, tautomer, N-oxide, stereoisomer, or a pharmaceutically acceptable salt thereof, wherein R$^5$ and R$^6$, together with the nitrogen to which they are attached, form a C$_{2-9}$heterocycloalkyl ring substituted with one or two R$^{10}$ independently selected from C$_{1-6}$alkyl, C$_{3-8}$cycloalkyl, C$_{1-6}$haloalkyl, halogen, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$. In another embodiment is a compound of Formula (I), or a solvate, hydrate, tautomer, N-oxide, stereoisomer, or a pharmaceutically acceptable salt thereof, wherein p is 2. In another embodiment is a compound of Formula (V), or a solvate, hydrate, tautomer, N-oxide, stereoisomer, or a pharmaceutically acceptable salt thereof, wherein R$^5$ and R$^6$, together with the nitrogen to which they are attached, form a C$_{2-9}$heterocycloalkyl ring substituted with one or two R$^{10}$ independently selected from C$_{1-6}$alkyl and —CO$_2$H. In another embodiment is a compound of Formula (V), or a solvate, hydrate, tautomer, N-oxide, stereoisomer, or a pharmaceutically acceptable salt thereof, wherein R$^5$ and R$^6$, together with the nitrogen to which they are attached, form an unsubstituted C$_{2-9}$heterocycloalkyl ring. In another embodiment is a compound of Formula (V), or a solvate, hydrate, tautomer, N-oxide, stereoisomer, or a pharmaceutically acceptable salt thereof, wherein R$^5$ and R$^6$, together with the nitrogen to which they are attached, form a C$_{2-9}$heterocycloalkyl ring selected from:

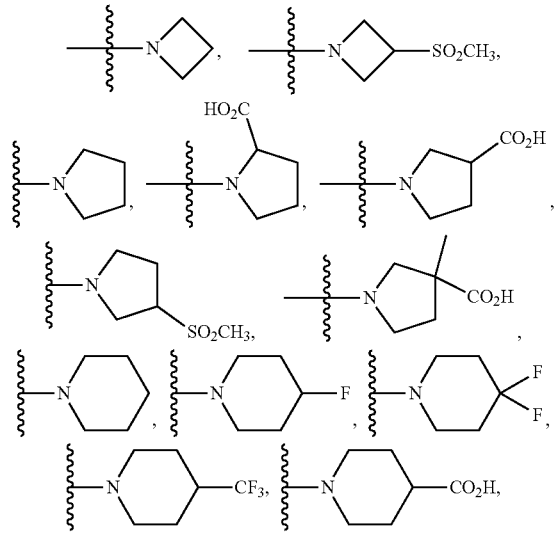

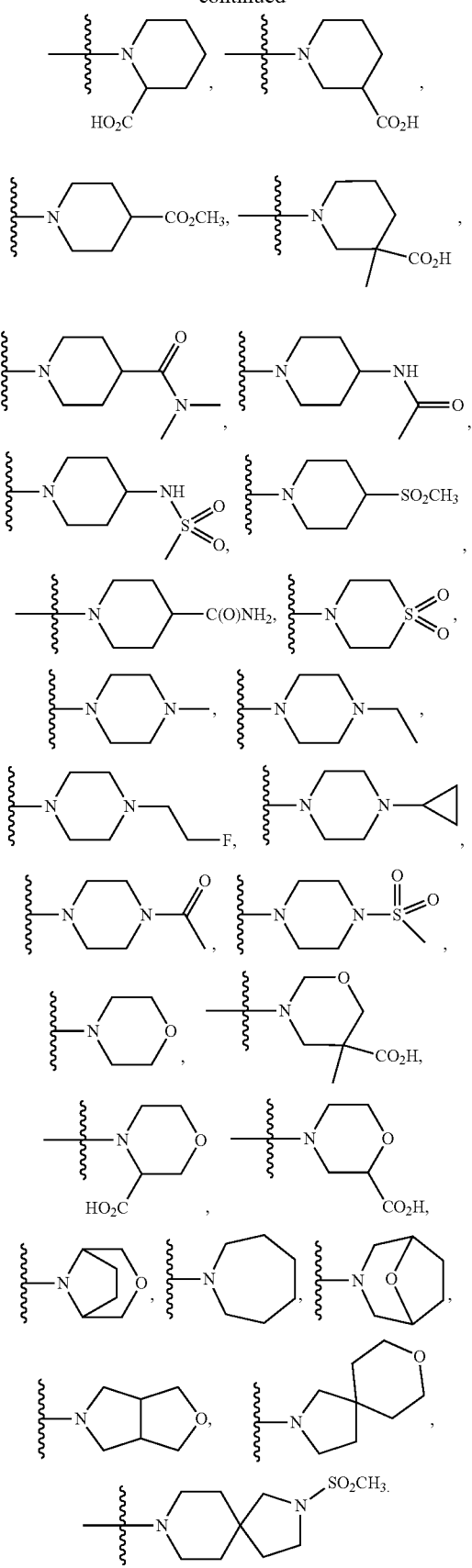

In another aspect is a compound having the structure of Formula (V'):

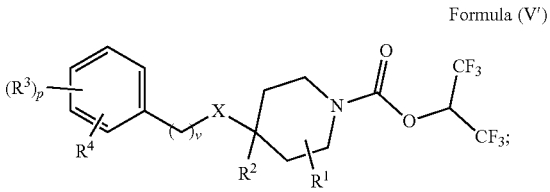

wherein:
X is —O— or —N(R$^{11}$)—;
R$^1$ is H or C$_{1-6}$alkyl;
R$^2$ is C$_{1-6}$alkyl;
each R$^3$ is independently selected from C$_{1-6}$alkyl, halogen, —CN, C$_{1-6}$haloalkyl, C$_{3-8}$cycloalkyl, —SF$_5$, —OR$^7$, and —C(O)NR$^8$R$^9$;
R$^4$ is selected from

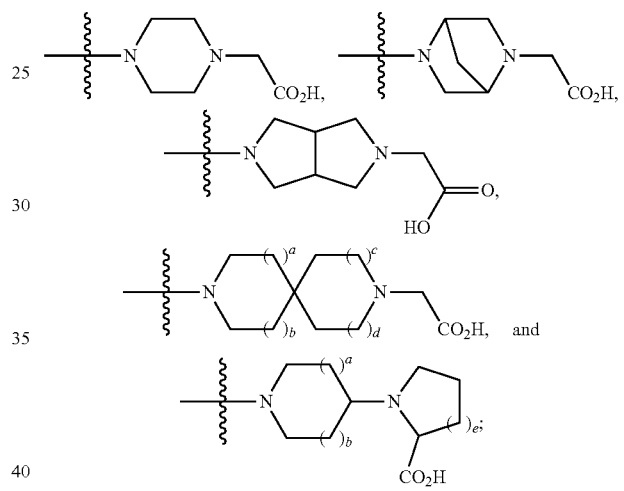

each R$^7$ is independently selected from H, C$_{1-6}$alkyl, C$_{1-6}$haloalkyl, C$_{3-8}$cycloalkyl, and -C$_{1-6}$alkyl-C$_{3-8}$cycloalkyl;
each R$^8$ and R$^9$ is independently selected from H, C$_{1-6}$alkyl, and C$_{3-8}$cycloalkyl;
R$^{11}$ is H or C$_{1-6}$alkyl;
a, b, c, and d are independently 0 or 1;
e is 0, 1, or 2;
p is 0, 1, 2, 3, or 4; and
v is 0 or 1;
or a solvate, hydrate, tautomer, N-oxide, stereoisomer, or pharmaceutically acceptable salt thereof.

In another embodiment is a compound of Formula (V'), or a solvate, hydrate, tautomer, N-oxide, stereoisomer, or a pharmaceutically acceptable salt thereof, wherein R$^4$ is

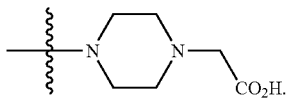

In another embodiment is a compound of Formula (V'), or a solvate, hydrate, tautomer, N-oxide, stereoisomer, or a pharmaceutically acceptable salt thereof, wherein R$^4$ is

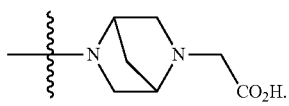

In another embodiment is a compound of Formula (V'), or a solvate, hydrate, tautomer, N-oxide, stereoisomer, or a pharmaceutically acceptable salt thereof, wherein $R^4$ is

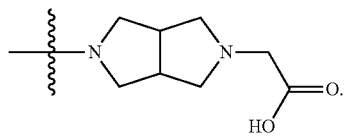 [SMILES: *N1CC2CN(CC(=O)O)CC2C1]

In another embodiment is a compound of Formula (V'), or a solvate, hydrate, tautomer, N-oxide, stereoisomer, or a pharmaceutically acceptable salt thereof, wherein $R^4$ is

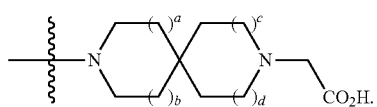

In another embodiment is a compound of Formula (V'), or a solvate, hydrate, tautomer, N-oxide, stereoisomer, or a pharmaceutically acceptable salt thereof, wherein $R^4$ is selected from

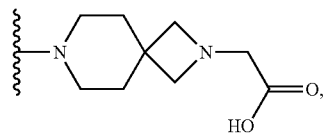

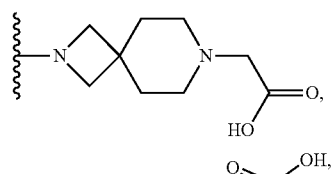

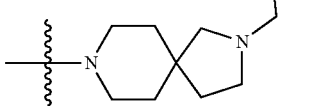

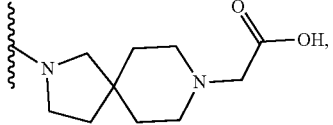

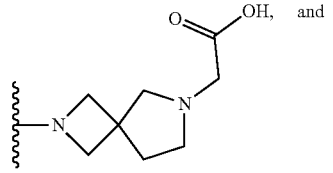

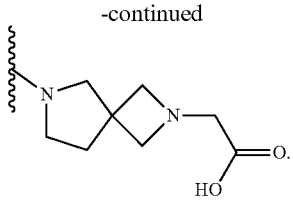

In another embodiment is a compound of Formula (V'), or a solvate, hydrate, tautomer, N-oxide, stereoisomer, or a pharmaceutically acceptable salt thereof, wherein $R^4$ is

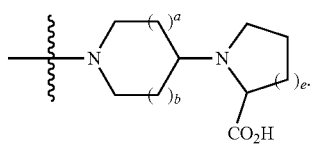

In another embodiment is a compound of Formula (V'), or a solvate, hydrate, tautomer, N-oxide, stereoisomer, or a pharmaceutically acceptable salt thereof, wherein $R^4$ is selected from

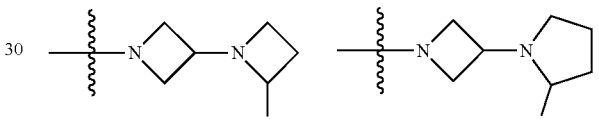

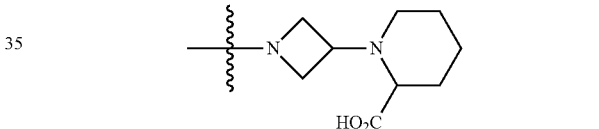

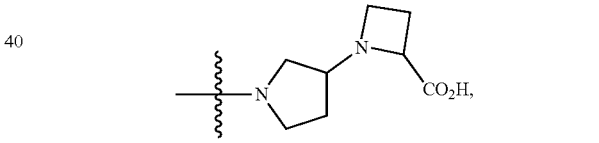

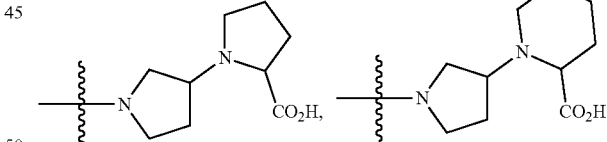

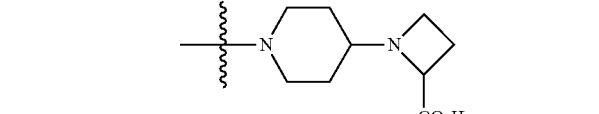

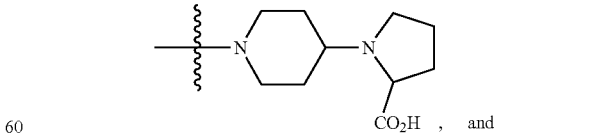

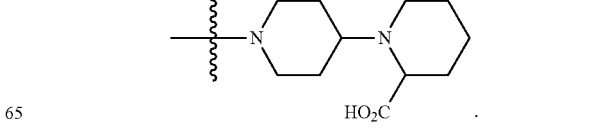

In another embodiment is a compound of Formula (V) or (V'), or a solvate, hydrate, tautomer, N-oxide, stereoisomer, or a pharmaceutically acceptable salt thereof, wherein v is 0. In another embodiment is a compound of Formula (V) or (V'), or a solvate, hydrate, tautomer, N-oxide, stereoisomer, or a pharmaceutically acceptable salt thereof, wherein v is 1. In another embodiment is a compound of Formula (V) or (V'), or a solvate, hydrate, tautomer, N-oxide, stereoisomer, or a pharmaceutically acceptable salt thereof, wherein X is —O—. In another embodiment is a compound of Formula (V) or (V'), or a solvate, hydrate, tautomer, N-oxide, stereoisomer, or a pharmaceutically acceptable salt thereof, wherein X is —N(CH$_3$)—. In another embodiment is a compound of Formula (V) or (V'), or a solvate, hydrate, tautomer, N-oxide, stereoisomer, or a pharmaceutically acceptable salt thereof, wherein R$^2$ is —CH$_3$. In another embodiment is a compound of Formula (V) or (V'), or a solvate, hydrate, tautomer, N-oxide, stereoisomer, or a pharmaceutically acceptable salt thereof, wherein R$^1$ is H. In another embodiment is a compound of Formula (V) or (V'), or a solvate, hydrate, tautomer, N-oxide, stereoisomer, or a pharmaceutically acceptable salt thereof, wherein R$^1$ is —CH$_3$. In another embodiment is a compound of Formula (II), (III), (IV), (V), (V'), or (VI), or a solvate, hydrate, tautomer, N-oxide, stereoisomer, or a pharmaceutically acceptable salt thereof, wherein p is 2. In another embodiment is a compound of Formula (II), (III), (IV), (V), (V'), or (VI), or a solvate, hydrate, tautomer, N-oxide, stereoisomer, or a pharmaceutically acceptable salt thereof, wherein p is 1.

In another aspect is a compound having the structure of Formula (VII):

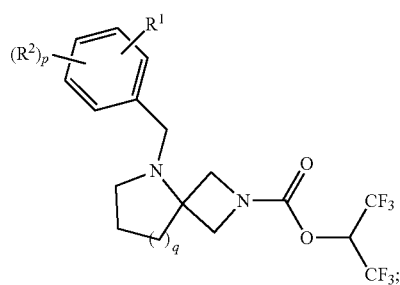

Formula (VII)

wherein:

R$^1$ is selected from

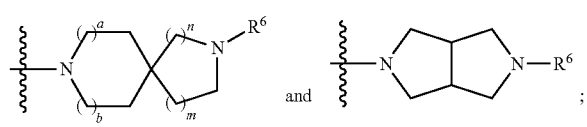

each R$^2$ is independently selected from C$_{1-6}$alkyl, halogen, —CN, C$_{1-6}$haloalkyl, C$_{3-8}$cycloalkyl, —SF$_5$, —OR$^3$, and —C(O)NR$^4$R$^5$;

each R$^3$ is independently selected from H, C$_{1-6}$alkyl, C$_{1-6}$haloalkyl, C$_{3-8}$cycloalkyl, and -C$_{1-6}$alkyl-C$_{3-8}$cycloalkyl;

each R$^4$ and R$^5$ is independently selected from H, C$_{1-6}$alkyl, and C$_{3-8}$cycloalkyl;

R$^6$ is selected from C$_{1-6}$alkyl, —C(O)-C$_{1-6}$alkyl, and —S(O)$_2$-C$_{1-6}$alkyl;

a is 0 or 1;
b is 0 or 1;
m is 0, 1, or 2;
n is 0, 1, or 2; provided that when n is 0, then m is 2;
p is 0, 1, 2, 3, or 4, and
q is 1 or 2;

or a solvate, hydrate, tautomer, N-oxide, stereoisomer, or pharmaceutically acceptable salt thereof.

In another embodiment is a compound of Formula (VII), or a solvate, hydrate, tautomer, N-oxide, stereoisomer, or a pharmaceutically acceptable salt thereof, wherein q is 1. In another embodiment is a compound of Formula (VII), or a solvate, hydrate, tautomer, N-oxide, stereoisomer, or a pharmaceutically acceptable salt thereof, wherein q is 2.

In another aspect is a compound having the structure of Formula (VIII):

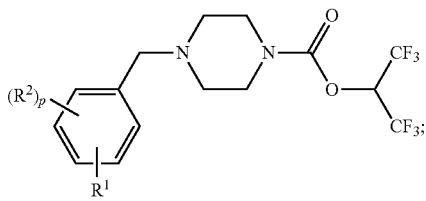

Formula (VIII)

wherein:

R$^1$ is selected from

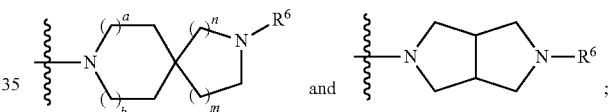

each R$^2$ is independently selected from C$_{1-6}$alkyl, halogen, —CN, C$_{1-6}$haloalkyl, C$_{3-8}$cycloalkyl, —SF$_5$, —OR$^3$, and —C(O)NR$^4$R$^5$;

each R$^3$ is independently selected from H, C$_{1-6}$alkyl, C$_{1-6}$haloalkyl, C$_{3-8}$cycloalkyl, and -C$_{1-6}$alkyl-C$_{3-8}$cycloalkyl;

each R$^4$ and R$^5$ is independently selected from H, C$_{1-6}$alkyl, and C$_{3-8}$cycloalkyl;

R$^6$ is selected from C$_{1-6}$alkyl, —C(O)-C$_{1-6}$alkyl, and —S(O)$_2$-C$_{1-6}$alkyl;

a is 0 or 1;
b is 0 or 1;
m is 0, 1, or 2;
n is 0, 1, or 2; provided that when n is 0, then m is 2; and
p is 0, 1, 2, 3, or 4;

or a solvate, hydrate, tautomer, N-oxide, stereoisomer, or pharmaceutically acceptable salt thereof.

In another embodiment is a compound of Formula (VII) or (VIII), or a solvate, hydrate, tautomer, N-oxide, stereoisomer, or a pharmaceutically acceptable salt thereof, wherein R$^1$ is

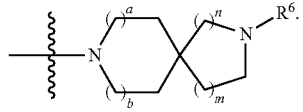

In another embodiment is a compound of Formula (VII) or (VIII), or a solvate, hydrate, tautomer, N-oxide, stereoisomer, or a pharmaceutically acceptable salt thereof, wherein R¹ is

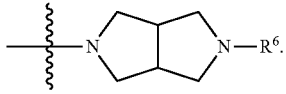

In another embodiment is a compound of Formula (VII) or (VIII), or a solvate, hydrate, tautomer, N-oxide, stereoisomer, or a pharmaceutically acceptable salt thereof, wherein R⁶ is $C_{1-6}$alkyl In another embodiment is a compound of Formula (VII) or (VIII), or a solvate, hydrate, tautomer, N-oxide, stereoisomer, or a pharmaceutically acceptable salt thereof, wherein R⁶ is —C(O)-$C_{1-6}$alkyl. In another embodiment is a compound of Formula (VII) or (VIII), or a solvate, hydrate, tautomer, N-oxide, stereoisomer, or a pharmaceutically acceptable salt thereof, wherein R⁶ is —S(O)$_2$-$C_{1-6}$alkyl. In another embodiment is a compound of Formula (VII) or (VIII), or a solvate, hydrate, tautomer, N-oxide, stereoisomer, or a pharmaceutically acceptable salt thereof, wherein each R³ is independently selected from halogen and $C_{1-6}$haloalkyl. In another embodiment is a compound of Formula (VII) or (VIII), or a solvate, hydrate, tautomer, N-oxide, stereoisomer, or a pharmaceutically acceptable salt thereof, wherein each R³ is independently selected from halogen. In another embodiment is a compound of Formula (VII) or (VIII), or a solvate, hydrate, tautomer, N-oxide, stereoisomer, or a pharmaceutically acceptable salt thereof, wherein each R³ is —Cl. In another embodiment is a compound of Formula (VII) or (VIII), or a solvate, hydrate, tautomer, N-oxide, stereoisomer, or a pharmaceutically acceptable salt thereof, wherein each R³ is independently selected from $C_{1-6}$haloalkyl. In another embodiment is a compound of Formula (VII) or (VIII), or a solvate, hydrate, tautomer, N-oxide, stereoisomer, or a pharmaceutically acceptable salt thereof, wherein each R³ is —CF$_3$. In another embodiment is a compound of Formula (VII) or (VIII), or a solvate, hydrate, tautomer, N-oxide, stereoisomer, or a pharmaceutically acceptable salt thereof, wherein p is 1. In another embodiment is a compound of Formula (VII) or (VIII), or a solvate, hydrate, tautomer, N-oxide, stereoisomer, or a pharmaceutically acceptable salt thereof, wherein p is 0.

In another aspect is a pharmaceutical composition comprising a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, and at least one pharmaceutically acceptable excipient.

In another aspect is a method of treating pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof. In some embodiments is a method of treating pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, wherein the pain is neuropathic pain. In some embodiments is a method of treating pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, wherein the pain is inflammatory pain.

In another embodiment is a method of treating a disease or disorder in a patient comprising administering to the patient in need thereof a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof, wherein the disease is selected from migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating epilepsy/seizure disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating neuromyelitis optica (NMO) in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating Tourette syndrome in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating persistent motor tic disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating persistent vocal tic disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof. In another embodiment is a method of treating abdominal pain associated with irritable bowel syndrome in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a solvate, hydrate, tautomer, N-oxide, or a pharmaceutically acceptable salt thereof.

DETAILED DESCRIPTION OF THE INVENTION

This disclosure is directed, at least in part, to MAGL modulators or inhibitors. For example, provided herein are compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aminoalkyl" refers to a radical of the formula —$R^c$—$N(R^a)_2$ or —$R^c$—$N(R^a)$—$R^c$, where each $R^c$ is independently an alkylene chain as defined above, for example, methylene, ethylene, and the like; and each $R^a$ is independently hydrogen, alkyl, fluoroalkyl, cycloalkyl, aryl, aralkyl, heterocycloalkyl, or heteroaryl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Bickel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl is saturated, (i.e., containing single C—C bonds only) or partially unsaturated (i.e., containing one or more double bonds). Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, $-OR^a$, $-SR^a$, $-OC(O)-R^f$, $-N(R^a)_2$, $-C(O)R^a$, $-C(O)OR^a$, $-C(O)N(R^a)_2$, $-N(R^a)C(O)OR^f$, $-OC(O)-NR^aR^f$, $-N(R^a)C(O)R^f$, $-N(R^a)S(O)_tR^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, haloalkyl, cycloalkyl, aryl, aralkyl, heterocycloalkyl, heteroaryl, or heteroarylalkyl, and each R$^f$ is independently alkyl, haloalkyl, cycloalkyl, aryl, aralkyl, heterocycloalkyl, heteroaryl, or heteroarylalkyl.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl, or heteroarylalkyl, each R$^b$ is independently a direct bond or a straight or branched alkylene or alkenylene chain, and R$^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

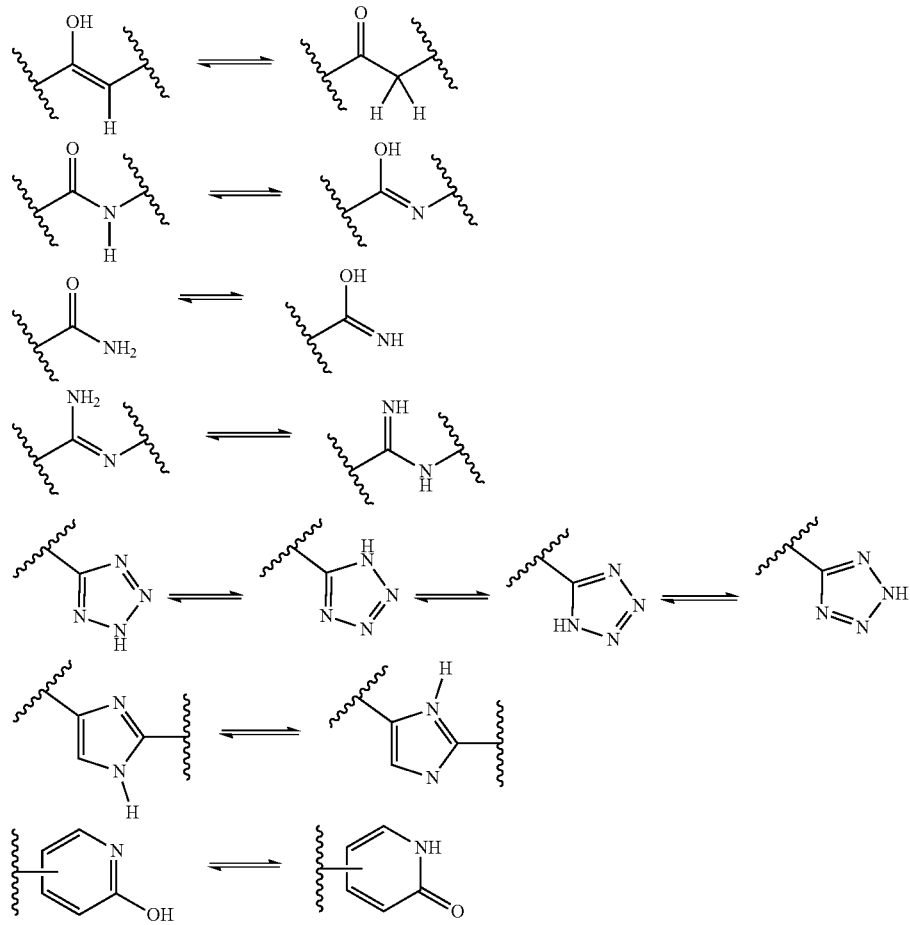

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating " or "palliating" or "ameliorating" are used
interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Ib), (I'), (Ia'), (Ib'), (II), (III), (IV), (V), (Va), (V'), (Va'), (VI), (VII), or (VIII) described herein are modulators of MAGL. In some embodiments, the compounds are inhibitors of MAGL. The compounds of Formula (I), (Ia), (Ib), (I'), (Ia'), (Ib'), (II), (III), (IV), (V), (Va), (V'), (Va'), (VI), (VII), or (VIII) described herein, and compositions comprising these compounds, are useful for the treatment of pain.

In some embodiments is a compound having the structure of Formula (I):

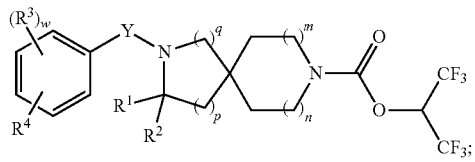

Formula (I)

wherein:
Y is —CH$_2$— or —C(O)—;
R$^1$ is H or C$_{1-6}$alkyl;
R$^2$ is H or C$_{1-6}$alkyl;
each R$^3$ is independently selected from C$_{1-6}$alkyl, halogen, —CN, C$_{1-6}$haloalkyl, —SF$_5$, and —OR$^7$;
R$^4$ is selected from —C≡C-C$_{1-6}$alkyl-CO$_2$H and —C$_{3-8}$cycloalkyl-CO$_2$H;

each R$^7$ is independently selected from H, C$_{1-6}$alkyl, C$_{1-6}$haloalkyl, C$_{1-6}$aminoalkyl, C$_{3-8}$cycloalkyl, and -C$_{1-6}$alkyl-C$_{3-8}$cycloalkyl;
w is 0, 1, 2, 3, or 4;
n is 0 or 1;
m is 0 or 1;
p is 0, 1, or 2; and
q is 0, 1, or 2; provided that when q is 0, then p is 2;
or a solvate, hydrate, tautomer, N-oxide, stereoisomer, or pharmaceutically acceptable salt thereof.

In another embodiment is a compound of Formula (I), wherein m is 0, n is 0, p is 1, and q is 2. In another embodiment is a compound of Formula (I), wherein m is 0, n is 1, p is 1, and q is 1. In another embodiment is a compound of Formula (I), wherein m is 1, n is 0, p is 1, and q is 1. In another embodiment is a compound of Formula (I), wherein m is 1, n is 1, p is 0, and q is 1. In another embodiment is a compound of Formula (I), wherein m is 1, n is 1, p is 1, and q is 1. In another embodiment is a compound of Formula (I), or a solvate, hydrate, tautomer, N-oxide, stereoisomer, or a pharmaceutically acceptable salt thereof, wherein m is 1, n is 1, p is 2 and q is 0.

In some embodiments is a compound of Formula (I), or a solvate, hydrate, tautomer, N-oxide, stereoisomer, or a pharmaceutically acceptable salt thereof, wherein Y is —CH$_2$—. In some embodiments is a compound of Formula (I), or a solvate, hydrate, tautomer, N-oxide, stereoisomer, or a pharmaceutically acceptable salt thereof, wherein Y is —C(O)—.

In some embodiments is a compound of Formula (I), or a solvate, hydrate, tautomer, N-oxide, stereoisomer, or a pharmaceutically acceptable salt thereof, wherein R$^1$ is H. In some embodiments is a compound of Formula (I), or a solvate, hydrate, tautomer, N-oxide, stereoisomer, or a pharmaceutically acceptable salt thereof, wherein R$^2$ is H. In some embodiments is a compound of Formula (I), or a solvate, hydrate, tautomer, N-oxide, stereoisomer, or a pharmaceutically acceptable salt thereof, wherein R$^1$ and R$^2$ are both H. In some embodiments is a compound of Formula (I), or a solvate, hydrate, tautomer, N-oxide, stereoisomer, or a pharmaceutically acceptable salt thereof, wherein R$^1$ is C$_{1-6}$alkyl. In some embodiments is a compound of Formula (I), or a solvate, hydrate, tautomer, N-oxide, stereoisomer, or a pharmaceutically acceptable salt thereof, wherein R$^1$ is —CH$_3$. In some embodiments is a compound of Formula (I), or a solvate, hydrate, tautomer, N-oxide, stereoisomer, or a pharmaceutically acceptable salt thereof, wherein R$^2$ is C$_{1-6}$alkyl. In some embodiments is a compound of Formula (I), or a solvate, hydrate, tautomer, N-oxide, stereoisomer, or a pharmaceutically acceptable salt thereof, wherein R$^2$ is —CH$_3$. In some embodiments is a compound of Formula (I), or a solvate, hydrate, tautomer, N-oxide, stereoisomer, or a pharmaceutically acceptable salt thereof, wherein R$^1$ and R$^2$ are both C$_{1-6}$alkyl. In some embodiments is a compound of Formula (I), or a solvate, hydrate, tautomer, N-oxide, stereoisomer, or a pharmaceutically acceptable salt thereof, wherein R$^1$ and R$^2$ are both —CH$_3$.

In another embodiment is a compound of Formula (I), or a solvate, hydrate, tautomer, N-oxide, stereoisomer, or a pharmaceutically acceptable salt thereof, wherein w is 0, 1, 2, or 3. In another embodiment is a compound of Formula (I), or a solvate, hydrate, tautomer, N-oxide, stereoisomer, or a pharmaceutically acceptable salt thereof, wherein w is 0, 1, or 2. In another embodiment is a compound of Formula (I), or a solvate, hydrate, tautomer, N-oxide, stereoisomer, or a pharmaceutically acceptable salt thereof, wherein w is 0 or 1. In another embodiment is a compound of Formula (I), or a solvate, hydrate, tautomer, N-oxide, stereoisomer, or a pharmaceutically acceptable salt thereof, wherein w is 1 or 2. In another embodiment is a compound of Formula (I), or a solvate, hydrate, tautomer, N-oxide, stereoisomer, or a pharmaceutically acceptable salt thereof, wherein w is 0. In another embodiment is a compound of Formula (I), or a solvate, hydrate, tautomer, N-oxide, stereoisomer, or a pharmaceutically acceptable salt thereof, wherein w is 1. In another embodiment is a compound of Formula (I), or a solvate, hydrate, tautomer, N-oxide, stereoisomer, or a pharmaceutically acceptable salt thereof, wherein w is 2. In another embodiment is a compound of Formula (I), or a solvate, hydrate, tautomer, N-oxide, stereoisomer, or a pharmaceutically acceptable salt thereof, wherein w is 3. In another embodiment is a compound of Formula (I), or a solvate, hydrate, tautomer, N-oxide, stereoisomer, or a pharmaceutically acceptable salt thereof, wherein w is 4.

In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H. In another embodiment is a compound of Formula (I), or a solvate, hydrate, tautomer, N-oxide, stereoisomer, or a pharmaceutically acceptable salt thereof, wherein $R^4$ is —$C_{3-8}$cycloalkyl-$CO_2$H.

In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is selected from $C_{1-6}$alkyl, halogen, $C_{1-6}$haloalkyl, —$SF_5$, and —$OR^7$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is selected from halogen, $C_{1-6}$haloalkyl, and —$OR^7$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is selected from halogen and $C_{1-6}$haloalkyl. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is $C_{1-6}$alkyl. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$CH_3$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is halogen. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —Cl. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —CN. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is $C_{1-6}$haloalkyl. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$CF_3$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$SF_5$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$OR^7$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$OCH_3$.

In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from $C_{1-6}$alkyl, halogen, $C_{1-6}$haloalkyl, —$SF_5$, and —$OR^7$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from halogen, $C_{1-6}$haloalkyl, and —$OR^7$. In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from halogen and $C_{1-6}$haloalkyl.

In another embodiment is a compound of Formula (I), or a solvate, hydrate, tautomer, N-oxide, stereoisomer, or a pharmaceutically acceptable salt thereof, wherein $R^4$ is —C≡C-$C_{1-6}$cycloalkyl-$CO_2$H, w is 1, and $R^3$ is selected from $C_{1-6}$alkyl, halogen, $C_{1-6}$haloalkyl, —$SF_5$, and —$OR^7$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is selected from halogen, $C_{1-6}$haloalkyl, and —$OR^7$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is selected from halogen and $C_{3-6}$haloalkyl. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is $C_{1-6}$alkyl. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$CH_3$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is halogen. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —Cl. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —CN. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is $C_{1-6}$haloalkyl. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$CF_3$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —$SF_5$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —$OR^7$. In another embodiment is a compound of Formula (I), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —$OCH_3$.

In another embodiment is a compound of Formula (I), or a solvate, hydrate, tautomer, N-oxide, stereoisomer, or a pharmaceutically acceptable salt thereof, wherein $R^4$ -$C_{3-8}$cycloalkyl-$CO_2H$, w is 2, and each $R^3$ is independently selected from $C_{1-6}$alkyl, halogen, $C_{1-6}$haloalkyl, —$SF_5$, and —$OR^7$. In another embodiment is a compound of Formula (I), or a solvate, hydrate, tautomer, N-oxide, stereoisomer, or a pharmaceutically acceptable salt thereof, wherein $R^4$ is —$C_{3-8}$cycloalkyl-$CO_2H$, w is 2, and each $R^3$ is independently selected from halogen, $C_{1-6}$haloalkyl, and —$OR^7$. In another embodiment is a compound of Formula (I), or a solvate, hydrate, tautomer, N-oxide, stereoisomer, or a pharmaceutically acceptable salt thereof, wherein $R^4$ -$C_{3-8}$cycloalkyl-$CO_2H$, w is 2, and each $R^3$ is independently selected from halogen and $C_{1-6}$haloalkyl.

In some embodiments is a compound having the structure of Formula (Ia):

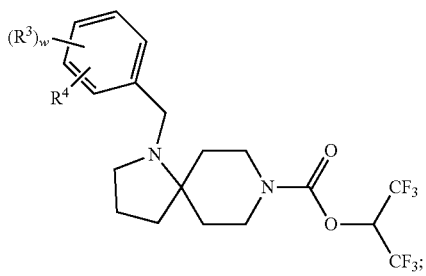

Formula (Ia)

wherein:
each $R^3$ is independently selected from $C_{1-6}$alkyl, halogen, —CN, $C_{1-6}$haloalkyl, —$SF_5$, and —$OR^7$;
$R^4$ is selected from —C≡C-$C_{1-6}$alkyl-$CO_2H$ and -$C_{3-8}$cycloalkyl-$CO_2H$;
each $R^7$ is independently selected from H, $C_{1-6}$alkyl, $C_{1-6}$haloalkyl, $C_{1-6}$aminoalkyl, $C_{3-8}$cycloalkyl, and -$C_{1-6}$alkyl-$C_{3-8}$cycloalkyl; and
w is 0, 1, 2, 3, or 4;
or a solvate, hydrate, tautomer, N-oxide, stereoisomer, or pharmaceutically acceptable salt thereof.

In another embodiment is a compound of Formula (Ia), or a solvate, hydrate, tautomer, N-oxide, stereoisomer, or a pharmaceutically acceptable salt thereof, wherein w is 0, 1, 2, or 3. In another embodiment is a compound of Formula (Ia), or a solvate, hydrate, tautomer, N-oxide, stereoisomer, or a pharmaceutically acceptable salt thereof, wherein w is 0, 1, or 2. In another embodiment is a compound of Formula (Ia), or a solvate, hydrate, tautomer, N-oxide, stereoisomer, or a pharmaceutically acceptable salt thereof, wherein w is 0 or 1. In another embodiment is a compound of Formula (Ia), or a solvate, hydrate, tautomer, N-oxide, stereoisomer, or a pharmaceutically acceptable salt thereof, wherein w is 1 or 2. In another embodiment is a compound of Formula (Ia), or a solvate, hydrate, tautomer, N-oxide, stereoisomer, or a pharmaceutically acceptable salt thereof, wherein w is 0. In another embodiment is a compound of Formula (Ia), or a solvate, hydrate, tautomer, N-oxide, stereoisomer, or a pharmaceutically acceptable salt thereof, wherein w is 1. In another embodiment is a compound of Formula (Ia), or a solvate, hydrate, tautomer, N-oxide, stereoisomer, or a pharmaceutically acceptable salt thereof, wherein w is 2. In another embodiment is a compound of Formula (Ia), or a solvate, hydrate, tautomer, N-oxide, stereoisomer, or a pharmaceutically acceptable salt thereof, wherein w is 3. In another embodiment is a compound of Formula (Ia), or a solvate, hydrate, tautomer, N-oxide, stereoisomer, or a pharmaceutically acceptable salt thereof, wherein w is 4.

In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$. In another embodiment is a compound of Formula (Ia), or a solvate, hydrate, tautomer, N-oxide, stereoisomer, or a pharmaceutically acceptable salt thereof, wherein $R^4$ is —$C_{3-8}$cycloalkyl-$CO_2H$.

In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$ and w is 0. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2H$ and w is 0.

In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from $C_{1-6}$alkyl, halogen, $C_{1-6}$haloalkyl, —$SF_5$, and —$OR^7$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from halogen, $C_{1-6}$haloalkyl, and —$OR^7$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from halogen and $C_{1-6}$haloalkyl. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is $C_{1-6}$alkyl. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$CH_3$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is halogen. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —Cl. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —CN. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is $C_{1-6}$haloalkyl. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$CF_3$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$SF_5$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$OR^7$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 1, and $R^3$ is —$OCH_3$.

In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from $C_{1-6}$alkyl, halogen, $C_{1-6}$haloalkyl, —$SF_5$, and —$OR^7$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from halogen, $C_{1-6}$haloalkyl, and —$OR^7$. In another embodiment is a compound of Formula (Ia), or a solvate, hydrate, tautomer, N-oxide, stereoisomer, or a pharmaceutically acceptable salt thereof, wherein $R^4$ is —C≡C-$C_{1-6}$alkyl-$CO_2$H, w is 2, and each $R^3$ is independently selected from halogen and $C_{1-6}$haloalkyl In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is selected from $C_{1-6}$alkyl, halogen, $C_{1-6}$haloalkyl, —$SF_5$, and —$OR^7$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is selected from halogen, $C_{1-6}$haloalkyl, and —$OR^7$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is selected from halogen and $C_{1-6}$haloalkyl. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is $C_{1-6}$alkyl. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$CH_3$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is halogen. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —Cl. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —CN. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is $C_{1-6}$haloalkyl. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$CF_3$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$SF_5$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$OR^7$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 1, and $R^3$ is —$OCH_3$.

In another embodiment is a compound of Formula (Ia), or a solvate, hydrate, tautomer, N-oxide, stereoisomer, or a pharmaceutically acceptable salt thereof, wherein $R^4$ -$C_{3-8}$cycloalkyl-$CO_2$H, w is 2, and each $R^3$ is independently selected from $C_{1-6}$alkyl, halogen, $C_{1-6}$haloalkyl, —$SF_5$, and —$OR^7$. In another embodiment is a compound of Formula (Ia), or a solvate, hydrate, tautomer, N-oxide, stereoisomer, or a pharmaceutically acceptable salt thereof, wherein $R^4$ is -$C_{3-8}$cycloalkyl-$CO_2$H, w is 2, and each $R^3$ is independently selected from halogen, $C_{1-6}$haloalkyl, and —$OR^7$. In another embodiment is a compound of Formula (Ia), or a solvate, hydrate, tautomer, N-oxide, stereoisomer, or a pharmaceutically acceptable salt thereof, wherein $R^4$ -$C_{3-8}$cycloalkyl-$CO_2$H, w is 2, and each $R^3$ is independently selected from halogen and $C_{1-6}$haloalkyl.

In some embodiments is a compound having the structure of Formula (Ib):

Formula (Ib)

wherein:
  each $R^3$ is independently selected from $C_{1-6}$alkyl, halogen, —CN, $C_{1-6}$haloalkyl, —$SF_5$, and —$OR^7$;
  $R^4$ is selected from —C≡C-$C_{1-6}$alkyl-$CO_2$H and -$C_{3-8}$cycloalkyl-$CO_2$H;
  each $R^7$ is independently selected from H, $C_{1-6}$alkyl, $C_{1-6}$haloalkyl, $C_{1-6}$aminoalkyl, $C_{3-8}$cycloalkyl, and -$C_{1-6}$alkyl-$C_{3-8}$cycloalkyl; and
  w is 0, 1, 2, 3, or 4;
or a solvate, hydrate, tautomer, N-oxide, stereoisomer, or pharmaceutically acceptable salt thereof.

In another embodiment is a compound of Formula (Ib), or a solvate, hydrate, tautomer, N-oxide, stereoisomer, or a pharmaceutically acceptable salt thereof, wherein w is 0, 1, 2, or 3. In another embodiment is a compound of Formula (Ib), or a solvate, hydrate, tautomer, N-oxide, stereoisomer, or a pharmaceutically acceptable salt thereof, wherein w is 0, 1, or 2. In another embodiment is a compound of Formula (Ib), or a solvate, hydrate, tautomer, N-oxide, stereoisomer, or a pharmaceutically acceptable salt thereof, wherein w is 0 or 1. In another embodiment is a compound of Formula (Ib), or a solvate, hydrate, tautomer, N-oxide, stereoisomer, or a pharmaceutically acceptable salt thereof, wherein w is 1 or 2. In another embodiment is a compound of Formula (Ib), or a solvate, hydrate, tautomer, N-oxide, stereoisomer, or a pharmaceutically acceptable salt thereof, wherein w is 0. In another embodiment is a compound of Formula (Ib), or a solvate, hydrate, tautomer, N-oxide, stereoisomer, or a pharmaceutically acceptable salt thereof, wherein w is 1. In another embodiment is a compound of Formula (Ib), or a solvate, hydrate, tautomer, N-oxide, stereoisomer, or a pharmaceutically acceptable salt thereof, wherein w is 2. In another embodiment is a compound of Formula (Ib), or a solvate, hydrate, tautomer, N-oxide, stereoisomer, or a pharmaceutically acceptable salt thereof, wherein w is 3. In another embodiment is a compound of Formula (Ib), or a solvate, hydrate, tautomer, N-oxide, stereoisomer, or a pharmaceutically acceptable salt thereof, wherein w is 4.

In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$.

In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$ and w is 0. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$ and w is 0.

In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from $C_{1-6}$alkyl, halogen, $C_{1-6}$haloalkyl, —$SF_5$, and —$OR^7$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from halogen, $C_{1-6}$haloalkyl, and —$OR^7$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is selected from halogen and $C_{1-6}$haloalkyl. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is $C_{1-6}$alkyl. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$CH_3$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is halogen. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —Cl. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —CN. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is $C_{1-6}$haloalkyl. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$CF_3$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$SF_5$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$OR^7$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 1, and $R^3$ is —$OCH_3$.

In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 2, and each $R^3$ is independently selected from $C_{1-6}$alkyl, halogen, $C_{1-6}$haloalkyl, —$SF_5$, and —$OR^7$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 2, and each $R^3$ is independently selected from halogen, $C_{1-6}$haloalkyl, and —$OR^7$. In another embodiment is a compound of Formula (Ib), or a solvate, hydrate, tautomer, N-oxide, stereoisomer, or a pharmaceutically acceptable salt thereof, wherein $R^4$ is —C≡C-$C_{1-6}$alkyl-$CO_2H$, w is 2, and each $R^3$ is independently selected from halogen and $C_{1-6}$haloalkyl.

In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is selected from $C_{1-6}$alkyl, halogen, $C_{1-6}$haloalkyl, —$SF_5$, and —$OR^7$. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is selected from halogen, $C_{1-6}$haloalkyl, and —$OR^7$. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is selected from halogen and $C_{1-6}$haloalkyl. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is $C_{1-6}$alkyl. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —$CH_3$. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is halogen. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —Cl. In another embodiment is a compound of Formula (Ib), or a solvate, hydrate, tautomer, N-oxide, stereoisomer, or a pharmaceutically acceptable salt thereof, wherein $R^4$ is -$C_{3-8}$cycloalkyl-$CO_2H$, w is 1, and $R^3$ is —CN. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 1, and R³ is $C_{1-6}$haloalkyl. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 1, and R³ is —$CF_3$. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 1, and R³ is —$SF_5$. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 1, and R³ is —$OR^7$. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 1, and R³ is —$OCH_3$.

In another embodiment is a compound of Formula (Ib), or a solvate, hydrate, tautomer, N-oxide, stereoisomer, or a pharmaceutically acceptable salt thereof, wherein R⁴ -$C_{3-8}$cycloalkyl-$CO_2H$, w is 2, and each R³ is independently selected from $C_{1-6}$alkyl, halogen, $C_{1-6}$haloalkyl, —$SF_5$, and —$OR^7$. In another embodiment is a compound of Formula (Ib), or a solvate, hydrate, tautomer, N-oxide, stereoisomer, or a pharmaceutically acceptable salt thereof, wherein R⁴ is -$C_{3-8}$cycloalkyl-$CO_2H$, w is 2, and each R³ is independently selected from halogen, $C_{1-6}$haloalkyl, and —$OR^7$. In another embodiment is a compound of Formula (Ib), or a solvate, hydrate, tautomer, N-oxide, stereoisomer, or a pharmaceutically acceptable salt thereof, wherein R⁴ -$C_{3-8}$cycloalkyl-$CO_2H$, w is 2, and each R³ is independently selected from halogen and $C_{1-6}$haloalkyl.

In some embodiments is a compound having the structure of Formula (I'):

Formula (I')

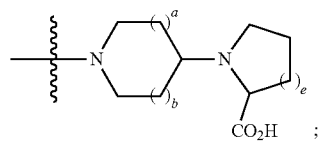

wherein:
Y is —$CH_2$—;
R¹ is H or $C_{1-6}$alkyl;
R² is H or $C_{1-6}$alkyl;
each R³ is independently selected from $C_{1-6}$alkyl, halogen, —CN, $C_{1-6}$haloalkyl, —$SF_5$, and —$OR^7$;
R⁴ is selected from

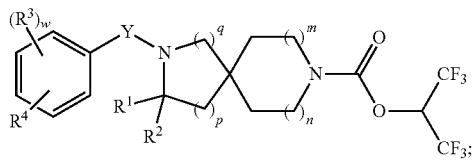

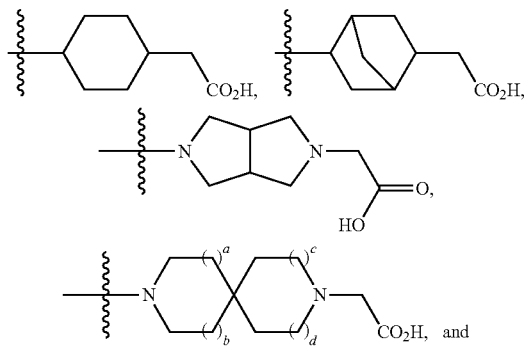

each R⁷ is independently selected from H, $C_{1-6}$alkyl, $C_{1-6}$haloalkyl, $C_{3-8}$cycloalkyl, and -$C_{1-6}$alkyl-$C_{3-8}$cycloalkyl;
a, b, c, and d are independently 0 or 1;
e is 0, 1, or 2;
w is 0, 1, 2, 3, or 4;
n is 0 or 1;
m is 0 or 1;
p is 0, 1, or 2; and
q is 0, 1, or 2; provided that when q is 0, then p is 2;
or a solvate, hydrate, tautomer, N-oxide, stereoisomer, or pharmaceutically acceptable salt thereof.

In another embodiment is a compound of Formula (I'), wherein m is 0, n is 0, p is 1, and q is 2. In another embodiment is a compound of Formula (I'), wherein m is 0, n is 1, p is 1, and q is 1. In another embodiment is a compound of Formula (I'), wherein m is 1, n is 0, p is 1, and q is 1. In another embodiment is a compound of Formula (I'), wherein m is 1, n is 1, p is 0, and q is 1. In another embodiment is a compound of Formula (I'), wherein m is 1, n is 1, p is 1, and q is 1. In another embodiment is a compound of Formula (I'), or a solvate, hydrate, tautomer, N-oxide, stereoisomer, or a pharmaceutically acceptable salt thereof, wherein m is 1, n is 1, p is 2 and q is 0.

In some embodiments is a compound of Formula (I'), or a solvate, hydrate, tautomer, N-oxide, stereoisomer, or a pharmaceutically acceptable salt thereof, wherein R¹ is H. In some embodiments is a compound of Formula (I'), or a solvate, hydrate, tautomer, N-oxide, stereoisomer, or a pharmaceutically acceptable salt thereof, wherein R² is H. In some embodiments is a compound of Formula (I'), or a solvate, hydrate, tautomer, N-oxide, stereoisomer, or a pharmaceutically acceptable salt thereof, wherein R¹ and R² are both H. In some embodiments is a compound of Formula (I'), or a solvate, hydrate, tautomer, N-oxide, stereoisomer, or a pharmaceutically acceptable salt thereof, wherein R¹ is $C_{1-6}$alkyl. In some embodiments is a compound of Formula (I'), or a solvate, hydrate, tautomer, N-oxide, stereoisomer, or a pharmaceutically acceptable salt thereof, wherein R¹ is —$CH_3$. In some embodiments is a compound of Formula (I'), or a solvate, hydrate, tautomer, N-oxide, stereoisomer, or a pharmaceutically acceptable salt thereof, wherein R² is $C_{1-6}$alkyl. In some embodiments is a compound of Formula (I'), or a solvate, hydrate, tautomer, N-oxide, stereoisomer, or a pharmaceutically acceptable salt thereof, wherein R² is —$CH_3$. In some embodiments is a compound of Formula (I'), or a solvate, hydrate, tautomer, N-oxide, stereoisomer, or a pharmaceutically acceptable salt thereof, wherein R¹ and R² are both $C_{1-6}$alkyl. In some embodiments is a compound of Formula (I'), or a solvate, hydrate, tautomer, N-oxide, stereoisomer, or a pharmaceutically acceptable salt thereof, wherein R¹ and R² are both —$CH_3$.

In another embodiment is a compound of Formula (I'), or a solvate, hydrate, tautomer, N-oxide, stereoisomer, or a pharmaceutically acceptable salt thereof, wherein w is 0, 1, 2, or 3. In another embodiment is a compound of Formula (I'), or a solvate, hydrate, tautomer, N-oxide, stereoisomer, or a pharmaceutically acceptable salt thereof, wherein w is 0, 1, or 2. In another embodiment is a compound of Formula (I'), or a solvate, hydrate, tautomer, N-oxide, stereoisomer, or a pharmaceutically acceptable salt thereof, wherein w is 0 or 1. In another embodiment is a compound of Formula (I'), or a solvate, hydrate, tautomer, N-oxide, stereoisomer, or a pharmaceutically acceptable salt thereof, wherein w is 1 or 2. In another embodiment is a compound of Formula (I'), or a solvate, hydrate, tautomer, N-oxide, stereoisomer, or a pharmaceutically acceptable salt thereof, wherein w is 0. In another embodiment is a compound of Formula (I'), or a solvate, hydrate, tautomer, N-oxide, stereoisomer, or a pharmaceutically acceptable salt thereof, wherein w is 1. In another embodiment is a compound of Formula (I'), or a solvate, hydrate, tautomer, N-oxide, stereoisomer, or a pharmaceutically acceptable salt thereof, wherein w is 2. In another embodiment is a compound of Formula (I'), or a solvate, hydrate, tautomer, N-oxide, stereoisomer, or a pharmaceutically acceptable salt thereof, wherein w is 3. In another embodiment is a compound of Formula (I'), or a solvate, hydrate, tautomer, N-oxide, stereoisomer, or a pharmaceutically acceptable salt thereof, wherein w is 4.

In another embodiment is a compound of Formula (I'), or a solvate, hydrate, tautomer, N-oxide, stereoisomer, or a pharmaceutically acceptable salt thereof, wherein $R^4$ is

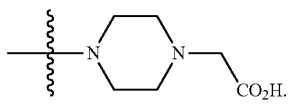

In another embodiment is a compound of Formula (I'), or a solvate, hydrate, tautomer, N-oxide, stereoisomer, or a pharmaceutically acceptable salt thereof, wherein $R^4$ is

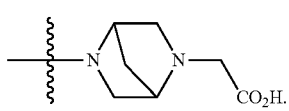 [SMILES: *N1CC2CC1CN2CC(=O)O]

In another embodiment is a compound of Formula (I'), or a solvate, hydrate, tautomer, N-oxide, stereoisomer, or a pharmaceutically acceptable salt thereof, wherein $R^4$ is

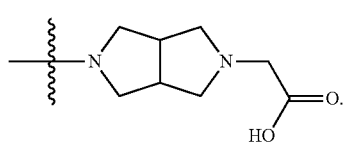 [SMILES: *N1CC2CN(CC(=O)O)CC2C1]

In another embodiment is a compound of Formula (I'), or a solvate, hydrate, tautomer, N-oxide, stereoisomer, or a pharmaceutically acceptable salt thereof, wherein $R^4$ is

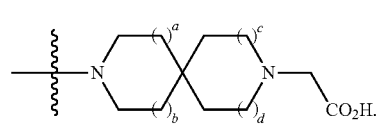

In another embodiment is a compound of Formula (I'), or a solvate, hydrate, tautomer, N-oxide, stereoisomer, or a pharmaceutically acceptable salt thereof, wherein $R^4$ is

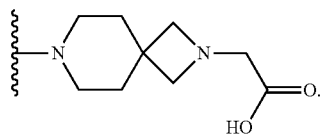 [SMILES: *N1CCC2(CC1)CN(CC(=O)O)C2]

In another embodiment is a compound of Formula (I'), or a solvate, hydrate, tautomer, N-oxide, stereoisomer, or a pharmaceutically acceptable salt thereof, wherein $R^4$ is

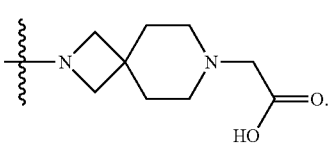 [SMILES: *N1CC2(CCN(CC(=O)O)CC2)C1]

In another embodiment is a compound of Formula (I'), or a solvate, hydrate, tautomer, N-oxide, stereoisomer, or a pharmaceutically acceptable salt thereof, wherein $R^4$ is

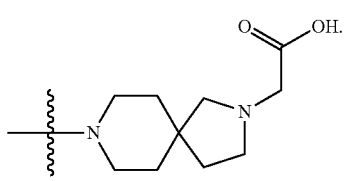 [SMILES: *N1CCC2(CC1)CCN(CC(=O)O)C2]

In another embodiment is a compound of Formula (I'), or a solvate, hydrate, tautomer, N-oxide, stereoisomer, or a pharmaceutically acceptable salt thereof, wherein $R^4$ is

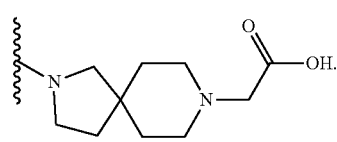 [SMILES: *N1CCC2(CCN(CC(=O)O)CC2)C1]

In another embodiment is a compound of Formula (I'), or a solvate, hydrate, tautomer, N-oxide, stereoisomer, or a pharmaceutically acceptable salt thereof, wherein $R^4$ is

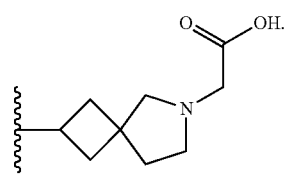 [SMILES: *C1CC2(CCN(CC(=O)O)C2)C1]

In another embodiment is a compound of Formula (I'), or a solvate, hydrate, tautomer, N-oxide, stereoisomer, or a pharmaceutically acceptable salt thereof, wherein $R^4$ is

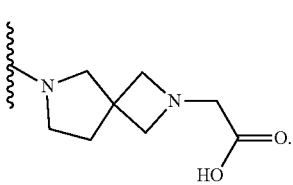 [SMILES: *N1CCC2(C1)CN(CC(=O)O)C2]

In another embodiment is a compound of Formula (I'), or a solvate, hydrate, tautomer, N-oxide, stereoisomer, or a pharmaceutically acceptable salt thereof, wherein $R^4$ is

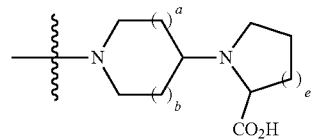

In another embodiment is a compound of Formula (I'), or a solvate, hydrate, tautomer, N-oxide, stereoisomer, or a pharmaceutically acceptable salt thereof, wherein $R^4$ is

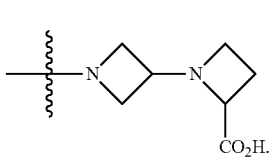 [SMILES: *N1CC(N2CCC2C(=O)O)C1]

In another embodiment is a compound of Formula (I'), or a solvate, hydrate, tautomer, N-oxide, stereoisomer, or a pharmaceutically acceptable salt thereof, wherein $R^4$ is

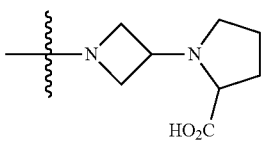

In another embodiment is a compound of Formula (I'), or a solvate, hydrate, tautomer, N-oxide, stereoisomer, or a pharmaceutically acceptable salt thereof, wherein $R^4$ is

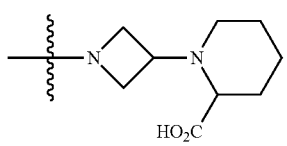

In another embodiment is a compound of Formula (I'), or a solvate, hydrate, tautomer, N-oxide, stereoisomer, or a pharmaceutically acceptable salt thereof, wherein $R^4$ is

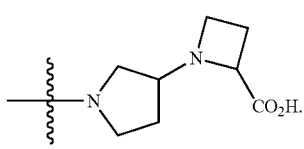 [SMILES: *N1CCC(N2CCC2C(=O)O)C1]

In another embodiment is a compound of Formula (I'), or a solvate, hydrate, tautomer, N-oxide, stereoisomer, or a pharmaceutically acceptable salt thereof, wherein $R^4$ is

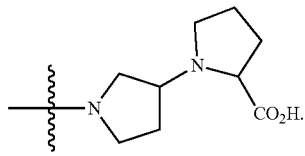 [SMILES: *N1CCC(N2CCCC2C(=O)O)C1]

In another embodiment is a compound of Formula (I'), or a solvate, hydrate, tautomer, N-oxide, stereoisomer, or a pharmaceutically acceptable salt thereof, wherein $R^4$ is

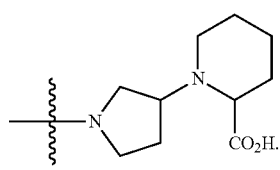 [SMILES: *N1CCC(N2CCCCC2C(=O)O)C1]

In another embodiment is a compound of Formula (I'), or a solvate, hydrate, tautomer, N-oxide, stereoisomer, or a pharmaceutically acceptable salt thereof, wherein $R^4$ is

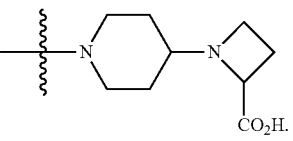 [SMILES: *N1CCC(N2CCC2C(=O)O)CC1]

In another embodiment is a compound of Formula (I'), or a solvate, hydrate, tautomer, N-oxide, stereoisomer, or a pharmaceutically acceptable salt thereof, wherein $R^4$ is

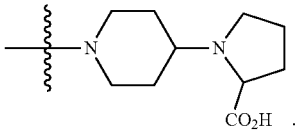

In another embodiment is a compound of Formula (I'), or a solvate, hydrate, tautomer, N-oxide, stereoisomer, or a pharmaceutically acceptable salt thereof, wherein $R^4$ is

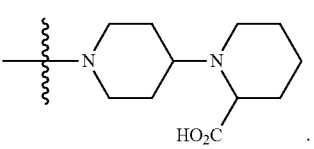 [SMILES: *N1CCC(N2CCCCC2C(=O)O)CC1]

In another embodiment is a compound of Formula (I'), or a solvate, hydrate, tautomer, N-oxide, stereoisomer, or a pharmaceutically acceptable salt thereof, wherein $R^4$ is selected from

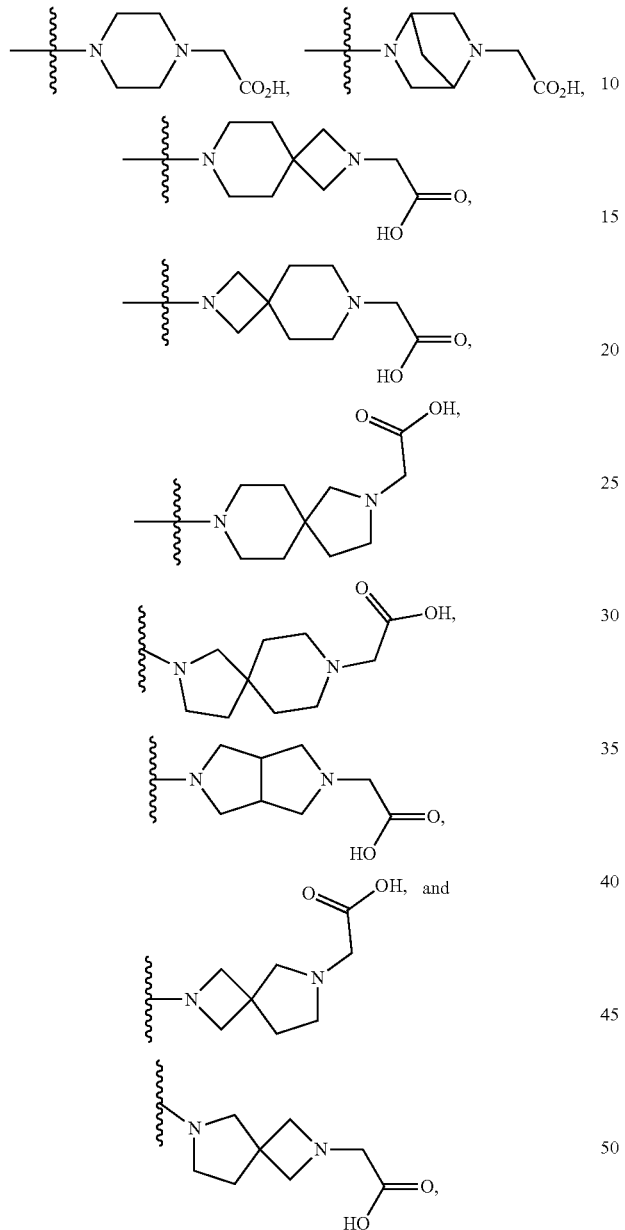

and w is 0. In another embodiment is a compound of Formula (I'), or a solvate, hydrate, tautomer, N-oxide, stereoisomer, or a pharmaceutically acceptable salt thereof, wherein $R^4$ is selected from

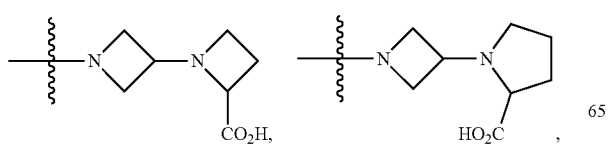

-continued

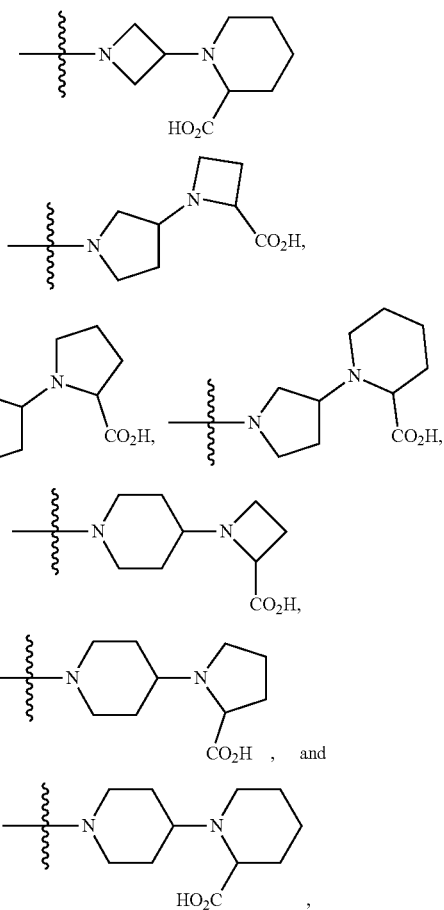

and w is 0.

In another embodiment is a compound of Formula (I'), or a solvate, hydrate, tautomer, N-oxide, stereoisomer, or a pharmaceutically acceptable salt thereof, wherein $R^4$ is selected from

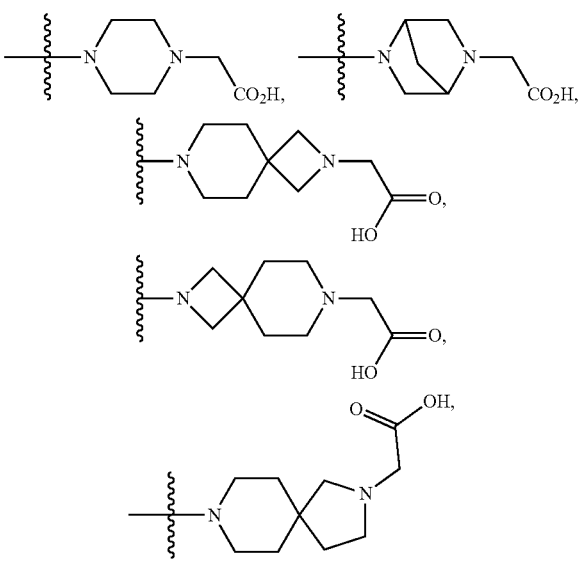

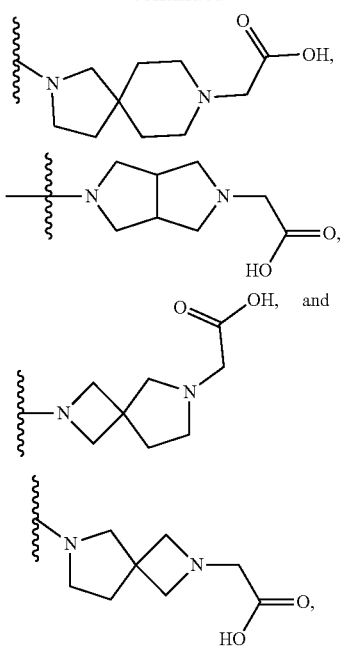

and w is 1. In another embodiment is a compound of Formula (I'), or a solvate, hydrate, tautomer, N-oxide, stereoisomer, or a pharmaceutically acceptable salt thereof, wherein $R^4$ is selected from selected from

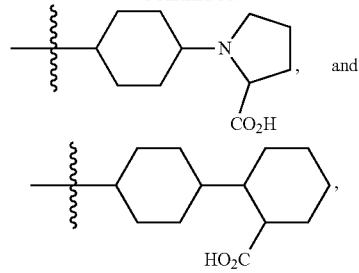

and w is 1.

In another embodiment is a compound of Formula (I'), or a solvate, hydrate, tautomer, N-oxide, stereoisomer, or a pharmaceutically acceptable salt thereof, wherein w is 1 and $R^3$ is selected from $C_{1-6}$alkyl, halogen, $C_{1-6}$haloalkyl, —$SF_5$, and —$OR^7$. In another embodiment is a compound of Formula (I'), or a solvate, hydrate, tautomer, N-oxide, stereoisomer, or a pharmaceutically acceptable salt thereof, wherein w is 1 and $R^3$ is selected from halogen, $C_{1-6}$haloalkyl, and —$OR^7$. In another embodiment is a compound of Formula (I'), or a solvate, hydrate, tautomer, N-oxide, stereoisomer, or a pharmaceutically acceptable salt thereof, wherein w is 1 and $R^3$ is selected from halogen and $C_{1-6}$haloalkyl. In another embodiment is a compound of Formula (I'), or a solvate, hydrate, tautomer, N-oxide, stereoisomer, or a pharmaceutically acceptable salt thereof, wherein w is 1 and $R^3$ is $C_{1-6}$alkyl. In another embodiment is a compound of Formula (I'), or a solvate, hydrate, tautomer, N-oxide, stereoisomer, or a pharmaceutically acceptable salt thereof, wherein w is 1 and $R^3$ is —$CH_3$. In another embodiment is a compound of Formula (I'), or a solvate, hydrate, tautomer, N-oxide, stereoisomer, or a pharmaceutically acceptable salt thereof, wherein w is 1 and $R^3$ is halogen. In another embodiment is a compound of Formula (I'), or a solvate, hydrate, tautomer, N-oxide, stereoisomer, or a pharmaceutically acceptable salt thereof, wherein w is 1 and $R^3$ is —Cl. In another embodiment is a compound of Formula (I'), or a solvate, hydrate, tautomer, N-oxide, stereoisomer, or a pharmaceutically acceptable salt thereof, wherein w is 1 and $R^3$ is —CN. In another embodiment is a compound of Formula (I'), or a solvate, hydrate, tautomer, N-oxide, stereoisomer, or a pharmaceutically acceptable salt thereof, wherein w is 1 and $R^3$ is $C_{1-6}$haloalkyl. In another embodiment is a compound of Formula (I'), or a solvate, hydrate, tautomer, N-oxide, stereoisomer, or a pharmaceutically acceptable salt thereof, wherein w is 1 and $R^3$ is —$CF_3$. In another embodiment is a compound of Formula (I'), or a solvate, hydrate, tautomer, N-oxide, stereoisomer, or a pharmaceutically acceptable salt thereof, wherein w is 1 and $R^3$ is —$SF_5$. In another embodiment is a compound of Formula (I'), or a solvate, hydrate, tautomer, N-oxide, stereoisomer, or a pharmaceutically acceptable salt thereof, wherein w is 1 and $R^3$ is —$OR^7$. In another embodiment is a compound of Formula (I'), or a solvate, hydrate, tautomer, N-oxide, stereoisomer, or a pharmaceutically acceptable salt thereof, wherein w is 1 and $R^3$ is —$OCH_3$.

In another embodiment is a compound of Formula (I'), or a solvate, hydrate, tautomer, N-oxide, stereoisomer, or a pharmaceutically acceptable salt thereof, wherein w is 2 and each $R^3$ is independently selected from $C_{1-6}$alkyl, halogen, $C_{1-6}$haloalkyl, —$SF_5$, and —$OR^7$. In another embodiment is a compound of Formula (I'), or a solvate, hydrate, tautomer, N-oxide, stereoisomer, or a pharmaceutically acceptable salt thereof, wherein w is 2 and each $R^3$ is independently selected from halogen, $C_{1-6}$haloalkyl, and —$OR^7$. In another embodiment is a compound of Formula (I'), or a solvate, hydrate, tautomer, N-oxide, stereoisomer, or a pharmaceutically acceptable salt thereof, wherein w is 2 and each $R^3$ is independently selected from halogen and $C_{1-6}$haloalkyl.

In some embodiments is a compound having the structure of Formula (Ia'):

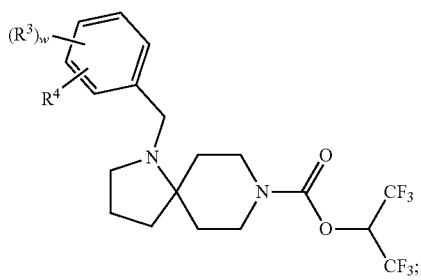

Formula (Ia')

wherein:
each $R^3$ is independently selected from $C_{1-6}$alkyl, halogen, —CN, $C_{1-6}$haloalkyl, —$SF_5$, and —$OR^7$;
$R^4$ is selected from

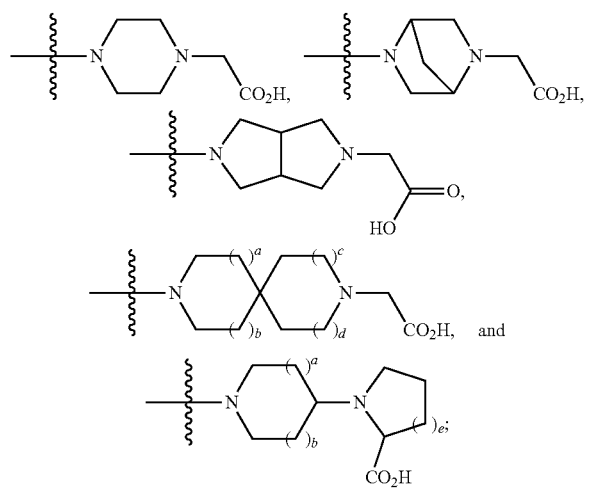

each $R^7$ is independently selected from H, $C_{1-6}$alkyl, $C_{1-6}$haloalkyl, $C_{3-8}$cycloalkyl, and -$C_{1-6}$alkyl-$C_{3-8}$cycloalkyl;
a, b, c, and d are independently 0 or 1;
e is 0, 1, or 2; and
w is 0, 1, 2, 3, or 4;
or a solvate, hydrate, tautomer, N-oxide, stereoisomer, or pharmaceutically acceptable salt thereof.

In another embodiment is a compound of Formula (Ia'), or a solvate, hydrate, tautomer, N-oxide, stereoisomer, or a pharmaceutically acceptable salt thereof, wherein w is 0, 1, 2, or 3. In another embodiment is a compound of Formula (Ia'), or a solvate, hydrate, tautomer, N-oxide, stereoisomer, or a pharmaceutically acceptable salt thereof, wherein w is 0, 1, or 2. In another embodiment is a compound of Formula (Ia'), or a solvate, hydrate, tautomer, N-oxide, stereoisomer, or a pharmaceutically acceptable salt thereof, wherein w is 0 or 1. In another embodiment is a compound of Formula (Ia'), or a solvate, hydrate, tautomer, N-oxide, stereoisomer, or a pharmaceutically acceptable salt thereof, wherein w is 1 or 2. In another embodiment is a compound of Formula (Ia'), or a solvate, hydrate, tautomer, N-oxide, stereoisomer, or a pharmaceutically acceptable salt thereof, wherein w is 0. In another embodiment is a compound of Formula (Ia'), or a solvate, hydrate, tautomer, N-oxide, stereoisomer, or a pharmaceutically acceptable salt thereof, wherein w is 1. In another embodiment is a compound of Formula (Ia'), or a solvate, hydrate, tautomer, N-oxide, stereoisomer, or a pharmaceutically acceptable salt thereof, wherein w is 2. In another embodiment is a compound of Formula (Ia'), or a solvate, hydrate, tautomer, N-oxide, stereoisomer, or a pharmaceutically acceptable salt thereof, wherein w is 3. In another embodiment is a compound of Formula (Ia'), or a solvate, hydrate, tautomer, N-oxide, stereoisomer, or a pharmaceutically acceptable salt thereof, wherein w is 4.

In another embodiment is a compound of Formula (Ia'), or a solvate, hydrate, tautomer, N-oxide, stereoisomer, or a pharmaceutically acceptable salt thereof, wherein $R^4$ is

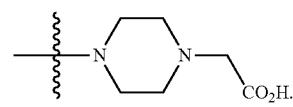 [SMILES: *N1CCN(CC(=O)O)CC1]

In another embodiment is a compound of Formula (Ia'), or a solvate, hydrate, tautomer, N-oxide, stereoisomer, or a pharmaceutically acceptable salt thereof, wherein $R^4$ is

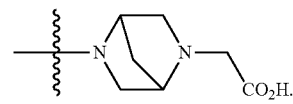 [SMILES: *N1CC2CC1CN2CC(=O)O]

In another embodiment is a compound of Formula (Ia'), or a solvate, hydrate, tautomer, N-oxide, stereoisomer, or a pharmaceutically acceptable salt thereof, wherein $R^4$ is

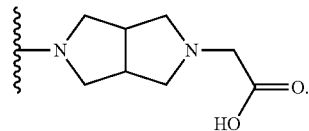 [SMILES: *N1CC2CN(CC(=O)O)CC2C1]

In another embodiment is a compound of Formula (Ia'), or a solvate, hydrate, tautomer, N-oxide, stereoisomer, or a pharmaceutically acceptable salt thereof, wherein $R^4$ is

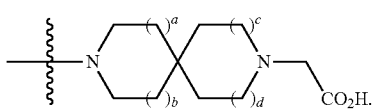

In another embodiment is a compound of Formula (Ia'), or a solvate, hydrate, tautomer, N-oxide, stereoisomer, or a pharmaceutically acceptable salt thereof, wherein $R^4$ is

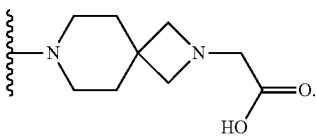 [SMILES: *N1CCC2(CC1)CN(CC(=O)O)C2]

In another embodiment is a compound of Formula (Ia'), or a solvate, hydrate, tautomer, N-oxide, stereoisomer, or a pharmaceutically acceptable salt thereof, wherein $R^4$ is

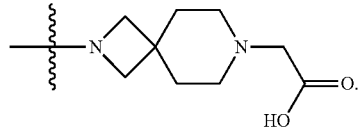

In another embodiment is a compound of Formula (Ia'), or a solvate, hydrate, tautomer, N-oxide, stereoisomer, or a pharmaceutically acceptable salt thereof, wherein $R^4$ is

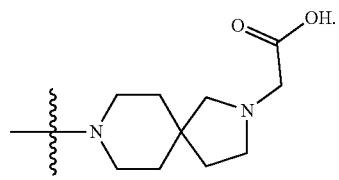 [SMILES: *N1CCC2(CC1)CCN(CC(=O)O)C2]

In another embodiment is a compound of Formula (Ia'), or a solvate, hydrate, tautomer, N-oxide, stereoisomer, or a pharmaceutically acceptable salt thereof, wherein $R^4$ is

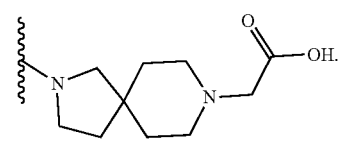 [SMILES: *N1CCC2(CCN(CC(=O)O)CC2)C1]

In another embodiment is a compound of Formula (Ia'), or a solvate, hydrate, tautomer, N-oxide, stereoisomer, or a pharmaceutically acceptable salt thereof, wherein $R^4$ is

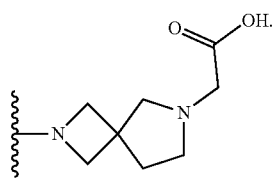 [SMILES: *N1CC2(CCN(CC(=O)O)C2)C1]

In another embodiment is a compound of Formula (Ia'), or a solvate, hydrate, tautomer, N-oxide, stereoisomer, or a pharmaceutically acceptable salt thereof, wherein $R^4$ is

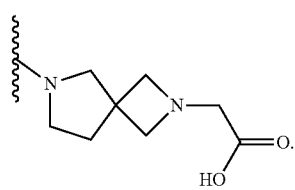 [SMILES: *N1CCC2(C1)CN(CC(=O)O)C2]

In another embodiment is a compound of Formula (Ia'), or a solvate, hydrate, tautomer, N-oxide, stereoisomer, or a pharmaceutically acceptable salt thereof, wherein $R^4$ is

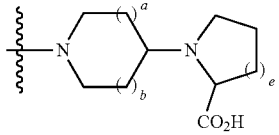

In another embodiment is a compound of Formula (Ia'), or a solvate, hydrate, tautomer, N-oxide, stereoisomer, or a pharmaceutically acceptable salt thereof, wherein $R^4$ is

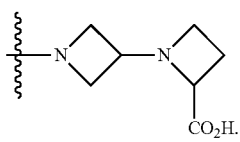 [SMILES: *N1CC(N2CCC2C(=O)O)C1]

In another embodiment is a compound of Formula (Ia'), or a solvate, hydrate, tautomer, N-oxide, stereoisomer, or a pharmaceutically acceptable salt thereof, wherein $R^4$ is

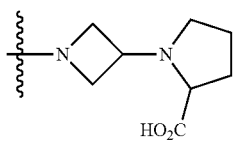

In another embodiment is a compound of Formula (Ia'), or a solvate, hydrate, tautomer, N-oxide, stereoisomer, or a pharmaceutically acceptable salt thereof, wherein $R^4$ is

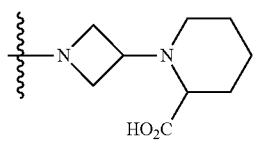

In another embodiment is a compound of Formula (Ia'), or a solvate, hydrate, tautomer, N-oxide, stereoisomer, or a pharmaceutically acceptable salt thereof, wherein $R^4$ is

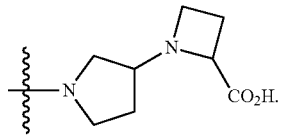

In another embodiment is a compound of Formula (Ia'), or a solvate, hydrate, tautomer, N-oxide, stereoisomer, or a pharmaceutically acceptable salt thereof, wherein $R^4$ is

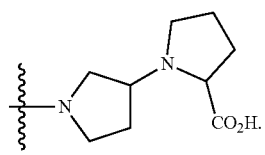 [SMILES: *N1CCC(N2CCCC2C(=O)O)C1]

In another embodiment is a compound of Formula (Ia'), or a solvate, hydrate, tautomer, N-oxide, stereoisomer, or a pharmaceutically acceptable salt thereof, wherein R⁴ is

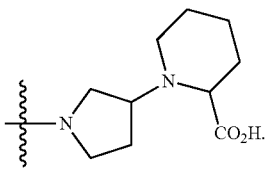 [SMILES: *N1CCC(N2CCCCC2C(=O)O)C1]

In another embodiment is a compound of Formula (Ia'), or a solvate, hydrate, tautomer, N-oxide, stereoisomer, or a pharmaceutically acceptable salt thereof, wherein R⁴ is

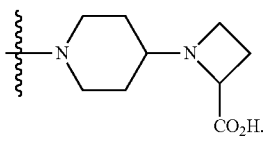 [SMILES: *N1CCC(N2CCC2C(=O)O)CC1]

In another embodiment is a compound of Formula (Ia'), or a solvate, hydrate, tautomer, N-oxide, stereoisomer, or a pharmaceutically acceptable salt thereof, wherein R⁴ is

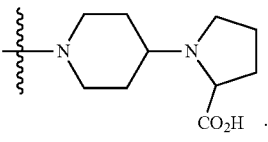

In another embodiment is a compound of Formula (Ia'), or a solvate, hydrate, tautomer, N-oxide, stereoisomer, or a pharmaceutically acceptable salt thereof, wherein R⁴ is

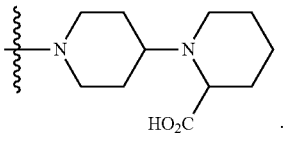

In another embodiment is a compound of Formula (Ia'), or a solvate, hydrate, tautomer, N-oxide, stereoisomer, or a pharmaceutically acceptable salt thereof, wherein R⁴ is selected from

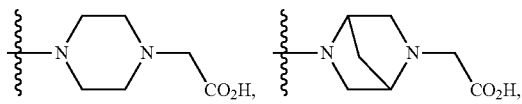

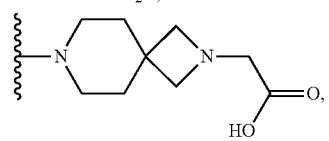

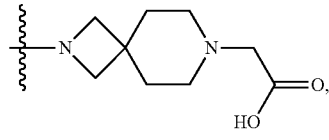

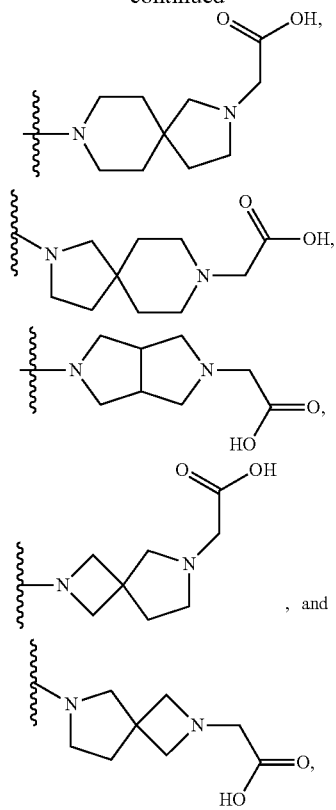

and w is 0. In another embodiment is a compound of Formula (Ia'), or a solvate, hydrate, tautomer, N-oxide, stereoisomer, or a pharmaceutically acceptable salt thereof, wherein R⁴ is selected from

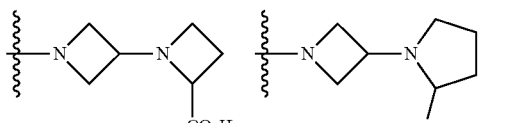

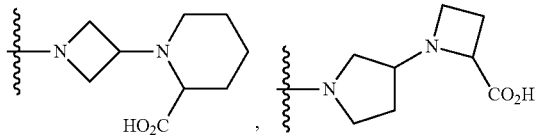

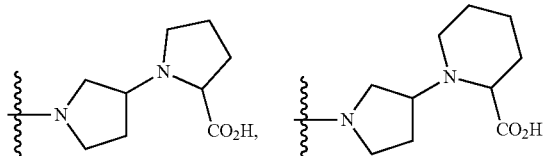

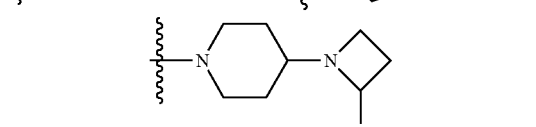

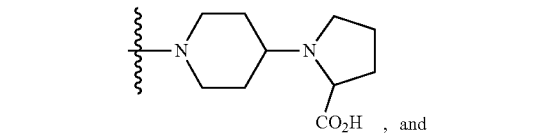

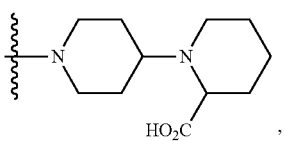

and w is 0.

In another embodiment is a compound of Formula (Ia'), or a solvate, hydrate, tautomer, N-oxide, stereoisomer, or a pharmaceutically acceptable salt thereof, wherein $R^4$ is selected from

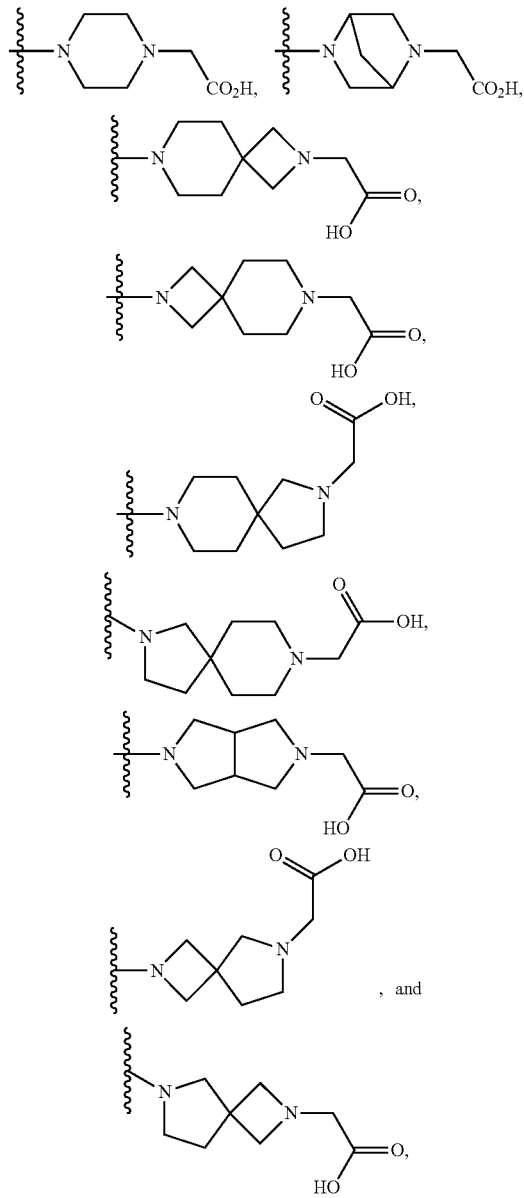

and w is 1. In another embodiment is a compound of Formula (Ia'), or a solvate, hydrate, tautomer, N-oxide, stereoisomer, or a pharmaceutically acceptable salt thereof, wherein $R^4$ is selected from selected from

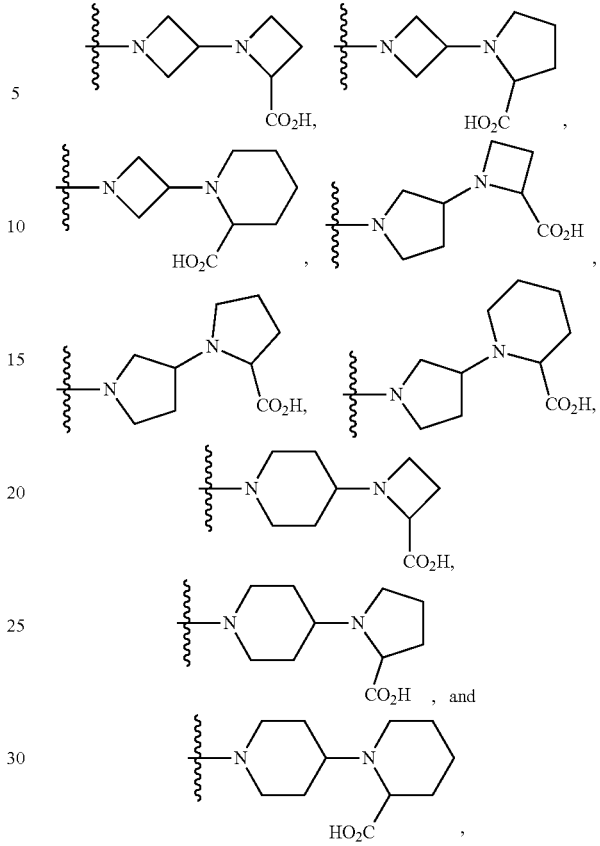

and w is 1.

In another embodiment is a compound of Formula (Ia'), or a solvate, hydrate, tautomer, N-oxide, stereoisomer, or a pharmaceutically acceptable salt thereof, wherein w is 1 and $R^3$ is selected from $C_{1-6}$alkyl, halogen, $C_{1-6}$haloalkyl, —$SF_5$, and —$OR^7$. In another embodiment is a compound of Formula (Ia'), or a solvate, hydrate, tautomer, N-oxide, stereoisomer, or a pharmaceutically acceptable salt thereof, wherein w is 1 and $R^3$ is selected from halogen, $C_{1-6}$haloalkyl, and —$OR^7$. In another embodiment is a compound of Formula (Ia'), or a solvate, hydrate, tautomer, N-oxide, stereoisomer, or a pharmaceutically acceptable salt thereof, wherein w is 1 and $R^3$ is selected from halogen and $C_{1-6}$haloalkyl. In another embodiment is a compound of Formula (Ia'), or a solvate, hydrate, tautomer, N-oxide, stereoisomer, or a pharmaceutically acceptable salt thereof, wherein w is 1 and $R^3$ is $C_{1-6}$alkyl. In another embodiment is a compound of Formula (Ia'), or a solvate, hydrate, tautomer, N-oxide, stereoisomer, or a pharmaceutically acceptable salt thereof, wherein w is 1 and $R^3$ is —$CH_3$. In another embodiment is a compound of Formula (Ia'), or a solvate, hydrate, tautomer, N-oxide, stereoisomer, or a pharmaceutically acceptable salt thereof, wherein w is 1 and $R^3$ is halogen. In another embodiment is a compound of Formula (Ia'), or a solvate, hydrate, tautomer, N-oxide, stereoisomer, or a pharmaceutically acceptable salt thereof, wherein w is 1 and $R^3$ is —Cl. In another embodiment is a compound of Formula (Ia'), or a solvate, hydrate, tautomer, N-oxide, stereoisomer, or a pharmaceutically acceptable salt thereof, wherein w is 1 and $R^3$ is —CN. In another embodiment is a compound of Formula (Ia'), or a solvate, hydrate, tautomer, N-oxide, stereoisomer, or a pharmaceutically acceptable salt thereof, wherein w is 1 and $R^3$ is $C_{1-6}$haloalkyl. In another embodiment is a compound of Formula (Ia'), or a solvate, hydrate, tautomer, N-oxide, stereoisomer, or a pharmaceutically acceptable salt thereof, wherein w is 1 and $R^3$ is —$CF_3$. In another embodiment is a compound of Formula (Ia'), or a solvate, hydrate, tautomer, N-oxide, stereoisomer, or a pharmaceutically acceptable salt thereof, wherein w is 1 and $R^3$ is —$SF_5$. In another embodiment is a compound of Formula (Ia'), or a solvate, hydrate, tautomer, N-oxide, stereoisomer, or a pharmaceutically acceptable salt thereof, wherein w is 1 and $R^3$ is —$OR^7$. In another embodiment is a compound of Formula (Ia'), or a solvate, hydrate, tautomer, N-oxide, stereoisomer, or a pharmaceutically acceptable salt thereof, wherein w is 1 and $R^3$ is —$OCH_3$.

In another embodiment is a compound of Formula (Ia'), or a solvate, hydrate, tautomer, N-oxide, stereoisomer, or a pharmaceutically acceptable salt thereof, wherein w is 2 and each $R^3$ is independently selected from $C_{1-6}$alkyl, halogen, $C_{1-6}$haloalkyl, —$SF_5$, and —$OR^7$. In another embodiment is a compound of Formula (Ia'), or a solvate, hydrate, tautomer, N-oxide, stereoisomer, or a pharmaceutically acceptable salt thereof, wherein w is 2 and each $R^3$ is independently selected from halogen, $C_{1-6}$haloalkyl, and —$OR^7$. In another embodiment is a compound of Formula (Ia'), or a solvate, hydrate, tautomer, N-oxide, stereoisomer, or a pharmaceutically acceptable salt thereof, wherein w is 2 and each $R^3$ is independently selected from halogen and $C_{1-6}$haloalkyl.

In some embodiments is a compound having the structure of Formula (Ib'):

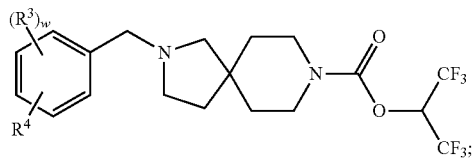

Formula (Ib')

wherein:
each $R^3$ is independently selected from $C_{1-6}$alkyl, halogen, —CN, $C_{1-6}$haloalkyl, —$SF_5$, and —$OR^7$;
$R^4$ is selected from

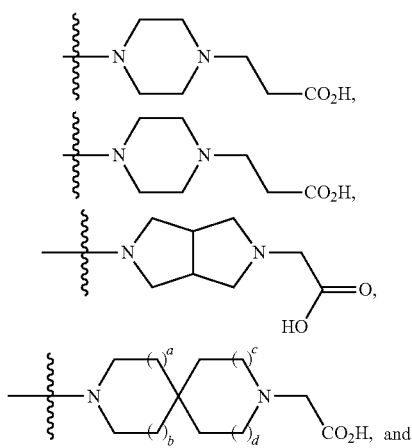

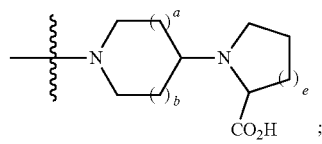

each $R^7$ is independently selected from H, $C_{1-6}$alkyl, $C_{1-6}$haloalkyl, $C_3$-cycloalkyl, and -$C_{1-6}$alkyl-$C_{3-8}$cycloalkyl;
a, b, c, and d are independently 0 or 1;
e is 0, 1, or 2; and
w is 0, 1, 2, 3, or 4;
or a solvate, hydrate, tautomer, N-oxide, stereoisomer, or pharmaceutically acceptable salt thereof.

In another embodiment is a compound of Formula (Ib'), or a solvate, hydrate, tautomer, N-oxide, stereoisomer, or a pharmaceutically acceptable salt thereof, wherein w is 0, 1, 2, or 3. In another embodiment is a compound of Formula (Ib'), or a solvate, hydrate, tautomer, N-oxide, stereoisomer, or a pharmaceutically acceptable salt thereof, wherein w is 0, 1, or 2. In another embodiment is a compound of Formula (Ib'), or a solvate, hydrate, tautomer, N-oxide, stereoisomer, or a pharmaceutically acceptable salt thereof, wherein w is 0 or 1. In another embodiment is a compound of Formula (Ib'), or a solvate, hydrate, tautomer, N-oxide, stereoisomer, or a pharmaceutically acceptable salt thereof, wherein w is 1 or 2. In another embodiment is a compound of Formula (Ib'), or a solvate, hydrate, tautomer, N-oxide, stereoisomer, or a pharmaceutically acceptable salt thereof, wherein w is 0. In another embodiment is a compound of Formula (Ib'), or a solvate, hydrate, tautomer, N-oxide, stereoisomer, or a pharmaceutically acceptable salt thereof, wherein w is 1. In another embodiment is a compound of Formula (Ib'), or a solvate, hydrate, tautomer, N-oxide, stereoisomer, or a pharmaceutically acceptable salt thereof, wherein w is 2. In another embodiment is a compound of Formula (Ib'), or a solvate, hydrate, tautomer, N-oxide, stereoisomer, or a pharmaceutically acceptable salt thereof, wherein w is 3. In another embodiment is a compound of Formula (Ib'), or a solvate, hydrate, tautomer, N-oxide, stereoisomer, or a pharmaceutically acceptable salt thereof, wherein w is 4.

In another embodiment is a compound of Formula (Ib'), or a solvate, hydrate, tautomer, N-oxide, stereoisomer, or a pharmaceutically acceptable salt thereof, wherein $R^4$ is

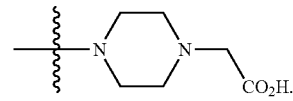

In another embodiment is a compound of Formula (Ib'), or a solvate, hydrate, tautomer, N-oxide, stereoisomer, or a pharmaceutically acceptable salt thereof, wherein $R^4$ is

In another embodiment is a compound of Formula (Ib'), or a solvate, hydrate, tautomer, N-oxide, stereoisomer, or a pharmaceutically acceptable salt thereof, wherein $R^4$ is

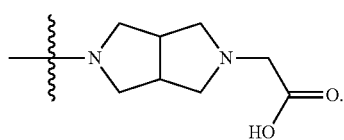 [SMILES: *N1CC2CN(CC(=O)O)CC2C1]

In another embodiment is a compound of Formula (Ib'), or a solvate, hydrate, tautomer, N-oxide, stereoisomer, or a pharmaceutically acceptable salt thereof, wherein $R^4$ is

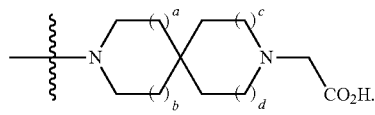

In another embodiment is a compound of Formula (Ib'), or a solvate, hydrate, tautomer, N-oxide, stereoisomer, or a pharmaceutically acceptable salt thereof, wherein $R^4$ is

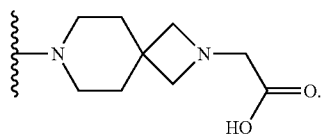 [SMILES: *N1CCC2(CC1)CN(CC(=O)O)C2]

In another embodiment is a compound of Formula (Ib'), or a solvate, hydrate, tautomer, N-oxide, stereoisomer, or a pharmaceutically acceptable salt thereof, wherein $R^4$ is

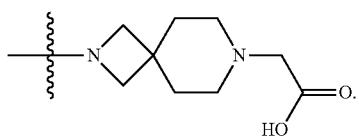 [SMILES: *N1CC2(CCN(CC(=O)O)CC2)C1]

In another embodiment is a compound of Formula (Ib'), or a solvate, hydrate, tautomer, N-oxide, stereoisomer, or a pharmaceutically acceptable salt thereof, wherein $R^4$ is

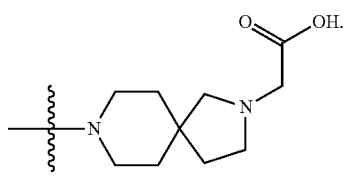 [SMILES: *N1CCC2(CC1)CCN(CC(=O)O)C2]

In another embodiment is a compound of Formula (Ib'), or a solvate, hydrate, tautomer, N-oxide, stereoisomer, or a pharmaceutically acceptable salt thereof, wherein $R^4$ is

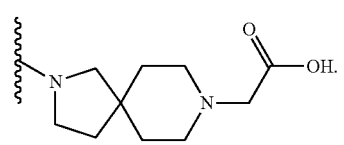 [SMILES: *N1CCC2(CCN(CC(=O)O)CC2)C1]

In another embodiment is a compound of Formula (Ib'), or a solvate, hydrate, tautomer, N-oxide, stereoisomer, or a pharmaceutically acceptable salt thereof, wherein $R^4$ is

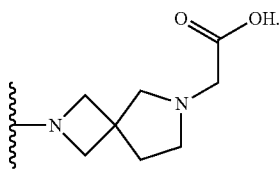 [SMILES: *N1CC2(CCN(CC(=O)O)C2)C1]

In another embodiment is a compound of Formula (Ib'), or a solvate, hydrate, tautomer, N-oxide, stereoisomer, or a pharmaceutically acceptable salt thereof, wherein $R^4$ is

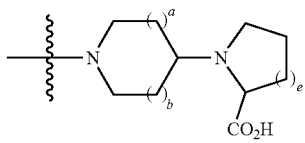

In another embodiment is a compound of Formula (Ib'), or a solvate, hydrate, tautomer, N-oxide, stereoisomer, or a pharmaceutically acceptable salt thereof, wherein $R^4$ is

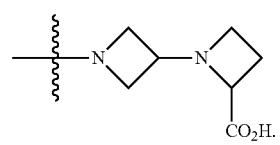

In another embodiment is a compound of Formula (Ib'), or a solvate, hydrate, tautomer, N-oxide, stereoisomer, or a pharmaceutically acceptable salt thereof, wherein $R^4$ is

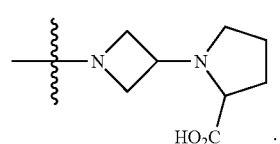

In another embodiment is a compound of Formula (Ib'), or a solvate, hydrate, tautomer, N-oxide, stereoisomer, or a pharmaceutically acceptable salt thereof, wherein $R^4$ is

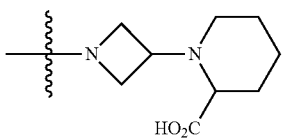

In another embodiment is a compound of Formula (Ib'), or a solvate, hydrate, tautomer, N-oxide, stereoisomer, or a pharmaceutically acceptable salt thereof, wherein $R^4$ is

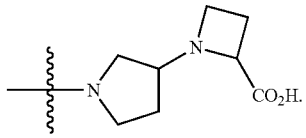 [SMILES: *N1CCC(N2CCC2C(=O)O)C1]

In another embodiment is a compound of Formula (Ib'), or a solvate, hydrate, tautomer, N-oxide, stereoisomer, or a pharmaceutically acceptable salt thereof, wherein $R^4$ is

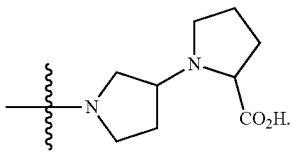

In another embodiment is a compound of Formula (Ib'), or a solvate, hydrate, tautomer, N-oxide, stereoisomer, or a pharmaceutically acceptable salt thereof, wherein $R^4$ is

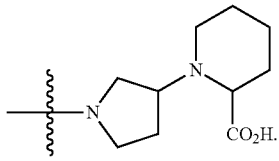 [SMILES: *N1CCC(N2CCCCC2C(=O)O)C1]

In another embodiment is a compound of Formula (Ib'), or a solvate, hydrate, tautomer, N-oxide, stereoisomer, or a pharmaceutically acceptable salt thereof, wherein $R^4$ is

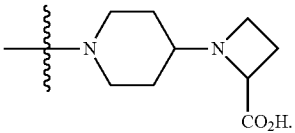

In another embodiment is a compound of Formula (Ib'), or a solvate, hydrate, tautomer, N-oxide, stereoisomer, or a pharmaceutically acceptable salt thereof, wherein $R^4$ is

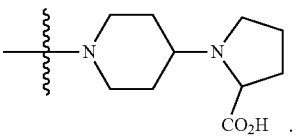

In another embodiment is a compound of Formula (Ib'), or a solvate, hydrate, tautomer, N-oxide, stereoisomer, or a pharmaceutically acceptable salt thereof, wherein $R^4$ is

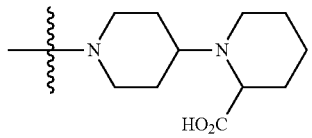

In another embodiment is a compound of Formula (Ib'), or a solvate, hydrate, tautomer, N-oxide, stereoisomer, or a pharmaceutically acceptable salt thereof, wherein $R^4$ is selected from

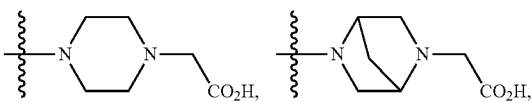

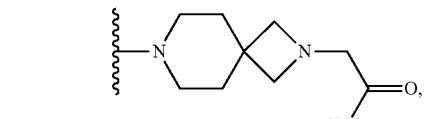

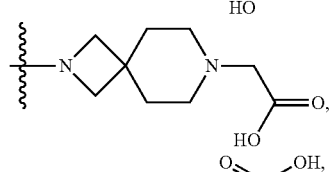

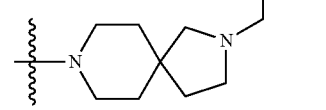

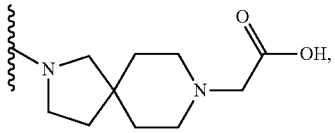

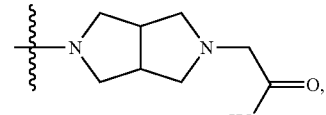

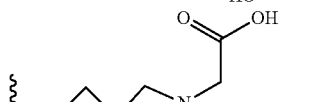

, and

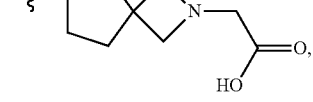

and w is 0. In another embodiment is a compound of Formula (Ib'), or a solvate, hydrate, tautomer, N-oxide, stereoisomer, or a pharmaceutically acceptable salt thereof, wherein $R^4$ is selected from

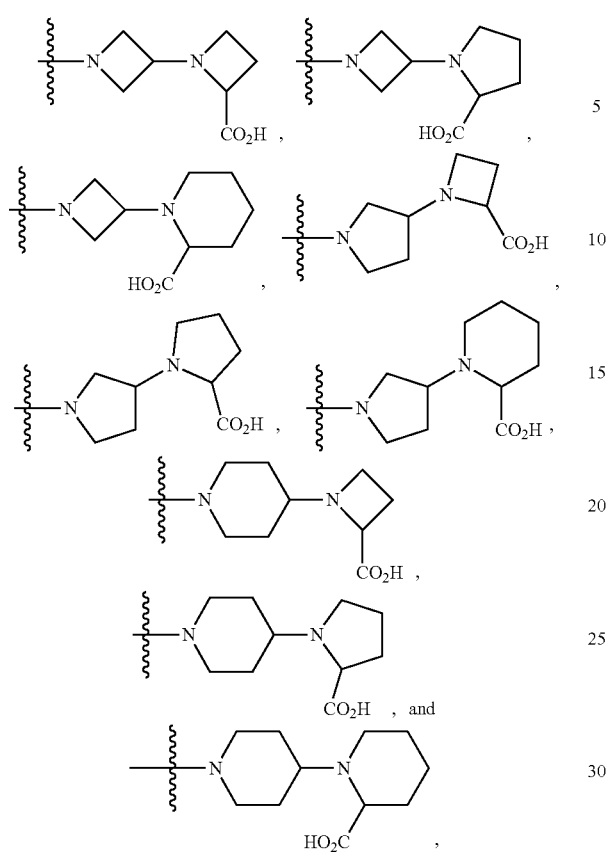

and w is 0

In another embodiment is a compound of Formula (Ib'), or a solvate, hydrate, tautomer, N-oxide, stereoisomer, or a pharmaceutically acceptable salt thereof, wherein $R^4$ is selected from

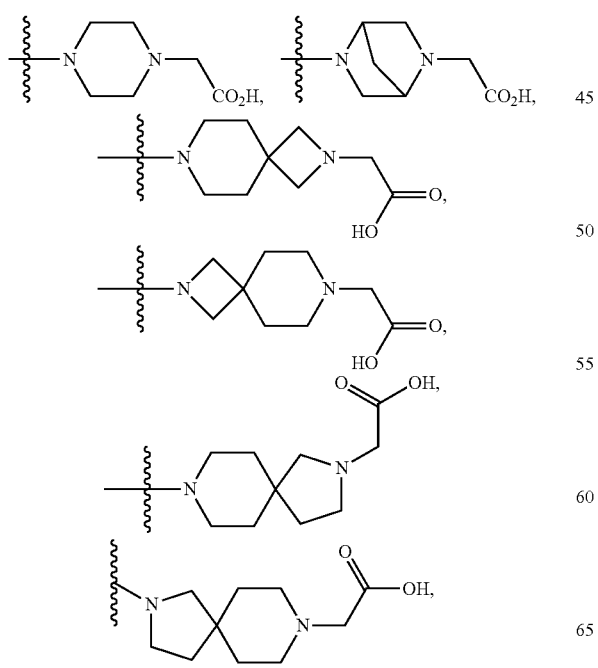

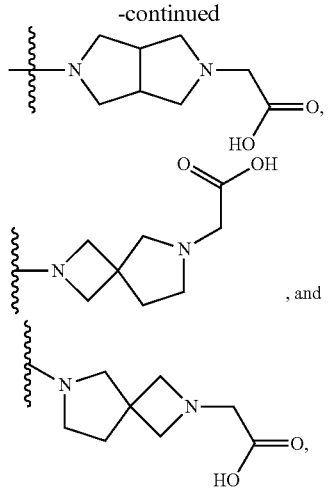

and w is 1. In another embodiment is a compound of Formula (Ib'), or a solvate, hydrate, tautomer, N-oxide, stereoisomer, or a pharmaceutically acceptable salt thereof, wherein $R^4$ is selected from selected from

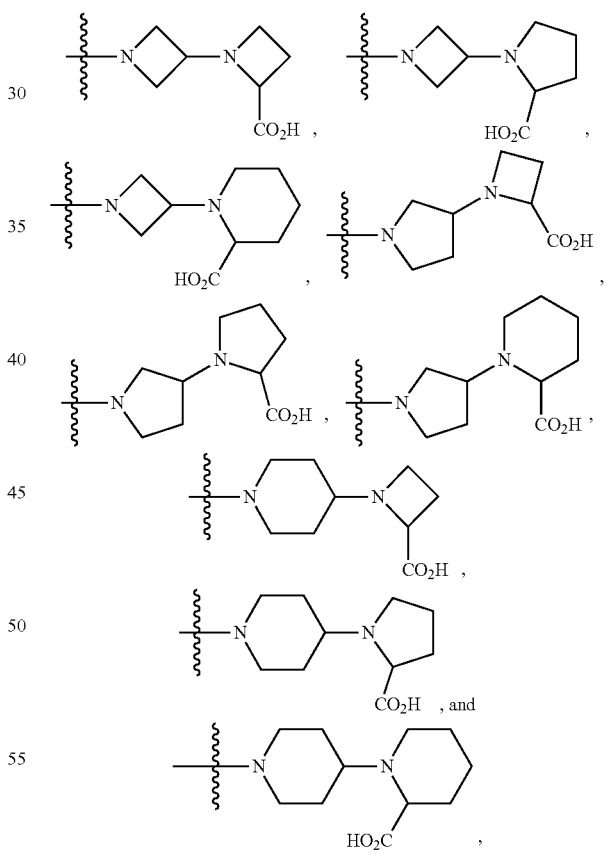

and w is 1.

In another embodiment is a compound of Formula (Ib'), or a solvate, hydrate, tautomer, N-oxide, stereoisomer, or a pharmaceutically acceptable salt thereof, wherein w is 1 and $R^3$ is selected from $C_{1-6}$alkyl, halogen, $C_{1-6}$haloalkyl, —$SF_5$, and —$OR^7$. In another embodiment is a compound of Formula (Ib'), or a solvate, hydrate, tautomer, N-oxide, stereoisomer, or a pharmaceutically acceptable salt thereof, wherein w is 1 and $R^3$ is selected from halogen, $C_{1-6}$haloalkyl, and —$OR^7$. In another embodiment is a compound of Formula (Ib'), or a solvate, hydrate, tautomer, N-oxide, stereoisomer, or a pharmaceutically acceptable salt thereof, wherein w is 1 and $R^3$ is selected from halogen and $C_{1-6}$haloalkyl. In another embodiment is a compound of Formula (Ib'), or a solvate, hydrate, tautomer, N-oxide, stereoisomer, or a pharmaceutically acceptable salt thereof, wherein w is 1 and $R^3$ is $C_{1-6}$alkyl. In another embodiment is a compound of Formula (Ib'), or a solvate, hydrate, tautomer, N-oxide, stereoisomer, or a pharmaceutically acceptable salt thereof, wherein w is 1 and $R^3$ is —$CH_3$. In another embodiment is a compound of Formula (Ib'), or a solvate, hydrate, tautomer, N-oxide, stereoisomer, or a pharmaceutically acceptable salt thereof, wherein w is 1 and $R^3$ is halogen. In another embodiment is a compound of Formula (Ib'), or a solvate, hydrate, tautomer, N-oxide, stereoisomer, or a pharmaceutically acceptable salt thereof, wherein w is 1 and $R^3$ is —Cl. In another embodiment is a compound of Formula (Ib'), or a solvate, hydrate, tautomer, N-oxide, stereoisomer, or a pharmaceutically acceptable salt thereof, wherein w is 1 and $R^3$ is —CN. In another embodiment is a compound of Formula (Ib'), or a solvate, hydrate, tautomer, N-oxide, stereoisomer, or a pharmaceutically acceptable salt thereof, wherein w is 1 and $R^3$ is $C_{1-6}$haloalkyl. In another embodiment is a compound of Formula (Ib'), or a solvate, hydrate, tautomer, N-oxide, stereoisomer, or a pharmaceutically acceptable salt thereof, wherein w is 1 and $R^3$ is —$CF_3$. In another embodiment is a compound of Formula (Ib'), or a solvate, hydrate, tautomer, N-oxide, stereoisomer, or a pharmaceutically acceptable salt thereof, wherein w is 1 and $R^3$ is —$SF_5$. In another embodiment is a compound of Formula (Ib'), or a solvate, hydrate, tautomer, N-oxide, stereoisomer, or a pharmaceutically acceptable salt thereof, wherein w is 1 and $R^3$ is —$OR^7$. In another embodiment is a compound of Formula (Ib'), or a solvate, hydrate, tautomer, N-oxide, stereoisomer, or a pharmaceutically acceptable salt thereof, wherein w is 1 and $R^3$ is —$OCH_3$.

In another embodiment is a compound of Formula (Ib'), or a solvate, hydrate, tautomer, N-oxide, stereoisomer, or a pharmaceutically acceptable salt thereof, wherein w is 2 and each $R^3$ is independently selected from $C_{1-6}$alkyl, halogen, $C_{1-6}$haloalkyl, —$SF_5$, and —$OR^7$. In another embodiment is a compound of Formula (Ib'), or a solvate, hydrate, tautomer, N-oxide, stereoisomer, or a pharmaceutically acceptable salt thereof, wherein w is 2 and each $R^3$ is independently selected from halogen, $C_{1-6}$haloalkyl, and —$OR^7$. In another embodiment is a compound of Formula (Ib'), or a solvate, hydrate, tautomer, N-oxide, stereoisomer, or a pharmaceutically acceptable salt thereof, wherein w is 2 and each $R^3$ is independently selected from halogen and $C_{1-6}$haloalkyl.

In some embodiments is a compound having the structure of Formula (II):

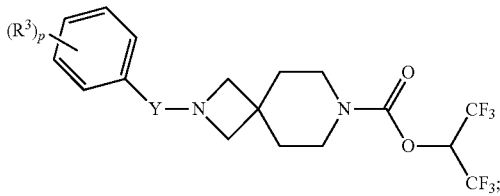

Formula (II)

wherein:
Y is —$CH_2$— or —C(O)—;
each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, -$C_{1-6}$alkyl($C_{2-9}$heterocycloalkyl), $C_{6-10}$aryl, $C_{1-9}$heteroaryl, —$SF_5$, —$NR^5R^6$, —$OR^7$, —$CO_2R^8$, and —$C(O)NR^8R^9$, wherein -$C_{1-6}$alkyl($C_{2-9}$heterocycloalkyl) and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
each $R^4$ is independently selected from $C_{1-6}$alkyl, $C_{1-6}$haloalkyl, $C_{3-8}$cycloalkyl, halogen, oxo, —CN, —$CO_2R^8$, -$C_{1-6}$alkyl-$CO_2R^8$, —$C(O)R^8$, —$C(O)NR^8R^9$, —$SO_2R^8$, —$NR^9C(O)R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-$C(O)(C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-$C(O)(C_{2-9}$heterocycloalkyl), $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, $CO_2H$, and $C(O)NH_2$;
each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2H$, and $C(O)NH_2$;
each $R^{10}$ is independently selected from halogen, $C_{1-6}$alkyl, -$C_{1-6}$alkyl-$CO_2R^8$, -$C_{1-6}$haloalkyl, $C_{3-8}$cycloalkyl, oxo, —CN, —$CO_2R^8$, —$C(O)R^8$, —$C(O)NR^8R^9$, —$SO_2R^8$, —$NR^9C(O)R^8$, and —$NR^9SO_2R^8$; and
p is 0, 1, 2, 3, 4, or 5;
or a solvate, hydrate, tautomer, N-oxide, stereoisomer, or pharmaceutically acceptable salt thereof.

In some embodiments is a compound of Formula (II), or a solvate, hydrate, tautomer, N-oxide, stereoisomer, or a pharmaceutically acceptable salt thereof, wherein Y is —$CH_2$—. In some embodiments is a compound of Formula (II), or a solvate, hydrate, tautomer, N-oxide, stereoisomer, or a pharmaceutically acceptable salt thereof, wherein Y is —C(O)—.

In another embodiment is a compound of Formula (II), or a solvate, hydrate, tautomer, N-oxide, stereoisomer, or a pharmaceutically acceptable salt thereof, wherein p is 0, 1, 2, or 3. In another embodiment is a compound of Formula (II), or a solvate, hydrate, tautomer, N-oxide, stereoisomer, or a pharmaceutically acceptable salt thereof, wherein p is 0, 1, or 2. In another embodiment is a compound of Formula (II), or a solvate, hydrate, tautomer, N-oxide, stereoisomer, or a pharmaceutically acceptable salt thereof, wherein p is 0 or 1. In another embodiment is a compound of Formula (II), or a solvate, hydrate, tautomer, N-oxide, stereoisomer, or a pharmaceutically acceptable salt thereof, wherein p is 1 or 2. In another embodiment is a compound of Formula (II), or a solvate, hydrate, tautomer, N-oxide, stereoisomer, or a pharmaceutically acceptable salt thereof, wherein p is 0. In another embodiment is a compound of Formula (II), or a solvate, hydrate, tautomer, N-oxide, stereoisomer, or a pharmaceutically acceptable salt thereof, wherein p is 1. In another embodiment is a compound of Formula (II), or a solvate, hydrate, tautomer, N-oxide, stereoisomer, or a pharmaceutically acceptable salt thereof, wherein p is 2. In another embodiment is a compound of Formula (II), or a solvate, hydrate, tautomer, N-oxide, stereoisomer, or a pharmaceutically acceptable salt thereof, wherein p is 3. In another embodiment is a compound of Formula (II), or a solvate, hydrate, tautomer, N-oxide, stereoisomer, or a pharmaceutically acceptable salt thereof, wherein p is 4.

In another embodiment is a compound of Formula (II), or a solvate, hydrate, tautomer, N-oxide, stereoisomer, or a pharmaceutically acceptable salt thereof, wherein p is 2 and each $R^3$ is independently selected from $C_{1-6}$alkyl, halogen, —CN, $C_{1-6}$haloalkyl, $C_{1-6}$aminoalkyl, -$C_{1-6}$alkyl(heterocycloalkyl), —SF$_5$, —NR$^5$R$^6$, and —OR$^7$; wherein -$C_{1-6}$alkyl (heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (II), or a solvate, hydrate, tautomer, N-oxide, stereoisomer, or a pharmaceutically acceptable salt thereof, wherein p is 2 and each $R^3$ is independently selected halogen, $C_{1-6}$alkyl, $C_{1-6}$haloalkyl, -$C_{1-6}$alkyl($C_{2-9}$heterocycloalkyl), —NR$^5$R$^6$, —OR$^7$, —CO$_2$R$^8$, and —C(O)NR$^8$R$^9$. In another embodiment is a compound of Formula (II), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —NR$^5$R$^6$, and —OR$^7$. In another embodiment is a compound of Formula (II), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, —NR$^5$R$^6$, and —OR$^7$. In another embodiment is a compound of Formula (II), or a solvate, hydrate, tautomer, N-oxide, stereoisomer, or a pharmaceutically acceptable salt thereof, wherein p is 2 and each $R^3$ is independently selected from halogen, —NR$^5$R$^6$, and $C_{1-6}$haloalkyl. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein R$^5$ and R$^6$, together with the nitrogen to which they are attached, form a $C_{2-9}$heterocycloalkyl ring optionally substituted with one, two, or three $R^{10}$. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein R$^5$ and R$^6$, together with the nitrogen to which they are attached, form an unsubstitued $C_{2-9}$heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein R$^5$ and R$^6$, together with the nitrogen to which they are attached, form a $C_{2-9}$heterocycloalkyl ring substituted with one or two $R^{10}$. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein R$^5$ and R$^6$, together with the nitrogen to which they are attached, form a $C_{2-9}$heterocycloalkyl ring substituted with one or two $R^{10}$ selected from $C_{1-6}$alkyl and —CO$_2$H. In another embodiment is a compound of Formula (II), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein R$^5$ and R$^6$, together with the nitrogen to which they are attached, form a $C_{2-9}$heterocycloalkyl ring substituted with —CO$_2$H. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein R$^5$ and R$^6$, together with the nitrogen to which they are attached, form a $C_{2-9}$heterocycloalkyl ring optionally substituted with one, two, or three $R^{10}$. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein R$^5$ and R$^6$, together with the nitrogen to which they are attached, form an unsubstitued $C_{2-9}$heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein R$^5$ and R$^6$, together with the nitrogen to which they are attached, form a $C_{2-9}$heterocycloalkyl ring substituted with one or two $R^{10}$. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein R$^5$ and R$^6$, together with the nitrogen to which they are attached, form a $C_{2-9}$heterocycloalkyl ring substituted with one or two $R^{10}$ selected from $C_{1-6}$alkyl and —CO$_2$H. In another embodiment is a compound of Formula (II), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein R$^5$ and R$^6$, together with the nitrogen to which they are attached, form a $C_{2-9}$heterocycloalkyl ring substituted with —CO$_2$H. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein R$^5$ and R$^6$, together with the nitrogen to which they are attached, form a $C_{2-9}$heterocycloalkyl ring optionally substituted with one, two, or three $R^{10}$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein R$^5$ and R$^6$, together with the nitrogen to which they are attached, form an unsubstitued $C_{2-9}$heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein R$^5$ and R$^6$, together with the nitrogen to which they are attached, form a $C_{2-9}$heterocycloalkyl ring substituted with one or two $R^{10}$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (II), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (II), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (II), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (II), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (II), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (II), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (II), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (II), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (II), or a solvate, hydrate, tautomer, N-oxide, stereoisomer, or a pharmaceutically acceptable salt thereof, wherein p is 1 and $R^3$ is halogen. In another embodiment is a compound of Formula (II), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (II), or a solvate, hydrate, tautomer, N-oxide, stereoisomer, or a pharmaceutically acceptable salt thereof, wherein p is 1 and $R^3$ is —$OR^7$. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstitued $C_{2-9}$heterocycloalkyl ring. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (II), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (II), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

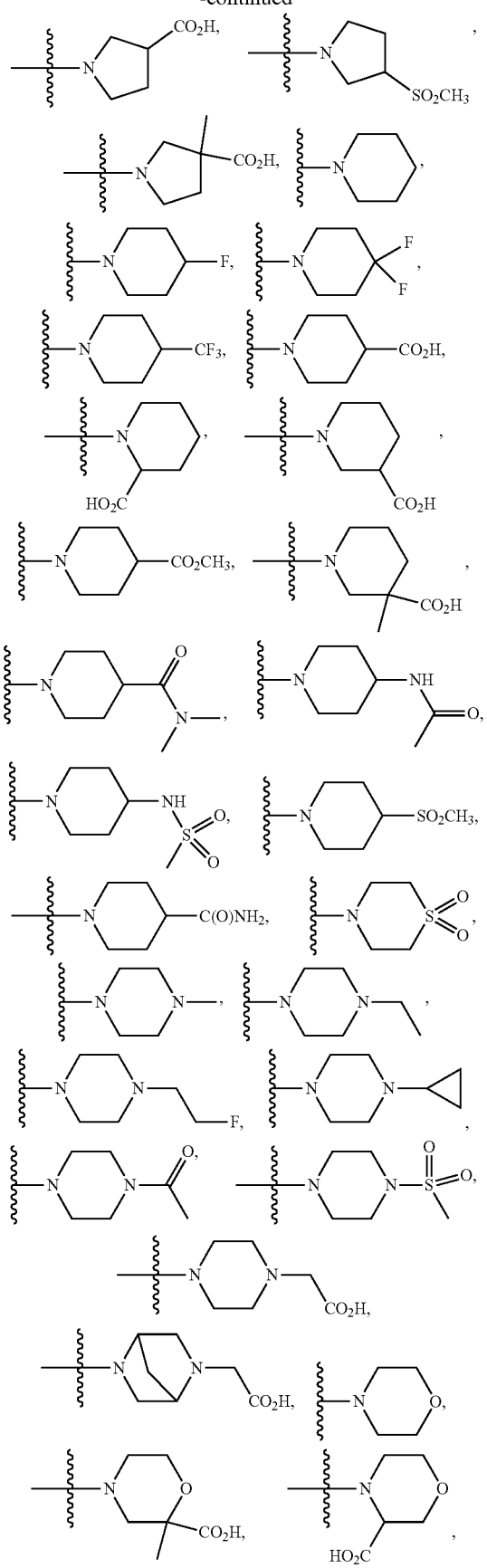
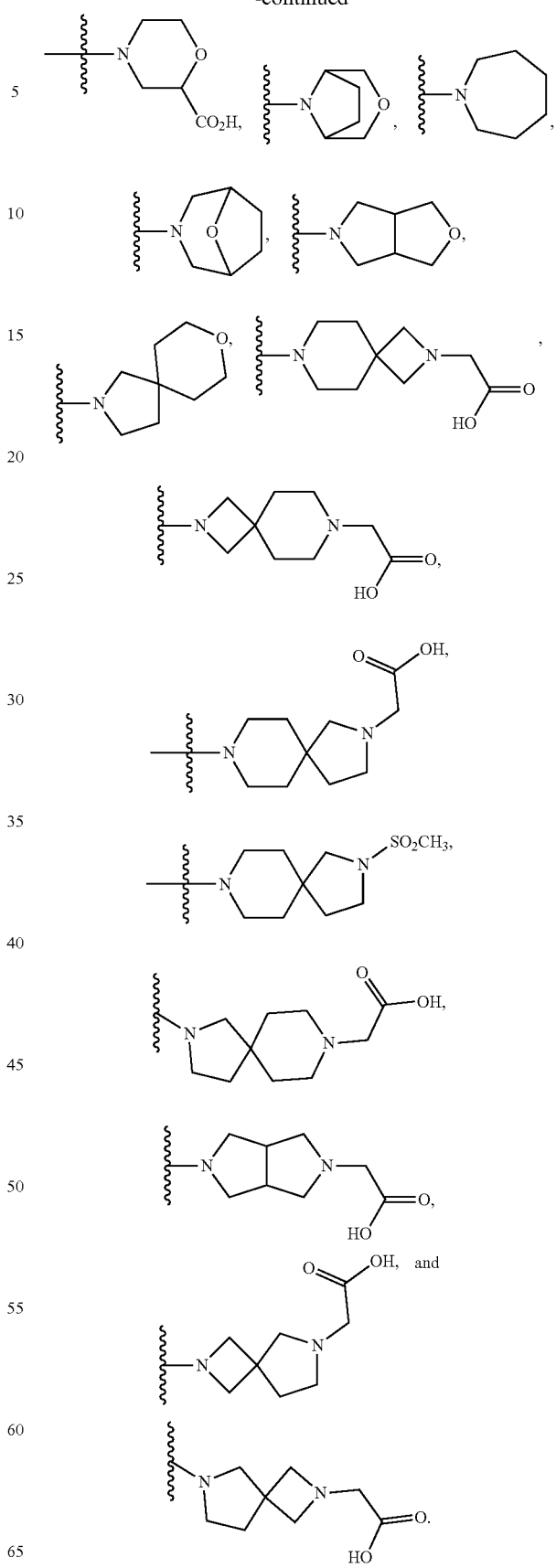

In some embodiments is a compound having the structure of Formula (III):

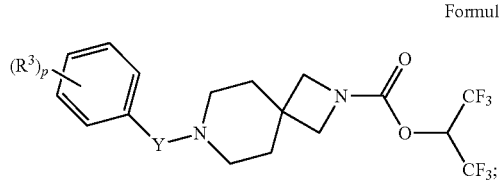

Formula (III)

wherein:
  Y is —CH$_2$— or —C(O)—;
  each R$^3$ is independently selected from C$_{1-6}$alkyl, C$_{1-6}$alkenyl, C$_{1-6}$alkynyl, halogen, —CN, C$_{1-6}$haloalkyl, C$_{1-6}$aminoalkyl, -C$_{1-6}$alkyl(C$_{2-9}$heterocycloalkyl), C$_{6-10}$aryl, C$_{1-9}$heteroaryl, —SF$_5$, —NR$^5$R$^6$, —OR$^7$, —CO$_2$R$^8$, and —C(O)NR$^8$R$^9$, wherein -C$_{1-6}$alkyl(C$_{2-9}$heterocycloalkyl) and C$_{1-9}$heteroaryl are optionally substituted with one or two R$^4$; or two adjacent R$^3$ form a C$_{2-9}$heterocycloalkyl ring, wherein the C$_{2-9}$heterocycloalkyl ring is optionally substituted with one, two, or three R$^4$;
  each R$^4$ is independently selected from C$_{1-6}$alkyl, C$_{1-6}$haloalkyl, C$_{3-8}$cycloalkyl, halogen, oxo, —CN, —CO$_2$R$^8$, -C$_{1-6}$alkyl-CO$_2$R$^8$, —C(O)R$^8$, —C(O)NR$^8$R$^9$, —SO$_2$R$^8$, —NR$^9$C(O)R$^8$, and —NR$^9$SO$_2$R$^8$;
  each R$^5$ and R$^6$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl; or R$^5$ and R$^6$, together with the nitrogen to which they are attached, form a C$_{2-9}$heterocycloalkyl ring optionally substituted with one, two, or three R$^{10}$;
  each R$^7$ is independently selected from H, C$_{1-6}$alkyl, C$_{1-6}$haloalkyl, C$_{1-6}$aminoalkyl, C$_{3-8}$cycloalkyl, -C$_{1-6}$alkyl(C$_{2-9}$heterocycloalkyl), -C$_{1-6}$alkyl-C(O)(C$_{2-9}$heterocycloalkyl), C$_{2-9}$heterocycloalkyl, C$_{6-10}$aryl, and C$_{1-9}$heteroaryl, wherein C$_{2-9}$heterocycloalkyl, C$_{6-10}$aryl, and C$_{1-9}$heteroaryl are optionally substituted with one or two groups selected from oxo, C$_{1-6}$alkyl, C$_{1-6}$haloalkyl, CO$_2$H, and C(O)NH$_2$;
  each R$^8$ and R$^9$ is independently selected from H, C$_{1-6}$alkyl, C$_{1-6}$haloalkyl, C$_{3-8}$cycloalkyl, C$_{6-10}$aryl, and C$_{1-9}$heteroaryl; or R$^8$ and R$^9$, together with the nitrogen to which they are attached, form a C$_{2-9}$heterocycloalkyl ring optionally substituted with one or two groups selected from C$_{1-6}$alkyl, C$_{1-6}$haloalkyl, CO$_2$H, and C(O)NH$_2$;
  each R$^{10}$ is independently selected from halogen, C$_{1-6}$alkyl, -C$_{1-6}$alkyl-CO$_2$R$^8$, C$_{1-6}$haloalkyl, C$_{3-8}$cycloalkyl, oxo, —CN, —CO$_2$R$^8$, —C(O)R$^8$, —C(O)NR$^8$R$^9$, —SO$_2$R$^8$, —NR$^9$C(O)R$^8$, and —NR$^9$SO$_2$R$^8$; and
  p is 0, 1, 2, 3, 4, or 5;
or a solvate, hydrate, tautomer, N-oxide, stereoisomer, or pharmaceutically acceptable salt thereof.

In some embodiments is a compound of Formula (III), or a solvate, hydrate, tautomer, N-oxide, stereoisomer, or a pharmaceutically acceptable salt thereof, wherein Y is —CH$_2$—. In some embodiments is a compound of Formula (III), or a solvate, hydrate, tautomer, N-oxide, stereoisomer, or a pharmaceutically acceptable salt thereof, wherein Y is —C(O)—.

In another embodiment is a compound of Formula (III), or a solvate, hydrate, tautomer, N-oxide, stereoisomer, or a pharmaceutically acceptable salt thereof, wherein p is 0, 1, 2, or 3. In another embodiment is a compound of Formula (III), or a solvate, hydrate, tautomer, N-oxide, stereoisomer, or a pharmaceutically acceptable salt thereof, wherein p is 0, 1, or 2. In another embodiment is a compound of Formula (III), or a solvate, hydrate, tautomer, N-oxide, stereoisomer, or a pharmaceutically acceptable salt thereof, wherein p is 0 or 1. In another embodiment is a compound of Formula (III), or a solvate, hydrate, tautomer, N-oxide, stereoisomer, or a pharmaceutically acceptable salt thereof, wherein p is 1 or 2. In another embodiment is a compound of Formula (III), or a solvate, hydrate, tautomer, N-oxide, stereoisomer, or a pharmaceutically acceptable salt thereof, wherein p is 0. In another embodiment is a compound of Formula (III), or a solvate, hydrate, tautomer, N-oxide, stereoisomer, or a pharmaceutically acceptable salt thereof, wherein p is 1. In another embodiment is a compound of Formula (III), or a solvate, hydrate, tautomer, N-oxide, stereoisomer, or a pharmaceutically acceptable salt thereof, wherein p is 2. In another embodiment is a compound of Formula (III), or a solvate, hydrate, tautomer, N-oxide, stereoisomer, or a pharmaceutically acceptable salt thereof, wherein p is 3. In another embodiment is a compound of Formula (III), or a solvate, hydrate, tautomer, N-oxide, stereoisomer, or a pharmaceutically acceptable salt thereof, wherein p is 4.

In another embodiment is a compound of Formula (III), or a solvate, hydrate, tautomer, N-oxide, stereoisomer, or a pharmaceutically acceptable salt thereof, wherein p is 2 and each R$^3$ is independently selected from C$_{1-6}$alkyl, halogen, —CN, C$_{1-6}$haloalkyl, C$_{1-6}$aminoalkyl, -C$_{1-6}$alkyl(heterocycloalkyl), —SF$_5$, —NR$^5$R$^6$, and —OR$^7$; wherein -C$_{1-6}$alkyl (heterocycloalkyl) is optionally substituted with one or two groups selected from halogen, C$_{1-6}$alkyl, C$_{1-6}$haloalkyl, C$_{3-8}$cycloalkyl, and oxo. In another embodiment is a compound of Formula (III), or a solvate, hydrate, tautomer, N-oxide, stereoisomer, or a pharmaceutically acceptable salt thereof, wherein p is 2 and each R$^3$ is independently selected halogen, C$_{1-6}$alkyl, C$_{1-6}$haloalkyl, -C$_{1-6}$alkyl(C$_{2-9}$heterocycloalkyl), —NR$^5$R$^6$, —OR$^7$, —CO$_2$R$^8$, and —C(O)NR$^8$R$^9$. In another embodiment is a compound of Formula (III), or a solvate, hydrate, tautomer, N-oxide, stereoisomer, or a pharmaceutically acceptable salt thereof, wherein p is 2 and each R$^3$ is independently selected from C$_{1-6}$alkyl, halogen, C$_{1-6}$haloalkyl, —NR$^5$R$^6$, and —OR$^7$. In another embodiment is a compound of Formula (III), or a solvate, hydrate, tautomer, N-oxide, stereoisomer, or a pharmaceutically acceptable salt thereof, wherein p is 2 and each R$^3$ is independently selected from halogen, C$_{1-6}$haloalkyl, —NR$^5$R$^6$, and —OR$^7$. In another embodiment is a compound of Formula (III), or a solvate, hydrate, tautomer, N-oxide, stereoisomer, or a pharmaceutically acceptable salt thereof, wherein p is 2 and each R$^3$ is independently selected from halogen, —NR$^5$R$^6$, and C$_{1-6}$haloalkyl. In another embodiment is a compound of Formula (III), or a solvate, hydrate, tautomer, N-oxide, stereoisomer, or a pharmaceutically acceptable salt thereof, wherein p is 2, one R$^3$ is halogen and one R$^3$ is —NR$^5$R$^6$. In another embodiment is a compound of Formula (III), or a solvate, hydrate, tautomer, N-oxide, stereoisomer, or a pharmaceutically acceptable salt thereof, wherein p is 2, one R$^3$ is halogen and one R$^3$ is —NR$^5$R$^6$ wherein R$^5$ and R$^6$, together with the nitrogen to which they are attached, form a C$_{2-9}$heterocycloalkyl ring optionally substituted with one, two, or three R$^{10}$. In another embodiment is a compound of Formula (III), or a solvate, hydrate, tautomer, N-oxide, stereoisomer, or a pharmaceutically acceptable salt thereof, wherein p is 2, one R$^3$ is halogen and one R$^3$ is —NR$^5$R$^6$ wherein R$^5$ and R$^6$, together with the nitrogen to which they are attached, form an unsubstitued C$_{2-9}$heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (III), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form an unsubstituted $C_{2-9}$heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (III), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (III), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (III), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (III), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (III), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (III), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (III), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (III), or a solvate, hydrate, tautomer, N-oxide, stereoisomer, or a pharmaceutically acceptable salt thereof, wherein p is 1 and $R^3$ is halogen. In another embodiment is a compound of Formula (III), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (III), or a solvate, hydrate, tautomer, N-oxide, stereoisomer, or a pharmaceutically acceptable salt thereof, wherein p is 1 and $R^3$ is —$OR^7$. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstitued $C_{2-9}$heterocycloalkyl ring. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (III), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (III), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

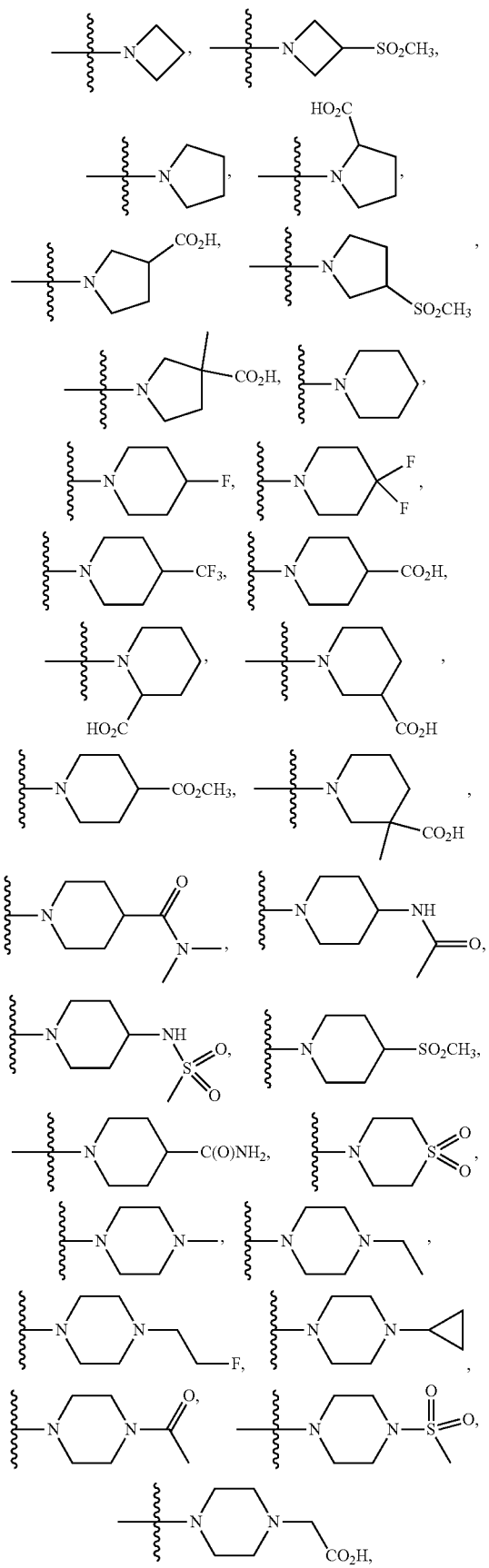

-continued

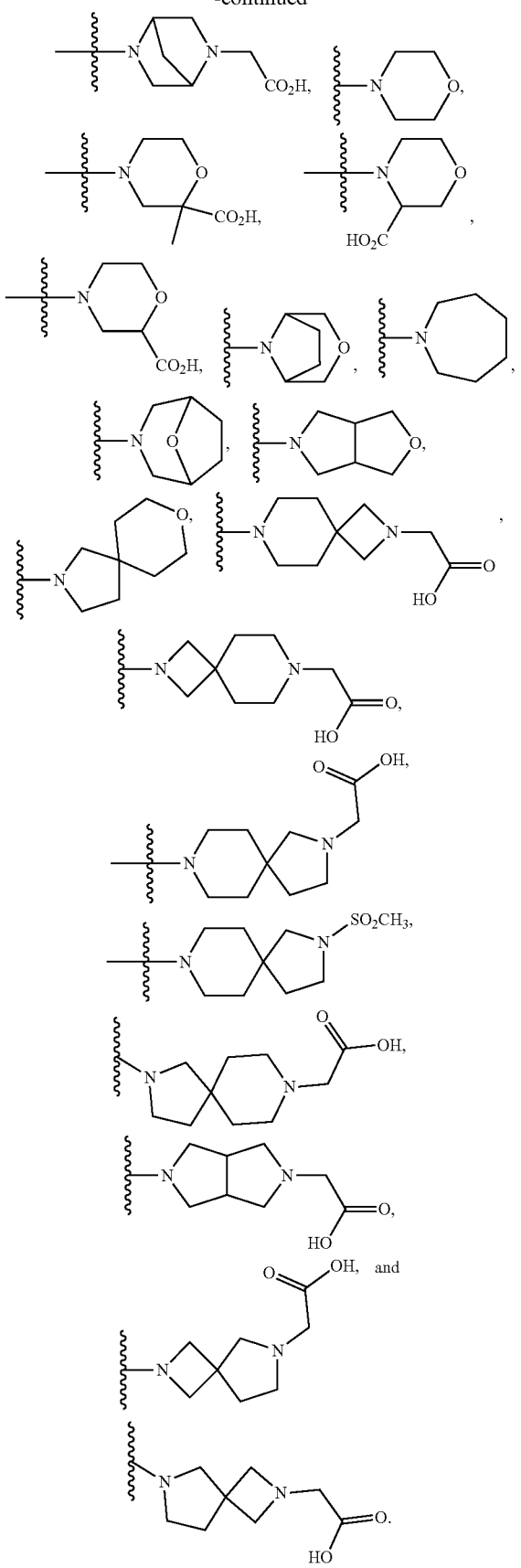

In some embodiments is a compound having the structure of Formula (IV):

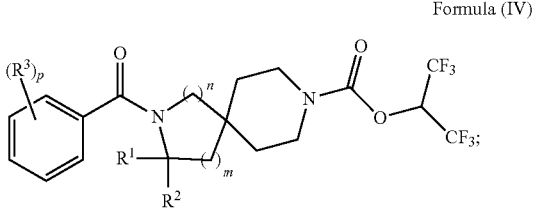

Formula (IV)

wherein:
Y is —$CH_2$— or —C(O)—;
each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, -$C_{1-6}$alkyl($C_{2-9}$heterocycloalkyl), $C_{6-10}$aryl, $C_{1-9}$heteroaryl, —$SF_5$, —$NR^5R^6$, —$OR^7$, —$CO_2R^8$, and —C(O)$NR^8R^9$, wherein -$C_{1-6}$alkyl($C_{2-9}$heterocycloalkyl) and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
each $R^4$ is independently selected from $C_{1-6}$alkyl, $C_{1-6}$haloalkyl, $C_{3-8}$cycloalkyl, halogen, oxo, —CN, —$CO_2R^8$, -$C_{1-6}$alkyl-$CO_2R^8$, —C(O)$R^8$, —C(O)$NR^8R^9$, —$SO_2R^8$, —$NR^9$C(O)$R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, $CO_2H$, and C(O)$NH_2$;
each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2H$, and C(O)$NH_2$;
each $R^{10}$ is independently selected from halogen, $C_{1-6}$alkyl, -$C_{1-6}$alkyl-$CO_2R^8$, $C_{1-6}$haloalkyl, $C_{3-8}$cycloalkyl, oxo, —CN, —$CO_2R^8$,—C(O)$R^8$, —C(O)$NR^8R^9$, —$SO_2R^8$, —$NR^9$C(O)$R^8$, and —$NR^9SO_2R^8$; and
p is 0, 1, 2, 3, 4, or 5;
or a solvate, hydrate, tautomer, N-oxide, stereoisomer, or pharmaceutically acceptable salt thereof.

In another embodiment is a compound of Formula (IV), or a solvate, hydrate, tautomer, N-oxide, stereoisomer, or pharmaceutically acceptable salt thereof, wherein p is 0, 1, 2, or 3. In another embodiment is a compound of Formula (IV), or a solvate, hydrate, tautomer, N-oxide, stereoisomer, or a pharmaceutically acceptable salt thereof, wherein p is 0, 1, or 2. In another embodiment is a compound of Formula (IV), or a solvate, hydrate, tautomer, N-oxide, stereoisomer, or a pharmaceutically acceptable salt thereof, wherein p is 0 or 1. In another embodiment is a compound of Formula (IV), or a solvate, hydrate, tautomer, N-oxide, stereoisomer, or a pharmaceutically acceptable salt thereof, wherein p is 1 or 2. In another embodiment is a compound of Formula (IV), or a solvate, hydrate, tautomer, N-oxide, stereoisomer, or a pharmaceutically acceptable salt thereof, wherein p is 0. In another embodiment is a compound of Formula (IV), or a solvate, hydrate, tautomer, N-oxide, stereoisomer, or a pharmaceutically acceptable salt thereof, wherein p is 1. In another embodiment is a compound of Formula (IV), or a solvate, hydrate, tautomer, N-oxide, stereoisomer, or a pharmaceutically acceptable salt thereof, wherein p is 2. In another embodiment is a compound of Formula (IV), or a solvate, hydrate, tautomer, N-oxide, stereoisomer, or a pharmaceutically acceptable salt thereof, wherein p is 3. In another embodiment is a compound of Formula (IV), or a solvate, hydrate, tautomer, N-oxide, stereoisomer, or a pharmaceutically acceptable salt thereof, wherein p is 4.

In another embodiment is a compound of Formula (IV), or a solvate, hydrate, tautomer, N-oxide, stereoisomer, or a pharmaceutically acceptable salt thereof, wherein p is 2 and each $R^3$ is independently selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl (heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (IV), or a solvate, hydrate, tautomer, N-oxide, stereoisomer, or a pharmaceutically acceptable salt thereof, wherein p is 2 and each $R^3$ is independently selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (IV), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$NR^5R^6$, and —$OR^7$. In another embodiment is a compound of Formula (IV), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, —$NR^5R^6$, and —$OR^7$. In another embodiment is a compound of Formula (IV), or a solvate, hydrate, tautomer, N-oxide, stereoisomer, or a pharmaceutically acceptable salt thereof, wherein p is 2 and each $R^3$ is independently selected from halogen, —$NR^5R^6$, and $C_{1-6}$haloalkyl. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two le selected from $C_{1-6}$alkyl and —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form an unsubstituted $C_{2-9}$heterocycloalkyl ring. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (IV), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (IV), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (IV), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (IV), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (IV), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (IV), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (IV), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (IV), or a solvate, hydrate, tautomer, N-oxide, stereoisomer, or a pharmaceutically acceptable salt thereof, wherein p is 1 and $R^3$ is halogen. In another embodiment is a compound of Formula (IV), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (IV), or a solvate, hydrate, tautomer, N-oxide, stereoisomer, or a pharmaceutically acceptable salt thereof, wherein p is 1 and $R^3$ is —$OR^7$. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstitued $C_{2-9}$heterocycloalkyl ring. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (IV), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (IV), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

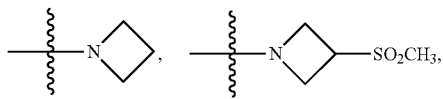

-continued
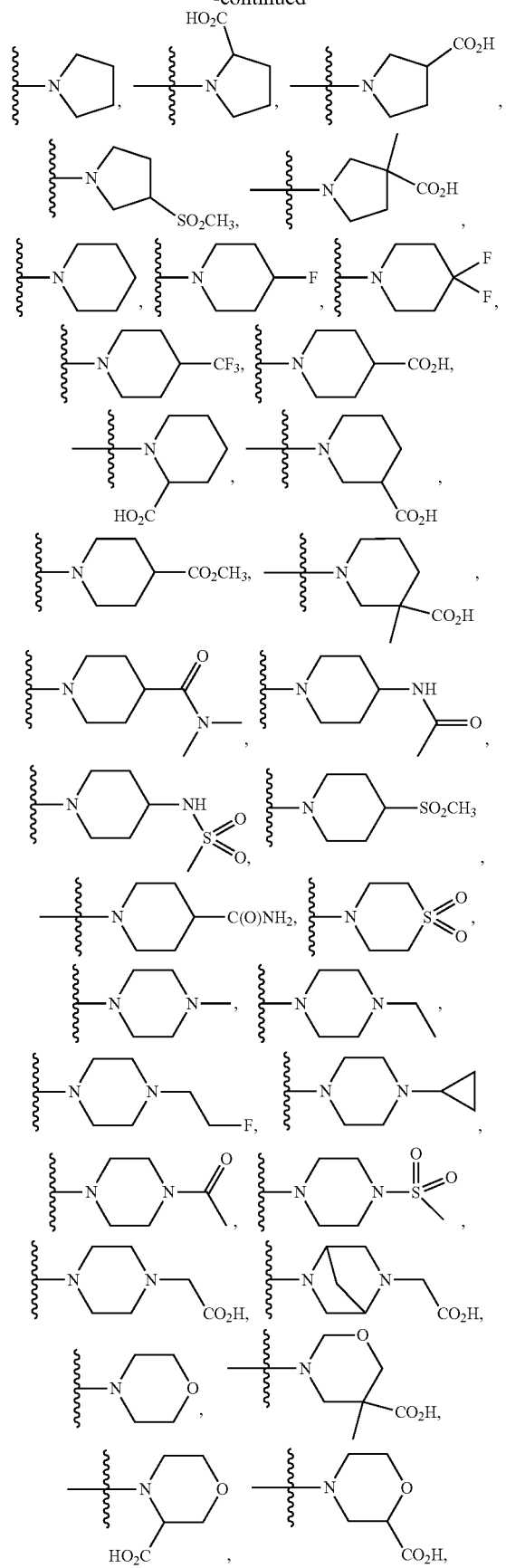
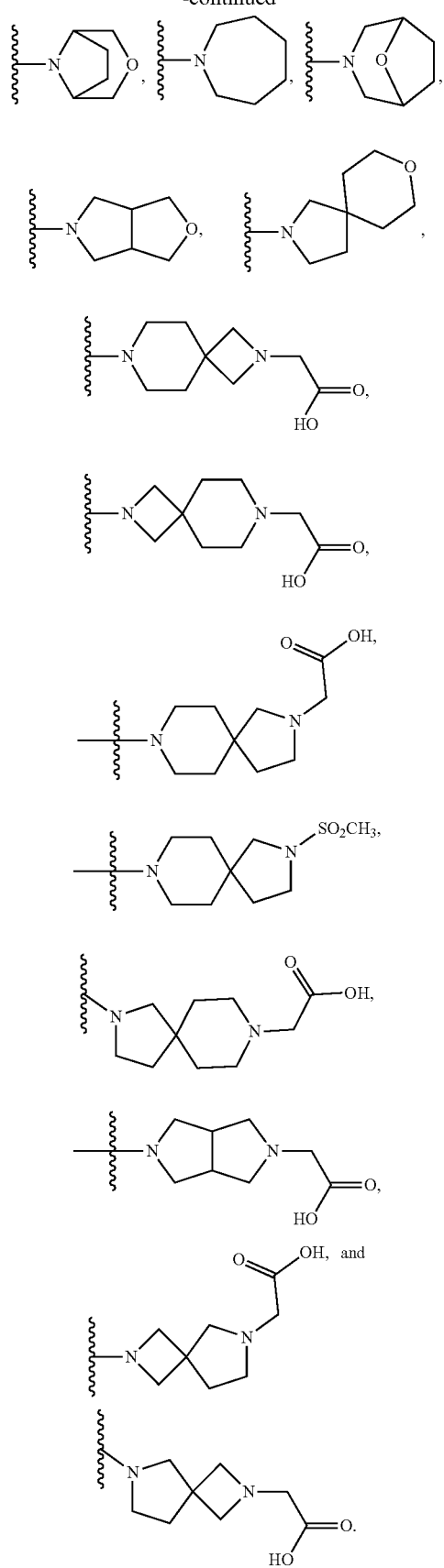

In some embodiments is a compound having the structure of Formula (V):

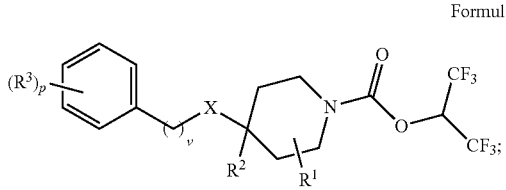

Formula (V)

wherein:
X is —O— or —N($R^{11}$)—;
$R^1$ is H or $C_{1-6}$alkyl;
$R^2$ is $C_{1-6}$alkyl;
each $R^3$ is independently selected from $C_{1-6}$alkyl, $C_{2-6}$alkenyl, $C_{2-6}$alkynyl, —C≡C-$C_{1-6}$alkyl-$CO_2$H, halogen, —CN, $C_{1-6}$haloalkyl, $C_{1-6}$aminoalkyl, $C_{3-8}$cycloalkyl, -$C_{1-6}$alkyl($C_{2-9}$heterocycloalkyl), $C_{1-9}$heteroaryl, —$SF_5$, —$NR^5R^6$, —$OR^7$, —$CO_2R^8$, and —C(O)$NR^8R^9$, wherein $C_{3-8}$cycloalkyl, -$C_{1-6}$alkyl($C_{2-9}$heterocycloalkyl), and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
each $R^4$ is independently selected from $C_{1-6}$alkyl, $C_{3-8}$cycloalkyl, $C_{1-6}$haloalkyl, halogen, oxo, —CN, —$CO_2R^8$, —C(O)$R^8$, —C(O)$NR^8R^9$, —$SO_2R^8$, —$NR^9C(O)R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), -$C_{1-6}$alkyl-$CO_2$H, $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, $CO_2$H, and $CO_2NH_2$;
each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2$H, and $CO_2NH_2$;
each $R^{10}$ is independently selected from halogen, $C_{1-6}$alkyl, $C_{1-6}$haloalkyl, $C_{3-8}$cycloalkyl, oxo, —CN, —$CO_2R^8$, —C(O)$R^8$, —C(O)$NR^8R^9$, —$SO_2R^8$, —$NR^9C(O)R^8$, and —$NR^9SO_2R^8$;
$R^{11}$ is H, $C_{1-6}$alkyl, —C(O)-$C_{1-6}$alkyl, or —$CH_2CO_2$H;
p is 0, 1, 2, 3, 4, or 5; and
v is 0 or 1;
or a solvate, hydrate, tautomer, N-oxide, stereoisomer, or pharmaceutically acceptable salt thereof.

In some embodiments is a compound of Formula (V), or a solvate, hydrate, tautomer, N-oxide, stereoisomer, or a pharmaceutically acceptable salt thereof, wherein X is —O—. In some embodiments is a compound of Formula (V), or a solvate, hydrate, tautomer, N-oxide, stereoisomer, or a pharmaceutically acceptable salt thereof, wherein X is —N($R^{11}$)—. In some embodiments is a compound of Formula (V), or a solvate, hydrate, tautomer, N-oxide, stereoisomer, or a pharmaceutically acceptable salt thereof, wherein X is —N($R^{11}$)— and $R^{11}$ is H. In some embodiments is a compound of Formula (V), or a solvate, hydrate, tautomer, N-oxide, stereoisomer, or a pharmaceutically acceptable salt thereof, wherein X is —N($R^{11}$)— and $R^{11}$ is $C_{1-6}$alkyl. In some embodiments is a compound of Formula (V), or a solvate, hydrate, tautomer, N-oxide, stereoisomer, or a pharmaceutically acceptable salt thereof, wherein X is —N($R^{11}$)— and $R^{11}$ is —$CH_3$. In some embodiments is a compound of Formula (V), or a solvate, hydrate, tautomer, N-oxide, stereoisomer, or a pharmaceutically acceptable salt thereof, wherein X is —N($R^{11}$)— and $R^{11}$ is —C(O)-$C_{1-6}$alkyl. In some embodiments is a compound of Formula (V), or a solvate, hydrate, tautomer, N-oxide, stereoisomer, or a pharmaceutically acceptable salt thereof, wherein X is —N($R^{11}$)— and $R^{11}$ is —$CH_2CO_2$H.

In some embodiments is a compound of Formula (V), or a solvate, hydrate, tautomer, N-oxide, stereoisomer, or a pharmaceutically acceptable salt thereof, wherein $R^1$ is H. In some embodiments is a compound of Formula (V), or a solvate, hydrate, tautomer, N-oxide, stereoisomer, or a pharmaceutically acceptable salt thereof, wherein $R^1$ is $C_{1-6}$alkyl. In some embodiments is a compound of Formula (V), or a solvate, hydrate, tautomer, N-oxide, stereoisomer, or a pharmaceutically acceptable salt thereof, wherein $R^1$ and $R^2$ are both $C_{1-6}$alkyl. In some embodiments is a compound of Formula (V), or a solvate, hydrate, tautomer, N-oxide, stereoisomer, or a pharmaceutically acceptable salt thereof, wherein $R^2$ is —$CH_3$. In some embodiments is a compound of Formula (V), or a solvate, hydrate, tautomer, N-oxide, stereoisomer, or a pharmaceutically acceptable salt thereof, wherein $R^1$ and $R^2$ are both —$CH_3$. In some embodiments is a compound of Formula (V), or a solvate, hydrate, tautomer, N-oxide, stereoisomer, or a pharmaceutically acceptable salt thereof, wherein $R^1$ is H and $R^2$ is —$CH_3$.

In another embodiment is a compound of Formula (V), or a solvate, hydrate, tautomer, N-oxide, stereoisomer, or a pharmaceutically acceptable salt thereof, wherein p is 0, 1, 2, or 3. In another embodiment is a compound of Formula (V), or a solvate, hydrate, tautomer, N-oxide, stereoisomer, or a pharmaceutically acceptable salt thereof, wherein p is 0, 1, or 2. In another embodiment is a compound of Formula (V), or a solvate, hydrate, tautomer, N-oxide, stereoisomer, or a pharmaceutically acceptable salt thereof, wherein p is 0 or 1. In another embodiment is a compound of Formula (V), or a solvate, hydrate, tautomer, N-oxide, stereoisomer, or a pharmaceutically acceptable salt thereof, wherein p is 1 or 2. In another embodiment is a compound of Formula (V), or a solvate, hydrate, tautomer, N-oxide, stereoisomer, or a pharmaceutically acceptable salt thereof, wherein p is 0. In another embodiment is a compound of Formula (V), or a solvate, hydrate, tautomer, N-oxide, stereoisomer, or a pharmaceutically acceptable salt thereof, wherein p is 1. In another embodiment is a compound of Formula (V), or a solvate, hydrate, tautomer, N-oxide, stereoisomer, or a pharmaceutically acceptable salt thereof, wherein p is 2. In another embodiment is a compound of Formula (V), or a solvate, hydrate, tautomer, N-oxide, stereoisomer, or a pharmaceutically acceptable salt thereof, wherein p is 3. In another embodiment is a compound of Formula (V), or a solvate, hydrate, tautomer, N-oxide, stereoisomer, or a pharmaceutically acceptable salt thereof, wherein p is 4.

In another embodiment is a compound of Formula (V), or a solvate, hydrate, tautomer, N-oxide, stereoisomer, or a pharmaceutically acceptable salt thereof, wherein p is 2 and each $R^3$ is independently selected from $C_{1-6}$alkyl, halogen, —CN, $C_{1-6}$haloalkyl, $C_{1-6}$aminoalkyl, -$C_{1-6}$alkyl(heterocycloalkyl), —SF$_5$, —NR$^5$R$^6$, and —OR$^7$; wherein -$C_{1-6}$alkyl (heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (V), or a solvate, hydrate, tautomer, N-oxide, stereoisomer, or a pharmaceutically acceptable salt thereof, wherein p is 2 and each $R^3$ is independently selected halogen, $C_{1-6}$alkyl, $C_{1-6}$haloalkyl, -$C_{1-6}$alkyl($C_{2-9}$heterocycloalkyl), —NR$^5$R$^6$, —OR$^7$, —CO$_2$R$^8$, and —C(O)NR$^8$R$^9$. In another embodiment is a compound of Formula (V), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —NR$^5$R$^6$, and —OR$^7$. In another embodiment is a compound of Formula (V), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, —NR$^5$R$^6$, and —OR$^7$. In another embodiment is a compound of Formula (V), or a solvate, hydrate, tautomer, N-oxide, stereoisomer, or a pharmaceutically acceptable salt thereof, wherein p is 2 and each $R^3$ is independently selected from halogen, —NR$^5$R$^6$, and $C_{1-6}$haloalkyl. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein $R^5$ and $R^6$, together with the nitrogen to which they are attached, form an unsubstitued $C_{2-9}$heterocycloalkyl ring. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein $R^5$ and $R^6$, together with the nitrogen to which they are attached, form a $C_{2-9}$heterocycloalkyl ring substituted with one or two $R^{10}$. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is halogen and one $R^3$ is —NR$^5$R$^6$ wherein $R^5$ and $R^6$, together with the nitrogen to which they are attached, form a $C_{2-9}$heterocycloalkyl ring substituted with —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein $R^5$ and $R^6$, together with the nitrogen to which they are attached, form an unsubstitued $C_{2-9}$heterocycloalkyl ring. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein $R^5$ and $R^6$, together with the nitrogen to which they are attached, form a $C_{2-9}$heterocycloalkyl ring substituted with one or two $R^{10}$. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is —Cl and one $R^3$ is —NR$^5$R$^6$ wherein $R^5$ and $R^6$, together with the nitrogen to which they are attached, form a $C_{2-9}$heterocycloalkyl ring substituted with —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein $R^5$ and $R^6$, together with the nitrogen to which they are attached, form an unsubstituted $C_{2-9}$heterocycloalkyl ring. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein $R^5$ and $R^6$, together with the nitrogen to which they are attached, form a $C_{2-9}$heterocycloalkyl ring substituted with one or two $R^{10}$. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$, together with the nitrogen to which they are attached, form a $C_{2-9}$heterocycloalkyl ring substituted with one or two $R^{10}$ selected from $C_{1-6}$alkyl and —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —NR$^5$R$^6$ wherein $R^5$ and $R^6$, together with the nitrogen to which they are attached, form a $C_{2-9}$heterocycloalkyl ring substituted with —CO$_2$H. In another embodiment is a compound of Formula (V), or a solvate, hydrate, tautomer, N-oxide, stereoisomer, or a pharmaceutically acceptable salt thereof, wherein p is 2, one $R^3$ is —CF$_3$ and one $R^3$ is —NR$^5$R$^6$. In another embodiment is a compound of Formula (V), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (V), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (V), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (V), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (V), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (V), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (V), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl ($C_{2-9}$heterocycloalkyl), —$NR^5R^6$, —$OR^7$, —$CO_2R^8$, and —$C(O)NR^8R^9$. In another embodiment is a compound of Formula (V), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (V), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (V), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (V), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (V), or a solvate, hydrate, tautomer, N-oxide, stereoisomer, or a pharmaceutically acceptable salt thereof, wherein p is 1 and $R^3$ is halogen. In another embodiment is a compound of Formula (V), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (V), or a solvate, hydrate, tautomer, N-oxide, stereoisomer, or a pharmaceutically acceptable salt thereof, wherein p is 1 and $R^3$ is —$OR^7$. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstitued $C_{2-9}$heterocycloalkyl ring. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (V), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (V), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

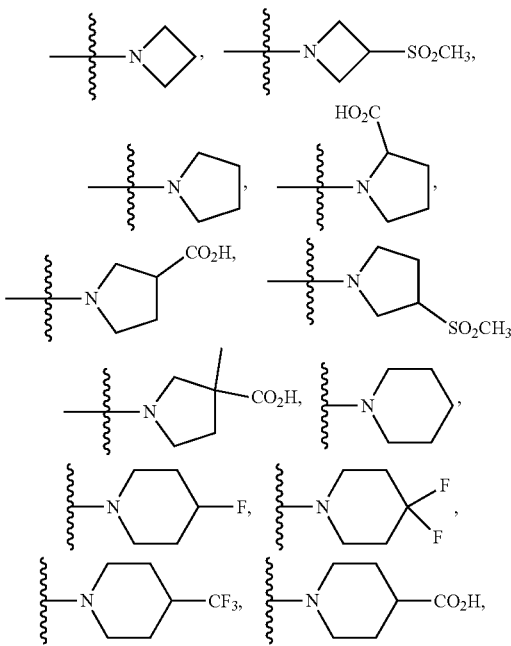

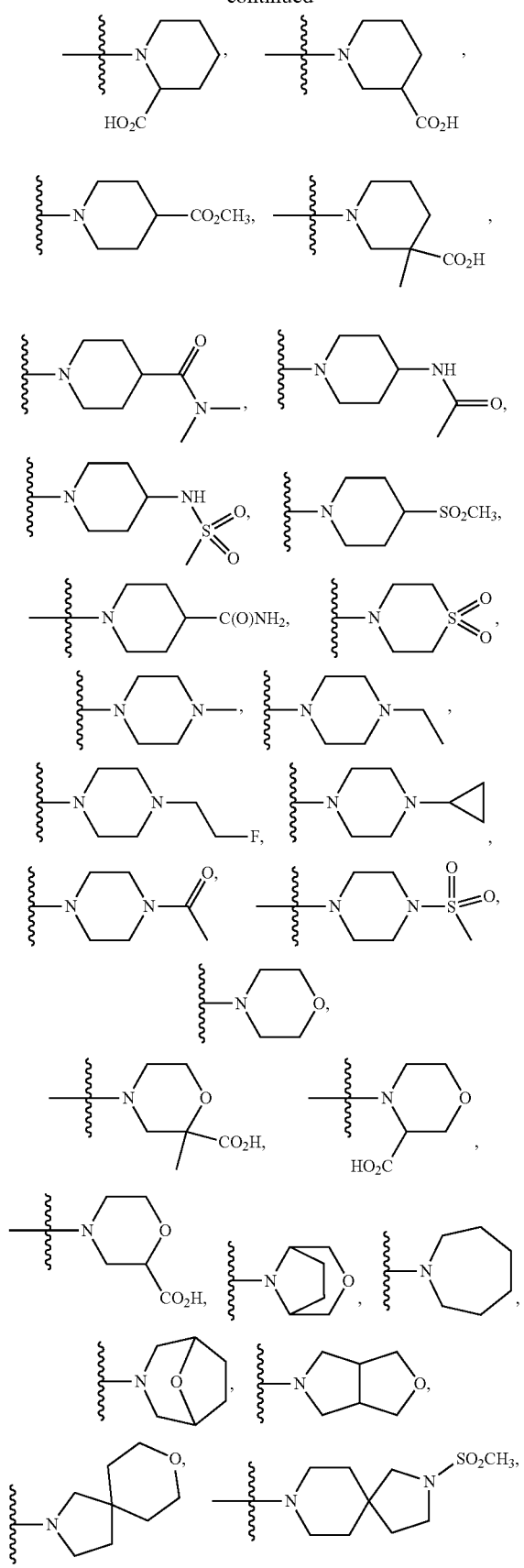

In some embodiments is a compound having the structure of Formula (Va):

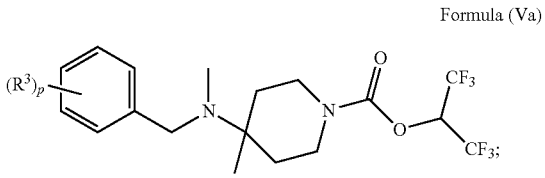

Formula (Va)

wherein:
each $R^3$ is independently selected from $C_{1-6}$alkyl, $C_{2-6}$alkenyl, $C_{2-6}$alkynyl, —C≡C-$C_{1-6}$alkyl-$CO_2$H, halogen, —CN, $C_{1-6}$haloalkyl, $C_{1-6}$aminoalkyl, $C_{3-8}$cycloalkyl, -$C_{1-6}$alkyl($C_{2-9}$heterocycloalkyl), $C_{1-9}$heteroaryl, —$SF_5$, —$NR^5R^6$, —$OR^7$, —$CO_2R^8$, and —C(O)$NR^8R^9$, wherein $C_{3-8}$cycloalkyl, -$C_{1-6}$alkyl($C_{2-9}$heterocycloalkyl), and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;
each $R^4$ is independently selected from $C_{1-6}$alkyl, $C_{3-8}$cycloalkyl, $C_{1-6}$haloalkyl, halogen, oxo, —CN, —$CO_2R^8$, —C(O)$R^8$, —C(O)$NR^8R^9$, —$SO_2R^8$, —$NR^5C(O)R^8$, and —$NR^9SO_2R^8$;
each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;
each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-C(O)($C_{2-9}$heterocycloalkyl), -$C_{1-6}$alkyl-$CO_2$H, $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, $CO_2$H, and $CO_2NH_2$;
each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2$H, and $CO_2NH_2$;
each $R^{10}$ is independently selected from halogen, $C_{1-6}$alkyl, $C_{1-6}$haloalkyl, $C_{3-8}$cycloalkyl, oxo, —CN, —$CO_2R^8$, —C(O)$R^8$, —C(O)$NR^8R^9$, —$SO_2R^8$, —$NR^5C(O)R^8$, and —$NR^9SO_2R^8$;
p is 0, 1, 2, 3, 4, or 5;
or a solvate, hydrate, tautomer, N-oxide, stereoisomer, or pharmaceutically acceptable salt thereof.

In another embodiment is a compound of Formula (Va), or a solvate, hydrate, tautomer, N-oxide, stereoisomer, or pharmaceutically acceptable salt thereof, wherein p is 0, 1, 2, or 3. In another embodiment is a compound of Formula (Va), or a solvate, hydrate, tautomer, N-oxide, stereoisomer, or a pharmaceutically acceptable salt thereof, wherein p is 0, 1, or 2. In another embodiment is a compound of Formula (Va), or a solvate, hydrate, tautomer, N-oxide, stereoisomer, or a pharmaceutically acceptable salt thereof, wherein p is 0 or 1. In another embodiment is a compound of Formula (Va), or a solvate, hydrate, tautomer, N-oxide, stereoisomer, or a pharmaceutically acceptable salt thereof, wherein p is 1 or 2. In another embodiment is a compound of Formula (Va), or a solvate, hydrate, tautomer, N-oxide, stereoisomer, or a pharmaceutically acceptable salt thereof, wherein p is 0. In another embodiment is a compound of Formula (Va), or a solvate, hydrate, tautomer, N-oxide, stereoisomer, or a pharmaceutically acceptable salt thereof, wherein p is 1. In another embodiment is a compound of Formula (Va), or a solvate, hydrate, tautomer, N-oxide, stereoisomer, or a pharmaceutically acceptable salt thereof, wherein p is 2. In another embodiment is a compound of Formula (Va), or a solvate, hydrate, tautomer, N-oxide, stereoisomer, or a pharmaceutically acceptable salt thereof, wherein p is 3. In another embodiment is a compound of Formula (Va), or a solvate, hydrate, tautomer, N-oxide, stereoisomer, or a pharmaceutically acceptable salt thereof, wherein p is 4.

In another embodiment is a compound of Formula (Va), or a solvate, hydrate, tautomer, N-oxide, stereoisomer, or a pharmaceutically acceptable salt thereof, wherein p is 2 and each $R^3$ is independently selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl (heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (Va), or a solvate, hydrate, tautomer, N-oxide, stereoisomer, or a pharmaceutically acceptable salt thereof, wherein p is 2 and each $R^3$ is independently selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (Va), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$NR^5R^6$, and —$OR^7$. In another embodiment is a compound of Formula (Va), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, —$NR^5R^6$, and —$OR^7$. In another embodiment is a compound of Formula (Va), or a solvate, hydrate, tautomer, N-oxide, stereoisomer, or a pharmaceutically acceptable salt thereof, wherein p is 2 and each $R^3$ is independently selected from halogen, —$NR^5R^6$, and $C_{1-6}$haloalkyl. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form an unsubstituted $C_{2-9}$heterocycloalkyl ring. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two le selected from $C_{1-6}$alkyl and —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (Va), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (Va), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (Va), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (Va), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (Va), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (Va), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (Va), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (Va), or a solvate, hydrate, tautomer, N-oxide, stereoisomer, or a pharmaceutically acceptable salt thereof, wherein p is 1 and $R^3$ is halogen. In another embodiment is a compound of Formula (Va), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (Va), or a solvate, hydrate, tautomer, N-oxide, stereoisomer, or a pharmaceutically acceptable salt thereof, wherein p is 1 and $R^3$ is —$OR^7$. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstitued $C_{2-9}$heterocycloalkyl ring. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (Va), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (Va), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

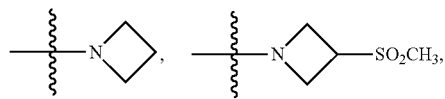

-continued

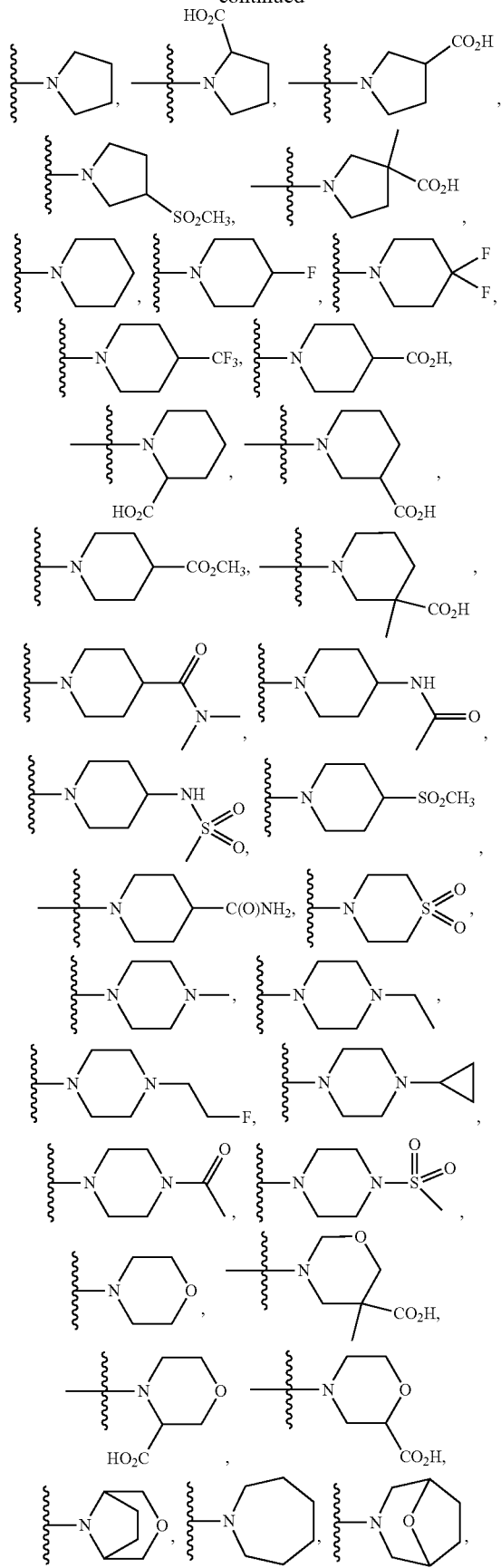

-continued

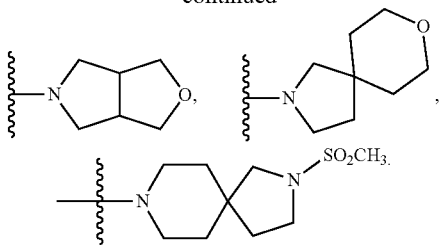

In some embodiments is a compound having the structure of Formula (V'):

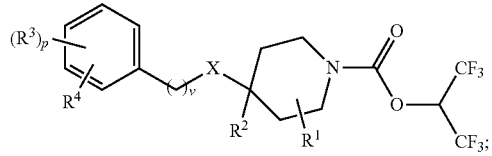

Formula (V')

wherein:
X is —O— or —N($R^{11}$)—;
$R^1$ is H or $C_{1-6}$alkyl;
$R^2$ is $C_{1-6}$alkyl;
each $R^3$ is independently selected from $C_{1-6}$alkyl, halogen, —CN, $C_{1-6}$haloalkyl, $C_{3-8}$cycloalkyl, —SF$_5$, —OR$^7$, and —C(O)NR$^8$R$^9$;
$R^4$ is selected from

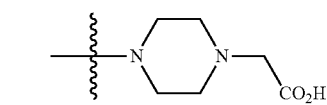

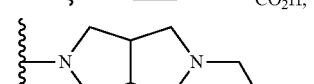

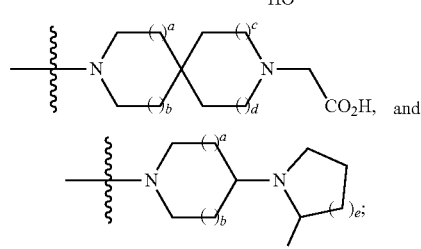

each $R^7$ is independently selected from H, $C_{1-6}$alkyl, $C_{1-6}$haloalkyl, $C_{3-8}$cycloalkyl, and -$C_{1-6}$alkyl-$C_{3-8}$cycloalkyl;
each $R^8$ and $R^9$ is independently selected from H, $C_{1-6}$alkyl, and $C_{3-8}$cycloalkyl;
$R^{11}$ is H or $C_{1-6}$alkyl;
a, b, c, and d are independently 0 or 1;
e is 0, 1, or 2;
p is 0, 1, 2, 3, or 4; and
v is 0 or 1;
or a solvate, hydrate, tautomer, N-oxide, stereoisomer, or pharmaceutically acceptable salt thereof.

In some embodiments is a compound of Formula (V'), or a solvate, hydrate, tautomer, N-oxide, stereoisomer, or a pharmaceutically acceptable salt thereof, wherein X is —O—. In some embodiments is a compound of Formula (V'), or a solvate, hydrate, tautomer, N-oxide, stereoisomer, or a pharmaceutically acceptable salt thereof, wherein X is —N($R^{11}$)—. In some embodiments is a compound of Formula (V'), or a solvate, hydrate, tautomer, N-oxide, stereoisomer, or a pharmaceutically acceptable salt thereof, wherein X is —N($R^{11}$)— and $R^{11}$ is H. In some embodiments is a compound of Formula (V'), or a solvate, hydrate, tautomer, N-oxide, stereoisomer, or a pharmaceutically acceptable salt thereof, wherein X is —N($R^{11}$)— and $R^{11}$ is $C_{1-6}$alkyl. In some embodiments is a compound of Formula (V'), or a solvate, hydrate, tautomer, N-oxide, stereoisomer, or a pharmaceutically acceptable salt thereof, wherein X is —N($R^{11}$)— and is —$CH_3$. In some embodiments is a compound of Formula (V'), or a solvate, hydrate, tautomer, N-oxide, stereoisomer, or a pharmaceutically acceptable salt thereof, wherein X is —N($R^{11}$)— and is —C(O)-$C_{1-6}$alkyl. In some embodiments is a compound of Formula (V'), or a solvate, hydrate, tautomer, N-oxide, stereoisomer, or a pharmaceutically acceptable salt thereof, wherein X is —N($R^{11}$)— and $R^{11}$ is —$CH_2CO_2H$.

In some embodiments is a compound of Formula (V'), or a solvate, hydrate, tautomer, N-oxide, stereoisomer, or a pharmaceutically acceptable salt thereof, wherein $R^1$ is H. In some embodiments is a compound of Formula (V'), or a solvate, hydrate, tautomer, N-oxide, stereoisomer, or a pharmaceutically acceptable salt thereof, wherein $R^1$ is $C_{1-6}$alkyl. In some embodiments is a compound of Formula (V'), or a solvate, hydrate, tautomer, N-oxide, stereoisomer, or a pharmaceutically acceptable salt thereof, wherein $R^1$ and $R^2$ are both $C_{1-6}$alkyl. In some embodiments is a compound of Formula (V'), or a solvate, hydrate, tautomer, N-oxide, stereoisomer, or a pharmaceutically acceptable salt thereof, wherein $R^2$ is —$CH_3$. In some embodiments is a compound of Formula (V'), or a solvate, hydrate, tautomer, N-oxide, stereoisomer, or a pharmaceutically acceptable salt thereof, wherein $R^1$ and $R^2$ are both —$CH_3$. In some embodiments is a compound of Formula (V'), or a solvate, hydrate, tautomer, N-oxide, stereoisomer, or a pharmaceutically acceptable salt thereof, wherein $R^1$ is H and $R^2$ is —$CH_3$.

In another embodiment is a compound of Formula (V'), or a solvate, hydrate, tautomer, N-oxide, stereoisomer, or a pharmaceutically acceptable salt thereof, wherein p is 0, 1, 2, or 3. In another embodiment is a compound of Formula (V'), or a solvate, hydrate, tautomer, N-oxide, stereoisomer, or a pharmaceutically acceptable salt thereof, wherein p is 0, 1, or 2. In another embodiment is a compound of Formula (V'), or a solvate, hydrate, tautomer, N-oxide, stereoisomer, or a pharmaceutically acceptable salt thereof, wherein p is 0 or 1. In another embodiment is a compound of Formula (V'), or a solvate, hydrate, tautomer, N-oxide, stereoisomer, or a pharmaceutically acceptable salt thereof, wherein p is 1 or 2. In another embodiment is a compound of Formula (V'), or a solvate, hydrate, tautomer, N-oxide, stereoisomer, or a pharmaceutically acceptable salt thereof, wherein p is 0. In another embodiment is a compound of Formula (V'), or a solvate, hydrate, tautomer, N-oxide, stereoisomer, or a pharmaceutically acceptable salt thereof, wherein p is 1. In another embodiment is a compound of Formula (V'), or a solvate, hydrate, tautomer, N-oxide, stereoisomer, or a pharmaceutically acceptable salt thereof, wherein p is 2. In another embodiment is a compound of Formula (V'), or a solvate, hydrate, tautomer, N-oxide, stereoisomer, or a pharmaceutically acceptable salt thereof, wherein p is 3. In another embodiment is a compound of Formula (V'), or a solvate, hydrate, tautomer, N-oxide, stereoisomer, or a pharmaceutically acceptable salt thereof, wherein p is 4.

In another embodiment is a compound of Formula (V'), or a solvate, hydrate, tautomer, N-oxide, stereoisomer, or a pharmaceutically acceptable salt thereof, wherein $R^4$ is

[Chemical structure: piperazine ring with N-CH2-CO2H substituent]

In another embodiment is a compound of Formula (V'), or a solvate, hydrate, tautomer, N-oxide, stereoisomer, or a pharmaceutically acceptable salt thereof, wherein $R^4$ is

[Chemical structure: bicyclic diazabicyclo with N-CH2-CO2H substituent]

In another embodiment is a compound of Formula (V'), or a solvate, hydrate, tautomer, N-oxide, stereoisomer, or a pharmaceutically acceptable salt thereof, wherein $R^4$ is

[Chemical structure: octahydropyrrolo[3,4-c]pyrrole with N-CH2-C(O)OH substituent]

In another embodiment is a compound of Formula (V'), or a solvate, hydrate, tautomer, N-oxide, stereoisomer, or a pharmaceutically acceptable salt thereof, wherein $R^4$ is

[Chemical structure: spiro diazaspiro ring with subscripts a, b, c, d and N-CH2-CO2H substituent]

In another embodiment is a compound of Formula (V'), or a solvate, hydrate, tautomer, N-oxide, stereoisomer, or a pharmaceutically acceptable salt thereof, wherein $R^4$ is

[Chemical structure: diazaspiro ring system with N-CH2-C(O)OH substituent]

In another embodiment is a compound of Formula (V'), or a solvate, hydrate, tautomer, N-oxide, stereoisomer, or a pharmaceutically acceptable salt thereof, wherein $R^4$ is

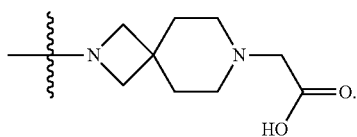 [SMILES: *N1CC2(CCN(CC(=O)O)CC2)C1]

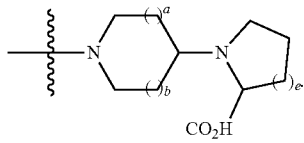

In another embodiment is a compound of Formula (V'), or a solvate, hydrate, tautomer, N-oxide, stereoisomer, or a pharmaceutically acceptable salt thereof, wherein R⁴ is In another embodiment is a compound of Formula (V'), or a solvate, hydrate, tautomer, N-oxide, stereoisomer, or a pharmaceutically acceptable salt thereof, wherein R⁴ is

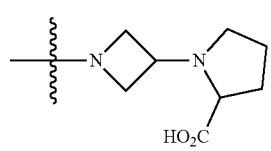

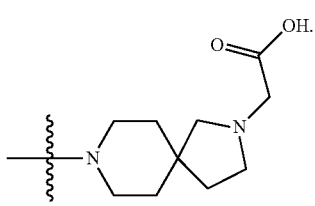 [SMILES: *N1CCC2(CC1)CCN(CC(=O)O)C2]

In another embodiment is a compound of Formula (V'), or a solvate, hydrate, tautomer, N-oxide, stereoisomer, or a pharmaceutically acceptable salt thereof, wherein R⁴ is In another embodiment is a compound of Formula (V'), or a solvate, hydrate, tautomer, N-oxide, stereoisomer, or a pharmaceutically acceptable salt thereof, wherein R⁴ is

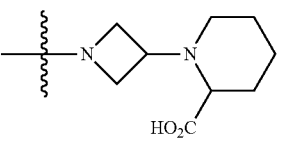

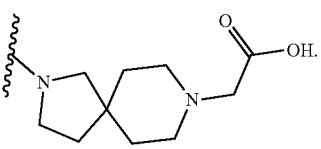 [SMILES: *N1CCC2(CCN(CC(=O)O)CC2)C1]

In another embodiment is a compound of Formula (V'), or a solvate, hydrate, tautomer, N-oxide, stereoisomer, or a pharmaceutically acceptable salt thereof, wherein R⁴ is In another embodiment is a compound of Formula (V'), or a solvate, hydrate, tautomer, N-oxide, stereoisomer, or a pharmaceutically acceptable salt thereof, wherein R⁴ is

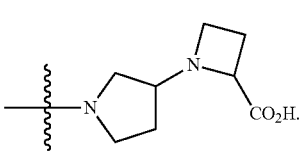

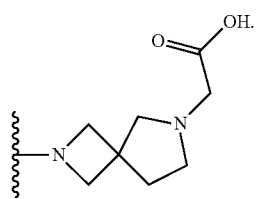 [SMILES: *N1CC2(CCN(CC(=O)O)C2)C1]

In another embodiment is a compound of Formula (V'), or a solvate, hydrate, tautomer, N-oxide, stereoisomer, or a pharmaceutically acceptable salt thereof, wherein R⁴ is In another embodiment is a compound of Formula (V'), or a solvate, hydrate, tautomer, N-oxide, stereoisomer, or a pharmaceutically acceptable salt thereof, wherein R⁴ is

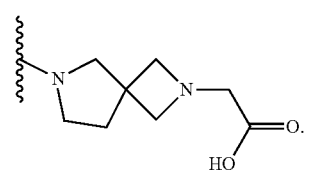 [SMILES: *N1CCC2(C1)CN(CC(=O)O)C2]

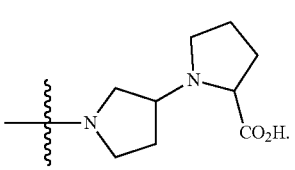 [SMILES: *N1CCC(N2CCCC2C(=O)O)C1]

In another embodiment is a compound of Formula (V'), or a solvate, hydrate, tautomer, N-oxide, stereoisomer, or a pharmaceutically acceptable salt thereof, wherein R⁴ is In another embodiment is a compound of Formula (V'), or a solvate, hydrate, tautomer, N-oxide, stereoisomer, or a pharmaceutically acceptable salt thereof, wherein R⁴ is

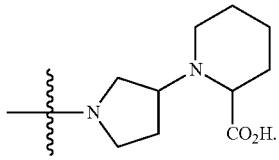 [SMILES: *N1CCC(N2CCCCC2C(=O)O)C1]

In another embodiment is a compound of Formula (V'), or a solvate, hydrate, tautomer, N-oxide, stereoisomer, or a pharmaceutically acceptable salt thereof, wherein R⁴ is

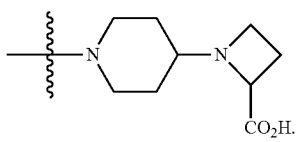 [SMILES: *N1CCC(N2CCC2C(=O)O)CC1]

In another embodiment is a compound of Formula (V'), or a solvate, hydrate, tautomer, N-oxide, stereoisomer, or a pharmaceutically acceptable salt thereof, wherein R⁴ is

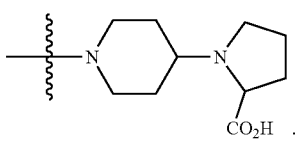

In another embodiment is a compound of Formula (V'), or a solvate, hydrate, tautomer, N-oxide, stereoisomer, or a pharmaceutically acceptable salt thereof, wherein R⁴ is

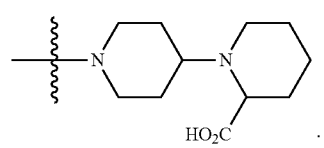

In another embodiment is a compound of Formula (V'), or a solvate, hydrate, tautomer, N-oxide, stereoisomer, or a pharmaceutically acceptable salt thereof, wherein R⁴ is selected from

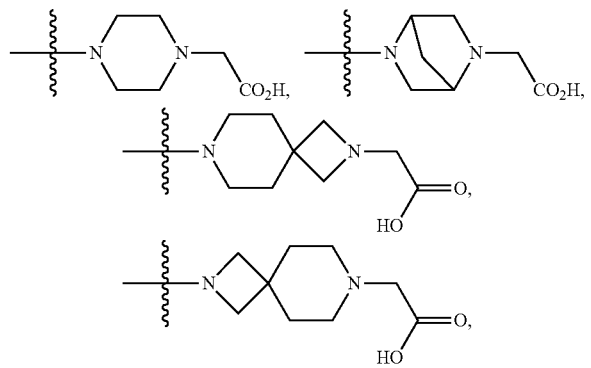

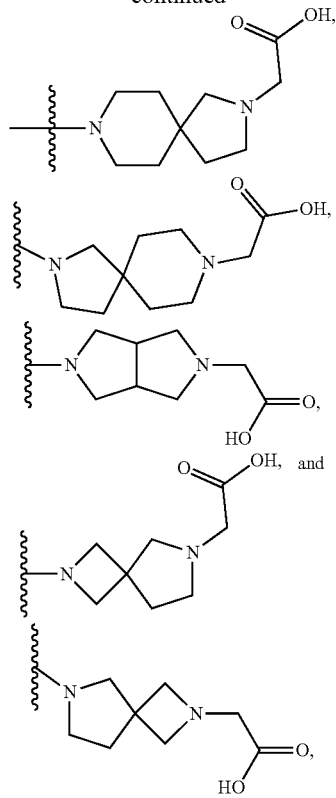

and p is 0. In another embodiment is a compound of Formula (V'), or a solvate, hydrate, tautomer, N-oxide, stereoisomer, or a pharmaceutically acceptable salt thereof, wherein R⁴ is selected from

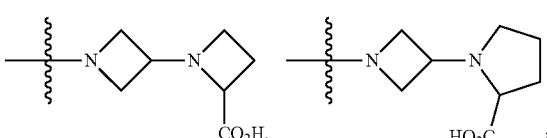

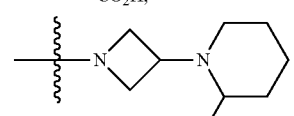

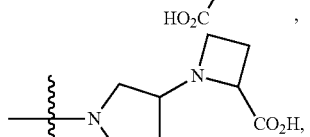

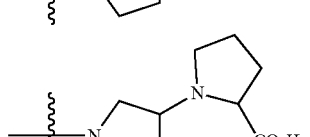

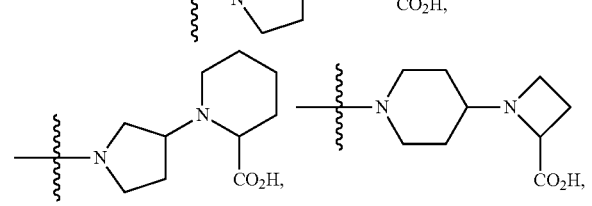

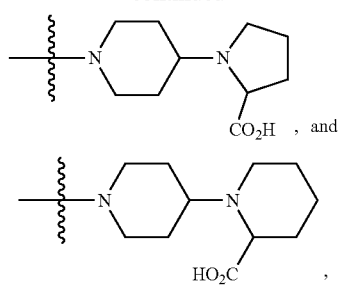

and p is 0.

In another embodiment is a compound of Formula (V'), or a solvate, hydrate, tautomer, N-oxide, stereoisomer, or a pharmaceutically acceptable salt thereof, wherein $R^4$ is selected from

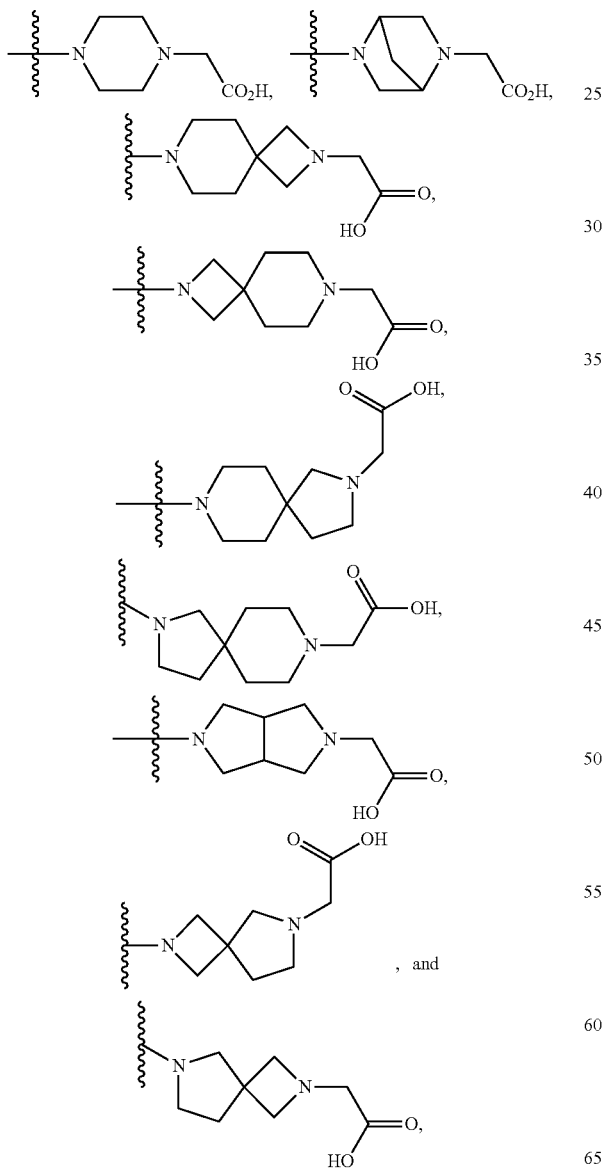

and p is 1. In another embodiment is a compound of Formula (V'), or a solvate, hydrate, tautomer, N-oxide, stereoisomer, or a pharmaceutically acceptable salt thereof, wherein $R^4$ is selected from selected from

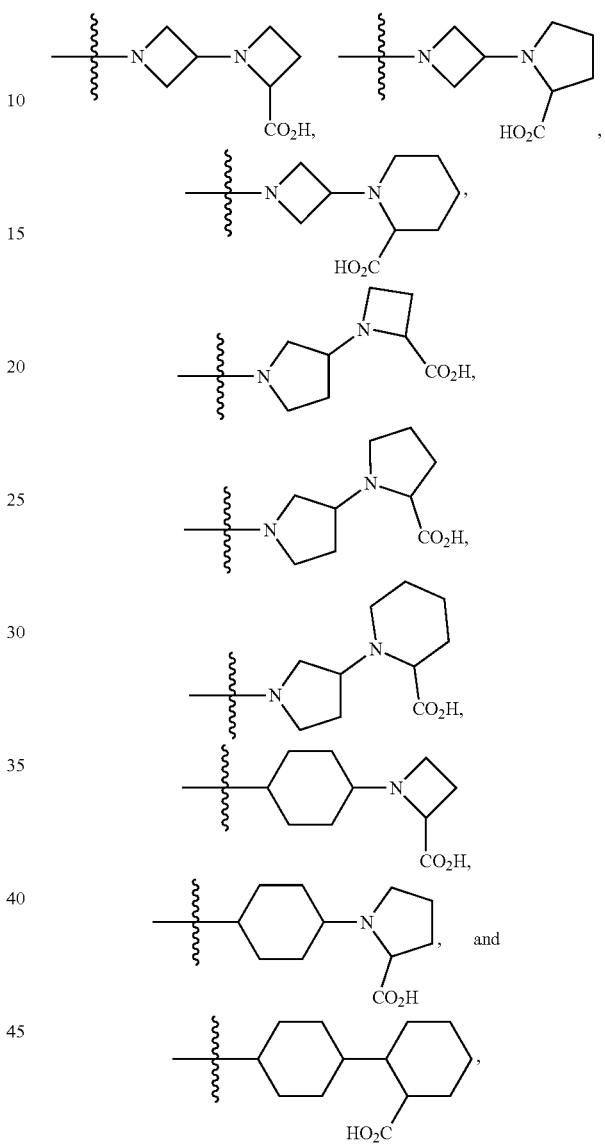

and p is 1.

In another embodiment is a compound of Formula (V'), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$SF_5$, and —$OR^7$. In another embodiment is a compound of Formula (V'), or a solvate, hydrate, tautomer, N-oxide, stereoisomer, or a pharmaceutically acceptable salt thereof, wherein p is 1 and $R^3$ is selected from halogen, $C_{1-6}$haloalkyl, and —$OR^7$. In another embodiment is a compound of Formula (V'), or a solvate, hydrate, tautomer, N-oxide, stereoisomer, or a pharmaceutically acceptable salt thereof, wherein p is 1 and $R^3$ is selected from halogen and $C_{1-6}$haloalkyl. In another embodiment is a compound of Formula (V'), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (V'), or a solvate, hydrate, tautomer, N-oxide, stereoisomer, or a pharmaceutically acceptable salt thereof, wherein p is 1 and $R^3$ is —$CH_3$. In another embodiment is a compound of Formula (V'), or a solvate, hydrate, tautomer, N-oxide, stereoisomer, or a pharmaceutically acceptable salt thereof, wherein p is 1 and $R^3$ is halogen. In another embodiment is a compound of Formula (V'), or a solvate, hydrate, tautomer, N-oxide, stereoisomer, or a pharmaceutically acceptable salt thereof, wherein p is 1 and $R^3$ is —Cl. In another embodiment is a compound of Formula (V'), or a solvate, hydrate, tautomer, N-oxide, stereoisomer, or a pharmaceutically acceptable salt thereof, wherein p is 1 and $R^3$ is —CN. In another embodiment is a compound of Formula (V'), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (V'), or a solvate, hydrate, tautomer, N-oxide, stereoisomer, or a pharmaceutically acceptable salt thereof, wherein p is 1 and $R^3$ is —$CF_3$. In another embodiment is a compound of Formula (V'), or a solvate, hydrate, tautomer, N-oxide, stereoisomer, or a pharmaceutically acceptable salt thereof, wherein p is 1 and $R^3$ is —$SF_5$. In another embodiment is a compound of Formula (V'), or a solvate, hydrate, tautomer, N-oxide, stereoisomer, or a pharmaceutically acceptable salt thereof, wherein p is 1 and $R^3$ is —$OR^7$. In another embodiment is a compound of Formula (V'), or a solvate, hydrate, tautomer, N-oxide, stereoisomer, or a pharmaceutically acceptable salt thereof, wherein p is 1 and $R^3$ is —$OCH_3$. In another embodiment is a compound of Formula (V'), or a solvate, hydrate, tautomer, N-oxide, stereoisomer, or a pharmaceutically acceptable salt thereof, wherein p is 1 and $R^3$ is $C_{3-8}$cycloalkyl. In another embodiment is a compound of Formula (V'), or a solvate, hydrate, tautomer, N-oxide, stereoisomer, or a pharmaceutically acceptable salt thereof, wherein p is 1 and $R^3$ is —$C(O)NR^8R^9$.

In another embodiment is a compound of Formula (V'), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$SF_5$, and —$OR^7$. In another embodiment is a compound of Formula (V'), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, and —$OR^7$. In another embodiment is a compound of Formula (V'), or a solvate, hydrate, tautomer, N-oxide, stereoisomer, or a pharmaceutically acceptable salt thereof, wherein p is 2 and each $R^3$ is independently selected from halogen and $C_{1-6}$haloalkyl.

In some embodiments is a compound having the structure of Formula (Va'):

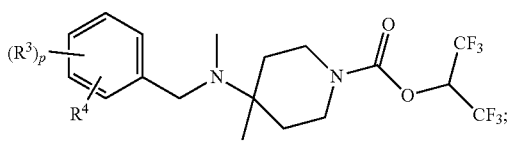

Formula (Va')

wherein:
  each $R^3$ is independently selected from $C_{1-6}$alkyl, halogen, —CN, $C_{1-6}$haloalkyl, $C_{3-8}$cycloalkyl, —$SF_5$, —$OR^7$, and —$C(O)NR^8R^9$;

$R^4$ is selected from

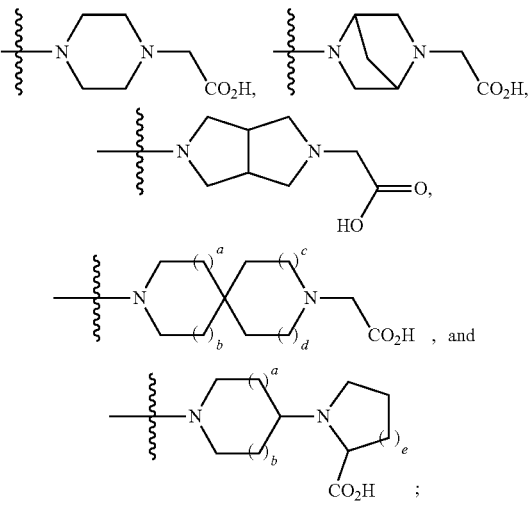

each $R^7$ is independently selected from H, $C_{1-6}$alkyl, $C_{1-6}$haloalkyl, $C_{3-8}$cycloalkyl, and -$C_{1-6}$alkyl-$C_{3-8}$cycloalkyl;

each $R^8$ and $R^9$ is independently selected from H, $C_{1-6}$alkyl, and $C_{3-8}$cycloalkyl;

a, b, c, and d are independently 0 or 1;

e is 0, 1, or 2; and p is 0, 1, 2, 3, or 4;

or a solvate, hydrate, tautomer, N-oxide, stereoisomer, or pharmaceutically acceptable salt thereof.

In another embodiment is a compound of Formula (Va'), or a solvate, hydrate, tautomer, N-oxide, stereoisomer, or a pharmaceutically acceptable salt thereof, wherein p is 0, 1, 2, or 3. In another embodiment is a compound of Formula (Va'), or a solvate, hydrate, tautomer, N-oxide, stereoisomer, or a pharmaceutically acceptable salt thereof, wherein p is 0, 1, or 2. In another embodiment is a compound of Formula (Va'), or a solvate, hydrate, tautomer, N-oxide, stereoisomer, or a pharmaceutically acceptable salt thereof, wherein p is 0 or 1. In another embodiment is a compound of Formula (Va'), or a solvate, hydrate, tautomer, N-oxide, stereoisomer, or a pharmaceutically acceptable salt thereof, wherein p is 1 or 2. In another embodiment is a compound of Formula (Va'), or a solvate, hydrate, tautomer, N-oxide, stereoisomer, or a pharmaceutically acceptable salt thereof, wherein p is 0. In another embodiment is a compound of Formula (Va'), or a solvate, hydrate, tautomer, N-oxide, stereoisomer, or a pharmaceutically acceptable salt thereof, wherein p is 1. In another embodiment is a compound of Formula (Va'), or a solvate, hydrate, tautomer, N-oxide, stereoisomer, or a pharmaceutically acceptable salt thereof, wherein p is 2. In another embodiment is a compound of Formula (Va'), or a solvate, hydrate, tautomer, N-oxide, stereoisomer, or a pharmaceutically acceptable salt thereof, wherein p is 3. In another embodiment is a compound of Formula (Va'), or a solvate, hydrate, tautomer, N-oxide, stereoisomer, or a pharmaceutically acceptable salt thereof, wherein p is 4.

In another embodiment is a compound of Formula (Va'), or a solvate, hydrate, tautomer, N-oxide, stereoisomer, or a pharmaceutically acceptable salt thereof, wherein $R^4$ is

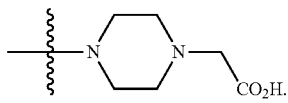

In another embodiment is a compound of Formula (Va'), or a solvate, hydrate, tautomer, N-oxide, stereoisomer, or a pharmaceutically acceptable salt thereof, wherein $R^4$ is

In another embodiment is a compound of Formula (Va'), or a solvate, hydrate, tautomer, N-oxide, stereoisomer, or a pharmaceutically acceptable salt thereof, wherein $R^4$ is

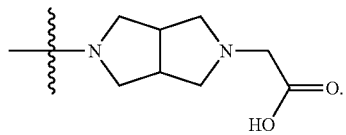 [SMILES: *N1CC2CN(CC(=O)O)CC2C1]

In another embodiment is a compound of Formula (Va'), or a solvate, hydrate, tautomer, N-oxide, stereoisomer, or a pharmaceutically acceptable salt thereof, wherein $R^4$ is

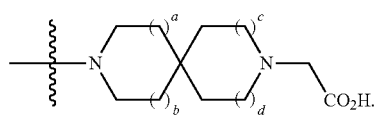

In another embodiment is a compound of Formula (Va'), or a solvate, hydrate, tautomer, N-oxide, stereoisomer, or a pharmaceutically acceptable salt thereof, wherein $R^4$ is

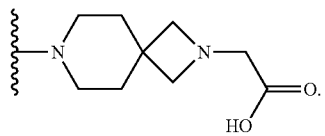 [SMILES: *N1CCC2(CC1)CN(CC(=O)O)C2]

In another embodiment is a compound of Formula (Va'), or a solvate, hydrate, tautomer, N-oxide, stereoisomer, or a pharmaceutically acceptable salt thereof, wherein $R^4$ is

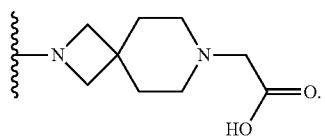 [SMILES: *N1CC2(CCN(CC(=O)O)CC2)C1]

In another embodiment is a compound of Formula (Va'), or a solvate, hydrate, tautomer, N-oxide, stereoisomer, or a pharmaceutically acceptable salt thereof, wherein $R^4$ is

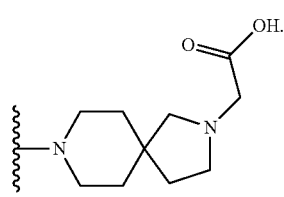 [SMILES: *N1CCC2(CC1)CCN(CC(=O)O)C2]

In another embodiment is a compound of Formula (Va'), or a solvate, hydrate, tautomer, N-oxide, stereoisomer, or a pharmaceutically acceptable salt thereof, wherein $R^4$ is

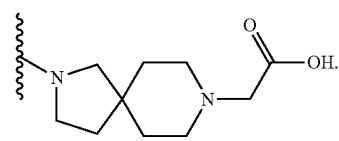 [SMILES: *N1CCC2(CCN(CC(=O)O)CC2)C1]

In another embodiment is a compound of Formula (Va'), or a solvate, hydrate, tautomer, N-oxide, stereoisomer, or a pharmaceutically acceptable salt thereof, wherein $R^4$ is

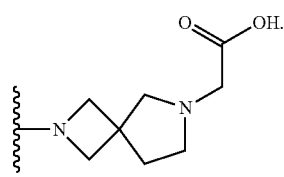 [SMILES: *N1CC2(CCN(CC(=O)O)C2)C1]

In another embodiment is a compound of Formula (Va'), or a solvate, hydrate, tautomer, N-oxide, stereoisomer, or a pharmaceutically acceptable salt thereof, wherein $R^4$ is

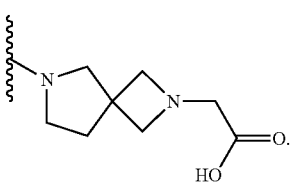 [SMILES: *N1CCC2(C1)CN(CC(=O)O)C2]

In another embodiment is a compound of Formula (Va'), or a solvate, hydrate, tautomer, N-oxide, stereoisomer, or a pharmaceutically acceptable salt thereof, wherein $R^4$ is

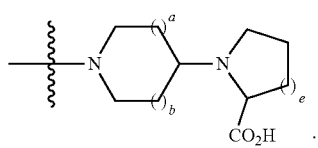

In another embodiment is a compound of Formula (Va'), or a solvate, hydrate, tautomer, N-oxide, stereoisomer, or a pharmaceutically acceptable salt thereof, wherein $R^4$ is

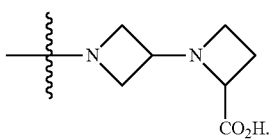 [SMILES: *N1CC(N2CCC2C(=O)O)C1]

In another embodiment is a compound of Formula (Va'), or a solvate, hydrate, tautomer, N-oxide, stereoisomer, or a pharmaceutically acceptable salt thereof, wherein $R^4$ is

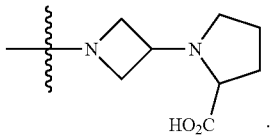 [SMILES: *N1CC(N2CCCC2C(=O)O)C1]

In another embodiment is a compound of Formula (Va'), or a solvate, hydrate, tautomer, N-oxide, stereoisomer, or a pharmaceutically acceptable salt thereof, wherein $R^4$ is

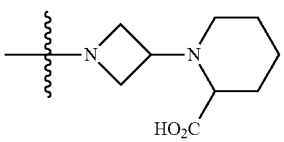

In another embodiment is a compound of Formula (Va'), or a solvate, hydrate, tautomer, N-oxide, stereoisomer, or a pharmaceutically acceptable salt thereof, wherein $R^4$ is

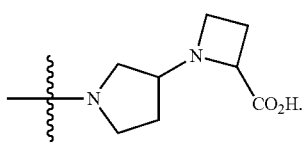 [SMILES: *N1CCC(N2CCC2C(=O)O)C1]

In another embodiment is a compound of Formula (Va'), or a solvate, hydrate, tautomer, N-oxide, stereoisomer, or a pharmaceutically acceptable salt thereof, wherein $R^4$ is

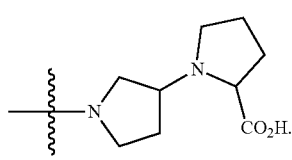

In another embodiment is a compound of Formula (Va'), or a solvate, hydrate, tautomer, N-oxide, stereoisomer, or a pharmaceutically acceptable salt thereof, wherein $R^4$ is

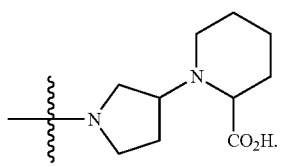 [SMILES: *N1CCC(N2CCCCC2C(=O)O)C1]

In another embodiment is a compound of Formula (Va'), or a solvate, hydrate, tautomer, N-oxide, stereoisomer, or a pharmaceutically acceptable salt thereof, wherein $R^4$ is

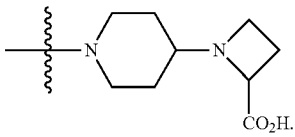

In another embodiment is a compound of Formula (Va'), or a solvate, hydrate, tautomer, N-oxide, stereoisomer, or a pharmaceutically acceptable salt thereof, wherein $R^4$ is

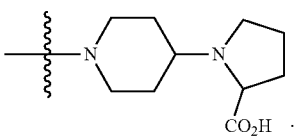 [SMILES: *N1CCC(N2CCCC2C(=O)O)CC1]

In another embodiment is a compound of Formula (Va'), or a solvate, hydrate, tautomer, N-oxide, stereoisomer, or a pharmaceutically acceptable salt thereof, wherein $R^4$ is

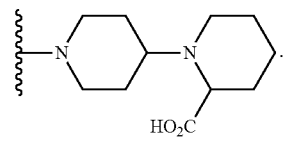

In another embodiment is a compound of Formula (Va'), or a solvate, hydrate, tautomer, N-oxide, stereoisomer, or a pharmaceutically acceptable salt thereof, wherein $R^4$ is selected from

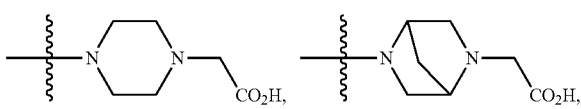

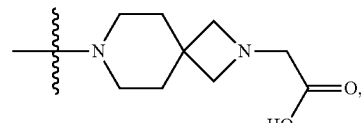

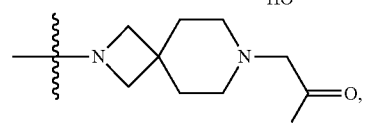

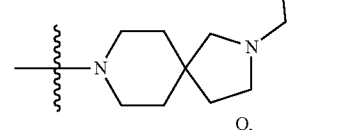

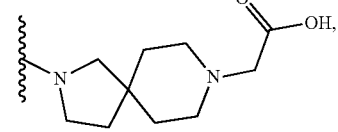

-continued

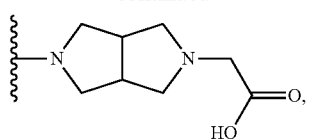

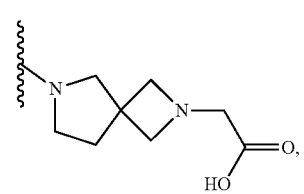

and p is 0. In another embodiment is a compound of Formula (Va'), or a solvate, hydrate, tautomer, N-oxide, stereoisomer, or a pharmaceutically acceptable salt thereof, wherein $R^4$ is selected from

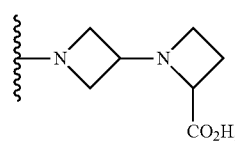 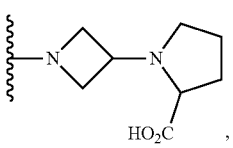

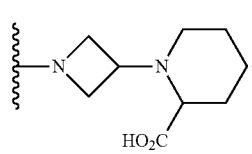 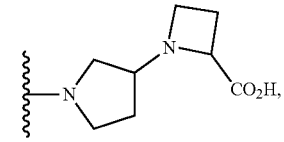

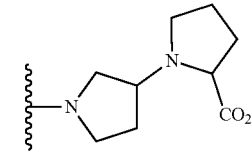 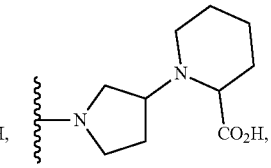

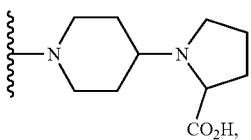

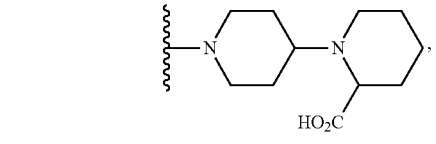 [SMILES: *N1CCC(N2CCCCC2C(=O)O)CC1]

and p is 0.

In another embodiment is a compound of Formula (Va'), or a solvate, hydrate, tautomer, N-oxide, stereoisomer, or a pharmaceutically acceptable salt thereof, wherein $R^4$ is selected from

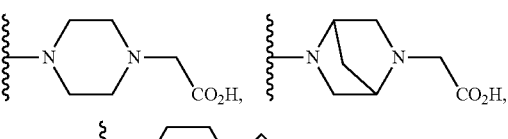

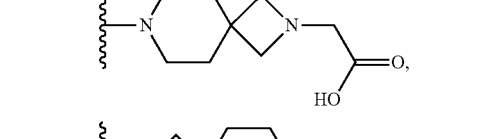

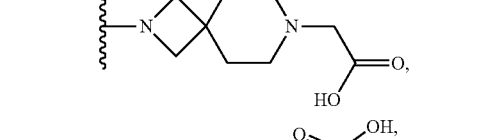

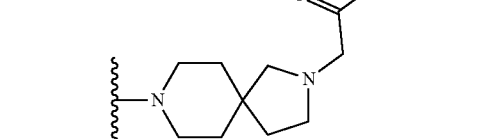

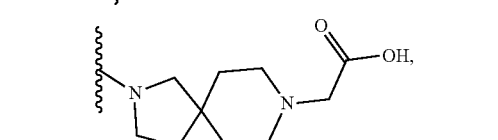

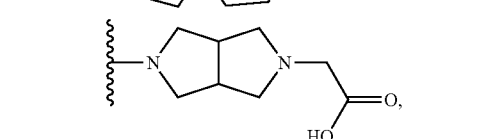

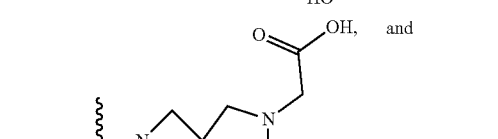

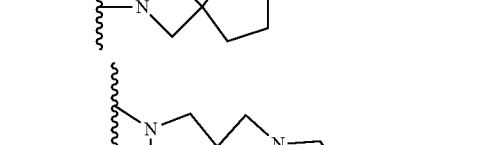

and p is 1. In another embodiment is a compound of Formula (Va'), or a solvate, hydrate, tautomer, N-oxide, stereoisomer, or a pharmaceutically acceptable salt thereof, wherein $R^4$ is selected from selected from

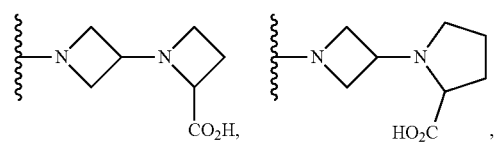

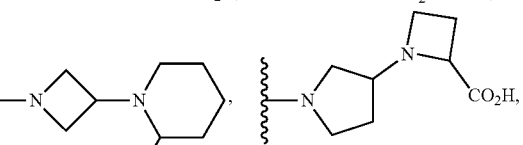

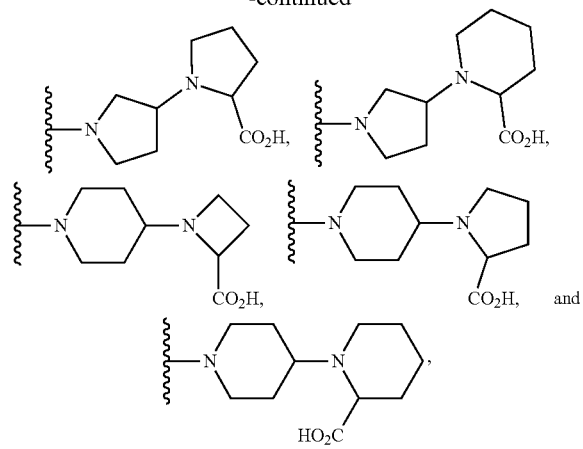

and p is 1.

In another embodiment is a compound of Formula (Va'), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$SF_5$, and —$OR^7$. In another embodiment is a compound of Formula (Va'), or a solvate, hydrate, tautomer, N-oxide, stereoisomer, or a pharmaceutically acceptable salt thereof, wherein p is 1 and $R^3$ is selected from halogen, $C_{1-6}$haloalkyl, and —$OR^7$. In another embodiment is a compound of Formula (Va'), or a solvate, hydrate, tautomer, N-oxide, stereoisomer, or a pharmaceutically acceptable salt thereof, wherein p is 1 and $R^3$ is selected from halogen and $C_{1-6}$haloalkyl. In another embodiment is a compound of Formula (Va'), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (Va'), or a solvate, hydrate, tautomer, N-oxide, stereoisomer, or a pharmaceutically acceptable salt thereof, wherein p is 1 and $R^3$ is —$CH_3$. In another embodiment is a compound of Formula (Va'), or a solvate, hydrate, tautomer, N-oxide, stereoisomer, or a pharmaceutically acceptable salt thereof, wherein p is 1 and $R^3$ is halogen. In another embodiment is a compound of Formula (Va'), or a solvate, hydrate, tautomer, N-oxide, stereoisomer, or a pharmaceutically acceptable salt thereof, wherein p is 1 and $R^3$ is —Cl. In another embodiment is a compound of Formula (Va'), or a solvate, hydrate, tautomer, N-oxide, stereoisomer, or a pharmaceutically acceptable salt thereof, wherein p is 1 and $R^3$ is —CN. In another embodiment is a compound of Formula (Va'), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (Va'), or a solvate, hydrate, tautomer, N-oxide, stereoisomer, or a pharmaceutically acceptable salt thereof, wherein p is 1 and $R^3$ is —$CF_3$. In another embodiment is a compound of Formula (Va'), or a solvate, hydrate, tautomer, N-oxide, stereoisomer, or a pharmaceutically acceptable salt thereof, wherein p is 1 and $R^3$ is —$SF_5$. In another embodiment is a compound of Formula (Va'), or a solvate, hydrate, tautomer, N-oxide, stereoisomer, or a pharmaceutically acceptable salt thereof, wherein p is 1 and $R^3$ is —$OR^7$. In another embodiment is a compound of Formula (Va'), or a solvate, hydrate, tautomer, N-oxide, stereoisomer, or a pharmaceutically acceptable salt thereof, wherein p is 1 and $R^3$ is —$OCH_3$. In another embodiment is a compound of Formula (Va'), or a solvate, hydrate, tau-tomer, N-oxide, stereoisomer, or a pharmaceutically acceptable salt thereof, wherein p is 1 and $R^3$ is $C_{3-8}$cycloalkyl. In another embodiment is a compound of Formula (Va'), or a solvate, hydrate, tautomer, N-oxide, stereoisomer, or a pharmaceutically acceptable salt thereof, wherein p is 1 and $R^3$ is —$C(O)NR^8R^9$.

In another embodiment is a compound of Formula (Va'), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$SF_5$, and —$OR^7$. In another embodiment is a compound of Formula (Va'), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, and —$OR^7$. In another embodiment is a compound of Formula (Va'), or a solvate, hydrate, tautomer, N-oxide, stereoisomer, or a pharmaceutically acceptable salt thereof, wherein p is 2 and each $R^3$ is independently selected from halogen and $C_{1-6}$haloalkyl.

In some embodiments is a compound having the structure of Formula (VI):

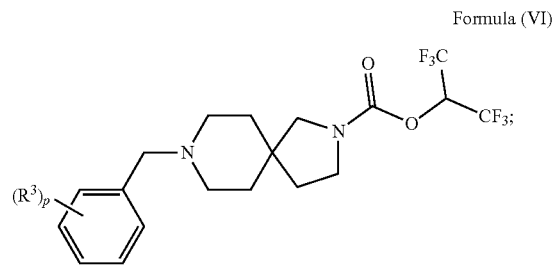

Formula (VI)

wherein:

each $R^3$ is independently selected from $C_{1-6}$alkyl, $C_{1-6}$alkenyl, $C_{1-6}$alkynyl, halogen, —CN, $C_{1-6}$haloalkyl, $C_{1-6}$aminoalkyl, -$C_{1-6}$alkyl($C_{2-9}$heterocycloalkyl), $C_{6-10}$aryl, $C_{1-9}$heteroaryl, —$SF_5$, —$NR^5R^6$, —$OR^7$, —$CO_2R^8$, and —$C(O)NR^8R^9$, wherein -$C_{1-6}$alkyl($C_{2-9}$heterocycloalkyl) and $C_{1-9}$heteroaryl are optionally substituted with one or two $R^4$; or two adjacent $R^3$ form a $C_{2-9}$heterocycloalkyl ring, wherein the $C_{2-9}$heterocycloalkyl ring is optionally substituted with one, two, or three $R^4$;

each $R^4$ is independently selected from $C_{1-6}$alkyl, $C_{1-6}$haloalkyl, $C_{3-8}$cycloalkyl, halogen, oxo, —CN, —$CO_2R^8$, -$C_{1-6}$alkyl-$CO_2R^8$, —$C(O)R^8$, —$C(O)NR^8R^9$, —$SO_2R^8$, —$NR^9C(O)R^8$, and —$NR^9SO_2R^8$;

each $R^5$ and $R^6$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-$C(O)(C_{2-9}$heterocycloalkyl), $C_{2-9}$heterocycloalkyl, $C_{6-10}$aryl, and $C_{1-9}$heteroaryl; or $R^5$ and $R^6$, together with the nitrogen to which they are attached, form a $C_{2-9}$heterocycloalkyl ring optionally substituted with one, two, or three $R^{10}$;

each $R^7$ is independently selected from H, $C_{1-6}$alkyl, $C_{1-6}$haloalkyl, $C_{1-6}$aminoalkyl, $C_{3-8}$cycloalkyl, -$C_{1-6}$alkyl($C_{2-9}$heterocycloalkyl), -$C_{1-6}$alkyl-$C(O)(C_{2-9}$heterocycloalkyl), $C_{2-9}$heterocycloalkyl, $C_{6-10}$aryl, and $C_{1-9}$heteroaryl, wherein $C_{2-9}$heterocycloalkyl, $C_{6-10}$aryl, and $C_{1-9}$heteroaryl are optionally substituted with one or two groups selected from oxo, $C_{1-6}$alkyl, $C_{1-6}$haloalkyl, $CO_2H$, and $C(O)NH_2$;

each $R^8$ and $R^9$ is independently selected from H, $C_{1-6}$alkyl, $C_{1-6}$haloalkyl, $C_{3-8}$cycloalkyl, $C_{6-10}$aryl, and $C_{1-9}$heteroaryl; or $R^8$ and $R^9$, together with the nitrogen to which they are attached, form a $C_{2-9}$heterocycloalkyl ring optionally substituted with one or two groups selected from $C_{1-6}$alkyl, $C_{1-6}$haloalkyl, $CO_2H$, and $C(O)NH_2$;

each $R^{10}$ is independently selected from halogen, $C_{1-6}$alkyl, $-C_{1-6}$alkyl-$CO_2R^8$, $C_{1-6}$haloalkyl, $C_{3-8}$cycloalkyl, oxo, —CN, —$CO_2R^8$, —$C(O)R^8$, —$C(O)NR^8R^9$, —$SO_2R^8$, —$NR^9C(O)R^8$, and —$NR^9SO_2R^8$; and p is 0, 1, 2, 3, 4, or 5;

or a solvate, hydrate, tautomer, N-oxide, stereoisomer, or pharmaceutically acceptable salt thereof.

In another embodiment is a compound of Formula (VI), or a solvate, hydrate, tautomer, N-oxide, stereoisomer, or a pharmaceutically acceptable salt thereof, wherein p is 0, 1, 2, or 3. In another embodiment is a compound of Formula (VI), or a solvate, hydrate, tautomer, N-oxide, stereoisomer, or a pharmaceutically acceptable salt thereof, wherein p is 0, 1, or 2. In another embodiment is a compound of Formula (VI), or a solvate, hydrate, tautomer, N-oxide, stereoisomer, or a pharmaceutically acceptable salt thereof, wherein p is 0 or 1. In another embodiment is a compound of Formula (VI), or a solvate, hydrate, tautomer, N-oxide, stereoisomer, or a pharmaceutically acceptable salt thereof, wherein p is 1 or 2. In another embodiment is a compound of Formula (VI), or a solvate, hydrate, tautomer, N-oxide, stereoisomer, or a pharmaceutically acceptable salt thereof, wherein p is 0. In another embodiment is a compound of Formula (VI), or a solvate, hydrate, tautomer, N-oxide, stereoisomer, or a pharmaceutically acceptable salt thereof, wherein p is 1. In another embodiment is a compound of Formula (VI), or a solvate, hydrate, tautomer, N-oxide, stereoisomer, or a pharmaceutically acceptable salt thereof, wherein p is 2. In another embodiment is a compound of Formula (VI), or a solvate, hydrate, tautomer, N-oxide, stereoisomer, or a pharmaceutically acceptable salt thereof, wherein p is 3. In another embodiment is a compound of Formula (VI), or a solvate, hydrate, tautomer, N-oxide, stereoisomer, or a pharmaceutically acceptable salt thereof, wherein p is 4.

In another embodiment is a compound of Formula (VI), or a solvate, hydrate, tautomer, N-oxide, stereoisomer, or a pharmaceutically acceptable salt thereof, wherein p is 2 and each $R^3$ is independently selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl (heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (VI), or a solvate, hydrate, tautomer, N-oxide, stereoisomer, or a pharmaceutically acceptable salt thereof, wherein p is 2 and each $R^3$ is independently selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (VI), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$NR^5R^6$, and —$OR^7$. In another embodiment is a compound of Formula (VI), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, —$NR^5R^6$, and —$OR^7$. In another embodiment is a compound of Formula (VI), or a solvate, hydrate, tautomer, N-oxide, stereoisomer, or a pharmaceutically acceptable salt thereof, wherein p is 2 and each $R^3$ is independently selected from halogen, —$NR^5R^6$, and $C_{1-6}$haloalkyl. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is halogen and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is —Cl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is $C_{1-6}$haloalkyl and one $R^3$ is —$NR^5R^6$ wherein $R^5$ and $R^6$, together with the nitrogen to which they are attached, form a $C_{2-9}$heterocycloalkyl ring substituted with —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring optionally substituted with one, two, or three $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form an unsubstitued $C_{2-9}$heterocycloalkyl ring. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (VI), or a solvate, hydrate, tautomer, N-oxide, stereoisomer, or a pharmaceutically acceptable salt thereof, wherein p is 2, one $R^3$ is —$CF_3$ and one $R^3$ is —$NR^5R^6$ wherein $R^5$ and $R^6$, together with the nitrogen to which they are attached, form a $C_{2-9}$heterocycloalkyl ring substituted with —$CO_2H$.

In another embodiment is a compound of Formula (VI), or a solvate, hydrate, tautomer, N-oxide, stereoisomer, or a pharmaceutically acceptable salt thereof, wherein p is 1 and $R^3$ is selected from $C_{1-6}$alkyl, halogen, —CN, $C_{1-6}$haloalkyl, $C_{1-6}$aminoalkyl, -$C_{1-6}$alkyl(heterocycloalkyl), —$SF_5$, —$NR^5R^6$, and —$OR^7$; wherein -$C_{1-6}$alkyl(heterocycloalkyl) is optionally substituted with one or two groups selected from halogen, $C_{1-6}$alkyl, $C_{1-6}$haloalkyl, $C_{3-8}$cycloalkyl, and oxo. In another embodiment is a compound of Formula (VI), or a solvate, hydrate, tautomer, N-oxide, stereoisomer, or a pharmaceutically acceptable salt thereof, wherein p is 1 and $R^3$ is selected halogen, $C_{1-6}$alkyl, $C_{1-6}$haloalkyl, -$C_{1-6}$alkyl($C_{2-9}$heterocycloalkyl), —$NR^5R^6$, —$OR^7$, —$CO_2R^8$, and —$C(O)NR^8R^9$. In another embodiment is a compound of Formula (VI), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$NR^5R^6$, and —$OR^7$. In another embodiment is a compound of Formula (VI), or a solvate, hydrate, tautomer, N-oxide, stereoisomer, or a pharmaceutically acceptable salt thereof, wherein p is 1 and $R^3$ is selected from halogen, $C_{1-6}$haloalkyl, —$NR^5R^6$, and —$OR^7$. In another embodiment is a compound of Formula (VI), or a solvate, hydrate, tautomer, N-oxide, stereoisomer, or a pharmaceutically acceptable salt thereof, wherein p is 1 and $R^3$ is selected from halogen, —$NR^5R^6$, and $C_{1-6}$haloalkyl. In another embodiment is a compound of Formula (VI), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (VI), or a solvate, hydrate, tautomer, N-oxide, stereoisomer, or a pharmaceutically acceptable salt thereof, wherein p is 1 and $R^3$ is halogen. In another embodiment is a compound of Formula (VI), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (VI), or a solvate, hydrate, tautomer, N-oxide, stereoisomer, or a pharmaceutically acceptable salt thereof, wherein p is 1 and $R^3$ is —$OR^7$. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring optionally substituted with one, two, or three $R^{10}$. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form an unsubstituted $C_{2-9}$heterocycloalkyl ring. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with one or two $R^{10}$ selected from $C_{1-6}$alkyl and —$CO_2H$. In another embodiment is a compound of Formula (VI), or a solvate, hydrate, tautomer, N-oxide, stereoisomer, or a pharmaceutically acceptable salt thereof, wherein p is 1 and $R^3$ is —$NR^5R^6$, wherein $R^5$ and $R^6$, together with the nitrogen to which they are attached, form a $C_{2-9}$heterocycloalkyl ring substituted with —$CO_2H$.

In another embodiment is a compound of Formula (VI), or a solvate, hydrate, tautomer, N-oxide, stereoisomer, or a pharmaceutically acceptable salt thereof, wherein $R^5$ and $R^6$, together with the nitrogen to which they are attached, form a $C_{2-9}$heterocycloalkyl ring selected from:

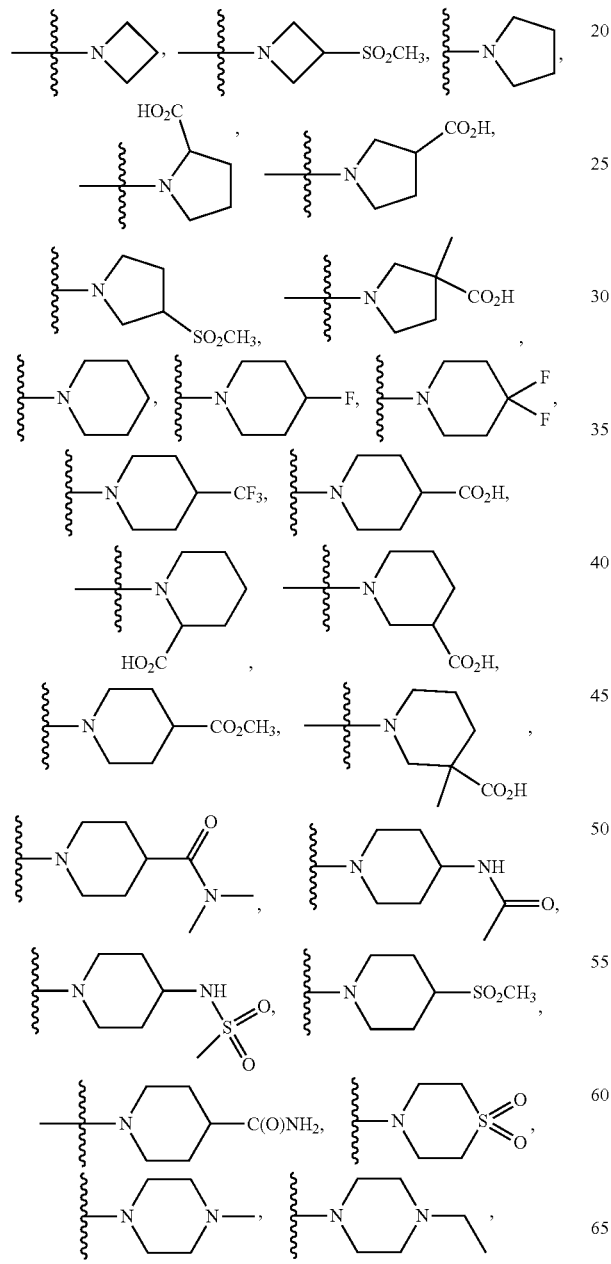

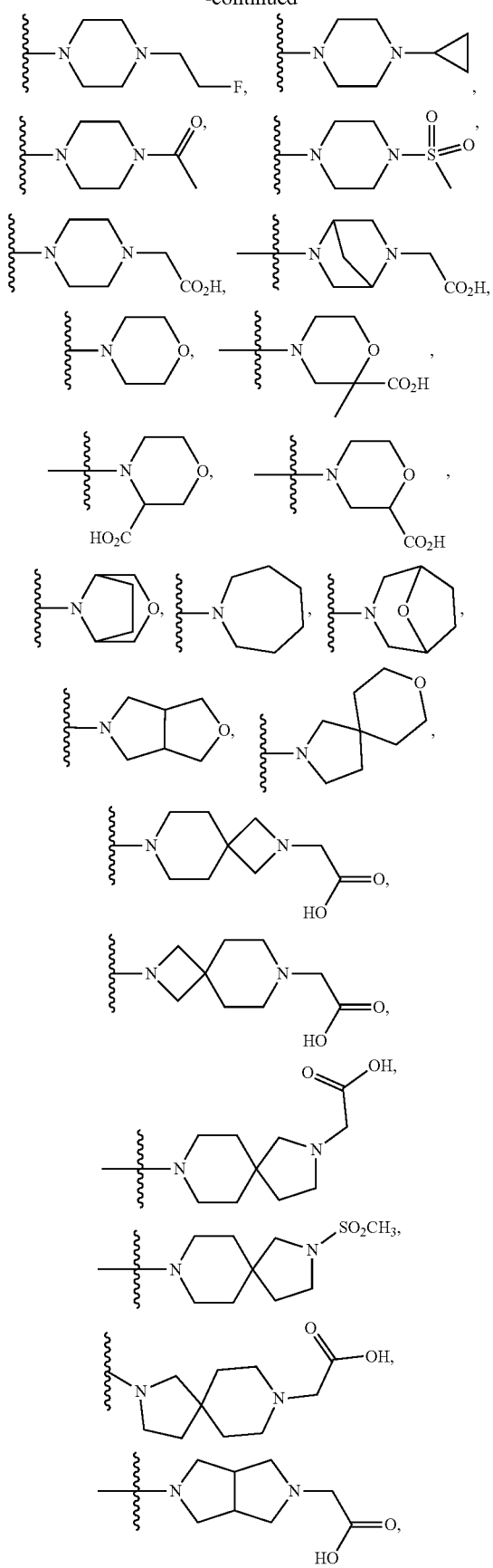

-continued

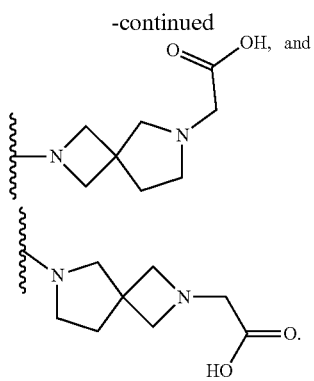

In some embodiments is a compound having the structure of Formula (VII):

Formula (VII)

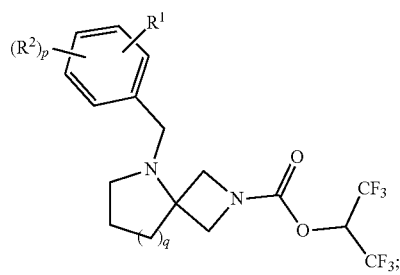

wherein:
R$^1$ is selected from

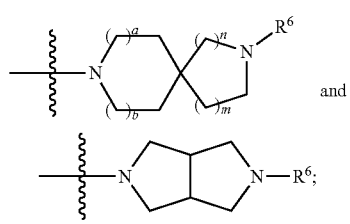

and each R$^2$ is independently selected from C$_{1-6}$alkyl, halogen, —CN, C$_{1-6}$haloalkyl, C$_{3-8}$cycloalkyl, —SF$_5$, —OR$^3$, and —C(O)NR$^4$R$^5$;
each R$^3$ is independently selected from H, C$_{1-6}$alkyl, C$_{1-6}$haloalkyl, C$_{3-8}$cycloalkyl, and -C$_{1-6}$alkyl-C$_{3-8}$cycloalkyl;
each R$^4$ and R$^5$ is independently selected from H, C$_{1-6}$alkyl, and C$_{3-8}$cycloalkyl;
R$^6$ is selected from C$_{1-6}$alkyl, —C(O)-C$_{1-6}$alkyl, and —S(O)$_2$-C$_{1-6}$alkyl;
a is 0 or 1;
b is 0 or 1;
m is 0, 1, or 2;
n is 0, 1, or 2; provided that when n is 0, then m is 2;
p is 0, 1, 2, 3, or 4; and
q is 1 or 2;
or a solvate, hydrate, tautomer, N-oxide, stereoisomer, or pharmaceutically acceptable salt thereof.

In another embodiment is a compound of Formula (VII), or a solvate, hydrate, tautomer, N-oxide, stereoisomer, or a pharmaceutically acceptable salt thereof, wherein q is 1. In another embodiment is a compound of Formula (VII), or a solvate, hydrate, tautomer, N-oxide, stereoisomer, or a pharmaceutically acceptable salt thereof, wherein q is 2.

In another embodiment is a compound of Formula (VII), or a solvate, hydrate, tautomer, N-oxide, stereoisomer, or a pharmaceutically acceptable salt thereof, wherein p is 0, 1, 2, or 3. In another embodiment is a compound of Formula (VII), or a solvate, hydrate, tautomer, N-oxide, stereoisomer, or a pharmaceutically acceptable salt thereof, wherein p is 0, 1, or 2. In another embodiment is a compound of Formula (VII), or a solvate, hydrate, tautomer, N-oxide, stereoisomer, or a pharmaceutically acceptable salt thereof, wherein p is 0 or 1. In another embodiment is a compound of Formula (VII), or a solvate, hydrate, tautomer, N-oxide, stereoisomer, or a pharmaceutically acceptable salt thereof, wherein p is 1 or 2. In another embodiment is a compound of Formula (VII), or a solvate, hydrate, tautomer, N-oxide, stereoisomer, or a pharmaceutically acceptable salt thereof, wherein p is 0. In another embodiment is a compound of Formula (VII), or a solvate, hydrate, tautomer, N-oxide, stereoisomer, or a pharmaceutically acceptable salt thereof, wherein p is 1. In another embodiment is a compound of Formula (VII), or a solvate, hydrate, tautomer, N-oxide, stereoisomer, or a pharmaceutically acceptable salt thereof, wherein p is 2. In another embodiment is a compound of Formula (VII), or a solvate, hydrate, tautomer, N-oxide, stereoisomer, or a pharmaceutically acceptable salt thereof, wherein p is 3. In another embodiment is a compound of Formula (VII), or a solvate, hydrate, tautomer, N-oxide, stereoisomer, or a pharmaceutically acceptable salt thereof, wherein p is 4.

In another embodiment is a compound of Formula (VII), or a solvate, hydrate, tautomer, N-oxide, stereoisomer, or a pharmaceutically acceptable salt thereof, wherein R$^1$ is

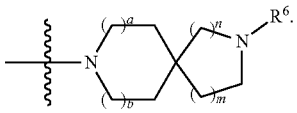

In another embodiment is a compound of Formula (VII), or a solvate, hydrate, tautomer, N-oxide, stereoisomer, or a pharmaceutically acceptable salt thereof, wherein R$^1$ is

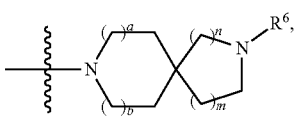

a is 1, b is 1, m is 1, and n is 1. In another embodiment is a compound of Formula (VII), or a solvate, hydrate, tautomer, N-oxide, stereoisomer, or a pharmaceutically acceptable salt thereof, wherein R$^1$ is

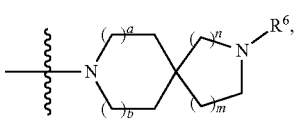

a is 1, b is 1, m is 0, and n is 1. In another embodiment is a compound of Formula (VII), or a solvate, hydrate, tautomer, N-oxide, stereoisomer, or a pharmaceutically acceptable salt thereof, wherein R¹ is

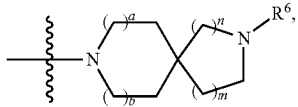

a is 1, b is 1, m is 2, and n is 0. In another embodiment is a compound of

Formula (VII), or a solvate, hydrate, tautomer, N-oxide, stereoisomer, or a pharmaceutically acceptable salt thereof, wherein R¹ is

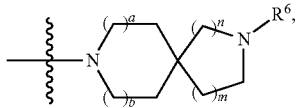

a is 0, b is 1, m is 1, and n is 1. In another embodiment is a compound of Formula (VII), or a solvate, hydrate, tautomer, N-oxide, stereoisomer, or a pharmaceutically acceptable salt thereof, wherein R¹ is

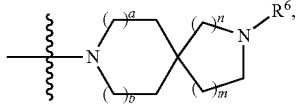

a is 0, b is 1, m is 1, and n is 2. In another embodiment is a compound of Formula (VII), or a solvate, hydrate, tautomer, N-oxide, stereoisomer, or a pharmaceutically acceptable salt thereof, wherein R¹ is

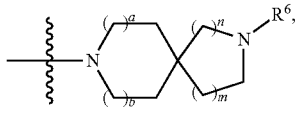

a is 0, b is 1, m is 0, and n is 1. In another embodiment is a compound of Formula (VII), or a solvate, hydrate, tautomer, N-oxide, stereoisomer, or a pharmaceutically acceptable salt thereof, wherein R¹ is

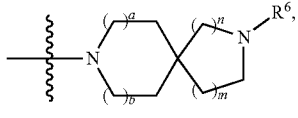

a is 0, b is 0, m is 1, and n is 1. In another embodiment is a compound of Formula (VII), or a solvate, hydrate, tautomer, N-oxide, stereoisomer, or a pharmaceutically acceptable salt thereof, wherein R¹ is

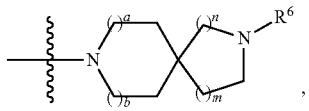

a is 0, b is 0, m is 1, and n is 2.

In another embodiment is a compound of Formula (VII), or a solvate, hydrate, tautomer, N-oxide, stereoisomer, or a pharmaceutically acceptable salt thereof, wherein R¹ is

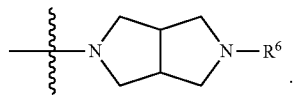

In another embodiment is a compound of Formula (VII), or a solvate, hydrate, tautomer, N-oxide, stereoisomer, or a pharmaceutically acceptable salt thereof, wherein $R^6$ is $C_{1-6}$alkyl. In another embodiment is a compound of Formula (VII), or a solvate, hydrate, tautomer, N-oxide, stereoisomer, or a pharmaceutically acceptable salt thereof, wherein $R^6$ is —$CH_3$. In another embodiment is a compound of Formula (VII), or a solvate, hydrate, tautomer, N-oxide, stereoisomer, or a pharmaceutically acceptable salt thereof, wherein $R^6$ is —$CH_2CH_3$. In another embodiment is a compound of Formula (VII), or a solvate, hydrate, tautomer, N-oxide, stereoisomer, or a pharmaceutically acceptable salt thereof, wherein $R^6$ is —C(O)-$C_{1-6}$alkyl. In another embodiment is a compound of Formula (VII), or a solvate, hydrate, tautomer, N-oxide, stereoisomer, or a pharmaceutically acceptable salt thereof, wherein $R^6$ is —C(O)$CH_3$. In another embodiment is a compound of Formula (VII), or a solvate, hydrate, tautomer, N-oxide, stereoisomer, or a pharmaceutically acceptable salt thereof, wherein $R^6$ is —$S(O)_2$-$C_{1-6}$alkyl. In another embodiment is a compound of Formula (VII), or a solvate, hydrate, tautomer, N-oxide, stereoisomer, or a pharmaceutically acceptable salt thereof, wherein $R^6$ is —$S(O)_2CH_3$.

In another embodiment is a compound of Formula (VII), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$SF_5$, and —$OR^7$. In another embodiment is a compound of Formula (VII), or a solvate, hydrate, tautomer, N-oxide, stereoisomer, or a pharmaceutically acceptable salt thereof, wherein p is 1 and $R^3$ is selected from halogen, $C_{1-6}$haloalkyl, and —$OR^7$. In another embodiment is a compound of Formula (VII), or a solvate, hydrate, tautomer, N-oxide, stereoisomer, or a pharmaceutically acceptable salt thereof, wherein p is 1 and $R^3$ is selected from halogen and $C_{1-6}$haloalkyl. In another embodiment is a compound of Formula (VII), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (VII), or a solvate, hydrate, tautomer, N-oxide, stereoisomer, or a pharmaceutically acceptable salt thereof, wherein p is 1 and $R^3$ is —$CH_3$. In another embodiment is a compound of Formula (VII), or a solvate, hydrate, tautomer, N-oxide, stereoisomer, or a pharmaceutically acceptable salt thereof, wherein p is 1 and $R^3$ is halogen. In another embodiment is a compound of Formula (VII), or a solvate, hydrate, tautomer, N-oxide, stereoisomer, or a pharmaceutically acceptable salt thereof, wherein p is 1 and $R^3$ is —Cl. In another embodiment is a compound of Formula (VII), or a solvate, hydrate, tautomer, N-oxide, stereoisomer, or a pharmaceutically acceptable salt thereof, wherein p is 1 and $R^3$ is —CN. In another embodiment is a compound of Formula (VII), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (VII), or a solvate, hydrate, tautomer, N-oxide, stereoisomer, or a pharmaceutically acceptable salt thereof, wherein p is 1 and $R^3$ is —$CF_3$. In another embodiment is a compound of Formula (VII), or a solvate, hydrate, tautomer, N-oxide, stereoisomer, or a pharmaceutically acceptable salt thereof, wherein p is 1 and $R^3$ is —$SF_5$. In another embodiment is a compound of Formula (VII), or a solvate, hydrate, tautomer, N-oxide, stereoisomer, or a pharmaceutically acceptable salt thereof, wherein p is 1 and $R^3$ is —$OR^7$. In another embodiment is a compound of Formula (VII), or a solvate, hydrate, tautomer, N-oxide, stereoisomer, or a pharmaceutically acceptable salt thereof, wherein p is 1 and $R^3$ is —$OCH_3$. In another embodiment is a compound of Formula (VII), or a solvate, hydrate, tautomer, N-oxide, stereoisomer, or a pharmaceutically acceptable salt thereof, wherein p is 1 and $R^3$ is $C_{3-8}$cycloalkyl. In another embodiment is a compound of Formula (VII), or a solvate, hydrate, tautomer, N-oxide, stereoisomer, or a pharmaceutically acceptable salt thereof, wherein p is 1 and $R^3$ is —$C(O)NR^8R^9$.

In another embodiment is a compound of Formula (VII), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$SF_5$, and —$OR^7$. In another embodiment is a compound of Formula (VII), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, and —$OR^7$. In another embodiment is a compound of Formula (VII), or a solvate, hydrate, tautomer, N-oxide, stereoisomer, or a pharmaceutically acceptable salt thereof, wherein p is 2 and each $R^3$ is independently selected from halogen and $C_{1-6}$haloalkyl.

In some embodiments is a compound having the structure of Formula (VIII):

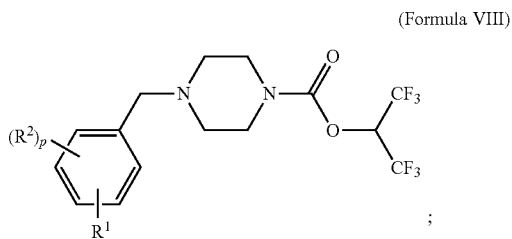

(Formula VIII)

wherein:
$R^1$ is selected from

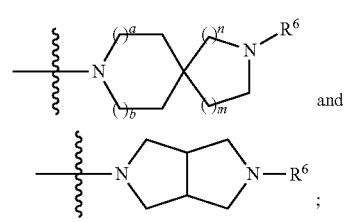

each $R^2$ is independently selected from $C_{1-6}$alkyl, halogen, —CN, $C_{1-6}$haloalkyl, $C_{3-8}$cycloalkyl, —$SF_5$, —$OR^3$, and —$C(O)NR^4R^5$;
each $R^3$ is independently selected from H, $C_{1-6}$alkyl, $C_{1-6}$haloalkyl, $C_{3-8}$cycloalkyl, and -$C_{1-6}$alkyl-$C_{3-8}$cycloalkyl;
each $R^4$ and $R^5$ is independently selected from H, $C_{1-6}$alkyl, and $C_{3-8}$cycloalkyl;
$R^6$ is selected from $C_{1-6}$alkyl, —$C(O)$-$C_{1-6}$alkyl, and —$S(O)_2$-$C_{1-6}$alkyl;
a is 0 or 1;
b is 0 or 1;
m is 0, 1, or 2;
n is 0, 1, or 2; provided that when n is 0, then m is 2; and
p is 0, 1, 2, 3, or 4;
or a solvate, hydrate, tautomer, N-oxide, stereoisomer, or pharmaceutically acceptable salt thereof.

In another embodiment is a compound of Formula (VIII), or a solvate, hydrate, tautomer, N-oxide, stereoisomer, or a pharmaceutically acceptable salt thereof, wherein q is 1. In another embodiment is a compound of Formula (VIII), or a solvate, hydrate, tautomer, N-oxide, stereoisomer, or a pharmaceutically acceptable salt thereof, wherein q is 2.

In another embodiment is a compound of Formula (VIII), or a solvate, hydrate, tautomer, N-oxide, stereoisomer, or a pharmaceutically acceptable salt thereof, wherein p is 0, 1, 2, or 3. In another embodiment is a compound of Formula (VIII), or a solvate, hydrate, tautomer, N-oxide, stereoisomer, or a pharmaceutically acceptable salt thereof, wherein p is 0, 1, or 2. In another embodiment is a compound of Formula (VIII), or a solvate, hydrate, tautomer, N-oxide, stereoisomer, or a pharmaceutically acceptable salt thereof, wherein p is 0 or 1. In another embodiment is a compound of Formula (VIII), or a solvate, hydrate, tautomer, N-oxide, stereoisomer, or a pharmaceutically acceptable salt thereof, wherein p is 1 or 2. In another embodiment is a compound of Formula (VIII), or a solvate, hydrate, tautomer, N-oxide, stereoisomer, or a pharmaceutically acceptable salt thereof, wherein p is 0. In another embodiment is a compound of Formula (VIII), or a solvate, hydrate, tautomer, N-oxide, stereoisomer, or a pharmaceutically acceptable salt thereof, wherein p is 1. In another embodiment is a compound of Formula (VIII), or a solvate, hydrate, tautomer, N-oxide, stereoisomer, or a pharmaceutically acceptable salt thereof, wherein p is 2. In another embodiment is a compound of Formula (VIII), or a solvate, hydrate, tautomer, N-oxide, stereoisomer, or a pharmaceutically acceptable salt thereof, wherein p is 3. In another embodiment is a compound of Formula (VIII), or a solvate, hydrate, tautomer, N-oxide, stereoisomer, or a pharmaceutically acceptable salt thereof, wherein p is 4.

In another embodiment is a compound of Formula (VIII), or a solvate, hydrate, tautomer, N-oxide, stereoisomer, or a pharmaceutically acceptable salt thereof, wherein $R^1$ is

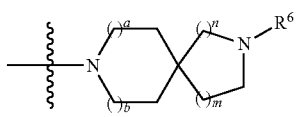

In another embodiment is a compound of Formula (VIII), or a solvate, hydrate, tautomer, N-oxide, stereoisomer, or a pharmaceutically acceptable salt thereof, wherein $R^1$ is

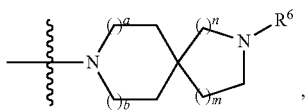

a is 1, b is 1, m is 1, and n is 1. In another embodiment is a compound of Formula (VIII), or a solvate, hydrate, tautomer, N-oxide, stereoisomer, or a pharmaceutically acceptable salt thereof, wherein $R^1$ is

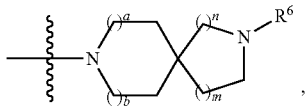

a is 1, b is 1, m is 0, and n is 1. In another embodiment is a compound of Formula (VIII), or a solvate, hydrate, tautomer, N-oxide, tereoisomer, or a pharmaceutically acceptable salt thereof, wherein $R^1$ is

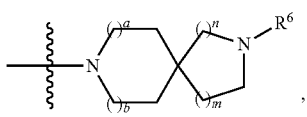

a is 1, b is 1, m is 2, and n is 0. In another embodiment is a compound of Formula (VIII), or a solvate, hydrate, tautomer, N-oxide, stereoisomer, or a pharmaceutically acceptable salt thereof, wherein $R^1$ is

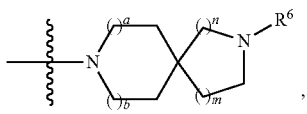

a is 0, b is 1, m is 1, and n is 1. In another embodiment is a compound of Formula (VIII), or a solvate, hydrate, tautomer, N-oxide, stereoisomer, or a pharmaceutically acceptable salt thereof, wherein $R^1$ is

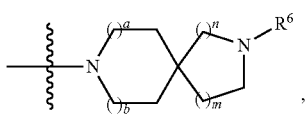

a is 0, b is 1, m is 1, and n is 2. In another embodiment is a compound of Formula (VIII), or a solvate, hydrate, tautomer, N-oxide, stereoisomer, or a pharmaceutically acceptable salt thereof, wherein $R^1$ is

a is 0, b is 1, m is 0, and n is 1. In another embodiment is a compound of Formula (VIII), or a solvate, hydrate, tautomer, N-oxide, stereoisomer, or a pharmaceutically acceptable salt thereof, wherein $R^1$ is

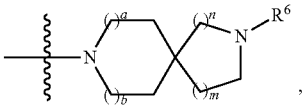

a is 0, b is 0, m is 1, and n is 1. In another embodiment is a compound of Formula (VIII), or a solvate, hydrate, tautomer, N-oxide, stereoisomer, or a pharmaceutically acceptable salt thereof, wherein $R^1$ is

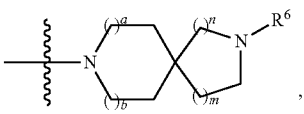

a is 0, b is 0, m is 1, and n is 2.

In another embodiment is a compound of Formula (VIII), or a solvate, hydrate, tautomer, N-oxide, stereoisomer, or a pharmaceutically acceptable salt thereof, wherein $R^1$ is

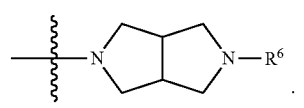

In another embodiment is a compound of Formula (VIII), or a solvate, hydrate, tautomer, N-oxide, stereoisomer, or a pharmaceutically acceptable salt thereof, wherein $R^6$ is $C_{1-6}$alkyl. In another embodiment is a compound of Formula (VIII), or a solvate, hydrate, tautomer, N-oxide, stereoisomer, or a pharmaceutically acceptable salt thereof, wherein $R^6$ is —$CH_3$. In another embodiment is a compound of Formula (VIII), or a solvate, hydrate, tautomer, N-oxide, stereoisomer, or a pharmaceutically acceptable salt thereof, wherein $R^6$ is —$CH_2CH_3$. In another embodiment is a compound of Formula (VIII), or a solvate, hydrate, tautomer, N-oxide, stereoisomer, or a pharmaceutically acceptable salt thereof, wherein $R^6$ is —C(O)-$C_{1-6}$alkyl. In another embodiment is a compound of Formula (VIII), or a solvate, hydrate, tautomer, N-oxide, stereoisomer, or a pharmaceutically acceptable salt thereof, wherein $R^6$ is —C(O)$CH_3$. In another embodiment is a compound of Formula (VIII), or a solvate, hydrate, tautomer, N-oxide, stereoisomer, or a pharmaceutically acceptable salt thereof, wherein $R^6$ is —$S(O)_2$-$C_{1-6}$alkyl. In another embodiment is a compound of Formula (VIII), or a solvate, hydrate, tautomer, N-oxide, stereoisomer, or a pharmaceutically acceptable salt thereof, wherein $R^6$ is —$S(O)_2CH_3$.

In another embodiment is a compound of Formula (VIII), or a solvate, hydrate, tautomer, N-oxide, stereoisomer, or a pharmaceutically acceptable salt thereof, wherein p is 1 and $R^3$ is selected from $C_{1-6}$alkyl, halogen, $C_{1-6}$haloalkyl, —$SF_5$, and —$OR^7$. In another embodiment is a compound of Formula (VIII), or a solvate, hydrate, tautomer, N-oxide, stereoisomer, or a pharmaceutically acceptable salt thereof, wherein p is 1 and $R^3$ is selected from halogen, $C_{1-6}$haloalkyl, and —$OR^7$. In another embodiment is a compound of Formula (VIII), or a solvate, hydrate, tautomer, N-oxide, stereoisomer, or a pharmaceutically acceptable salt thereof, wherein p is 1 and $R^3$ is selected from halogen and $C_{1-6}$haloalkyl. In another embodiment is a compound of Formula (VIII), or a solvate, hydrate, tautomer, N-oxide, stereoisomer, or a pharmaceutically acceptable salt thereof, wherein p is 1 and $R^3$ is $C_{1-6}$alkyl. In another embodiment is a compound of Formula (VIII), or a solvate, hydrate, tautomer, N-oxide, stereoisomer, or a pharmaceutically acceptable salt thereof, wherein p is 1 and $R^3$ is —$CH_3$. In another embodiment is a compound of Formula (VIII), or a solvate, hydrate, tautomer, N-oxide, stereoisomer, or a pharmaceutically acceptable salt thereof, wherein p is 1 and $R^3$ is halogen. In another embodiment is a compound of Formula (VIII), or a solvate, hydrate, tautomer, N-oxide, stereoisomer, or a pharmaceutically acceptable salt thereof, wherein p is 1 and $R^3$ is —Cl. In another embodiment is a compound of Formula (VIII), or a solvate, hydrate, tautomer, N-oxide, stereoisomer, or a pharmaceutically acceptable salt thereof, wherein p is 1 and $R^3$ is —CN. In another embodiment is a compound of Formula (VIII), or a solvate, hydrate, tautomer, N-oxide, stereoisomer, or a pharmaceutically acceptable salt thereof, wherein p is 1 and $R^3$ is $C_{1-6}$haloalkyl. In another embodiment is a compound of Formula (VIII), or a solvate, hydrate, tautomer, N-oxide, stereoisomer, or a pharmaceutically acceptable salt thereof, wherein p is 1 and $R^3$ is —$CF_3$. In another embodiment is a compound of Formula (VIII), or a solvate, hydrate, tautomer, N-oxide, stereoisomer, or a pharmaceutically acceptable salt thereof, wherein p is 1 and $R^3$ is —$SF_5$. In another embodiment is a compound of Formula (VIII), or a solvate, hydrate, tautomer, N-oxide, stereoisomer, or a pharmaceutically acceptable salt thereof, wherein p is 1 and $R^3$ is —$OR^7$. In another embodiment is a compound of Formula (VIII), or a solvate, hydrate, tautomer, N-oxide, stereoisomer, or a pharmaceutically acceptable salt thereof, wherein p is 1 and $R^3$ is —$OCH_3$. In another embodiment is a compound of Formula (VIII), or a solvate, hydrate, tautomer, N-oxide, stereoisomer, or a pharmaceutically acceptable salt thereof, wherein p is 1 and $R^3$ is $C_{3-8}$cycloalkyl. In another embodiment is a compound of Formula (VIII), or a solvate, hydrate, tautomer, N-oxide, stereoisomer, or a pharmaceutically acceptable salt thereof, wherein p is 1 and $R^3$ is —$C(O)NR^8R^9$.

In another embodiment is a compound of Formula (VIII), or a solvate, hydrate, tautomer, N-oxide, stereoisomer, or a pharmaceutically acceptable salt thereof, wherein p is 2 and each $R^3$ is independently selected from $C_{1-6}$alkyl, halogen, $C_{1-6}$haloalkyl, —$SF_5$, and —$OR^7$. In another embodiment is a compound of Formula (VIII), or a solvate, hydrate, tautomer, N-oxide, stereoisomer, or a pharmaceutically acceptable salt thereof, wherein p is 2 and each $R^3$ is independently selected from halogen, $C_{1-6}$haloalkyl, and —$OR^7$. In another embodiment is a compound of Formula (VIII), or a solvate, hydrate, tautomer, N-oxide, stereoisomer, or a pharmaceutically acceptable salt thereof, wherein p is 2 and each $R^3$ is independently selected from halogen and $C_{1-6}$haloalkyl.

Further embodiments provided herein include combinations of one or more of the particular embodiments set forth above.

In some embodiments, the compound disclosed herein is selected from examples 1-242.

In another embodiment is a compound having the structure:

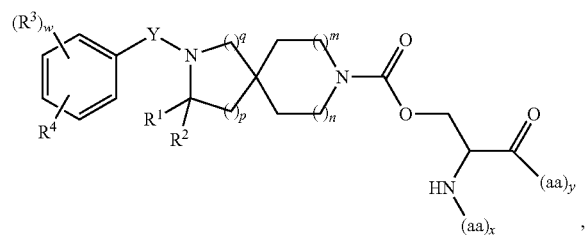

wherein $R^1$, $R^2$, $R^3$, $R^4$, Y, m, n, p, q and w are defined as in Formula (I) described herein, and x and y are at least one amino acid (aa). In another embodiment is a compound having the structure

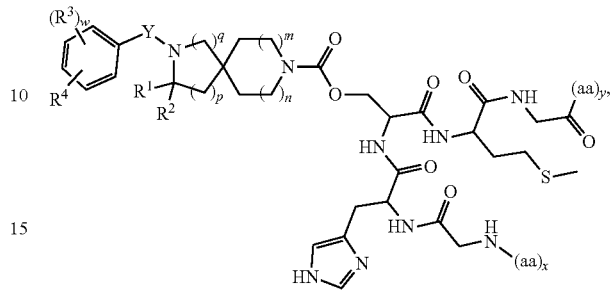

wherein $R^1$, $R^2$, $R^3$, $R^4$, Y, m, n, p, q and w are defined as in Formula (I) described herein, and x and y are at least one amino acid (aa).

In another embodiment is a compound having the structure:

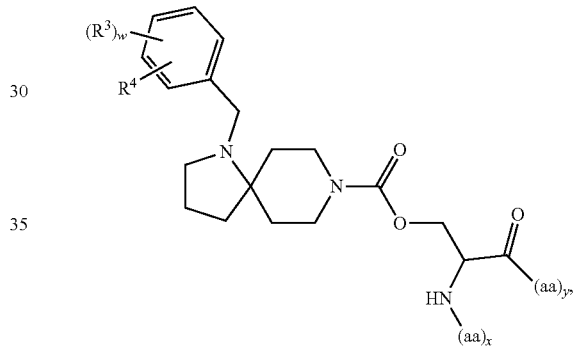

wherein $R^3$, $R^4$, and w are defined as in Formula (Ia) described herein, and x and y are at least one amino acid (aa). In another embodiment is a compound having the structure:

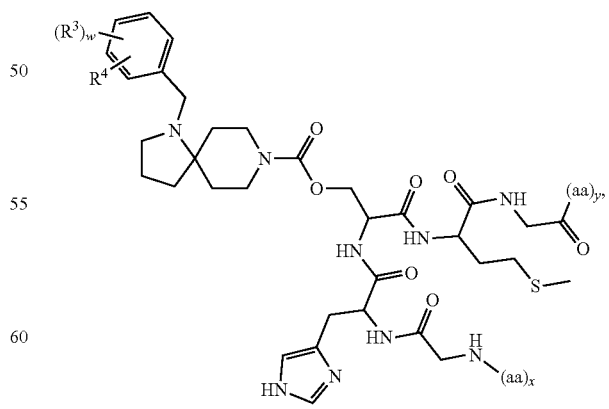

wherein $R^3$, $R^4$, and w are defined as in Formula (Ia) described herein, and x and y are at least one amino acid (aa).

In another embodiment is a compound having the structure:

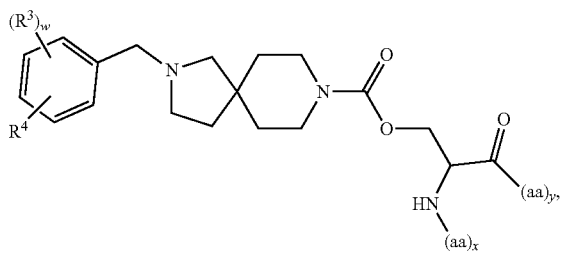

wherein R³, R⁴, and w are defined as in Formula (Ib) described herein, and x and y are at least one amino acid (aa). In another embodiment is a compound having the structure:

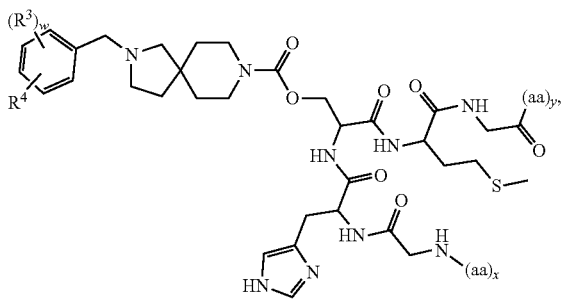

wherein R³, R⁴, and w are defined as in Formula (Ib) described herein, and x and y are at least one amino acid (aa).

In another embodiment is a compound having the structure:

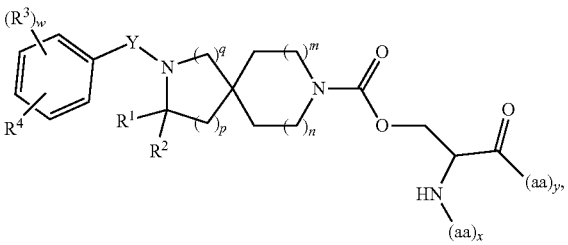

wherein R¹, R², R³, R⁴, Y, m, n, p, q and w are defined as in Formula (I') described herein, and x and y are at least one amino acid (aa). In another embodiment is a compound having the structure:

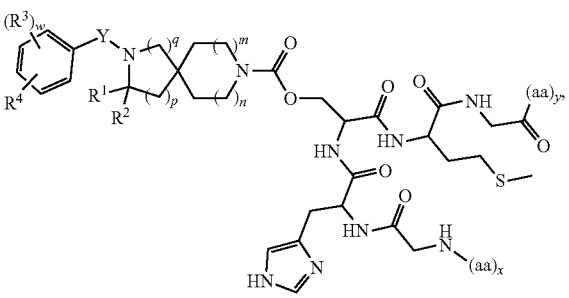

wherein R¹, R², R³, R⁴, Y, m, n, p, q and w are defined as in Formula (I') described herein, and x and y are at least one amino acid (aa).

In another embodiment is a compound having the structure:

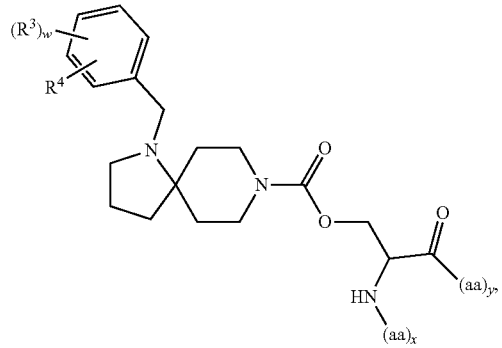

wherein R³, R⁴, and w are defined as in Formula (Ia') described herein, and x and y are at least one amino acid (aa). In another embodiment is a compound having the structure:

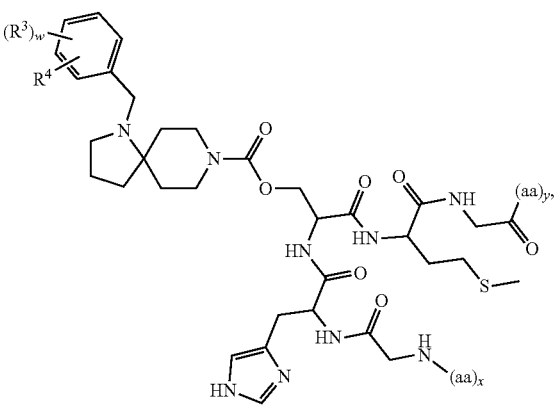

wherein R³, R⁴, and w are defined as in Formula (Ia') described herein, and x and y are at least one amino acid (aa).

In another embodiment is a compound having the structure:

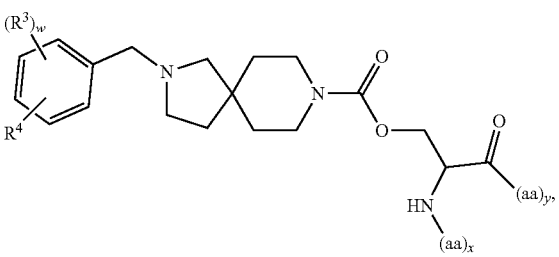

wherein R³, R⁴, and w are defined as in Formula (Ib') described herein, and x and y are at least one amino acid (aa). In another embodiment is a compound having the structure:

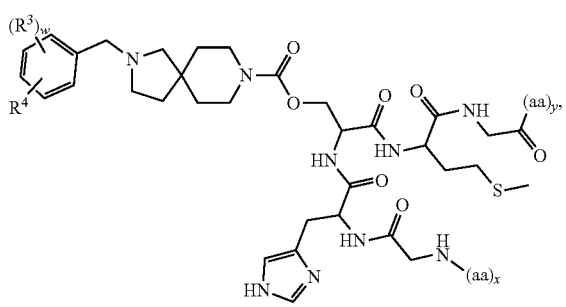

wherein $R^3$, $R^4$, and w are defined as in Formula (Ib') described herein, and x and y are at least one amino acid (aa).

In another embodiment is a compound having the structure:

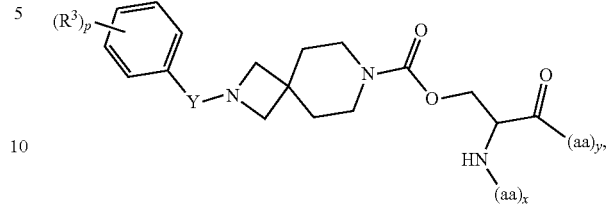

wherein $R^3$, Y, and p are defined as in Formula (II) described herein, and x and y are at least one amino acid (aa). In another embodiment is a compound having the structure:

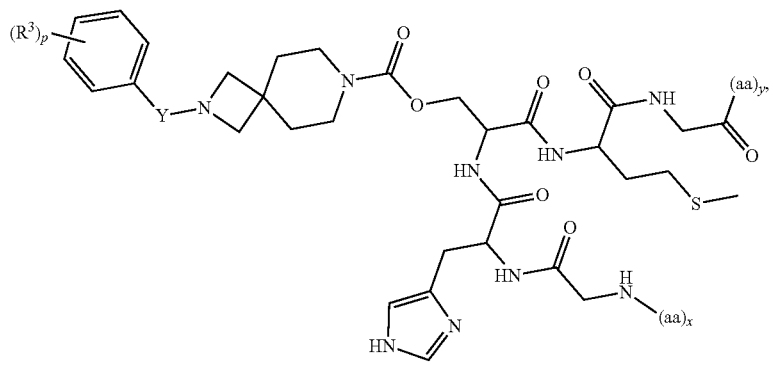

wherein $R^3$, Y, and p are defined as in Formula (II) described herein, and x and y are at least one amino acid (aa).

In another embodiment is a compound having the structure:

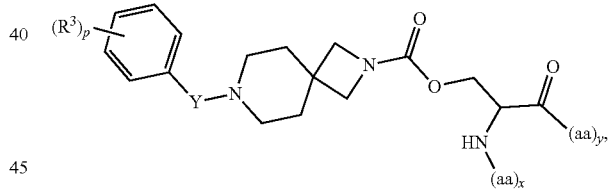

wherein $R^3$, Y, and p are defined as in Formula (III) described herein, and x and y are at least one amino acid (aa). In another embodiment is a compound having the structure:

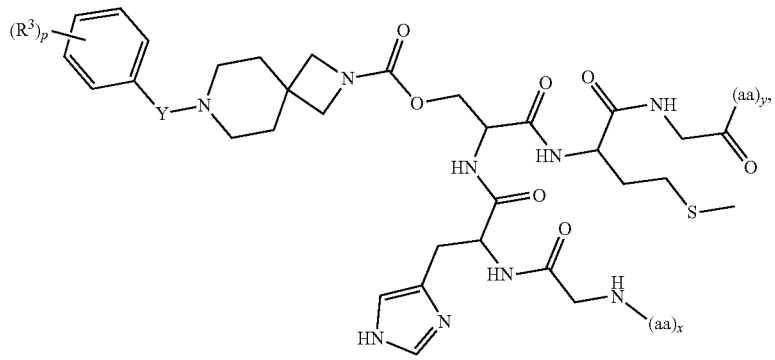

wherein R³, Y, and p are defined as in Formula (III) described herein, and x and y are at least one amino acid (aa).

In another embodiment is a compound having the structure:

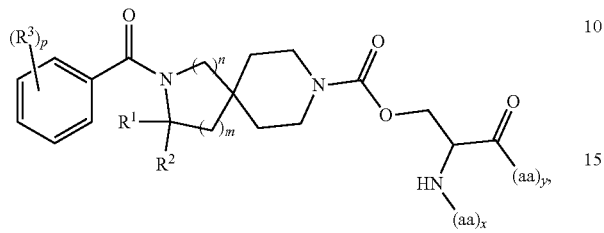

wherein R¹, R², R³, m, n, and p are defined as in Formula (IV) described herein, and x and y are at least one amino acid (aa). In another embodiment is a compound having the structure:

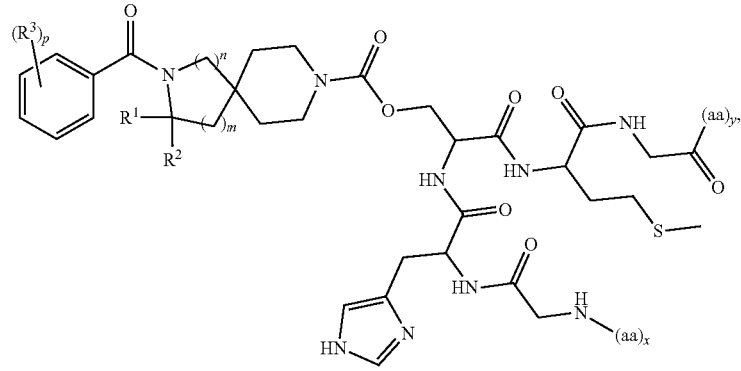

wherein R¹, R², R³, m, n, and p are defined as in Formula (IV) described herein, and x and y are at least one amino acid (aa).

In another embodiment is a compound having the structure:

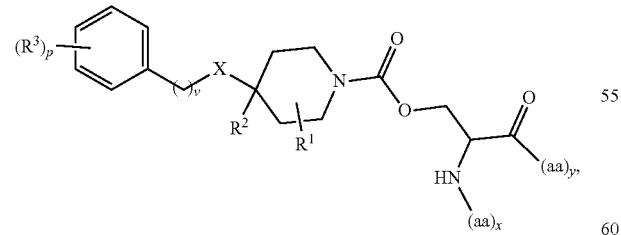

wherein R¹, R², R³, X, p, and v are defined as in Formula (V) described herein, and x and y are at least one amino acid (aa). In another embodiment is a compound having the structure:

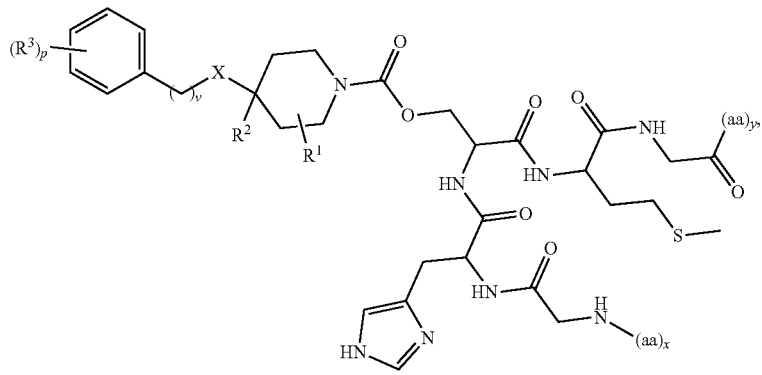

wherein $R^1$, $R^2$, $R^3$, X, p, and v are defined as in Formula (V) described herein, and x and y are at least one amino acid (aa).

In another embodiment is a compound having the structure:

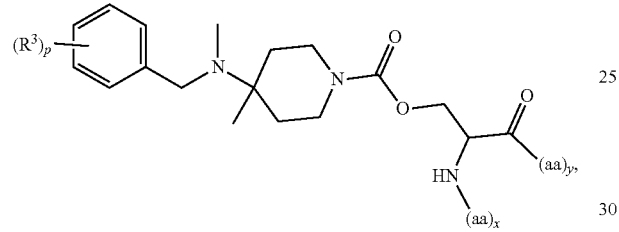

wherein $R^3$ and p are defined as in Formula (Va) described herein, and x and y are at least one amino acid (aa). In another embodiment is a compound having the structure:

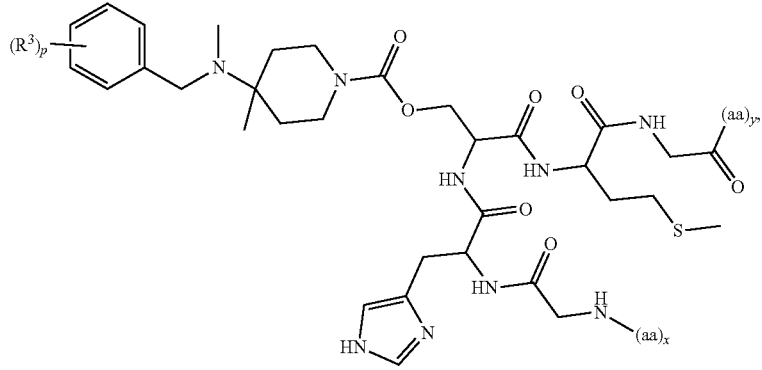

wherein $R^3$ and p are defined as in Formula (Va) described herein, and x and y are at least one amino acid (aa).

In another embodiment is a compound having the structure:

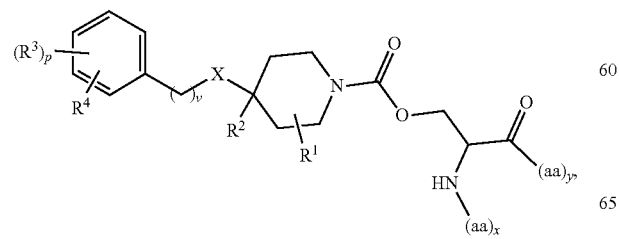

wherein $R^1$, $R^2$, $R^3$, $R^4$, X, p, and v are defined as in Formula (V') described herein, and x and y are at least one amino acid (aa). In another embodiment is a compound having the structure:

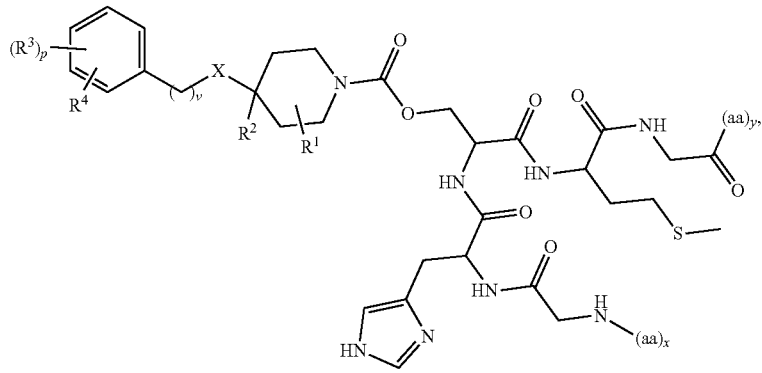

wherein $R^1$, $R^2$, $R^3$, $R^4$, X, p, and v are defined as in Formula (V') described herein, and x and y are at least one amino acid (aa).

In another embodiment is a compound having the structure:

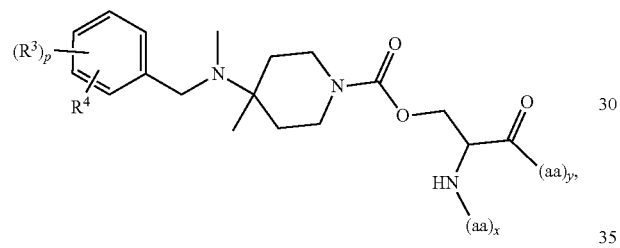

wherein $R^3$, $R^4$, and p are defined as in Formula (Va') described herein, and x and y are at least one amino acid (aa). In another embodiment is a compound having the structure:

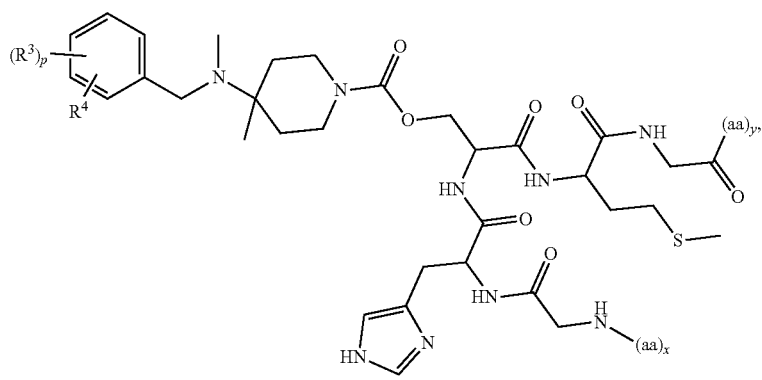

wherein $R^3$, $R^4$, and p are defined as in Formula (Va') described herein, and x and y are at least one amino acid (aa).

Described herein are inhibitors of monoacylglycerol lipase (MAGL) having the structure of Formula (I), (Ia), (Ib), (I'), (Ia'), (Ib'), (II), (III), (IV), (V), (Va), (V'), (Va'), (VI), (VII), or (VIII). In one embodiment, the inhibitors of MAGL are covalent inhibitors of MAGL, that is, the compounds of Formula (I), (Ia), (Ib), (I'), (Ia'), (Ib'), (II), (III), (IV), (V), (Va), (V'), (Va'), (VI), (VII), or (VIII) react with a serine residue of MAGL to form a modified serine residue, comprising the staying group of Formula (I), (Ia), (Ib), (I'), (Ia'), (Ib'), (II), (III), (IV), (V), (Va), (V'), (Va'), (VI), (VII), or (VIII); in such an embodiment, the leaving group of Formula (I), (Ia), (Ib), (I'), (Ia'), (Ib'), (II), (III), (IV), (V), (Va), (V'), (Va'), (VI), (VII), or (VIII) is removed from the compound of Formula (I), (Ia), (Ib), (I'), (Ia'), (Ib'), (II), (III), (IV), (V), (Va), (V'), (Va'), (VI), (VII), or (VIII). In a further embodiment, the covalent inhibitors of MAGL react irreversibly with a serine residue of MAGL to form the modified serine residue.

The staying group portion of the compounds of Formula (I) is

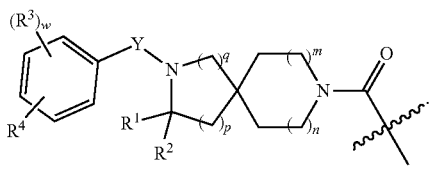

The staying group portion of the compounds of Formula (Ia) is

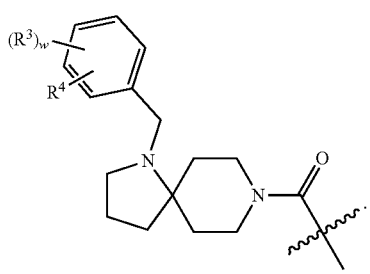

The staying group portion of the compounds of Formula (Ib) is

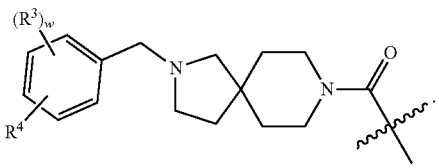

The staying group portion of the compounds of Formula (I') is

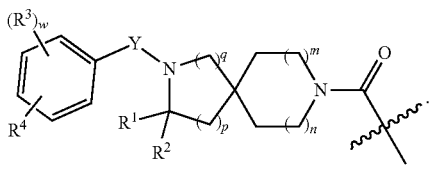

The staying group portion of the compounds of Formula (Ia') is

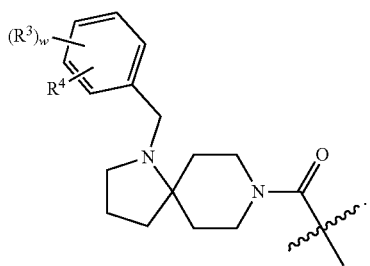

The staying group portion of the compounds of Formula (Ib') is

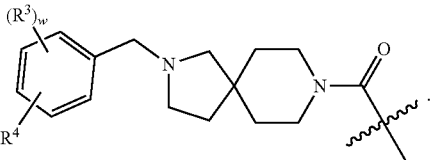

The staying group portion of the compounds of Formula (II) is

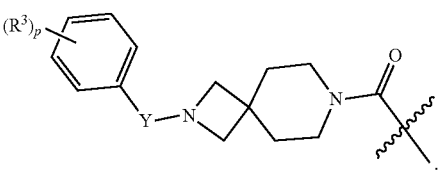

The staying group portion of the compounds of Formula (III) is

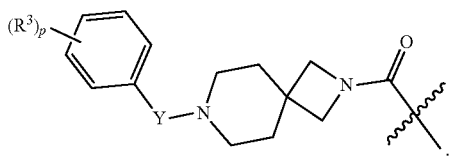

The staying group portion of the compounds of Formula (IV) is

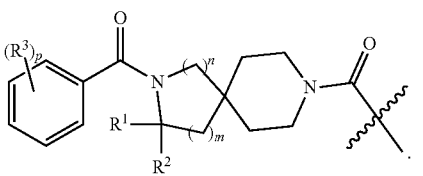

The staying group portion of the compounds of Formula (V) is

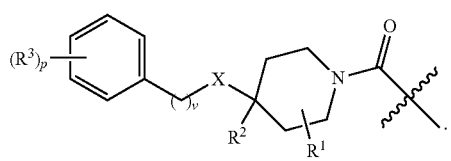

The staying group portion of the compounds of Formula (Va) is

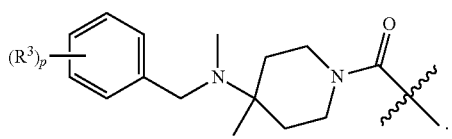

The staying group portion of the compounds of Formula (V') is

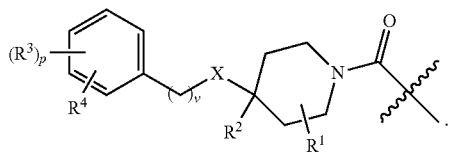

The staying group portion of the compounds of Formula (Va') is

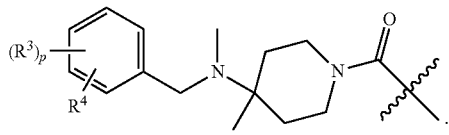

The leaving group portion of the compounds of Formula (I), (Ia), (Ib), (I'), (Ia'), (Ib'), (II), (III), (IV), (V), (Va), (V'), (Va'), (VI), (VII), or (VIII) is:

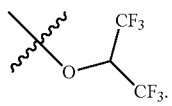

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, CN), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include, for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvates, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy, or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine, and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters, disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to the following groups and combinations of groups:

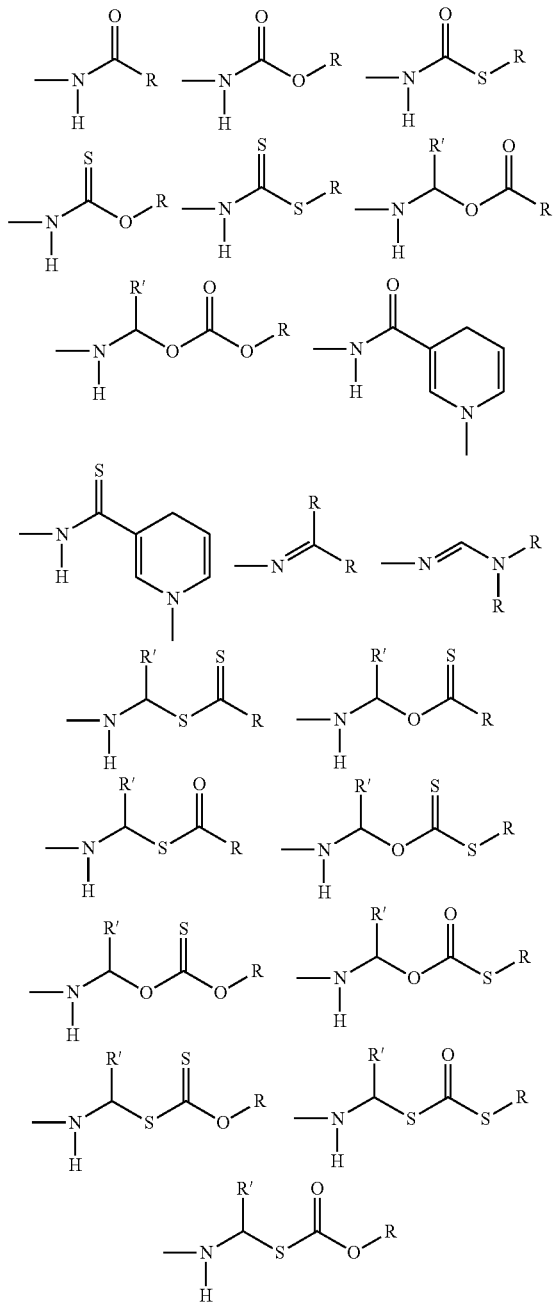

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), (Ib), (Ia'), (Ib'), (II), (III), (IV), (V), (Va), (V'), (Va'), (VI), (VII), or (VIII) described herein is administered as a pure chemical. In other embodiments, the compound of Formula (I), (Ia), (Ib), (I'), (Ia'), (Ib'), (II), (III), (IV), (V), (Va), (V'), (Va'), (VI), (VII), or (VIII) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), (Ib), (I'), (Ia'), (Ib'), (II), (III), (IV), (V), (Va), (V'), (Va'), (VI), (VII), or (VIII) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

One embodiment provides a pharmaceutical composition comprising a pharmaceutically acceptable carrier and a compound of Formula (Ia), or a pharmaceutically acceptable salt thereof.

One embodiment provides a pharmaceutical composition comprising a pharmaceutically acceptable carrier and a compound of Formula (Ib), or a pharmaceutically acceptable salt thereof.

One embodiment provides a pharmaceutical composition comprising a pharmaceutically acceptable carrier and a compound of Formula (I'), or a pharmaceutically acceptable salt thereof.

One embodiment provides a pharmaceutical composition comprising a pharmaceutically acceptable carrier and a compound of Formula (Ia'), or a pharmaceutically acceptable salt thereof.

One embodiment provides a pharmaceutical composition comprising a pharmaceutically acceptable carrier and a compound of Formula (Ib'), or a pharmaceutically acceptable salt thereof.

One embodiment provides a pharmaceutical composition comprising a pharmaceutically acceptable carrier and a compound of Formula (II), or a pharmaceutically acceptable salt thereof.

One embodiment provides a pharmaceutical composition comprising a pharmaceutically acceptable carrier and a compound of Formula (III), or a pharmaceutically acceptable salt thereof.

One embodiment provides a pharmaceutical composition comprising a pharmaceutically acceptable carrier and a compound of Formula (IV), or a pharmaceutically acceptable salt thereof.

One embodiment provides a pharmaceutical composition comprising a pharmaceutically acceptable carrier and a compound of Formula (V), or a pharmaceutically acceptable salt thereof.

One embodiment provides a pharmaceutical composition comprising a pharmaceutically acceptable carrier and a compound of Formula (Va), or a pharmaceutically acceptable salt thereof.

One embodiment provides a pharmaceutical composition comprising a pharmaceutically acceptable carrier and a compound of Formula (V'), or a pharmaceutically acceptable salt thereof.

One embodiment provides a pharmaceutical composition comprising a pharmaceutically acceptable carrier and a compound of Formula (Va'), or a pharmaceutically acceptable salt thereof.

One embodiment provides a pharmaceutical composition comprising a pharmaceutically acceptable carrier and a compound of Formula (VI), or a pharmaceutically acceptable salt thereof.

One embodiment provides a pharmaceutical composition comprising a pharmaceutically acceptable carrier and a compound of Formula (VII), or a pharmaceutically acceptable salt thereof.

One embodiment provides a pharmaceutical composition comprising a pharmaceutically acceptable carrier and a compound of Formula (VIII), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof. Another embodiment provides a pharmaceutical composition consisting essentially of a pharmaceutically acceptable carrier and a compound of Formula (Ia), or a pharmaceutically acceptable salt thereof. Another embodiment provides a pharmaceutical composition consisting essentially of a pharmaceutically acceptable carrier and a compound of Formula (Ib), or a pharmaceutically acceptable salt thereof. Another embodiment provides a pharmaceutical composition consisting essentially of a pharmaceutically acceptable carrier and a compound of Formula (I'), or a pharmaceutically acceptable salt thereof. Another embodiment provides a pharmaceutical composition consisting essentially of a pharmaceutically acceptable carrier and a compound of Formula (Ia'), or a pharmaceutically acceptable salt thereof. Another embodiment provides a pharmaceutical composition consisting essentially of a pharmaceutically acceptable carrier and a compound of Formula (Ib'), or a pharmaceutically acceptable salt thereof. Another embodiment provides a pharmaceutical composition consisting essentially of a pharmaceutically acceptable carrier and a compound of Formula (II), or a pharmaceutically acceptable salt thereof. Another embodiment provides a pharmaceutical composition consisting essentially of a pharmaceutically acceptable carrier and a compound of Formula (III), or a pharmaceutically acceptable salt thereof. Another embodiment provides a pharmaceutical composition consisting essentially of a pharmaceutically acceptable carrier and a compound of Formula (IV), or a pharmaceutically acceptable salt thereof. Another embodiment provides a pharmaceutical composition consisting essentially of a pharmaceutically acceptable carrier and a compound of Formula (V), or a pharmaceutically acceptable salt thereof. Another embodiment provides a pharmaceutical composition consisting essentially of a pharmaceutically acceptable carrier and a compound of Formula (Va), or a pharmaceutically acceptable salt thereof. Another embodiment provides a pharmaceutical composition consisting essentially of a pharmaceutically acceptable carrier and a compound of Formula (V'), or a pharmaceutically acceptable salt thereof. Another embodiment provides a pharmaceutical composition consisting essentially of a pharmaceutically acceptable carrier and a compound of Formula (Va'), or a pharmaceutically acceptable salt thereof. Another embodiment provides a pharmaceutical composition consisting essentially of a pharmaceutically acceptable carrier and a compound of Formula (VI), or a pharmaceutically acceptable salt thereof. Another embodiment provides a pharmaceutical composition consisting essentially of a pharmaceutically acceptable carrier and a compound of Formula (VII), or a pharmaceutically acceptable salt thereof. Another embodiment provides a pharmaceutical composition consisting essentially of a pharmaceutically acceptable carrier and a compound of Formula (VIII), or a pharmaceutically acceptable salt thereof.

In certain embodiments, the compound of Formula (I), (Ia), (Ib), (I'), (Ia'), (Ib'), (III), (IV), (V), (Va), (V'), (Va'), (VI), (VII), or (VIII) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These compositions described herein include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches, and inhalants. In some embodiments, the active component is mixed under sterile conditions with a pharmaceutically acceptable carrier, and with any preservatives, buffers, or propellants as required.

In some embodiments, the ointments, pastes, creams, and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, and amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5, and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Ib), (I'), (Ia'), (Ib'), (II), (III), (IV), (V), (Va), (V'), (Va'), (VI), (VII), or (VIII) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (Ib), (I'), (Ia'), (Ib'), (II), (III), (IV), (V), (Va), (V'), (Va'), (VI), (VII), or (VIII). In some embodiments, provided herein is a compound of Formula (I), (Ia), (Ib), (I'), (Ia'), (Ib'), (II), (III), (IV), (V), (Va), (V'), (Va'), (VI), (VII), or (VIII) wherein the compound is a MAGL inhibitor. In some embodiments, provided herein is a compound of Formula (I), (Ia), (Ib), (I'), (Ia'), (Ib'), (II), (III), (IV), (V), (Va), (V'), (Va'), (VI), (VII), or (VIII) wherein the compound is a selective MAGL inhibitor. The ability of compounds described herein to modulate or inhibit MAGL is evaluated by procedures known in the art and/or described herein. Another aspect of this disclosure provides methods of treating a disease associated with expression or activity of MAGL in a patient. In some embodiments, provided herein is a compound of Formula (I), (Ia), (Ib), (I'), (Ia'), (Ib'), (II), (III), (IV), (V), (Va), (V'), (Va'), (VI), (VII), or (VIII) wherein the compound is selective in inhibiting MAGL as compared to inhibition of other serine hydrolases. In some embodiments, provided herein is a compound of Formula (I), (Ia), (Ib), (I'), (Ia'), (Ib'), (II), (III), (IV), (V), (Va), (V'), (Va'), (VI), (VII), or (VIII) wherein the compound is 10, 100, or 1000-fold selective in inhibiting MAGL as compared to inhibition of other serine hydrolases.

In some embodiments is a method of treating pain in a patient, comprising administering a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, to a patient in need thereof to treat said pain. In some embodiments is a method of treating pain in a patient, comprising administering a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, to a patient in need thereof to treat said pain, wherein the pain is neuropathic pain. In some embodiments is a method of treating pain in a patient, comprising administering a therapeutically effective amount of a compound of Formula (I), (Ia), (Ib), (I'), (Ia'), (Ib'), (II), (III), (IV), (V), (Va), (V'), (Va'), (VI), (VII), or (VIII), or a solvate, hydrate, tautomer, N-oxide, stereoisomer, or a pharmaceutically acceptable salt thereof, to a patient in need thereof to treat said pain, wherein the pain is inflammatory pain.

Also contemplated herein in some embodiments are methods of treating and/or preventing in a patient in need thereof a disorder such as one or more of acute or chronic pain, bone cancer pain, rheumatoid arthritis pain, pruritus, vomiting or nausea, Down's syndrome, Parkinson's disease, epilepsy, NSAID-induced ulcers, opioid withdrawal, cannabis withdrawal, nicotine withdrawal, traumatic brain injury, ischemia, renal ischemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), liver injury, lung injury, skeletal muscle contusions, inflammatory disorders, and/or anxiety disorders. Contemplated methods include administering a pharmaceutically effective amount of a disclosed compound.

In some embodiments, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that result in liver damage, in a patient in need thereof.

In some embodiments, provide herein is a method for treating chronic pain such as inflammatory pain, visceral pain, back pain, post operative pain, and pain related to migraine, osteoarthritis, or rheumatoid arthritis.

In some embodiments, provide herein are methods for ameliorating cognitive function in a patient suffering from Down's syndrome or Alzheimer's disease, comprising administering an effective amount of a disclosed compound. Exemplary patients suffering from Down's syndrome are a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). In some embodiments, such patients also suffer from further cognitive impairment and/or dementia, and/or seizures which, in some embodiments are due to production of prostaglandins and/or amyloid beta. For example, such patients also are suffering from, or have one or more of the following symptoms associated with early-mid or late stage cognitive impairment: loss of language, impairment of social skills, progressive loss of activities of daily living, and include psychotic behavior. Provided herein, for example, is a method for treating a patient having Down's syndrome or Alzheimer's disease with cognitive impairment, comprising administering an effective amount of a disclosed compound. Such disclosed methods result in cognitive improvement, for example, measured by IQ or the Arizona Cognitive Test Battery (e.g., measured with a cognitive test battery designed for use in individuals with Down's syndrome). For example, a treated patient using a disclosed method has at least one of: increased memory, improved memory or improved speech. In some embodiments, such disclosed methods result in a patient having an increased quality of life as measured by an adaptive behavior scale after said administration.

In other embodiments, a method for at least partially providing a Down's syndrome patient a neuroprotective (such as a disclosed compounds), that results in delayed onset of neurodegeneration or substantially prevents neurodegeneration, is provided. Administration to a patient is initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In another embodiment is a method of treating a disease or disorder in a patient in need thereof, comprising administering to the patient in need thereof a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof, wherein the disease or disorder is selected from the group consisting of migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating epilepsy/seizure disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating neuromyelitis optica (NMO) in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating Tourette syndrome in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating persistent motor tic disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating persistent vocal tic disorder in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating abdominal pain associated with irritable bowel syndrome in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating pain associated with irritable bowel disease in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating pain associated with Crohn's disease in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

In another embodiment is a method of treating cancer pain, pain caused by peripheral neuropathy, central pain, fibromyalgia, migraine, vasoocclussive painful crises in sickle cell disease, functional chest pain, rheumatoid arthritis, osteoarthritis, functional dyspepsia, or spasticity, pain, sleep disturbance, or bladder dysfunction associated with multiple sclerosis, in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating central pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating migraine in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating spasticity, pain, sleep disturbance, or bladder dysfunction associated with multiple sclerosis in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (Ib), (I'), (Ia'), (Ib'), (II), (III), (IV), (V), (Va), (V'), (Va'), (VI), (VII), or (VIII) described herein, or a pharmaceutically acceptable salt or solvate thereof.

Also disclosed herein are methods of treating and/or preventing in a patient in need thereof a disorder such as one or more of acute or chronic pain and neuropathy. Disclosed methods include administering a pharmaceutically effective amount of a compound described herein.

In certain embodiments, a disclosed compound utilized by one or more of the foregoing methods is one of the generic, subgeneric, or specific compounds described herein, such as a compound of Formula (I), (Ia), (Ib), (I'), (Ia'), (Ib'), (II), (III), (IV), (V), (Va), (V'), (Va'), (VI), (VII), or (VIII).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane (Cl $CH_2CH_2$Cl)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Example 1: 4-(2-Chloro-6-((8-((((1,1,1,3,3,3-hexafluoropropan-2-yl)oxy)carbonyl)-1,8-diazaspiro[4.5]decan-1-yl)methyl)phenyl)-2,2-dimethylbut-3-ynoic acid

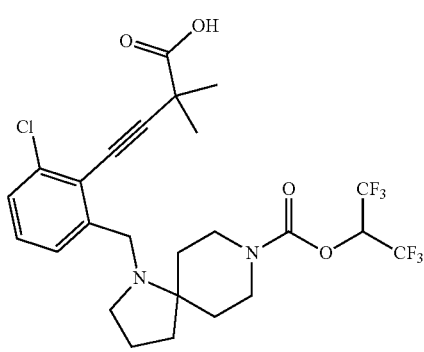 [SMILES: CC(C)(C#Cc1c(Cl)cccc1CN1CCCC12CCN(C(=O)OC(C(F)(F)F)C(F)(F)F)CC2)C(=O)O]

Step 1: Synthesis of tert-butyl 1-(2-bromo-3-chlorobenzyl)-1,8-diazaspiro[4.5]decane-8-carboxylate

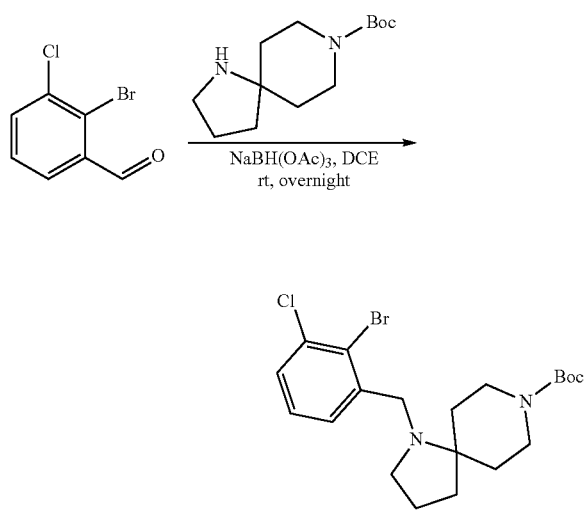

A 100-mL round-bottom flask was charged with 2-bromo-3-chlorobenzaldehyde (0.500 g, 2.28 mmol, 1.00 equiv), tert-butyl 1,8-diazaspiro[4.5]decane-8-carboxylate (0.660 g, 2.75 mmol, 1.20 equiv), and 1,2-dichloroethane (15 mL). The mixture was stirred for 1 hour at room temperature, prior to addition of sodium triacetoxyborohydride (1.93 g, 9.12 mmol, 4.00 equiv). The reaction mixture was stirred overnight at room temperature and quenched with water (10 mL). The resulting solution was extracted with dichloromethane (3×15 mL) and the organic layers were combined, washed with brine (1×20 mL), dried over anhydrous Na$_2$SO$_4$, filtered and concentrated under reduced pressure. The residue was chromatographed on a silica gel column to provide 640 mg (63% yield) of tert-butyl 1-(2-bromo-3-chlorobenzyl)-1,8-diazaspiro[4.5]decane-8-carboxylate. LCMS (ESI, m/z): 443 [M+H]$^+$.

Step 2: Synthesis of tert-butyl 1-(3-chloro-2-(4-ethoxy-3,3-dimethyl-4-oxobut-1-yn-1-yl)benzyl)-1,8-diazaspiro[4.5]decane-8-carboxylate

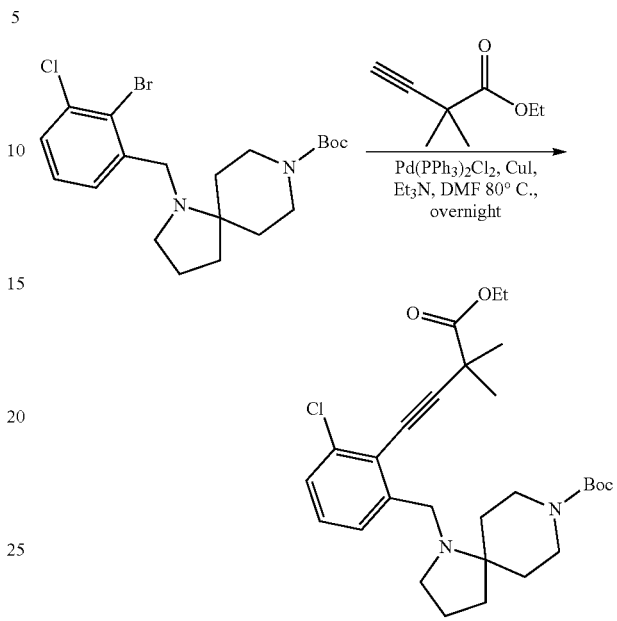

A 100-mL round-bottom flask was charged with tert-butyl 1-(2-bromo-3-chlorobenzyl)-1,8-diazaspiro[4.5]decane-8-carboxylate (540 mg, 1.22 mmol, 1.00 equiv), ethyl 2,2-dimethylbut-3-ynoate (223 mg, 1.59 mmol, 1.30 equiv), bis(triphenylphosphine)palladium(II) chloride (42.8 mg, 0.0610 mmol, 0.05 equiv), copper(I) iodide (23.2 mg, 0.122 mmol, 0.10 equiv), triethylamine (370 mg, 3.66 mmol, 3.00 equiv), and N,N-dimethylformamide (10 mL) under nitrogen. The reaction mixture was stirred overnight at 80° C. and then quenched with water (10 mL). The resulting mixture was extracted with dichloromethane (3×30 mL) and the organic layers were combined, washed with brine (1×30 mL), dried over anhydrous Na$_2$SO$_4$, filtered and concentrated under reduced pressure. The residue was chromatographed on a silica gel column to provide 460 mg (75% yield) of tert-butyl 1-(3-chloro-2-(4-ethoxy-3,3-dimethyl-4-oxobut-1-yn-1-yl)benzyl)-1,8-diazaspiro[4.5]decane-8-carboxylate. LCMS (ESI, m/z): 503 [M+H]$^+$.

Step 3: Synthesis of 4-(2-((8-(tert-butoxycarbonyl)-1,8-diazaspiro[4.5]decan-1-yl)methyl)-6-chlorophenyl)-2,2-dimethylbut-3-ynoic acid

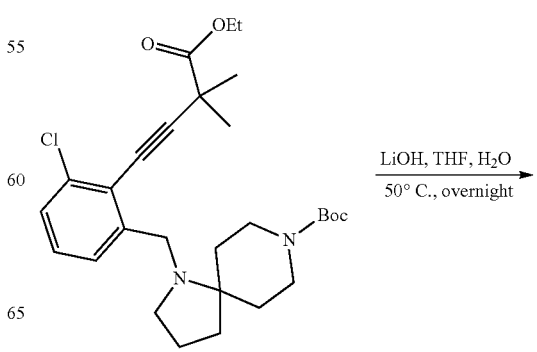

-continued

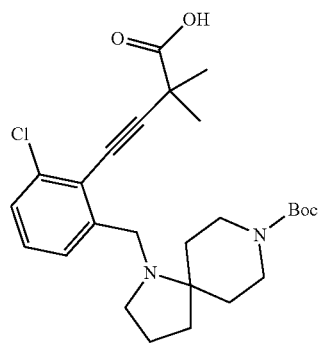

A 100-mL round-bottom flask was charged with tert-butyl 1-(3-chloro-2-(4-ethoxy-3,3-dimethyl-4-oxobut-1-yn-1-yl)benzyl)-1,8-diazaspiro[4.5]decane-8-carboxylate (550 mg, 1.09 mmol, 1.00 equiv), lithium hydroxide (262 mg, 10.9 mmol, 10.0 equiv), tetrahydrofuran (10 mL), and water (2 mL). The resulting solution was stirred overnight at 50° C. and quenched with water (5 mL). The pH of the solution was adjusted to 5 with hydrochloric acid (1M). The resulting solution was extracted with dichloromethane (3×20 mL) and the organic layers were combined, washed with brine (1×20 mL), dried over anhydrous Na$_2$SO$_4$, filtered and concentrated under reduced pressure to provide 460 mg (crude) of 4-(2((8-(tert-butoxycarbonyl)-1,8-diazaspiro[4.5]decan-1-yl)methyl)-6-chlorophenyl)-2,2-dimethylbut-3-ynoic acid. LCMS (ESI, m/z): 475 [M+H]$^+$.

Step 4: Synthesis of 4-(2-((1,8-diazaspiro[4.5]decan-1-yl)methyl)-6-chlorophenyl)-2,2-dimethylbut-3-ynoic acid

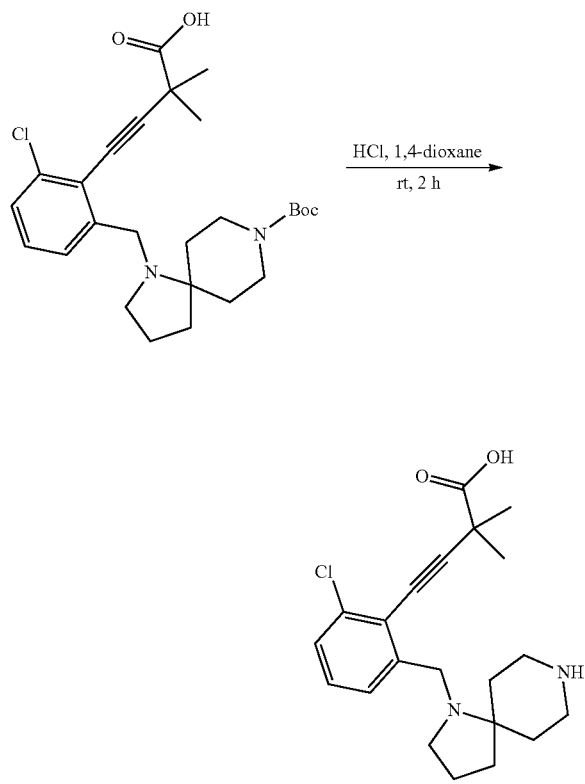 [SMILES: CC(C)(C)OC(=O)N1CCC2(CCCN2Cc2cccc(Cl)c2C#CC(C)(C)C(=O)O)CC1 ; CC(C)(C#Cc1c(Cl)cccc1CN1CCCC12CCNCC2)C(=O)O]

A 100-mL round-bottom flask was charged with 4-(2-((8-(tert-butoxycarbonyl)-1,8-diazaspiro[4.5]decan-1-yl)methyl)-6-chlorophenyl)-2,2-dimethylbut-3-ynoic acid (460 mg, 0.97 mmol, 1.00 equiv), 1,4-dioxane (10 mL), concentrated hydrochloric acid (1 mL). The resulting solution was stirred for 2 hours at room temperature and concentrated under reduced pressure to provide 363 mg (quantitative) of 4-(2-((1,8-diazaspiro[4.5]decan-1-yl)methyl)-6-chorophenyl)-2,2-dimethylbut-3-ynoic acid. LCMS (ESI, m/z): 375 [M+H]$^+$.

Step 5: Synthesis of 4-(2-chloro-6-((8-(((1,1,1,3,3,3-hexafluoropropan-2-yl)oxy)carbonyl)-1,8-diazaspiro[4.5]decan-1-yl)methyl)phenyl)-2,2-dimethylbut-3-ynoic acid

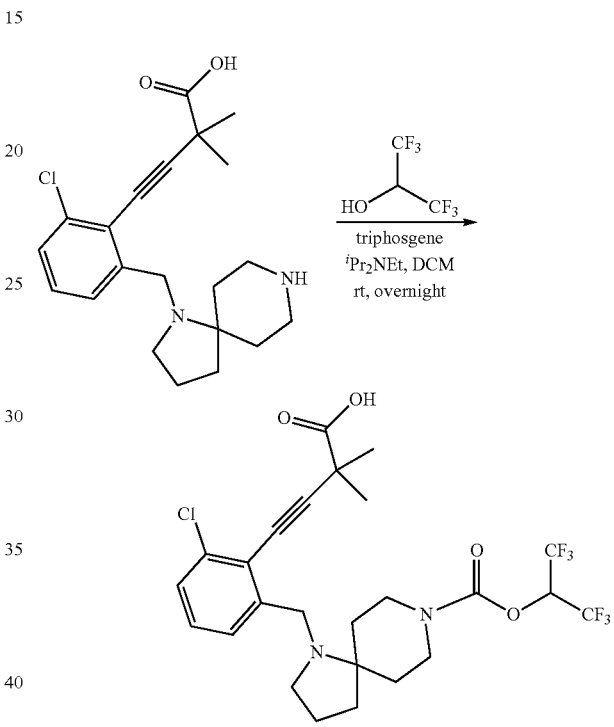

A 100-mL round-bottom flask was charged with triphosgene (139 mg, 0.470 mmol, 0.70 equiv) and dichloromethane (10 mL). 1,1,1,3,3,3-Hexafluoropropan-2-ol (225 mg, 1.34 mmol, 2.00 equiv) and N,N-diisopropylethylamine (346 mg, 2.68 mmol, 4.00 equiv) were added sequentially at 0° C. The mixture was stirred for 2 hours at room temperature prior to the addition of 4-(2-chloro-6-[1,8-diazaspiro[4.5]decan-1-ylmethyl]phenyl)-2,2-dimethylbut-3-ynoic acid (253 mg, 0.670 mmol, 1.00 equiv). The reaction mixture was stirred overnight at room temperature and quenched with water (10 mL). The resulting solution was extracted with dichloromethane (3×15 mL) and the organic layers were combined, washed with brine (1×20 mL), dried over anhydrous Na$_2$SO$_4$, filtered and concentrated under reduced pressure. The crude product (400 mg) was purified by preparative HPLC to afford 119.3 mg (31% yield) of 4-(2-chloro-6-((8-(((1,1,1,3,3,3-hexafluoropropan-2-yl)oxy)carbonyl)-1,8-diazaspiro[4.5]decan-1-yl)methyl)phenyl)-2,2-dimethylbut-3-ynoic acid as a white solid. $^1$H NMR (300 MHz, Methanol-d$_4$) δ 7.43-7.48 (m, 2H), 7.28-7.34 (m, 1H), 6.10-6.18 (m, 1H), 4.23 (br, 4H), 3.05-3.21 (m, 4H), 2.16-2.21 (m, 2H), 1.98-2.05 (m, 4H), 1.82-1.86 (m, 2H), 1.55 (s, 6H). LCMS (ESI, m/z): 569 [M+H]$^+$.

Example 2: 2-(4-(3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)piperazin-1-yl)acetic acid

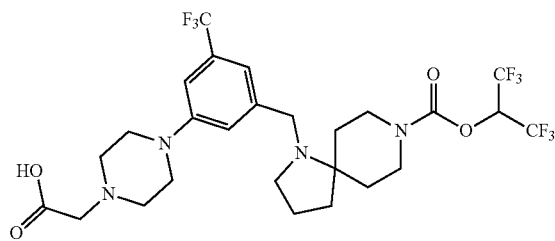 [SMILES: O=C(O)CN1CCN(c2cc(CN3CCCC34CCN(C(=O)OC(C(F)(F)F)C(F)(F)F)CC4)cc(C(F)(F)F)c2)CC1]

Step 1: Synthesis of tert-butyl 2-(4-(3-formyl-5-(trifluoromethyl)phenyl)piperazin-1-yl)acetate

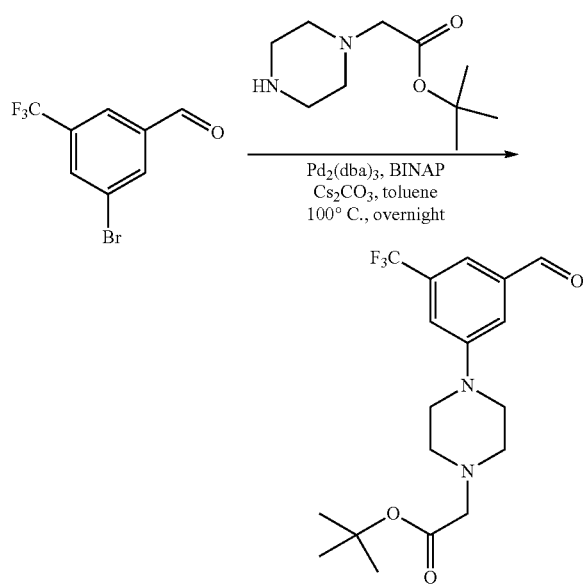

A 50-mL round-bottom flask was charged with 3-bromo-5-(trifluoromethyl)benzaldehyde (300 mg, 1.19 mmol, 1.00 equiv), tert-butyl 2-(piperazin-1-yl)acetate (476 mg, 2.38 mmol, 2.00 equiv), tris(dibenzylideneacetone)dipalladium (54.4 mg, 0.0595 mmol, 0.05 equiv), 2,2'-bis(diphenylphosphino)-1,1'-binaphthyl (148 mg, 0.238 mmol, 0.20 equiv), cesium carbonate (1.16 g, 3.56 mmol, 3.00 equiv), and toluene (10 mL) under nitrogen. The reaction mixture was stirred overnight at 100° C. and quenched with water (10 mL). The resulting solution was extracted with ethyl acetate (3×15 mL) and the organic layers were combined, washed with brine (2×15 mL), dried over anhydrous Na$_2$SO$_4$, filtered and concentrated under reduced pressure. The residue was chromatographsed on a silica gel column to provide 310 mg (70% yield) of tert-butyl 2-(4-(3-formyl-5-(trifluoromethyl)phenyl)piperazin-1-yl)acetate. LCMS (ESI, m/z): 373 [M+H]$^+$.

Step 2: Synthesis of 1,1,1,3,3,3-hexafluoropropan-2-yl 1-(3-(4-(2-(tert-butoxy)-2-oxoethyl)piperazin-1-yl)-5-(trifluoromethyl)benzyl)-1,8-diazaspiro[4.5]decane-8-carboxylate

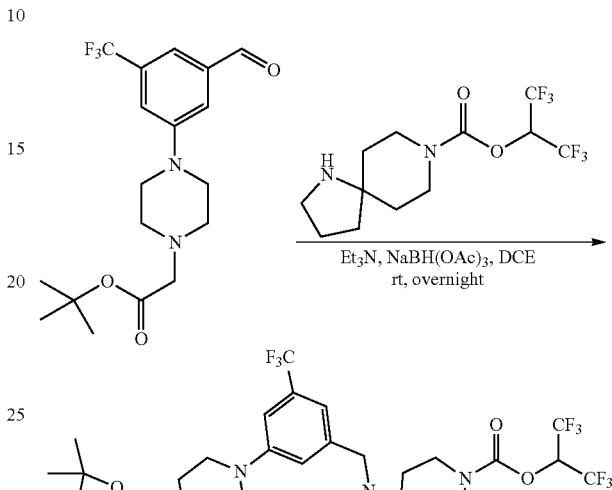

A 50-mL round-bottom flask was charged with tert-butyl 2-(4-(3-formyl-5-(trifluoromethyl)phenyl)piperazin-1-yl) acetate (310 mg, 0.833 mmol, 1.00 equiv), 1,1,1,3,3,3-hexafluoropropan-2-yl 1,8-diazaspiro[4.5]decane-8-carboxylate (306 mg, 0.916 mmol, 1.10 equiv), 1,2-dichloroethane (10 mL), and triethylamine (252 mg, 2.49 mmol, 3.00 equiv). The resulting solution was stirred for 1 hour at room temperature prior to the addition of sodium triacetoxyborohydride (530 mg, 2.50 mmol, 3.00 equiv). The reaction mixture was stirred overnight at room temperature and quenched with water (10 mL). The mixture was extracted with dichloromethane (3×10 mL) and the organic layers were combined, washed with brine (2×15 mL), dried over anhydrous Na$_2$SO$_4$, filtered and concentrated under reduced pressure. The residue was applied onto a silica gel column to provide 370 mg (64% yield) of 1,1,1,3,3,3-hexafluoropropan-2-yl 1-(3-(4-(2-(tert-butoxy)-2-oxoethyl)piperazin-1-yl)-5-(trifluoromethyl)benzyl)-1,8-diazaspiro[4.5]decane-8-carboxylate as a yellow solid. LCMS (ESI, m/z): 691 [M+H]$^+$.

Step 3: Synthesis of 2-(4-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperazin-1-yl)acetic acid

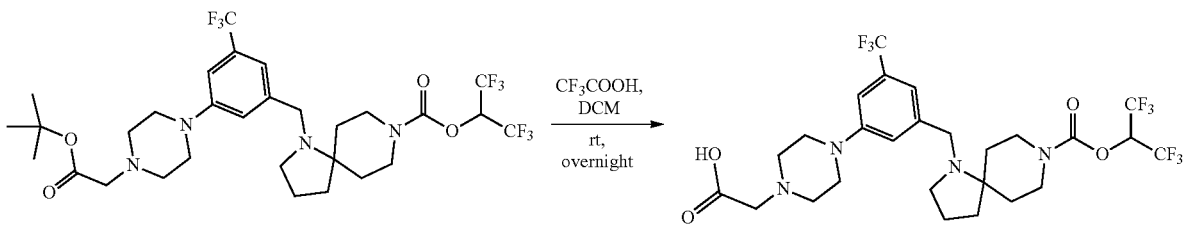 [SMILES: CC(C)(C)OC(=O)CN1CCN(c2cc(CN3CCCC34CCN(C(=O)OC(C(F)(F)F)C(F)(F)F)CC4)cc(C(F)(F)F)c2)CC1 ; O=C(O)CN1CCN(c2cc(CN3CCCC34CCN(C(=O)OC(C(F)(F)F)C(F)(F)F)CC4)cc(C(F)(F)F)c2)CC1]

A 40-mL round-bottom flask was charged with 1,1,1,3,3,3-hexafluoropropan-2-yl 1-(3-(4-(2-(tert-butoxy)-2-oxoethyl)piperazin-1-yl)-5-(trifluoromethyl)benzyl)-1,8-diazaspiro[4.5]decane-8-carboxylate (370 mg, 0.536 mmol, 1.00 equiv), dichloromethane (10 mL), and trifluoroacetic acid (2 mL). The reaction mixture was stirred overnight at room temperature and concentrated under reduced pressure. The mixture was quenched with saturated NaHCO₃ solution (10 mL). The resulting solution was extracted with dichloromethane (3×10 mL) and the organic layers were combined, washed with brine (2×15 mL), dried over anhydrous Na₂SO₄, filtered and concentrated under reduced pressure. The crude product (350 mg) was purified by preparative HPLC to provide 196.1 mg (58% yield) of 2-(4-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperazin-1-yl)acetic acid. ¹H NMR (300 MHz, Methanol-d₄) δ 7.14-7.22 (m, 3H), 6.11-6.15 (m, 1H), 4.16-4.18 (m, 2H), 3.62-3.70 (m, 4H), 3.35-3.50 (m, 8H), 3.05-3.12 (m, 2H), 2.72-2.76 (m, 2H), 1.76-1.94 (m, 6H), 1.54-1.59 (m, 2H). LCMS (ESI, m/z): 635 [M+H]⁺.

Example 3: 2-(4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)piperazin-1-yl)acetic acid

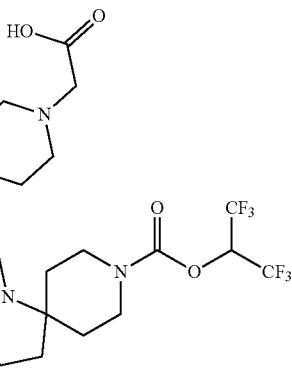

Step 1: Synthesis of tert-butyl 2-(4-(2-formyl-5-(trifluoromethyl)phenyl)piperazin-1-yl)acetate

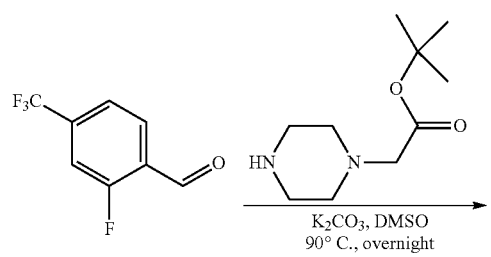

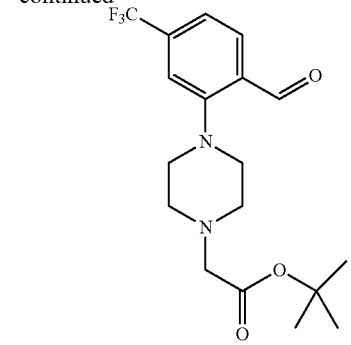

A 50-mL round-bottom flask was charged with 2-fluoro-4-(trifluoromethyl)benzaldehyde (250 mg, 1.30 mmol, 1.00 equiv), dimethyl sulfoxide (10 mL), tert-butyl 2-(piperazin-1-yl)acetate (520 mg, 2.60 mmol, 2.00 equiv), and potassium carbonate (538 mg, 3.89 mmol, 3.00 equiv). The resulting solution was stirred overnight at 90° C. and quenched with water (10 mL). The mixture was extracted with ethyl acetate (3×10 mL) and the organic layers were combined, washed with brine (2×15 mL), dried over anhydrous Na₂SO₄, filtered and concentrated under reduced pressure. The residue was chromatographed on a silica gel column to provide 480 mg (99% yield) of tert-butyl 2-(4-(2-formyl-5-(trifluoromethyl)phenyl)piperazin-1-yl)acetate. LCMS (ESI, m/z): 373 [M+H]⁺.

Step 2: Synthesis of 1,1,1,3,3,3-hexafluoropropan-2-yl 1-(2-(4-(2-(tert-butoxy)-2-oxoethyl)piperazin-1-yl)-4-(trifluoromethyl)benzyl)-1,8-diazaspiro[4.5]decane-8-carboxylate

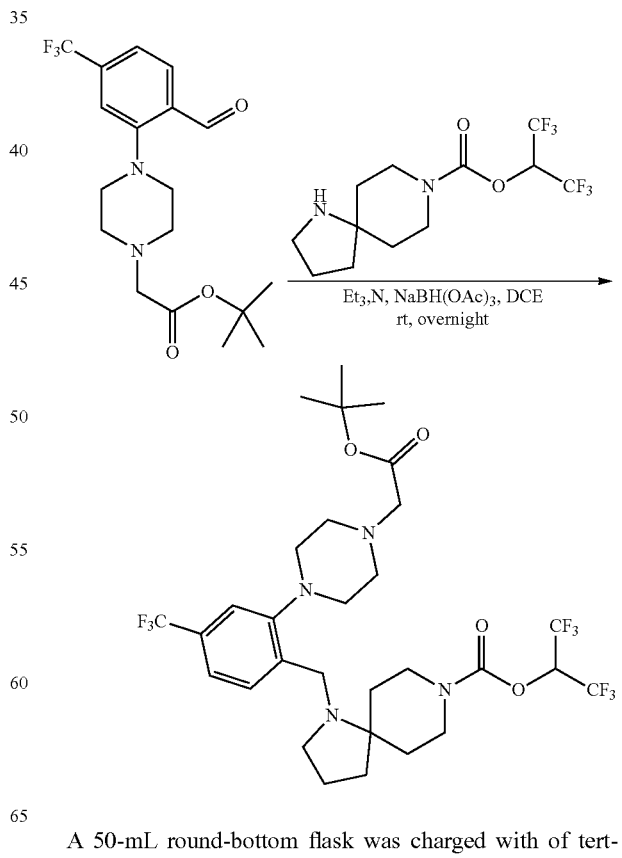

A 50-mL round-bottom flask was charged with of tert-butyl 2-(4-(2-formyl-5-(trifluoromethyl)phenyl)piperazin- 1-yl)acetate (190 mg, 0.510 mmol, 1.00 equiv), 1,2-dichloroethane (10 mL), 1,1,1,3,3,3-hexafluoropropan-2-yl 1,8-diazaspiro[4.5]decane-8-carboxylate (255 mg, 0.760 mmol, 1.50 equiv), and triethylamine (154 mg, 1.52 mmol, 3.00 equiv). The resulting solution was stirred for 1 hour at room temperature prior to the addition of sodium triacetoxyborohydride (324 mg, 1.53 mmol, 3.00 equiv). The reaction mixture was stirred overnight at room temperature and quenched with water (10 mL). The mixture was extracted with dichloromethane (3×10 mL) and the organic layers were combined, washed with brine (2×15 mL), dried over anhydrous Na$_2$SO$_4$, filtered and concentrated under reduced pressure. The residue was chromatographed on a silica gel column to provide 280 mg (79% yield) of 1,1,1,3,3,3-hexafluoropropan-2-yl 1-(2-(4-(2-(tert-butoxy)-2-oxoethyl)piperazin-1-yl)-4-(trifluoromethyl)benzyl)-1,8-diazaspiro[4.5]decane-8-carboxylate. LCMS (ESI, m/z): 691 [M+H]$^+$.

Step 3: Synthesis of 2-(4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperazin-1-yl)acetic acid

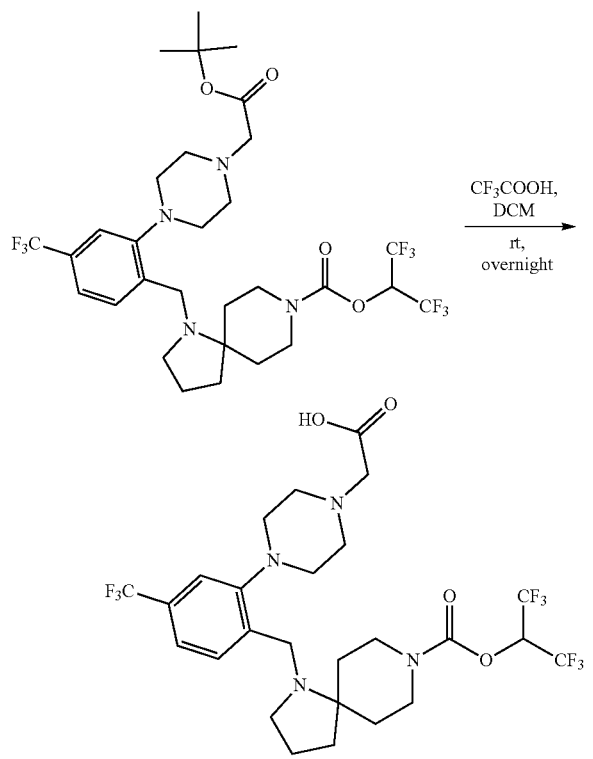

A 50-mL round-bottom flask was charged with 1,1,1,3,3,3-hexafluoropropan-2-yl 1-(2-(4-(2-(tert-butoxy)-2-oxoethyl)piperazin-1-yl)-4-(trifluoromethyl)benzyl)-1,8-diazaspiro[4.5]decane-8-carboxylate (280 mg, 0.410 mmol, 1.00 equiv), dichloromethane (5 mL), and trifluoroacetic acid (1 mL). The reaction mixture was stirred overnight at room temperature and concentrated under reduced pressure. After quenching with saturated NaHCO$_3$ (10 mL), the resulting solution was extracted with dichloromethane (3×10 mL) and the organic layers were combined, washed with brine (2×15 mL), dried over anhydrous Na$_2$SO$_4$, filtered and concentrated under reduced pressure. The crude product (400 mg) was purified by preparative HPLC to afford 91.3 mg (35% yield) of 2-(4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)piperazin-1-yl)acetic acid. $^1$H NMR (300 MHz, Methanol-d$_4$) δ 7.72-7.75 (m, 1H), 7.41-7.43 (m, 2H), 6.08-6.21 (m, 1H), 4.15-4.22 (m, 2H), 3.75-3.86 (m, 2H), 3.67 (s, 2H), 3.44 (br, 4H), 3.01-3.32 (m, 6H), 2.66-2.73 (m, 2H), 1.90-1.94 (m, 6H), 1.82-1.85 (m, 2H). LCMS (ESI, m/z): 635 [M+H]$^+$.

Example 4: 1-(3-Fluoro-5-((8-(((1,1,1,3,3,3-hexafluoropropan-2-yl)oxy)carbonyl)-1,8-diazaspiro[4.5]decan-1-yl)methyl)phenyl)cyclopentane-1-carboxylic acid

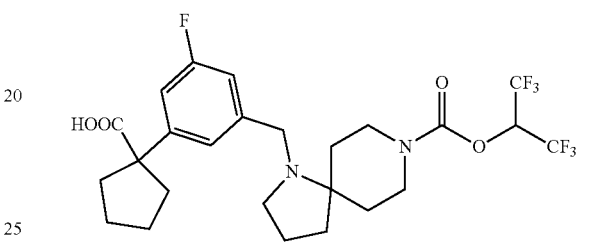

Step 1: Synthesis of potassium 3-(tert-butoxy)-3-oxopropanoate

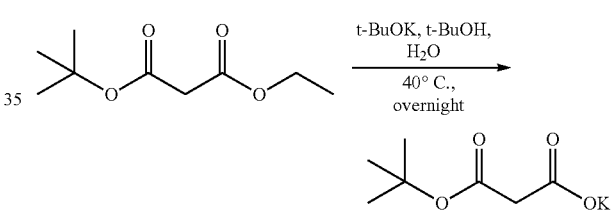

A 250-mL round-bottom flask was charged with 1-tert-butyl 3-ethyl propanedioate (6.20 g, 32.9 mmol, 1.10 equiv), tert-butanol (50 mL), and water (553 mg, 30.6 mmol, 1.02 equiv). The mixture was stirred for 30 min at 40° C., at which point a solution of (tert-butoxy)potassium (3.36 g, 30.0 mmol, 1.00 equiv) in tert-butanol (50 mL) was added dropwise over 30 min. The reaction mixture was stirred overnight at 40° C. and concentrated under reduced pressure. The resulting mixture was triturated with ether (50 mL) and the solids were collected by filtration to provide 4.70 g (79% yield) of 3-(tert-butoxy)-3-oxopropanoate as a white solid. LCMS (ESI, m/z): 159 [M−K]$^-$.

Step 2: Synthesis of tert-butyl 1-(3-bromo-5-fluorobenzyl)-1,8-diazaspiro[4.5]decane-8-carboxylate

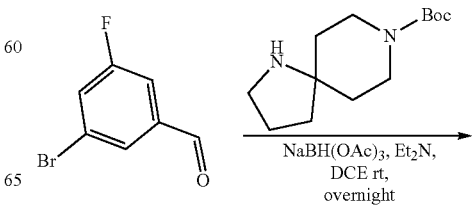

-continued

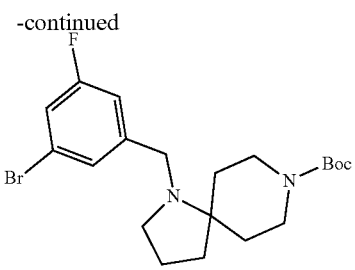

A 25-mL round-bottom flask was charged with 3-bromo-5-fluorobenzaldehyde (609 mg, 3.00 mmol, 1.20 equiv), tert-butyl 1,8-diazaspiro[4.5]decane-8-carboxylate (600 mg, 2.50 mmol, 1.00 equiv), triethylamine (758 mg, 7.49 mmol, 3.00 equiv), and 1,2-dichloroethane (15 mL). The mixture was stirred for 30 min at room temperature prior to the addition of sodium triacetoxyborohydride (1.59 g, 7.50 mmol, 3.00 equiv). The reaction mixture was stirred overnight at room temperature and quenched with water (15 mL). The resulting solution was extracted with dichloromethane (3×20 mL) and the organic layers were combined, washed with brine (2×15 mL), dried over anhydrous Na$_2$SO$_4$, filtered and concentrated under reduced pressure. The residue was chromatographed on a silica gel column to provide 980 mg (92% yield) of tert-butyl 1-(3-bromo-5-fluorobenzyl)-1,8-diazaspiro[4.5]decane-8-carboxylate. LCMS (ESI, m/z): 427 [M+H]$^+$.

Step 3: Synthesis of tert-butyl 1-(3-(2-(tert-butoxy)-2-oxoethyl)-5-fluorobenzyl)-1,8-diazaspiro[4.5]decane-8-carboxylate

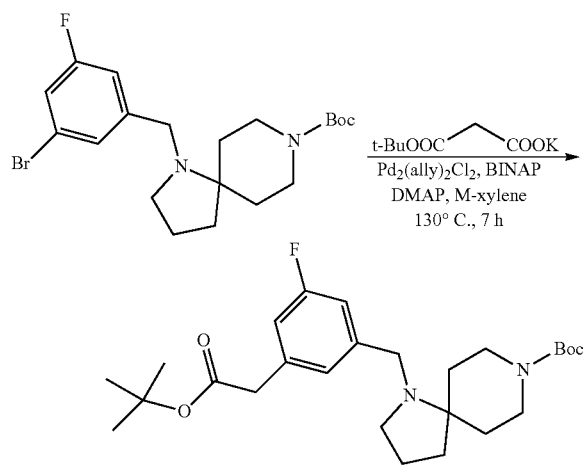

A 50-mL round-bottom flask was charged with tert-butyl 1-(3-bromo-5-fluorobenzyl)-1,8-diazaspiro[4.5]decane-8-carboxylate (980 mg, 2.29 mmol, 1.00 equiv), 3-(tert-butoxy)-3-oxopropanoate (909 mg, 4.58 mmol, 2.00 equiv), allylpalladium(II) chloride dimer (33.6 mg, 0.0918 mmol, 0.04 equiv), 2,2'-bis(diphenylphosphino)-1,1'-binaphthyl (153 mg, 0.246 mmol, 0.12 equiv), 4-dimethylaminopyridine (28.0 mg, 0.230 mmol, 0.10 equiv), and M-xylene (20 mL) under nitrogen. The reaction mixture was stirred for 7 h at 130° C. and quenched with water (20 mL). The resulting solution was extracted with dichloromethane (3×30 mL) and the organic layers were combined, washed with brine (2×15 mL), dried over anhydrous Na$_2$SO$_4$, filtered and concentrated under reduced pressure. The residue was chromatographed on a silica gel column to provide 390 mg (37% yield) of tert-butyl 1-(3-(2-(tert-butoxy)-2-oxoethyl)-5-fluorobenzyl)-1,8-diazaspiro[4.5]decane-8-carboxylate. LCMS (ESI, m/z): 463 [M+H]$^+$.

Step 4: Synthesis of tert-butyl 1-(3-(1-(tert-butoxycarbonyl)cyclopentyl)-5-fluorobenzyl)-1,8-diazaspiro[4.5]decane-8-carboxylate

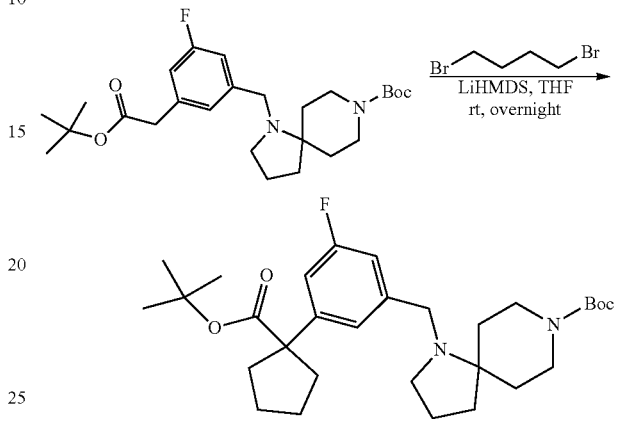

A 10-mL round-bottom flask was charged with tert-butyl 1-([3-[2-(tert-butoxy)-2-oxoethyl]-5-fluorophenyl]methyl)-1,8-diazaspiro[4.5]decane-8-carboxylate (100 mg, 0.216 mmol, 1.00 equiv) and tetrahydrofuran (2 mL) under nitrogen. Lithium bis(trimethylsilyl)amide (0.864 mL, 0.864 mmol, 4.00 equiv, 1M) was added dropwise at 0° C., followed by addition of 1,4-dibromobutane (93.3 mg, 0.432 mmol, 2.00 equiv). The reaction mixture was stirred overnight at room temperature and quenched with water (5 mL). The resulting solution was extracted with ethyl acetate (3×10 mL) and the organic layers were combined, washed with brine (2×5 mL), dried over anhydrous Na$_2$SO$_4$, filtered and concentrated under reduced pressure. The residue was chromatographed on a silica gel column to provide 50.0 mg (45% yield) of tert-butyl 1-(3-(1-(tert-butoxycarbonyl)cyclopentyl)-5-fluorobenzyl)-1,8-diazaspiro[4.5]decane-8-carboxylate as colorless oil. LCMS (ESI, m/z): 517 [M+H]$^+$.

Step 5: Synthesis of 1-(3-((1,8-diazaspiro[4.5]decan-1-yl)methyl)-5-fluorophenyl)cyclopentane-1-carboxylic acid

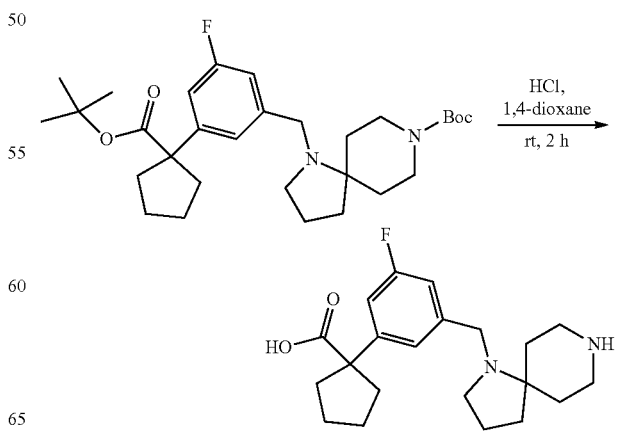

A 10-mL round-bottom flask was charged with tert-butyl 1-(3-(1-(tert-butoxycarbonyl)cyclopentyl)-5-fluorobenzyl)-1,8-diazaspiro[4.5]decane-8-carboxylate (50.0 mg, 0.967 mmol, 1.00 equiv), 1,4-dioxane (2 mL), and concentrated hydrochloric acid (0.5 mL). The resulting solution was stirred for 2 h at room temperature and concentrated under reduced pressure to provide 45.0 mg (crude) of 1-(3-((1,8-diazaspiro[4.5]decan-1-yl)methyl)-5-fluorophenyl)cyclopentane-1-carboxylic acid. LCMS (ESI, m/z): 361 [M+H]+.

Step 6: Synthesis of 1-(3-fluoro-5-((8-(((1,1,1,3,3,3-hexafluoropropan-2-yl)oxy)carbonyl)-1,8-diazaspiro[4.5]decan-1-yl)methyl)phenyl)cyclopentane-1-carboxylic acid

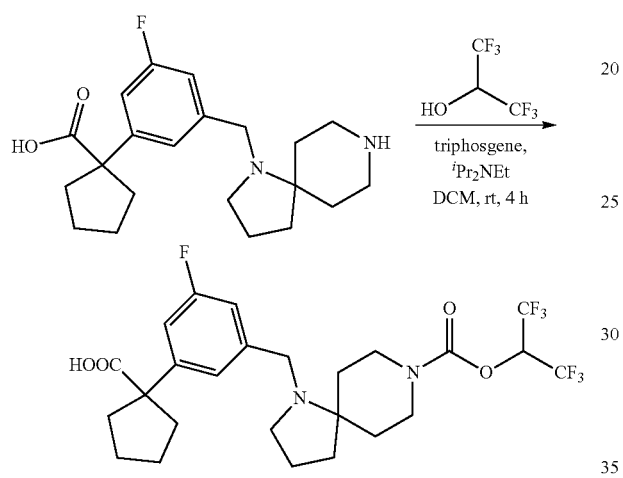

A 10-mL round-bottom flask was charged with triphosgene (14.0 mg, 0.0471 mmol, 0.50 equiv), dichloromethane (2 mL), and 1,1,1,3,3,3-hexafluoropropan-2-ol (31.7 mg, 0.189 mmol, 2.00 equiv). N,N-Diisopropylethylamine (48.7 mg, 0.378 mmol, 4.00 equiv) was added dropwise at 0° C., and the mixture was stirred for 2 h at room temperature prior to the addition of 1-(3-((1,8-diazaspiro[4.5]decan-1-yl)methyl)-5-fluorophenyl)cyclopentane-1-carboxylic acid (34.0 mg, 0.0944 mmol, 1.00 equiv). The reaction mixture was stirred for 2 h at room temperature and quenched with water (5 mL). The resulting solution was extracted with dichloromethane (3×10 mL) and the organic layers were combined, washed with brine (2×5 mL), dried over anhydrous Na$_2$SO$_4$, filtered and concentrated under reduced pressure. The crude product (60.0 mg) was purified by preparative HPLC to provide 10.6 mg (20% yield) of 1-(3-fluoro-5-((8-(((1,1,1,3,3,3-hexafluoropropan-2-yl)oxy)carbonyl)-1,8-diazaspiro[4.5]decan-1-yl)methyl)phenyl)cyclopentane-1-carboxylic acid. $^1$H NMR (300 MHz, Methanol-d$_4$) δ 7.22 (s, 1H), 7.05 (d, J=10.5 Hz, 1H), 6.95 (d, J=9.6 Hz, 1H), 6.11-6.19 (m, 1H), 4.21 (br, 2H), 3.74 (br, 2H), 3.02-3.18 (m, 2H), 2.82-2.86 (m, 2H), 2.760-2.64 (m, 2H), 1.95-2.00 (m, 2H), 1.72-1.90 (m, 10H), 1.58-1.62 (m, 2H). LCMS (ESI, m/z): 555 [M+H]+.

Example 5: 4-(2-((8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,2-dimethylbut-3-ynoic acid

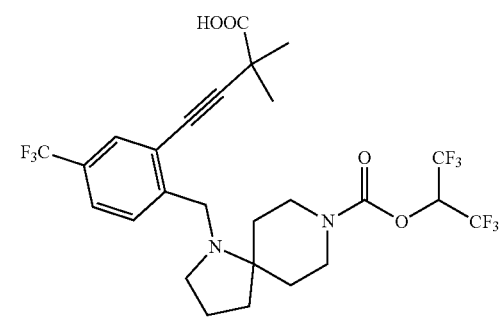 [SMILES: CC(C)(C#Cc1cc(C(F)(F)F)ccc1CN1CCCC12CCN(C(=O)OC(C(F)(F)F)C(F)(F)F)CC2)C(=O)O]

Step 1: Synthesis of tert-butyl 1-(2-iodo-4-(trifluoromethyl)benzyl)-1,8-diazaspiro[4.5]decane-8-carboxylate

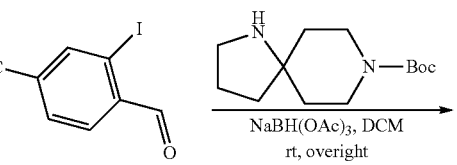

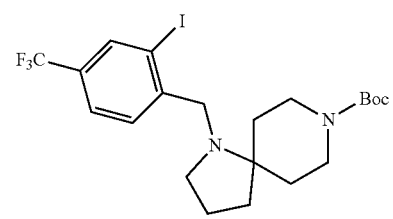

A 100-mL round-bottom flask was charged with 2-iodo-4-(trifluoromethyl)benzaldehyde (1.00 g, 3.33 mmol, 1.00 equiv), tert-butyl 1,8-diazaspiro[4.5]decane-8-carboxylate (0.960 g, 4.00 mmol, 1.20 equiv), and dichloromethane (25 mL). The mixture was stirred for 1 h at room temperature prior to addition of sodium triacetoxyborohydride (2.12 g, 10.0 mmol, 3.00 equiv). The reaction mixture was stirred overnight at room temperature and quenched with water (30 mL). The resulting solution was extracted with dichloromethane (3×50 mL) and the organic layers were combined, washed with brine (2×50 mL), dried over anhydrous Na$_2$SO$_4$, filtered and concentrated under reduced pressure. The residue was chromatographed on a silica gel column to provide 1.06 g (61% yield) of tert-butyl 1-(2-iodo-4-(trifluoromethyl)benzyl)-1,8-diazaspiro[4.5]decane-8-carboxylate. LCMS (ESI, m/z): 525 [M+H]+.

Step 2: Synthesis of tert-butyl 1-(2-(4-ethoxy-3,3-dimethyl-4-oxobut-1-yn-1-yl)-4-(trifluoromethyl)benzyl)-1,8-diazaspiro[4.5]decane-8-carboxylate

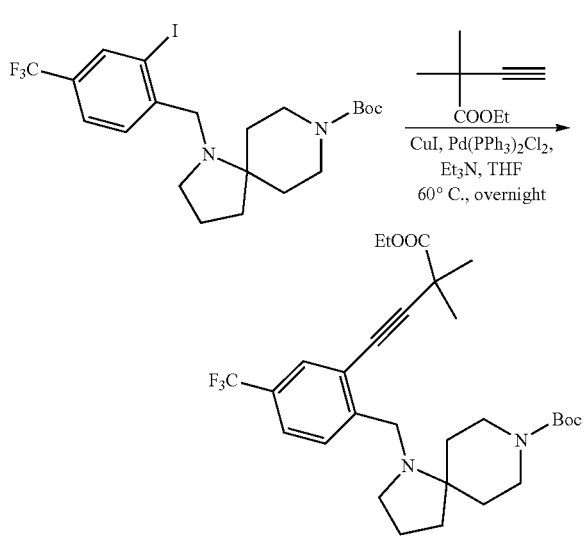

A 50-mL round-bottom flask was charged with tert-butyl 1-(2-iodo-4-(trifluoromethyl)benzyl)-1,8-diazaspiro[4.5]decane-8-carboxylate (498 mg, 0.950 mmol, 1.00 equiv), ethyl 2,2-dimethylbut-3-ynoate (200 mg, 1.43 mmol, 1.50 equiv), copper(I) iodide (18.1 mg, 0.0950 mmol, 0.10 equiv), bis(triphenylphosphine)palladium(II) chloride (133 mg, 0.190 mmol, 0.20 equiv), triethylamine (288 mg, 2.85 mmol, 3.00 equiv), and tetrahydrofuran (6 mL). The resulting solution was stirred overnight at 60° C. and quenched with water (15 mL). The mixture was extracted with DCM (3×30 mL) and the organic layers were combined, washed with brine (1×30 mL), dried over anhydrous Na$_2$SO$_4$, filtered and concentrated under reduced pressure. The residue was chromatographed on a silica gel column to provide 400 mg (78% yield) of tert-butyl 1-(2-(4-ethoxy-3,3-dimethyl-4-oxobut-1-yn-1-yl)-4-(trifluoromethyl)benzyl)-1,8-diazaspiro[4.5]decane-8-carboxylate. LCMS (ESI, m/z): 537 [M+H]$^+$.

Step 3: Synthesis of 4-(2-((8-(tert-butoxycarbonyl)-1,8-diazaspiro[4.5]decan-1-yl)methyl)-5-(trifluoromethyl)phenyl)-2,2-dimethylbut-3-ynoic acid

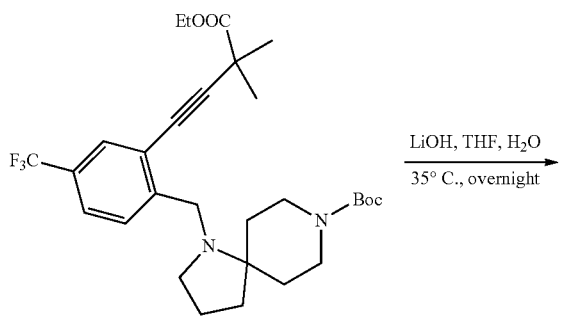

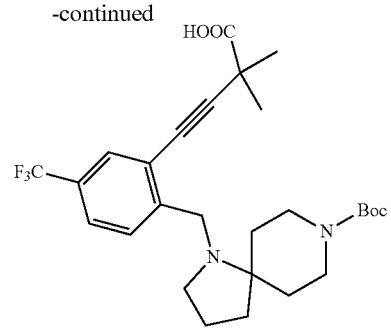

A 50-mL round-bottom flask was charged with tert-butyl 1-[[2-(4-ethoxy-3,3-dimethyl-4-oxobut-1-yn-1-yl)-4-(trifluoromethyl)phenyl]methyl]-1,8-diazaspiro[4.5]decane-8-carboxylate (400 mg, 0.746 mmol, 1.00 equiv), lithium hydroxide (269 mg, 11.2 mmol, 15.00 equiv), tetrahydrofuran (5 mL), and water (2 mL). The reaction mixture was stirred overnight at 35° C. and quenched with water (10 mL). The pH of the solution was adjusted to 6 with hydrochloric acid (1M). The resulting solution was extracted with dichloromethane (3×20 mL) and the organic layers were combined, washed with brine (1×40 mL), dried over anhydrous Na$_2$SO$_4$, filtered and concentrated under reduced pressure to provide 200 mg (53% yield) of 4-(2-((8-(tert-butoxycarbonyl)-1,8-diazaspiro[4.5]decan-1-yl)methyl)-5-(trifluoromethyl)phenyl)-2,2-dimethylbut-3-ynoic acid. LCMS (ESI, m/z): 509 [M+H]$^+$.

Step 4: Synthesis of 4-(2-((1,8-diazaspiro[4.5]decan-1-yl)methyl)-5-(trifluoromethyl)phenyl)-2,2-dimethylbut-3-ynoic acid

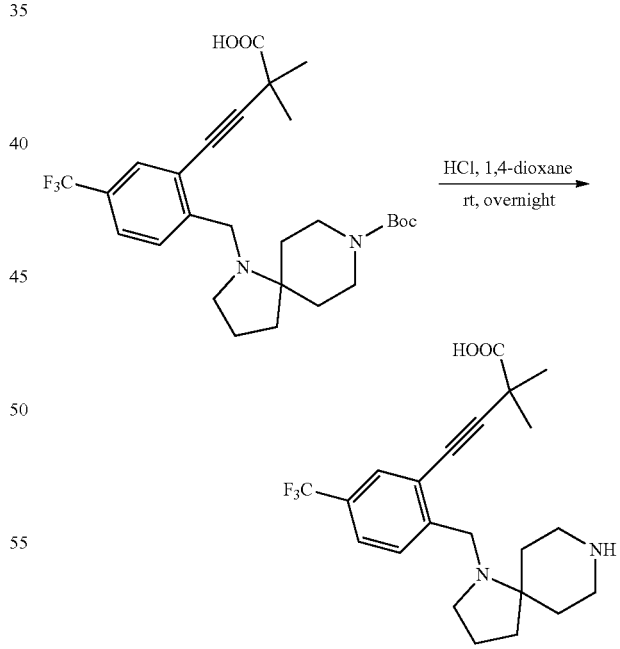

A 50-mL round-bottom flask was charged with 4-(2-((8-(tert-butoxycarbonyl)-1,8-diazaspiro[4.5]decan-1-yl)methyl)-5-(trifluoromethyl)phenyl)-2,2-dimethylbut-3-ynoic acid (200 mg, 0.394 mmol, 1.00 equiv), concentrated hydrochloride acid (2 mL), and 1,4-dioxane (8 mL). The resulting solution was stirred overnight at room temperature and concentrated under reduced pressure to provide 190 mg (crude) of 4-(2-((1,8-diazaspiro[4.5]decan-1-yl)methyl)-5-(trifluoromethyl)phenyl)-2,2-dimethylbut-3-ynoic acid. LCMS (ESI, m/z): 409 [M+H]+.

Step 5: Synthesis of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2,2-dimethylbut-3-ynoic acid

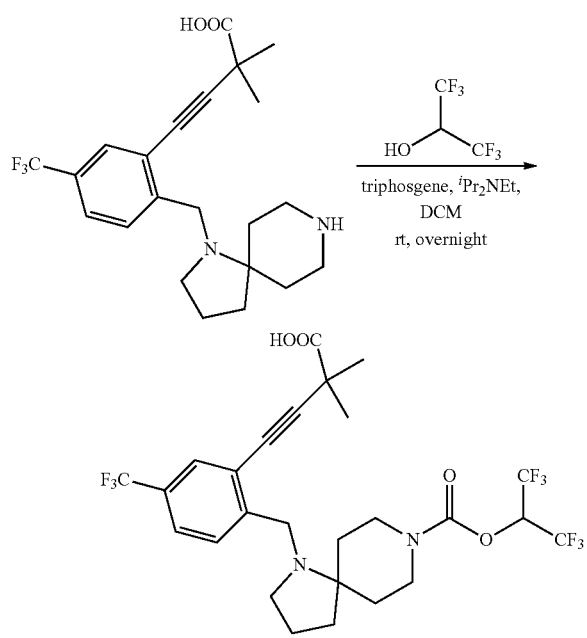

A 50-mL round-bottom flask was charged with triphosgene (76.6 mg, 0.258 mmol, 0.70 equiv) and dichloromethane (5 mL). 1,1,1,3,3,3-Hexafluoropropan-2-ol (124 mg, 0.736 mmol, 2.00 equiv) and N,N-diisopropylethylamine (191 mg, 1.48 mmol, 4.00 equiv) were added sequentially at 0° C. The mixture was stirred for 2 h at room temperature prior to the addition of 4-(2-((1,8-diazaspiro[4.5]decan-1-yl)methyl)-5-(trifluoromethyl)phenyl)-2,2-dimethylbut-3-ynoic acid (150 mg, 0.368 mmol, 1.00 equiv). The reaction mixture was stirred overnight at room temperature and quenched with water (50 mL). The resulting solution was extracted with dichloromethane (3×50 mL) and the organic layers were combined, washed with brine (1×100 mL), dried over anhydrous Na$_2$SO$_4$, filtered and concentrated under reduced pressure. The crude product (400 mg) was purified by preparative HPLC to provide 105 mg (47% yield) of 4-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2,2-dimethylbut-3-ynoic acid. $^1$H NMR (300 MHz, Methanol-d$_4$) δ 7.69-7.73 (m, 2H), 7.63 (d, J=8.4 Hz, 1H), 6.10-6.19 (m, 1H), 4.23-4.28 (m, 4H), 3.05-3.16 (m, 4H), 2.13-2.18 (m, 2H), 1.89-2.04 (m, 4H), 1.78-1.82 (m, 2H), 1.55 (s, 6H). LCMS (ESI, m/z): 603 [M+H]+.

Example 6: 2-(5-(2-((8-(((1,1,1,3,3,3-hexafluoropropan-2-yl)oxy)carbonyl)4,8-diazaspiro[4.5]decan-1-yl)methyl)-5-(trifluoromethyl)phenyl)-2,5-diazabicyclo[2.2.1]heptan-2-yl)acetic acid

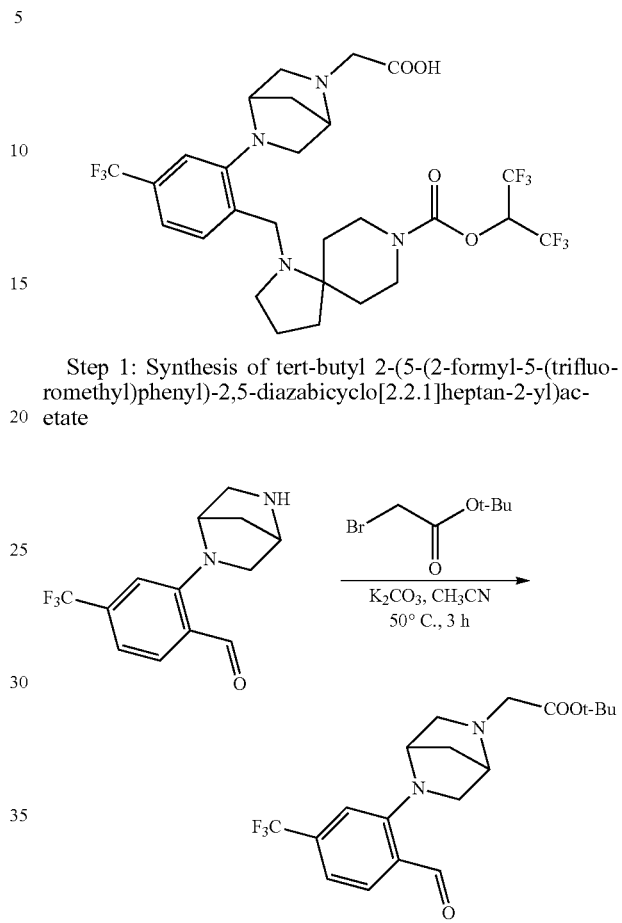

Step 1: Synthesis of tert-butyl 2-(5-(2-formyl-5-(trifluoromethyl)phenyl)-2,5-diazabicyclo[2.2.1]heptan-2-yl)acetate A 50-mL round-bottom flask was charged with 2-[2,5-diazabicyclo[2.2.1]heptan-2-yl]-4-(trifluoromethyl)benzaldehyde (1.00 g, 3.70 mmol, 1.00 equiv), acetonitrile (15 mL), tert-butyl 2-bromoacetate (0.861 g, 4.41 mmol, 1.20 equiv), and potassium carbonate (1.53 g, 11.1 mmol, 3.00 equiv) The reaction mixture was stirred for 3 h at 50° C. and quenched with water (50 mL). The resulting solution was extracted with ethyl acetate (2×80 mL) and the organic layers were combined, washed with brine (2×50 mL), dried over anhydrous Na$_2$SO$_4$, filtered and concentrated under reduced pressure. The residue was chromatographed on a silica gel column to provide 800 mg (56% yield) of tert-butyl 2-(5-(2-formyl-5-(trifluoromethyl)phenyl)-2,5-diazabicyclo[2.2.1]heptan-2-yl)acetate. LCMS (ESI, m/z): 385 [M+H]+.

Step 2: Synthesis of 1,1,1,3,3,3-hexafluoropropan-2-yl 1-(2-(5-(2-(tert-butoxy)-2-oxoethyl)-2,5-diazabicyclo[2.2.1]heptan-2-yl)-4-(trifluoromethyl)benzyl)-1,8-diazaspiro[4.5]decane-8-carboxylate

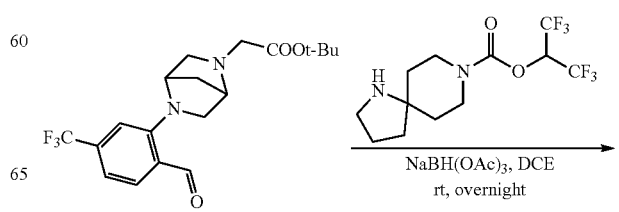

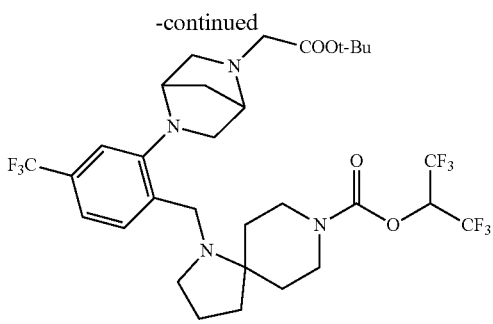

A 50-mL round-bottom flask was charged with tert-butyl 2-(5-(2-formyl-5-(trifluoromethyl)phenyl)-2,5-diazabicyclo[2.2.1]heptan-2-yl)acetate (384 mg, 1.00 mmol, 1.00 equiv), 1,1,1,3,3,3-hexafluoropropan-2-yl 1,8-diazaspiro[4.5]decane-8-carboxylate (334 mg, 1.00 mmol, 1.00 equiv), and 1,2-dichloroethane (10 mL). The mixture was stirred for 1 h at room temperature prior to the addition of sodium triacetoxyborohydride (636 mg, 3.00 mmol, 3.00 equiv). The resulting solution was stirred overnight at room temperature and quenched with water (10 mL). The mixture was extracted with ethyl acetate (3×30 mL) and the organic layers were combined, washed with brine (2×30 mL), dried over anhydrous $Na_2SO_4$, filtered and concentrated under reduced pressure. The residue was chromatographed on a silica gel column to provide 470 mg (67% yield) of 1,1,1,3,3,3-hexafluoropropan-2-yl 1-(2-(5-(2-(tert-butoxy)-2-oxoethyl)-2,5-diazabicyclo[2.2.1]heptan-2-yl)-4-(trifluoromethyl)benzyl)-1,8-diazaspiro[4.5]decane-8-carboxylate. LCMS (ESI, m/z): 703 [M+H]+.

Step 3: Synthesis of 2-(5-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2,5-diazabicyclo[2.2.1]heptan-2-yl)acetic acid

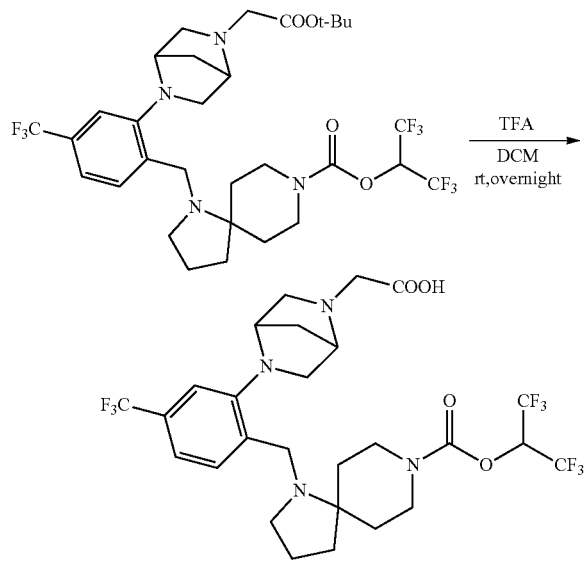

A 50-mL round-bottom flask was charged with 1,1,1,3,3,3-hexafluoropropan-2-yl 1-[(2-[5-[2-(tert-butoxy)-2-oxoethyl]-2,5-diazabicyclo[2.2.1]heptan-2-yl]-4-(trifluoromethyl)phenyl)methyl]-1,8-diazaspiro[4.5]decane-8-carboxylate (200 mg, 0.280 mmol, 1.00 equiv), dichloromethane (5 mL), and trifluoroacetic acid (1 mL). The resulting solution was stirred overnight at room temperature and concentrated under reduced pressure. The crude product (600 mg) was purified by preparative HPLC to afford 87.6 mg (48% yield) of 2-(5-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)-2,5-diazabicyclo[2.2.1]heptan-2-yl)acetic acid. $^1$H NMR (300 MHz, Methanol-$d_4$) δ 7.75 (d, J=8.0 Hz, 1H), 7.22-7.24 (m, 2H), 6.08-6.16 (m, 1H), 4.42-4.86 (m, 2H), 4.17-4.22 (m, 2H), 3.66-3.83 (m, 6H), 3.47-3.61 (m, 1H), 3.31-3.37 (m, 1H), 3.08-3.16 (m, 2H), 2.63-2.67 (m, 2H), 2.20-2.31 (m, 2H), 1.94-1.98 (m, 2H), 1.78-1.89 (m, 4H), 1.57 -1.70 (m, 2H). LCMS (ESI, m/z): 647 [M+H]+.

Example 7: 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)cyclopentane-1-carboxylic acid

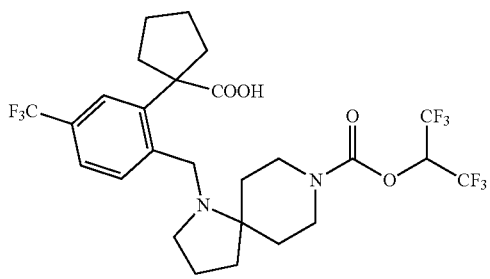 [SMILES: O=C(OC(C(F)(F)F)C(F)(F)F)N1CCC2(CCCN2Cc2ccc(C(F)(F)F)cc2C2(C(=O)O)CCCC2)CC1]

Step 1: Synthesis of tert-butyl 1-(2-(2-(tert-butoxy)-2-oxoethyl)-4-(trifluoromethyl)benzyl)-1,8-diazaspiro[4.5]decane-8-carboxylate

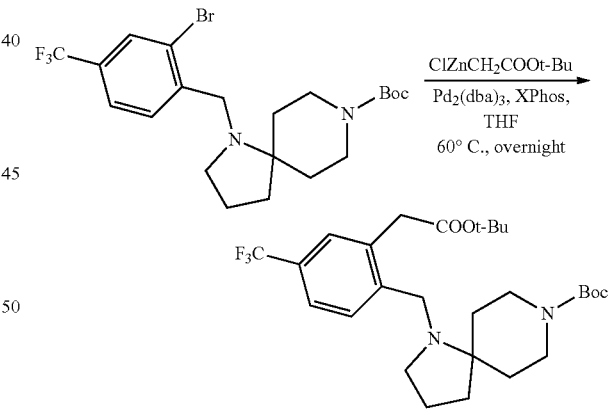

A 50-mL round-bottom flask was charged with tert-butyl 1-[[2-bromo-4-(trifluoromethyl)phenyl]methyl]-1,8-diazaspiro[4.5]decane-8-carboxylate (270 mg, 0.567 mmol, 1.00 equiv), (2-tert-butoxy-2-oxoethyl)zinc(II) chloride (3.4 mL, 3.00 equiv, 0.5M in ethylether), tris(dibenzylideneacetone)dipalladium (51.8 mg, 0.0567 mmol, 0.10 equiv), 2-(dicyclohexylphosphino)-2',4',6'-triisopropylbiphenyl (Xphos, 54.0 mg, 0.113 mmol, 0.20 equiv), and tetrahydrofuran (5 mL). The reaction mixture was stirred overnight at 60° C. and quenched with water (5 mL). The resulting solution was extracted with ethyl acetate (3×10 mL) and the organic layers were combined, washed with brine (2×5 mL), dried over anhydrous Na₂SO₄, filtered and concentrated under reduced pressure. The residue was chromatographed on a silica gel column to provide 300 mg (crude) of tert-butyl 1-([2-[2-(tert-butoxy)-2-oxoethyl]-4-(trifluoromethyl)phenyl]methyl)-1,8-diazaspiro[4.5]decane-8-carboxylate as brown oil. LCMS (ESI, m/z): 513 [M+H]⁺.

Step 2: Synthesis of 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)cyclopentane-1-carboxylic acid

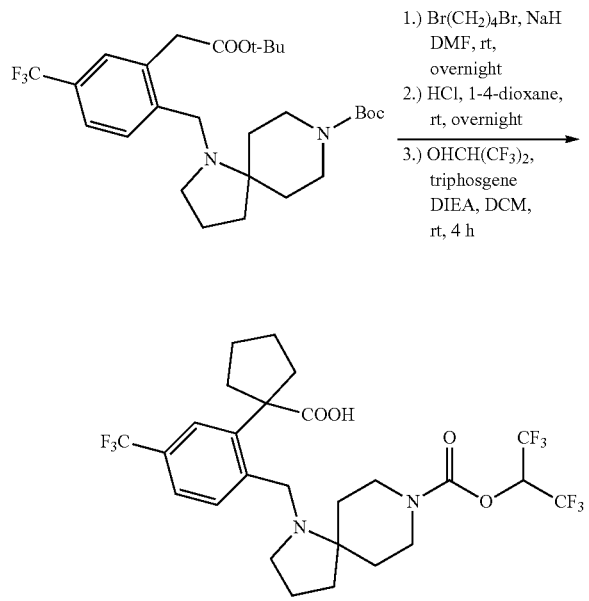

The target compound was prepared as described in Example 4, Steps 4 through 6 (using NaH instead of LiHMDS in Step 4) to provide 9.1 mg (9% yield) of 1-(2-((8-(((1,1,1,3,3,3-hexafluoropropan-2-yl)oxy)carbonyl)-1,8-diazaspiro[4.5]decan-1-yl)methyl)-5-(trifluoromethyl)phenyl)cyclopentane-1-carboxylic acid. ¹H NMR (300 MHz, Methanol-d₄) δ 7.80 (s, 1H), 7.70 (d, J=7.8 Hz, 1H), 7.57 (d, J=7.8 Hz, 1H), 6.17-6.25 (m, 1H), 4.27-4.39 (m, 4H), 3.11-3.28 (m, 2H), 2.88-2.93 (m, 4H), 1.83-2.26 (m, 14H). LCMS (ESI, m/z): 605 [M+H]⁺.

Example 8: 1-(3-((8-(((1,1,1,3,3,3-Hexafluoropropan-2-yl)oxy)carbonyl)-1,8-diazaspiro[4.5]decan-1-yl)methyl)-5-(trifluoromethyl)phenyl)cyclopentane-1-carboxylic acid

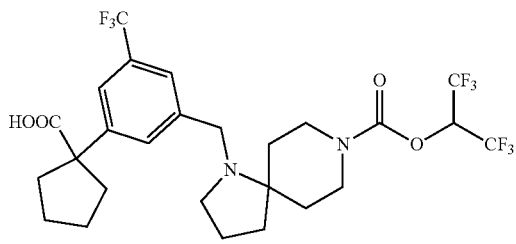 [SMILES: O=C(OC(C(F)(F)F)C(F)(F)F)N1CCC2(CCCN2Cc2cc(C(F)(F)F)cc(C3(C(=O)O)CCCC3)c2)CC1]

Step 1: Synthesis of tert-butyl 2-(3-bromo-5-(trifluoromethyl)phenyl)acetate

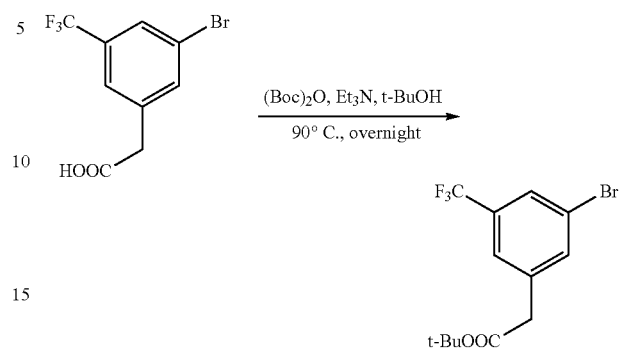

A 250-mL round-bottom flask was charged with 2-[3-bromo-5-(trifluoromethyl)phenyl]acetic acid (6.00 g, 21.2 mmol, 1.00 equiv), tert-butanol (80 mL), triethylamine (6.45 g, 63.7 mmol, 3.00 equiv), and di-tert-butyl dicarbonate (9.28 g, 42.5 mmol, 2.00 equiv). The reaction mixture was stirred overnight at 90° C. and quenched with water (60 mL). The resulting mixture was extracted with ethyl acetate (3×90 mL) and the organic layers were combined, washed with brine (2×100 mL), dried over anhydrous Na₂SO₄, filtered and concentrated under reduced pressure. The residue was chromatographed on a silica gel column to provide 4.80 g (67% yield) of tert-butyl 2-(3-bromo-5-(trifluoromethyl)phenyl)acetate. ¹H NMR (300 MHz, Chloroform-d) δ 7.67 (s, 1H), 7.62 (s, 1H), 7.48 (s, 1H), 3.56 (s, 2H), 1.45 (s, 9H).

Step 2: Synthesis of tert-butyl 1-(3-bromo-5-(trifluoromethyl)phenyl)cyclopentane-1-carboxylate

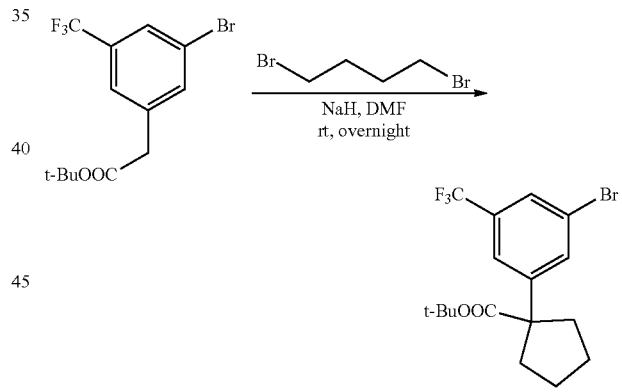

A 100-mL round-bottom flask was charged with tert-butyl 2-(3-bromo-5-(trifluoromethyl)phenyl)acetate (4.80 g, 14.2 mmol, 1.00 equiv), N,N-dimethylformamide (40 mL). Sodium hydride (2.27 g, 60% in mineral oil, 56.7 mmol, 4.00 equiv) was added at 0° C. and the mixture was stirred for 10 min at 0° C. prior to the subsequent addition of 1,4-dibromobutane (4.56 g, 21.3 mmol, 1.50 equiv). The reaction mixture was stirred overnight at room temperature and quenched with water (60 mL). The resulting solution was extracted with ethyl acetate (3×100 mL) and the organic layers were combined, washed with brine (1×100 mL), dried over anhydrous Na₂SO₄, filtered and concentrated under reduced pressure. The residue was chromatographed on a silica gel column to provide 3.10 g (56% yield) of tert-butyl 1-(3-bromo-5-(trifluoromethyl)phenyl)cyclopentane-1-carboxylate. ¹H NMR (400 MHz, Chloroform-d) δ 7.69 (s, 1H), 7.65 (s, 1H), 7.55 (s, 1H), 2.62-2.67 (m, 2H), 1.75-1.86 (m, 6H), 1.37 (s, 9H).

Step 3: Synthesis of tert-butyl 1-(3-formyl-5-(trifluoromethyl)phenyl)cyclopentane-1-carboxylate

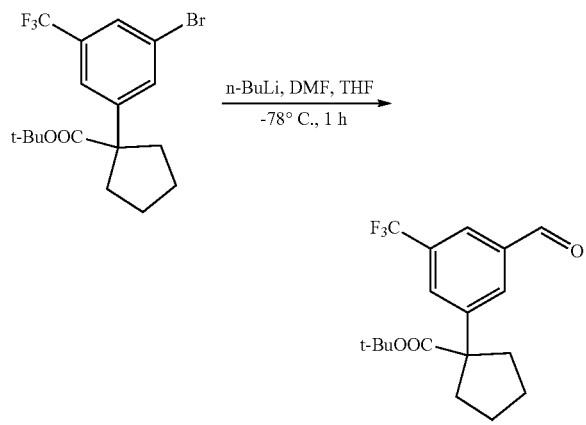

A 100-mL round-bottom flask was charged with tert-butyl 1-(3-bromo-5-(trifluoromethyl)phenyl)cyclopentane-1-carboxylate (3.10 g, 7.89 mmol, 1.00 equiv), and tetrahydrofuran (30 mL) under nitrogen. n-Butyllithium (4.11 mL, 2.5M in n-hexane, 10.3 mmol, 1.30 equiv) was added dropwise at −78° C., and the resulting solution was stirred for 30 min at −78° C. N,N-Dimethylformamide (2.89 g, 39.5 mmol, 5.00 equiv) was added at −78° C., and the reaction mixture was stirred for 30 min at −78° C. before quenching with saturated NH₄Cl solution (30 mL). The resulting solution was extracted with ethyl acetate (3×100 mL) and the organic layers were combined, washed with brine (1×100 mL), dried over anhydrous Na₂SO₄, filtered and concentrated under reduced pressure. The residue was chromatographed on a silica gel column to provide 2.00 g (74% yield) of tert-butyl 1-(3-formyl-5-(trifluoromethyl)phenyl)cyclopentane-1-carboxylate. ¹H NMR (300 MHz, Chloroform-d) δ 10.03 (s, 1H), 8.07 (s, 1H), 8.03 (s, 1H), 7.90 (s, 1H), 2.69-2.75 (m, 2H), 1.78-1.93 (m, 6H), 1.45 (s, 9H).

Step 4: Synthesis of 1,1,1,3,3,3-hexafluoropropan-2-yl 1-(3-(1-(tert-butoxycarbonyl)cyclopentyl)-5-(trifluoromethyl)benzyl)-1,8-diazaspiro[4.5]decane-8-carboxylate

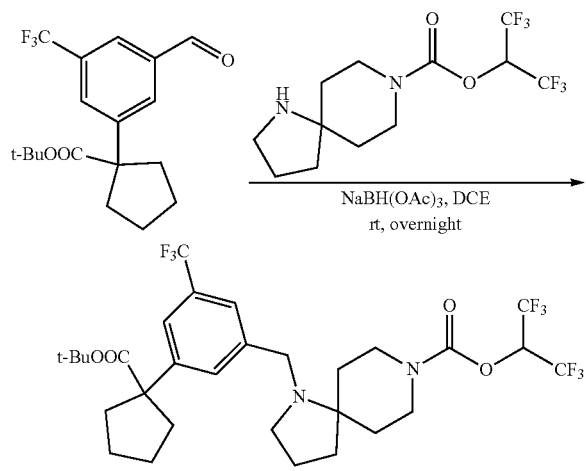

A 50-mL round-bottom flask was charged with tert-butyl 1-(3-formyl-5-(trifluoromethyl)phenyl)cyclopentane-1-carboxylate (1.75 g, 5.11 mmol, 1.00 equiv), 1,1,1,3,3,3-hexafluoropropan-2-yl 1,8-diazaspiro[4.5]decane-8-carboxylate (1.88 g, 5.62 mmol, 1.10 equiv), and 1,2-dichloroethane (30 mL). The mixture was stirred for 1 h at room temperature prior to addition of sodium triacetoxyborohydride (3.25 g, 15.3 mmol, 3.00 equiv). The reaction mixture was stirred overnight at room temperature and quenched with water (50 mL). The resulting solution was extracted with dichloromethane (3×100 mL) and the organic layers were combined, washed with brine (1×100 mL), dried over anhydrous Na₂SO₄, filtered and concentrated under reduced pressure. The residue was chromatographed on a silica gel column to provide 2.10 g (62% yield) of 1,1,1,3,3,3-hexafluoropropan-2-yl 1-(3-(1-(tert-butoxycarbonyl)cyclopentyl)-5-(trifluoromethyl)benzyl)-1,8-diazaspiro[4.5]decane-8-carboxylate. LCMS (ESI, m/z): 661 [M+H]⁺.

Step 5: Synthesis of 1-(3-((8-(((1,1,1,3,3,3-hexafluoropropan-2-yl)oxy)carbonyl)-1,8-diazaspiro[4.5]decan-1-yl)methyl)-5-(trifluoromethyl)phenyl)cyclopentane-1-carboxylic acid

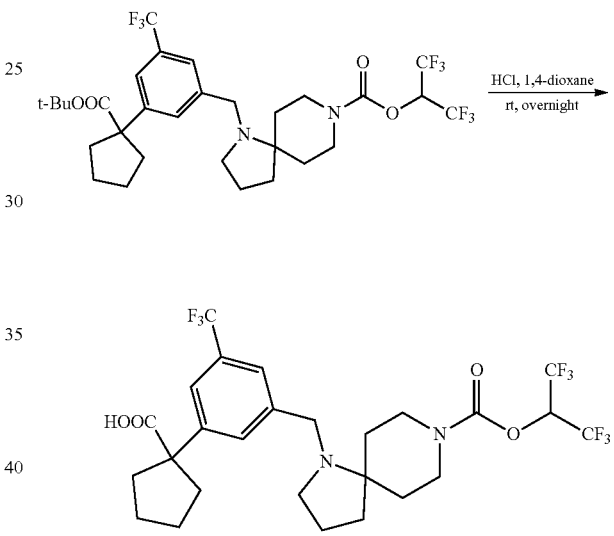

A 250-mL round-bottom flask was charged with 1,1,1,3,3,3-hexafluoropropan-2-yl 1-(3-(1-(tert-butoxycarbonyl)cyclopentyl)-5-(trifluoromethyl)benzyl)-1,8-diazaspiro[4.5]decane-8-carboxylate (2.10 g, 3.18 mmol, 1.00 equiv), 1,4-dioxane (90 mL), and concentrated hydrochloric acid (60 mL). The reaction mixture was stirred overnight at room temperature and concentrated under reduced pressure. The crude product was dissolved in saturated aqueous NaHCO₃ (60 mL). The resulting mixture was extracted with dichloromethane (3×80 mL) and the organic layers were combined, washed with brine (1×80 mL), dried over anhydrous Na₂SO₄, filtered and concentrated under reduced pressure. The crude product (2.00 g) was purified by preparative HPLC to afford 1.11 g (58% yield) of 1-[3-[(8-[[(1,1,1,3,3,3-hexafluoropropan-2-yl)oxy]carbonyl]-1,8-diazaspiro[4.5]decan-1-yl)methyl]-5-(trifluoromethyl)phenyl]cyclopentane-1-carboxylic acid as a white solid. ¹H NMR (400 MHz, Methanol-d₄) δ 7.69 (s, 1H), 7.61 (s, 1H), 7.57 (s, 1H), 6.12-6.22 (m, 1H), 4.21-4.26 (m, 2H), 3.91 (s, 2H), 3.06-3.20 (m, 2H), 2.88-2.91 (m, 2H), 2.68-2.73 (m, 2H), 2.01-2.05 (m, 2H), 1.82-1.96 (m, 6H), 1.70-1.80 (m, 4H), 1.63-1.69 (m, 2H). LCMS (ESI, m/z): 605 [M+H]⁺.

Example 9: 1-(2-Chloro-6-(((1-(((1,1,1,3,3,3-hexafluoropropan-2-yl)oxy)carbonyl)-4-methylpiperidin-4-yl)(methyl)amino)methyl)phenyl)cyclopentane-1-carboxylic acid

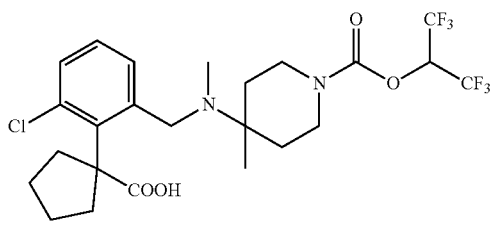 [SMILES: CN(Cc1cccc(Cl)c1C1(C(=O)O)CCCC1)C1(C)CCN(C(=O)OC(C(F)(F)F)C(F)(F)F)CC1]

Step 1: Synthesis of tert-butyl 4-((2-bromo-3-chlorobenzyl)amino)-4-methylpiperidine-1-carboxylate

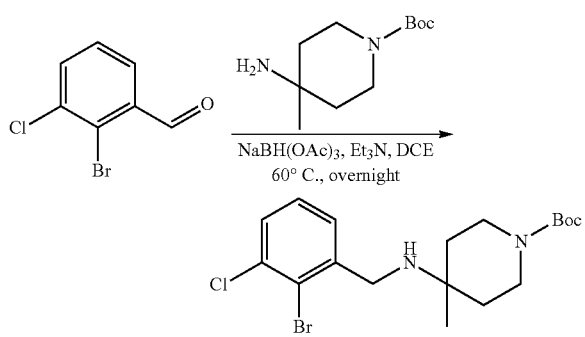

A 100-mL round-bottom flask was charged with 2-bromo-3-chlorobenzaldehyde (1.00 g, 4.56 mmol, 1.00 equiv), tert-butyl 4-amino-4-methylpiperidine-1-carboxylate (1.08 g, 5.04 mmol, 1.10 equiv), 1,2-dichloroethane (20 mL), and triethylamine (1.39 g, 13.7 mmol, 3.00 equiv). The mixture was stirred for 1 h at 60° C. prior to addition of sodium triacetoxyborohydride (2.92 g, 13.8 mmol, 3.00 equiv). The reaction mixture was stirred overnight at 60° C. and quenched with water (20 mL). The resulting solution was extracted with dichloromethane (3×20 mL) and the organic layers were combined, washed with brine (2×20 mL), dried over anhydrous Na$_2$SO$_4$, filtered and concentrated under reduced pressure to provide 2.10 g (crude) of tert-butyl 4-((2-bromo-3-chlorobenzyl)amino)-4-methylpiperidine-1-carboxylate. LCMS (ESI, m/z): 417 [M+H]$^+$.

Step 2: Synthesis of tert-butyl 4-((2-bromo-3-chlorobenzyl)(methyl)amino)-4-methylpiperidine-1-carboxylate

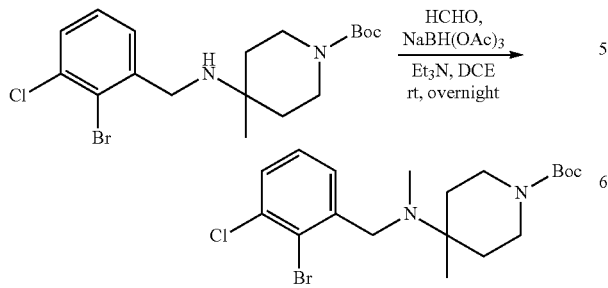

A 100-mL round-bottom flask was charged with tert-butyl 4-((2-bromo-3-chlorobenzyl)amino)-4-methylpiperidine-1-carboxylate (1.91 g, 4.57 mmol, 1.00 equiv), paraformaldehyde (1.38 g, 46.0 mmol, 10.0 equiv), 1,2-dichloroethane (20 mL), and triethylamine (1.39 g, 13.8 mmol, 3.00 equiv). The resulting solution was stirred for 1 h at room temperature prior to addition of sodium triacetoxyborohydride (2.93 g, 13.8 mmol, 3.00 equiv). The reaction mixture was stirred overnight at room temperature and quenched with water (20 mL). The resulting solution was extracted with dichloromethane (3×20 mL) and the organic layers were combined, washed with brine (2×20 mL), dried over anhydrous Na$_2$SO$_4$, filtered and concentrated under reduced pressure. The residue was chromatographed on a silica gel column to provide 1.12 g (57% yield) of tert-butyl 4-((2-bromo-3-chlorobenzyl)(methyl)amino)-4-methylpiperidine-1-carboxylate. LCMS (ESI, m/z): 431 [M+H]$^+$.

Step 3: Synthesis of tert-butyl 4-((2-(2-(tert-butoxy)-2-oxoethyl)-3-chlorobenzyl)(methyl)amino)-4-methylpiperidine-1-carboxylate

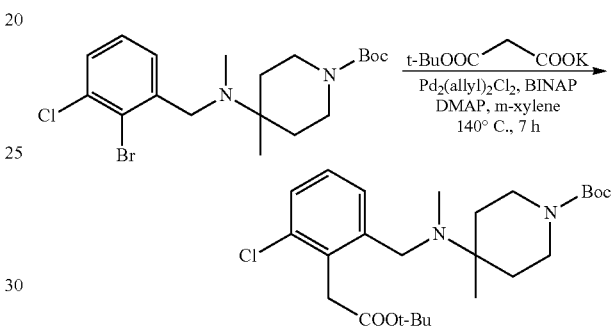

A 100-mL round-bottom flask was charged with tert-butyl 4-((2-bromo-3-chlorobenzyl)(methyl)amino)-4-methylpiperidine-1-carboxylate (1.12 g, 2.59 mmol, 1.00 equiv), potassium 3-(tert-butoxy)-3-oxopropanoate (1.03 g, 6.84 mmol, 2.00 equiv), allylpalladium chloride dimer (38.1 mg, 0.100 mmol, 0.04 equiv), 2,2'-bis(diphenylphosphino)-1,1'-binaphthyl (194 mg, 0.310 mmol, 0.12 equiv), 4-dimethylaminopyridine (31.7 mg, 0.260 mmol, 0.10 equiv), and m-xylene (10 mL). The resulting solution was stirred for 7 h at 140° C. and concentrated under reduced pressure. The residue was chromatographed on a silica gel column to provide 534 mg (51% yield) of tert-butyl 4-((2-(2-(tert-butoxy)-2-oxoethyl)-3-chlorobenzyl)(methyl)amino)-4-methylpiperidine-1-carboxylate. LCMS (ESI, m/z): 467 [M+H]$^+$.

Step 4: Synthesis of tert-butyl 4-((2-(1-(tert-butoxycarbonyl)cyclopentyl)-3-chlorobenzyl)(methyl)amino)-4-methylpiperidine-1-carboxylate

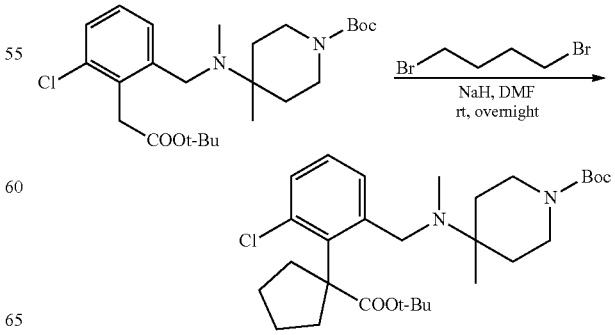

A 100-mL round-bottom flask was charged with tert-butyl 4-((2-(2-(tert-butoxy)-2-oxoethyl)-3-chlorobenzyl)(methyl)amino)-4-methylpiperidine-1-carboxylate (534 mg, 1.14 mmol, 1.00 equiv), N,N-dimethylformamide (10 mL), sodium hydride (183 mg, 4.58 mmol, 4.00 equiv, 60% in mineral oil), and 1,4-dibromobutane (492 mg, 2.28 mmol, 2.00 equiv). The reaction mixture was stirred overnight at room temperature and quenched with water (10 mL). The resulting solution was extracted with ethyl acetate (3×10 mL) and the organic layers were combined, washed with brine (2×10 mL), dried over Na$_2$SO$_4$, filtered and concentrated under reduced pressure. The residue was chromatographed on a silica gel column to provide 209 mg (35% yield) tert-butyl 4-((2-(1-(tert-butoxycarbonyl)cyclopentyl)-3-chlorobenzyl)(methyl)amino)-4-methylpiperidine-1-carboxylate. LCMS (ESI, m/z): 521 [M+H]$^+$.

Step 5: Synthesis of 1-(2-chloro-6-((methyl(4-methylpiperidin-4-yl)amino)methyl)phenyl)cyclopentane-1-carboxylic acid

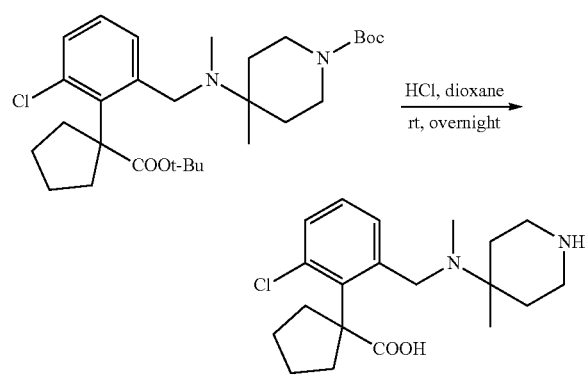

A 50-mL round-bottom flask was charged tert-butyl 4-((2-(1-(tert-butoxycarbonyl)cyclopentyl)-3-chlorobenzyl)(methyl)amino)-4-methylpiperidine-1-carboxylate (209 mg, 0.400 mmol, 1.00 equiv), 1,4-dioxane (5 mL), and concentrated hydrochloric acid (1 mL). The resulting solution was stirred overnight at room temperature and concentrated under reduced pressure to provide 200 mg (crude) of 1-(2-chloro-6-((methyl(4-methylpiperidin-4-yl)amino)methyl)phenyl)cyclopentane-1-carboxylic acid. LCMS (ESI, m/z): 365 [M+H]$^+$.

Step 6: Synthesis of 1-(2-chloro-6-(((1-(((1,1,1,3,3,3-hexafluoropropan-2-yl)oxy)carbonyl)-4-methylpiperidin-4-yl)(methyl)amino)methyl)phenyl)cyclopentane-1-carboxylic acid

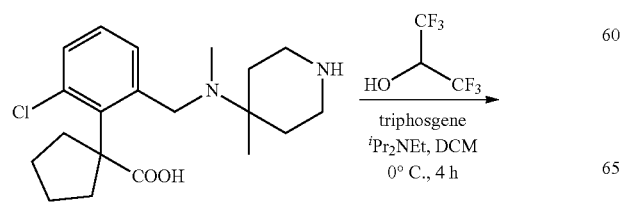

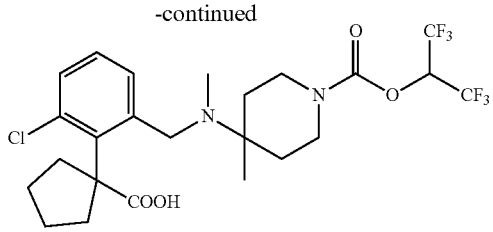

A 50-mL round-bottom flask was charged with triphosgene (83.6 mg, 0.280 mmol, 0.70 equiv), dichloromethane (10 mL), and 1,1,1,3,3,3-hexafluoropropan-2-ol (142 mg, 0.850 mmol, 2.10 equiv). N,N-Diisopropylethylamine (156 mg, 1.21 mmol, 3.00 equiv) was added dropwise at 0° C., and the resulting solution was stirred for 2 h at 0° C. prior to addition of 1-(2-chloro-6-((methyl(4-methylpiperidin-4-yl)amino)methyl)phenyl)cyclopentane-1-carboxylic acid (146 mg, 0.400 mmol, 1.00 equiv). The reaction mixture was stirred for 2 h at 0° C. and quenched with water (10 mL). The mixture was extracted with dichloromethane (3×10 mL) and the organic layers were combined, washed with brine (2×10 mL), dried over anhydrous Na$_2$SO$_4$, filtered and concentrated under reduced pressure. The crude product (300 mg) was purified by preparative HPLC to afford 110.2 mg (49% yield) of 1-(2-chloro-6-(((1-(((1,1,1,3,3,3-hexafluoropropan-2-yl)oxy)carbonyl)-4-methylpiperidin-4-yl)(methyl)amino)methyl)phenyl)cyclopentane-1-carboxylic acid. $^1$H NMR (300 MHz, Methanol-d$_4$) δ 7.47-7.45 (m, 1H), 7.37-7.40 (m, 1H), 7.16-7.21 (m, 1H), 6.10-6.19 (m, 1H), 4.37 (br, 2H), 3.96-4.00 (m, 2H), 3.35-3.43 (m, 2H), 3.04 (br, 2H), 1.96-2.01 (m, 9H), 1.71-1.79 (m, 4H), 1.39 (s, 3H). LCMS (ESI, m/z): 559 [M+H]$^+$.

Example 10: 1-(2-(8-(((1,1,1,3,3,3-Hexafluoropropan-2-yl)oxy)carbonyl)-1,8-diazaspiro[4.5]decane-1-carbonyl)-5-(trifluoromethyl)benzyl)piperidine-4-carboxylic acid

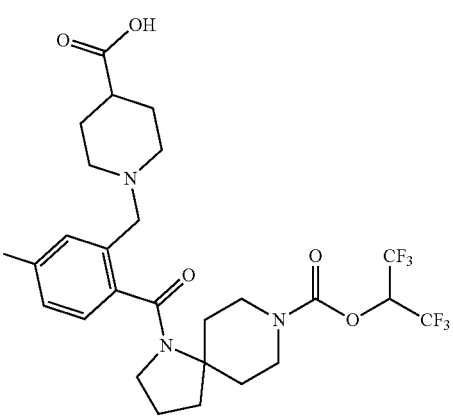

Step 1: Synthesis of tert-butyl 1-(2-bromo-4-(trifluoromethyl)benzoyl)-1,8-diazaspiro[4.5]decane-8-carboxylate

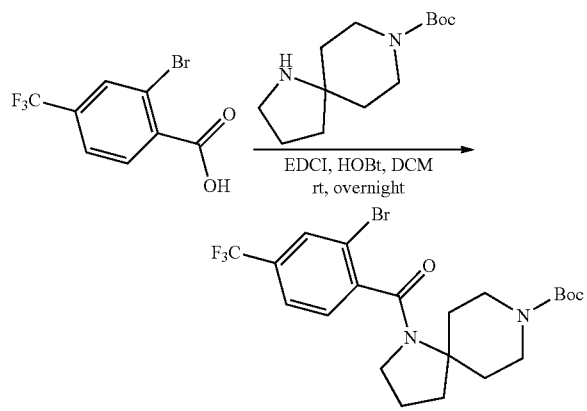

A 100-mL round-bottom flask was charged with 2-bromo-4-(trifluoromethyl)benzoic acid (1.00 g, 3.72 mmol, 1.00 equiv), dichloromethane (25 mL), N-(3-dimethylaminopropyl)-N'-ethylcarbodiimide hydrochloride (856 mg, 4.46 mmol, 1.20 equiv), and 1-hydroxybenzotrizole (602 mg, 4.46 mmol, 1.20 equiv). The mixture was stirred for 2 h at room temperature prior to addition of tert-butyl 1,8-diazaspiro[4.5]decane-8-carboxylate (1.07 g, 4.46 mmol, 1.20 equiv). The reaction mixture was stirred overnight at room temperature and quenched with water (20 mL). The resulting solution was extracted with DCM (3×35 mL) and the organic layers were combined, washed with brine (1×30 mL), dried over anhydrous Na$_2$SO$_4$, filtered and concentrated under reduced pressure. The residue was chromatographed on a silica gel column to provide 1.10 g (60% yield) of tert-butyl 1-(2-bromo-4-(trifluoromethyl)benzoyl)-1,8-diazaspiro[4.5]decane-8-carboxylate. LCMS (ESI, m/z): 491 [M+H]$^+$.

Step 2: Synthesis of tert-butyl 1-(2-formyl-4-(trifluoromethyl)benzoyl)-1,8-diazaspiro[4.5]decane-8-carboxylate

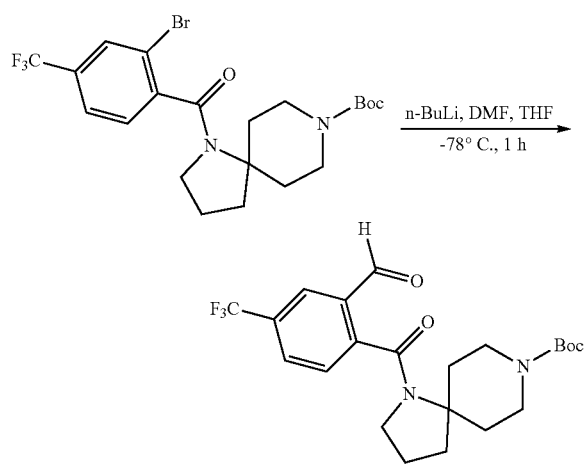

A 100-mL round-bottom flask was charged with tert-butyl 1-(2-bromo-4-(trifluoromethyl)benzoyl)-1,8-diazaspiro[4.5]decane-8-carboxylate (400 mg, 0.815 mmol, 1.00 equiv), and THF (15 mL) under nitrogen. n-Butyllithium (1.3 mL, 2.5 M in hexane, 3.26 mmol, 4.00 equiv) was added at −78° C. and the mixture was stirred for 30 min at −78° C. prior to addition of N,N-dimethylformamide (179 mg, 2.45 mmol, 3.00 equiv). The mixture continued to stir for 30 min at −78° C., then quenched with saturated ammonium chloride solution (10 mL). The resulting solution was extracted with DCM (3×30 mL) and the organic layers were combined, washed with brine (1×30 mL), dried over anhydrous Na$_2$SO$_4$, filtered and concentrated under reduced pressure. The residue was chromatographed on a silica gel column to provide 130 mg (36% yield) of tert-butyl 1-(2-formyl-4-(trifluoromethyl)benzoyl)-1,8-diazaspiro[4.5]decane-8-carboxylate. LCMS (ESI, m/z): 441 [M+H]$^+$.

Step 3: Synthesis of tert-butyl 1-(2-((4-(tert-butoxycarbonyl)piperidin-1-yl)methyl)-4-(trifluoromethyl)benzoyl)-1,8-diazaspiro[4.5]decane-8-carboxylate

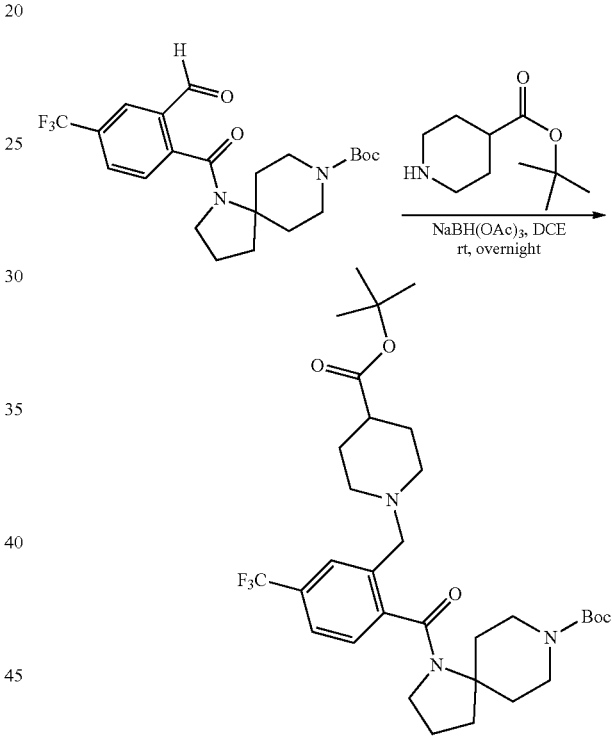

A 100-mL round-bottom flask was charged with tert-butyl 1-(2-formyl-4-(trifluoromethyl)benzoyl)-1,8-diazaspiro[4.5]decane-8-carboxylate (260 mg, 0.590 mmol, 1.00 equiv), tert-butyl piperidine-4-carboxylate (131 mg, 0.710 mmol, 1.20 equiv), and 1,2-dichloroethane (15 mL). The mixture was stirred for 1 h at room temperature prior to addition of sodium triacetoxyborohydride (500 mg, 2.36 mmol, 4.00 equiv). The reaction mixture was stirred overnight at room temperature and quenched with water (10 mL). The resulting solution was extracted with DCM (3×15 mL) and the organic layers were combined, washed with brine (1×20 mL), dried over anhydrous Na$_2$SO$_4$, filtered and concentrated under reduced pressure. The residue was chromatographed on a silica gel column to provide 100 mg (28% yield) of tert-butyl 1-(2-((4-(tert-butoxycarbonyl)piperidin-1-yl)methyl)-4-(trifluoromethyl)benzoyl)-1,8-diazaspiro[4.5]decane-8-carboxylate. LCMS (ESI, m/z): 610 [M+H]$^+$.

Step 4: Synthesis of 1-(2-(1,8-diazaspiro[4.5]decane-1-carbonyl)-5-(trifluoromethyl)benzyl)piperidine-4-carboxylic acid

Step 5: Synthesis of 1-(2-(8-(((1,1,1,3,3,3-hexafluoropropan-2-yl)oxy)carbonyl)-1,8-diazaspiro[4.5]decane-1-carbonyl)-5-(trifluoromethyl)benzyl)piperidine-4-carboxylic acid

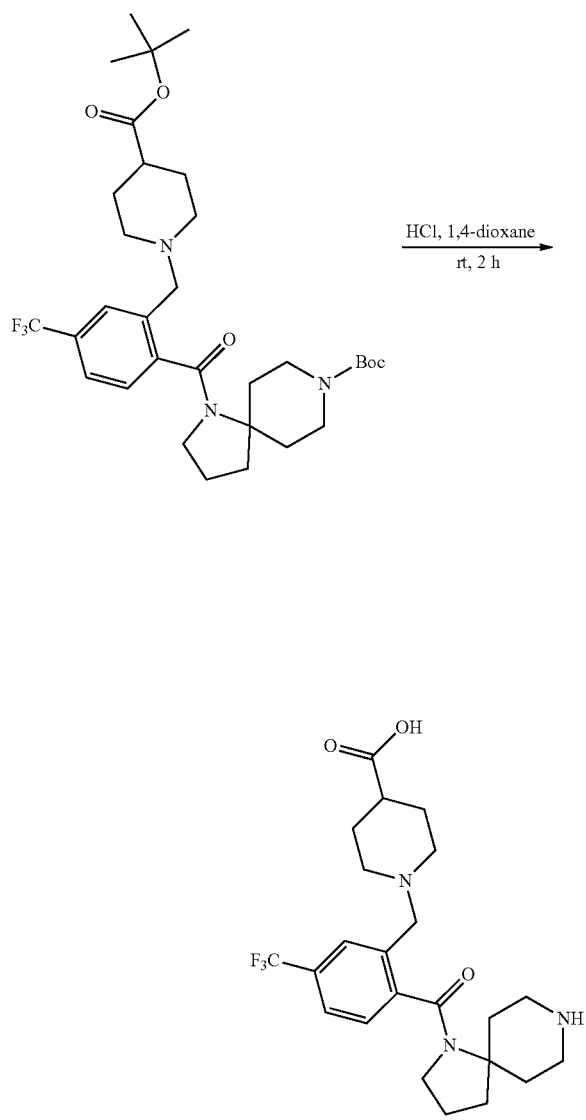

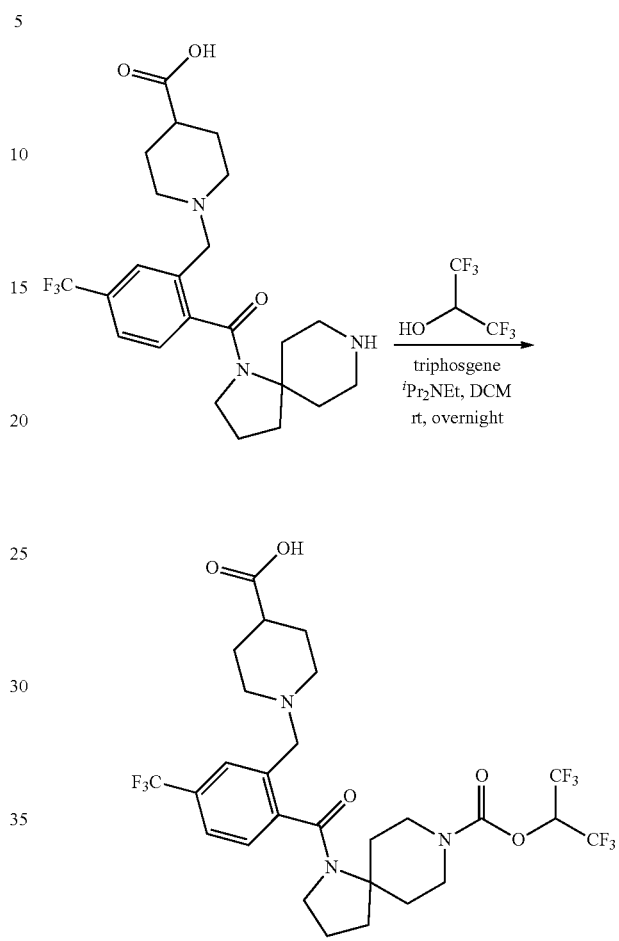

A 100-mL round-bottom flask was charged with tert-butyl 1-(2-((4-(tert-butoxycarbonyl)piperidin-1-yl)methyl)-4-(trifluoromethyl)benzoyl)-1,8-diazaspiro[4.5]decane-8-carboxylate (80.0 mg, 0.130 mmol, 1.00 equiv), 1,4-dioxane (10 mL), and concentrated hydrochloric acid (1 mL). The resulting solution was stirred for 2 h at room temperature and concentrated under reduced pressure to provide 100 mg (crude) of 1-(2-(1,8-diazaspiro[4.5]decane-1-carbonyl)-5-(trifluoromethyl)benzyl)piperidine-4-carboxylic acid. LCMS (ESI, m/z): 454 [M+H]$^+$.

A 100-mL round-bottom flask was charged with triphosgene (39.0 mg, 0.130 mmol, 0.70 equiv), and DCM (15 mL). 1,1,1,3,3,3-Hexafluoropropan-2-ol (67.0 mg, 0.400 mmol, 2.20 equiv) and DIPEA (93.0 mg, 0.720 mmol, 4.00 equiv) were added sequentially at 0° C. The mixture was stirred for 1 h at room temperature prior to the addition of 1-(2-(1,8-diazaspiro[4.5]decane-1-carbonyl)-5-(trifluoromethyl)benzyl)piperidine-4-carboxylic acid (80.0 mg, 0.180 mmol, 1.00 equiv). The resulting solution was stirred overnight at room temperature and quenched with water (10 mL). The mixture was extracted with DCM (3×15 mL) and the organic layers were combined, washed with brine (1×20 mL), dried over anhydrous Na$_2$SO$_4$, filtered and concentrated under reduced pressure. The crude product (400 mg) was purified by preparative HPLC to afford 17.4 mg (15% yield) of 1-(2-(8-(((1,1,1,3,3,3-hexafluoropropan-2-yl)oxy)carbonyl)-1,8-diazaspiro[4.5]decane-1-carbonyl)-5-(trifluoromethyl)benzyl)piperidine-4-carboxylic acid. $^1$H NMR (300 MHz, Methanol-d$_4$) δ 7.65-7.70 (m, 2H), 7.44-7.47 (m, 1H), 6.09-6.18 (m, 1H), 4.15-4.21 (m, 2H), 3.60 (br, 2H), 3.33-3.38 (m, 2H), 3.06-3.14 (m, 4H), 2.81-2.85 (m, 2H), 2.16-2.31 (m, 5H), 1.86-1.90 (m, 4H), 1.63-1.70 (m, 4H). LCMS (ESI, m/z): 648 [M+H]$^+$.

Example 11: 1-(3-Chloro-5-(8-(((1,1,1,3,3,3-hexafluoropropan-2-yl)oxy)carbonyl)-1,8-diazaspiro[4.5]decane-1-carbonyl)benzyl)piperidine-4-carboxylic acid

Step 1: Synthesis of 1,1,1,3,3,3-hexafluoropropan-2-yl 1-(3-bromo-5-chlorobenzoyl)-1,8-diazaspiro[4.5]decane-8-carboxylate

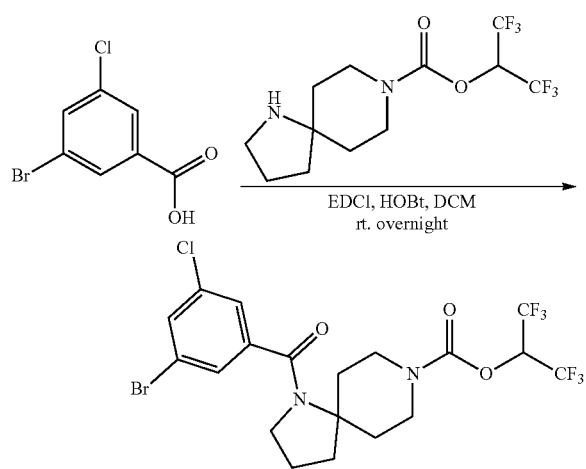

A 50-mL round-bottom flask was charged with 3-bromo-5-chlorobenzoic acid (180 mg, 0.760 mmol, 1.00 equiv), DCM (10 mL), N-(3-dimethylaminopropyl)-N'-ethylcarbodiimide hydrochloride (219 mg, 1.14 mmol, 1.50 equiv), and 1-hydroxybenzotrizole (154 mg, 1.14 mmol, 1.50 equiv). The resulting solution was stirred 1 h at room temperature prior to addition of 1,1,1,3,3,3-hexafluoropropan-2-yl 1,8-diazaspiro[4.5]decane-8-carboxylate (305 mg, 0.912 mmol, 1.20 equiv). The reaction mixture was stirred overnight at room temperature and quenched with water (30 mL). The resulting solution was extracted with DCM (2×50 mL) and the organic layers were combined, washed with brine (2×30 mL), dried over anhydrous Na$_2$SO$_4$, filtered and concentrated under reduced pressure. The residue was chromatographed on a silica gel column to provide 200 mg (47% yield) of 1,1,1,3,3,3-hexafluoropropan-2-yl 1-(3-bromo-5-chlorobenzoyl)-1,8-diazaspiro[4.5]decane-8-carboxylate. LCMS (ESI, m/z): 551 [M+H]$^+$.

Step 2: Synthesis of 1,1,1,3,3,3-hexafluoropropan-2-yl 1-(3-((4-(tert-butoxycarbonyl)piperidin-1-yl)methyl)-5-chlorobenzoyl)-1,8-diazaspiro[4.5]decane-8-carboxylate

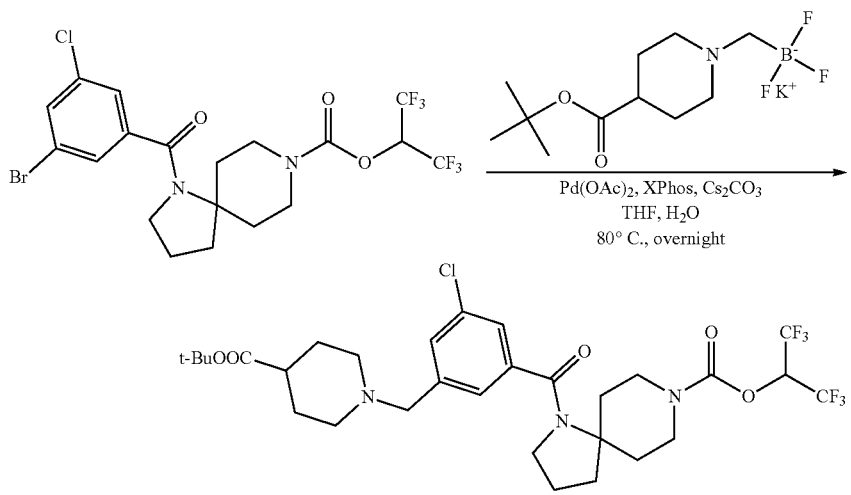

A 50-mL round-bottom flask was charged with 1,1,1,3,3,3-hexafluoropropan-2-yl 1-(3-bromo-5-chlorobenzoyl)-1,8-diazaspiro[4.5]decane-8-carboxylate (200 mg, 0.360 mmol, 1.00 equiv), (4-[(tert-butoxy)carbonyl]piperidin-1-ylmethyl) potassium trifluoroborate (132 mg, 0.432 mmol, 1.20 equiv), palladium acetate (2.00 mg, 0.0108 mmol, 0.03 equiv), XPhos (10.0 mg, 0.0216 mmol, 0.06 equiv), cesium carbonate (236 mg, 0.720 mmol, 2.00 equiv), THF (10 mL), and water (2 mL) under nitrogen. The reaction mixture was stirred overnight at 80° C. and quenched with water (30 mL). The resulting solution was extracted with DCM (2×50 mL) and the organic layers were combined, washed with brine (2×30 mL), dried over anhydrous Na$_2$SO$_4$, filtered and concentrated under reduced pressure. The residue was chromatographed on a silica gel column to provide 50.0 mg (21% yield) of 1,1,1,3,3,3-hexafluoropropan-2-yl 1-(3-((4-(tert-butoxycarbonyl)piperidin-1-yl)methyl)-5-chlorobenzoyl)-1,8-diazaspiro[4 5]decane-8-carboxylate. LCMS (ESI, m/z): 670 [M+H]$^+$.

Step 3: Synthesis of 1-(3-chloro-5-(8-(((1,1,1,3,3,3-hexafluoropropan-2-yl)oxy)carbonyl)-1,8-diazaspiro[4.5]decane-1-carbonyl)benzyl)piperidine-4-carboxylic acid

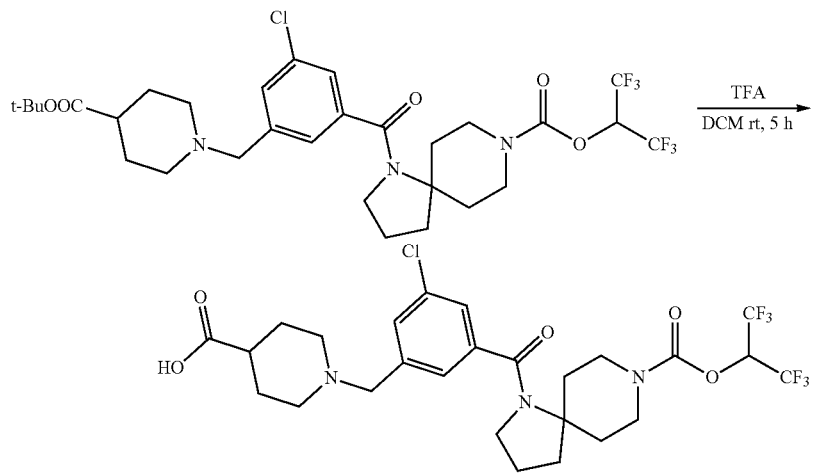

A 50-mL round-bottom flask was charged with 1,1,1,3,3,3-hexafluoropropan-2-yl 1-(3-((4-(tert-butoxycarbonyl)piperidin-1-yl)methyl)-5-chlorobenzoyl)-1,8-diazaspiro[4.5]decane-8-carboxylate (50.0 mg, 0.0800 mmol, 1.00 equiv), DCM (10 mL), and TFA (2 mL). The resulting solution was stirred for 5 h at room temperature and concentrated under reduced pressure. The crude product (100 mg) was purified by preparative HPLC to provide 11.4 mg (25% yield) of 1-(3-chloro-5-(8-(((1,1,1,3,3,3-hexafluoropropan-2-yl)oxy)carbonyl)-1,8-diazaspiro[4.5]decane-1-carbonyl)benzyl)piperidine-4-carboxylic acid. $^1$H NMR (400 MHz, Methanol-$d_4$) δ 7.52 (s, 1H), 7.43 (s, 1H), 7.36 (s, 1H), 6.11-6.17 (m, 1H), 4.13-4.19 (m, 2H), 3.79 (s, 2H), 3.43 (t, J=6.8 Hz, 2H), 2.99-3.18 (m, 6H), 2.28-2.65 (m, 3H), 2.15 (t, J=6.8 Hz, 2H), 1.74-1.97 (m, 6H), 1.57-1.60 (m, 2H). LCMS (ESI, m/z): 614 [M+H]$^+$.

Example 12: 1,1,1,3,3,3-Hexafluoropropan-2-yl 2-(4-cyano-3-(trifluoromethyl)benzoyl)-2,8-diazaspiro[4.5]decane-8-carboxylate

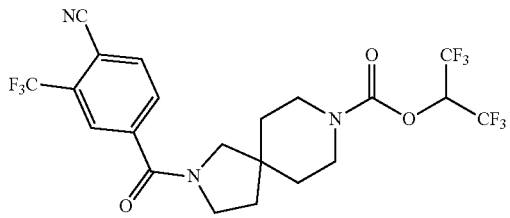 [SMILES: N#Cc1ccc(C(=O)N2CCC3(CCN(C(=O)OC(C(F)(F)F)C(F)(F)F)CC3)C2)cc1C(F)(F)F]

Step 1: Synthesis of tert-butyl 2-(4-bromo-3-(trifluoromethyl)benzoyl)-2,8-diazaspiro[4.5]decane-8-carboxylate

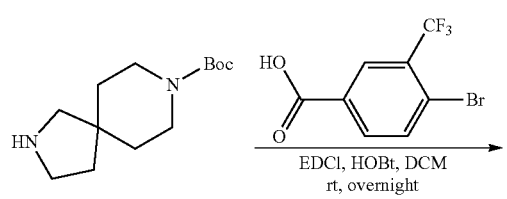

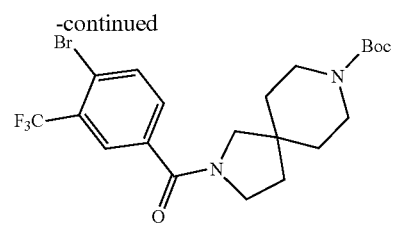

A 100-mL round-bottom flask was charged with 4-bromo-3-(trifluoromethyl)benzoic acid (482 mg, 1.79 mmol, 1.20 equiv), DCM (15 mL), N-(3-dimethylaminopropyl)-N'-ethylcarbodiimide hydrochloride (518 mg, 2.70 mmol, 1.80 equiv), and 1-hydroxybenzotrizole (365 mg, 2.70 mmol, 1.80 equiv). The mixture was stirred for 2 h at room temperature prior to addition of tert-butyl 2,8-diazaspiro[4.5]decane-8-carboxylate (350 mg, 1.46 mmol, 1.00 equiv). The reaction mixture was stirred overnight at room temperature and quenched with water (10 mL). The resulting mixture was extracted with DCM (3×15 mL) and the organic layers were combined, washed with brine (2×50 mL), dried over anhydrous Na$_2$SO$_4$, filtered and concentrated under reduced pressure. The residue was chromatographed on a silica gel column to provide 660 mg (75% yield) of tert-butyl 2-(4-bromo-3-(trifluoromethyl)benzoyl)-2,8-diazaspiro[4.5]decane-8-carboxylate. LCMS (ESI, m/z): 491 [M+H]$^+$.

Step 2: Synthesis of tert-butyl 2-(4-cyano-3-(trifluoromethyl)benzoyl)-2,8-diazaspiro[4.5]decane-8-carboxylate

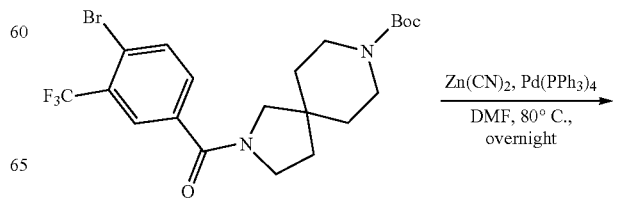

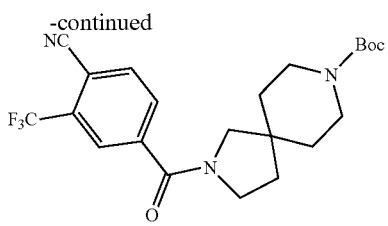

A 50-mL round-bottom flask was charged with tert-butyl 2-(4-bromo-3-(trifluoromethyl)benzoyl)-2,8-diazaspiro[4.5]decane-8-carboxylate (200 mg, 0.410 mmol, 1.00 equiv), zinccyanide (72.0 mg, 0.620 mmol, 1.50 equiv), tetrakis(triphenylphosphine)palladium (46.0 mg, 0.0400 mmol, 0.10 equiv), and N,N-dimethylformamide (10 mL) under nitrogen. The reaction mixture was stirred overnight at 80° C. and then quenched with water (15 mL). The resulting solution was extracted with ethyl acetate (3×25 mL) and the organic layers were combined, washed with brine (1×75 mL), dried over anhydrous $Na_2SO_4$, filtered and concentrated under reduced pressure. The residue was chromatographed on a silica gel column to provide 160 mg (90% yield) of tert-butyl 2-(4-cyano-3-(trifluoromethyl)benzoyl)-2,8-diazaspiro[4.5]decane-8-carboxylate. LCMS (ESI, m/z): 438 $[M+H]^+$.

Step 3: Synthesis of 1,1,1,3,3,3-hexafluoropropan-2-yl 2-(4-cyano-3-(trifluoromethyl)benzoyl)-2,8-diazaspiro[4.5]decane-8-carboxylate

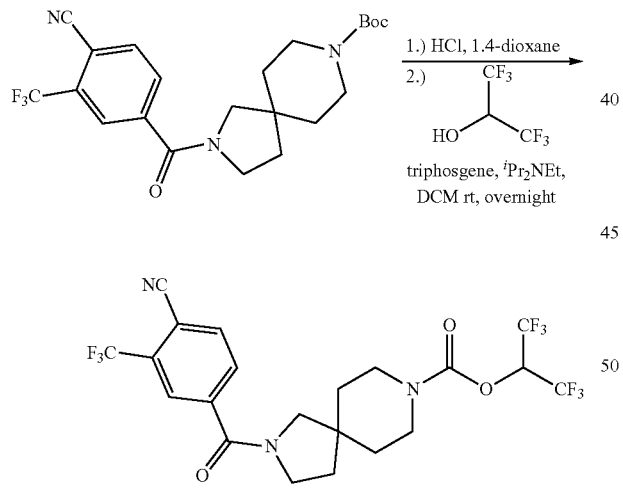

The title compound was prepared as described in Example 11, Steps 4-5, using analogous starting materials to provide 37.4 mg (22% yield) of 1,1,1,3,3,3-hexafluoropropan-2-yl 2-(4-cyano-3-(trifluoromethyl)benzoyl)-2,8-diazaspiro[4.5]decane-8-carboxylate. $^1$H NMR (300 MHz, Chloroform-d) δ 7.91-7.94 (m, 2H), 7.78-7.83 (m, 1H), 5.68-5.80 (m, 1H), 3.71-2.81 (m, 2H), 3.42-3.60 (m, 5H), 3.27 (s, 1H), 1.87-1.98 (m, 2H), 1.57-1.71 (m, 4H). LCMS (ESI, m/z): 532 $[M+H]^+$.

Example 13: 1,1,1,3,3,3-Hexafluoropropan-2-yl 1-(4-chlorobenzoyl)-1,8-diazaspiro[4.5]decane-8-carboxylate

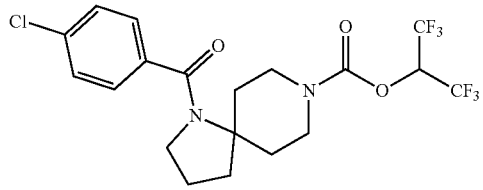 [SMILES: O=C(OC(C(F)(F)F)C(F)(F)F)N1CCC2(CCCN2C(=O)c2ccc(Cl)cc2)CC1]

Step 1: Synthesis of 4-chlorobenzoyl chloride

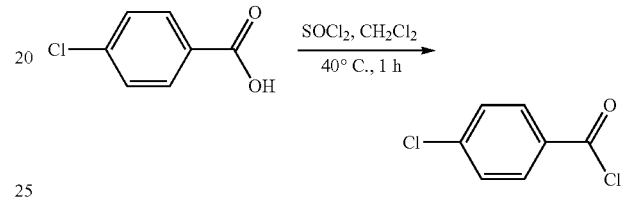

A 40-mL round-bottom flask was charged with 4-chlorobenzoic acid (78.0 mg, 0.497 mmol, 1.00 equiv), DCM (5 mL), and thionyl chloride (119 mg, 0.994 mmol, 2.00 equiv). The resulting solution was stirred for 1 h at 40° C. The resulting mixture was concentrated under reduced pressure to provide 87.0 mg (99% yield) of 4-chlorobenzoyl chloride.

Step 2: Synthesis of 1,1,1,3,3,3-hexafluoropropan-2-yl 1-(4-chlorobenzoyl)-1,8-diazaspiro[4.5]decane-8-carboxylate

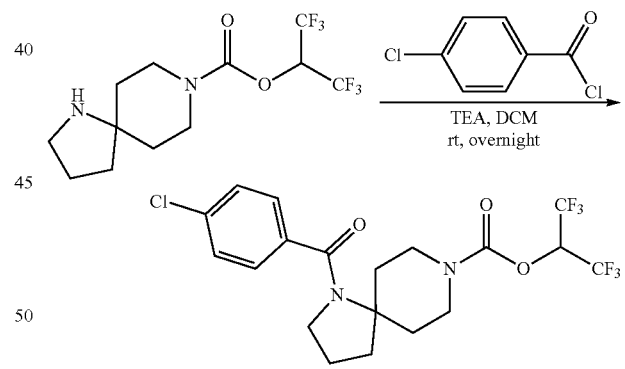

A 40-mL round-bottom flask was charged with 4-chlorobenzoyl chloride (87.0 mg, 0.497 mmol, 1.00 equiv), 1,1,1,3,3,3-hexafluoropropan-2-yl 1,8-diazaspiro[4.5]decane-8-carboxylate (167 mg, 0.497 mmol, 1.00 equiv), triethylamine (156 mg, 1.50 mmol, 3.00 equiv), and DCM (5 mL). The resulting solution was stirred overnight at room temperature and quenched with water (20 mL). The mixture was extracted with DCM (3×30 mL) and the organic layers were combined, washed with brine (3×30 mL), dried over anhydrous $Na_2SO_4$, filtered and concentrated under reduced pressure. The crude product (103 mg) was purified by preparative HPLC to provide 54.5 mg (23% yield) of 1,1,1,3,3,3-hexafluoropropan-2-yl 2-(4-cyano-3-(trifluoromethyl)benzoyl)-2,8-diazaspiro[4.5]decane-8-carboxylate. $^1$H NMR (400 MHz, Chloroform-d) δ 7.36 (br, 4H), 5.71-5.81 (m, 1H), 4.17-4.25 (m, 2H), 3.42 (t, J=6.8 Hz, 2H), 2.94-3.44 (m, 4H), 1.98-2.11 (m, 2H), 1.83-1.86 (m, 2H), 1.41-1.51 (m, 2H). LCMS (ESI, m/z): 473 [M+H]$^+$.

Example 14: 1-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)piperidine-4-carboxylic acid

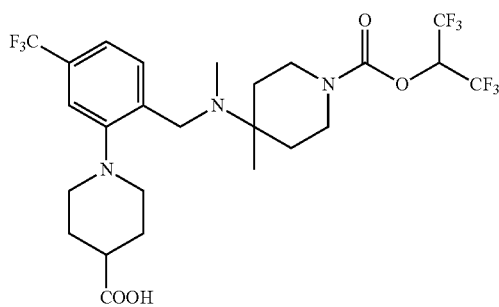 [SMILES: CN(Cc1ccc(C(F)(F)F)cc1N1CCC(C(=O)O)CC1)C1(C)CCN(C(=O)OC(C(F)(F)F)C(F)(F)F)CC1]

Step 1: Synthesis of tert-butyl 1-(2-formyl-5-(trifluoromethyl)phenyl)piperidine-4-carboxylate

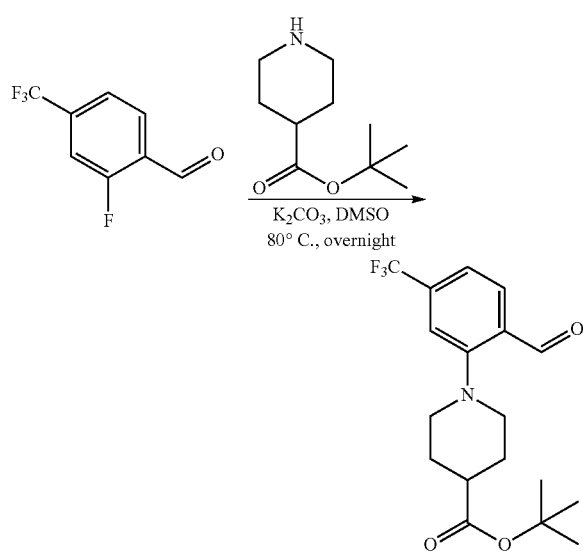

A round-bottom flask was charged with 2-fluoro-4-(trifluoromethyl)benzaldehyde (1.00 g, 5.21 mmol, 1.00 equiv), potassium carbonate (2.16 g, 15.6 mmol, 3.00 equiv), tert-butyl piperidine-4-carboxylate (1.93 g, 10.4 mmol, 2.00 equiv), and dimethyl sulfoxide (20 mL) under nitrogen. The reaction mixture was stirred overnight at 80° C. and quenched with water (20 mL). The resulting solution was extracted with ethyl acetate (3×20 mL) and the organic layers were combined, washed with brine (2×20 mL), dried over anhydrous sodium sulfate, filtered and concentrated under reduced pressure. The residue was chromatographed on a silica gel column to provide 380 mg (20% yield) of tert-butyl 1-(2-formyl-5-(trifluoromethyl)phenyl)piperidine-4-carboxylate. LCMS (ESI, m/z): 358 [M+H]$^+$.

Step 2: Synthesis of tert-butyl 4-((2-(4-(tert-butoxycarbonyl)piperidin-1-yl)-4-(trifluoromethyl)benzyl)amino)-4-methylpiperidine-1-carboxylate

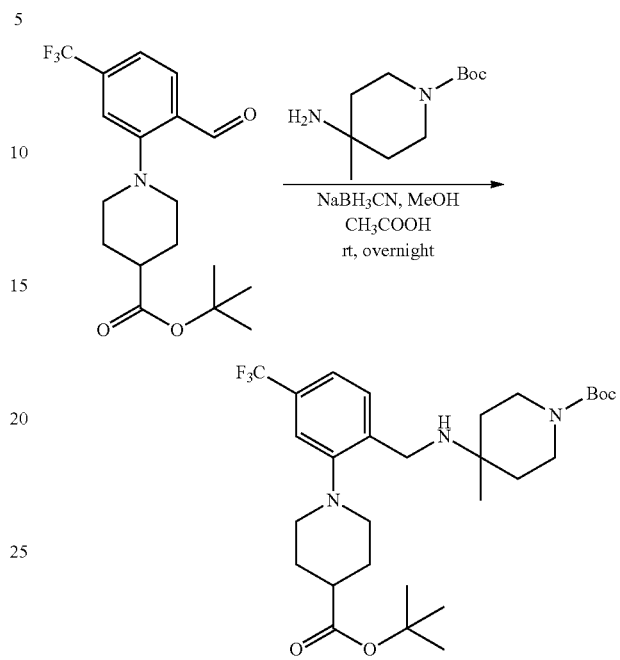

A round-bottom flask was charged with tert-butyl 1-(2-formyl-5-(trifluoromethyl)phenyl)piperidine-4-carboxylate (380 mg, 1.06 mmol, 1.00 equiv), methanol (10 mL), acetic acid (191 mg, 3.18 mmol, 3.00 equiv), and tert-butyl 4-amino-4-methylpiperidine-1-carboxylate (295 mg, 1.38 mmol, 1.30 equiv). The resulting solution was stirred for 30 min at room temperature prior to addition of sodium cyanoborohydride (200 mg, 3.18 mmol, 3.00 equiv). The reaction mixture was stirred overnight at room temperature and quenched with water (10 mL). The resulting solution was extracted with dichloromethane (3×10 mL) and the organic layers were combined, washed with brine (2×10 mL), dried over anhydrous sodium sulfate, filtered and concentrated under reduced pressure. The residue was chromatographed on a silica gel column to yield 300 mg (51% yield) of tert-butyl 4-((2-(4-(tert-butoxycarbonyl)piperidin-1-yl)-4-(trifluoromethyl)benzyp amino)-4-methylpiperidine-1-carboxylate. LCMS (ESI, m/z): 556 [M+H]$^+$.

Step 3: Synthesis of tert-butyl 4-((2-(4-(tert-butoxycarbonyl)piperidin-1-yl)-4-(trifluoromethyl)benzyl)(methyl)amino)-4-methylpiperidine-1-carboxylate

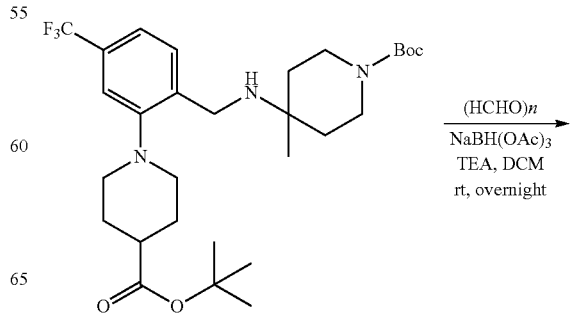

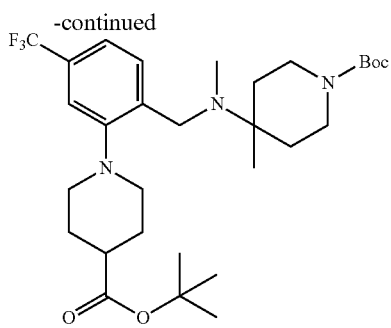

A round-bottom flask was charged with tert-butyl 4-((2-(4-(tert-butoxycarbonyl)piperidin-1-yl)-4-(trifluoromethyl)benzypamino)-4-methylpiperidine-1-carboxylate (300 mg, 0.540 mmol, 1.00 equiv), paraformaldehyde (162 mg, 5.06 mmol, 10.0 equiv), triethylamine (164 mg, 1.62 mmol, 3.00 equiv), and 1,2-dichloroethane (10 mL). The resulting solution was stirred for 30 min at room temperature prior to addition of sodium triacetoxyborohydride (343 mg, 1.62 mmol, 3.00 equiv). The resulting solution was stirred overnight at room temperature and quenched with water (10 mL). The reaction mixture was extracted with dichloromethane (3×10 mL) and the organic layers were combined, washed with brine (2×10 mL), dried over anhydrous sodium sulfate, filtered and concentrated under reduced pressure. The residue was chromatographed on a silica gel column with dichloromethane/methanol (20/1) to yield 230 mg (75% yield) of tert-butyl 4-((2-(4-(tert-butoxycarbonyl)piperidi-1-yl)-4-(trifluoromethyl)benzyl)(methyl)amino)-4-methylpiperidine-1-carboxylate. LCMS (ESI, m/z): 570 [M+H]$^+$.

Step 4: Synthesis of 1-(2-((methyl(4-methylpiperidin-4-yl)amino)methyl)-5-(trifluoromethyl)phenyl)piperidine-4-carboxylic acid

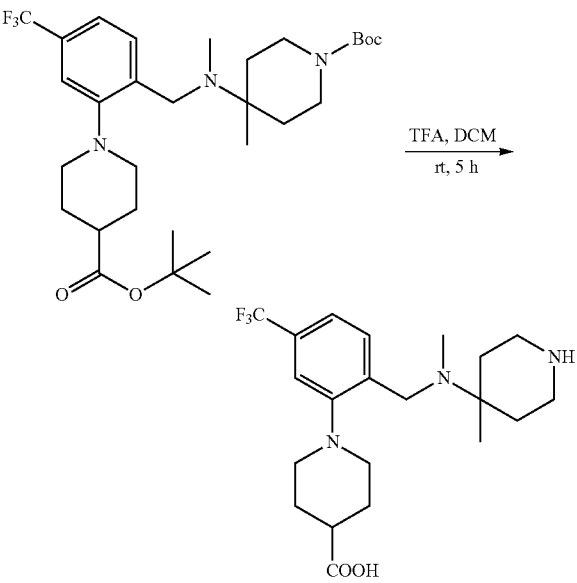

A round-bottom flask was charged with tert-butyl 4-((2-(4-(tert-butoxycarbonyl)piperidin-1-yl)-4-(trifluoromethyl) benzyl)(methyl)amino)-4-methylpiperidine-1-carboxylate (230 mg, 0.400 mmol, 1.00 equiv), dichloromethane (5 mL), and trifluoroacetic acid (3 mL). The resulting solution was stirred for 5 h at room temperature and concentrated under reduced pressure to yield 266 mg (crude) of 1-(2-((methyl (4-methylpiperidin-4-yl)amino)methyl)-5-(trifluoromethyl) phenyl)piperidine-4-carboxylic acid. LCMS (ESI, m/z): 414 [M+H]$^+$.

Step 5: Synthesis of 1-(2-(((1-(((1,1,1,3,3,3-hexafluoropropan-2-yl)oxy)carbonyl)-4-methylpiperidin-4-yl)(methyl) amino)methyl)-5-(trifluoromethyl)phenyl)piperidine-4-carboxylic acid

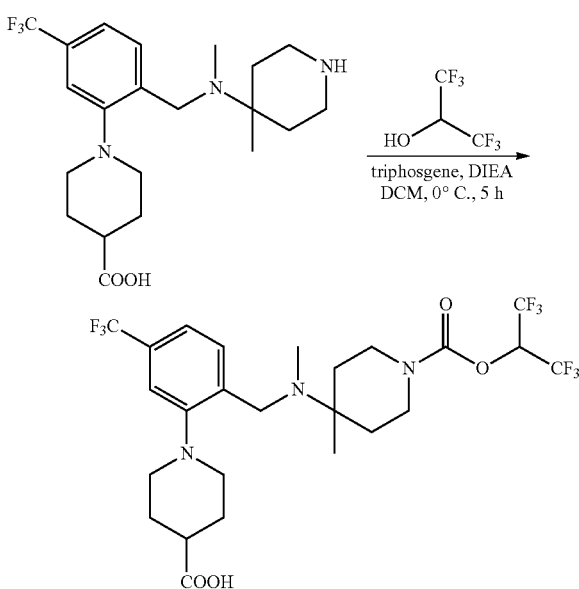

A round-bottom flask was charged with triphosgene (60.0 mg, 0.200 mmol, 0.50 equiv), dichloromethane (5 mL), and 1,1,1,3,3,3-hexafluoropropan-2-ol (101 mg, 0.600 mmol, 1.50 equiv) under nitrogen. N,N-Diisopropylethyl amine (156 mg, 1.21 mmol, 3.00 equiv) was added dropwise at 0° C. The resulting solution was stirred for 2 h at 0° C. prior to addition of 1-(2-[[methyl(4-methylpiperidin-4-yl)amino] methyl]-5-(trifluoromethyl)phenyl)piperidine-4-carboxylic acid (166 mg, 0.400 mmol, 1.00 equiv) in dichloromethane (5 mL). The reaction mixture was stirred for 3 h at 0° C. and quenched with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (400 mg) was purified by preparative HPLC to afford 125.1 mg (51% yield) of 1-(2-(((1-(((1,1,1,3,3,3-hexafluoropropan-2-yl)oxy)carbonyl)-4-methylpiperidin-4-yl)(methyl)amino)methyl)-5-(trifluoromethyl)phenyl)piperidine-4-carboxylic acid. $^1$H NMR (300 MHz, Methanol-d$_4$) δ 7.76-7.78 (m, 1H), 7.33-7.37 (m, 2H), 6.05-6.14 (m, 1H), 3.77 (br, 2H), 3.57-3.67 (m, 4H), 3.02-3.06 (m, 2H), 2.69-2.77 (m, 2H), 2.36-2.46 (m, 1H), 2.14 (s, 3H), 1.94-2.03 (m, 4H), 1.75-1.90 (m, 2H), 1.51-1.64 (m, 2H), 1.25 (s, 3H). LCMS (ESI, m/z): 608 [M+H]$^+$.

Example 15: 1,1,1,3,3,3-Hexafluoropropan-2-yl 2-((1-acetyl-1,2,3,4-tetrahydroquinolin-8-yl)methyl)-2,7-diazaspiro[3.5]nonane-7-carboxylate

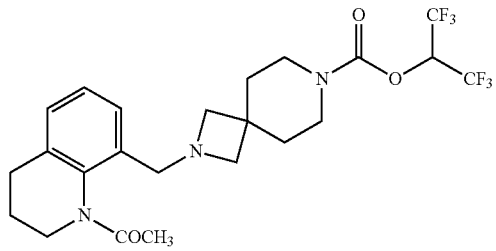 [SMILES: CC(=O)N1CCCc2cccc(CN3CC4(CCN(C(=O)OC(C(F)(F)F)C(F)(F)F)CC4)C3)c21]

Step 1: Synthesis of tert-butyl 2-((1,2,3,4-tetrahydroquinolin-8-yl)methyl)-2,7-diazaspiro[3.5]nonane-7-carboxylate

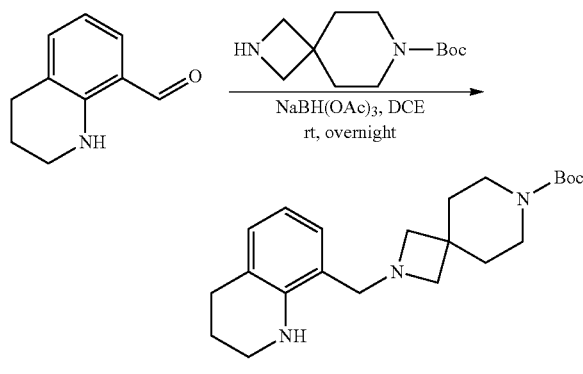

A round-bottom flask was charged with 1,2,3,4-tetrahydroquinoline-8-carbaldehyde (1.50 g, 9.31 mmol, 1.00 equiv), tert-butyl 2,7-diazaspiro[3.5]nonane-7-carboxylate (2.53 g, 11.2 mmol, 1.20 equiv), and 1,2-dichloroethane (30 mL).The resulting solution was stirred for 1 h at room temperature prior to addition of sodium triacetoxyborohydride (5.92 g, 27.9 mmol, 3.00 equiv). The reaction mixture was stirred overnight at room temperature and quenched with water (15 mL). The resulting solution was extracted with dichloromethane (3×20 mL) and the organic layers were combined, dried over anhydrous sodium sulfate, filtered and concentrated under reduced pressure. The residue was chromatographed on a silica gel column to provide 2.50 g (72% yield) of tert-butyl 2-((1,2,3,4-tetrahydroquinolin-8-yl)methyl)-2,7-diazaspiro[3.5]nonane-7-carboxylate. LCMS (ESI, m/z): 372 [M+H]+.

Step 2: Synthesis of tert-butyl 2-((1-acetyl-1,2,3,4-tetrahydroquinolin-8-yl)methyl)-2,7-diazaspiro[3.5]nonane-7-carboxylate

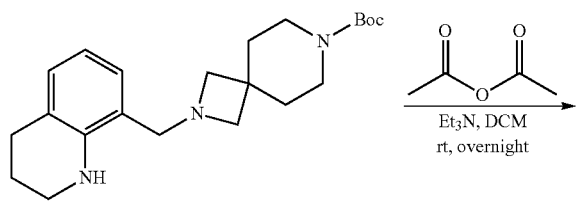

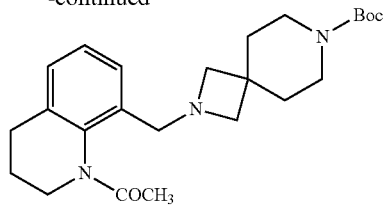

A round-bottom flask was charged with tert-butyl 2-((1,2,3,4-tetrahydroquinolin-8-yl)methyl)-2,7-diazaspiro[3.5]nonane-7-carboxylate (500 mg, 1.35 mmol, 1.00 equiv), acetyl acetate (206 mg, 2.02 mmol, 1.50 equiv), dichloromethane (10 mL), and triethylamine (407 mg, 4.02 mmol, 3.00 equiv). The reaction mixture was stirred overnight at room temperature and quenched with water (10 mL). The resulting solution was extracted with dichloromethane (3×15 mL) and the organic layers were combined, dried over anhydrous sodium sulfate, filtered and concentrated under reduced pressure. The residue was chromatographed on a silica gel column to provide 480 mg (86% yield) of tert-butyl 2-((1-acetyl-1,2,3,4-tetrahydroquinolin-8-yl)methyl)-2,7-diazaspiro[3.5]nonane-7-carboxylate. LCMS (ESI, m/z): 414 [M+H]+.

Step 3: Synthesis of 1-(8-((2,7-diazaspiro[3.5]nonan-2-yl)methyl)-3,4-dihydroquinolin-1(2H)-yl)ethan-1-one

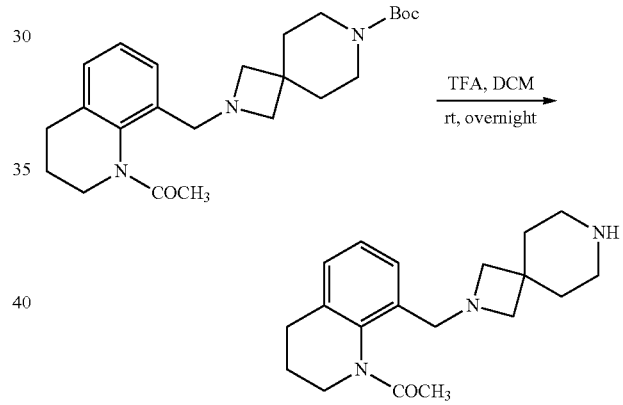

A round-bottom flask was charged with tert-butyl 2-((1-acetyl-1,2,3,4-tetrahydroquinolin-8-yl)methyl)-2,7-diazaspiro[3.5]nonane-7-carboxylate (480 mg, 1.16 mmol, 1.00 equiv), dichloromethane (9 mL), and trifluoroacetic acid (1.5 mL). The resulting solution was stirred overnight at room temperature and concentrated under reduced pressure to provide 360 mg (99% yield) of 1-(8-((2,7-diazaspiro[3.5]nonan-2-yl)methyl)-3,4-dihydroquinolin-1(2H)-yl)ethan-1-one. LCMS (ESI, m/z): 314 [M+H]+.

Step 4: Synthesis of 1,1,1,3,3,3-hexafluoropropan-2-yl 2-((1-acetyl-1,2,3,4-tetrahydroquinolin-8-yl)methyl)-2,7-diazaspiro[3.5]nonane-7-carboxylate

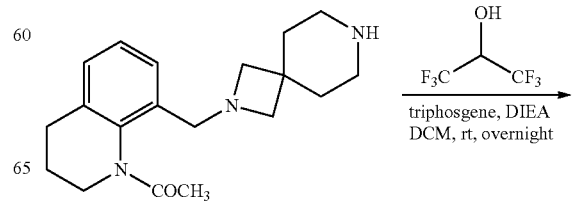

-continued

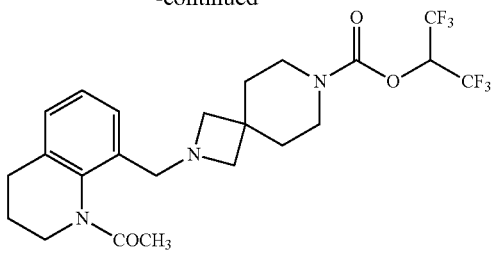

A round-bottom flask was charged with triphosgene (120 mg, 0.400 mmol, 0.70 equiv) and dichloromethane (10 mL). 1,1,1,3,3,3-Hexafluoropropan-2-ol (193 mg, 1.15 mmol, 2.00 equiv) and N,N-diisopropylethylamine (222 mg, 1.72 mmol, 3.00 equiv) were added sequentially at 0° C. The resulting solution was stirred for 1 h at room temperature prior to addition of 1-(8-[2,7-diazaspiro[3.5]nonan-2-ylmethyl]-1,2,3,4-tetrahydroquinolin-1-yl)ethan-1-one (180 mg, 0.570 mmol, 1.00 equiv). The crude product (300 mg) was purified by preparative HPLC to afford 68.6 mg (24% yield) of 1,1,1,3,3,3-hexafluoropropan-2-yl 2-((1-acetyl-1,2,3,4-tetrahydroquinolin-8-yl)methyl)-2,7-diazaspiro[3.5]nonane-7-carboxylate. $^1$H NMR (300 MHz, DMSO-d$_6$) δ 7.29 (br, 1H), 7.08-7.16 (m, 2H), 6.20-6.33 (m, 1H), 4.07-4.60 (m, 1H), 3.13-3.74 (m, 7H), 2.94 (br, 4H), 2.62 (br, 2H), 1.77-2.04 (m, 9H). LCMS (ESI, m/z): 508 [M+H]$^+$.

Example 16: 1,1,1,3,3,3-Hexafluoropropan-2-yl 2-((1-ethyl-1,2,3,4-tetrahydroquinolin-8-yl)methyl)-2,7-diazaspiro[3.5]nonane-7-carboxylate

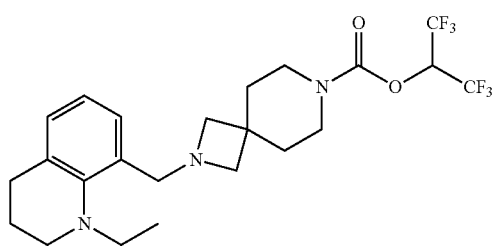 [SMILES: CCN1CCCc2cccc(CN3CC4(CCN(C(=O)OC(C(F)(F)F)C(F)(F)F)CC4)C3)c21]

Step 1: Synthesis of (1,2,3,4-tetrahydroquinolin-8-yl)methanol

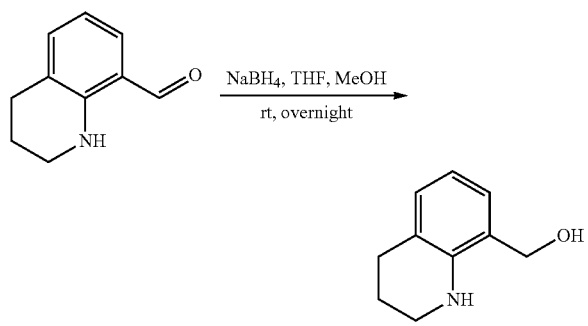

A round-bottom flask was charged with 1,2,3,4-tetrahydroquinoline-8-carbaldehyde (2.50 g, 15.5 mmol, 1.00 equiv) and tetrahydrofuran (20 mL). Sodium tetrahydroborate (590 mg, 15.6 mmol, 1.01 equiv) and methanol (0.5 mL) were added sequentially at 0° C. The reaction mixture was stirred overnight at room temperature and quenched with water (15 mL). The resulting solution was extracted with dichloromethane (3×30 mL) and the organic layers were combined, dried over anhydrous sodium sulfate, filtered and concentrated under reduced pressure. The residue was chromatographed on a silica gel column to provide 2.30 g (91% yield) of 1,2,3,4-tetrahydroquinolin-8-ylmethanol. LCMS (ESI, m/z): 164 [M+H]$^+$.

Step 2: Synthesis of 8-(((tert-butyldimethylsilyl)oxy)methyl)-1,2,3,4-tetrahydroquinoline

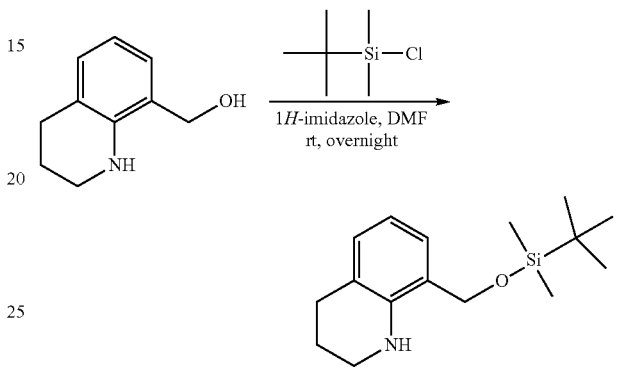

A round-bottom flask was charged with 1,2,3,4-tetrahydroquinolin-8-ylmethanol (2.30 g, 14.1 mmol, 1.00 equiv), N,N-dimethylformamide (25 mL), 1H-imidazole (1.44 g, 21.2 mmol, 1.50 equiv), and tert-butyl(chloro)dimethylsilane (2.77 g, 18.4 mmol, 1.30 equiv). The reaction mixture was stirred overnight at room temperature and quenched with water (20 mL). The resulting solution was extracted with ethyl acetate (3×30 mL) and the organic layers were combined, dried over anhydrous sodium sulfate, filtered and concentrated under reduced pressure. The residue was chromatographed on a silica gel column to provide 3.18 g (81% yield) of 8-(((tert-butyldimethylsilyl)oxy)methyl)-1,2,3,4-tetrahydroquinoline. LCMS (ESI, m/z): 278 [M+H]$^+$.

Step 3: Synthesis of 8-(((tert-butyldimethylsilyl)oxy)methyl)-1-ethyl-1,2,3,4-tetrahydroquinoline

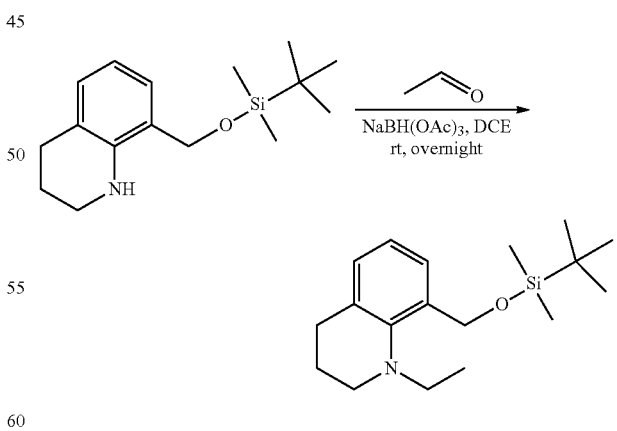

A round-bottom flask was charged with 8-(((tert-butyldimethylsilyl)oxy)methyl)-1,2,3,4-tetrahydroquinoline (4.00 g, 14.4 mmol, 1.00 equiv), acetaldehyde (1.91 g, 43.4 mmol, 3.00 equiv), and 1,2-dichloroethane (50 mL). The resulting solution was stirred for 30 min at room temperature prior to addition of sodium triacetoxyborohydride (9.18 g, 43.3 mmol, 3.00 equiv). The reaction mixture was stirred overnight at room temperature and quenched with water (30 mL). The resulting solution was extracted with dichloromethane (3×50 mL) and the organic layers were combined, dried over anhydrous sodium sulfate, filtered and concentrated under reduced pressure. The residue was chromatographed on a silica gel column to provide 2.91 g (66% yield) of 8-(((tert-butyldimethylsilyl)oxy)methyl)-1-ethyl-1, 2,3,4-tetrahydroquinoline. LCMS (ESI, m/z): 306 [M+H]+.

Step 4: Synthesis of (1-ethyl-1,2,3,4-tetrahydroquinolin-8-yl)methanol

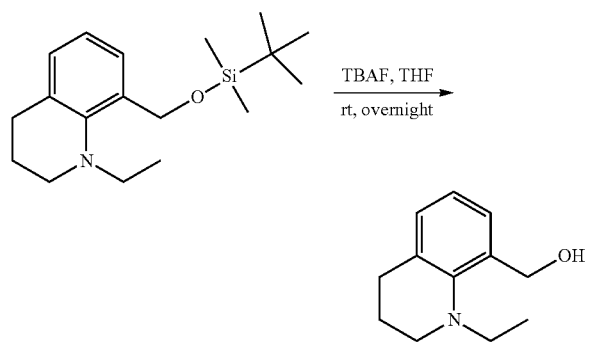

A 100-mL round-bottom flask was charged with 8-(((tert-butyldimethylsilyl)oxy)methyl)-1-ethyl-1,2,3,4-tetrahydroquinoline (2.90 g, 9.49 mmol, 1.00 equiv), tetrahydrofuran (40 mL), and tetrabutylammonium fluoride (4.95 g, 18.9 mmol, 2.00 equiv). The reaction mixture was stirred overnight at room temperature and quenched with water (30 mL). The resulting solution was extracted with dichloromethane (3×50 mL) and the organic layers were combined, dried over anhydrous sodium sulfate, filtered and concentrated under reduced pressure. The residue was chromatographed on a silica gel column to provide 1.40 g (77% yield) of (1-ethyl-1,2,3,4-tetrahydroquinolin-8-yl)methanol. LCMS (ESI, m/z): 192 [M+H]+.

Step 5: Synthesis of 1-ethyl-1,2,3,4-tetrahydroquinoline-8-carbaldehyde

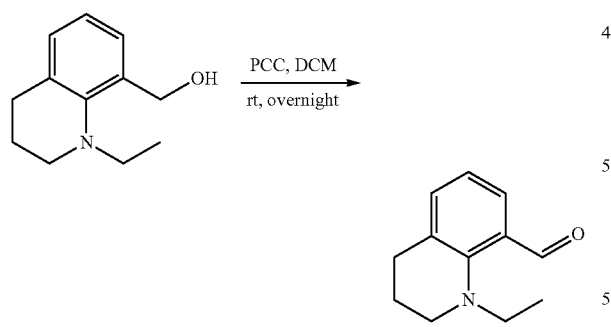

A round-bottom flask was charged with (1-ethyl-1,2,3,4-tetrahydroquinolin-8-yl)methanol (360 mg, 1.88 mmol, 1.00 equiv), dichloromethane (15 mL), and pyridinium chlorochromate (814 mg, 3.78 mmol, 2.00 equiv). The reaction mixture was stirred overnight at room temperature and quenched with water (15 mL). The resulting solution was extracted with dichloromethane (3×20 mL) and the organic layers were combined, dried over anhydrous sodium sulfate, filtered and concentrated under reduced pressure. The residue was chromatographed on a silica gel column to provide 90 mg (25% yield) of 1-ethyl-1,2,3,4-tetrahydroquinoline-8-carbaldehyde. LCMS (ESI, m/z): 190 [M+H]+.

Step 6: Synthesis of tert-butyl 2-((1-ethyl-1,2,3,4-tetrahydroquinolin-8-yl)methyl)-2,7-diazaspiro[3.5]nonane-7-carboxylate

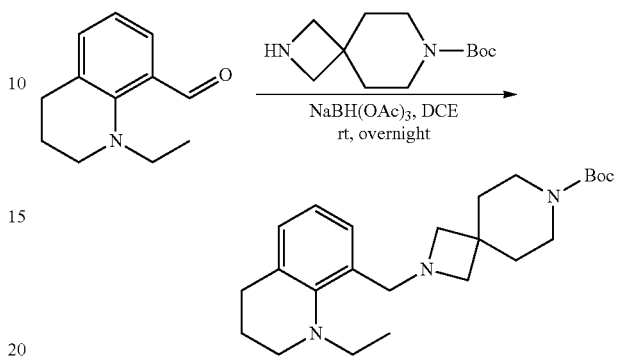

A round-bottom flask was charged with 1-ethyl-1,2,3,4-tetrahydroquinoline-8-carbaldehyde (90.0 mg, 0.480 mmol, 1.00 equiv), tert-butyl 2,7-diazaspiro[3.5]nonane-7-carboxylate (129 mg, 0.570 mmol, 1.20 equiv), and 1,2-dichloroethane (10 mL). The resulting solution was stirred for 30 min at room temperature prior to addition of sodium triacetoxyborohydride (303 mg, 1.43 mmol, 3.00 equiv). The reaction mixture was stirred overnight at room temperature and quenched with water (10 mL). The resulting solution was extracted with dichloromethane (3×15 mL) and the organic layers were combined, dried over anhydrous sodium sulfate, filtered and concentrated under reduced pressure. The residue was chromatographed on a silica gel column to provide 110 mg (58% yield) of tert-butyl 2-((1-ethyl-1,2,3,4-tetrahydroquinolin-8-yl)methyl)-2,7-diazaspiro[3.5]nonane-7-carboxylate. LCMS (ESI, m/z): 400 [M+H]+.

Step 7: Synthesis of 8-((2,7-diazaspiro[3.5]nonan-2-yl)methyl)-1-ethyl-1,2,3,4-tetrahydroquinoline

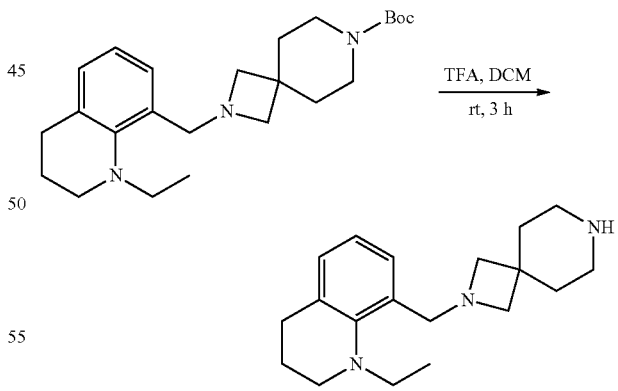

A round-bottom flask was charged with tert-butyl 2-[(1-ethyl-1,2,3,4-tetrahydroquinolin-8-yl)methyl]-2,7-diazaspiro[3.5]nonane-7-carboxylate (110 mg, 0.280 mmol, 1.00 equiv), dichloromethane (10 mL), and trifluoroacetic acid (2 mL). The resulting solution was stirred for 3 h at room temperature and concentrated under reduced pressure to provide 80 mg (97% yield) of 8-((2,7-diazaspiro[3.5]nonan-2-yl)methyl)-1-ethyl-1,2,3,4-tetrahydroquinoline. LCMS (ESI, m/z): 300 [M+H]+.

Step 8: Synthesis of 1,1,1,3,3,3-hexafluoropropan-2-yl 2-((1-ethyl-1,2,3,4-tetrahydroquinolin-8-yl)methyl)-2,7-diazaspiro[3.5]nonane-7-carboxylate

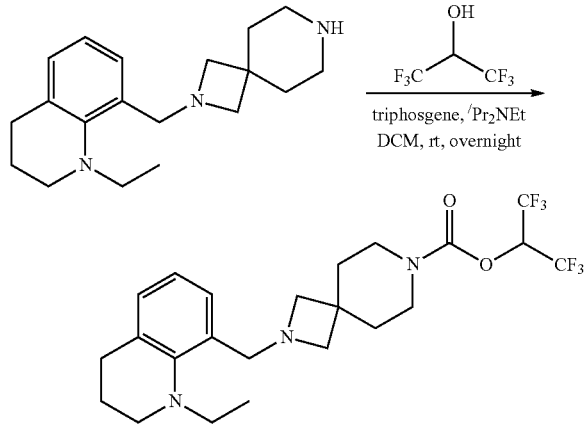

A round-bottom flask was charged with triphosgene (56.0 mg, 0.190 mmol, 0.70 equiv), dichloromethane (10 mL). 1,1,1,3,3,3-Hexafluoropropan-2-ol (90.0 mg, 0.540 mmol, 2.00 equiv) and N,N-diisopropylethylamine (104 mg, 0.800 mmol, 3.00 equiv) were added sequentially at 0° C. The resulting solution was stirred for 1 h at 0° C. prior to addition of 8-((2,7-diazaspiro[3.5]nonan-2-yl)methyl)-1-ethyl-1,2,3,4-tetrahydroquinoline (80.0 mg, 0.270 mmol, 1.00 equiv). The reaction mixture was stirred for 2 h at room temperature and concentrated under reduced pressure. The crude product (150 mg) was purified by preparative HPLC to provide 66.9 mg (51% yield) of 1,1,1,3,3,3-hexafluoropropan-2-yl 2-((1-ethyl-1,2,3,4-tetrahydroquinolin-8-yl)methyl)-2,7-diazaspiro[3.5]nonane-7-carboxylate. $^1$H NMR (300 MHz, Chloroform-d) δ 7.18-7.21 (m, 1H), 6.86-6.94 (m, 2H), 5.68-5.80 (m, 1H), 3.64 (br, 2H), 3.45 (t, J=5.6 Hz, 4H), 3.03-3.11 (m, 6H), 2.77-2.98 (m, 4H), 1.77-1.82 (m, 6H), 1.21 (t, J=6.0 Hz, 3H). LCMS (ESI, m/z): 494 [M+H]$^+$.

Example 17: 1,1,1,3,3,3-Hexafluoropropan-2-yl 7-(4-(pyrrolidin-1-yl)benzyl)-2,7-diazaspiro[3.5]nonane-2-carboxylate

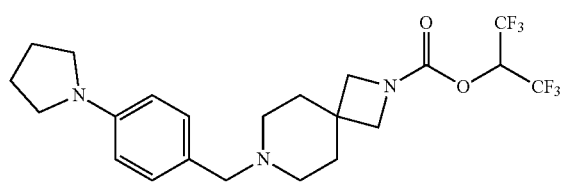 [SMILES: O=C(OC(C(F)(F)F)C(F)(F)F)N1CC2(CCN(Cc3ccc(N4CCCC4)cc3)CC2)C1]

Step 1: Synthesis of tert-butyl 7-(4-(pyrrolidin-1-yl)benzyl)-2,7-diazaspiro[3.5]nonane-2-carboxylate

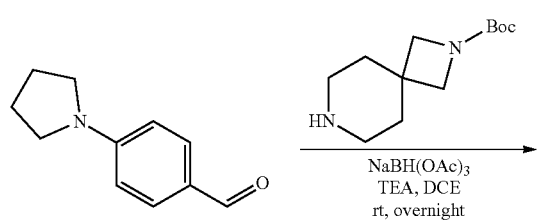

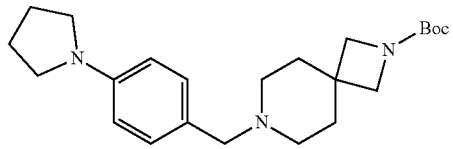

A round-bottom flask was charged with 4-(pyrrolidin-1-yl)benzaldehyde (700 mg, 3.99 mmol, 1.00 equiv) in 1,2-dichloroethane (20 mL), tert-butyl 2,7-diazaspiro[3.5]nonane-2-carboxylate (1.08 g, 4.77 mmol, 1.20 equiv), and triethylamine (1.21 g, 12.0 mmol, 3.00 equiv). The resulting solution was stirred for 30 min at room temperature prior to addition of sodium triacetoxyborohydride (2.54 g, 12.0 mmol, 3.00 equiv). The reaction mixture was stirred overnight at room temperature and quenched with water (20 mL). The resulting solution was extracted with dichloromethane (3×20 mL) and the organic layers were combined, washed with brine (2×20 mL), dried over anhydrous sodium sulfate, filtered and concentrated under reduced pressure. The residue was chromatographed on a silica gel column to yield 1.20 g (78% yield) of tert-butyl 7-(4-(pyrrolidin-1-yl)benzyl)-2,7-diazaspiro[3.5]nonane-2-carboxylate. LCMS (ESI, m/z): 386 [M+H]$^+$.

Step 2: Synthesis of 7-(4-(pyrrolidin-1-yl)benzyl)-2,7-diazaspiro[3.5]nonane

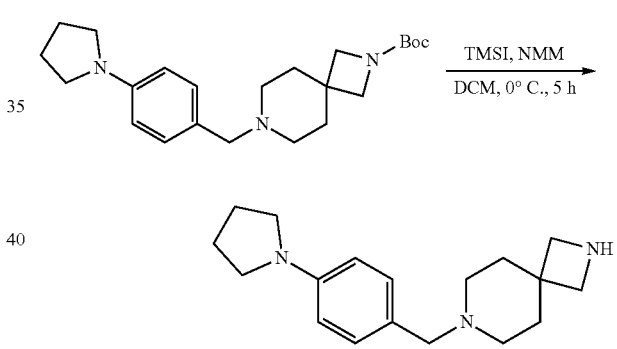

A round-bottom flask was charged with tert-butyl 7-(4-(pyrrolidin-1-yl)benzyl)-2,7-diazaspiro[3.5]nonane-2-carboxylate (1.20 g, 3.11 mmol, 1.00 equiv) in dichloromethane (20 mL). Trimethyiodosilane (936 mg, 4.68 mmol, 1.50 equiv) and N-methylmorpholine (945 mg, 9.34 mmol, 3.00 equiv) were added. The resulting solution was stirred for 5 h at 0° C. and concentrated under reduced pressure to yield 1.25 g (crude) of 7-(4-(pyrrolidin-1-yl)benzyl)-2,7-diazaspiro[3.5]nonane. LCMS (ESI, m/z): 286 [M+H]$^+$.

Step 3: Synthesis of 1,1,1,3,3,3-hexafluoropropan-2-yl 7-(4-(pyrrolidin-1-yl)benzyl)-2,7-diazaspiro[3.5]nonane-2-carboxylate

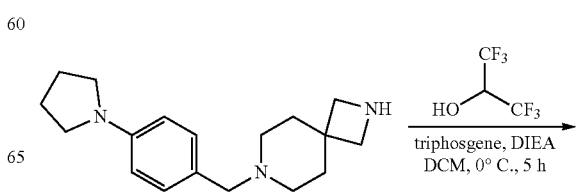

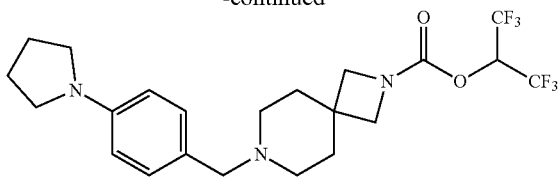

A round-bottom flask was charged with triphosgene (47.5 mg, 0.160 mmol, 0.35 equiv) in dichloromethane (5 mL) and 1,1,1,3,3,3-hexafluoropropan-2-ol (115 mg, 0.680 mmol, 1.50 equiv) under nitrogen. N,N-Diisopropylethylamine (177 mg, 1.37 mmol, 3.00 equiv) was added dropwise at 0° C. and the resulting solution was stirred for 2 h at 0° C. prior to dropwise addition of 7-(4-(pyrrolidin-1-yl)benzyl)-2,7-diazaspiro[3.5]nonane (130 mg, 0.460 mmol, 1.00 equiv) in dichloromethane (5 mL). The reaction mixture was stirred for 3 h at 0° C. and quenched with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (420 mg) was purified by preparative HPLC to afford 60.4 mg (28% yield) of 1,1,1,3,3,3-hexafluoropropan-2-yl 7-(4-(pyrrolidin-1-yl)benzyl)-2,7-diazaspiro[3.5]nonane-2-carboxylate. $^1$H NMR (300 MHz, Chloroform-d) δ 7.13 (d, J=6.0 Hz, 2H), 6.52 (d, J=9.0 Hz, 2H), 5.58-5.71 (m, 1H), 3.74-3.78 (m, 4H), 3.40 (s, 2H), 3.28 (t, J=7.5 Hz, 4H), 2.35 (br, 4H), 1.94-2.04 (m, 4H), 1.79-1.92 (m, 4H). LCMS (ESI, m/z): 160 $[C_{11}H_{14}N]^+$.

Example 18: 1,1,1,3,3,3-Hexafluoropropan-2-yl 7-(4-(morpholinomethyl)benzyl)-2,7-diazaspiro[3.5]nonane-2-carboxylate

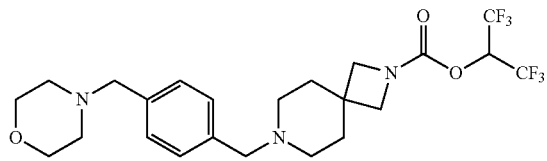 [SMILES: O=C(OC(C(F)(F)F)C(F)(F)F)N1CC2(CCN(Cc3ccc(CN4CCOCC4)cc3)CC2)C1]

Step 1: Synthesis of 4-(morpholinomethyl)benzonitrile

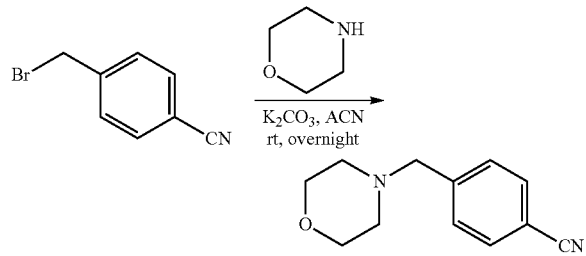

A round-bottom flask was charged with 4-(bromomethyl) benzonitrile (10.0 g, 51.0 mmol, 1.00 equiv), acetonitrile (30 mL), morpholine (6.70 g, 76.9 mmol, 1.50 equiv), and potassium carbonate (14.2 g, 103 mmol, 2.00 equiv) under nitrogen. The reaction mixture was stirred overnight at room temperature and diluted with water (20 mL). The resulting solution was extracted with ethyl acetate (3×50 mL) and the organic layers were combined, washed with brine (2×30 mL), dried over anhydrous sodium sulfate, filtered and concentrated under reduced pressure. The residue was chromatographed on a silica gel column to provide 8.84 g (86% yield) of 4-(morpholinomethyl)benzonitrile. LCMS (ESI, m/z): 203 $[M+H]^+$.

Step 2: Synthesis of 4-(morpholinomethyl)benzaldehyde

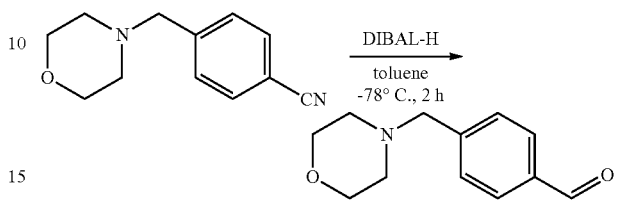

A round-bottom flask was charged with 4-(morpholinomethyl)benzonitrile (8.54 g, 42.2 mmol, 1.00 equiv) in toluene (50 mL) under nitrogen. Diisobutylaluminum hydride (84.5 mL, 84.5 mmol, 2.00 equiv, 1M in hexane) was added at −78° C. and the reaction mixture was stirred for 2 h at −78° C. before quenching with saturated NH$_4$Cl solution (50 mL). The resulting solution was extracted with ethyl acetate (3×50 mL) and the organic layers were combined, washed with brine (2×50 mL), dried over anhydrous sodium sulfate, filtered and concentrated under reduced pressure. The residue was chromatographed on a silica gel column to yield 8.50 g (98% yield) of 4-(morpholinomethyl)benzaldehyde. LCMS (ESI, m/z): 206 $[M+H]^+$.

Step 3: Synthesis of tert-butyl 7-(4-(morpholinomethyl) benzyl)-2,7-diazaspiro[3.5]nonane-2-carboxylate

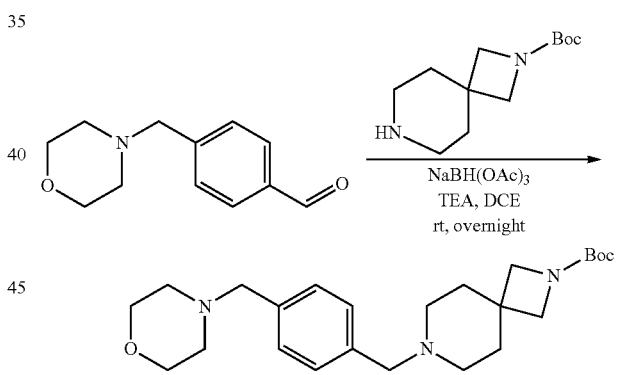

A round-bottom flask was charged with 4-(morpholinomethyl)benzaldehyde (900 mg, 4.38 mmol, 1.00 equiv) in 1,2-dichloroethane (30 mL). Tert-butyl 2,7-diazaspiro[3.5] nonane-2-carboxylate (992 mg, 4.38 mmol, 1.00 equiv) and triethylamine (1.33 g, 13.1 mmol, 3.00 equiv) were added. The reaction mixture was stirred for 30 min at room temperature prior to addition of sodium triacetoxyborohydride (2.80 g, 13.2 mmol, 3.00 equiv). The reaction mixture was stirred overnight at room temperature and quenched with water (30 mL). The resulting solution was extracted with dichloromethane (3×30 mL) and the organic layers were combined, washed with brine (2×30 mL), dried over anhydrous sodium sulfate, filtered and concentrated under reduced pressure. The residue was chromatographed on a silica gel column to yield 1.50 g (82% yield) of tert-butyl 7-(4-(morpholinomethyl)benzyl)-2,7-diazaspiro[3.5] nonane-2-carboxylate. LCMS (ESI, m/z): 416 $[M+H]^+$.

Step 4: Synthesis of 4-(4-((2,7-diazaspiro[3.5]nonan-7-yl)methyl)benzyl)morpholine

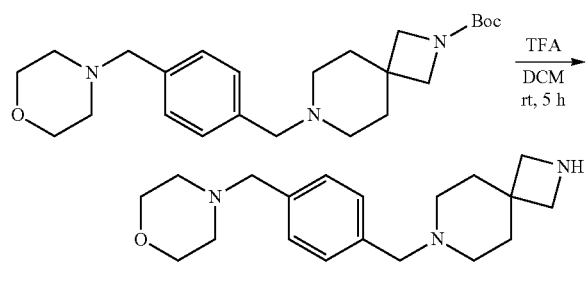

A round-bottom flask was charged with tert-butyl 7-(4-(morpholinomethyl)benzyl)-2,7-diazaspiro[3.5]nonane-2-carboxylate (1.50 g, 3.61 mmol, 1.00 equiv) in dichloromethane (20 mL). Trifluoroacetic acid (5 mL) was added. The resulting solution was stirred for 5 h at room temperature and concentrated under reduced pressure to yield 1.60 g (crude) of 4-(4-((2,7-diazaspiro[3.5]nonan-7-yl)methyl)benzyl)morpholine. LCMS (ESI, m/z): 316 [M+H]$^+$.

Step 5: Synthesis of 1,1,1,3,3,3-hexafluoropropan-2-yl 7-(4-(morpholinomethyl)benzyl)-2,7-diazaspiro[3.5]nonane-2-carboxylate

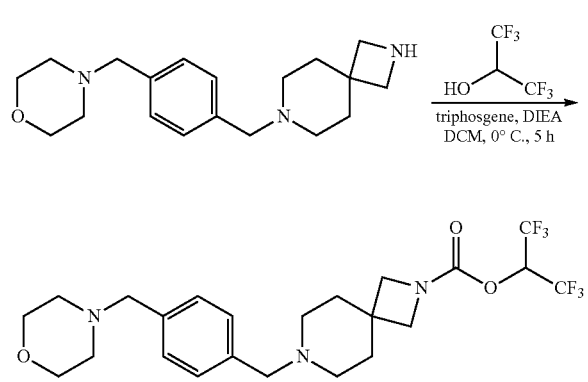

A round-bottom flask was charged with triphosgene (49.6 mg, 0.170 mmol, 0.35 equiv) in dichloromethane (5 mL) and 1,1,1,3,3,3-hexafluoropropan-2-ol (120 mg, 0.710 mmol, 1.50 equiv) under nitrogen. N,N-Diisopropylethylamine (184 mg, 1.43 mmol, 3.00 equiv) was added dropwise at 0° C. and the resulting solution was stirred for 2 h at 0° C. prior to dropwise addition of 4-(4-((2,7-diazaspiro[3.5]nonan-7-yl)methyl)benzyl)morpholine (150 mg, 0.480 mmol, 1.00 equiv) in dichloromethane (5 mL). The reaction mixture was stirred for 3 h at 0° C. and quenched with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (450 mg) was purified by preparative HPLC to afford 44.8 mg (18% yield) of 1,1,1,3,3,3-hexafluoropropan-2-yl 7-(4-(morpholinomethyl)benzyl)-2,7-diazaspiro[3.5]nonane-2-carboxylate. $^1$H NMR (300 MHz, Chloroform-d) δ 7.24-7.30 (m, 4H), 5.60-5.72 (m, 1H), 3.70-3.80 (m, 8H), 3.46-3.50 (m, 4H), 2.17-2.47 (m, 8H), 1.82 (t, J=4.5 Hz, 4H). LCMS (ESI, m/z): 510 [M+H]$^+$.

Example 19: 1,1,1,3,3,3-Hexafluoropropan-2-yl 7-((3-methyl-[1,1'-biphenyl]-4-yl)methyl)-2,7-diazaspiro[3.5]nonane-2-carboxylate

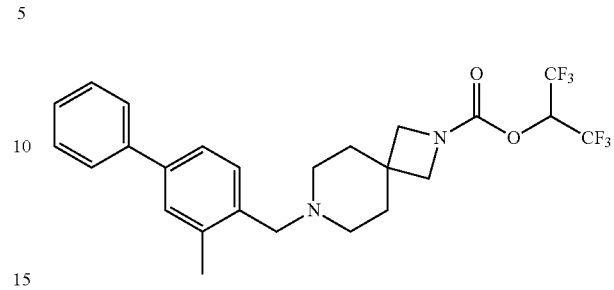

Step 1: Synthesis of 3-methyl-[1,1'-biphenyl]-4-carbaldehyde

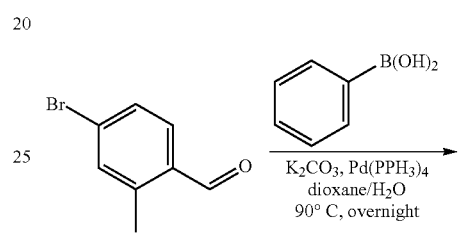

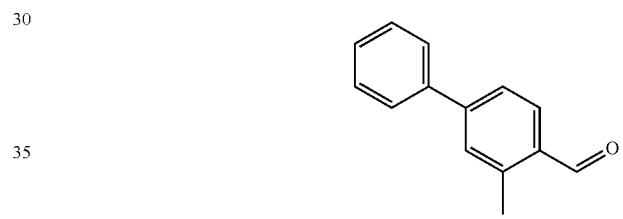

A round-bottom flask was charged with 4-bromo-2-methylbenzaldehyde (8.00 g, 40.4 mmol, 1.00 equiv), 1,4-dioxane/water (100/20 mL), phenylboronic acid (7.39 g, 60.6 mmol, 1.50 equiv), potassium carbonate (16.7 g, 121 mmol, 3.00 equiv), and tetrakis(triphenylphosphine)palladium (4.67 g, 4.04 mmol, 0.10 equiv) under nitrogen. The reaction mixture was stirred overnight at 90° C. and diluted with water (100 mL). The resulting solution was extracted with ethyl acetate (3×100 mL) and the organic layers were combined, washed with brine (2×100 mL), dried over anhydrous sodium sulfate, filtered and concentrated under reduced pressure. The residue was chromatographed on a silica gel column to provide 7.19 g (91% yield) of 3-methyl-[1,1'-biphenyl]-4-carbaldehyde.

Step 2: Synthesis of tert-butyl 7-((3-methyl-[1,1'-biphenyl]-4-yl)methyl)-2,7-diazaspiro[3.5]nonane-2-carboxylate

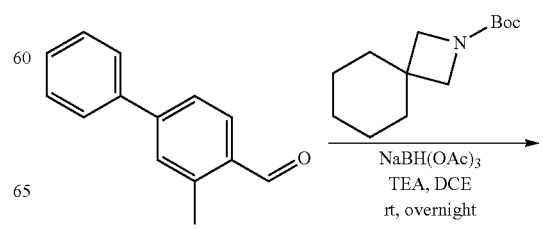

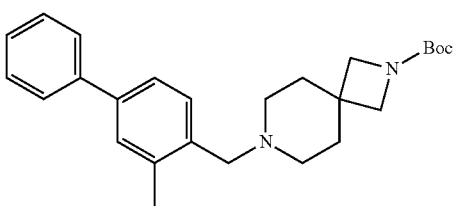

A round-bottom flask was charged with 3-methyl-[1,1'-biphenyl]-4-carbaldehyde (800 mg, 4.08 mmol, 1.00 equiv) in 1,2-dichloroethane (30 mL). Tert-butyl 2,7-diazaspiro[3.5]nonane-2-carboxylate (922 mg, 4.07 mmol, 1.00 equiv) and triethylamine (1.23 g, 12.2 mmol, 3.00 equiv) were added. The resulting solution was stirred for 30 min at room temperature prior to addition of sodium triacetoxyborohydride (2.59 g, 12.2 mmol, 3.00 equiv). The reaction mixture was stirred overnight at room temperature and quenched with water (30 mL). The resulting solution was extracted with dichloromethane (3×30 mL) and the organic layers were combined, washed with brine (2×30 mL), dried over anhydrous sodium sulfate, filtered and concentrated under reduced pressure. The residue was chromatographed on a silica gel column to yield 1.40 g (84% yield) of tert-butyl 7-((3-methyl[1,1'-biphenyl]-4-yl)methyl)-2,7-diazaspiro[3.5]nonane-2-carboxylate. LCMS (ESI, m/z): 407 [M+H]+.

Step 3: Synthesis of 7-((3-methyl-[1,1'-biphenyl]-4-yl)methyl)-2,7-diazaspiro[3.5]nonane

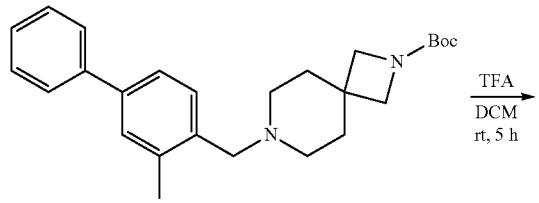

A round-bottom flask was charged with tert-butyl 7-((3-methyl-[1,1'-biphenyl]-4-yl)methyl)-2,7-diazaspiro[3.5]nonane-2-carboxylate (1.40 g, 3.44 mmol, 1.00 equiv) in dichloromethane (20 mL) and trifluoroacetic acid (5 mL). The resulting solution was stirred for 5 h at room temperature and concentrated under reduced pressure to yield 1.50 g (crude) of 7-((3-methyl-[1,1'-biphenyl]-4-yl)methyl)-2,7-diazaspiro[3.5]nonane. LCMS (ESI, m/z): 307 [M+H]+.

Step 4: Synthesis of 1,1,1,3,3,3-hexafluoropropan-2-yl 7-((3-methyl-[1,1'-biphenyl]-4-yl)methyl)-2,7-diazaspiro[3.5]nonane-2-carboxylate

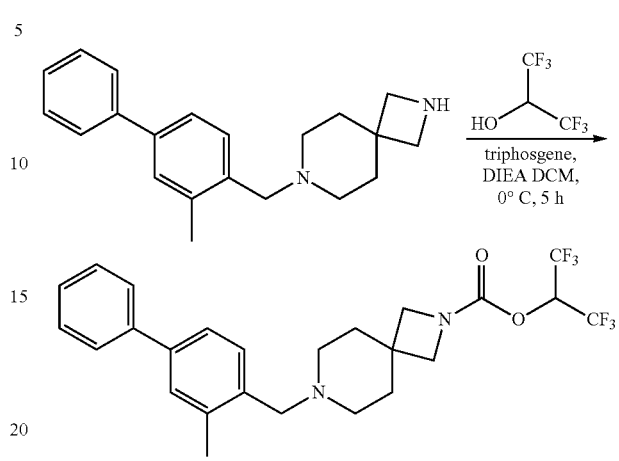

A round-bottom flask was charged with triphosgene (51.1 mg, 0.170 mmol, 0.35 equiv) in dichloromethane (5 mL) and 1,1,1,3,3,3-hexafluoropropan-2-ol (123 mg, 0.730 mmol, 1.50 equiv) under nitrogen. N-Ethyl-N-isopropylpropan-2-amine (190 mg, 1.47 mmol, 3.00 equiv) was added dropwise at 0° C. The resulting solution was stirred for 2 h at 0° C. and 7-((3-methyl-[1,1'-biphenyl]-4-yl)methyl)-2,7-diazaspiro[3.5]nonane (150 mg, 0.490 mmol, 1.00 equiv) in dichloromethane (5 mL) was added dropwise at 0° C. and the resulting solution was stirred for 3 h at 0° C. before quenching with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (460 mg) was purified by preparative HPLC to afford 109.8 mg (45% yield) of 1,1,1,3,3,3-hexafluoropropan-2-yl 7-((3-methyl-[1,1'-biphenyl]-4-yl)methyl)-2,7-diazaspiro[3.5]nonane-2-carboxylate. $^1$H NMR (300 MHz, Chloroform-d) δ 7.56-7.60 (m, 2H), 7.26-7.45 (m, 6H), 5.62-5.70 (m, 1H), 3.75-3.85 (m, 4H), 3.45 (s, 2H), 2.46 (br, 7H), 1.80 (br, 4H). LCMS (ESI, m/z): 501 [M+H]+.

Example 20: 4-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)morpholine-2-carboxylic acid

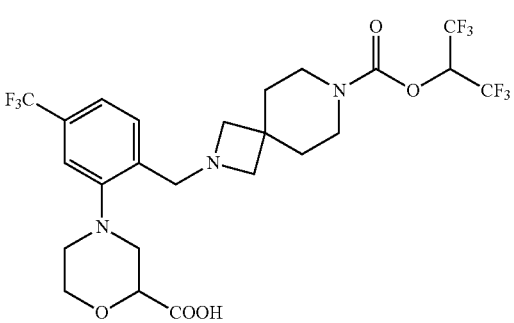 [SMILES: O=C(O)C1CN(c2cc(C(F)(F)F)ccc2CN2CC3(CCN(C(=O)OC(C(F)(F)F)C(F)(F)F)CC3)C2)CCO1]

Step 1: Synthesis of methyl 4-(2-formyl-5-(trifluoromethyl)phenyl)morpholine-2-carboxylate

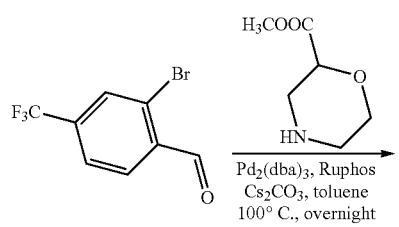

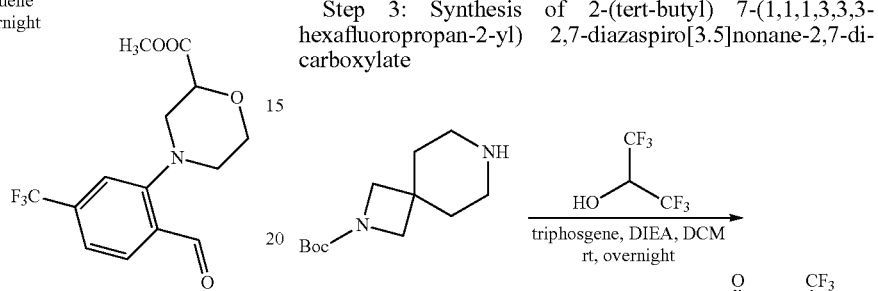

A round-bottom flask was charged with 2-bromo-4-(trifluoromethyl)benzaldehyde (1.20 g, 4.74 mmol, 1.00 equiv), methyl morpholine-2-carboxylate (1.38 g, 9.48 mmol, 2.00 equiv), tris(dibenzylideneacetone)dipalladium (0.218 g, 0.240 mmol, 0.05 equiv), dicyclohexyl(2',6'-diisopropoxybiphenyl-2-yl)phosphine (0.445 g, 0.950 mmol, 0.20 equiv), cesium carbonate (4.66 g, 14.3 mmol, 3.00 equiv), and toluene (30 mL) under nitrogen. The reaction mixture was stirred overnight at 100° C. and quenched with water (50 mL). The resulting solution was extracted with ethyl acetate (3×50 mL) and the organic layers were combined, washed with brine (3×100 mL), dried over anhydrous sodium sulfate, filtered and concentrated under reduced pressure. The residue was chromatographed on a silica gel column to provide 0.432 g (25% yield) of methyl 4-(2-formyl-5-(trifluoromethyl)phenyl)morpholine-2-carboxylate. LCMS (ESI, m/z): 318 [M+H]⁺.

Step 2: Synthesis of 4-(2-formyl-5-(trifluoromethyl)phenyl)morpholine-2-carboxylic acid

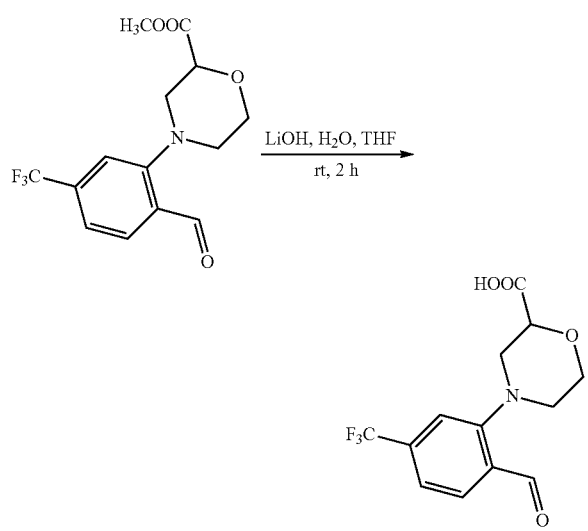

A round-bottom flask was charged with methyl 4-(2-formyl-5-(trifluoromethyl)phenyl)morpholine-2-carboxylate (432 mg, 1.36 mmol, 1.00 equiv), tetrahydrofuran (40 mL), lithium hydroxide (98.0 mg, 4.09 mmol, 3.00 equiv), and water (16 mL). The reaction mixture was stirred for 2 h at room temperature and quenched with water (20 mL). The pH of the solution was adjusted to 5 with hydrochloric acid (1M), and the resulting solution was extracted with dichloromethane (3×20 mL), organic layers were combined, washed with brine (2×20 mL), dried over anhydrous sodium sulfate, filtered and concentrated under reduced pressure to provide 410 mg (99% yield) of 4-(2-formyl-5-(trifluoromethyl)phenyl)morpholine-2-carboxylic acid. LCMS (ESI, m/z): 304 [M+H]⁺.

Step 3: Synthesis of 2-(tert-butyl) 7-(1,1,1,3,3,3-hexafluoropropan-2-yl) 2,7-diazaspiro[3.5]nonane-2,7-dicarboxylate

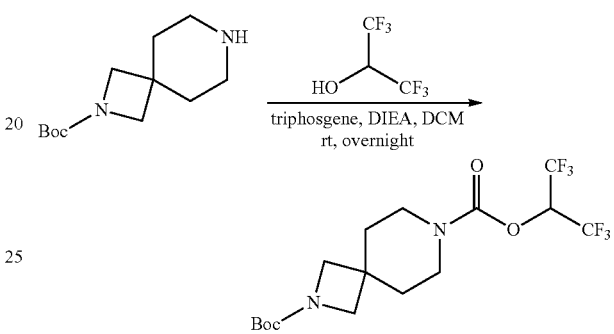

A round-bottom flask was charged with triphosgene (1.84 g, 6.19 mmol, 0.70 equiv) and dichloromethane (25 mL). 1,1,1,3,3,3-Hexafluoropropan-2-ol (2.97 g, 17.7 mmol, 2.00 equiv) and N,N-diisopropylethylamine (4.57 g, 35.4 mmol, 4.00 equiv) were added sequentially at 0° C. The mixture was stirred for 2 h at room temperature prior to addition of tert-butyl 2,7-diazaspiro[3.5]nonane-2-carboxylate (2.00 g, 8.84 mmol, 1.00 equiv). The reaction mixture was stirred overnight at room temperature and quenched with water (15 mL). The resulting solution was extracted with dichloromethane (3×25 mL) and the organic layers were combined, washed with brine (2×75 mL), dried over anhydrous sodium sulfate, filtered and concentrated under reduced pressure. The residue was chromatographed on a silica gel column to provide 1.90 g (51% yield) of 2-(tert-butyl) 7-(1,1,1,3,3,3-hexafluoropropan-2-yl) 2,7-diazaspiro[3.5] nonane-2,7-dicarboxylate. LCMS (ESI, m/z): 421 [M+H]⁺.

Step 4: Synthesis of 1,1,1,3,3,3-hexafluoropropan-2-yl 2,7-diazaspiro[3.5]nonane-7-carboxylate

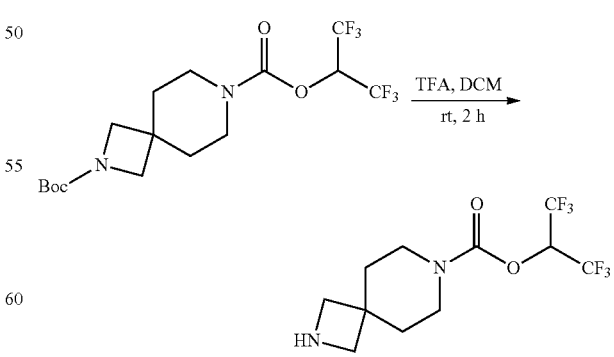

A round-bottom flask was charged with 2-(tert-butyl) 7-(1,1,1,3,3,3-hexafluoropropan-2-yl) 2,7-diazaspiro[3.5] nonane-2,7-dicarboxylate (482 mg, 1.15 mmol, 1.00 equiv), dichloromethane (40 mL), and trifluoroacetic acid (4 mL).

The resulting solution was stirred for 2 h at room temperature and concentrated under reduced pressure to provide 550 mg (crude) of 1,1,1,3,3,3-hexafluoropropan-2-yl 2,7-diazaspiro[3.5]nonane-7-carboxylate. LCMS (ESI, m/z): 321 [M+H]$^+$.

Step 5: Synthesis of 4-(2-((7-(((1,1,1,3,3,3-hexafluoropropan-2-yl)oxy)carbonyl)-2,7-diazaspiro[3.5]nonan-2-yl)methyl)-5-(trifluoromethyl)phenyl)morpholine-2-carboxylic acid

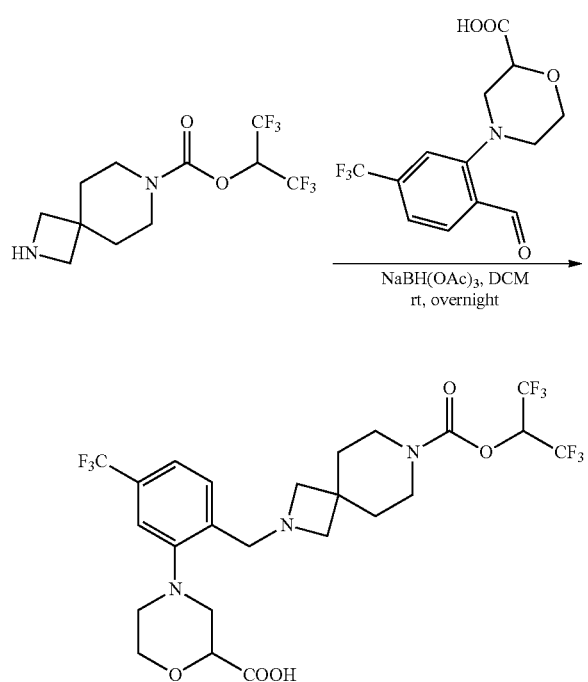 [SMILES: O=C(OC(C(F)(F)F)C(F)(F)F)N1CCC2(CC1)CNC2 ; O=Cc1ccc(C(F)(F)F)cc1N1CCOC(C(=O)O)C1 ; O=C(O)C1CN(c2cc(C(F)(F)F)ccc2CN2CC3(CCN(C(=O)OC(C(F)(F)F)C(F)(F)F)CC3)C2)CCO1]

A round-bottom flask was charged with 4-(2-formyl-5-(trifluoromethyl)phenyl)morpholine-2-carboxylic acid (136 mg, 0.450 mmol, 1.00 equiv), 1,1,1,3,3,3-hexafluoropropan-2-yl 2,7-diazaspiro[3.5]nonane-7-carboxylate (172 mg, 0.540 mmol, 1.20 equiv), and dichloromethane (20 mL). The mixture was stirred for 2 h at room temperature prior to addition of sodium triacetoxyborohydride (286 mg, 1.35 mmol, 3.00 equiv). The reaction mixture was stirred overnight at room temperature and quenched with water (20 mL). The resulting mixture was extracted with dichloromethane (3×20 mL) and the organic layers were combined, washed with brine (1×100 mL), dried over anhydrous sodium sulfate, filtered and concentrated under reduced pressure. The crude product (550 mg) was purified by preparative HPLC to afford 28.6 mg (10% yield) of 4-(2-((7-(((1,1,1,3,3,3-hexafluoropropan-2-yl)oxy)carbonyl)-2,7-diazaspiro[3.5]nonan-2-yl)methyl)-5-(trifluoromethyl)phenyl)morpholine-2-carboxylic acid. $^1$H NMR (300 MHz, Methanol-d$_4$) δ 7.55-7.69 (m, 3H), 6.11-6.20 (m, 1H), 4.46 (br, 2H), 4.24-4.26 (m, 1H), 4.08-4.14 (m, 1H), 3.81-3.90 (m, 5H), 3.53-3.55 (m, 4H), 3.22 (br, 2H), 3.02-3.09 (m, 1H), 2.90-2.94 (m, 1H), 1.97 (br, 4H). LCMS (ESI, m/z): 608 [M+H]$^+$.

Example 21: 5-((7-(((1,1,1,3,3,3-Hexafluoropropan-2-yl)oxy)carbonyl)-2,7-diazaspiro[3.5]nonan-2-yl)methyl)-2-(trifluoromethyl)benzoic acid

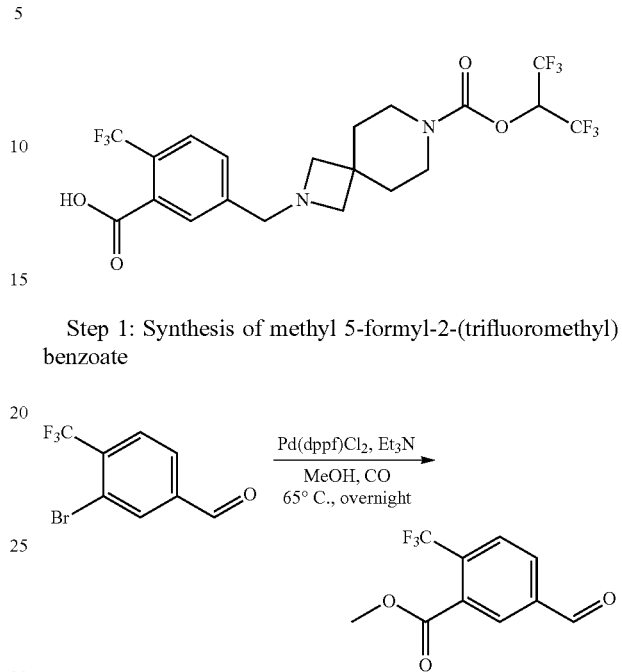

Step 1: Synthesis of methyl 5-formyl-2-(trifluoromethyl)benzoate

A 100-mL autoclave was charged with 3-bromo-4-(trifluoromethyl)benzaldehyde (3.00 g, 11.9 mmol, 1.00 equiv), 1,1'-bis(diphenylphosphino)ferrocenepalladiumdichloride (0.869 g, 1.19 mmol, 0.10 equiv), triethylamine (3.61 g, 35.7 mmol, 3.00 equiv), and methanol (50 mL). The contents of the autoclave were placed under an atmosphere of carbon monoxide (15 atm). The resulting solution was stirred overnight at 65° C. and quenched with water (50 mL). The reaction mixture was extracted with dichloromethane (3×50 mL) and the organic layers were combined, washed with brine (1×100 mL), dried over anhydrous sodium sulfate, filtered and concentrated under reduced pressure. The residue was chromatographed on a silica gel column to provide 2.00 g (73% yield) of methyl 5-formyl-2-(trifluoromethyl)benzoate. $^1$H NMR (300 MHz, Chloroform-d) δ 10.4 (s, 1H), 8.31 (s, 1H), 8.14 (d, J=8.1 Hz, 1H), 7.97 (d, J=8.1 Hz, 1H), 4.01 (s, 3H).

Step 2: Synthesis of tert-butyl 2-(3-(methoxycarbonyl)-4-(trifluoromethyl)benzyl)-2,7-diazaspiro[3.5]nonane-7-carboxylate

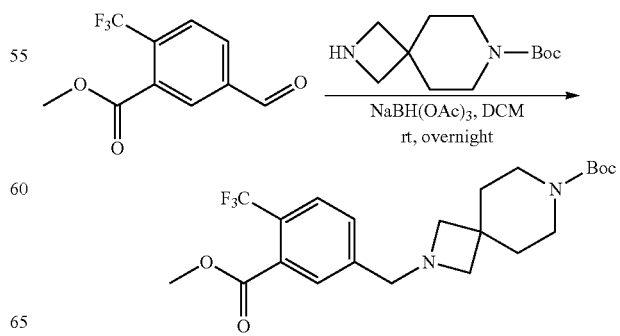

A round-bottom flask was charged with methyl 5-formyl-2-(trifluoromethyl)benzoate (0.300 g, 1.29 mmol, 1.00 equiv), tert-butyl 2,7-diazaspiro[3.5]nonane-7-carboxylate (0.585 g, 2.58 mmol, 2.00 equiv), and dichloromethane (15 mL). The mixture was stirred for 1 h at room temperature prior to addition of sodium triacetoxyborohydride (1.09 g, 5.16 mmol, 4.00 equiv). The reaction mixture was stirred overnight at room temperature and quenched with water (50 mL). The resulting mixture was extracted with dichloromethane (3×50 mL) and the organic layers were combined, washed with brine (1×100 mL), dried over anhydrous sodium sulfate, filtered and concentrated under reduced pressure. The residue was chromatographed on a silica gel column to provide 0.360 g (63% yield) of tert-butyl 2-(3-(methoxycarbonyl)-4-(trifluoromethyl)benzyl)-2,7-diazaspiro[3.5]nonane-7-carboxylate. LCMS (ESI, m/z): 443 [M+H]⁺.

Step 3: Synthesis of 5-((7-(tert-butoxycarbonyl)-2,7-diazaspiro[3.5]nonan-2-yl)methyl)-2-(trifluoromethyl)benzoic acid

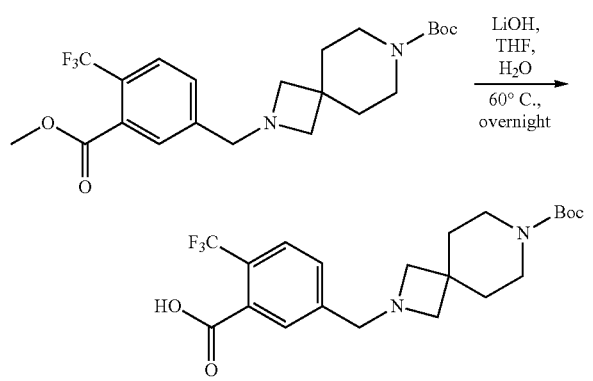

A round-bottom flask was charged with tert-butyl 2-(3-(methoxycarbonyl)-4-(trifluoromethyl)benzyl)-2,7-diazaspiro[3.5]nonane-7-carboxylate (360 mg, 0.814 mmol, 1.00 equiv), lithium hydroxide (195 mg, 8.14 mmol, 10.00 equiv), tetrahydrofuran (5 mL), and water (2 mL). The resulting solution was stirred overnight at 60° C. and quenched with water (10 mL). The pH of the solution was adjusted to 6 with hydrochloric acid (1M), and the resulting mixture was extracted with dichloromethane (3×50 mL). Organic layers were combined, washed with brine (30 mL), dried over anhydrous sodium sulfate, filtered and concentrated under reduced pressure to provide 280 mg (80% yield) of 5-((7-(tert-butoxycarbonyl)-2,7-diazaspiro[3.5]nonan-2-yl)methyl)-2-(trifluoromethyl)benzoic acid. LCMS (ESI, m/z): 429 [M+H]⁺.

Step 4: Synthesis of 5-((2,7-diazaspiro[3.5]nonan-2-yl)methyl)-2-(trifluoromethyl)benzoic acid

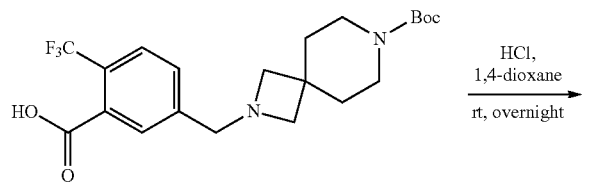

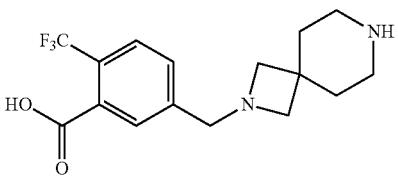

A round-bottom flask was charged with 5-((7-(tert-butoxycarbonyl)-2,7-diazaspiro[3.5]nonan-2-yl)methyl)-2-(trifluoromethyl)benzoic acid (280 mg, 0.650 mmol, 1.00 equiv), concentrated hydrochloride acid (3 mL), and 1,4-dioxane (12 mL). The resulting solution was stirred overnight at room temperature and concentrated under reduced pressure to provide 270 mg (crude) of 5-((2,7-diazaspiro[3.5]nonan-2-yl)methyl)-2-(trifluoromethyl)benzoic acid. LCMS (ESI, m/z): 329 [M+H]⁺.

Step 5: Synthesis of 5-((7-(((1,1,1,3,3,3-hexafluoropropan-2-yl)oxy)carbonyl)-2,7-diazaspiro[3.5]nonan-2-yl)methyl)-2-(trifluoromethyl)benzoic acid

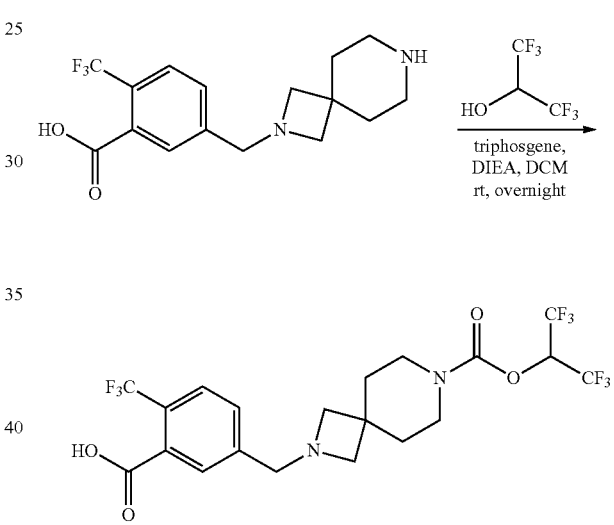

A round-bottom flask was charged with triphosgene (127 mg, 0.430 mmol, 0.70 equiv) and dichloromethane (5 mL). 1,1,1,3,3,3-Hexafluoropropan-2-ol (205 mg, 1.22 mmol, 2.00 equiv) and N,N-diisopropylethylamine (315 mg, 2.44 mmol, 4.00 equiv) were sequentially added at 0° C. The mixture was stirred for 2 h at room temperature prior to addition of 5-((2,7-diazaspiro[3.5]nonan-2-yl)methyl)-2-(trifluoromethyl)benzoic acid (200 mg, 0.610 mmol, 1.00 equiv). The reaction mixture was stirred overnight at room temperature and quenched with water (50 mL). The resulting mixture was extracted with dichloromethane (3×50 mL) and the organic layers were combined, washed with brine (1×100 mL), dried over anhydrous sodium sulfate, filtered and concentrated under reduced pressure. The crude product (400 mg) was purified by preparative HPLC to afford 29.1 mg (9% yield) of 5-((7-(((1,1,1,3,3,3-hexafluoropropan-2-yl)oxy)carbonyl)-2,7-diazaspiro[3.5]nonan-2-yl)methyl)-2-(trifluoromethyl)benzoic acid. ¹H NMR (300 MHz, Methanol-d₄) δ 7.79 (s, 1H), 7.71 (d, J=8.1 Hz, 1H), 7.58 (d, J=8.1 Hz, 1H), 6.10-6.18 (m, 1H), 4.47 (s, 2H), 3.99 (s, 4H), 3.52 (br, 4H), 1.97 (br, 4H). LCMS (ESI, m/z): 523 [M+H]⁺.

Example 22: 4-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-2-methylmorpholine-2-carboxylic acid

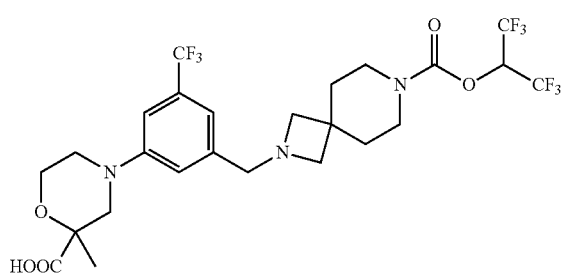 [SMILES: CC1(C(=O)O)CN(c2cc(CN3CC4(CCN(C(=O)OC(C(F)(F)F)C(F)(F)F)CC4)C3)cc(C(F)(F)F)c2)CCO1]

Step 1: Synthesis of 4-(tert-butyl) 2-ethyl 2-methylmorpholine-2,4-dicarboxylate

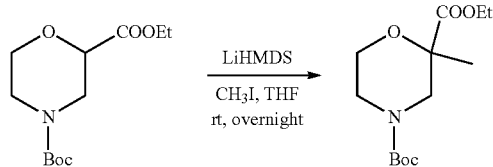 [SMILES: CCOC(=O)C1CN(C(=O)OC(C)(C)C)CCO1 ; CCOC(=O)C1(C)CN(C(=O)OC(C)(C)C)CCO1]

A round-bottom flask was charged with 4-tert-butyl 2-ethyl morpholine-2,4-dicarboxylate (2.59 g, 10.0 mmol, 1.00 equiv) and tetrahydrofuran (50 mL) under nitrogen. Lithium bis(trimethylsilyl)amide (30.0 mL, 30.0 mmol, 3.00 equiv, 1M in THF) was added dropwise over 1 h at −78° C. The mixture was stirred for 30 min at −78° C. prior to dropwise addition of iodomethane (4.26 g, 30.0 mmol, 3.00 equiv) over 20 min at −78° C. The reaction mixture was stirred overnight at room temperature and quenched with saturated NH$_4$Cl solution (50 mL). The resulting solution was extracted with ethyl acetate (2×80 mL) and the organic layers were combined, washed with brine (2×50 mL), dried over anhydrous sodium sulfate, filtered and concentrated under reduced pressure. The residue was chromatographed on a silica gel column to provide 1.81 g (66% yield) of 4-(tert-butyl) 2-ethyl 2-methylmorpholine-2,4-dicarboxylate. LCMS (ESI, m/z): 274 [M+H]$^+$.

Step 2: Synthesis of ethyl 2-methylmorpholine-2-carboxylate

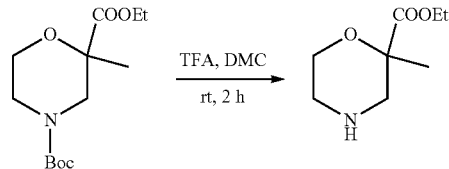 [SMILES: CCOC(=O)C1(C)CN(C(=O)OC(C)(C)C)CCO1 ; CCOC(=O)C1(C)CNCCO1]

A round-bottom flask was charged with 4-(tert-butyl) 2-ethyl 2-methylmorpholine-2,4-dicarboxylate (1.30 g, 4.76 mmol, 1.00 equiv), 1,4-dioxane (12 mL), and concentrated hydrochloric acid (4 mL). The resulting solution was stirred for 2 h at room temperature and concentrated under reduced pressure to provide 1.50 g (crude) of ethyl 2-methylmorpholine-2-carboxylate. LCMS (ESI, m/z): 174 [M+H]$^+$.

Step 3: Synthesis of 4-(3-((7-(((1,1,1,3,3,3-hexafluoropropan-2-yl)oxy)carbonyl)-2,7-diazaspiro[3.5]nonan-2-yl)methyl)-5-(trifluoromethyl)phenyl)-2-methylmorpholine-2-carboxylic acid

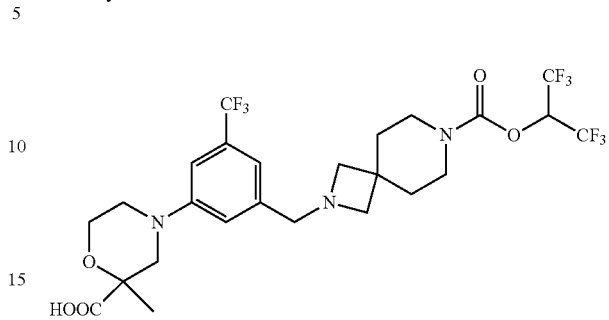

The title compound was synthesized as described in Example 21, Steps 2-5, using ethyl 2-methylmorpholine-2-carboxylate in Step 2. $^1$H NMR (400 MHz, Methanol-d$_4$) δ 7.11-7.14 (m, 2H), 7.02 (s, 1H), 6.06-6.14 (m, 1H), 4.06-4.13 (m, 2H), 3.80-3.83 (m, 1H), 3.74 (s, 2H), 3.45 (s, 4H), 3.31-3.36 (m, 1H), 3.19 (s, 4H), 2.83-2.90 (m, 1H), 2.65-2.70 (m, 1H), 1.78 (s, 4H), 1.40 (s, 3H). LCMS (ESI, m/z): 622 [M+H]$^+$.

Example 23: 1-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)piperidine-2-carboxylic acid

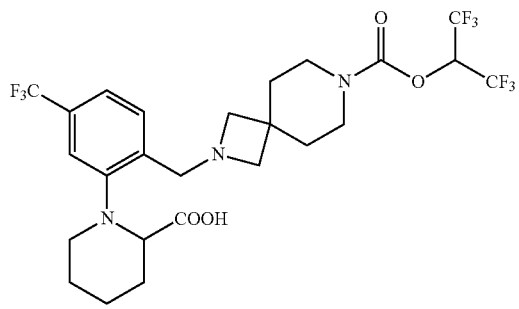 [SMILES: O=C(O)C1CCCCN1c1cc(C(F)(F)F)ccc1CN1CC2(CCN(C(=O)OC(C(F)(F)F)C(F)(F)F)CC2)C1]

Step 1: Synthesis of tert-butyl 2-(2-bromo-4-(trifluoromethyl)benzyl)-2,7-diazaspiro[3.5]nonane-7-carboxylate

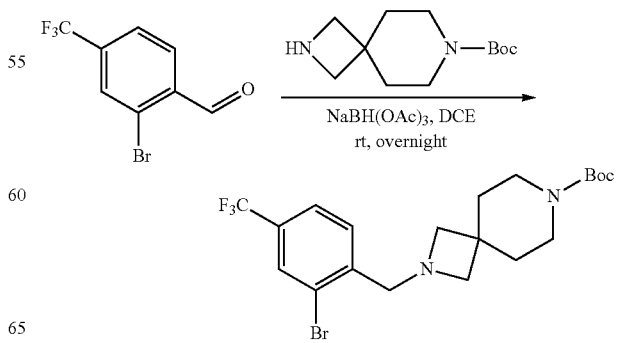

A round-bottom flask was charged with 2-bromo-4-(trifluoromethyl)benzaldehyde (506 mg, 2.00 mmol, 1.00 equiv), tert-butyl 2,7-diazaspiro[3.5]nonane-7-carboxylate (678 mg, 3.00 mmol, 1.50 equiv), and 1,2-dichloroethane (20 mL). The mixture was stirred for 1 h at room temperature prior to addition of sodium triacetoxyborohydride (1.27 g, 6.00 mmol, 3.00 equiv). The resulting solution was stirred overnight at room temperature and quenched with water (10 mL). The mixture was extracted with ethyl acetate (3×30 mL) and the organic layers were combined, washed with brine (2×30 mL), dried over anhydrous sodium sulfate, filtered and concentrated under reduced pressure. The residue was chromatographed on a silica gel column to provide 629 mg (68% yield) of tert-butyl 2-(2-bromo-4-(trifluoromethyl)benzyl)-2,7-diazaspiro[3.5]nonane-7-carboxylate. LCMS (ESI, m/z): 463 [M+H]$^+$.

Step 2: Synthesis of 1-(2-((7-(tert-butoxycarbonyl)-2,7-diazaspiro[3.5]nonan-2-yl)methyl)-5-(trifluoromethyl)phenyl)piperidine-2-carboxylic acid

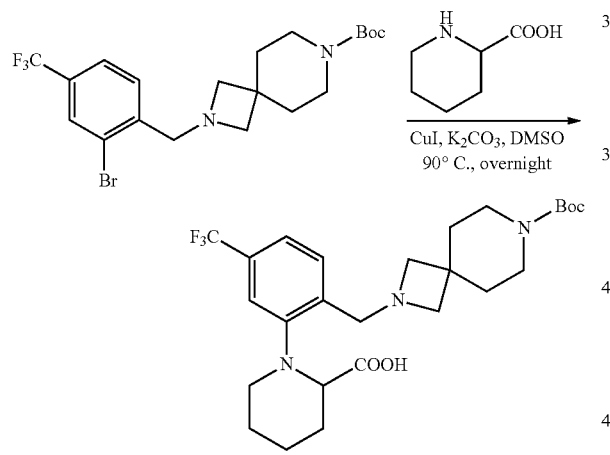

A round-bottom flask was charged with tert-butyl 2-(2-bromo-4-(trifluoromethyl)benzyl)-2,7-diazaspiro[3.5]nonane-7-carboxylate (232 mg, 0.500 mmol, 1.00 equiv), piperidine-2-carboxylic acid (194 mg, 1.50 mmol, 3.00 equiv), potassium carbonate (207 mg, 1.50 mmol, 3.00 equiv), copper(I) iodide (19.0 mg, 0.100 mmol, 0.20 equiv), and dimethyl sulfoxide (5 mL) under nitrogen. The resulting solution was stirred overnight at 90° C. and quenched with water (10 mL). The mixture was extracted with ethyl acetate (3×30 mL) and the organic layers were combined, washed with brine (2×30 mL), dried over anhydrous sodium sulfate, filtered and concentrated under reduced pressure. The residue was chromatographed on a silica gel column to provide 220 mg (86% yield) of 1-(2-((7-(tert-butoxycarbonyl)-2,7-diazaspiro[3.5]nonan-2-yl)methyl)-5-(trifluoromethyl)phenyl)piperidine-2-carboxylic acid. LCMS (ESI, m/z): 512 [M+H]$^+$.

Step 3: Synthesis of 1-(2-((7-(((1,1,1,3,3,3-hexafluoropropan-2-yl)oxy)carbonyl)-2,7-diazaspiro[3.5]nonan-2-yl)methyl)-5-(trifluoromethyl)phenyl)piperidine-2-carboxylic acid

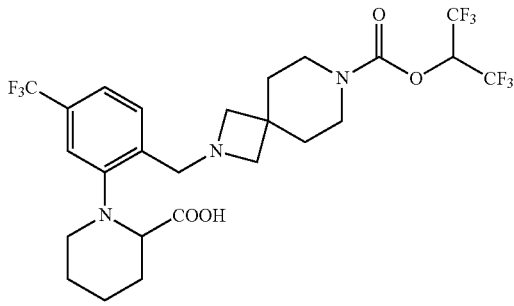 [SMILES: O=C(O)C1CCCCN1c1cc(C(F)(F)F)ccc1CN1CC2(CCN(C(=O)OC(C(F)(F)F)C(F)(F)F)CC2)C1]

The title compound was synthesized as described in Example 21, Steps 4-5, using 1-(2-((7-(tert-butoxycarbonyl)-2,7-diazaspiro[3.5]nonan-2-yl)methyl)-5-(trifluoromethyl)phenyl)piperidine-2-carboxylic acid in Step 4.

Example 24: 1,1,1,3,3,3-Hexafluoropropan-2-yl 4-((2-(1H-tetrazol-5-yl)-4-(trifluoromethyl)benzyl)(methyl)amino)-4-methylpiperidine-1-carboxylate Step 1: Synthesis of tert-butyl 4-((2-cyano-4-(trifluoromethyl)benzyl)(methyl)amino)-4-methylpiperidine-1-carboxylate

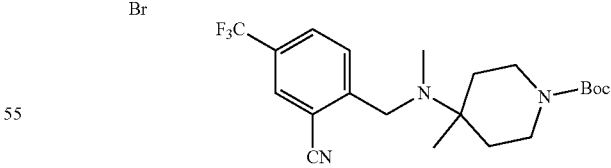

A round-bottom flask was charged with tert-butyl 4-((2-bromo-4-(trifluoromethyl)benzyl)(methyl)amino)-4-methylpiperidine-1-carboxylate (800 mg, 1.72 mmol, 1.00 equiv), tetrakis(triphenylphosphine)palladium (398 mg, 0.344 mmol, 0.20 equiv), N,N-dimethylformamide (10 mL), and zinc dicarbonitrile (800 mg, 6.81 mmol, 4.00 equiv) under nitrogen. The reaction mixture was stirred overnight at 90° C. and quenched with water (10 mL). The resulting solution was extracted with ethyl acetate (3×10 mL) and the organic layers were combined, washed with brine (2×10 mL), dried over anhydrous sodium sulfate, filtered and concentrated under reduced pressure. The residue was chromatographed on a silica gel column to provide 600 mg (85% yield) of tert-butyl 4-((2-cyano-4-(trifluoromethyl)benzyl) (methyl)amino)-4-methylpiperidine-1-carboxylate. LCMS (ESI, m/z): 412 [M+H]+.

Step 2: Synthesis of tert-butyl 4-((2-(1H-tetrazol-5-yl)-4-(trifluoromethyl)benzyl)(methyl)amino)-4-methylpiperidine-1-carboxylate

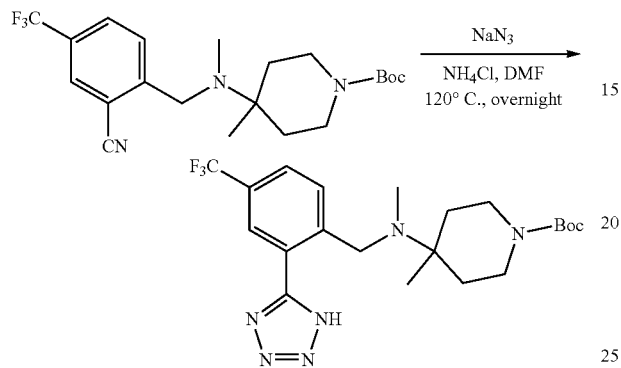

A round-bottom flask was charged with tert-butyl 4-((2-cyano-4-(trifluoromethyl)benzyl)(methyl)amino)-4-methylpiperidine-1-carboxylate (720 mg, 1.75 mmol, 1.00 equiv), ammonium chloride (557 mg, 10.4 mmol, 6.00 equiv), N,N-dimethylformamide (10 mL), and sodium azide (569 mg, 8.75 mmol, 5.00 equiv) under nitrogen. The reaction mixture was stirred overnight at 120° C. and quenched with water (10 mL). The resulting solution was extracted with ethyl acetate (3×10 mL) and the organic layers were combined, washed with brine (2×10 mL), dried over anhydrous sodium sulfate, filtered and concentrated under reduced pressure. The residue was chromatographed on a silica gel column to provide 600 mg (75% yield) of tert-butyl 4-((2-(1H-tetrazol-5-yl)-4-(trifluoromethyl)benzyl)(methyl)amino)-4-methylpiperidine-1-carboxylate. LCMS (ESI, m/z): 455 [M+H]+.

Step 3: Synthesis of 1,1,1,3,3,3-hexafluoropropan-2-yl 4-((2-(1H-tetrazol-5-yl)-4-(trifluoromethyl)benzyl)(methyl) amino)-4-methylpiperidine-1-carboxylate

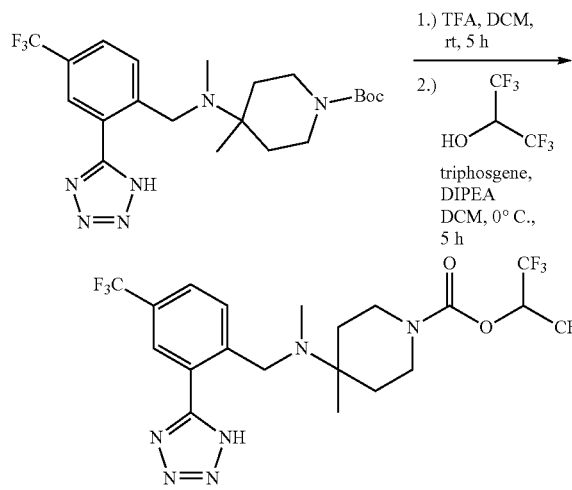

The title compound was synthesized as described in Example 14, Steps 3-4, using tert-butyl 4-((2-(1H-tetrazol-5-yl)-4-(trifluoromethyl)benzyl)(methyl)amino)-4-methylpiperidine-1-carboxylate in Step 3 to provide 1,1,1,3,3,3-hexafluoropropan-2-yl 4-((2-(1H-tetrazol-5-yl)-4-(trifluoromethyl)benzyl)(methyl)amino)-4-methylpiperidine-1-carboxylate. 1H NMR (300 MHz, Methanol-d4) δ 8.46 (s, 1H), 7.81-7.89 (m, 2H), 6.17-6.26 (m, 1H), 4.55 (br, 2H), 4.18-4.22 (m, 2H), 3.32-3.46 (m, 2H), 2.64 (s, 3H), 2.21 (br, 4H), 1.67 (s, 3H). LCMS (ESI, m/z): 549 [M+H]+.

Example 25: 1-(3-(((1-(((1,1,1,3,3,3-Hexafluoropropan-2-yl)oxy)carbonyl)-4-methylpiperidin-4-yl)oxy) methyl)-5-(trifluoromethyl)benzyl)piperidine-4-carboxylic acid

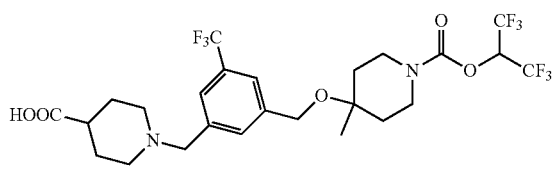 [SMILES: CC1(OCc2cc(CN3CCC(C(=O)O)CC3)cc(C(F)(F)F)c2)CCN(C(=O)OC(C(F)(F)F)C(F)(F)F)CC1]

Step 1: Synthesis of potassium ((4-(t-butoxycarbonyl)piperidin-1-yl)methyl)trifluoroborate

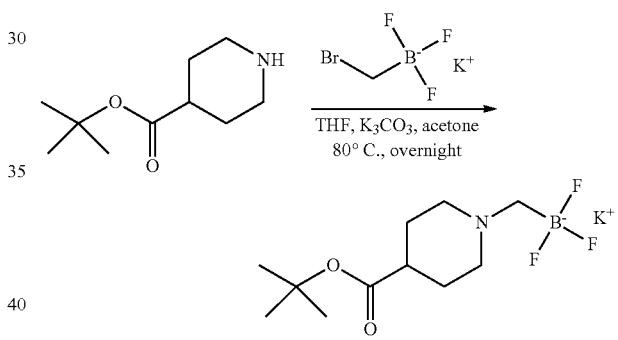

A flask was charged with t-butyl piperidine-4-carboxylate (7.00 g, 37.8 mmol, 1.00 equiv), potassium (bromomethyl) trifluoroborate (7.60 g, 37.8 mmol, 1.00 equiv), and THF (70 mL). The mixture was stirred overnight at 80° C. and concentrated under reduced pressure. Acetone (70 mL) and potassium carbonate (5.22 g, 37.8 mmol, 1.00 equiv) were added. The resulting solution was stirred for 1.5 h at room temperature and the solids were filtered. The eluent was concentrated under reduced pressure. The crude product was triturated with acetone/hexane (1/20) to provide 6.50 g (56% yield) of potassium ((4-(t-butoxycarbonyl)piperidin-1-yl) methyl)trifluoroborate as a yellow semi-solid. LCMS (ESI, m/z): 266 [M−K]−.

Step 2: Synthesis of t-butyl 4-((3-bromo-5-(trifluoromethyl)benzyl)oxy)-4-methylpiperidine-1-carboxylate

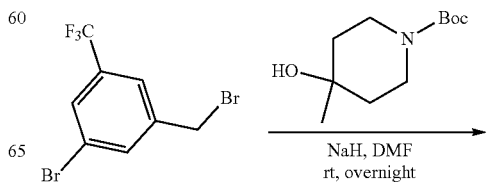

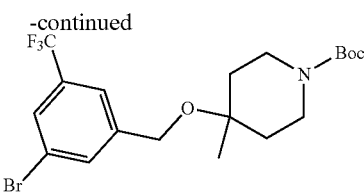

A flask was charged with t-butyl 4-hydroxy-4-methylpiperidine-1-carboxylate (1.11 g, 5.16 mmol, 1.10 equiv), DMF (10 mL), and sodium hydride (566 mg, 14.2 mmol, 3.00 equiv, 60% in mineral oil). The mixture was stirred for 30 min at 0° C. prior to addition of 1-bromo-3-(bromomethyl)-5-(trifluoromethyl)benzene (1.50 g, 4.72 mmol, 1.00 equiv). The resulting solution was stirred overnight at room temperature and quenched with water (10 mL). The mixture was extracted with EtOAc (3×20 mL) and the organic layers were combined, washed with brine (2×5 mL), dried over anhydrous $Na_2SO_4$, filtered and concentrated under reduced pressure. The residue was chromatographed on a silica gel column to provide 265 mg (12% yield) of t-butyl 4-((3-bromo-5-(trifluoromethyl)benzyl)oxy)-4-methylpiperidine-1-carboxylate as a yellow oil. LCMS (ESI, m/z): 454 [M+H]⁺.

Step 3: Synthesis of t-butyl 4-((3-((4-(t-butoxycarbonyl)piperidin-1-yl)methyl)-5-(trifluoromethyl)benzyl)oxy)-4-methylpiperidine-1-carboxylate

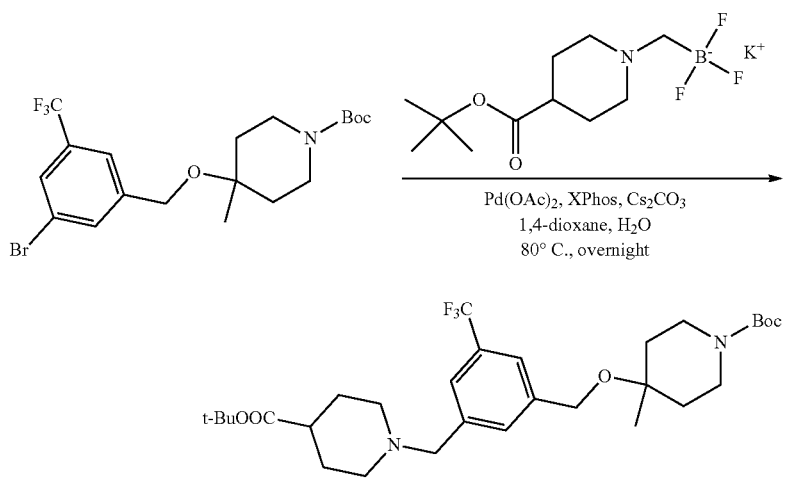

A flask was charged with t-butyl 4-((3-bromo-5-(trifluoromethyl)benzyl)oxy)-4-methylpiperidine-1-carboxylate (265 mg, 0.586 mmol, 1.00 equiv), potassium ((4-(t-butoxycarbonyl)piperidin-1-yl)methyl)trifluoroborate (358 mg, 1.17 mmol, 2.00 equiv), palladium acetate (4.00 mg, 0.0178 mmol, 0.03 equiv), 2-(dicyclohexylphosphino)-2',4',6'-triisopropylbiphenyl (16.8 mg, 0.0352 mmol, 0.06 equiv), cesium carbonate (573 mg, 1.76 mmol, 3.00 equiv), 1,4-dioxane (4 mL), and water (1 mL) under nitrogen. The resulting solution was stirred overnight at 80° C. and quenched with water (5 mL). The resulting solution was extracted with DCM (3×10 mL) and the organic layers were combined, washed with brine (2×5 mL), dried over anhydrous $Na_2SO_4$, filtered and concentrated under reduced pressure. The residue was chromatographed on a silica gel column to provide 190 mg (57% yield) of t-butyl 4-((3-((4-(t-butoxycarbonyl)piperidin-1-yl)methyl)-5-(trifluoromethyl)benzyl)oxy)-4-methylpiperidine-1-carboxylate as a yellow oil. LCMS (ESI, m/z): 571 [M+H]⁺.

Step 4: Synthesis of 1-(3-(((4-methylpiperidin-4-yl)oxy)methyl)-5-(trifluoromethyl)benzyl)piperidine-4-carboxylic acid

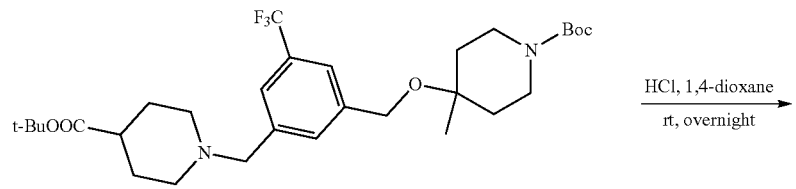

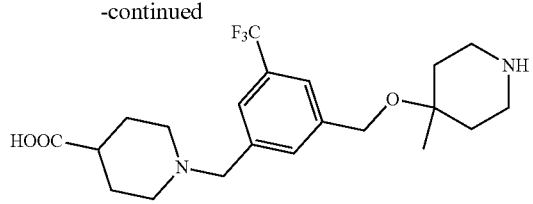

A flask was charged with t-butyl 4-((3((4-(t-butoxycarbonyl)piperidin-1-yl)methyl)-5-(trifluoromethyl)benzyl)oxy)-4-methylpiperidine-1-carboxylate (190 mg, 0.322 mmol, 1.00 equiv), 1,4-dioxane (4 mL), and concentrated hydrochloric acid (1 mL). The resulting solution was stirred overnight at room temperature and concentrated under reduced pressure to provide 140 mg (crude) of 1-(3-(((4-methylpiperidin-4-yl)oxy)methyl)-5-(trifluoromethyl)benzyl)piperidine-4-carboxylic acid as a yellow solid. LCMS (ESI, m/z): 415 [M+H]$^+$.

Step 5: Synthesis of 1-(3-(((1-(((1,1,1,3,3,3-hexafluoropropan-2-yl)oxy)carbonyl)-4-methylpiperidin-4-yl)oxy)methyl)-5-(trifluoromethyl)benzyl)piperidine-4-carboxylic acid

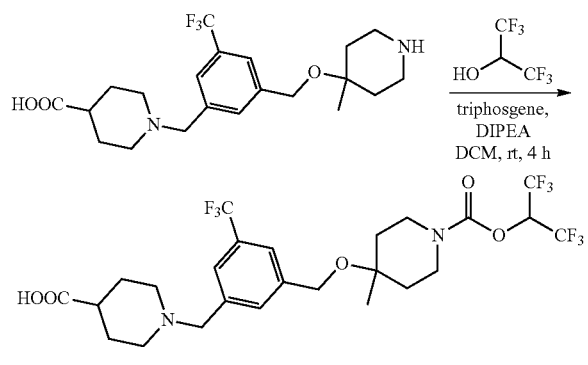

A flask was charged with triphosgene (50.2 mg, 0.169 mmol, 0.50 equiv), DCM (5 mL), and 1,1,1,3,3,3-hexafluoropropan-2-ol (114 mg, 0.678 mmol, 2.00 equiv). DIPEA (174 mg, 1.35 mmol, 4.00 equiv) was added dropwise at 0° C. The mixture was stirred for 2 h at room temperature prior to addition of 1-(3-(((4-methylpiperidin-4-yl)oxy)methyl)-5-(trifluoromethyl)benzyl)piperidine-4-carboxylic acid (140 mg, 0.338 mmol, 1.00 equiv). The reaction mixture was stirred for 2 h at room temperature and diluted with sodium bicarbonate (20%, 5 mL). The resulting solution was extracted with DCM (3×10 mL) and the organic layers were combined, washed with brine (2×5 mL), dried over anhydrous Na$_2$SO$_4$, filtered and concentrated under reduced pressure. The crude product (280 mg) was purified by preparative HPLC to provide 77.4 mg (38% yield) of 1-(3-(((1-(((1,1,1,3,3,3-hexafluoropropan-2-yl)oxy)carbonyl)-4-methylpiperidin-4-yl)oxy)methyl)-5-trifluoromethyl)benzyl)piperidine-4-carboxylic acid as a white solid. $^1$H NMR (300 MHz, Methanol-d$_4$) δ 7.73-7.68 (m, 3H), 6.17-6.13 (m, 1H), 4.62 (s, 2H), 3.97-3.88 (m, 4H), 3.45-3.40 (m, 2H), 3.15-3.11 (m, 2H), 2.61-2.54 (m, 2H), 2.37-2.36 (m, 1H), 2.03-1.98 (m, 4H), 1.90-1.82 (m, 2H), 1.64-1.61 (m, 2H), 1.36 (s, 3H). LCMS (ESI, m/z): 609 [M+H]$^+$.

Example 26: 2-(4-(2-(((1-(((1,1,1,3,3,3-Hexafluoropropan-2-yl)oxy)carbonyl)-4-methylpiperidin-4-yl) (methyl)amino)methyl)-5-(trifluoromethyl)phenyl) piperazin-1-yl)acetic acid

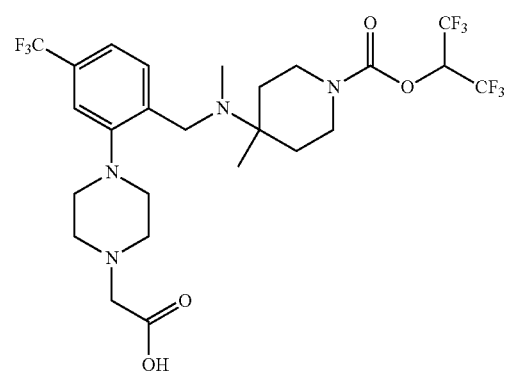 [SMILES: CN(Cc1ccc(C(F)(F)F)cc1N1CCN(CC(=O)O)CC1)C1(C)CCN(C(=O)OC(C(F)(F)F)C(F)(F)F)CC1]

Step 1: Synthesis of benzyl 4-((t-butoxycarbonyl)amino)-4-methylpiperidine-1-carboxylate

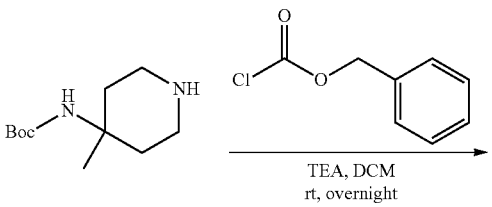

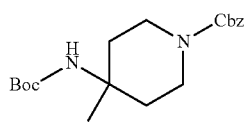

A flask was charged with t-butyl N-(4-methylpiperidin-4-yl)carbamate (3.21 g, 15.0 mmol, 1.00 equiv), benzyl chloroformate (3.06 g, 18.0 mmol, 1.20 equiv), DCM (20 mL), and TEA (4.54 g, 45.0 mmol, 3.00 equiv). The resulting solution was stirred overnight at room temperature, quenched with water (30 mL) and extracted with DCM (3×50 mL). The organic layers were combined, washed with brine (30 mL), dried over anhydrous Na$_2$SO$_4$, filtered and concentrated under reduced pressure. The residue was chromatographed on a silica gel column to provide 3.40 g (65% yield) of benzyl 4-((t-butoxycarbonyl)amino)-4-methylpiperidine-1-carboxylate as a colorless oil. LCMS (ESI, m/z): 349 [M+H]$^+$.

Step 2: Synthesis of benzyl 4-((t-butoxycarbonyl)(methyl)amino)-4-methylpiperidine-1-carboxylate

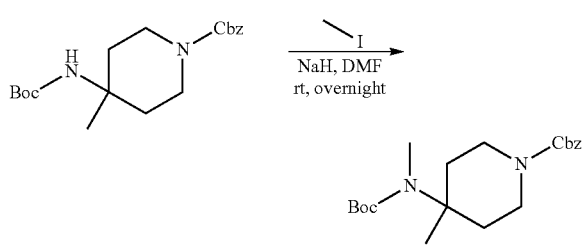

A flask was charged with benzyl 4-((t-butoxycarbonyl)amino)-4-methylpiperidine-1-carboxylate (1.39 g, 4.00 mmol, 1.00 equiv) and DMF (20 mL). Sodium hydride (480 mg, 12.0 mmol, 3.00 equiv, 60% in mineral oil) was added at 0° C. and the mixture was stirred for 10 min. Iodomethane (852 mg, 6.00 mmol, 1.50 equiv) was added and the resulting solution was stirred overnight at room temperature. The mixture was quenched with water (30 mL) and extracted with DCM (3×40 mL). The organic layers were combined, washed with brine (30 mL), dried over anhydrous Na$_2$SO$_4$, filtered and concentrated under reduced pressure. The residue was chromatographed on a silica gel column to provide 1.26 g (87% yield) of benzyl 4-((t-butoxycarbonyl)(methypamino)-4-methylpiperidine-1-carboxylate as a colorless oil. LCMS (ESI, m/z): 363 [M+H]$^+$.

Step 3: Synthesis of t-butyl methyl(4-methylpiperidin-4-yl)carbamate

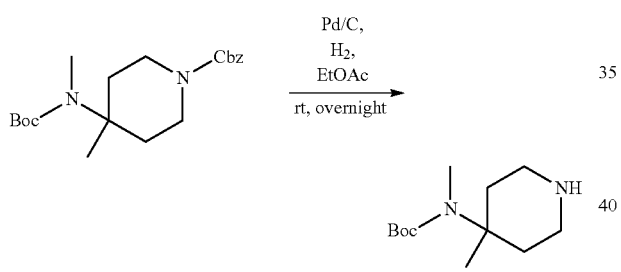

A flask was charged with benzyl 4-((t-butoxycarbonyl)(methyl)amino)-4-methylpiperidine-1-carboxylate (490 mg, 1.35 mmol, 1.00 equiv), palladium (10% on activated carbon, 245 mg), and EtOAc (10 mL). The contents of the flask were placed under an atmosphere of hydrogen (3 atm). The resulting solution was stirred overnight at room temperature. The solids were removed by filtration, and the resulting mixture was concentrated under reduced pressure to provide 285 mg (92% yield) of t-butyl methyl(4-methylpiperidin-4-yl)carbamate as a brown oil. LCMS (ESI, m/z): 229 [M+H]$^+$.

Step 4: Synthesis of 1,1,1,3,3,3-hexafluoropropan-2-yl 4-((t-butoxycarbonyl)(methyl)amino)-4-methylpiperidine-1-carboxylate

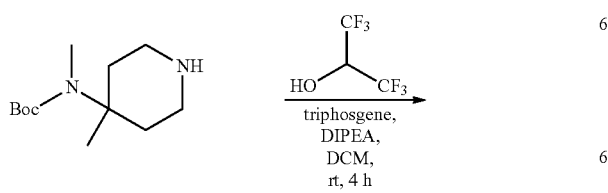

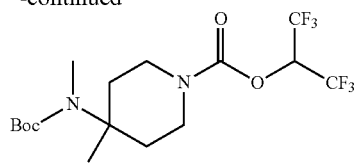

A flask was charged with triphosgene (186 mg, 0.625 mmol, 0.50 equiv), DCM (10 mL), and 1,1,1,3,3,3-hexafluoropropan-2-ol (420 mg, 2.50 mmol, 2.00 equiv). DIPEA (645 mg, 5.00 mmol, 4.00 equiv) was added dropwise at 0° C. The mixture was stirred for 2 h at room temperature. t-Butyl methyl(4-methylpiperidin-4-yl)carbamate (285 mg, 1.25 mmol, 1.00 equiv) was added. The resulting solution was stirred for 2 h at room temperature and quenched with water (10 mL). The mixture was extracted with DCM (3×20 mL) and the organic layers were combined, washed with brine (2×10 mL), dried over anhydrous Na$_2$SO$_4$, filtered and concentrated under reduced pressure. The residue was chromatographed on a silica gel column to provide 380 mg (72% yield) of 1,1,1,3,3,3-hexafluoropropan-2-yl 4-((t-butoxycarbonyl)(methypamino)-4-methylpiperidine-1-carboxylate as a colorless oil. LCMS (ESI, m/z): 423 [M+H]$^+$.

Step 5: Synthesis of 1,1,1,3,3,3-hexafluoropropan-2-yl 4-methyl-4-(methylamino)piperidine-1-carboxylate

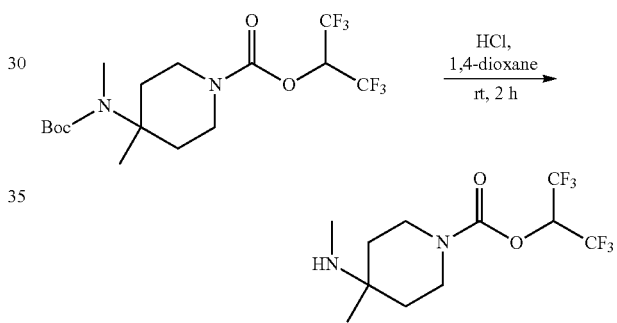

A flask was charged with 1,1,1,3,3,3-hexafluoropropan-2-yl 4-((t-butoxycarbonyl)(methypamino)-4-methylpiperidine-1-carboxylate (380 mg, 0.900 mmol, 1.00 equiv), 1,4-dioxane (10 mL), and concentrated hydrochloric acid (2 mL). The resulting solution was stirred for 2 h at room temperature and concentrated under reduced pressure to provide 290 mg (quantitative) of 1,1,1,3,3,3-hexafluoropropan-2-yl 4-methyl-4-(methylamino)piperidine-1-carboxylate as an off-white solid. LCMS (ESI, m/z): 323 [M+H]$^+$.

Step 6: Synthesis of t-butyl 2-(4-(2-formyl-5-(trifluoromethyl)phenyl)piperazin-1-yl)acetate

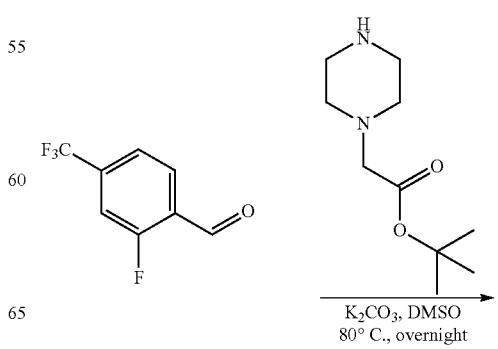

241

-continued

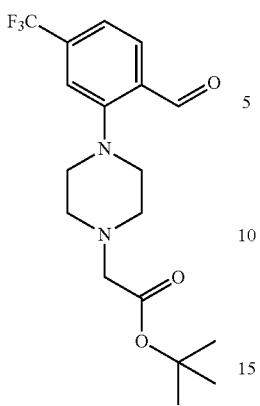

A flask was charged with 2-fluoro-4-(trifluoromethyl) benzaldehyde (500 mg, 2.60 mmol, 1.00 equiv), t-butyl 2-(piperazin-1-yl)acetate (625 mg, 3.13 mmol, 1.20 equiv), potassium carbonate (1.08 g, 7.80 mmol, 3.00 equiv), and DMSO (10 mL). The resulting solution was stirred overnight at 80° C. and quenched with water (20 mL). The mixture was extracted with EtOAc (3×20 mL) and the organic layers were combined, washed with brine (1×20 mL), dried over anhydrous Na$_2$SO$_4$, filtered and concentrated under reduced pressure. The residue was chromatographed on a silica gel column to provide 640 mg (66% yield) of t-butyl 2-(4-(2-formyl-5-(trifluoromethyl)phenyl)piperazin-1-yl)acetate as a yellow oil. LCMS (ESI, m/z): 373 [M+H]$^+$.

Step 7: Synthesis of 1,1,1,3,3,3-hexafluoropropan-2-yl 4-((2-(4-(2-(t-butoxy)-2-oxoethyl)piperazin-1-yl)-4-(trifluoromethyl)benzyl)(methyl)amino)-4-methylpiperidine-1-carboxylate

242

-continued

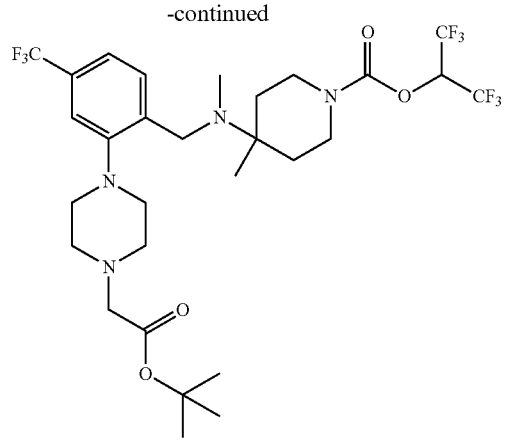

A flask was charged with 1,1,1,3,3,3-hexafluoropropan-2-yl 4-methyl-4-(methylamino)piperidine-1-carboxylate (104 mg, 0.323 mmol, 1.20 equiv), t-butyl 2-(4-(2-formyl-5-(trifluoromethyl)phenyl)piperazin-1-yl)acetate (100 mg, 0.269 mmol, 1.00 equiv), TEA (81.5 mg, 0.807 mmol, 3.00 equiv), and DCM (10 mL). The mixture was stirred for 2 h at room temperature and sodium triacetoxyborohydride (228 mg, 1.08 mmol, 4.00 equiv) was added. The resulting solution was stirred overnight at room temperature and quenched with water (20 mL). The mixture was extracted with DCM (3×20 mL) and the organic layers were combined, washed with brine (1×20 mL), dried over anhydrous Na$_2$SO$_4$, filtered and concentrated under reduced pressure. The residue was chromatographed on a silica gel column to provide 120 mg (66% yield) of 1,1,1,3,3,3-hexafluoropropan-2-yl 4-((2-(4-(2-(t-butoxy)-2-oxoethyl)piperazin-1-yl)-4-(trifluoromethyl)benzyl)(methyl)amino)-4-methylpiperidine-1-carboxylate as a yellow oil. LCMS (ESI, m/z): 679 [M+H]$^+$.

Step 8: Synthesis of 2-(4-(2-(((1-(((1,1,1,3,3,3-hexafluoropropan-2-yl)oxy)carbonyl)-4-methylpiperidin-4-yl)(methyl)amino)methyl)-5-(trifluoromethyl)phenyl)piperazin-1-yl)acetic acid

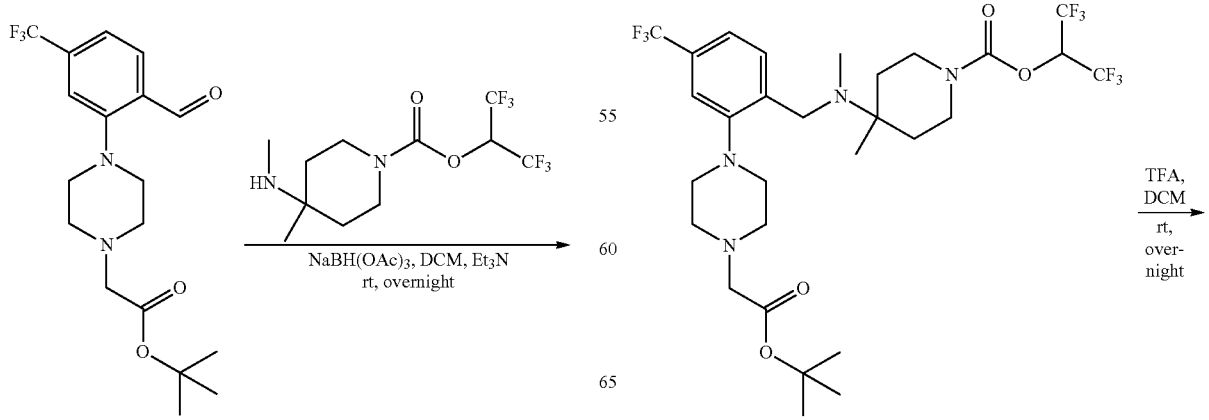

-continued

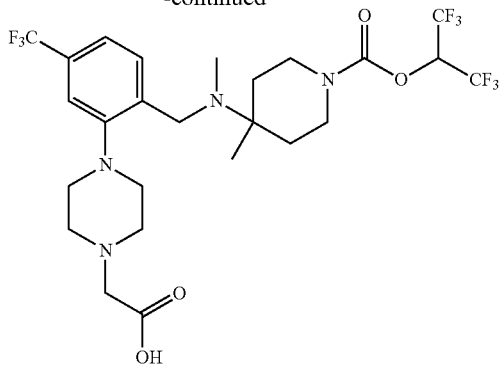

A flask was charged with 1,1,1,3,3,3-hexafluoropropan-2-yl 4-((2-(4-(2-(t-butoxy)-2-oxoethyl)piperazin-1-yl)-4-(trifluoromethyl)benzyl)(methyl)amino)-4-methylpiperidine-1-carboxylate (100 mg, 0.147 mmol, 1.00 equiv), DCM (8 mL), and trifluoroacetic acid (2 mL). The resulting solution was stirred overnight at room temperature and concentrated under reduced pressure. The crude product was dissolved in DCM (20 mL). The pH value of the solution was adjusted to 8 with saturated NaHCO$_3$ (20 mL) solution. The mixture was extracted with DCM (3×20 mL) and the organic layers were combined, washed with brine (1×20 mL), dried over anhydrous Na$_2$SO$_4$, filtered and concentrated under reduced pressure. The crude product (110 mg) was purified by preparative HPLC to provide 26.2 mg (29% yield) of 2-(4-(2-(((1-(((1,1,1,3,3,3-hexafluoropropan-2-yl)oxy)carbonyl)-4-methylpiperidin-4-yl)(methyl)amino)methyl)-5-(trifluoromethyl)phenyl)piperazin-1-yl)acetic acid as a white solid. $^1$H NMR (400 MHz, Methanol-d$_4$) δ 7.93-7.91 (m, 1H), 7.52-7.49 (m, 1H), 7.45 (s, 1H), 6.20-6.13 (m, 1H), 3.93-3.71 (m, 6H), 3.64-3.55 (m, 3H), 3.48 (s, 3H), 3.22-3.21 (m, 4H), 2.12 (s, 3H), 2.04-2.02 (m, 2H), 1.61-1.56 (m, 2H), 1.16 (s, 3H). LCMS (ESI, m/z): 623 [M+H]$^+$.

Example 27: 2-(5-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)-2,5-diazabicyclo[2.2.1]heptan-2-yl)acetic acid

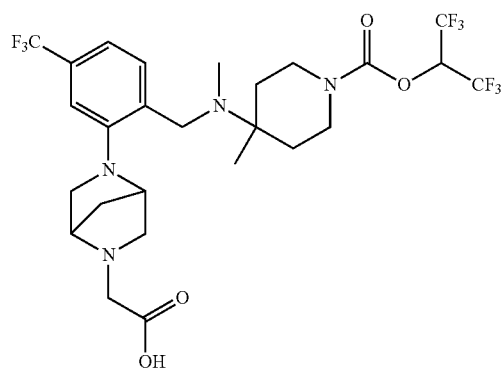 [SMILES: CN(Cc1ccc(C(F)(F)F)cc1N1CC2CC1CN2CC(=O)O)C1(C)CCN(C(=O)OC(C(F)(F)F)C(F)(F)F)CC1]

Step 1: Synthesis of t-butyl 5-(2-formyl-5-(trifluoromethyl)phenyl)-2,5-diazabicyclo[2.2.1]heptane-2-carboxylate

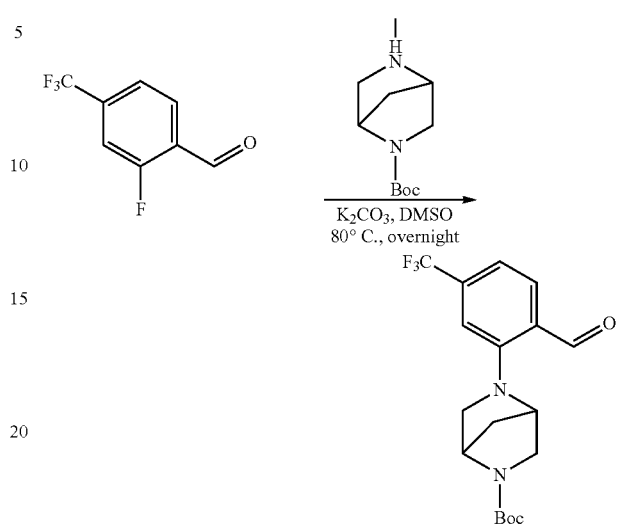

A flask was charged with 2-fluoro-4-(trifluoromethyl)benzaldehyde (768 mg, 4.00 mmol, 1.00 equiv), t-butyl 2,5-diazabicyclo[2.2.1]heptane-2-carboxylate (950 mg, 4.80 mmol, 1.20 equiv), DMSO (10 mL), and potassium carbonate (1.66 g, 12.0 mmol, 3.00 equiv). The resulting solution was stirred overnight at 80° C. and quenched with water (30 mL). The mixture was extracted with EtOAc (3×50 mL) and the organic layers were combined, washed with brine (2×30 mL), dried over anhydrous Na$_2$SO$_4$, filtered and concentrated under reduced pressure. The residue was chromatographed on a silica gel column to provide 500 mg (34% yield) of t-butyl 5-(2-formyl-5-(trifluoromethyl)phenyl)-2,5-diazabicyclo[2.2.1]heptane-2-carboxylate as a yellow oil. LCMS (ESI, m/z): 371 [M+H]$^+$.

Step 2: Synthesis of 2-(2,5-diazabicyclo[2.2.1]heptan-2-yl)-4-(trifluoromethyl)benzaldehyde

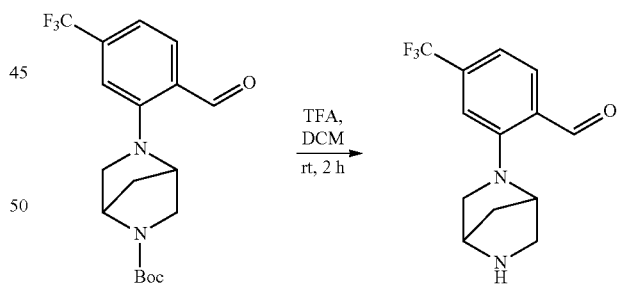

A flask was charged with t-butyl 5-(2-formyl-5-(trifluoromethyl)phenyl)-2,5-diazabicyclo[2.2.1]heptane-2-carboxylate (420 mg, 1.13 mmol, 1.00 equiv), DCM (10 mL), and trifluoroacetic acid (2 mL). The resulting solution was stirred for 2 h at room temperature and concentrated under reduced pressure. The crude product was dissolved in 1M NaOH solution (10 mL) and extracted with DCM (3×20 mL). The organic layers were combined, washed with brine (2×5 mL), dried over anhydrous Na$_2$SO$_4$, filtered and concentrated under reduced pressure to provide 308 mg (quantitative) of 2-(2,5-diazabicyclo[2.2.1]heptan-2-yl)-4-(trifluoromethyl)benzaldehyde as a yellow oil. LCMS (ESI, m/z): 271 [M+H]$^+$.

Step 3: Synthesis of t-butyl 2-(5-(2-formyl-5-(trifluoromethyl)phenyl)-2,5-diazabicyclo[2.2.1]heptan-2-yl)acetate

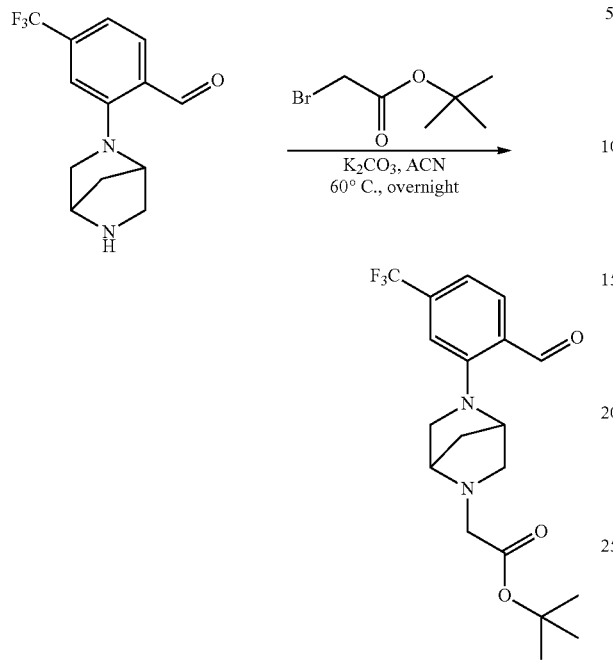

A flask was charged with 2-(2,5-diazabicyclo[2.2.1]heptan-2-yl)-4-(trifluoromethyl)benzaldehyde (308 mg, 1.14 mmol, 1.00 equiv), t-butyl 2-bromoacetate (221 mg, 1.13 mmol, 1.00 equiv), ACN (15 mL), and potassium carbonate (472 mg, 3.42 mmol, 3.00 equiv). The resulting solution was stirred overnight at 60° C. and quenched with water (20 mL). The resulting mixture was extracted with DCM (3×40 mL) and the organic layers were combined, washed with brine (30 mL), dried over anhydrous Na$_2$SO$_4$, filtered and concentrated under reduced pressure. The residue was chromatographed on a silica gel column to provide 380 mg (87% yield) of t-butyl 2-(5-(2-formyl-5-(trifluoromethyl)phenyl)-2,5-diazabicyclo[2.2.1]heptan-2-yl)acetate as a yellow oil. LCMS (ESI, m/z): 385 [M+H]$^+$.

Step 4: Synthesis of t-butyl 4-((2-(5-(2-(t-butoxy)-2-oxoethyl)-2,5-diazabicyclo[2.2.1]heptan-2-yl)-4-(trifluoromethyl)benzyl)amino)-4-methylpiperidine-1-carboxylate

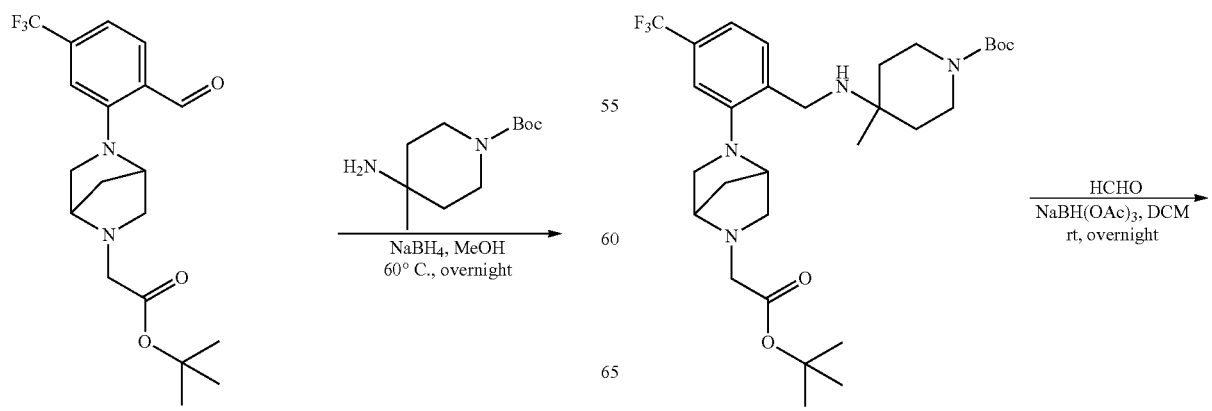

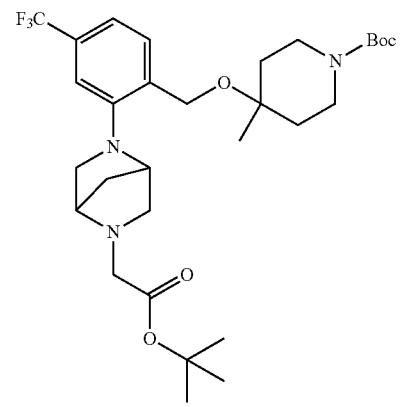

A flask was charged with t-butyl 2-(5-(2-formyl-5-(trifluoromethyl)phenyl)-2,5-diazabicyclo[2.2.1]heptan-2-yl)acetate (320 mg, 0.830 mmol, 1.00 equiv), t-butyl 4-amino-4-methylpiperidine-1-carboxylate (713 mg, 3.33 mmol, 4.00 equiv), and methanol (20 ml). The mixture was stirred for 4 h at 60° C. and sodium borohydride (127 mg, 3.36 mmol, 4.00 equiv) was added. The resulting solution was stirred overnight at 60° C. and quenched with water (20 mL). The resulting mixture was extracted with DCM (3×30 mL) and the organic layers were combined, washed with brine (30 mL), dried over anhydrous Na$_2$SO$_4$, filtered and concentrated under reduced pressure. The residue was chromatographed on a silica gel column to provide 400 mg (82% yield) of t-butyl 4-((2-(5-(2-(t-butoxy)-2-oxoethyl)-2,5-diazabicyclo[2.2.1]heptan-2-yl)-4-(trifluoromethyl)benzyl)amino)-4-methylpiperidine-1-carboxylate as a yellow oil. LCMS (ESI, m/z): 583 [M+H]$^+$.

Step 5: Synthesis of t-butyl 4-((2-(5-(2-(t-butoxy)-2-oxoethyl)-2,5-diazabicyclo[2.2.1]heptan-2-yl)-4-(trifluoromethyl)benzyl)(methyl)amino)-4-methylpiperidine-1-carboxylate

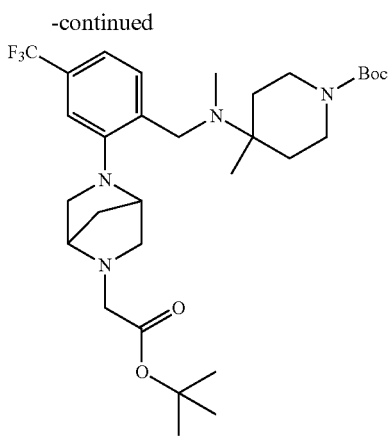

A flask was charged with t-butyl 4-((2-(5-(2-(t-butoxy)-2-oxoethyl)-2,5-diazabicyclo[2.2.1]heptan-2-yl)-4-(trifluoromethyl)benzyl)amino)-4-methylpiperidine-1-carboxylate (400 mg, 0.690 mmol, 1.00 equiv), paraformaldehyde (206 mg, 6.87 mmol, 10.00 equiv), and DCM (20 mL). The mixture was stirred for 4 h at room temperature and sodium triacetoxyborohydride (583 mg, 2.75 mmol, 4.00 equiv) was added. The reaction mixture was stirred overnight at room temperature and quenched with water (20 mL). The resulting solution was extracted with DCM (3×40 mL) and the organic layers were combined, washed with brine (30 mL), dried over anhydrous $Na_2SO_4$, filtered and concentrated under reduced pressure. The residue was chromatographed on a silica gel column to provide 380 mg (93% yield) of t-butyl 4-((2-(5-(2-(t-butoxy)-2-oxoethyl)-2,5-diazabicyclo[2.2.1]heptan-2-yl)-4-(trifluoromethyl)benzyl)(methyl)amino)-4-methylpiperidine-1-carboxylate as a yellow oil. LCMS (ESI, m/z): 597 $[M+H]^+$.

Step 6: Synthesis of 2-(5-(2-((methyl(4-methylpiperidin-4-yl)amino)methyl)-5-(trifluoromethyl)phenyl)-2,5-diazabicyclo[2.2.1]heptan-2-yl)acetic acid

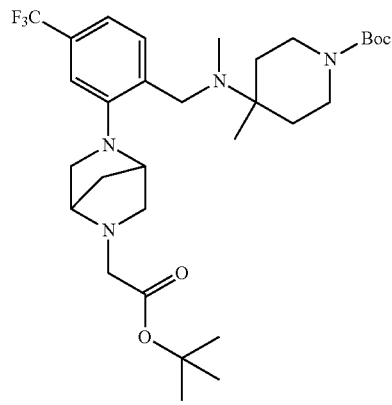

HCl, 1,4-dioxane
rt, 2 h

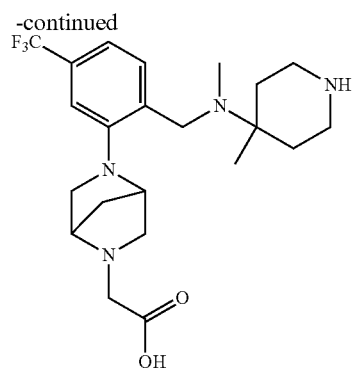

A flask was charged with t-butyl 4-((2-(5-(2-(t-butoxy)-2-oxoethyl)-2,5-diazabicyclo[2.2.1]heptan-2-yl)-4-(trifluoromethyl)benzyl)(methyl)amino)-4-methylpiperidine-1-carboxylate (180 mg, 0.300 mmol, 1.00 equiv), 1,4-dioxane (6 mL), and concentrated hydrochloric acid (2 mL). The resulting solution was stirred for 2 h at room temperature and concentrated under reduced pressure to provide 133 mg (quantitative) of 2-(5-(2-((methyl(4-methylpiperidin-4-yl)amino)methyl)-5-(trifluoromethyl)phenyl)-2,5-diazabicyclo[2.2.1]heptan-2-yl)acetic acid as a yellow oil. LCMS (ESI, m/z): 441 $[M+H]^+$.

Step 7: Synthesis of 2-(5-(2-(((1-(((1,1,1,3,3,3-hexafluoropropan-2-yl)oxy)carbonyl)-4-methylpiperidin-4-yl)(methyl)amino)methyl)-5-(trifluoromethyl)phenyl)-2,5-diazabicyclo[2.2.1]heptan-2-yl)acetic acid

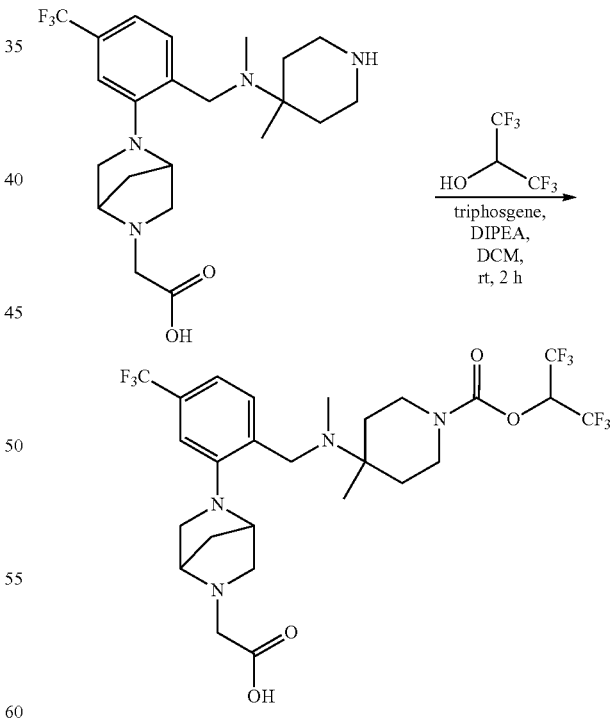

A flask was charged with triphosgene (62.8 mg, 0.210 mmol, 0.70 equiv), and DCM (10 mL). 1,1,1,3,3,3-Hexafluoropropan-2-ol (101 mg, 0.600 mmol, 2.00 equiv) and DIPEA (156 mg, 1.21 mmol, 4.00 equiv) were added at 0° C. The mixture was stirred for 1 h at room temperature prior to addition of 2-(5-(2-((Methyl(4-methylpiperidin-4- yl)amino)methyl)-5-(trifluoromethyl)phenyl)-2,5-diazabicyclo[2.2.1]heptan-2-yl)acetic acid (133 mg, 0.300 mmol, 1.00 equiv). The resulting solution was stirred for 1 h at room temperature and then quenched with saturated NaHCO$_3$ solution (10 mL). The mixture was extracted with DCM (3×30 mL) and the organic layers were combined, washed with brine (30 mL), dried over anhydrous Na$_2$SO$_4$, filtered and concentrated under reduced pressure. The crude product (200 mg) was purified by preparative HPLC to provide 37.1 mg (19% yield) of 2-(5-(2-(((1-(((1,1,1,3,3,3-hexafluoropropan-2-yl)oxy)carbonyl)-4-methylpiperidin-4-yl)(methyl)amino)methyl)-5-(trifluoromethyl)phenyl)-2,5-diazabicyclo[2.2.1]heptan-2-yl)acetic acid as an off-white solid. $^1$H NMR (400 MHz, Methanol-d$_4$) δ 7.92 (d, J=8.4 Hz, 1H), 7.34 (d, J=8.0 Hz, 1H), 7.28 (s, 1H), 6.18-6.12 (m, 1H), 4.44 (s, 1H), 4.37 (s, 1H), 3.85-3.62 (m, 7H), 3.58-3.54 (m, 3H), 3.46-3.38 (m, 2H), 2.33-2.30 (m, 1H), 2.25-2.22 (m, 1H), 2.12 (s, 3H), 2.05-2.02 (m, 2H), 1.59-1.52 (m, 2H), 1.16 (s, 3H). LCMS (ESI, m/z): 635 [M+H]$^+$.

Example 28: 1,1,1,3,3,3-Hexafluoropropan-2-yl 8-(4-chloro-2-(4-fluoropiperidin-1-yl)benzyl)-2,8-diazaspiro[4.5]decane-2-carboxylate

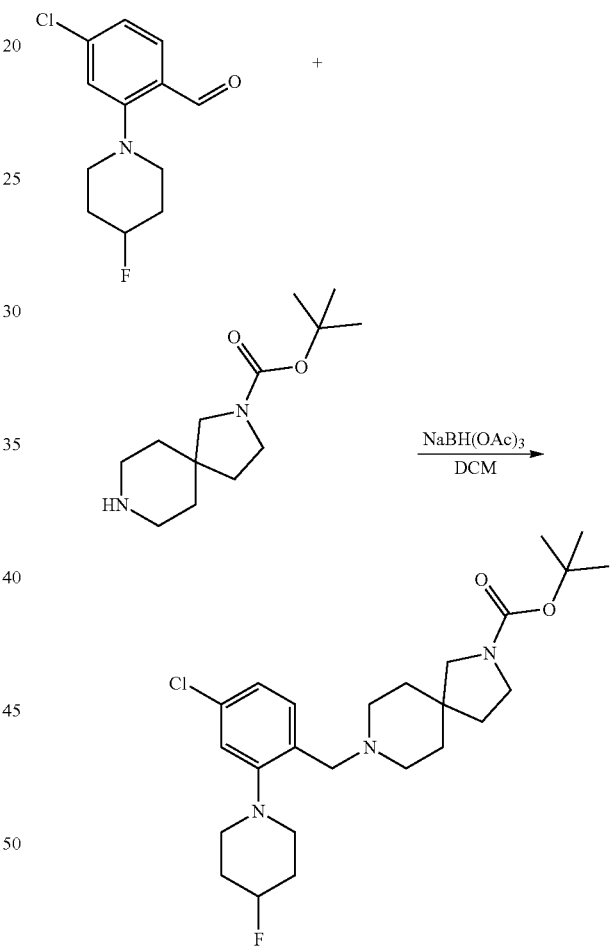

Step 1: Synthesis of 4-chloro-2-(4-fluoropiperidin-1-yl)benzaldehyde

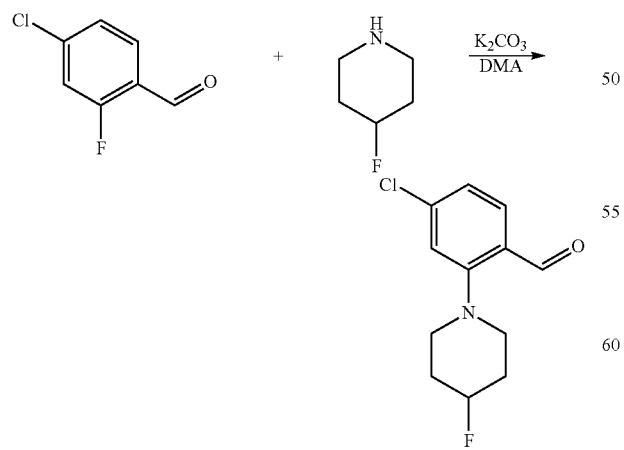

To a sealed tube vial was added 4-chloro-2-fluorobenzaldehyde (424 mg, 2.67 mmol, 1 equiv), 4-fluoropiperidine (330 mg, 3.21 mmol, 1.2 equiv), K$_2$CO$_3$ (1180 mg, 8.56 mmol, 3.2 equiv) and DMA (4 mL). The reaction was heated to 140° C. for 24 h. The mixture was cooled to room temperature, diluted with EtOAc (200 mL), washed with water (3×10 mL), and once with saturated ammonium chloride (10 mL). The organic layers were dried over Na$_2$SO$_4$, filtered and concentrated under reduced pressure to afford an oil which was purified by flash column chomatography to provide 4-chloro-2-(4-fluoropiperidin-1-yl)benzaldehyde as an oil (435 mg, 67% yield). $^1$H NMR (400 MHz, Chloroform-d) δ 10.22 (s, 1H), 7.81-7.71 (m, 1H), 7.14-7.06 (m, 2H), 5.02-4.81 (m, 1H), 3.36-3.21 (m, 2H), 3.12-3.00 (m, 2H), 2.22-1.99 (m, 4H). LCMS (ESI, m/z): 242 [M+H]$^+$.

Step 2: Synthesis of 1-butyl 8-(4-chloro-2-(4-fluoropiperidin-1-yl)benzyl)-2,8-diazaspiro[4.5]decane-2-carboxylate

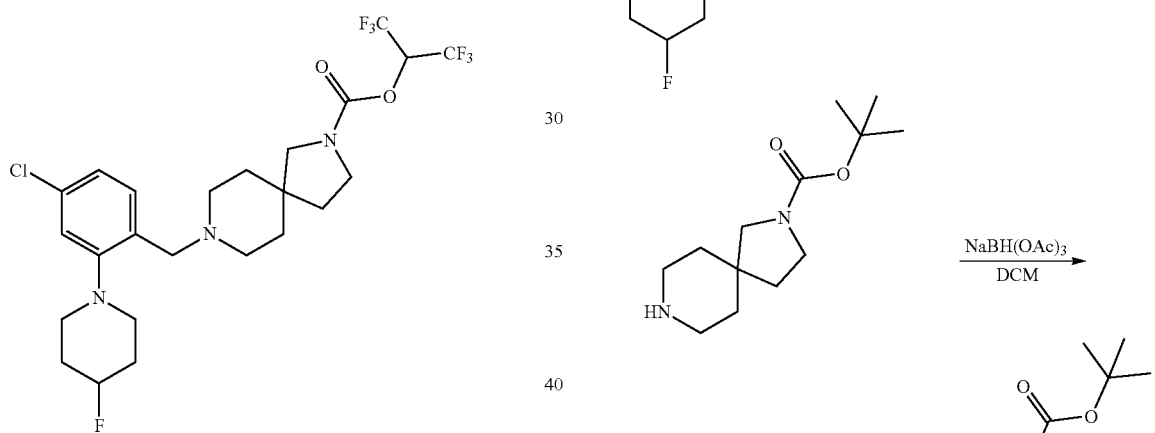

A flask was charged with 4-chloro-2-(4-fluoropiperidin-1-yl)benzaldehyde (244 mg, 1.00 mmol, 1 equiv) and DCM (5 mL). t-Butyl 2,8-diazaspiro[4.5]decane-2-carboxylate (266 mg, 1.11 mmol, 1.1 equiv) and molecular sieves (500 mg) were added. The reaction was purged with nitrogen and stirred at room temperature for 2 h. NaBH(OAc)$_3$ (235 mg, 1.11 mmol, 1.1 equiv) was added and the mixture stirred at room temperature overnight. The mixture was filtered over Celite, washed with brine (5 mL), dried over Na$_2$SO$_4$, and concentrated under reduced pressure to afford an oil which was purified by flash column chomatography to provide t-butyl 8-(4-chloro-2-(4-fluoropiperidin-1-yl)benzyl)-2,8- diazaspiro[4.5]decane-2-carboxylate as an oil (288 mg, 61% yield). ¹H NMR (400 MHz, Chloroform-d) δ 7.42-7.32 (m, 1H), 7.10-6.98 (m, 2H), 4.94-4.71 (m, 1H), 3.54-3.31 (m, 4H), 3.25-3.06 (m, 4H), 2.92-2.80 (m, 2H), 2.60-2.26 (m, 4H), 2.16-1.92 (m, 4H), 1.76-1.64 (m, 3H), 1.56 (s, 3H), 1.48 (s, 9H). LCMS (ESI, m/z): 467 [M+H]⁺.

Step 3: Synthesis of 8-(4-chloro-2-(4-fluoropiperidin-1-yl)benzyl)-2,8-diazaspiro[4.5]decane Step 4: Synthesis of 1,1,1,3,3,3-hexafluoropropan-2-yl 8-(4-chloro-2-(4-fluoropiperidin-1-yl)benzyl)-2,8-diazaspiro[4.5]decane-2-carboxylate

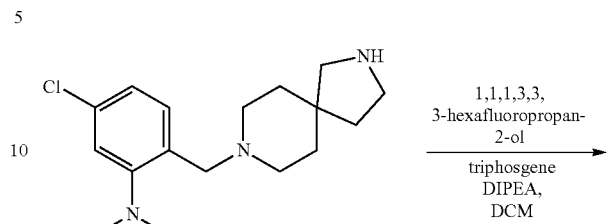

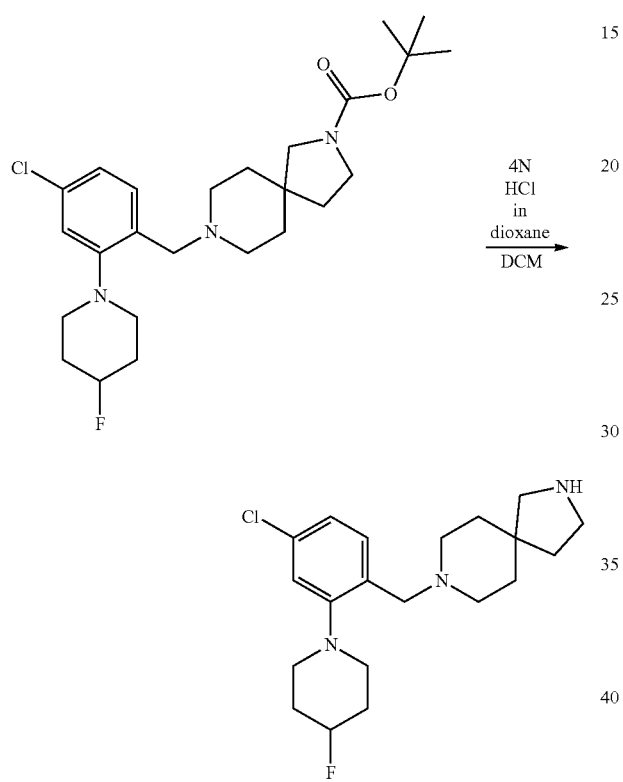

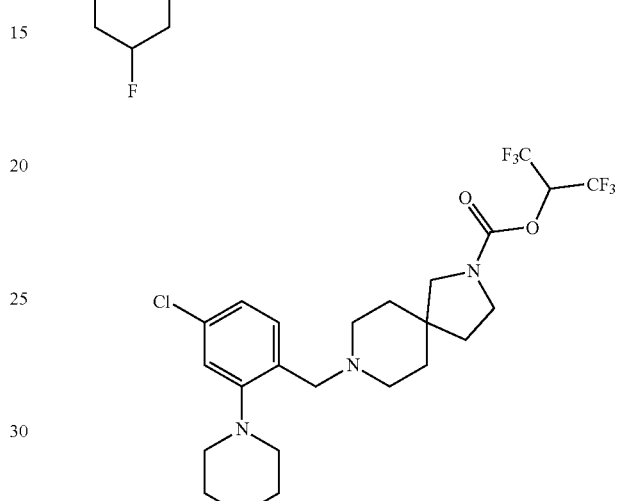

t-Butyl 8-(4-chloro-2-(4-fluoropiperidin-1-yl)benzyl)-2,8-diazaspiro[4.5]decane-2-carboxylate (288 mg, 0.618 mmol, 1 equiv) was dissolved in DCM (7 mL) and stirred. 4N HCl in dioxane (0.9270 mL, 3.71 mmol, 6 equiv) was added and the reaction stirred overnight at room temperature. The mixture was diluted with DCM (40 mL) and washed three times with saturated sodium carbonate. The aqueous layer was back-extracted with DCM (3×20 mL), and the organic layers were combined, dried over Na₂SO₄, and concentrated under reduced pressure to provide 8-(4-chloro-2-(4-fluoropiperidin-1-yl)benzyl)-2,8-diazaspiro [4.5]decane as an oil. ¹H NMR (400 MHz, Chloroform-d) δ 7.41-7.34 (m, 1H), 7.07-7.00 (m, 2H), 4.96-4.55 (m, 1H), 3.18-3.07 (m, 2H), 3.02-2.93 (m, 2H), 2.92-2.82 (m, 2H), 2.77-2.56 (m, 4H), 2.51-2.28 (m, 2H), 2.14-1.89 (m, 5H), 1.56 (dt, J=16.5, 6.3 Hz, 6H).

A vial was charged with triphosgene (366 mg, 1.23 mmol, 2 equiv) and DCM (5 mL). Once solids were solubilized, the solution was cooled to 0° C. and purged with N₂. 1,1,1,3,3,4-Hexafluoroisopropanol (492 µL, 4.01 mmol, 6.5 equiv) and DIPEA (1075 µL, 6.17 mmol, 10 equiv) were added. The mixture stirred for 2 h at room temperature and set aside. A separate vial was charged with 8-(4-chloro-2-(4-fluoropiperidin-1-yl)benzyl)-2,8-diazaspiro[4.5]decane (226 mg, 0.61 mmol, 1 equiv) and DCM (2 mL). The vial was purged with N₂, after which the contents were transferred to the HFIP chloroformate solution via syringe. The resulting solution was allowed to stir overnight at room temperature. The mixture was diluted with DCM (5 mL), washed with sat. NaHCO₃ (3×5 mL), dried over Na₂SO₄, concentrated under reduced pressure, and purified on silica gel by flash column chomatography to afford 1,1,1,3,3,3-hexafluoropropan-2-yl 8-(4-chloro-2-(4-fluoropiperidin-1-yl)benzyl)-2,8-diazaspiro[4.5]decane-2-carboxylate as an oil (176 mg, 50% yield). ¹H NMR (400 MHz, Chloroform-d) δ 7.37 (d, J=8.0 Hz, 1H), 7.09-7.01 (m, 2H), 5.82-5.72 (m, 1H), 4.82 (d, J=48.7, 5.1 Hz, 1H), 3.59-3.48 (m, 4H), 3.32 (d, J=13.9, 1.5 Hz, 2H), 3.19-3.07 (m, 2H), 2.92-2.79 (m, 2H), 2.62-2.25 (m, 4H), 2.13-1.93 (m, 4H), 1.81 (tdd, J=7.0, 5.2, 1.5 Hz, 2H), 1.59 (t, J=5.2 Hz, 4H). LCMS (ESI, m/z): 560 [M+H]⁺.

Example 29: 1,1,1,3,3,3-Hexafluoropropan-2-yl 4-(2-(8-acetyl-2,8-diazaspiro[4.5]decan-2-yl)-4-chlorobenzyl)piperazine-1-carboxylate

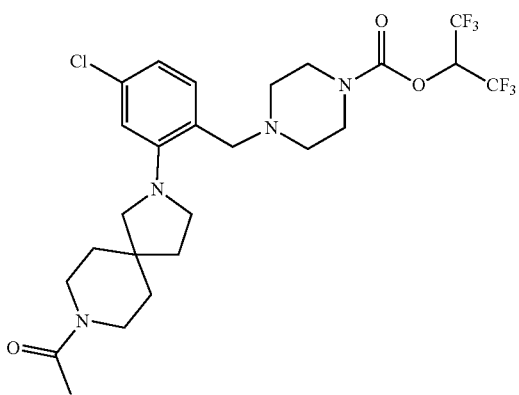 [SMILES: CC(=O)N1CCC2(CC1)CCN(c1cc(Cl)ccc1CN1CCN(C(=O)OC(C(F)(F)F)C(F)(F)F)CC1)C2]

Step 1: Synthesis of 1-butyl 2-(5-chloro-2-formylphenyl)-2,8-diazaspiro[4.5]decane-8-carboxylate

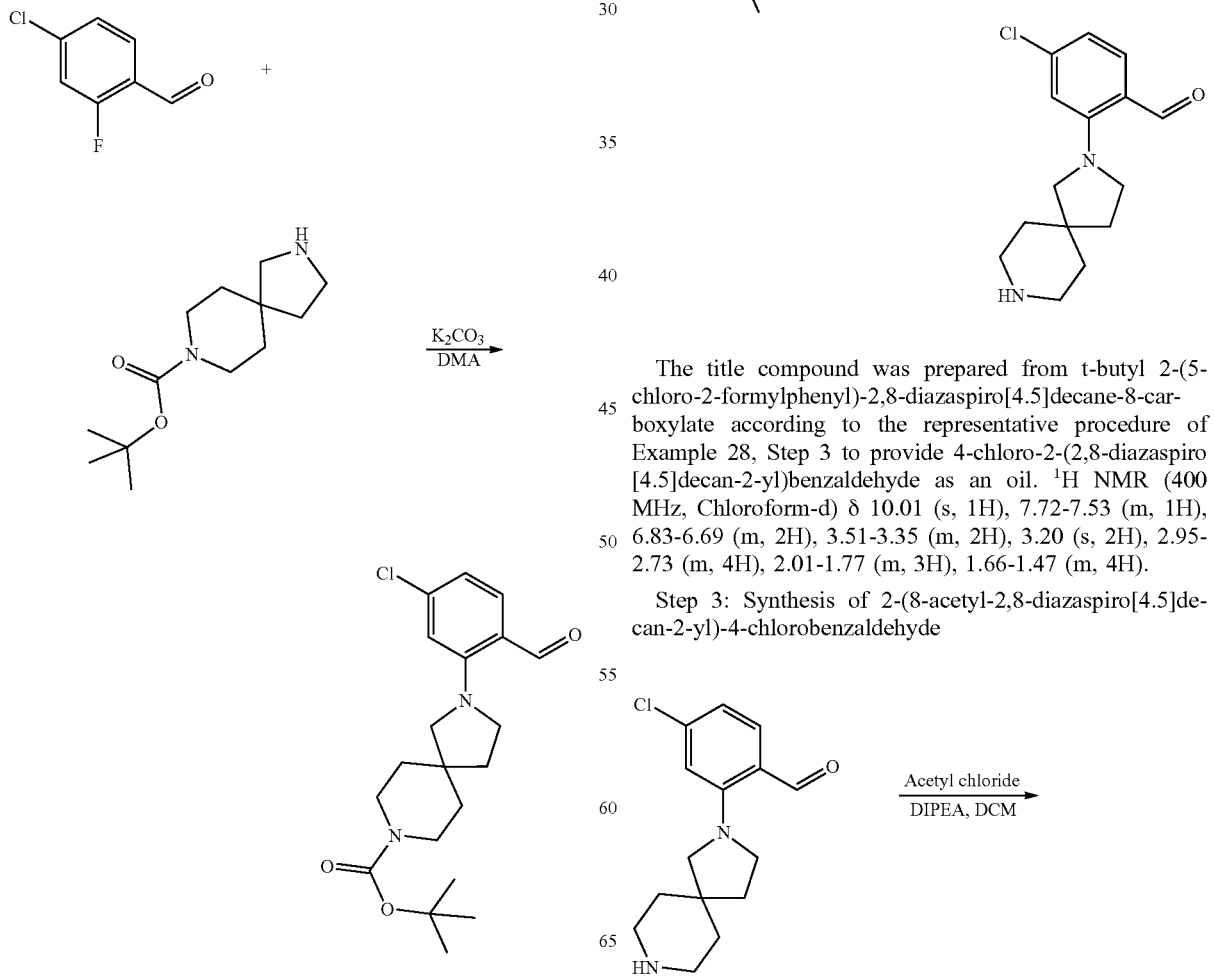

The title compound was prepared from 4-chloro-2-fluorobenzaldehyde and t-butyl 2,8-diazaspiro[4.5]decane-8-carboxylate according to the representative procedure of Example 28, Step 1 to provide t-butyl 2-(5-chloro-2-formylphenyl)-2,8-diazaspiro[4.5]decane-8-carboxylate as an oil (469 mg, 73% yield). $^1$H NMR (400 MHz, Chloroform-d) δ 10.01 (s, 1H), 7.68-7.59 (m, 1H), 6.85-6.77 (m, 2H), 3.53-3.43 (m, 4H), 3.42-3.34 (m, 2H), 3.21 (s, 2H), 1.96-1.89 (m, 2H), 1.62-1.56 (m, 4H), 1.49-1.46 (m, 9H). LCMS (ESI, m/z): 401 [M+Na]$^+$.

Step 2: Synthesis of 4-chloro-2-(2,8-diazaspiro[4.5]decan-2-yl)benzaldehyde

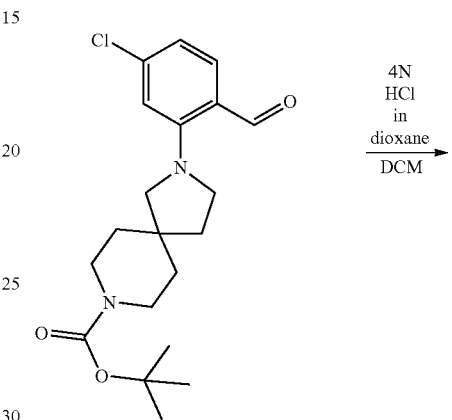

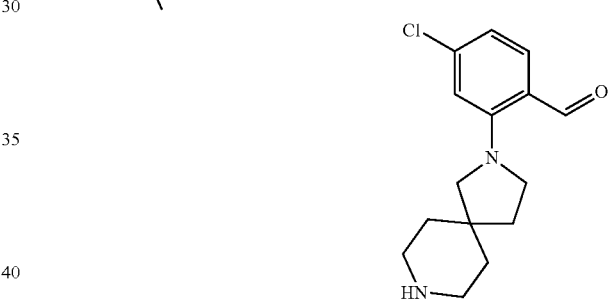

The title compound was prepared from t-butyl 2-(5-chloro-2-formylphenyl)-2,8-diazaspiro[4.5]decane-8-carboxylate according to the representative procedure of Example 28, Step 3 to provide 4-chloro-2-(2,8-diazaspiro[4.5]decan-2-yl)benzaldehyde as an oil. $^1$H NMR (400 MHz, Chloroform-d) δ 10.01 (s, 1H), 7.72-7.53 (m, 1H), 6.83-6.69 (m, 2H), 3.51-3.35 (m, 2H), 3.20 (s, 2H), 2.95-2.73 (m, 4H), 2.01-1.77 (m, 3H), 1.66-1.47 (m, 4H).

Step 3: Synthesis of 2-(8-acetyl-2,8-diazaspiro[4.5]decan-2-yl)-4-chlorobenzaldehyde

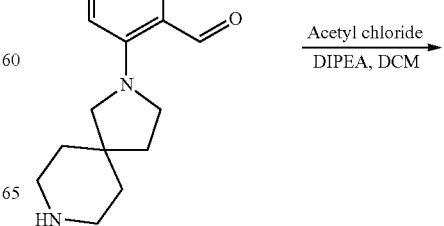

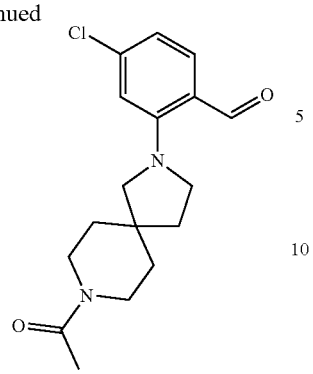

4-Chloro-2-(2,8-diazaspiro[4.5]decan-2-yl)benzaldehyde (166 mg, 0.597 mmol, 1 equiv), DCM (6 mL) and DIPEA (415 μL, 2.37 mmol, 4 equiv) were added to a vial. The reaction stirred 2 h, was cooled to 0° C. prior to dropwise addition of acetyl chloride (51 μL, 0.716 mmol, 1.2 equiv). The reaction was stirred for 3 h, diluted with DCM (10 mL), washed with saturated sodium bicarbonate (3×5 mL), dried over Na$_2$SO$_4$, filtered and concentrated under reduced pressure to provide an orange solid (223 mg, 95% yield) which was used without further purification. LCMS (ESI, m/z): 321 [M+H]$^+$.

Step 4: Synthesis of 1-(t-butyl) 4-(1,1,1,3,3,3-hexafluoropropan-2-yl) piperazine-1,4-dicarboxylate

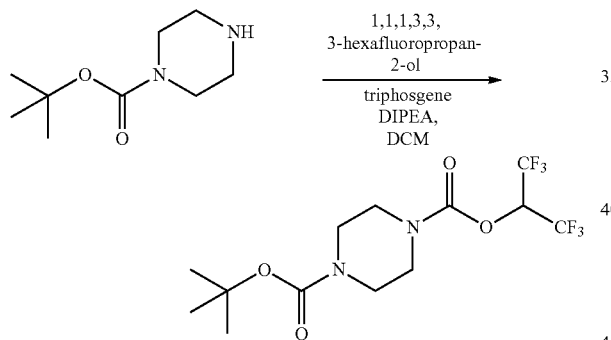

The title compound was prepared from commercially available t-butyl piperazine-1-carboxylate according to the representative procedure of Example 28, Step 4 to provide 1-(t-butyl) 4-(1,1,1,3,3,3-hexafluoropropan-2-yl) piperazine-1,4-dicarboxylate as a solid. (1.38 g, 91% yield). $^1$H NMR (400 MHz, Chloroform-d) δ 5.87-5.69 (m, 1H), 3.63-3.40 (m, 8H), 1.49 (s, 9H). LCMS (ESI, m/z): 381 [M+H]$^+$.

Step 5: Synthesis of 1,1,1,3,3,3-hexafluoropropan-2-yl piperazine-1-carboxylate

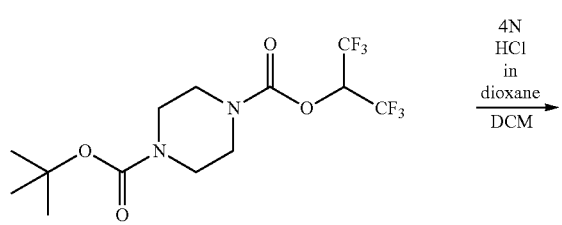

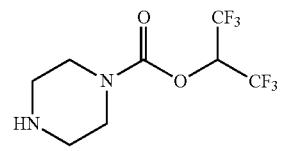

The title compound was prepared directly from 1-(t-butyl) 4-(1,1,1,3,3,3-hexafluoropropan-2-yl) piperazine-1,4-dicarboxylate according to the representative procedure of Example 28, Step 3 to provide 1,1,1,3,3,3-hexafluoropropan-2-yl piperazine-1-carboxylate as an oil (1 g, 98% yield). $^1$H NMR (400 MHz, Chloroform-d) δ 5.77-5.59 (m, 1H), 3.50-3.33 (m, 4H), 2.85-2.68 (m, 4H), 1.77 (s, 1H). LCMS (ESI, m/z): 381 [M+H]$^+$.

Step 6: Synthesis of 1,1,1,3,3,3-hexafluoropropan-2-yl 4-(2-(8-acetyl-2,8-diazaspiro[4.5]decan-2-yl)-4-chlorobenzyl)piperazine-1-carboxylate

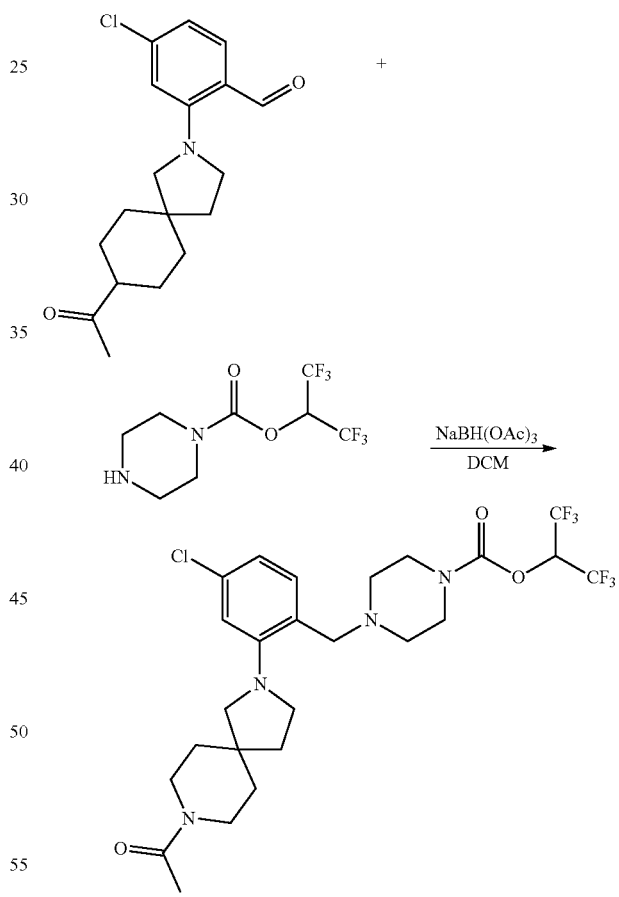

The title compound was prepared from 2-(8-acetyl-2,8-diazaspiro[4.5]decan-2-yl)-4-chlorobenzaldehyde and 1,1,1,3,3,3-hexafluoropropan-2-yl piperazine-1-carboxylate according to the representative procedure of Example 28, Step 2 to provide 1,1,1,3,3,3-hexafluoropropan-2-yl 4-(2-(8-acetyl-2,8-diazaspiro[4.5]decan-2-yl)-4-chlorobenzyl)piperazine-1-carboxylate as an oil (10 mg, 12% yield). $^1$H NMR (400 MHz, Chloroform-d) δ 7.28 (s, 1H), 6.86 (d, J=7.5 Hz, 2H), 5.83-5.72 (m, 1H), 3.66-3.41 (m, 10H), 3.38-3.29 (m, 2H), 3.18-3.09 (m, 2H), 2.52-2.39 (m, 4H), 2.13 (s, 3H), 1.88-1.81 (m, 2H), 1.71-1.59 (m, 4H). LCMS (ESI, m/z): 585 [M+H]$^+$.

Example 30: 1,1,1,3,3,3-Hexafluoropropan-2-yl 4-(4-chloro-2-(8-(methylsulfonyl)-2,8-diazaspiro[4.5]decan-2-yl)benzyl)piperazine-1-carboxylate

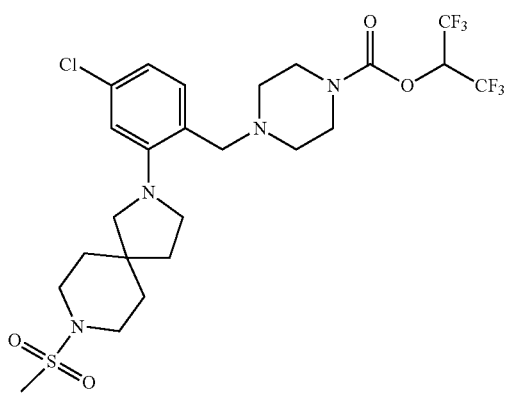 [SMILES: CS(=O)(=O)N1CCC2(CCN(c3cc(Cl)ccc3CN3CCN(C(=O)OC(C(F)(F)F)C(F)(F)F)CC3)C2)CC1]

Step 1: Synthesis of t-butyl 2-(5-chloro-2-formylphenyl)-2,8-diazaspiro[4.5]decane-8-carboxylate

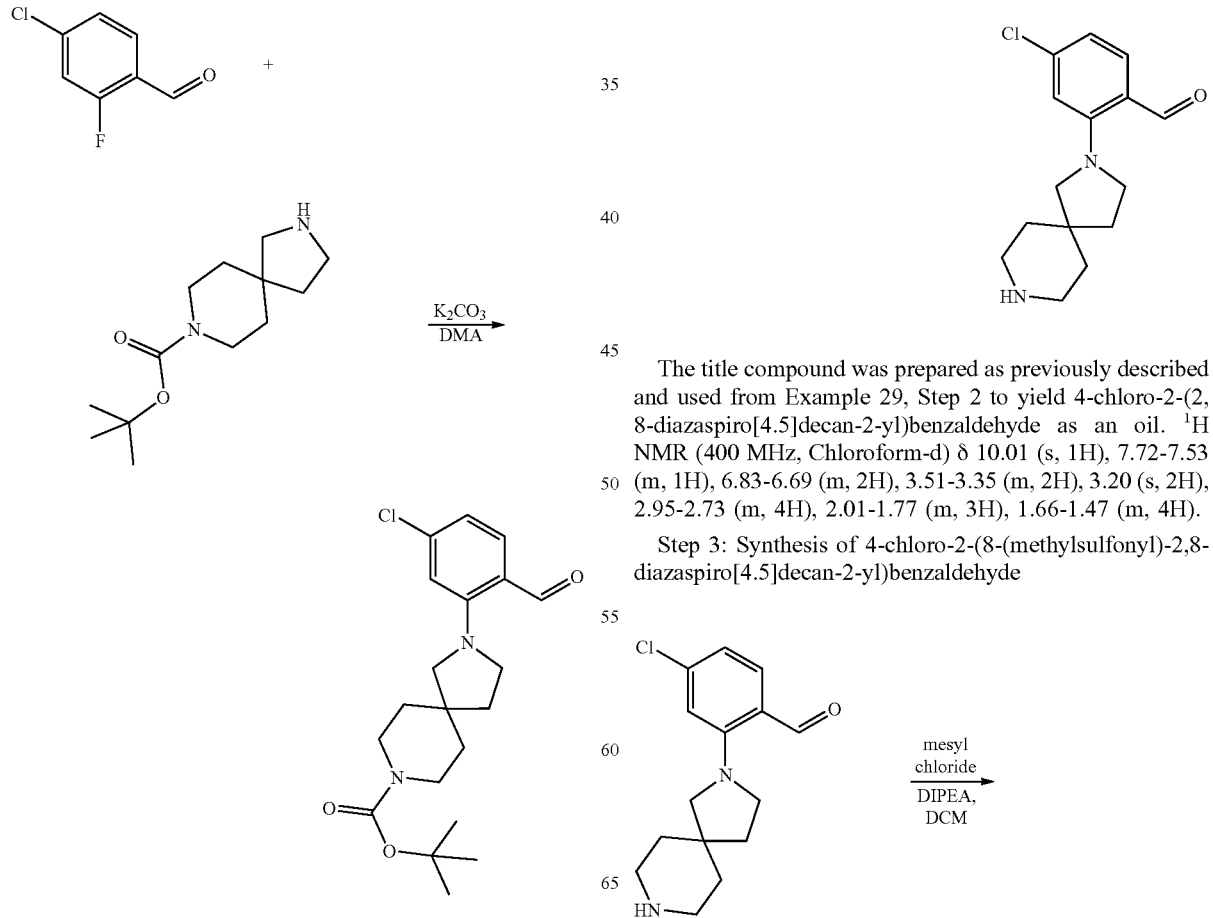

The title compound was prepared as previously described and used from Example 29, Step 1 to provide t-butyl 2-(5-chloro-2-formylphenyl)-2,8-diazaspiro[4.5]decane-8-carboxylate as an oil (469 mg, 73% yield). $^1$H NMR (400 MHz, Chloroform-d) δ 10.01 (s, 1H), 7.68-7.59 (m, 1H), 6.85-6.77 (m, 2H), 3.53-3.43 (m, 4H), 3.42-3.34 (m, 2H), 3.21 (s, 2H), 1.96-1.89 (m, 2H), 1.62-1.56 (m, 4H), 1.49-1.46 (m, 9H). LCMS (ESI, m/z): 401 [M+Na]$^+$.

Step 2: Synthesis of 4-chloro-2-(2,8-diazaspiro[4.5]decan-2-yl)benzaldehyde

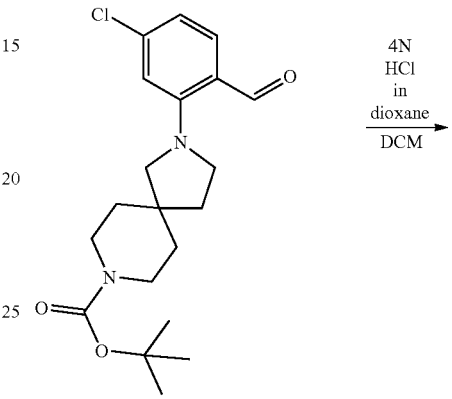

The title compound was prepared as previously described and used from Example 29, Step 2 to yield 4-chloro-2-(2,8-diazaspiro[4.5]decan-2-yl)benzaldehyde as an oil. $^1$H NMR (400 MHz, Chloroform-d) δ 10.01 (s, 1H), 7.72-7.53 (m, 1H), 6.83-6.69 (m, 2H), 3.51-3.35 (m, 2H), 3.20 (s, 2H), 2.95-2.73 (m, 4H), 2.01-1.77 (m, 3H), 1.66-1.47 (m, 4H).

Step 3: Synthesis of 4-chloro-2-(8-(methylsulfonyl)-2,8-diazaspiro[4.5]decan-2-yl)benzaldehyde

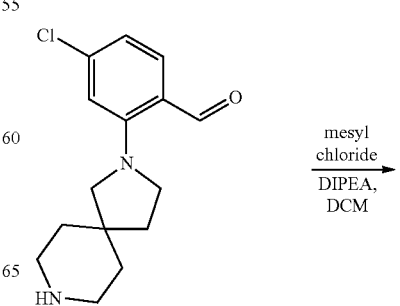

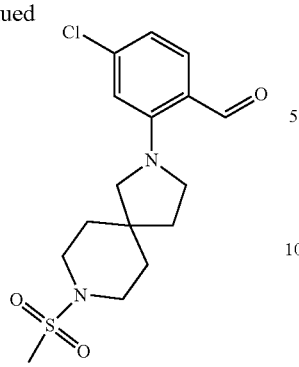

4-Chloro-2-(2,8-diazaspiro[4.5]decan-2-yl)benzaldehyde (175 mg, 0.630 mmol, 1 equiv) was added to a vial followed by DCM (6 mL) and DIPEA (439 µL, 2.52 mmol, 4 equiv). The reaction was stirred 2 h and cooled to 0° C. Mesyl chloride (58 µL, 0.756 mmol, 1.2 equiv) was added dropwise. The reaction stirred at rom temperature for 3 h, and was diluted with DCM (10 mL), washed with saturated sodium bicarbonate (3×5 mL), dried over $Na_2SO_4$, filtered and concentrated under reduced pressure to provide an oil which was purified by flash column chomatography to afford 4-chloro-2-(8-(methylsulfonyl)-2,8-diazaspiro[4.5]decan-2-yl)benzaldehyde as an oil. $^1$H NMR (400 MHz, Chloroform-d) δ 9.99 (s, 1H), 7.71-7.59 (m, 1H), 6.88-6.75 (m, 2H), 3.77-3.67 (m, 1H), 3.56-3.39 (m, 5H), 3.32-3.16 (m, 2H), 2.15-2.09 (m, 3H), 1.99-1.93 (m, 2H), 1.70-1.64 (m, 2H), 1.64-1.57 (m, 2H). LCMS (ESI, m/z): 357 [M+H]$^+$.

Step 4: Synthesis of 1-(t-butyl) 4-(1,1,1,3,3,3-hexafluoropropan-2-yl) piperazine-1,4-dicarboxylate

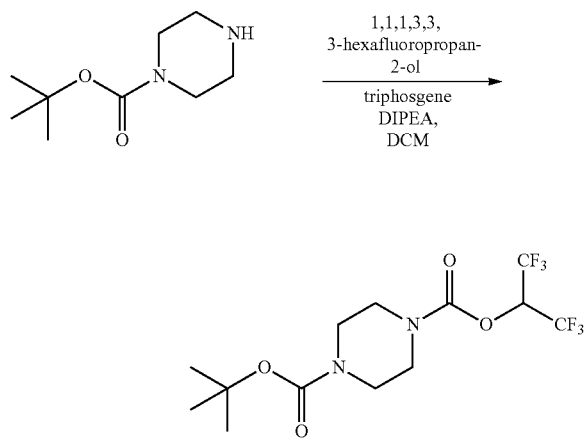

The title compound was prepared from commercially available t-butyl piperazine-1-carboxylate according to the representative procedure of Example 28, Step 4 to provide 1-(t-butyl) 4-(1,1,1,3,3,3-hexafluoropropan-2-yl) piperazine-1,4-dicarboxylate as a solid. (1.38 g, 91% yield). $^1$H NMR (400 MHz, Chloroform-d) δ 5.87-5.69 (m, 1H), 3.63-3.40 (m, 8H), 1.49 (s, 9H). LCMS (ESI, m/z): 381 [M+H]$^+$.

Step 5: Synthesis of 1,1,1,3,3,3-hexafluoropropan-2-yl piperazine-1-carboxylate

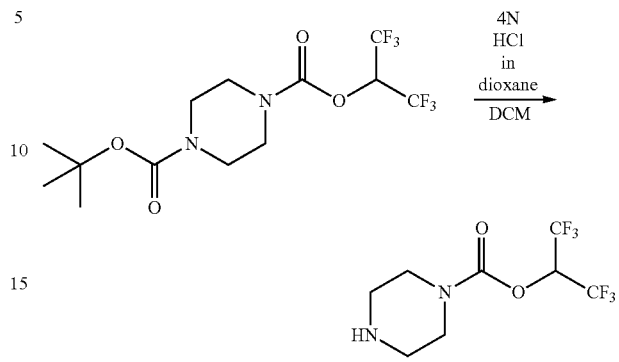

The title compound was prepared directly from 1-(t-butyl) 4-(1,1,1,3,3,3-hexafluoropropan-2-yl) piperazine-1,4-dicarboxylate according to the representative procedure of Example 28, Step 3 to afford 1,1,1,3,3,3-hexafluoropropan-2-yl piperazine-1-carboxylate as an oil (1 g, 98% yield). $^1$H NMR (400 MHz, Chloroform-d) δ 5.77-5.59 (m, 1H), 3.50-3.33 (m, 4H), 2.85-2.68 (m, 4H), 1.77 (s, 1H). LCMS (ESI, m/z): 381 [M+H]$^+$.

Step 6: Synthesis of 1,1,1,3,3,3-hexafluoropropan-2-yl 4-(4-chloro-2-(8-(methylsulfonyl)-2,8-diazaspiro[4.5]decan-2-yl)benzyl)piperazine-1-carboxylate

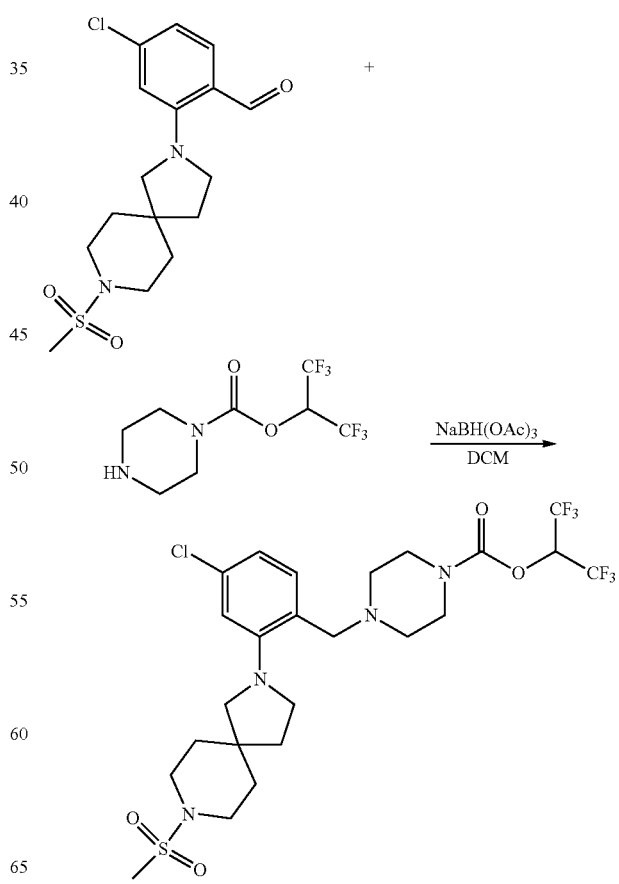

The title compound was prepared from 4-chloro-2-(8-(methylsulfonyl)-2,8-diazaspiro[4.5]decan-2-yl)benzaldehyde and 1,1,1,3,3,3-hexafluoropropan-2-yl piperazine-1-carboxylate according to the representative procedure of Example 28, Step 2 to provide 1,1,1,3,3,3-hexafluoropropan-2-yl 4-(4-chloro-2-(8-(methylsulfonyl)-2,8-diazaspiro[4.5]decan-2-yl)benzyl)piperazine-1-carboxylate as an oil (23 mg, 32% yield). $^1$H NMR (400 MHz, Chloroform-d) δ 7.28 (d, J=1.8 Hz, 1H), 6.94-6.81 (m, 2H), 5.83-5.70 (m, 1H), 3.62-3.45 (m, 6H), 3.37-3.21 (m, 6H), 3.11 (s, 2H), 2.82 (s, 3H), 2.50-2.39 (m, 4H), 1.87-1.75 (m, 6H). LCMS (ESI, m/z): 621 [M+H]$^+$.

Examples 31-242 were prepared by similar procedures as described in Examples 1-30.

| Ex | Structure | Name | NMR (¹H NMR, 300 MHz or 400 MHz, Methanol-d4) | MS [M+H]⁺ |
|---|---|---|---|---|
| 31 | 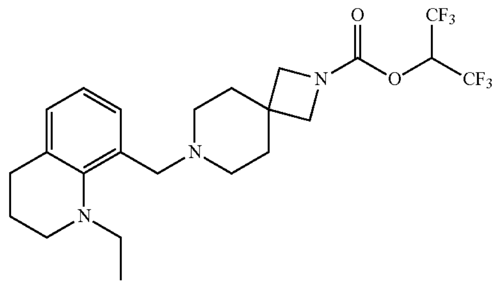 [SMILES: CCN1CCCc2cccc(CN3CCC4(CC3)CN(C(=O)OC(C(F)(F)F)C(F)(F)F)C4)c21] | 1,1,1,3,3,3-Hexafluoropropan-2-yl 7-((1-ethyl-1,2,3,4-tetrahydroquinolin-8-yl)methyl)-2,7-diazaspiro[3.5]nonane-2-carboxylate | δ 7.28 (br, 1H), 6.85-6.95 (m, 2H), 5.59-5.72 (m, 1H), 3.76-3.80 (m, 4H), 3.43 (br, 2H), 3.03,3.06 (m, 2H), 2.87-2.94 (m, 2H), 2.80 (t, J = 6.8 Hz, 2H), 2.39 (br, 4H), 1.77-1.83 (m, 6H), 1.21 (t, J = 6.0 Hz, 3H) | 494 |
| 32 | 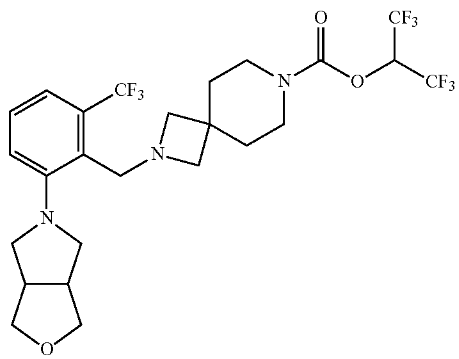 [SMILES: O=C(OC(C(F)(F)F)C(F)(F)F)N1CCC2(CC1)CN(Cc1c(N3CC4COCC4C3)cccc1C(F)(F)F)C2] | 1,1,1,3,3,3-Hexafluoropropan-2-yl 7-(2-(tetrahydro-1H-furo[3,4-c]pyrrol-5(3H)-yl)-6-(trifluoromethyl)benzyl)-2,7-diazaspiro[3.5]nonane-2-carboxylate | (Chloroform-d) δ 1.72-1.76 (m 4H), 2.97-2.99 (m, 4H), 3.13,3.15 (m, 6H), 3.42-3.45 (m, 4H), 3.69-3.72 (m, 2H), 3.95 (s, 2H), 3.99-4.03 (m, 2H), 5.62-5.87 (m, 1H), 7.33-7.40 (m, 2H), 7.43 (d, J = 7.6 Hz, 1H). | |
| 33 | 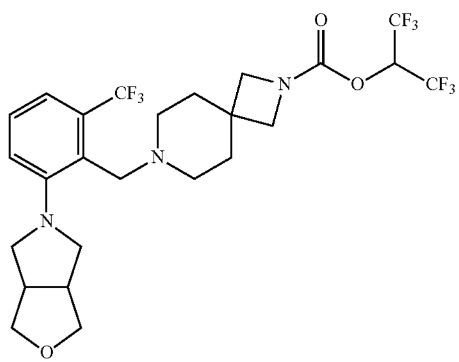 [SMILES: O=C(OC(C(F)(F)F)C(F)(F)F)N1CC2(CCN(Cc3c(N4CC5COCC5C4)cccc3C(F)(F)F)CC2)C1] | 1,1,1,3,3,3-Hexafluoropropan-2-yl 2-(4-chloro-2-(pyrrolidin-1-yl)benzyl)-2,7-diazaspiro[3.5]nonane-7-carboxylate | (Chloroform-d) δ 1.63-1.85 (m, 4H), 2.09-2.39 (m, 4H). 2.92-2.94 (m, 2H), 3.08-3.11 (m, 2H), 3.63 (m, 2H), 3.85-4.03 (m, 6H), 4.05-4.06 (m, 2H), 5.62-5.87 (m, 1H), 7.33-7.35 (m, 2H), 7.44 (m, 1H). | |

| Ex | Structure | Name | NMR (¹H NMR, 300 MHz or 400 MHz, Methanol-d4) | MS [M+ H]⁺ |
|---|---|---|---|---|
| 34 | 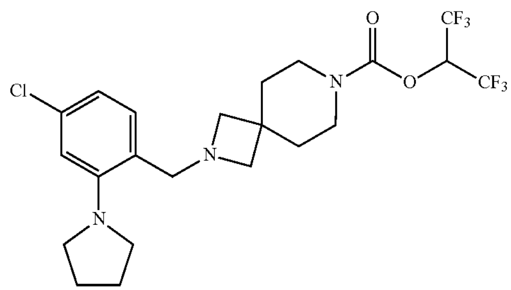 [SMILES: O=C(OC(C(F)(F)F)C(F)(F)F)N1CCC2(CC1)CN(Cc1ccc(Cl)cc1N1CCCC1)C2] | 1,1,1,3,3,3-Hexafluoropropan-2-yl 2-(2-(piperidin-1-yl)-4-(trifluoromethyl)benzyl)-2,7-diazaspiro[3.5]nonane-7-carboxylate | δ 7.22-7.25 (m, 1H), 6.81-6.84 (m, 2H), 5.68-5.78 (m, 1H), 3.62 (br, 2H), 3.45 (t, J = 5.6 Hz, 4H), 3.18 (t, J = 6.3 Hz, 4H), 3.05 (br, 4H), 1.91-2.00 (m, 4H), 1.75-1.82 (m, 4H) | 514 |
| 35 | 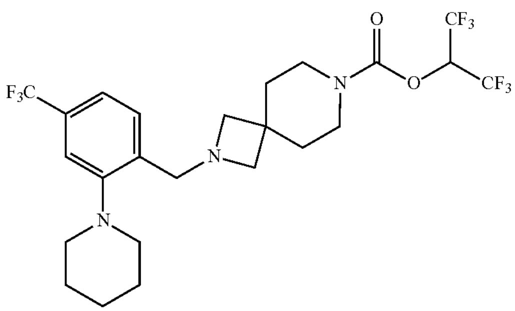 [SMILES: O=C(OC(C(F)(F)F)C(F)(F)F)N1CCC2(CC1)CN(Cc1ccc(C(F)(F)F)cc1N1CCCCC1)C2] | 1,1,1,3,3,3-Hexafluoropropan-2-yl 2-(2-morpholino-4-(trifluoromethyl)benzyl)-2,7-diazaspiro[3.5]nonane-7-carboxylate | δ 7.48 (d, J = 7.8 Hz, 1H), 7.25-7.28 (m, 2H), 5.71-5.79 (m, 1H), 3.72 (s, 2H), 3.46 (t, J = 5.4 Hz, 4H), 3.09 (s, 4H), 2.85 (t, J = 5.4 Hz, 4H), 1.69-1.83 (m, 8H), 1.59-1.62 (m, 2H) | 562 |
| 36 | 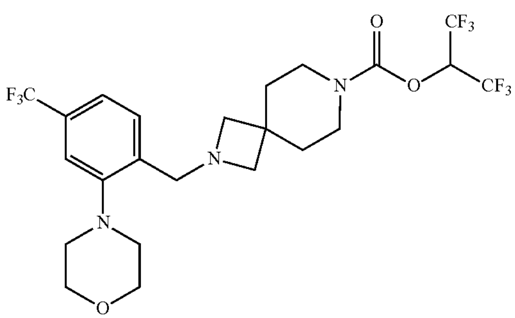 [SMILES: O=C(OC(C(F)(F)F)C(F)(F)F)N1CCC2(CC1)CN(Cc1ccc(C(F)(F)F)cc1N1CCOCC1)C2] | 1,1,1,3,3,3-Hexafluoropropan-2-yl 2-(2-morpholino-4-(trifluoromethyl)benzyl)-2,7-diazaspiro[3.5]nonane-7-carboxylate | δ 7.51 (d, J = 7.8 Hz, 1H), 7.31-7.34 (m, 2H), 5.68-5.81 (m, 1H), 3.86 (t, J = 4.5 Hz, 4H), 3.73 (br, 2H), 3.47 (t, J = 5.6 Hz, 4H), 2.97 (t, J = 4.5 Hz, 4H), 1.80 (br, 4H) | 564 |

| Ex | Structure | Name | NMR (¹H NMR, 300 MHz or 400 MHz, Methanol-d4) | MS [M+ H]⁺ |
|---|---|---|---|---|
| 37 | 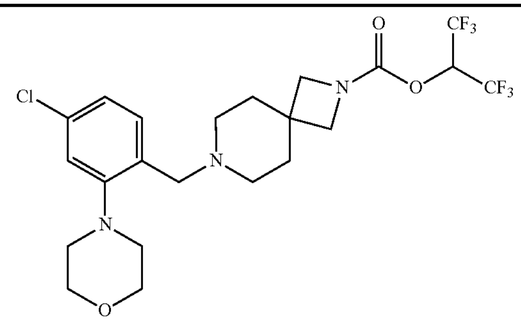 | 1,1,1,3,3,3-Hexafluoropropan-2-yl 7-(4-chloro-2-morpholinobenzyl)-2,7-diazaspiro[3.5]nonane-2-carboxylate | δ 7.34 (d, J = 8.1 Hz, 1H), 7.04-7.06 (m, 2H), 5.59-5.72 (m, 1H), 3.77-3.84 (m, 8H), 3.52 (br, 2H), 2.95 (t, J = 4.5 Hz, 4H), 2.37 (br, 4H), 1.76 (br, 4H) | 530 |
| 38 | 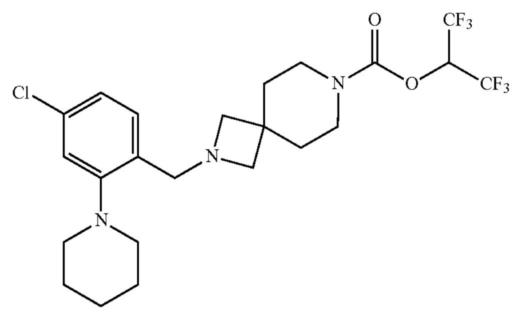 [SMILES: O=C(OC(C(F)(F)F)C(F)(F)F)N1CCC2(CC1)CN(Cc1ccc(Cl)cc1N1CCCCC1)C2] | 1,1,1,3,3,3-Hexafluoropropan-2-yl 2-(4-chloro-2-(piperidin-1-yl)benzyl)-2,7-diazaspiro[3.5]nonane-7-carboxylate | δ 7.24-7.31 (m, 1H), 7.00-7.02 (m, 2H), 2.69-5.79 (m, 1H), 3.69 (br, 2H), 3.46 (br, 4H), 3.13 (br, 4H), 2.82 (t, J = 5.0 Hz, 4H), 1.80-1.82 (m, 4H), 1.67-1.73 (m, 4H), 1.58-1.59 (m, 2H) | 528 |
| 39 | 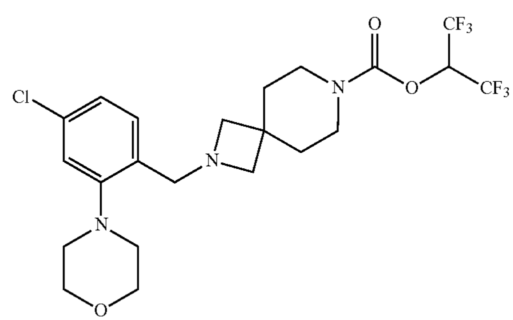 [SMILES: O=C(OC(C(F)(F)F)C(F)(F)F)N1CCC2(CC1)CN(Cc1ccc(Cl)cc1N1CCOCC1)C2] | 1,1,1,3,3,3-Hexafluoropropan-2-yl 2-(4-chloro-2-morpholinobenzyl)-2,7-diazaspiro[3.5]nonane-7-carboxylate | δ 7.30 (br, 1H), 7.00-7.07 (m, 2H), 5.69-5.79 (m, 1H), 3.84 (t, J = 4.4 Hz, 4H), 3.65 (br, 2H), 3.46 (br, 4H), 3.07 (br, 4H), 2.94 (t, J = 4.4 Hz, 4H), 1.79 (br, 4H) | 530 |

| Ex | Structure | Name | NMR (¹H NMR, 300 MHz or 400 MHz, Methanol-d4) | MS [M+ H]⁺ |
|---|---|---|---|---|
| 40 | 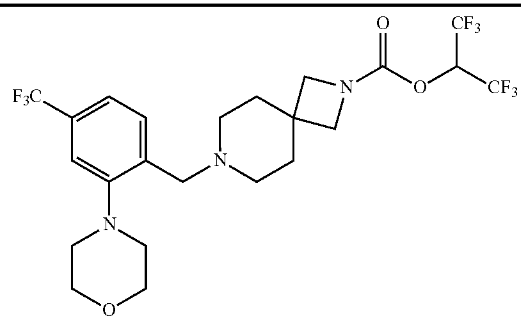 | 1,1,1,3,3,3-Hexafluoropropan-2-yl 7-(2-morpholino-4-(trifluoromethyl)benzyl)-2,7-diazaspiro[3.5]nonane-2-carboxylate | δ 7.58 (d, J = 7.8 Hz 1H), 7.29-7.34 (m, 2H), 5.59-5.72 (m, 1H), 3.78-3.86 (m, 8H), 3.53 (br, 2H), 2.97 (t, J = 4.4 Hz, 4H), 2.38 (br, 4H), 1.78 (t, J = 5.0 Hz, 4H) | 564 |
| 41 | 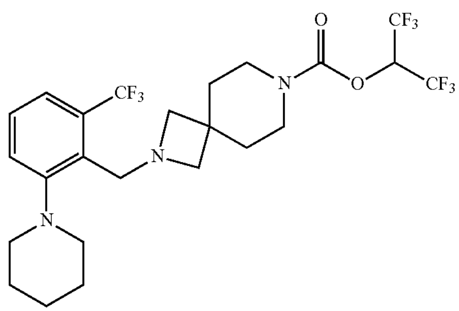 [SMILES: O=C(OC(C(F)(F)F)C(F)(F)F)N1CCC2(CC1)CN(Cc1c(N3CCCCC3)cccc1C(F)(F)F)C2] | 1,1,1,3,3,3-Hexafluoropropan-2-yl 2-(2-(piperidin-1-yl)-6-(trifluoromethyl)benzyl)-2,7-diazaspiro[3.5]nonane-7-carboxylate | δ 7.30-7.61 (m, 3H), 5.66-5.79 (m, 1H), 3.92 (br, 2H), 3.42 (t, J = 5.1 Hz, 4H), 3.16 (br, 4H), 2.83 (t, J = 4.8 Hz, 4H), 1.66-1.78 (m, 10H) | 562 |
| 42 | 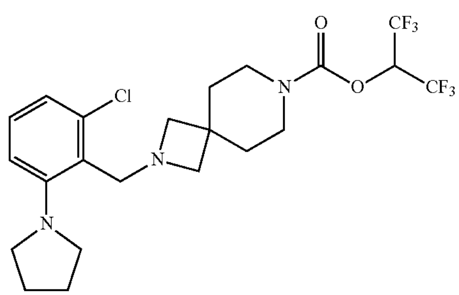 [SMILES: O=C(OC(C(F)(F)F)C(F)(F)F)N1CCC2(CC1)CN(Cc1c(Cl)cccc1N1CCCC1)C2] | 1,1,1,3,3,3-Hexafluoropropan-2-yl 2-(2-chloro-6-(pyrrolidin-1-yl)benzyl)-2,7-diazaspiro[3.5]nonane-7-carboxylate | δ 7.06-7.12 (m, 1H), 6.88-6.99 (m, 2H), 5.67-5.79 (m, 1H), 3.89 (s, 2H), 3.41-3.44 (m, 4H), 3.17-3.34 (m, 8H), 1.87-1.95 (m, 4H), 1.72-1.73 (m, 4H) | 514 |

-continued

| Ex | Structure | Name | NMR (¹H NMR, 300 MHz or 400 MHz, Methanol-d4) | MS [M+ H]⁺ |
|---|---|---|---|---|
| 43 | 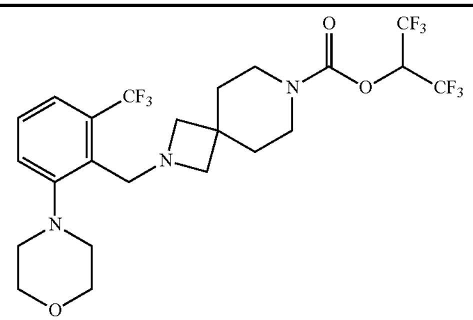 | 1,1,1,3,3,3-Hexafluoropropan-2-yl 2-(2-morpholino-6-(trifluoromethyl)benzyl)-2,7-diazaspiro[3.5]nonane-7-carboxylate | δ 7.34-7.61 (m, 3H), 5.63-5.76 (m, 1H), 3.88 (br, 6H), 3.43 (br, 5H), 3.18 (br, 2H), 2.74-2.97 (m, 5H), 1.61-1.90 (m, 4H) | 564 |
| 44 | 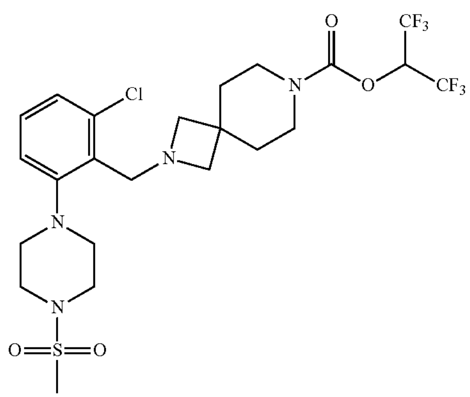 [SMILES: CS(=O)(=O)N1CCN(c2cccc(Cl)c2CN2CC3(CCN(C(=O)OC(C(F)(F)F)C(F)(F)F)CC3)C2)CC1] | 1,1,1,3,3,3-Hexafluoropropan-2-yl 2-(2-chloro-6-(4-(methylsulfonyl)piperazin-1-yl)benzyl)-2,7-diazaspiro[3.5]nonane-7-carboxylate | δ 7.02-7.18 (m, 2H), 6.91 (br, 1H), 5.69-5.79 (m, 1H), 3.96 (br, 2H), 3.38-3.69 (m, 8H), 3.17 (br, 8H), 2.87 (s, 3H), 1.72 (br, 4H) | 607 |
| 45 | 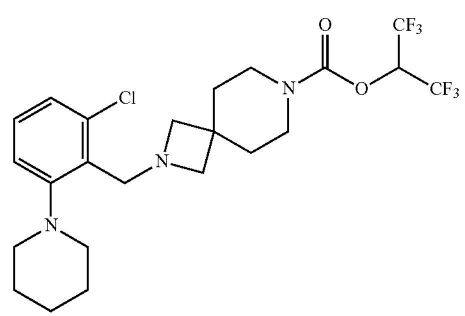 [SMILES: O=C(OC(C(F)(F)F)C(F)(F)F)N1CCC2(CC1)CN(Cc1c(Cl)cccc1N1CCCCC1)C2] | 1,1,1,3,3,3-Hexafluoropropan-2-yl 2-(2-chloro-6-(piperidin-1-yl)benzyl)-2,7-diazaspiro[3.5]nonane-7-carboxylate | δ 7.06-7.22 (m, 2H), 6.91-7.03 (m, 1H), 5.67-5.79 (m, 1H), 3.90 (br, 2H), 3.48-3.52 (m, 4H), 3.22 (br, 4H), 2.87-2.90 (m, 4H), 1.43-1.71 (m, 10H) | 528 |

-continued

| Ex | Structure | Name | NMR (¹H NMR, 300 MHz or 400 MHz, Methanol-d4) | MS [M+ H]⁺ |
|---|---|---|---|---|
| 46 | 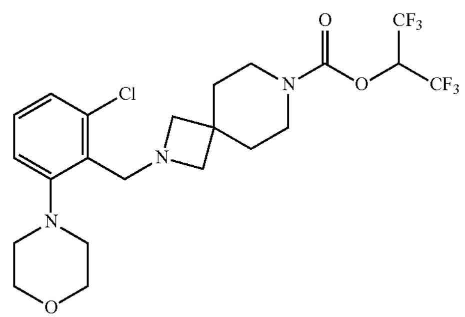 [SMILES: O=C(OC(C(F)(F)F)C(F)(F)F)N1CCC2(CC1)CN(Cc1c(Cl)cccc1N1CCOCC1)C2] | 1,1,1,3,3,3-Hexafluoropropan-2-yl 2-(2-chloro-6-morpholinobenzyl)-2,7-diazaspiro[3.5]nonane-7-carboxylate | δ 7.13-7.21 (m, 2H), 7.01-7.04 (m, 1H), 5.67-5.80 (m, 1H), 4.07 (m, 2H), 3.83 (t, J = 4.5 Hz, 4H), 3.41-3.45 (m, 4H), 3.19 (br, 4H), 3.04 (t, J = 4.5 Hz, 4H), 1.71-1.73 (m, 4H) | 530 |
| 47 | 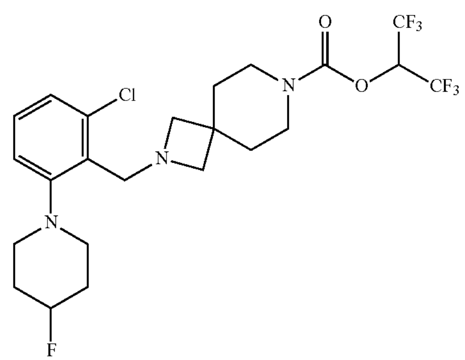 [SMILES: O=C(OC(C(F)(F)F)C(F)(F)F)N1CCC2(CC1)CN(Cc1c(Cl)cccc1N1CCC(F)CC1)C2] | 1,1,1,3,3,3-Hexafluoropropan-2-yl 2-(2-chloro-6-(4-fluoropiperidin-1-yl)benzyl)-2,7-diazaspiro[3.5]nonane-7-carboxylate | δ 7.11-7.19 (m, 2H), 7.01-7.04 (m, 1H), 5.67-5.80 (m, 1H), 4.85-4.91 (m, 1H), 3.89 (s, 2H), 3.43 (t, J = 5.4 Hz, 4H), 3.15-3.19 (m, 6H), 2.87-2.94 (m, 2H), 1.96-2.12 (m, 4H), 1.65-1.75 (m, 4H) | 546 |

-continued

| Ex | Structure | Name | NMR (¹H NMR, 300 MHz or 400 MHz, Methanol-d4) | MS [M+ H]⁺ |
|---|---|---|---|---|
| 48 | 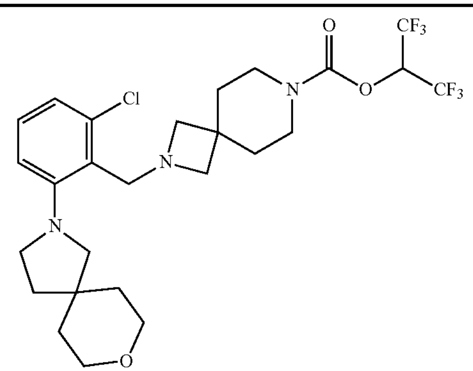 | 1,1,1,3,3,3-Hexafluoropropan-2-yl 2-(2-chloro-6-(8-oxa-2-azaspiro[4.5]decan-2-yl)benzyl)-2,7-diazaspiro[3.5]nonane-7-carboxylate | δ 7.08-7.16 (m, 1H), 6.98-7.01 (m, 1H), 6.88-6.91 (m, 1H), 5.67-5.77 (m, 1H), 3.87 (br, 2H), 3.70-3.76 (m, 4H), 3.36-3.48 (m, 4H), 3.23,3.30 (m, 2H), 3.05-3.21 (m, 6H), 1.82-1.90 (m, 2H), 1.65-1.80 (m, 8H) | 584 |
| 49 | 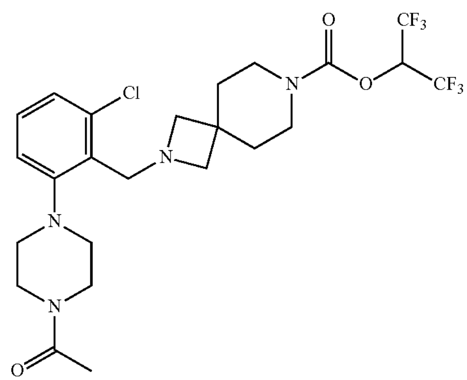 | 1,1,1,3,3,3-Hexafluoropropan-2-yl 2-(2-(4-acetylpiperazin-1-yl)-6-chlorobenzyl)-2,7-diazaspiro[3.5]nonane-7-carboxylate | δ 7.15-7.21 (m, 2H), 6.96-6.99 (m, 1H), 5.69-5.78 (m, 1H), 3.91 (br, 2H), 3.74 (br, 2H), 3.60-3.61 (m, 2H), 3.41-3.59 (m, 4H), 3.20 (br, 4H), 3.02-3.06 (m, 4H), 2.15 (s, 3H) 1.73-1.74 (m, 4H) | 571 |

| Ex | Structure | Name | NMR (¹H NMR, 300 MHz or 400 MHz, Methanol-d4) | MS [M+ H]⁺ |
|---|---|---|---|---|
| 50 | 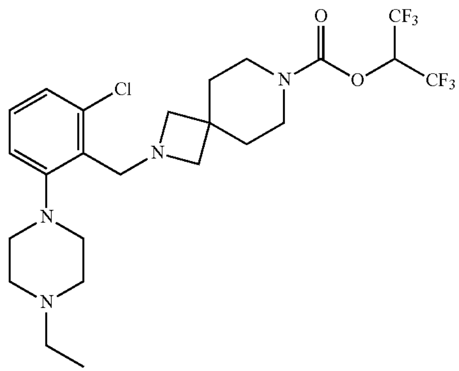 [SMILES: CCN1CCN(c2cccc(Cl)c2CN2CC3(CCN(C(=O)OC(C(F)(F)F)C(F)(F)F)CC3)C2)CC1] | 1,1,1,3,3,3-Hexafluoropropan-2-yl 2-(2-chloro-6-(4-ethylpiperazin-1-yl)benzyl)-2,7-diazaspiro[3.5]nonane-7-carboxylate | δ 7.10-7.19 (m, 2H), 7.02-7.05 (m, 1H), 5.69-5.78 (m, 1H), 3.88 (s, 2H), 3.42-3.45 (m, 4H), 3.19 (s, 4H), 3.08 (br, 4H), 2.46-2.61 (m, 6H), 1.69-1.75 (m, 4H), 1.15 (t, J = 7.2 Hz, 3H) | 557 |
| 51 | 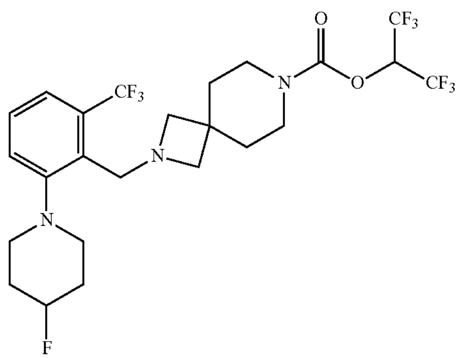 [SMILES: O=C(OC(C(F)(F)F)C(F)(F)F)N1CCC2(CC1)CN(Cc1c(N3CCC(F)CC3)cccc1C(F)(F)F)C2] | 1,1,1,3,3,3-Hexafluoropropan-2-yl 2-(2-(4-fluoropiperidin-1-yl)-6-(trifluoromethyl)benzyl)-2,7-diazaspiro[3.5]nonane-7-carboxylate | δ 7.48-7.54 (m, 1H), 7.36-7.46 (m, 2H), 5.70-5.80 (m, 1H), 4.78-4.90 (m, 1H), 3.91 (br, 2H), 3.44 (br, 4H), 3.25 (br, 6H), 2.82-2.84 (m, 2H), 1.91-2.09 (m, 4H), 1.74 (br, 4H) | 580 |

| Ex | Structure | Name | NMR (¹H NMR, 300 MHz or 400 MHz, Methanol-d4) | MS [M+ H]⁺ |
|---|---|---|---|---|
| 52 | 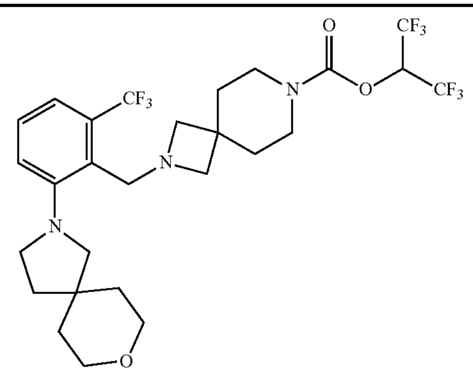 | 1,1,1,3,3,3-Hexafluoropropan-2-yl 2-(2-(8-oxa-2-azaspiro[4.5]decan-2-yl)-6-(trifluoromethyl)benzyl)-2,7-diazaspiro[3.5]nonane-7-carboxylate | δ 7.35 (s, 2H), 7.28 (br, 1H), 5.69-5.79 (m, 1H), 3.86 (br, 2H), 3.67-3.78 (m, 4H), 3.41 (br, 4H), 3.20-3.27 (m, 2H), 3.09 (s, 2H), 2.98 (br, 4H), 1.76-1.94 (m, 2H), 1.48-1.75 (m, 7H) | 618 |
| 53 | 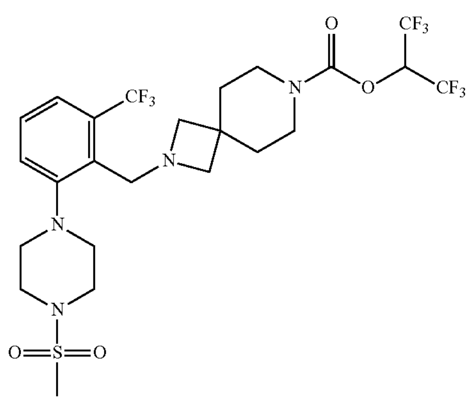 [SMILES: CS(=O)(=O)N1CCN(c2cccc(C(F)(F)F)c2CN2CC3(CCN(C(=O)OC(C(F)(F)F)C(F)(F)F)CC3)C2)CC1] | 1,1,1,3,3,3-Hexafluoropropan-2-yl 2-(2-(4-(methylsulfonyl)piperazin-1-yl)-6-(trifluoromethyl)benzyl)-2,7-diazaspiro[3.5]nonane-7-carboxylate | δ 7.51-7.54 (m, 1H), 7.40 (br, 2H), 5.71-5.78 (m, 1H), 3.90 (br, 2H), 3.44 (br, 8H), 3.20 (br, 8H), 2.90 (s, 3H), 1.72 (br, 4H) | 641 |

| Ex | Structure | Name | NMR (¹H NMR, 300 MHz or 400 MHz, Methanol-d4) | MS [M+ H]⁺ |
|---|---|---|---|---|
| 54 | 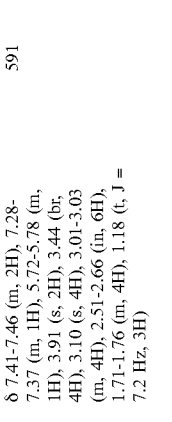 | 1,1,1,3,3,3-Hexafluoropropan-2-yl 2-(2-(4-ethylpiperazin-1-yl)-6-(trifluoromethyl)benzyl)-2,7-diazaspiro[3.5]nonane-7-carboxylate | δ 7.41-7.46 (m, 2H), 7.28-7.37 (m, 1H), 5.72-5.78 (m, 1H), 3.91 (s, 2H), 3.44 (br, 4H), 3.10 (s, 4H), 3.01-3.03 (m, 4H), 2.51-2.66 (m, 6H), 1.71-1.76 (m, 4H), 1.18 (t, J = 7.2 Hz, 3H) | 591 |
| 55 | 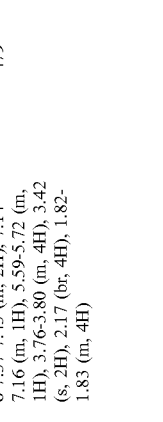 | 1,1,1,3,3,3-Hexafluoropropan-2-yl 7-(3,4-dichlorobenzyl)-2,7-diazaspiro[3.5]nonane-2-carboxylate | δ 7.37-7.43 (m, 2H), 7.14-7.16 (m, 1H), 5.59-5.72 (m, 1H), 3.76-3.80 (m, 4H), 3.42 (s, 2H), 2.17 (br, 4H), 1.82-1.83 (m, 4H) | 479 |
| 56 | 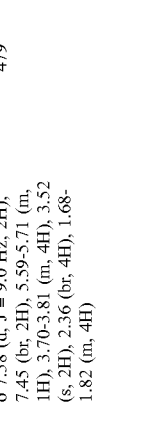 | 1,1,1,3,3,3-Hexafluoropropan-2-yl 7-(4-(trifluoromethyl)benzyl)-2,7-diazaspiro[3.5]nonane-2-carboxylate | δ 7.58 (d, J = 9.0 Hz, 2H), 7.45 (br, 2H), 5.59-5.71 (m, 1H), 3.70-3.81 (m, 4H), 3.52 (s, 2H), 2.36 (br, 4H), 1.68-1.82 (m, 4H) | 479 |

| Ex | Structure | Name | NMR (¹H NMR, 300 MHz or 400 MHz, Methanol-d4) | MS [M+H]⁺ |
|---|---|---|---|---|
| 57 | 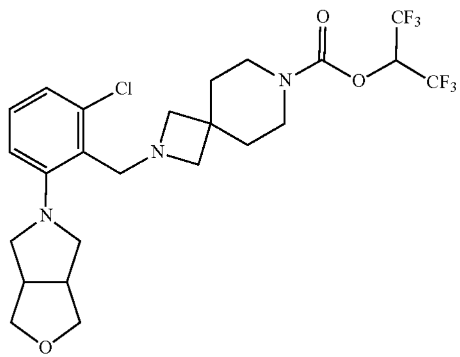 [SMILES: O=C(OC(C(F)(F)F)C(F)(F)F)N1CCC2(CC1)CN(Cc1c(Cl)cccc1N1CC3COCC3C1)C2] | 1,1,1,3,3,3-Hexafluoropropan-2-yl 2-(2-chloro-6-(tetrahydro-1H-furo[3,4-c]pyrrol-5(3H)-yl)benzyl)-2,7-diazaspiro[3.5]nonane-7-carboxylate | δ 7.12-7.23 (m, 2H), 7.02-7.06 (m, 1H), 5.70-5.80 (m, 1H), 4.04-4.06 (m, 2H), 3.92 (br, 2H), 3.60-3.64 (m, 2H), 3.45-3.46 (m, 4H), 3.24 (br, 4H), 3.02-3.15 (m, 5H), 2.93 (br, 2H), 1.76 (br, 4H) | 556 |
| 58 | 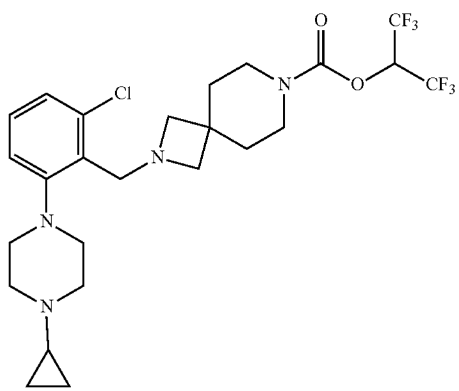 [SMILES: O=C(OC(C(F)(F)F)C(F)(F)F)N1CCC2(CC1)CN(Cc1c(Cl)cccc1N1CCN(C3CC3)CC1)C2] | 1,1,1,3,3,3-Hexafluoropropan-2-yl 2-(2-chloro-6-(4-cyclopropyl)piperazin-1-yl)benzyl)-2,7-diazaspiro[3.5]nonane-7-carboxylate | δ 7.16-7.26 (m, 2H), 7.03-7.05 (m, 1H), 5.66-5.85 (m, 1H), 3.96(br, 2H), 3.13,3.52 (m, 8H), 3.00 (br, 4H), 2.78 (br, 4H), 1.73 (br, 5H), 0.45-0.50. (m, 4H) | 569 |

| Ex | Structure | Name | NMR (¹H NMR, 300 MHz or 400 MHz, Methanol-d4) | MS [M+ H]⁺ |
|---|---|---|---|---|
| 59 | 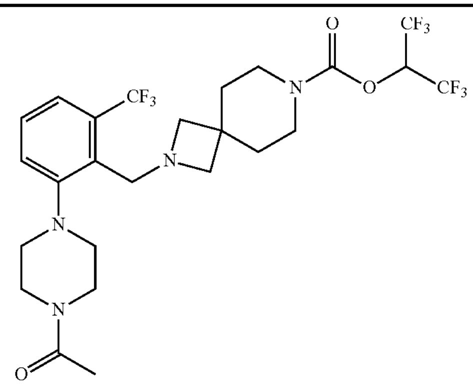 | 1,1,1,3,3,3-Hexafluoropropan-2-yl 2-(2-(4-acetylpiperazin-1-yl)-6-(trifluoromethyl)benzyl)-2,7-diazaspiro[3.5]nonane-7-carboxylate | δ 7.50-7.52 (m, 1H), 7.37 (br, 2H), 5.72-5.78 (m, 1H), 3.65-3.94 (m, 6H), 3.45 (br, 4H), 3.14 (br, 4H), 2.95-2.99 (m, 4H), 2.17 (s, 3H), 1.74 (br, 4H) | 605 |
| 60 | 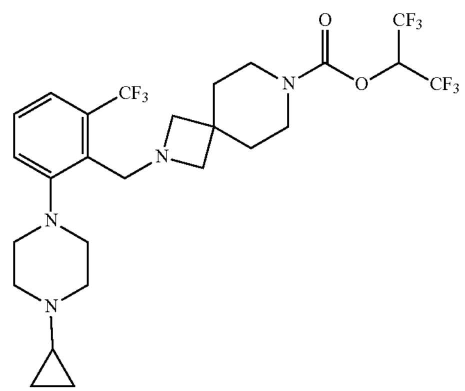 [SMILES: O=C(OC(C(F)(F)F)C(F)(F)F)N1CCC2(CC1)CN(Cc1c(N3CCN(C4CC4)CC3)cccc1C(F)(F)F)C2] | 1,1,1,3,3,3-Hexafluoropropan-2-yl 2-(2-(4-cyclopropylpiperazin-1-yl)-6-(trifluoromethyl)benzyl)-2,7-diazaspiro[3.5]nonane-7-carboxylate | δ 7.54-7.64 (m, 1H), 7.31-7.47 (m, 2H), 5.70-5.80 (m, 1H), 4.09 (br, 2H), 3.63 (br, 4H), 3.18 (br, 4H), 2.96 (br, 4H), 2.83 (br, 4H), 1.75 (br, 5H), 0.52-0.54 (m, 4H) | 603 |

| Ex | Structure | Name | NMR (¹H NMR, 300 MHz or 400 MHz, Methanol-d4) | MS [M+ H]⁺ |
|---|---|---|---|---|
| 61 | 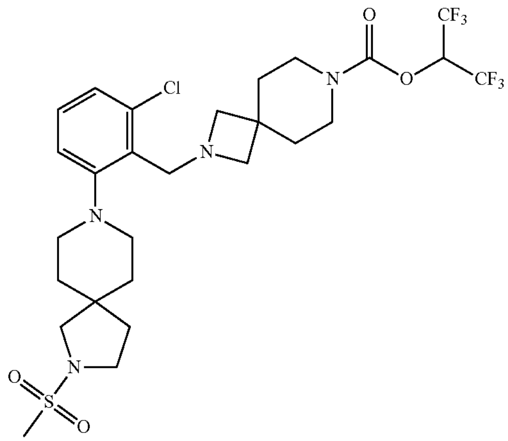 [SMILES: CS(=O)(=O)N1CCC2(CCN(c3cccc(Cl)c3CN3CC4(CCN(C(=O)OC(C(F)(F)F)C(F)(F)F)CC4)C3)CC2)C1] | 1,1,1,3,3,3-Hexafluoropropan-2-yl 2-(2-chloro-6-(2-(methylsulfonyl)-2,8-diazaspiro[4.5]decan-8-yl)benzyl)-2,7-diazaspiro[3.5]nonane-7-carboxylate | δ 7.12-7.18 (m, 2H), 7.00-7.02 (m, 1H), 5.69-5.77 (m, 1H), 3.89 (br, 2H), 3.42-3.47 (m, 6H), 3.21-3.35 (m, 6H), 3.00-3.09 (m, 2H), 2.90-2.92 (m, 2H), 2.86 (s, 3H), 1.89 (t, J = 7.2 Hz, 2H), 1.73-1.75 (m, 8H) | 661 |
| 62 | 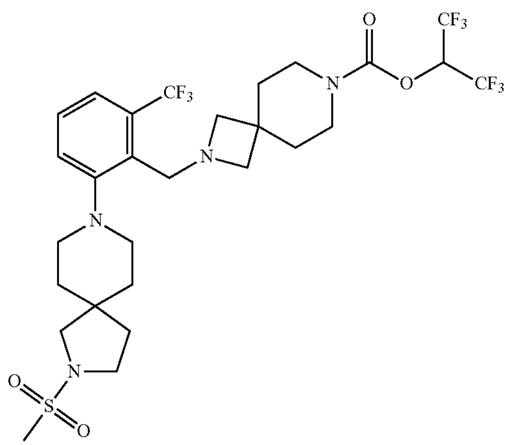 [SMILES: CS(=O)(=O)N1CCC2(CCN(c3cccc(C(F)(F)F)c3CN3CC4(CCN(C(=O)OC(C(F)(F)F)C(F)(F)F)CC4)C3)CC2)C1] | 1,1,1,3,3,3-Hexafluoropropan-2-yl 2-(2-(2-(methylsulfonyl)-2,8-diazaspiro[4.5]decan-8-yl)-6-(trifluoromethyl)benzyl)-2,7-diazaspiro[3.5]nonane-7-carboxylate | δ 7.45 (br, 1H), 7.36 (br, 2H), 5.69-5.77 (m, 1H), 3.90 (br, 2H), 3.62-3.67 (m, 6H), 3.43-3.48 (m, 2H), 3.11 (br, 4H), 2.92-2.96 (m, 2H), 2.82-2.87 (m, 5H), 1.92-1.98 (m, 2H), 1.72-1.78 (m, 8H) | 695 |

| Ex | Structure | Name | NMR (¹H NMR, 300 MHz or 400 MHz, Methanol-d4) | MS [M+ H]⁺ |
|---|---|---|---|---|
| 63 | 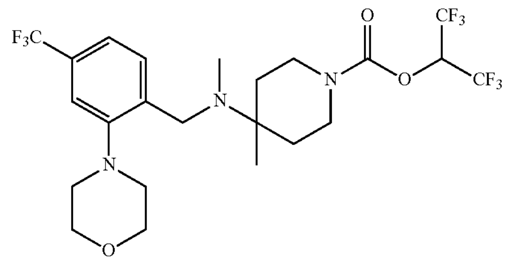 [SMILES: CN(Cc1ccc(C(F)(F)F)cc1N1CCOCC1)C1(C)CCN(C(=O)OC(C(F)(F)F)C(F)(F)F)CC1] | 1,1,1,3,3,3-Hexafluoropropan-2-yl 4-methyl-4-(methyl(2-morpholino-4-(trifluoromethyl)benzyl)amino)piperidine-1-carboxylate | (Chloroform-d) δ 7.73-7.66 (m, 1H), 7.34-7.29 (m, 1H), 7.25-7.20 (m, 1H), 5.76-5.64 (m, 1H), 3.82-3.75 (m, 4H), 3.71-3.59 (m, 2H), 3.59-3.53 (m, 2H), 3.51-3.37 (m, 2H), 2.87-2.77 (m, 4H), 2.01 (s, 3H), 1.95-1.81 (m, 2H), 1.57-1.35 (m, 3H), 1.01 (s, 3H). | 566 |
| 64 | 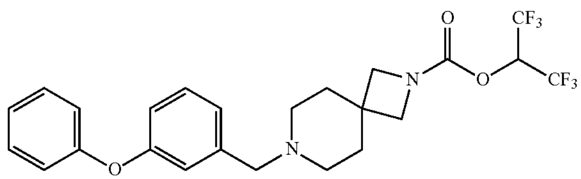 [SMILES: O=C(OC(C(F)(F)F)C(F)(F)F)N1CC2(CCN(Cc3cccc(Oc4ccccc4)c3)CC2)C1] | 1,1,1,3,3,3-Hexafluoropropan-2-yl 7-(3-phenoxybenzyl)-2,7-diazaspiro[3.5]nonane-2-carboxylate | δ 7.27-7.66 (m, 2H), 7.24-7.26 (m, 1H), 6.97-7.12 (m, 5H), 6.87-6.91 (m, 1H), 5.59-5.71 (m, 1H), 3.77 (d, J = 11.1 Hz, 4H), 3.45 (s, 2H), 2.35 (br, 4H), 1.79 (t, J = 5.1 Hz, 4H) | 503 |
| 65 | 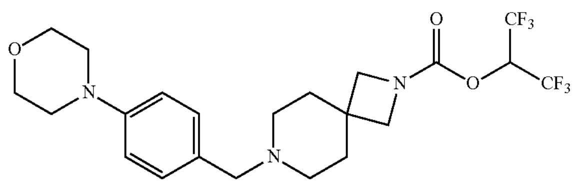 [SMILES: O=C(OC(C(F)(F)F)C(F)(F)F)N1CC2(CCN(Cc3ccc(N4CCOCC4)cc3)CC2)C1] | 1,1,1,3,3,3-Hexafluoropropan-2-yl 7-(4-morpholinobenzyl)-2,7-diazaspiro[3.5]nonane-2-carboxylate | δ 7.18-7.26 (m, 2H),6.86 (d, J = 8.7 Hz, 2H), 5.59-5.71 (m, 1H), 3.86 (t, J = 4.8 Hz, 4H), 3.74 (d, J = 11.1 Hz, 4H), 3.40 (s, 2H), 3.15 (t, J = 4.8 Hz, 4H), 2.34 (br, 4H), 1.80 (t, J = 5.1 Hz, 4H) | 496 |
| 66 | 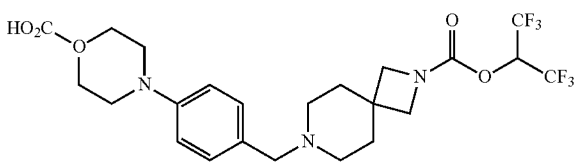 | 1-(4-((2-(((1,1,1,3,3,3-Hexafluoropropan-2-yl)oxy)carbonyl)-2,7-diazaspiro[3.5]nonan-7-yl)methyl)phenyl)piperidine-4-carboxylic acid | δ 7.16 (d, J = 9.0 Hz, 2H), 6.88 (d, J = 9.0 Hz, 2H), 5.58-5.68 (m, 1H), 3.80 (d, J = 12.0 Hz, 4H), 3.60-3.75 (m, 4H), 2.39-2.95 (m, 7H), 1.80-2.10 (m, 8H) | 538 |
| 67 | 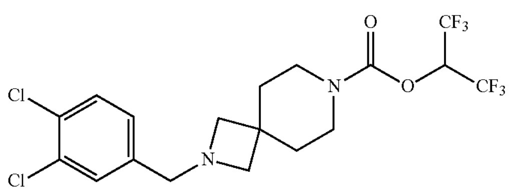 [SMILES: O=C(OC(C(F)(F)F)C(F)(F)F)N1CCC2(CC1)CN(Cc1ccc(Cl)c(Cl)c1)C2] | 1,1,1,3,3,3-Hexafluoropropan-2-yl 2-(3,4-dichlorobenzyl)-2,7-diazaspiro[3.5]nonane-7-carboxylate | δ 7.36-7.39 (m, 2H), 7.10-7.13 (m, 1H), 5.70-5.79 (m, 1H), 3.58 (s, 2H), 3.46 (t, J = 6.0 Hz, 4H), 3.05 (s, 4H), 1.75-1.82 (m, 4H) | 479 |

| Ex | Structure | Name | NMR (¹H NMR, 300 MHz or 400 MHz, Methanol-d4) | MS [M+ H]⁺ |
|---|---|---|---|---|
| 68 | 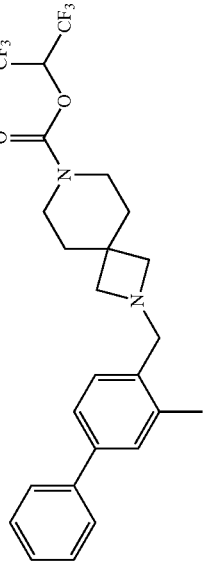 | 1,1,1,3,3,3-Hexafluoropropan-2-yl 2-((3-methyl-[1,1'-biphenyl]-4-yl)methyl)-2,7-diazaspiro[3,5]nonane-7-carboxylate | δ 7.59 (d, J = 1.5 Hz, 2H), 7.38-7.56 (m, 4H), 7.29-7.34 (m, 2H), 5.71-5.80(m, 1H), 3.65 (s, 2H), 3.46 (t, J = 6.0 Hz, 4H), 3.09 (s, 4H), 2.37 (s, 3H), 1.77-1.84 (m, 4H) | 501 |
| 69 | 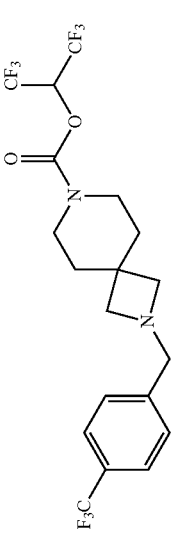 | 1,1,1,3,3,3-Hexafluoropropan-2-yl 2-(4-(trifluoromethyl)benzyl)-2,7-diazaspiro[3,5]nonane-7-carboxylate | δ 7.56 (d, J = 9.0 Hz, 2H), 7.40 (d, J = 9.0 Hz, 2H), 5.70-5.79 (m, 1H), 3.70 (s, 2H), 3.46 (t, J = 6.0 Hz, 4H), 3.08 (s, 4H), 1.76-1.83 (m, 4H) | 479 |
| 70 | 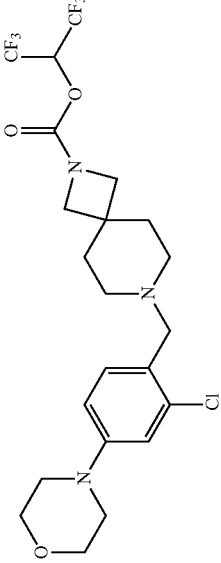 | 1,1,1,3,3,3-Hexafluoropropan-2-yl 7-(2-chloro-4-morpholinobenzyl)-2,7-diazaspiro[3,5]nonane-2-carboxylate | δ 7.29 (d, J = 8.4 Hz, 1H), 6.87 (d, J = 2.7 Hz, 1H), 6.76-6.79 (m, 1H), 5.59-5.71 (m, 1H), 3.76-3.86 (m, 8H), 3.51 (s, 2H), 3.14 (t, J = 3.6 Hz, 4H), 2.40 (br, 4H), 1.79 (t, J = 5.1 Hz, 4H) | 530 |
| 71 | 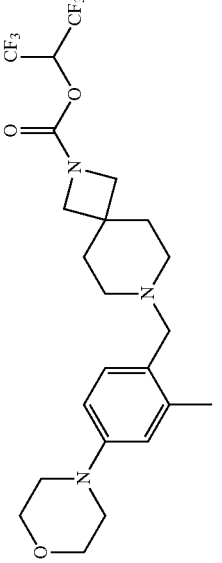 | 1,1,1,3,3,3-Hexafluoropropan-2-yl 7-(2-methyl-4-morpholinobenzyl)-2,7-diazaspiro[3,5]nonane-2-carboxylate | δ 7.10 (d, J = 5.1 Hz, 1H), 6.66-6.72 (m, 2H), 5.61-5.70 (m, 1H), 3.75-3.86 (m, 8H), 3.41 (br, 2H), 3.14 (t, J = 4.8 Hz, 4H), 2.32 (br, 7H), 1.76 (t, J = 5.1 Hz, 4H) | 190 [C₁₂H₁₆NO]⁺ |

| Ex | Structure | Name | NMR (¹H NMR, 300 MHz or 400 MHz, Methanol-d4) | MS [M+ H]⁺ |
|---|---|---|---|---|
| 72 | 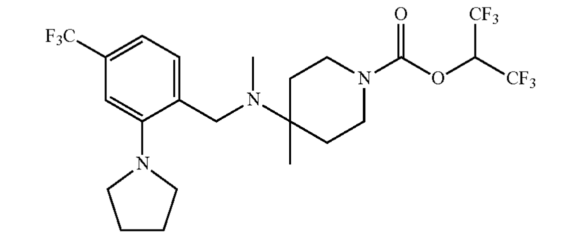 [SMILES: CN(Cc1ccc(C(F)(F)F)cc1N1CCCC1)C1(C)CCN(C(=O)OC(C(F)(F)F)C(F)(F)F)CC1] | 1,1,1,3,3,3-Hexafluoropropan-2-yl 4-(methyl(2-(pyrrolidin-1-yl)-4-(trifluoromethyl)benzyl)amino)piperidine-1-carboxylate | (Chloroform-d) δ 7.86-7.73 (m, 1H), 7.25-7.20 (m, 1H), 7.18-7.15 (m, 1H), 5.88-5.73 (m, 1H), 3.84-3.70 (m, 2H), 3.62-3.43 (m, 4H), 3.21-3.10 (m, 4H), 2.08 (s,3H), 2.04-1.93 (m, 6H), 1.58-1.43 (m, 2H), 1.13-1.06(m, 3H). | 550 |
| 73 | 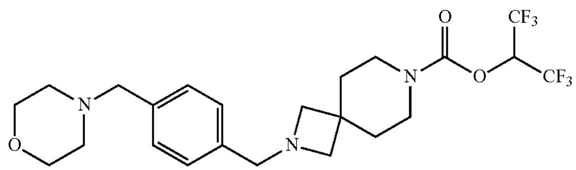 [SMILES: O=C(OC(C(F)(F)F)C(F)(F)F)N1CCC2(CC1)CN(Cc1ccc(CN3CCOCC3)cc1)C2] | 1,1,1,3,3,3-Hexafluoropropan-2-yl 2-(4-(morpholinomethyl)benzyl)-2,7-diazaspiro[3.5]nonane-7-carboxylate | δ 7.20-7.28 (m, 4H), 5.70-5.78 (m, 1H), 3.70 (t, J = 6.0 Hz, 4H), 3.62 (s, 2H), 3.43-3.47 (m, 6H), 3.06 (s, 4H), 2.44 (t, J = 4.5 Hz, 4H), 1.75-1.81 (m, 4H) | 510 |
| 74 | 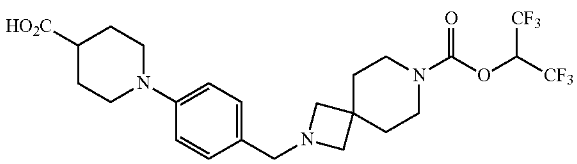 [SMILES: O=C(O)C1CCN(c2ccc(CN3CC4(CCN(C(=O)OC(C(F)(F)F)C(F)(F)F)CC4)C3)cc2)CC1] | 1-(4-((7-((1,1,1,3,3,3-Hexafluoropropan-2-yl)oxy)carbonyl)-2,7-diazaspiro[3.5]nonan-2-yl)methyl)phenyl)piperidine-4-carboxylic acid | δ 7.17 (d, J-6.0 Hz, 2H), 6.88 (d, J = 9.0 Hz, 2H), 5.68-5.76 (m, 1H), 3.82 (s, 2H), 3.56-3.69 (m, 2H), 3.42 (br, 8H), 2.86 (t, J = 12.0 Hz, 2H), 2.38-2.45 (m, 1H), 1.95-2.10 (m, 2H), 1.73-1.93 (m, 6H) | 538 |
| 75 | 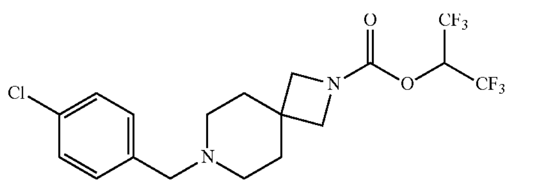 [SMILES: O=C(OC(C(F)(F)F)C(F)(F)F)N1CC2(CCN(Cc3ccc(Cl)cc3)CC2)C1] | 1,1,1,3,3,3-Hexafluoropropan-2-yl 7-(4-chlorobenzyl)-2,7-diazaspiro[3.5]nonane-2-carboxylate | (Acetonitrile-d3) δ 7.33-7.25 (m, 4H), 5.96-5.86 (m, 1H), 3.76 (s, 2H), 3.66 (s, 2H), 3.40 (s, 2H), 2.30 (brs,4H-overlapping with water peak), 1.73 (t, 4H, J = 5.3 Hz) | 441 |
| 76 | 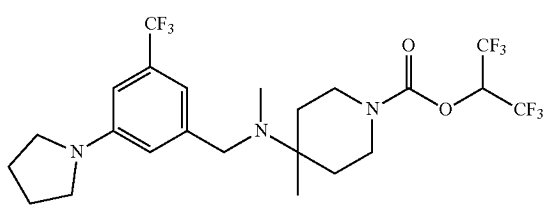 [SMILES: CN(Cc1cc(N2CCCC2)cc(C(F)(F)F)c1)C1(C)CCN(C(=O)OC(C(F)(F)F)C(F)(F)F)CC1] | 1,1,1,3,3,3-Hexafluoropropan-2-yl 4-(methyl(3-(pyrrolidin-1-yl)-5-(trifluoromethyl)benzyl)amino)piperidine-1-carboxylate | (Chloroform-d) δ 6.75 (s, 1H), 6.63 (s, 1H), 6.54 (s, 1H), 5.77-5.64 (m, 1H), 3.71-3.60 (m, 2H), 3.55-3.38 (m, 4H), 3.27-3.17 (m, 4H), 2.02 (s, 3H), 2.00-1.82 (m, 6H), 1.49-1.33 (m, 2H), 0.96 (s, 3H). | 550 |

-continued

| Ex | Structure | Name | NMR (¹H NMR, 300 MHz or 400 MHz, Methanol-d4) | MS [M+ H]⁺ |
|---|---|---|---|---|
| 77 | 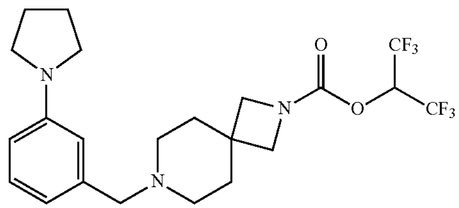 [SMILES: O=C(OC(C(F)(F)F)C(F)(F)F)N1CC2(CCN(Cc3cccc(N4CCCC4)c3)CC2)C1] | 1,1,1,3,3,3-Hexafluoropropan-2-yl 7-(3-(pyrrolidin-1-yl)benzyl)-2,7-diazaspiro[3.5]nonane-2-carboxylate | (Acetonitrile-d3) δ 7.09 (t, 1H, J = 7.8 Hz), 6.54-6.47 (m, 2H), 6.43 (dd, 1 H/ = 8.0,2.2 Hz), 5.91 (hept, 1H, J = 6.3 Hz), 3.76 (s, 2H), 3.70 (s, 2H), 3.34 (s, 2H), 3.25-3.18 (m, 4H), 2.29 (brs, 4H), 1.99-1.95 (m, 4H-overlaps with solvent peak), 1.77-1.69 (m, 1H) | 480 |
| 78 | 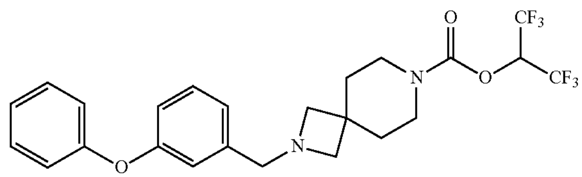 [SMILES: O=C(OC(C(F)(F)F)C(F)(F)F)N1CCC2(CC1)CN(Cc1cccc(Oc3ccccc3)c1)C2] | 1,1,1,3,3,3-Hexafluoropropan-2-yl 2-(3-phenoxybenzyl)-2,7-diazaspiro[3.5]nonane-7-carboxylate | δ 7.27-7.37 (m, 3H), 7.10-7.13 (m, 1H), 6.96-7.08 (m, 4H), 6.88-6.91 (m, 1H), 5.67-5.80 (m, 1H), 3.67 (s, 2H), 3.45 (t, J = 5.4 Hz, 4H), 3.12 (s,4H), 1.78 (t, J = 5.1 Hz 4H) | 503 |
| 79 | 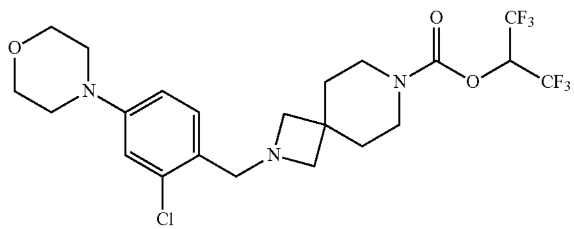 [SMILES: O=C(OC(C(F)(F)F)C(F)(F)F)N1CCC2(CC1)CN(Cc1ccc(N3CCOCC3)cc1Cl)C2] | 1,1,1,3,3,3-Hexafluoropropan-2-yl 2-(2-chloro-4-morpholinobenzyl)-2,7-diazaspiro[3.5]nonane-7-carboxylate | δ 7.43 (br, 1H), 6.91 (s, 1H). 6.80-6.88 (m, 1H), 5.69-5.77 (m, 1H), 3.83-4.08(m, 6H), 3.46 (t, J = 5.4 Hz, 4H), 3.29 (br, 3H), 3.14-3.18 (m, 5H), 1.85 (br, 4H) | 530 |
| 80 | 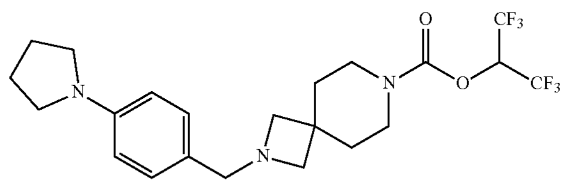 [SMILES: O=C(OC(C(F)(F)F)C(F)(F)F)N1CCC2(CC1)CN(Cc1ccc(N3CCCC3)cc1)C2] | 1,1,1,3,3,3-Hexafluoropropan-2-yl 2-(4-(pyrrolidin-1-yl)benzyl)-2,7-diazaspiro[3.5]nonane-7-carboxylate | δ 7.12 (d, J = 9.0 Hz, 2H), 6.52 (d, J = 9.0 Hz, 2H), 5.70-5.78 (m, 1H), 3.55 (s, 2H), 3.43 (t, J = 6.0 Hz, 4H), 3.26 (t, J = 7.5 Hz, 4H), 3.05 (s, 4H), 1.94-2.04 (m, 4H), 1.73-1.79(111. 4H) | 160 [C₁₁H₁₄N]⁺ |
| 81 | 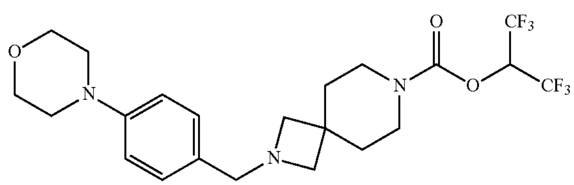 [SMILES: O=C(OC(C(F)(F)F)C(F)(F)F)N1CCC2(CC1)CN(Cc1ccc(N3CCOCC3)cc1)C2] | 1,1,1,3,3,3-Hexafluoropropan-2-yl 2-(4-morpholinobenzyl)-2,7-diazaspiro[3.5]nonane-7-carboxylate | δ 7.18 (d, J = 8.4 Hz, 2H), 6.86 (d, J = 7.5 Hz, 2H), 5.70-5.78 (m, 1H), 3.86 (t, J = 4.5 Hz, 4H), 3.57 (s, 2H), 3.44 (t, J = 5.4 Hz, 4H), 3.14 (t, J = 4.8 Hz, 4H), 3.04 (s, 4H), 1.74-1.80 (m, 4H) | 496 |

| Ex | Structure | Name | NMR (¹H NMR, 300 MHz or 400 MHz, Methanol-d4) | MS [M+ H]⁺ |
|---|---|---|---|---|
| 82 | 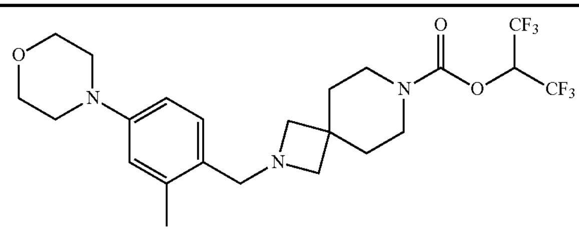 | 1,1,1,3,3,3-Hexafluoropropan-2-yl 2-(2-methyl-4-morpholinobenzyl)-2,7-diazaspiro[3.5]nonane-7-carboxylate | δ 7.14 (d, J = 8.1 Hz, 1H), 6.69-6.73 (m, 2H), 5.71-5.80 (m, 1H), 3.86 (t, J = 4.8 Hz, 4H), 3.56 (s, 2H), 3.46 (t, J = 5.7 Hz, 4H), 3.14 (t, J = 4.8 Hz, 4H), 3.04 (s, 4H), 2.31 (s, 3H), 1.76-1.82 (m, 4H) | 510 |
| 83 | 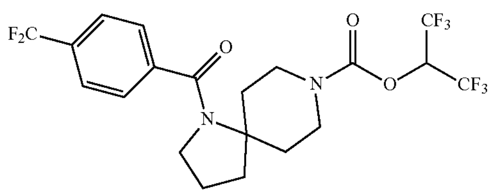 | 1,1,1,3,3,3-Hexafluoropropan-2-yl 1-(4-(trifluoromethyl)benzoyl)-1,8-diazaspiro[4.5]decane-8-carboxylate | (Chloroform-d) δ 7.66 (d, J = 8.0 Hz, 2H), 7.51 (d, J = 8.0 Hz, 2H), 5.71-5.81 (m, 1H), 4.18-4.27 (m, 2H), 3.39 (t, J = 6.4 Hz, 2H), 3.13-3.20 (m, 2H), 2.95-3.08 (m, 2H), 2.00-2.13 (m, 2H), 1.83-1.88 (m, 2H), 1.45-1.55 (m, 2H). | 507 |
| 84 | 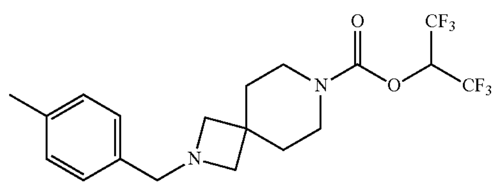 [SMILES: Cc1ccc(CN2CC3(CCN(C(=O)OC(C(F)(F)F)C(F)(F)F)CC3)C2)cc1] | 1,1,1,3,3,3-Hexafluoropropan-2-yl 2-(4-methylbenzyl)-2,7-diazaspiro[3.5]nonane-7-carboxylate | δ 7.14-7.21 (m, 4H), 5.73-5.82 (m, 1H), 3.63 (s, 2H), 3.48 (t, J = 5.7 Hz, 4H), 3.08 (s, 4H), 2.36 (s, 3H), 1.77-1.84 (m, 4H) | 425 |
| 85 | 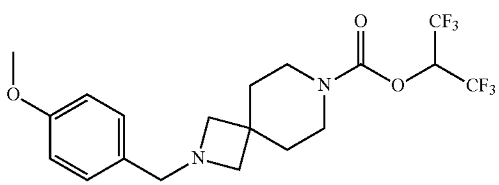 [SMILES: COc1ccc(CN2CC3(CCN(C(=O)OC(C(F)(F)F)C(F)(F)F)CC3)C2)cc1] | 1,1,1,3,3,3-Hexafluoropropan-2-yl 2-(4-methoxybenzyl)-2,7-diazaspiro[3.5]nonane-7-carboxylate | δ 7.20-7.24 (m, 2H), 6.86-6.90 (m, 2H), 5.73-5.82 (m, 1H), 3.82 (s, 3H), 3.60 (s, 2H), 3.47 (t, J = 5.6 Hz, 4H), 3.06 (s,4H), 1.77-1.83 (m, 4H) | 441 |
| 86 | 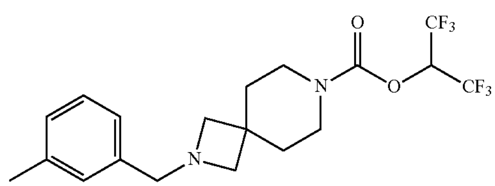 [SMILES: Cc1cccc(CN2CC3(CCN(C(=O)OC(C(F)(F)F)C(F)(F)F)CC3)C2)c1] | 1,1,1,3,3,3-Hexafluoropropan-2-yl 2-(3-methylbenzyl)-2,7-diazaspiro[3.5]nonane-7-carboxylate | δ 7.21-7.26 (m, 1H), 7.09-7.11 (m, 3H), 5.74-5.82 (m, 1H), 3.64 (s, 2H), 3.48 (t, J = 5.6 Hz, 4H), 3.10 (s,4H), 2.38 (s, 3H), 1.78-1.85 (m, 4H) | 425 |

-continued

| Ex | Structure | Name | NMR ($^1$H NMR, 300 MHz or 400 MHz, Methanol-d4) | MS [M+ H]$^+$ |
|---|---|---|---|---|
| 87 | 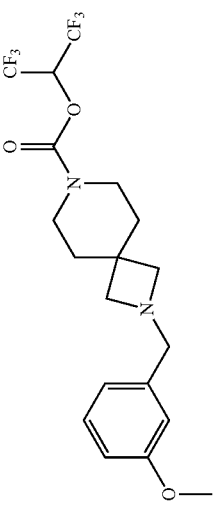 | 1,1,1,3,3,3-Hexafluoropropan-2-yl 2-(3-methoxybenzyl)-2,7-diazaspiro[3.5]nonane-7-carboxylate | δ 7.23-7.29 (m, 1H), 6.80-6.90 (m, 3H), 5.74-5.82 (m, 1H), 3.84 (s, 3H), 3.65 (s, 2H), 3.48 (t, J = 5.6 Hz, 4H) 3.09 (s, 4H), 1.78-1.84 (m, 4H) | 441 |
| 88 | 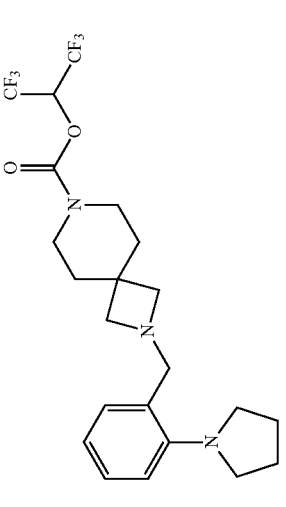 | 1,1,1,3,3,3-Hexafluoropropan-2-yl 2-(2-(pyrrolidin-1-yl)benzyl)-2,7-diazaspiro[3.5]nonane-7-carboxylate | δ 7.36-7.39 (m, 1H), 7.16-7.22 (m, 1H), 6.92-6.96 (m, 2H), 5.74-5.82 (m, 1H), 3.72 (s, 2H), 3.49 (t, J = 5.7 Hz, 4H), 3.12-3.22 (m, 8H), 1.91-2.01 (m, 4H), 1.79-1.86 (m, 4H) | 480 |
| 89 | 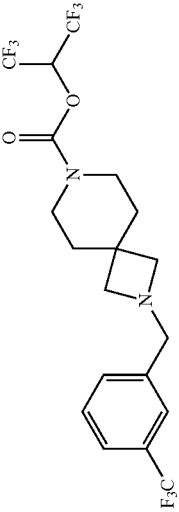 | 1,1,1,3,3,3-Hexafluoropropan-2-yl 2-(3-(trifluoromethyl)benzyl)-2,7-diazaspiro[3.5]nonane-7-carboxylate | δ 7.39-7.54 (m, 4H), 5.70-5.78 (m, 1H), 3.69 (s, 2H), 3.46 (t, J = 5.6 Hz, 4H), 3.07 (s, 4H), L.76-1.83 (m, 4H) | 479 |
| 90 | 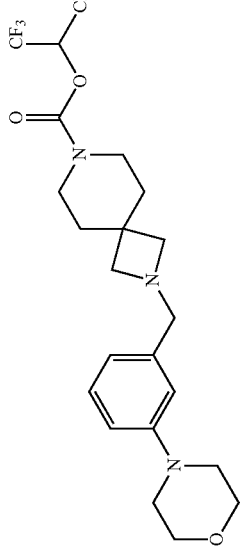 | 1,1,1,3,3,3-Hexafluoropropan-2-yl 2-(3-morpholinobenzyl)-2,7-diazaspiro[3.5]nonane-7-carboxylate | δ 7.19-7.24 (m, 1H), 6.85 (s, 1H), 6.78-6.80 (m, 2H), 5.70-5.78 (m, 1H), 3.86 (t, J = 4.8 Hz, 4H), 3.62 (s, 2H), 3.46 (t, J = 5.4 Hz, 4H), 3.16 (t, J = 4.8 Hz, 4H), 3.07 (s, 4H), 1.75-1.81 (m, 4H) | 496 |

| Ex | Structure | Name | NMR (¹H NMR, 300 MHz or 400 MHz, Methanol-d4) | MS [M+ H]⁺ |
|---|---|---|---|---|
| 91 | 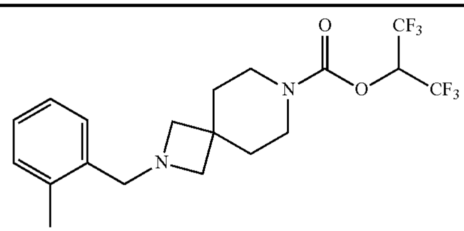 | 1,1,1,3,3,3-Hexafluoropropan-2-yl 2-(2-methylbenzyl)-2,7-diazaspiro[3.5]nonane-7-carboxylate | δ 7.23-7.26 (m, 1H), 7.14-7.17 (m, 3H), 5.70-5.78 (m, 1H), 3.62 (s, 2H), 3.45 (t, J = 5.7 Hz, 4H), 3.07 (s, 4H), 2.31 (s, 3H), 1.76-1.82 (m, 4H) | 425 |
| 92 | 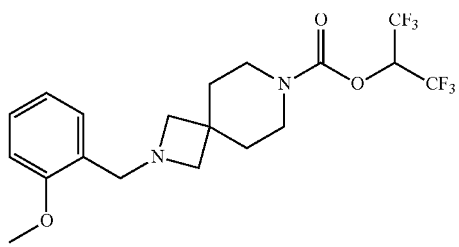 [SMILES: COc1ccccc1CN1CC2(CCN(C(=O)OC(C(F)(F)F)C(F)(F)F)CC2)C1] | 1,1,1,3,3,3-Hexafluoropropan-2-yl 2-(2-methoxybenzyl)-2,7-diazaspiro[3.5]nonane-7-carboxylate | δ 7.25-7.29 (m, 1H), 7.19-7.23 (m, 1H), 6.93-6.96(m, 1H), 6.84-6.91 (m, 1H), 5.70-5.79 (m, 1H), 3.82 (s, 3H), 3.68 (s, 2H), 3.45 (t, J = 5.6 Hz, 4H), 3.12 (s, 4H), 1.76-1.82 (m, 4H) | 441 |
| 93 | 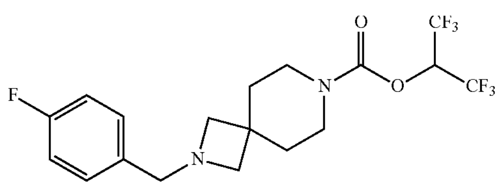 [SMILES: O=C(OC(C(F)(F)F)C(F)(F)F)N1CCC2(CC1)CN(Cc1ccc(F)cc1)C2] | 1,1,1,3,3,3-Hexafluoropropan-2-yl 2-(4-fluorobenzyl)-2,7-diazaspiro[3.5]nonane-7-carboxylate | δ 7.22-7.26 (m, 2H), 6.96-7.03 (m, 2H), 5.70-5.78 (m, 1H), 3.60 (s, 2H), 3.45 (t, J = 5.6 Hz, 4H), 3.05 (s, 4H), 1.75-1.81 (m, 4H) | 429 |
| 94 | 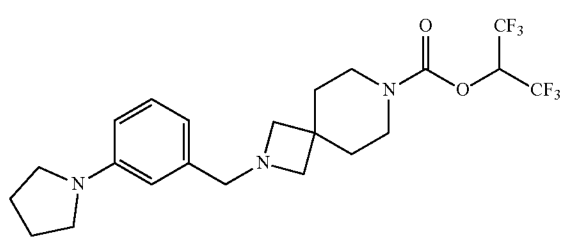 [SMILES: O=C(OC(C(F)(F)F)C(F)(F)F)N1CCC2(CC1)CN(Cc1cccc(N3CCCC3)c1)C2] | 1,1,1,3,3,3-Hexafluoropropan-2-yl 2-(3-(pyrrolidin-1-yl)benzyl)-2,7-diazaspiro[3.5]nonane-7-carboxylate | δ 7.11-7.15 (m, 1H), 6.49-6.58 (m, 3H), 6.07-6.17 (m, 1H), 3.66 (s, 2H), 3.50 (br, 4H), 3.29-3.38 (m, 4H), 3.20 (s, 4H), 2.00-2.07 (m, 4H), 1.72-1.80 (m, 4H) | 480 |

| Ex | Structure | Name | NMR (¹H NMR, 300 MHz or 400 MHz, Methanol-d4) | MS [M+ H]⁺ |
|---|---|---|---|---|
| 95 | 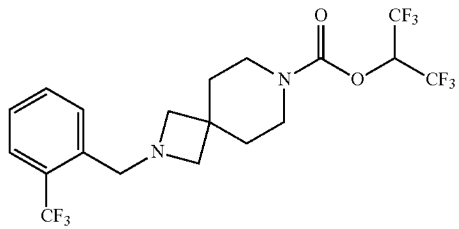 [SMILES: O=C(OC(C(F)(F)F)C(F)(F)F)N1CCC2(CC1)CN(Cc1ccccc1C(F)(F)F)C2] | 1,1,1,3,3,3-Hexafluoropropan-2-yl 2-(2-(trifluoro methyl)benzyl)-2,7-diazaspiro[3.5]nonane-7-carboxylate | δ 7.60-7.68 (m, 2H), 7.50-7.54 (m, 1H), 7.30-7.35 (m, 1H), 5.68-5.81 (m, 1H), 3.85 (s, 2H), 3.47 (t, J = 5.7 Hz, 4H), 3.12 (s, 4H), 1.79-1.86 (m, 4H) | 479 |
| 96 | 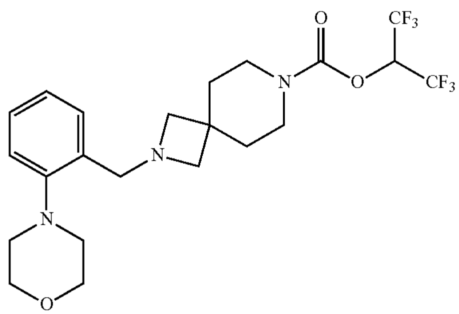 [SMILES: O=C(OC(C(F)(F)F)C(F)(F)F)N1CCC2(CC1)CN(Cc1ccccc1N1CCOCC1)C2] | 1,1,1,3,3,3-Hexafluoropropan-2-yl 2-(2-morpholinobenzyl)-2,7-diazaspiro[3.5]nonane-7-carboxylate | δ 7.34-7.37 (m, 1H), 7.26-7.27 (m, 0.2H), 7.22-7.25 (m, 0.8H), 7.06-7.10 (m, 2H), 5.70-5.79 (m, 1H), 3.85 (t, J = 4.5 Hz, 4H), 3.72 (s, 2H), 3.46 (t, J = 5.6 Hz, 4H), 3.09 (s, 4H), 2.96 (t, J = 4.6 Hz, 4H), 1.75-1.82 (m, 4H) | 496 |
| 97 | 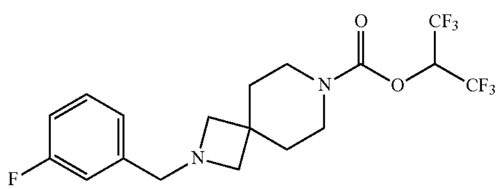 [SMILES: O=C(OC(C(F)(F)F)C(F)(F)F)N1CCC2(CC1)CN(Cc1cccc(F)c1)C2] | 1,1,1,3,3,3-Hexafluoropropan-2-yl 2-(3-fluorobenzyl)-2,7-diazaspiro[3.5]nonane-7-carboxylate | δ 7.28-7.30 (0.4 H), 7.23-7.25 (m, 0.6H), 6.90-7.05 (m, 3H), 5.70-5.78 (m, 1H), 3.63 (s, 2H), 3.45 (t, J = 5.7 Hz, 4H), 3.06 (s, 4H), 1.72-1.86 (m, 4H) | 429 |
| 98 | 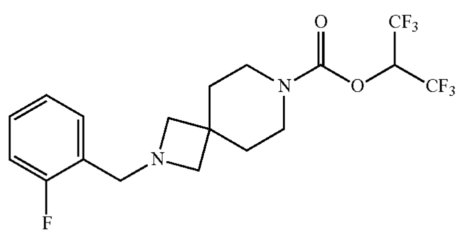 [SMILES: O=C(OC(C(F)(F)F)C(F)(F)F)N1CCC2(CC1)CN(Cc1ccccc1F)C2] | 1,1,1,3,3,3-Hexafluoropropan-2-yl 2-(2-fluorobenzyl)-2,7-diazaspiro[3.5]nonane-7-carboxylate | δ 5.31-7.36 (m, 1H), 7.20-7.25 (m, 1H), 7.08-7.13 (m, 1H), 6.99-7.06 (m, 1H), 5.70-5.78 (m, 1H), 3.70 (s, 2H), 3.45 (t, J = 5.7 Hz, 4H), 3.11 (s, 4H), 1.75-1.81 (m, 4H) | 429 |

| Ex | Structure | Name | NMR (¹H NMR, 300 MHz or 400 MHz, Methanol-d4) | MS [M+H]⁺ |
|---|---|---|---|---|
| 99 | 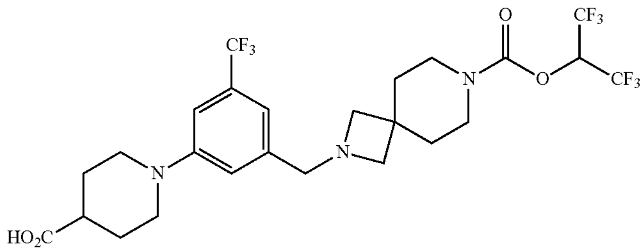 [SMILES: O=C(O)C1CCN(c2cc(CN3CC4(CCN(C(=O)OC(C(F)(F)F)C(F)(F)F)CC4)C3)cc(C(F)(F)F)c2)CC1] | 1-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)piperidine-4-carboxylic acid | δ 7.17 (s, 1H), 7.10 (s, 1H), 7.03 (s, 1H), 6.06-6.15 (m, 1H), 3.89 (s, 2H), 3.68-3.78 (m, 2H), 3.41-3.52 (m, 4H), 3.41 (s, 4H), 2.79-2.87 (m, 2H), 2.32-2.40 (m, 1H), 1.98-2.07 (m, 2H), 1.74-1.82 (m, 6H). | 606 |
| 100 | 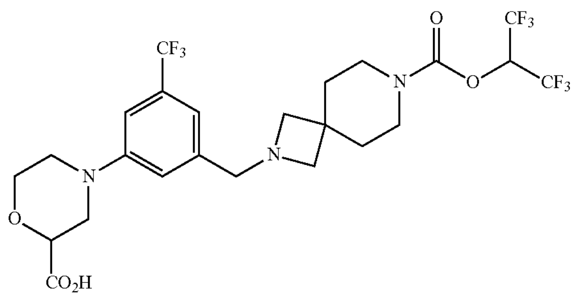 [SMILES: O=C(O)C1CN(c2cc(CN3CC4(CCN(C(=O)OC(C(F)(F)F)C(F)(F)F)CC4)C3)cc(C(F)(F)F)c2)CCO1] | 4-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)morpholine-2-carboxylic acid | δ 7.20-7.28 (m, 3H), 6.08-6.17 (m, 1H), 4.24 (s, 2H), 4.06-4.15 (m, 2H), 3.72-3.97 (m, 6H), 3.51-3.52 (m, 5H), 2.77-2.94 (m, 2H), 1.90 (br, 4H). | 608 |
| 101 | 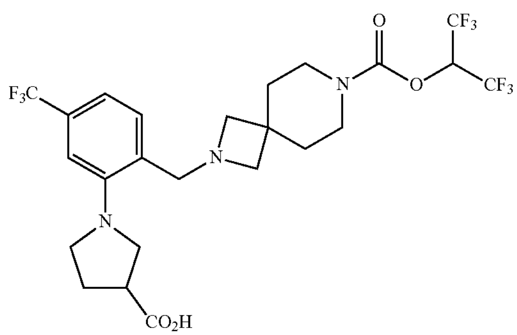 [SMILES: O=C(O)C1CCN(c2cc(C(F)(F)F)ccc2CN2CC3(CCN(C(=O)OC(C(F)(F)F)C(F)(F)F)CC3)C2)C1] | 1-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)pyrrolidine-3-carboxylic acid | δ 7.55-7.58 (m, 1H), 7.39-7.46 (m, 2H), 6.09-6.18 (m, 1H), 4.62-4.67 (m, 1H), 4.42-4.46 (m, 1H), 3.73-3.83 (m, 4H), 3.51-3.58 (m, 5H), 3.36-3.37 (m, 1H), 3.00-3.13 (m, 2H), 2.87-2.92 (m, 1H), 2.40-2.45 (m, 1H), 2.12-2.20 (m, 1H), 1.94-1.96 (m, 4H) | 592 |

| Ex | Structure | Name | NMR (¹H NMR, 300 MHz or 400 MHz, Methanol-d4) | MS [M+H]⁺ |
|---|---|---|---|---|
| 102 | 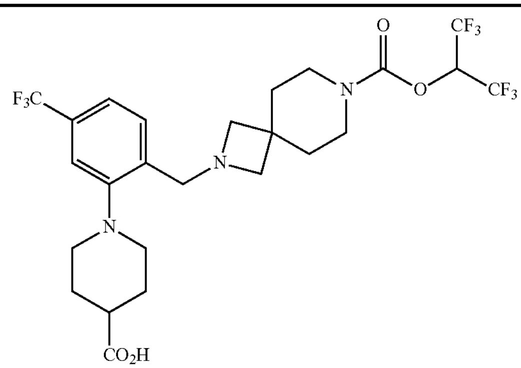 | 1-(2-((7-(((1,1,3,3,3-Hexafluoropropan-2-yl)oxy)carbonyl)-2,7-diazaspiro[3.5]nonan-2-yl)methyl)-5-(trifluoromethyl)phenyl)piperidine-4-carboxylic acid | δ 7.57-7.60 (m, 1H), 7.42-7.47 (m, 2H), 6.11-6.19 (m, 1H), 4.19 (s, 2H), 3.62 (s, 4H), 3.51-3.56 (m, 4H), 3.12-3.16 (m, 2H), 2.77-2.85 (m, 2H), 2.36-2.46 (m, 1H), 2.05-2.09 (m, 2H), 1.96-1.99 (m, 6H). | 606 |
| 103 | 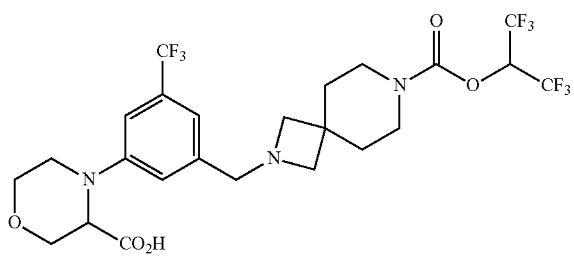 [SMILES: O=C(O)C1COCCN1c1cc(CN2CC3(CCN(C(=O)OC(C(F)(F)F)C(F)(F)F)CC3)C2)cc(C(F)(F)F)c1] | 4-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)morpholine-3-carboxylic acid | δ 7.14-7.20 (m, 2H), 7.02 (s, 1H), 6.08-6.17 (m, 1H), 4.48-4.52 (m, 1H), 4.30 (br, 1H), 4.15-4.22 (m, 2H), 3.97-4.03 (m, 1H), 3.66-3.87 (m, 6H), 3.48-3.55 (m, 6H), 1.84-1.89 (m, 4H). | 608 |
| 104 | 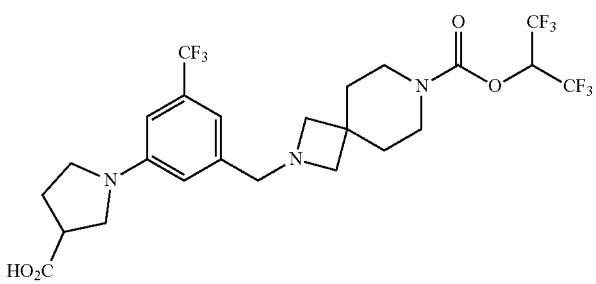 [SMILES: O=C(O)C1CCN(c2cc(CN3CC4(CCN(C(=O)OC(C(F)(F)F)C(F)(F)F)CC4)C3)cc(C(F)(F)F)c2)C1] | 1-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)pyrrolidine-3-carboxylic acid | δ 6.92-6.94 (m, 2H), 6.77 (s, 1H), 6.08-6.19 (m, 1H), 4.22 (br, 2H), 3.77 (br, 4H), 3.31-3.57 (m, 8H), 3.08-3.18 (m, 1H), 2.21-2.33 (m, 2H), 1.88 (br, 4H). | 592 |

| Ex | Structure | Name | NMR (¹H NMR, 300 MHz or 400 MHz, Methanol-d4) | MS [M+ H]⁺ |
|---|---|---|---|---|
| 105 | 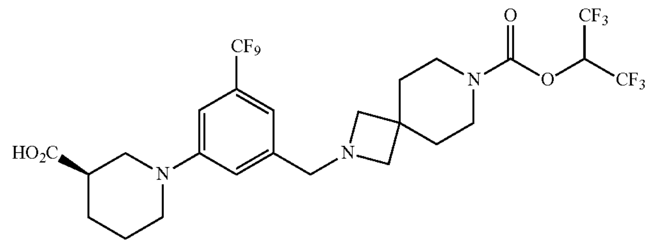 | (R)-1-(3-((7-(((1,1,1,3,3,3-Hexafluoropropan-2-yl)oxy)carbonyl)-2,7-diazaspiro[3,5]nonan-2-yl)methyl)-5-(trifluoromethyl)phenyl)piperidine-3-carboxylic acid | (Chloroform-d) δ 7.28 (s, 1H), 7.05 (s, 1H), 6.86 (s, 1H), 5.68-5.77 (m, 1H), 3.83-3.97 (m, 3H), 3.36-3.54 (m, 9H), 3.04-3.14 (m, 1H), 2.88-2.92 (m, 1H), 2.57-2.61 (m, 1H), 2.05-2.08 (m, 1H), 1.81-1.96 (m, 5H), 1.61-1.71 (m, 2H). | 606 |
| 106 | 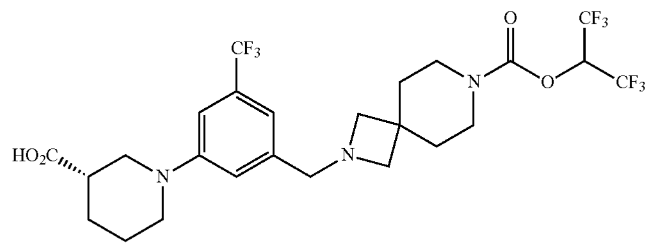 [SMILES: O=C(O)[C@H]1CCCN(c2cc(CN3CC4(CCN(C(=O)OC(C(F)(F)F)C(F)(F)F)CC4)C3)cc(C(F)(F)F)c2)C1] | (S)-1-(3-((7-(((1,1,1,3,3,3-Hexafluoropropan-2-yl)oxy)carbonyl)-2,7-diazaspiro[3,5]nonan-2-yl)methyl)-5-(trifluoromethyl)phenyl)piperidine-3-carboxylic acid | (Chloroform-d) δ 7.28 (s, 1H), 7.06 (s, 1H), 6.86 (s, 1H), 5.68-5.77 (m, 1H), 3.83-3.95 (m, 3H), 3.38-3.54 (m, 9H), 3.01-3.24 (m, 1H), 2.86-2.92 (m, 1H), 2.56-2.61 (m, 1H), 2.07-2.09 (m, 1H), 1.72-1.89 (m, 5H), 1.68-1.72 (m, 2H). | 606 |
| 107 | 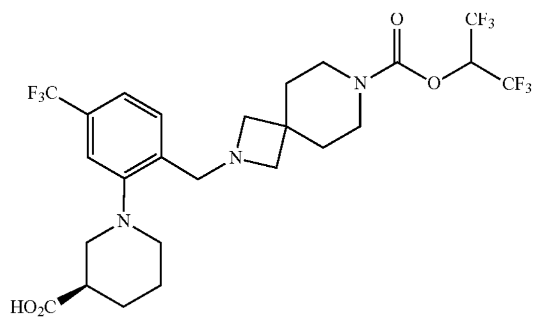 [SMILES: O=C(O)[C@@H]1CCCN(c2cc(C(F)(F)F)ccc2CN2CC3(CCN(C(=O)OC(C(F)(F)F)C(F)(F)F)CC3)C2)C1] | (R)-1-(2-((7-(((1,1,1,3,3,3-Hexafluoropropan-2-yl)oxy)carbonyl)-2,7-diazaspiro[3,5]nonan-2-yl)methyl)-5-(trifluoromethyl)phenyl)piperidine-3-carboxylic acid | δ 7.66-7.68 (m, 2H), 7.53-7.55 (m, 1H), 6.10-6.20 (m, 1H), 4.56-4.59 (m, 1H), 4.31-4.34 (m, 1H), 3.96 (br, 2H), 3.82-3.84 (m, 2H), 3.51-3.71 (m, 4H), 3.22-3.25 (m, 1H), 3.00-3.15 (m, 2H), 2.71-2.76(ia 1H), 2.66 (br, 1H), 2.28 (br, 1H), 2.02-2.03 (m, 4H), 1.76-1.86 (ia 3 H). | 606 |

| Ex | Structure | Name | NMR (¹H NMR, 300 MHz or 400 MHz, Methanol-d4) | MS [M+ H]⁺ |
|---|---|---|---|---|
| 108 | 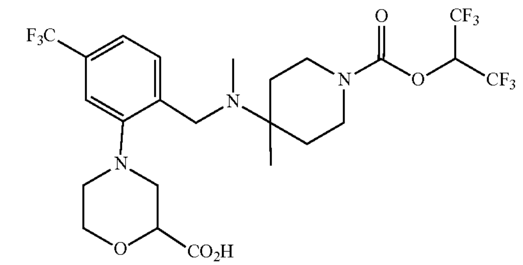 [SMILES: CN(Cc1ccc(C(F)(F)F)cc1N1CCOC(C(=O)O)C1)C1(C)CCN(C(=O)OC(C(F)(F)F)C(F)(F)F)CC1] | 4-(2-((1-(((1,1,1,3,3,3-Hexafluoropropan-2-yl)oxy)carbonyl)-4-methylpiperidin-4-yl)(methyl)amino)methyl)-5-(trifluoromethyl)phenyl)morpholine-2-carboxylic acid | δ 7.76-7.78 (m, 1H), 7.46-7.53 (m, 2H), 6.05-6.18(m, 1H), 4.09-4.18 (m, 4H), 3.75-3.82 (m, 3H), 3.46-3.51 (m, 2H), 3.17-3.28 (m, 1H), 2.89-3.05 (m, 3H), 2.32 (br, 3H), 1.97-2.00 (m, 2H), 1.82 (br, 2H), 1.35 (br, 3H). | 610 |
| 109 | 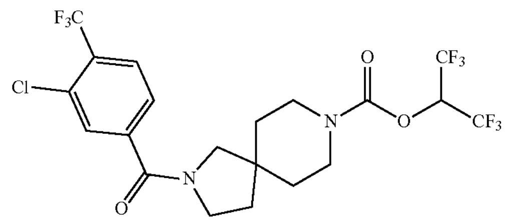 [SMILES: O=C(OC(C(F)(F)F)C(F)(F)F)N1CCC2(CC1)CCN(C(=O)c1ccc(C(F)(F)F)c(Cl)c1)C2] | 1,1,1,3,3,3-Hexafluoropropan-2-yl 2-(3-chloro-4-(trifluoromethyl)benzoyl)-2,8-diazaspiro[4.5]decane-8-carboxylate | (Chloroform-d) δ 7.74-7.77 (m, 1H), 7.63-7.64 (m, 1H), 7.45-7.50 (m, 1H), 5.66-5.82 (m, 1H), 3.71-3.78(m, 2H), 3.41-3.58 (m, 5H), 3.28 (s, 1H), 1.84-1.96 (m, 2H), 1.53-1.70 (m, 4H). LCMS (ESI, m/z): 541 [M+H]+. | 541 |
| 110 | 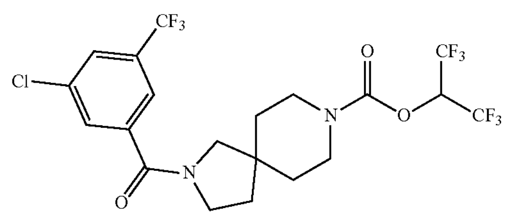 [SMILES: O=C(OC(C(F)(F)F)C(F)(F)F)N1CCC2(CC1)CCN(C(=O)c1cc(Cl)cc(C(F)(F)F)c1)C2] | 1,1,1,3,3,3-Hexafluoropropan-2-yl 2-(3-chloro-5-(trifluoromethyl)benzoyl)-2,8-diazaspiro[4.5]decane-8-carboxylate | (Chloroform-d) δ 7.66-7.69 (m, 3H), 5.68-5.80 (m, 1H), 3.71-3.78 (m, 2H), 3.47-3.59 (m, 5H), 3.29 (s, 1H), 1.85-1.96 (m, 2H), 1.56-1.72 (m, 4H). | 541 |
| 111 | 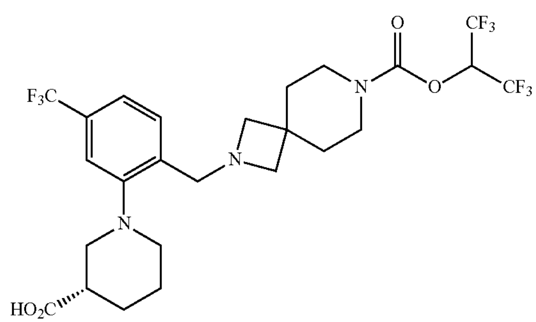 [SMILES: O=C(O)[C@H]1CCCN(c2cc(C(F)(F)F)ccc2CN2CC3(CCN(C(=O)OC(C(F)(F)F)C(F)(F)F)CC3)C2)C1] | (S)-1-(2-((7-(((1,1,1,3,3,3-hexafluoropropan-2-yl)oxy)carbonyl)-2,7-diazaspiro[3.5]nonan-2-yl)methyl)-5-(trifluoromethyl)phenyl)piperidine-3-carboxylic acid | δ 7.66-7.69 (m, 2H), 7.54-7.56 (m, 1H), 6.10-6.18(m, 1H), 4.57-4.62 (m, 1H), 4.32-4.37 (m, 1H), 3.98 (br, 2H), 3.84-3.87 (m, 2H), 3.53-3.55 (m, 4H), 3.24-3.28 (m, 1H), 3.02-3.07 (m, 2H), 2.68-2.78 (m, 2H), 2.29-2.32 (m, 1H), 2.03-2.04 (m, 4H), 1.73-1.84 (m, 3H). | 606 |

| Ex | Structure | Name | NMR (¹H NMR, 300 MHz or 400 MHz, Methanol-d4) | MS [M+ H]⁺ |
|---|---|---|---|---|
| 112 | 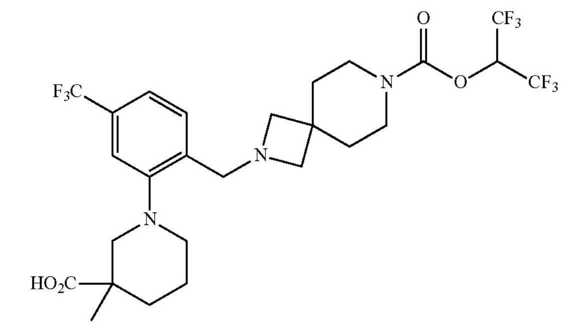 [SMILES: CC1(C(=O)O)CCCN(c2cc(C(F)(F)F)ccc2CN2CC3(CCN(C(=O)OC(C(F)(F)F)C(F)(F)F)CC3)C2)C1] | 1-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-3-methylpiperidine-3-carboxylic acid | δ 7.67-7.72 (m, 2H), 7.55-7.58 (m, 1H), 6.11-6.19 (m, 1H), 4.60-4.64 (m, 1H), 4.25-4.30 (m, 1H), 4.06-4.08 (m, 2H), 3.84-3.87 (m, 2H), 3.53-3.55 (m, 4H), 3.21-3.25 (m, 1H), 3.00-3.04 (m, 1H), 2.55-2.70 (m, 2H), 2.34-2.38 (m, 1H), 2.04-2.06 (m, 4H), 1.72-1.77 (m, 2H), 1.21-1.36 (m, 1H), 1.30 (s, 3H). | 620 |
| 113 | 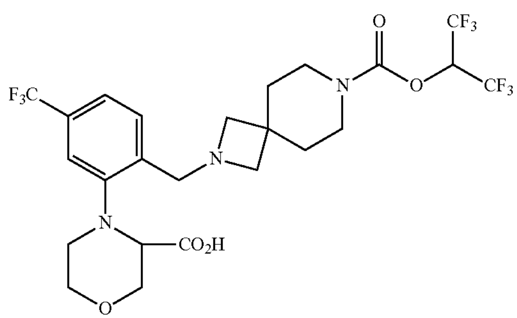 [SMILES: O=C(O)C1COCCN1c1cc(C(F)(F)F)ccc1CN1CC2(CCN(C(=O)OC(C(F)(F)F)C(F)(F)F)CC2)C1] | 4-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)morpholine-3-carboxylic acid | (Chloroform-d) δ 7.66 (s, 1H), 7.44-7.47 (m, 1H), 7.36-7.39 (m, 1H), 5.67-5.77 (m, 1H), 4.53-4.61 (m, 1H), 4.30-4.35 (m, 1H), 4.08-4.12 (m, 1H), 3.89-3.97 (m, 1H), 3.54-3.67 (m, 7H), 3.45 (br, 4H), 2.86-2.94 (m, 1H), 2.67-2.71 (m, 1H), 1.91 (br, 4H). | 608 |
| 114 | 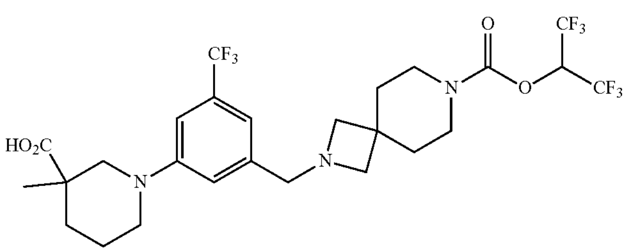 [SMILES: CC1(C(=O)O)CCCN(c2cc(CN3CC4(CCN(C(=O)OC(C(F)(F)F)C(F)(F)F)CC4)C3)cc(C(F)(F)F)c2)C1] | 1-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-3-methylpiperidine-3-carboxylic acid | δ 7.24 (s, 1H), 7.15 (s, 1H), 7.02 (s, 1H), 6.06-6.14 (m, 1H), 3.90-3.96 (m, 3H), 3.41-3.48 (m, 9H), 2.83-2.92 (m, 1H), 2.71-2.75 (m, 1H), 2.16-2.20 (m, 1H), 1.69-1.82 (m, 6H), 1.34-1.39 (m, 1H), 1.20 (s, 3H). | 620 |

-continued

| Ex | Structure | Name | NMR (¹H NMR, 300 MHz or 400 MHz, Methanol-d4) | MS [M+ H]⁺ |
|---|---|---|---|---|
| 115 | (structure) | 1-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-3-methylpyrrolidine-3-carboxylic acid | δ 7.53 (d, J = 7.8 Hz, 1H), 7.45 (s, 1H), 7.37 (d, J = 7.8 Hz, 1H), 6.07-6.15 (m, 1H), 4.61-4.66 (m, 1H), 4.42-4.46 (m, 1H), 3.75-3.78 (m, 4H), 3.65-3.75 (m, 1H), 3.35-3.49 (m, 4H), 3.31-3.33 (m, 1H), 3.11-3.19 (m, 1H), 2.62-2.65 (m, 1H), 2.40-2.46 (m, 1H), 1.86-1.95 (m, 5H), 1.38 (s, 3H). | 606 |
| 116 | (structure) | 1-(3-Chloro-5-((7-((((1,1,1,3,3,3-hexafluoropropan-2-yl)oxy)carbonyl)-2,7-diazaspiro[3.5]nonan-2-yl)methyl)phenyl)piperidine-4-carboxylic acid | δ 6.94-6.98 (m, 2H), 6.86(s, 1H), 6.09-6.18 (m, 1H), 4.08 (s, 2H), 3.86 (br, 6H), 3.41-3.61 (m, 4H), 2.80-2.84 (m, 2 H), 2.34-2.42 (m, 1H), 2.04-2.05 (m, 2H), 1.90-2.00 (m. 6H). | 572 |
| 117 | (structure) | 1-(3-Fluoro-5-((7-((((1,1,1,3,3,3-hexafluoropropan-2-yl)oxy)carbonyl)-2,7-diazaspiro[3.5]nonan-2-yl)methyl)phenyl)piperidine-4-carboxylic acid | δ 6.90 (s, 1H), 6.72-6.77 (m, 1H), 6.61-6.64 (m, 1H), 6.10-6.18 (m, 1H), 4.29 (s, 2H), 3.97 (s, 4H), 3.74-3.79 (m, 2H), 3.52-3.54 (m, 4H), 2.83-2.92 (m, 2H), 2.42-2.50 (m, 1H), 1.80-2.04 (m, 6H), 1.71-1.79 (m, 2H). | 556 |

| Ex | Structure | Name | NMR (¹H NMR, 300 MHz or 400 MHz, Methanol-d4) | MS [M+ H]⁺ |
|---|---|---|---|---|
| 118 | 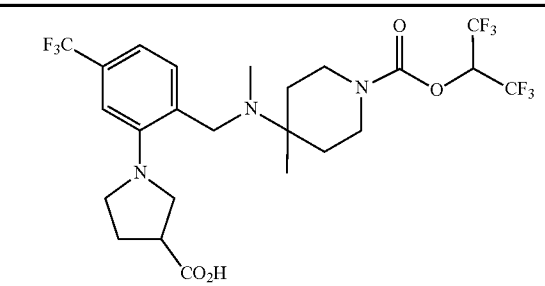 | 1-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)pyrrolidine-3-carboxylic acid | δ 7.77-7.80 (m, 1H), 7.30-7.32 (m, 2H), 6.07-6.20 (m, 1H), 3.80-3.92 (m, 2H), 3.60-3.68 (m, 4H), 3.45-3.49 (m, 1H), 3.06-3.32 (m, 4H), 2.23-2.31 (m, 5H), 1.92-2.09 (m, 2H), 1.51-1.70 (m, 2H), 1.25 (s, 3H). | 594 |
| 119 | 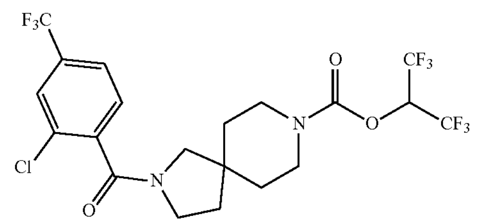 [SMILES: O=C(OC(C(F)(F)F)C(F)(F)F)N1CCC2(CC1)CCN(C(=O)c1ccc(C(F)(F)F)cc1Cl)C2] | 1,1,1,3,3,3-Hexafluoropropan-2-yl 2-(2-chloro-4-(trifluoromethyl)benzoyl)-2,8-diazaspiro[4.5]decane-8-carboxylate | (Dimethyl sulfoxide-d6) δ 7.99 (s, 1H), 7.80-7.83 (m, 1H), 7.61-7.69 (m, 1H), 6.50-6.62 (m, 1H), 3.40-3.59 (m, 6H), 3.15-3.20 (m, 1H), 3.03 (s, 1H), 1.78-1.88 (m, 2H), 1.48-1.60 (m, 4H). | 541 |
| 120 | 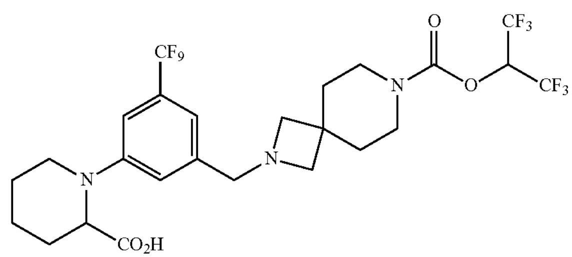 | 1-(3-((7-(((1,1,1,3,3,3-Hexafluoropropan-2-yl)oxy)carbonyl)-2,7-diazaspiro[3,5]nonan-2-yl)methyl)-5-(trifluoromethyl)phenyl)piperidine-2-carboxylic acid | δ 7.15 (s, 2H), 6.99 (s, 1H), 6.08-6.16 (m, 1H), 4.45 (s, 1H), 4.15-4.25 (m, 2H), 3.75-3.78 (m, 4H), 3.56-3.60 (m, 1H), 3.47 (br, 4H), 3.31-3.39 (m, 1H), 2.30-2.35 (m, 1H), 1.84 (br, 6H), 1.49-1.70 (m, 3H). | 606 |

| Ex | Structure | Name | NMR (¹H NMR, 300 MHz or 400 MHz, Methanol-d4) | MS [M+ H]⁺ |
|---|---|---|---|---|
| 121 | 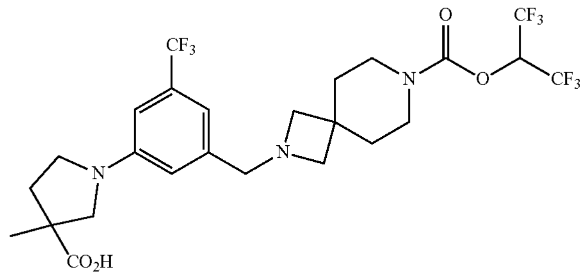 [SMILES: CC1(C(=O)O)CCN(c2cc(CN3CC4(CCN(C(=O)OC(C(F)(F)F)C(F)(F)F)CC4)C3)cc(C(F)(F)F)c2)C1] | 1-(3-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-3-methylpyrrolidine-3-carboxylic acid | δ 6.90-6.94 (m, 2H), 6.75 (s, 1H), 6.10-6.18 (m, 1H), 4.16-4.26 (m, 2H), 3.84-3.87 (m, 1H), 3.77 (s, 4H), 3.41-3.52 (m, 6H), 3.15-3.18 (m, 1H), 2.49-2.57 (m, 1H), 1.88-1.97 (m, 5H), 1.40 (s, 3H). | 606 |
| 122 | 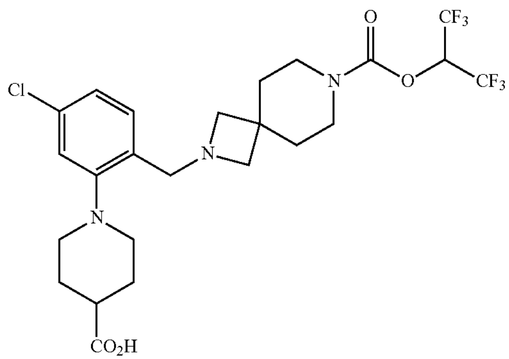 [SMILES: O=C(O)C1CCN(c2cc(Cl)ccc2CN2CC3(CCN(C(=O)OC(C(F)(F)F)C(F)(F)F)CC3)C2)CC1] | 1-(5-Chloro-2-((7-((((1,1,1,3,3,3-hexafluoropropan-2-yl)oxy)carbonyl)-2,7-diazaspiro[3.5]nonan-2-yl)methyl)phenyl)piperidine-4-carboxylic acid | δ 7.36-7.39 (m, 1H), 7.26 (s, 1H), 7.16-7.19 (m, 1H), 6.10-6.18 (m, 1H), 4.21 (s, 2H), 3.75 (s, 4H), 3.34-3.54 (m, 4H), 3.08-3.12 (m, 2H), 2.75-2.79 (m, 2H), 2.32-2.42 (m, 1H), 2.06-2.07 (m, 2H), 1.97-2.03 (m, 6H). | 572 |
| 123 | 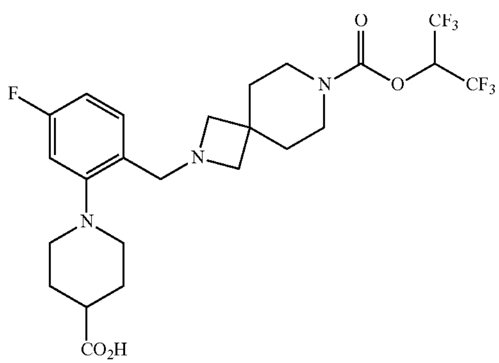 [SMILES: O=C(O)C1CCN(c2cc(F)ccc2CN2CC3(CCN(C(=O)OC(C(F)(F)F)C(F)(F)F)CC3)C2)CC1] | 1-(5-Fluoro-2-((7-((((1,1,1,3,3,3-hexafluoropropan-2-yl)oxy)carbonyl)-2,7-diazaspiro[3.5]nonan-2-yl)methyl)phenyl)piperidine-4-carboxylic acid | δ 7.42-7.44 (m, 1H), 7.03-7.04 (m, 1H), 6.88-6.95 (m, 1H), 6.10-6.18 (m, 1H), 4.26 (s, 2H), 3.88 (s, 4H), 3.54 (br, 4H), 3.09-3.13 (m, 2H), 2.74-2.78 (m, 2H), 2.31-2.41 (m, 1H), 2.07-2.08 (m, 2H), 1.97-2.03 (m, 6H). | 556 |

| Ex | Structure | Name | NMR (¹H NMR, 300 MHz or 400 MHz, Methanol-d4) | MS [M+ H]⁺ |
|---|---|---|---|---|
| 124 | 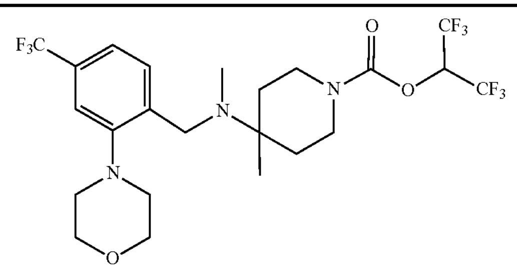 | N-(1-(((1,1,1,3,3,3-Hexafluoropropan-2-yl)oxy)carbonyl)-4-methyl)piperidin-4-yl)-N-(2-morpholino-4-(trifluoromethyl)benzyl) glycine | δ 7.77-7.80 (m, 1H), 7.63 (br, 1H), 7.51-7.54 (m, 1H), 6.16-6.24 (m, 1H), 4.45(br, 2H), 4.16-4.17 (m, 2H), 3.87-3.89 (m, 4H), 3.55 (br, 2H), 3.19-3.24 (m, 2H), 3.02-3.05 (m, 4H), 2.14 (br, 4H), 1.61 (s, 3H). | 610 |
| 125 | 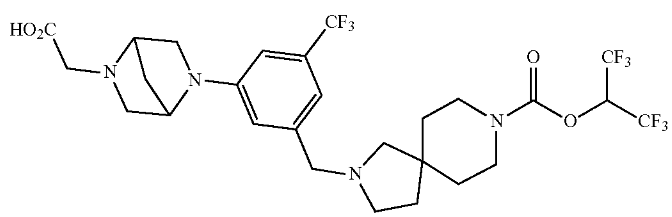 [SMILES: O=C(O)CN1CC2CC1CN2c1cc(CN2CCC3(CCN(C(=O)OC(C(F)(F)F)C(F)(F)F)CC3)C2)cc(C(F)(F)F)c1] | 2-(5-{3-[(8-{[(1,1,1,3,3,3-Hexafluoropropan-2-yl)oxy]carbonyl}-2,8-diazaspiro[4.5]decan-2-yl)methyl]-5-(trifluoromethyl)phenyl}-2,5-diazabicyclo[2.2.1]heptan-2-yl)acetic acid | δ 7.00 (s, 1H), 6.90 (s, 1H), 6.82 (s, 1H), 6.08-6.13 (m, 1H), 4.68 (br, 1H), 4.45 (br, 1H), 3.36-3.77 (m, 12H), 2.69 (t, J = 6.8 Hz, 2H), 2.51 (s, 2H), 2.22-2.35 (m, 2H), 1.75 (t, J = 6.9 Hz, 2H), 1.55-1.62 (m, 4H). | 647 |
| 126 | 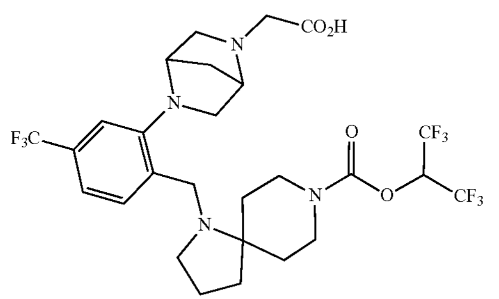 [SMILES: O=C(O)CN1CC2CC1CN2c1cc(C(F)(F)F)ccc1CN1CCCC12CCN(C(=O)OC(C(F)(F)F)C(F)(F)F)CC2] | 2-(5-{2-[(8-{[(1,1,1,3,3,3-Hexafluoropropan-2-yl)oxy]carbonyl}-1,8-diazaspiro[4.5]decan-1-yl) methyl]-5-(trifluoromethyl)phenyl}-2,5-diazabicyclo[2.2.1]heptan-2-yl)acetic acid | δ 7.75 (d, J = 8.0 Hz, 1H), 7.22-7.24 (m, 2H), 6.08-6.16 (m, 1H), 4.42-4.86(m, 2H), 4.17-4.22 (m, 2H), 3.66-3.83 (m, 6H), 3.47-3.61 (m, 1H), 3.31-3.37 (m, 1H), 3.08-3.16 (m, 2H), 2.63-2.67 (m, 2H), 2.20-2.31 (m, 2H), 1.94-1.98 (m, 2H), 1.78-1.89 (m, 4H), 1.57-1.70 (m, 2H). | 647 |

-continued

| Ex | Structure | Name | NMR (¹H NMR, 300 MHz or 400 MHz, Methanol-d4) | MS [M+ H]⁺ |
|---|---|---|---|---|
| 127 | 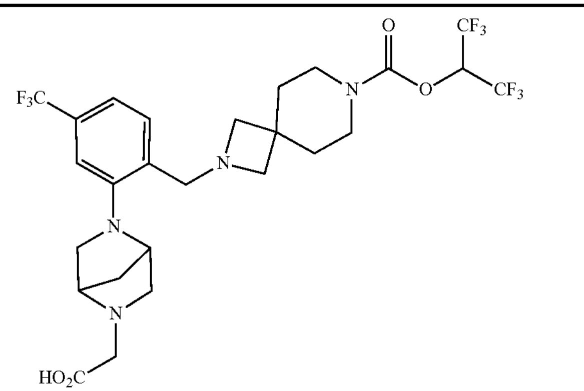 | 2-(5-{2-[(7-{[(1,1,1,3,3,3-Hexafluoropropan-2-yl)oxy]carbonyl}-2,7-diazaspiro[3.5]nonan-2-yl)methyl]-5-(trifluoromethyl)phenyl}-2,5-diazabicyclo[2.2.1]heptan-2-yl)acetic acid | δ 7.46-7.48 (m, 1H), 7.17-7.21 (m, 2H), 6.08-6.13 (m, 1H), 4.53 (s, 1H), 4.39 (s, 1H), 3.60-3.81 (m, 6H), 3.56-3.59 (m, 1H), 3.39-3.55 (m, 4H), 3.32-3.35 (m, 1H), 3.15 (s, 4H), 2.21-2.25 (m, 2H), 1.79 (br, 4H). | 633 |
| 128 | 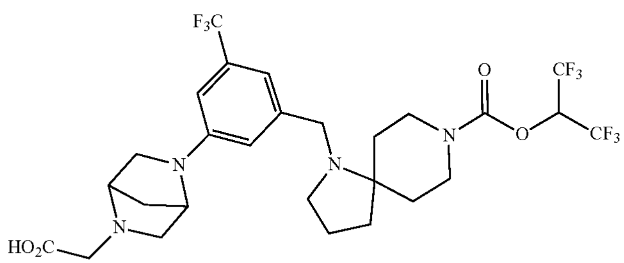 [SMILES: O=C(O)CN1CC2CC1CN2c1cc(CN2CCCC23CCN(C(=O)OC(C(F)(F)F)C(F)(F)F)CC3)cc(C(F)(F)F)c1] | 2-(5-{3-[(8-{[(1,1,1,3,3,3-Hexafluoropropan-2-yl)oxy]carbonyl}-1,8-diazaspiro[4.5]decan-1-yl)methyl]-5-(trifluoromethyl)phenyl}-2,5-diazabicyclo[2.2.1]heptan-2-yl)acetic acid | δ 7.00 (s, 1H), 6.87 (s, 1H), 6.78 (s, 1H), 6.09-6.17 (m, 1H), 4.69 (s, 1H), 4.48 (s, 1H), 4.16-4.20 (m, 2H), 3.53-3.79 (m, 7H), 3.31-3.37 (m, 1H), 3.00-3.16 (m, 2H), 2.70-2.74 (m, 2H), 2.23-2.36 (m, 2H), 1.92-1.95 (m, 2H), 1.70-1.82 (m, 4H), 1.50-1.62 (m, 2H). | 647 |
| 129 | 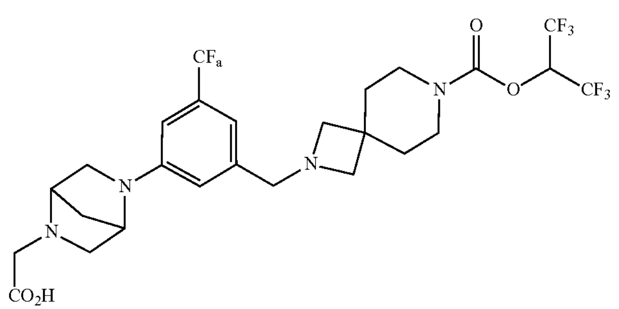 | 2-(5-{3-[(7-{[(1,1,1,3,3,3-Hexafluoropropan-2-yl)oxy]carbonyl}-2,7-diazaspiro[3.5]nonan-2-yl)methyl]-5-(trifluoromethyl)phenyl}-2,5-diazabicyclo[2.2.1]heptan-2-yl)acetic acid | δ 7.00 (s, 1H), 6.85-6.89 (m, 2H), 6.12-6.16 (m, 1H), 4.71 (s, 1H), 4.47 (s, 1H), 3.71-3.79 (m, 5H), 3.40-3.65 (m, 6H), 3.33,3.40 (m, 1H), 3.26 (s,4H), 2.34-2.39 (m, 1H), 2.24-2.28 (m, 1H), 1.81 (br, 4H). | 633 |

| Ex | Structure | Name | NMR (¹H NMR, 300 MHz or 400 MHz, Methanol-d4) | MS [M+ H]⁺ |
|---|---|---|---|---|
| 130 | 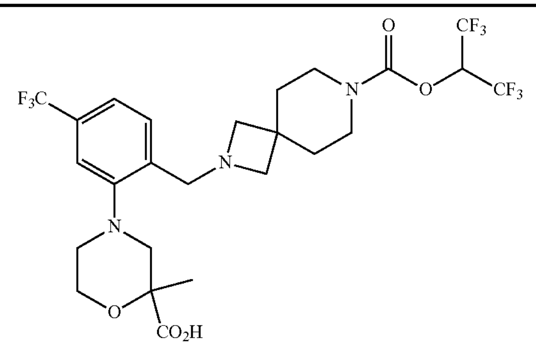 | 4-(2-((7-(((1,1,1,3,3,3-Hexafluoropropan-2-yl)oxy)carbonyl)-2,7-diazaspiro[3.5]nonan-2-yl)methyl)-5-(trifluoromethyl)phenyl)-2-methylmorpholine-2-carboxylic acid | δ 7.70-7.72 (m, 2H), 7.60 (d, J = 8.4 Hz, 1H), 6.10-6.18 (m, 1H), 4.57-4.71 (m, 2H), 4.08-4.11 (m, 2H), 3.85-3.97 (m, 4H), 3.46-3.53 (m, 5H), 2.96-3.05 (m, 1H), 2.85-2.89 (m, 1H), 2.74-2.77 (m, 1H), 1.99 (br, 4H), 1.38 (s, 3H). | 622 |
| 131 | 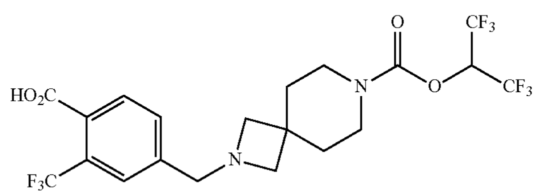 | 4-(7-(((1,1,1,3,3,3-Hexafluoropropan-2-yl)oxy)carbonyl)-2,7-diazaspiro[3.5]nonan-2-yl)methyl)-2-(trifluoromethyl)benzoic acid | δ 7.84 (s, 1H), 7.73-7.75 (m, 1H), 7.57-7.59 (m, 1H), 6.08-6.18 (m, 1H), 4.42 (s, 2H), 3.93 (s,4H), 3.52-3.53 (m, 4H), 1.93 (br, 4H). | 523 |
| 132 | 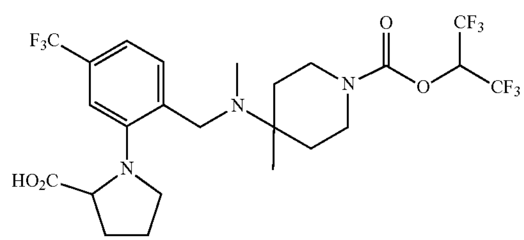 [SMILES: CN(Cc1ccc(C(F)(F)F)cc1N1CCCC1C(=O)O)C1(C)CCN(C(=O)OC(C(F)(F)F)C(F)(F)F)CC1] | (2-((1-(((1,1,1,3,3,3-Hexafluoropropan-2-yl)oxy)carbonyl)-4-methylpiperidin-4-yl)(methyl)amino)methyl)-5-(trifluoromethyl)phenyl)proline | δ 7.80 (s, 1H), 7.63-7.66 (m, 1H), 7.54-7.57 (m, 1H), 6.15-6.19 (m, 1H), 4.90 (br, 1H), 4.07-4.26 (m, 3H), 3.75-3.79 (m, 1H), 3.48-3.52 (m, 1H), 3.15-3.30 (m, 2H), 2.72-2.81 (m, 1H), 2.41-2.55 (m, 5H), 2.22-2.26 (m, 1H), 1.85-2.13 (m, 5H), 1.60 (s, 3H). | 594 |
| 133 | 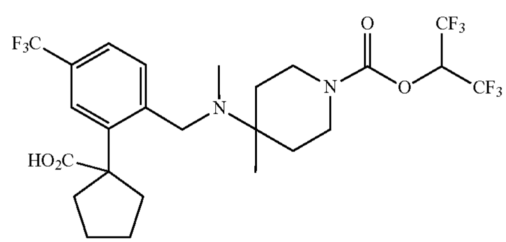 [SMILES: CN(Cc1ccc(C(F)(F)F)cc1C1(C(=O)O)CCCC1)C1(C)CCN(C(=O)OC(C(F)(F)F)C(F)(F)F)CC1] | 1-(2-{[(1-{[(1,1,1,3,3,3-Hexafluoropropan-2-yl)oxy]carbonyl}-4-methylpiperidin-4-yl)(methyl)amino]methyl}-5-(trifluoromethyl)phenyl)cyclopentane-1-carboxylic acid | δ 7.90-7.93 (m, 1H), 7.67 (s, 1H), 7.55-7.58 (m, 1H), 6.10-6.18 (m, 1H), 3.90 (br, 2H), 3.30-3.71 (br, 4H), 2.61-2.66 (m, 2H), 2.15 (s, 3H), 1.93-2.03 (m, 4H), 1.72-1.89 (m, 6H), 1.21 (s, 3H). | 593 |

-continued

| Ex | Structure | Name | NMR (¹H NMR, 300 MHz or 400 MHz, Methanol-d4) | MS [M+ H]⁺ |
|---|---|---|---|---|
| 134 | 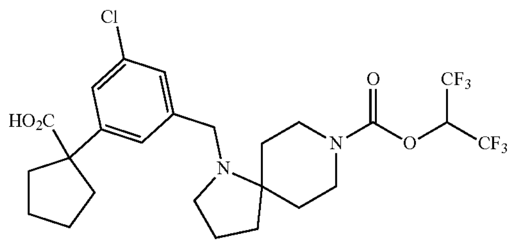 [SMILES: O=C(OC(C(F)(F)F)C(F)(F)F)N1CCC2(CCCN2Cc2cc(Cl)cc(C3(C(=O)O)CCCC3)c2)CC1] | 1-{3-Chloro-5-[(8-{[(1,1,1,3,3,3-hexafluoropropan-2-yl)oxy]carbonyl}-1,8-diazaspiro[4.5]decan-1-yl)methyl]phenyl}cyclopentane-1-carboxylic acid | δ 7.24-7.32 (m, 3H), 6.09-6.20 (m, 1H), 4.19-4.22 (m, 2H), 3.77 (s, 2H), 3.02-3.18 (m, 2H), 2.84-2.88 (m, 2H), 2.59-2.65 (m, 2H), 1.97-2.02 (m, 2H), 1.73-1.92 (m, 10H), 1.60-1.64 (m, 2H). | 571 |
| 135 | 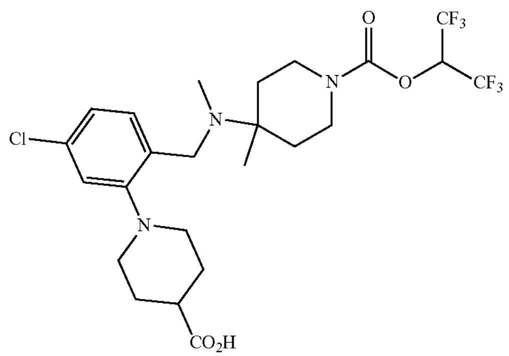 [SMILES: CN(Cc1ccc(Cl)cc1N1CCC(C(=O)O)CC1)C1(C)CCN(C(=O)OC(C(F)(F)F)C(F)(F)F)CC1] | 1-(5-Chloro-2-(((1-((((1,1,1,3,3,3-hexafluoropropan-2-yl)oxy)carbonyl)-4-methyl)piperidin-4-yl)(methyl)amino)methyl)phenyl)piperidine-4-carboxylic acid | (Chloroform-d) δ 7.56 (d, J = 8.8 Hz, 1H), 7.05-7.08 (m, 2H), 6.06-6.15 (m, 1H), 3.51-3.66 (m, 6H), 3.00-3.04 (m, 2H), 2.64-2.71 (m, 2H), 2.26-2.33 (m, 1H), 2.11 (s, 3H), 1.91-2.00 (m, 6H), 1.55 (br, 2H), 1.20-1.32 (m, 1H), 1.13 (s, 3H). | 574 |
| 136 | 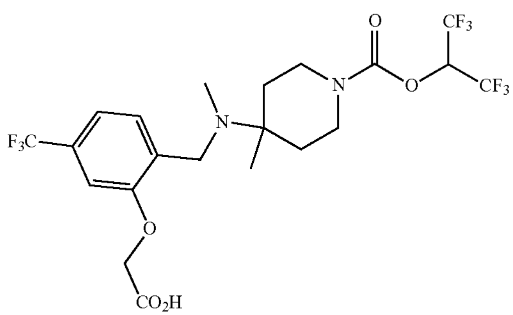 [SMILES: CN(Cc1ccc(C(F)(F)F)cc1OCC(=O)O)C1(C)CCN(C(=O)OC(C(F)(F)F)C(F)(F)F)CC1] | 2-(2-(((1-(((1,1,1,3,3,3-Hexafluoropropan-2-yl)oxy)carbonyl)-4-methyl)piperidin-4-yl)(methyl)amino)methyl)-5-(trifluoromethyl)phenoxy)acetic acid | δ 7.62 (d, J = 7,8 Hz, 1H), 7.48 (s, 1H), 7.37 (d, J = 7.8 Hz, 1H), 6.11-6.19 (m, 1H), 4.65-4.69 (m, 3H), 4.18 (br, 2H), 3.70-4.00 (m, 1H), 3.20-3.31 (m, 2H), 2.61 (s, 3H), 2.07 (br, 4H), 1.58 (s, 3H). | 555 |

| Ex | Structure | Name | NMR (¹H NMR, 300 MHz or 400 MHz, Methanol-d4) | MS [M+ H]⁺ |
|---|---|---|---|---|
| 137 | 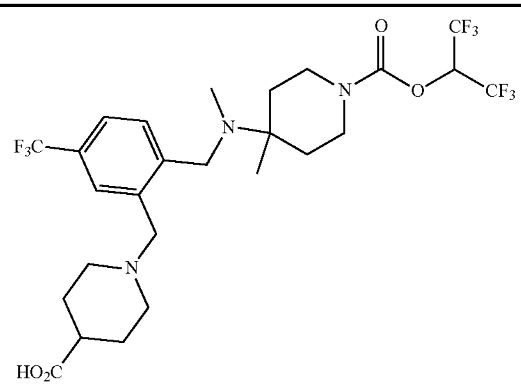 | 1-(2-(((1-(((1,1,1,3,3,3-Hexafluoropropan-2-yl)oxy)carbonyl)-4-methylpiperidin-4-yl)(methyl)amino)methyl)-5-(trifluoromethyl)benzyl)piperidine-4-carboxylic acid | δ 7.83-7.74 (m, 3H), 6.16-6.22 (m, 1H), 4.16-4.05 (m, 2H), 3.71-4.04 (m, 4H), 3.54-3.42 (m, 2H), 3.03 (br, 2H), 2.63 (br, 2H), 2.48-2.39 (m, 1H), 2.31 (s, 3H), 1.82-2.08 (m, 6 H), 1.76-1.78 (m, 2H), 1.39 (s, 3 H). | 623 |
| 138 | 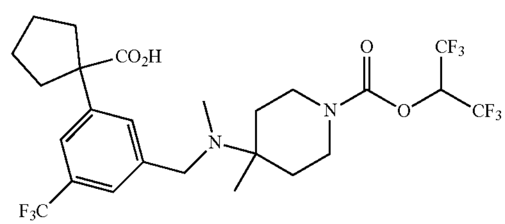 [SMILES: CN(Cc1cc(C(F)(F)F)cc(C2(C(=O)O)CCCC2)c1)C1(C)CCN(C(=O)OC(C(F)(F)F)C(F)(F)F)CC1] | 1-(3-{[(1-{[(1,1,1,3,3,3-Hexafluoropropan-2-yl)oxy]carbonyl}-4-methylpiperidin-4-yl)(methyl)amino]methyl}-5-(trifluoromethyl)phenyl)cyclopentane-1-carboxylic acid | δ 7.71 (s, 1H), 7.52-7.55 (m, 2H), 6.10-6.19 (m, 1H), 3.62-3.77 (m, 6H), 2.64-2.70 (m, 2H), 2.18 (s, 3H), 1.74-2.02 (m, 10H), 1.18 (s, 3H). | 593 |
| 139 | 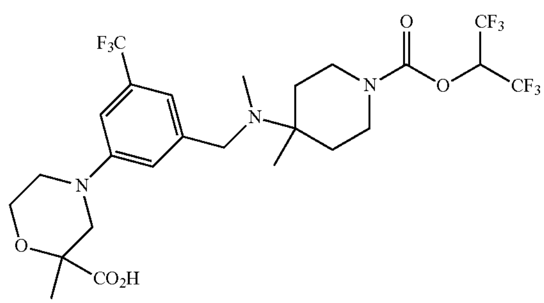 [SMILES: CN(Cc1cc(N2CCOC(C)(C(=O)O)C2)cc(C(F)(F)F)c1)C1(C)CCN(C(=O)OC(C(F)(F)F)C(F)(F)F)CC1] | 4-(3-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)-2-methylmorpholine-2-carboxylic acid | δ 7.24 (s, 1H), 7.10 (d, J = 11.4 Hz,2H), 6.09-6.18 (m, 1H), 4.02-4.09 (m, 2H), 3.76-3.85 (m, 5H), 3.56 (br, 2H), 3.32-3.37 (m, 1H),2.85-2.93 (br, 1H), 2.71-2.74 (m, 1H), 2.26 (s, 3H), 1.97-1.98 (m, 2H), 1.73 (br, 2H), 1.29 (s, 3H), 1.21 (s, 3H). | 624 |

| Ex | Structure | Name | NMR (¹H NMR, 300 MHz or 400 MHz, Methanol-d4) | MS [M+ H]⁺ |
|---|---|---|---|---|
| 140 | 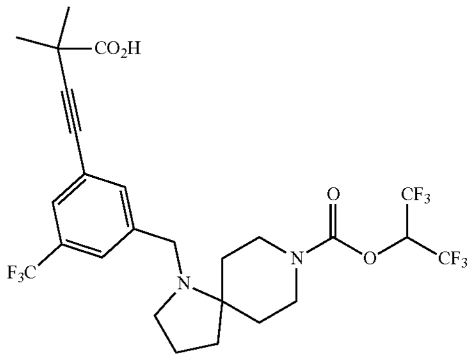 [SMILES: CC(C)(C#Cc1cc(CN2CCCC23CCN(C(=O)OC(C(F)(F)F)C(F)(F)F)CC3)cc(C(F)(F)F)c1)C(=O)O] | 4-{3-[(8-{[(1,1,1,3,3,3-Hexafluoropropan-2-yl)oxy]carbonyl}-1,8-diazaspiro[4.5]decan-1-yl)methyl]-5-(trifluoromethyl)phenyl}-2,2-dimethylbut-3-ynoic acid | δ 7.64-7.71 (m, 3H), 6.14-6.20 (m, 1H), 4.22-4.28 (m, 2H), 3.93 (br, 2H), 3.06-3.21 (m, 2H), 2.92 (br, 2H), 2.05-2.06 (m, 2H), 1.80-1.94 (m, 4H), 1.67-1.70 (m, 2H), 1.56 (s, 6H). | 603 |
| 141 | 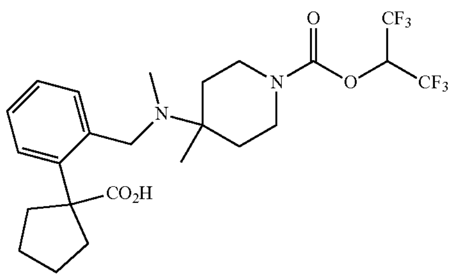 [SMILES: CN(Cc1ccccc1C1(C(=O)O)CCCC1)C1(C)CCN(C(=O)OC(C(F)(F)F)C(F)(F)F)CC1] | 1-(2-{[(1-{[(1,1,1,3,3,3-Hexafluoropropan-2-yl)oxy]carbonyl}-4-methylpiperidin-4-yl)(methyl)amino]methyl}phenyl)cyclopentane-1-carboxylic acid | δ 7.47-7.55 (m, 2H), 7.23-7.34 (m,2H),6.11-6.20(m, 1H), 4.27 (br, 2H), 4.03-4.07 (m, 2H), 3.29-3.43 (m, 2H), 2.79-2.80 (m, 2H), 2.23 (s, 3H), 1.93-2.09 (m, 4H), 1.76-1.87 (m, 6H), 1.45 (s, 3H). | 525 |
| 142 | 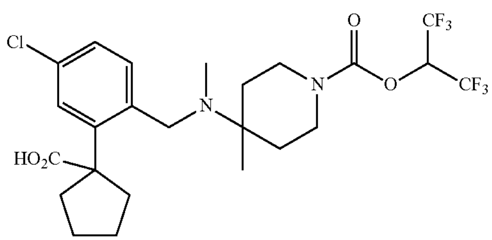 [SMILES: CN(Cc1ccc(Cl)cc1C1(C(=O)O)CCCC1)C1(C)CCN(C(=O)OC(C(F)(F)F)C(F)(F)F)CC1] | 1-(5-Chloro-2-{[(1-{[(1,1,1,3,3,3-hexafluoropropan-2-yl)oxy]carbonyl}-4-methylpiperidin-4-yl)(methyl)amino]methyl}phenyl)cyclopentane-1-carboxylic acid | δ 7.57-7.60 (m, 1H), 7.46 (d, y = 2.1 Hz, 1H), 7.25-7.28 (m, 1H), 6.10-6.19 (m, 1H), 3.86-4.03 (m, 4H), 3.42-3.48 (m, 2H), 2.67-2.71 (m, 2H), 2.20 (s, 3H), 2.02-2.07 (m, 2H), 1.77-1.90 (m, 8H), 1.32 (s, 3H). | 559 |

| Ex | Structure | Name | NMR (¹H NMR, 300 MHz or 400 MHz, Methanol-d4) | MS [M+ H]⁺ |
|---|---|---|---|---|
| 143 | 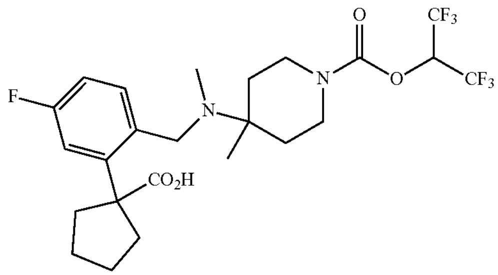 [SMILES: CN(Cc1ccc(F)cc1C1(C(=O)O)CCCC1)C1(C)CCN(C(=O)OC(C(F)(F)F)C(F)(F)F)CC1] | 1-(5-Fluoro-2-{[(1-{[(1,1,1,3,3,3-hexafluoropropan-2-yl)oxy]carbonyl}-4-methylpiperidin-4-yl)(methyl)amino]methyl}phenyl)cyclopentane-1-carboxylic acid | δ 7.53-7.58 (m, 1H), 7.22-7.27 (m, 1H), 6.98-7.04 (m, 1H), 6.11-6.20 (m, 1H), 4.20 (br, 2H), 3.99-4.04 (m, 2H), 3.37-3.45 (m, 2H), 2.72-2.76 (m, 2H), 2.25 (s, 3H), 1.83-2.10 (m, 10H), 1.40 (s, 3H). | 543 |
| 144 | 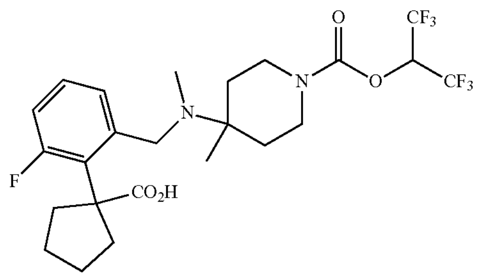 [SMILES: CN(Cc1cccc(F)c1C1(C(=O)O)CCCC1)C1(C)CCN(C(=O)OC(C(F)(F)F)C(F)(F)F)CC1] | 1-(2-Fluoro-6-{[(1-{[(1,1,1,3,3,3-hexafluoropropan-2-yl)oxy]carbonyl}-4-methylpiperidin-4-yl)(methyl)amino]methyl}phenyl)cyclopentane-1-carboxylic acid | δ 7.40-7.43 (m, 1H), 7.22-7.29 (m, 1H), 7.01-7.08(m, 1H), 6.10-6.19 (m, 1H), 4.17 (br, 2H), 3.90-3.94 (m, 2H), 3.38-3.49 (m, 2H), 2.82-2.85 (m, 2H), 2.13 (s, 3H), 1.97-2.08 (m, 4H), 1.89-1.95 (m, 2H), 1.75-1.77 (m, 4H), 1.35 (s, 3H). | 543 |
| 145 | 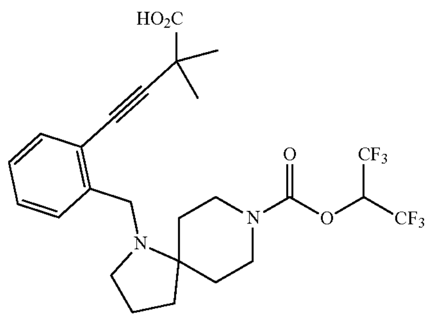 [SMILES: CC(C)(C#Cc1ccccc1CN1CCCC12CCN(C(=O)OC(C(F)(F)F)C(F)(F)F)CC2)C(=O)O] | 4-{2-[(8-{[(1,1,1,3,3,3-Hexafluoropropan-2-yl)oxy]carbonyl}-1,8-diazaspiro[4.5]decan-1-yl)methyl]phenyl}-2,2-dimethylbut-3-ynoic acid | δ 7.48-7.52 (m, 2H), 7.34-7.39 (m, 2H), 6.11-6.19 (m, 1H), 4.22-4.33 (m, 4H), 3.35 (br, 2H), 3.06-3.22 (m, 2H), 2.25-2.31 (m, 2H), 2.00-2.1 (m, 4H), 1.90-1.94 (m, 2H), 1.52 (s, 6H). | 535 |

-continued

| Ex | Structure | Name | NMR (¹H NMR, 300 MHz or 400 MHz, Methanol-d4) | MS [M+ H]⁺ |
|---|---|---|---|---|
| 146 | 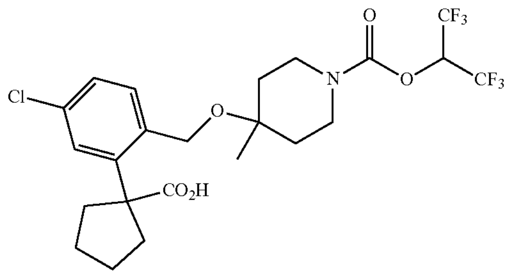 [SMILES: CC1(OCc2ccc(Cl)cc2C2(C(=O)O)CCCC2)CCN(C(=O)OC(C(F)(F)F)C(F)(F)F)CC1] | 1-(5-Chloro-2-{[(1-{[(1,1,1,3,3,3-hexafluoropropan-2-yl)oxy]carbonyl}-4-methylpiperidin-4-yl)oxy]methyl}phenyl)cyclopentane-1-carboxylic acid | δ 7.54 (d, J = 8.4 Hz, 1H), 7.36 (d, 2.1 Hz, 1H), 7.19-7.23 (m, 1H), 6.08-6.17 (m, 1H), 4.53 (s, 2H), 3.86-3.90 (m, 2H), 3.28-3.37 (m, 2H), 2.48-2.56 (m, 2H), 1.99 (br, 2H), 1.95 (br, 2H), 1.80-1.88 (m, 2H), 1.66-1.77 (m, 2H), 1.52-1.62 (m, 2H), 1.32 (s, 3H). | 568 [M + Na]⁺ |
| 147 | 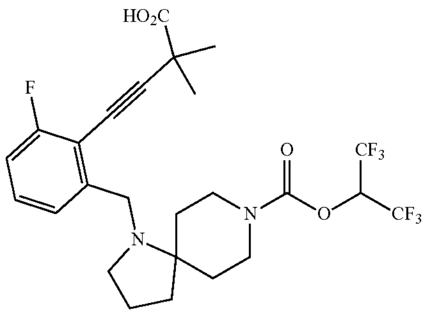 [SMILES: CC(C)(C#Cc1c(F)cccc1CN1CCCC12CCN(C(=O)OC(C(F)(F)F)C(F)(F)F)CC2)C(=O)O] | 4-{2-Fluoro-6-[(8-{[(1,1,1,3,3,3-hexafluoropropan-2-yl)oxy]carbonyl}-1,8-diazaspiro[4.5]decan-1-yl)methyl]phenyl}-2,2-dimethylbut-3-ynoic acid | δ 7.31-7.41 (m, 2H), 7.15-7.21 (m, 1H), 6.10-6.19 (m, 1H), 4.21-4.26 (m, 4H), 3.05-3.26 (m, 4H), 2.18-2.23 (m, 2H), 1.99-2.07 (m, 4H), 1.84-1.88 (m, 2H), 1.53 (s, 6H) | 553 |
| 148 | 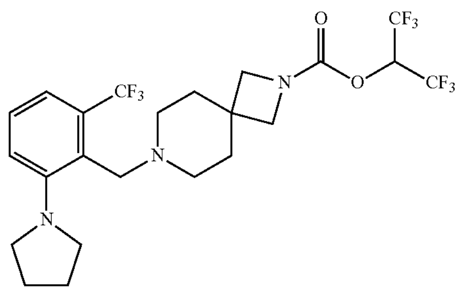 [SMILES: O=C(OC(C(F)(F)F)C(F)(F)F)N1CC2(CCN(Cc3c(N4CCCC4)cccc3C(F)(F)F)CC2)C1] | 1,1,1,3,3,3-Hexafluoropropan-2-yl 7-(2-(pyrrolidin-1-yl)-4-(trifluoromethyl)benzyl)-2,7-diazaspiro[3.5]nonane-2-carboxylate | δ 7.17-7.20 (m, 2H), 7.22-7.30 (m, 1H), 5.58-5.71 (m, 1H), 3.72-3.86 (m, 4H), 3.64 (s, 2H), 3.08 (t, J = 5.8 Hz, 4H), 2.23 (s, 4H), 1.92 (t, J = 6.2 Hz, 4H), 1.68 (t, J = 5.2 Hz, 4H) | 548 |

| Ex | Structure | Name | NMR (¹H NMR, 300 MHz or 400 MHz, Methanol-d4) | MS [M+ H]⁺ |
|---|---|---|---|---|
| 149 | 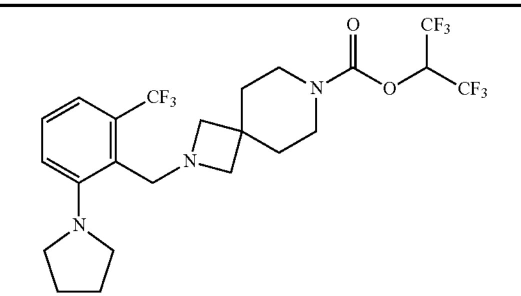 | 1,1,1,3,3,3-Hexafluoropropan-2-yl 2-(2-(pyrrolidin-1-yl)-4-(trifluoromethyl)benzyl)-2,7-diazaspiro[3.5]nonane-7-carboxylate | δ 7.25-7.30 (m, 1H), 7.20-7.25 (m, 2H), 5.66-5.79 (m, 1H), 3.85 (s, 2H), 3.40 (t, J = 4.2 Hz, 4H), 3.13 (t, J = 6.0 Hz, 4H), 2.99 (s, 4H), 1.94 (t, J = 6.0 Hz, 4H), 1.69-1.71 (m, 4H) | 548 |
| 150 | 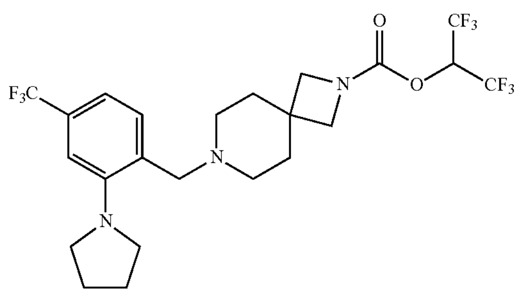 [SMILES: O=C(OC(C(F)(F)F)C(F)(F)F)N1CC2(CCN(Cc3ccc(C(F)(F)F)cc3N3CCCC3)CC2)C1] | 1,1,1,3,3,3-Hexafluoropropan-2-yl 7-(2-(pyrrolidin-1-yl)-4-(trifluoromethyl)benzyl)-2,7-diazaspiro[3.5]nonane-2-carboxylate | δ 7.51-7.60 (m, 1H), 7.08-7.20 (m, 2H), 5.59-5.69 (m, 1H), 3.71-3.81 (m, 4H), 3.48 (s, 2H), 3.22 (s, 4H), 2.35 (s, 4H), 1.94 (s, 4H), 1.80 (s, 4H) | 548 |
| 151 | 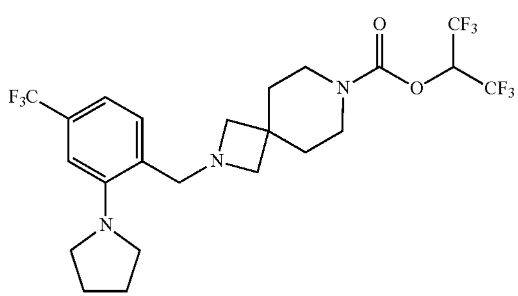 [SMILES: O=C(OC(C(F)(F)F)C(F)(F)F)N1CCC2(CC1)CN(Cc1ccc(C(F)(F)F)cc1N1CCCC1)C2] | 1,1,1,3,3,3-Hexafluoropropan-2-yl 2-(2-(pyrrolidin-1-yl)-4-(trifluoromethyl)benzyl)-2,7-diazaspiro[3.5]nonane-7-carboxylate | δ 7.45 (d, t, Jr = 7.8 Hz, 1H), 7.07-7.12 (m, 2H), 5.68-5.81 (m, 1H), 3.69 (s, 2H), 3.46 (t, J = 5.6 Hz, 4H), 3.22 (t, J = 6.4 Hz, 4H), 3.07 (s, 4H), 1.91-2.01 (m, 4H), 1.77-1.90 (m, 4H) | 548 |

| Ex | Structure | Name | NMR (1H NMR, 300 MHz or 400 MHz, Methanol-d4) | MS [M+ H]+ |
|---|---|---|---|---|
| 152 | 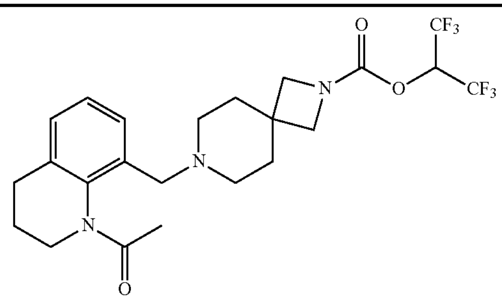 | 1,1,1,3,3,3-Hexafluoropropan-2-yl 7-((1-acetyl-1,2,3,4-tetrahydroquinolin-8-yl)methyl)-2,7-diazaspiro[3.5]nonane-2-carboxylate | (DMSO-d6) δ 7.30-7.32 (m, 1H), 7.10-7.14 (m, 2H), 6.16-6.24 (m, 1H), 3.71-4.95 (m, 5H), 3.30 (s, 3H), 2.62 (s, 2H), 1.67-2.21 (m, 13H) | 508 |
| 153 | 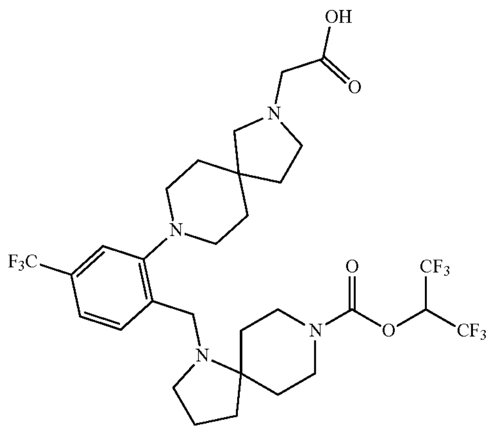 [SMILES: O=C(O)CN1CCC2(CCN(c3cc(C(F)(F)F)ccc3CN3CCCC34CCN(C(=O)OC(C(F)(F)F)C(F)(F)F)CC4)CC2)C1] | 2-(8-(2-(8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,8-diazaspiro[4.5]decan-2-yl)acetic acid | (Chloroform-d) δ 7.67-7.54 (m, 1H), 7.33-7.31 (m, 1H), 7.28-7.27 (m, 1H), 5.83-5.74 (m, 1H), 4.27-4.19 (m, 2H), 3.74-3.70 (m, 4H), 3.57-3.41 (m, 4H), 3.06-2.87 (m, 6H), 2.69 (s, 2H), 2.10-2.03 (m, 2H), 1.93-1.81 (m, 5H), 1.79-1.72 (m, 4H), 1.55-1.52 (m, 2H) | 689 |

| Ex | Structure | Name | NMR (¹H NMR, 300 MHz or 400 MHz, Methanol-d4) | MS [M+ H]⁺ |
|---|---|---|---|---|
| 154 | 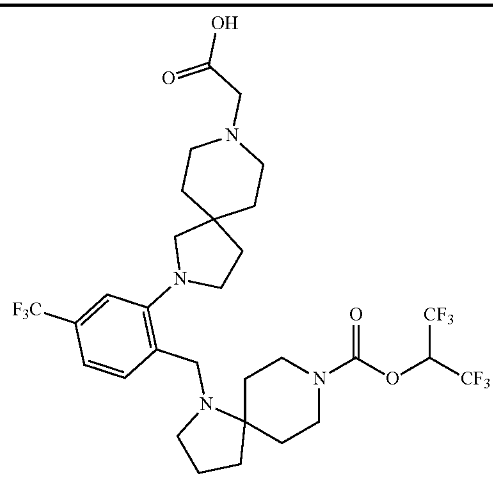 | 2-(2-(2-(8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,1-diazaspiro[4.5]decan-8-yl)acetic acid | (Chloroform-d) δ 7.70 (d, J = 7.8 Hz, 1H), 7.20 (d, J = 7.8 Hz, 1H), 7.12 (s, 1H), 5.70-5.81 (m, 1H), 4.25-4.16 (m, 2H), 3.65 (s, 2H), 3.56 (s, 2H), 3.44-3.24 (m, 6H), 3.24-2.92 (m, 4H), 2.65 (s, 2H), 2.17-1.66 (m, 12H), 1.61-1.43 (m, 2H) | 689 |
| 155 | 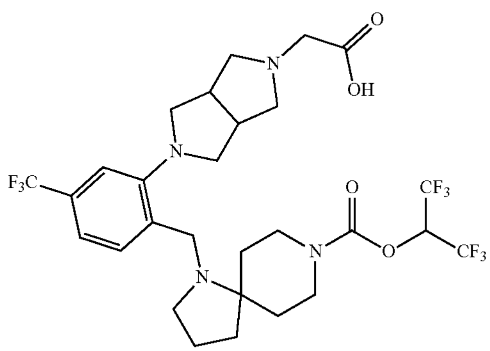 [SMILES: O=C(O)CN1CC2CN(c3cc(C(F)(F)F)ccc3CN3CCCC34CCN(C(=O)OC(C(F)(F)F)C(F)(F)F)CC4)CC2C1] | 2-(5-(2-(8-(((1,1,1,3,3,3-Hexafluoropropan-2-yl)oxy)carbonyl)-1,8-diazaspiro[4.5]decan-1-yl)methyl)-5-(trifluoromethyl)cyclohexyl)hexahydropyrrolo[3,4-c]pyrrol-2(1H)-yl)acetic acid | (Chloroform-d) δ 7.83 (s, 1H), 7.36-7.26 (m, 2H), 5.80-5.70 (m, 1H), 4.26-4.10(m, 2H), 4.01-3.81 (m, 3H), 3.74-3.60 (m, 2H), 3.55-3.55 (m, 1H), 3.40-3.23 (m, 3H), 3.06-2.68 (m, 9H), 1.89 (s, 4H), 1.78-1.59 (m, 4H) | 661 |

| Ex | Structure | Name | NMR (¹H NMR, 300 MHz or 400 MHz, Methanol-d4) | MS [M+ H]⁺ |
|---|---|---|---|---|
| 156 | 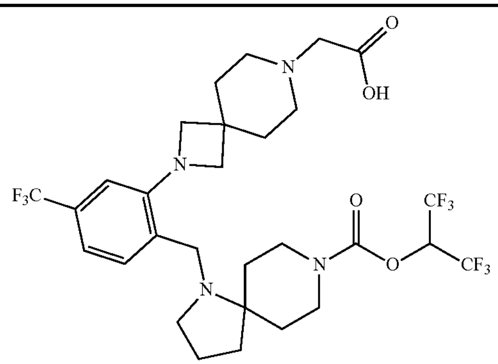 | 2-(2-(2-(8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,7-diazaspiro[3.5]nonan-7-yl)acetic acid | δ 7.63 (d, J = 8.0 Hz, 1H), 7.08 (d, j = 8.0 Hz, 1H), 6.75 (s, 1H), 6.19-6.12 (m, 1H), 4.18-4.16 (m, 2H), 3.81 (s, 4H), 3.64-3.59 (m, 4H), 3.33 (s, 4H), 3.17-3.07 (m, 2H), 2.71 (t, J = 6.8 Hz, 2H), 2.17-2.14 (m, 4H), 1.96-1.92 (m, 2H), 1.87-1.80 (m, 2H), 1.77-1.68 (m, 2H), 1.58-1.55 (m, 2H) | 675 |
| 157 | 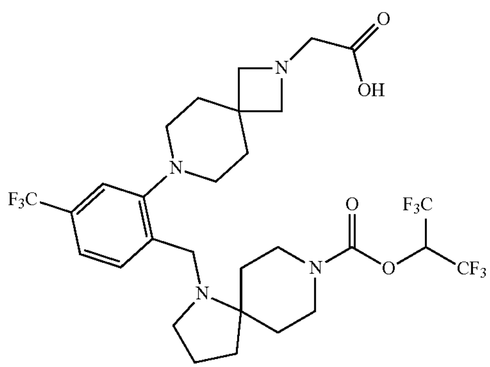 [SMILES: O=C(O)CN1CC2(CCN(c3cc(C(F)(F)F)ccc3CN3CCCC34CCN(C(=O)OC(C(F)(F)F)C(F)(F)F)CC4)CC2)C1] | 2-(7-(2-(8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,7-diazaspiro[3.5]nonan-2-yl)acetic acid | δ 7.67 (d, J = 8.0 Hz, 1H), 7.39-7.36 (m, 2H), 6.18-6.12 (m, 1H), 4.18-4.15 (m, 2H), 4.02 (s, 4H), 3.84-3.80 (m, 4H), 3.09-3.02 (m, 2H), 2.87 (s, 6H), 2.08 (s, 4H), 1.95-1.75 (m, 6H), 1.59-1.52 (m, 2H) | 675 |
| 158 | 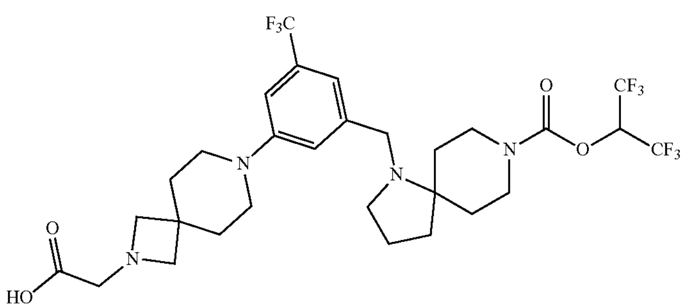 [SMILES: O=C(O)CN1CC2(CCN(c3cc(CN4CCCC45CCN(C(=O)OC(C(F)(F)F)C(F)(F)F)CC5)cc(C(F)(F)F)c3)CC2)C1] | 2-(7-(3-(8-(((1,1,1,3,3,3-Hexafluoropropan-2-yl)oxy)carbonyl)-1,8-diazaspiro[4.5]decan-1-yl)methyl)-5-(trifluoromethyl)phenyl)-2,7-diazaspiro[3.5]nonan-2-yl)acetic acid | δ 7.15 (s, 1H), 7.08-7.03 (m, 2H), 6.13-6.10 (m, 1H), 4.20-4.17 (m, 2H), 3.97 (s, 4H), 3.77 (s, 2H), 3.63 (s, 2H), 3.28-3.20 (m, 4H), 3.07-3.03 (m, 2H), 2.68 (t, J = 6.6 Hz, 2H), 2.02-2.00 (m, 4H), 1.93-1.91 (m, 2H), 1.82-1.74 (m, 4H), 1.72-1.51 (m, 2H) | 675 |

| Ex | Structure | Name | NMR (¹H NMR, 300 MHz or 400 MHz, Methanol-d4) | MS [M+ H]⁺ |
|---|---|---|---|---|
| 159 | 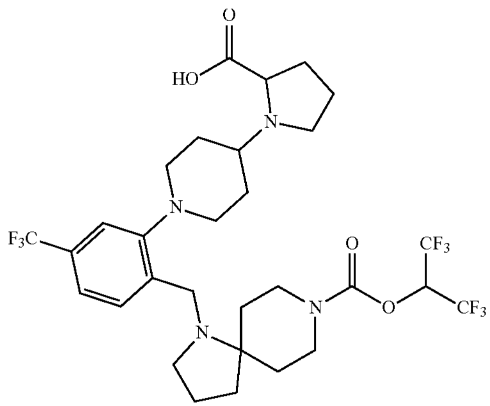 | (1-(2-(8-(1,1,1,3,3,3-Hexafluoropropan-2-yl)oxy)carbonyl)-1,8-diazaspiro[4.5]decan-1-yl)methyl)-5-(trifluoromethyl)phenyl)piperidin-4-yl)proline | δ 7.73 (d, J = 8.4 Hz, 1H), 7.38-7.37 (m, 2H), 6.22-6.11 (m, 1H), 4.38-4.11 (m, 2H), 4.11-4.09 (m, 1H), 3.80-3.76 (m, 3H), 3.40-3.37 (m, 1H), 3.34-3.07 (m, 5H), 2.82-2.80 (m, 2H), 2.72-2.71 (m, 2H), 2.49-2.30 (m, 1H), 2.25-2.21 (m, 2H), 2.14-2.11 (m, 2H), 2.00-1.92 (m, 6H), 1.89-1.80 (m, 2H), 1.79-1.70 (m, 1H), 1.58-1.56 (m, 2H) | 689 |
| 160 | 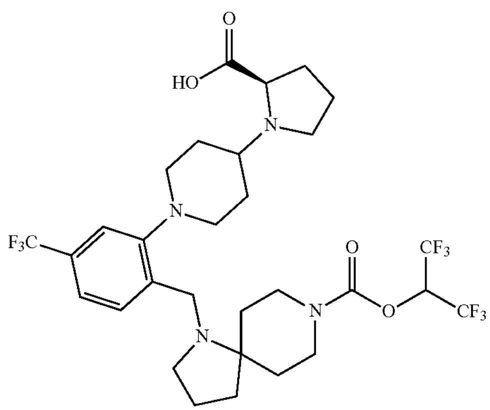 [SMILES: O=C(O)[C@H]1CCCN1C1CCN(c2cc(C(F)(F)F)ccc2CN2CCCC23CCN(C(=O)OC(C(F)(F)F)C(F)(F)F)CC3)CC1] | (1-(2-(((1,1,1,3,3,3-Hexafluoropropan-2-yl)oxy)carbonyl)-1,8-diazaspiro[4.5]decan-1-yl)methyl)-5-(trifluoromethyl)phenyl)piperidin-4-yl)-D-proline | δ 7.73 (d, J = 8.0 Hz, 1H), 7.38-7.37 (m, 2H), 6.16-6.11 (m, 1H), 4.25-4.15 (m, 2H), 4.08-4.05 (m, 1H), 3.80-3.77 (m, 3H), 3.38-3.33 (m, 1H), 3.29-3.07 (m, 5H), 2.82-2.71 (m, 4H), 2.49-2.30 (m, 1H), 2.26-2.10 (m, 4H), 2.00-1.82 (m, 9H), 1.58-1.56 (m, 2H) | 689 |

| Ex | Structure | Name | NMR (¹H NMR, 300 MHz or 400 MHz, Methanol-d4) | MS [M+ H]⁺ |
|---|---|---|---|---|
| 161 | 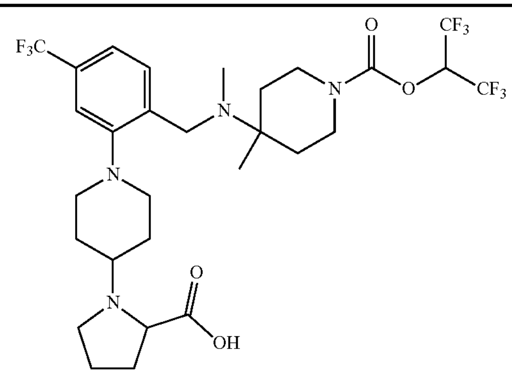 | (1-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)piperidin-4-yl)proline | δ 7.87 (d, J = 8.0 Hz, 1H), 7.43 (d, J = 8.0 Hz, 1H), 7.37 (s, 1H), 6.17-6.14 (m, 1H), 4.09-4.05 (m, 1H), 3.78-3.69 (m, 5H), 3.60-3.57 (m, 2H), 3.34-3.30 (m, 1H), 3.26-3.24 (m, 1H), 3.21-3.18 (m, 2H), 2.85-2.78 (m, 2H), 2.50-2.34 (m, 1H), 2.26-2.23 (m, 2H), 2.18-2.09 (m, 5H), 2.04-1.93 (m, 5H), 1.57-1.54 (m, 2H), 1.15 (s, 3H) | 677 |
| 162 | 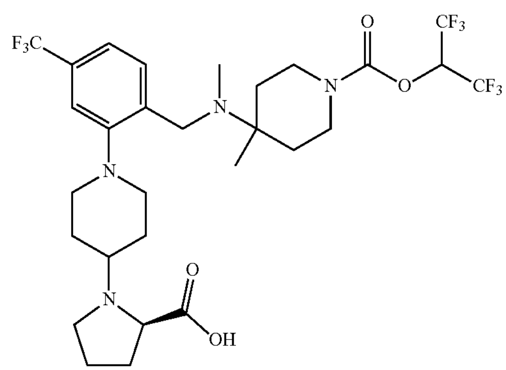 [SMILES: CN(Cc1ccc(C(F)(F)F)cc1N1CCC(N2CCC[C@@H]2C(=O)O)CC1)C1(C)CCN(C(=O)OC(C(F)(F)F)C(F)(F)F)CC1] | (1-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)piperidin-4-yl)-D-proline | δ 7.87 (d, J = 8.4 Hz, 1H), 7.43 (d, J = 8.4 Hz, 1H), 7.36 (s, 1H), 6.16-6.12 (m, 1H), 4.08-4.05(m, 1H), 3.78-3.69 (m, 5H), 3.59-3.56 (m, 2H), 3.38-3.32 (m, 1H), 3.27-3.18 (m, 3H), 2.83-2.79 (m, 2H), 2.41-2.39 (m, 1H), 2.26-2.23 (m, 2H), 2.14-2.09 (m, 5H), 2.04-1.93 (m, 5H), 1.57-1.54 (m, 2H), 1.14 (s, 3H) | 677 |

| Ex | Structure | Name | NMR (¹H NMR, 300 MHz or 400 MHz, Methanol-d4) | MS [M+ H]⁺ |
|---|---|---|---|---|
| 163 | 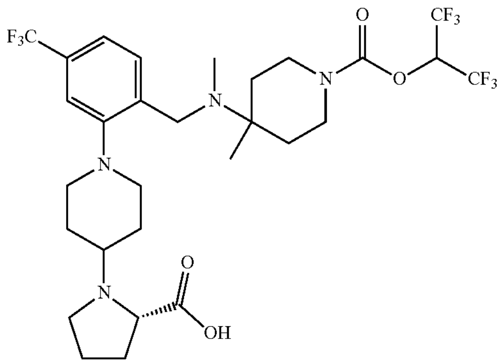 [SMILES: CN(Cc1ccc(C(F)(F)F)cc1N1CCC(N2CCC[C@H]2C(=O)O)CC1)C1(C)CCN(C(=O)OC(C(F)(F)F)C(F)(F)F)CC1] | (1-(2-(((1-(((1,1,1,3,3,3-Hexafluoropropan-2-yl)oxy)carbonyl)-4-methylpiperidin-4-yl)(methyl)amino)methyl)-5-(trifluoromethyl)phenyl)piperidin-4-yl)-L-proline | δ 7.87 (d, J = 8.4 Hz, 1H), 7.43 (d,J = 8.4 Hz, 1H), 7.36 (s, 1H), 6.15-6.12 (m, 1H), 4.08-4.05 (m, 1H), 3.78-3.69 (m, 5H), 3.62-3.56 (m, 2H), 3.37-3.29 (m, 1H), 3.27-3.17 (m, 3H), 2.85-2.78 (m, 2H), 2.42-2.39 (m, 1H), 2.26-2.23 (m, 2H), 2.15-2.11 (m, 5H), 2.04-1.93 (m, 5H), 1.56-1.54 (m, 2H), 1.14 (s, 3H) | 677 |
| 164 | 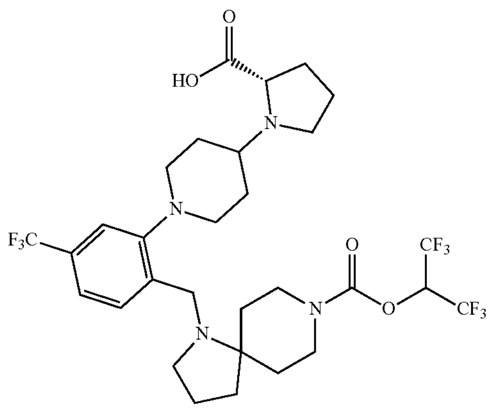 | (1-(2-(8-(((1,1,1,3,3,3-Hexafluoropropan-2-yl)oxy)carbonyl)-1,8-diazaspiro[4.5]decan-1-yl)methyl)-5-(trifluoromethyl)phenyl)piperidin-4-yl)-L-proline | δ 7.73 (d, J = 8.0 Hz, 1H), 7.38-7.37 (m, 2H), 6.16-6.11 (m, 1H), 4.21-4.15 (m, 2H), 4.08-4.05 (m, 1H), 3.80-3.76 (m, 3H), 3.37-3.32 (m, 1H), 3.28-3.07 (m, 5H), 2.84-2.71 (m, 4H), 2.49-2.30 (m, 1H), 2.26-2.10 (m, 4H), 2.03-1.73 (m, 9H), 1.58-1.56 (m, 2H) | 689 |

| Ex | Structure | Name | NMR (¹H NMR, 300 MHz or 400 MHz, Methanol-d4) | MS [M+ H]⁺ |
|---|---|---|---|---|
| 165 | 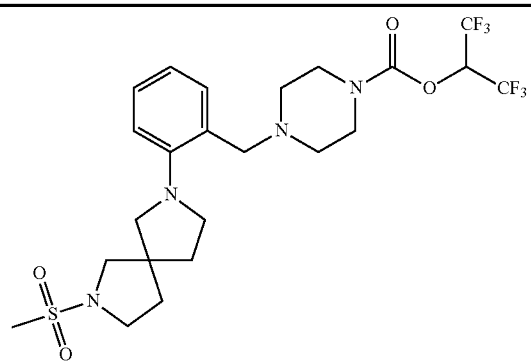 | 1,1,1,3,3,3-Hexafluoropropan-2-yl 4-(2-(7-(methylsulfonyl)-2,7-diazaspiro[4.4]nonan-2-yl)benzyl)piperazine-1-carboxylate | (Chloroform-d) δ 7.35-7.38 (m, 1H), 7.18-7.23 (m, 1H), 6.92-6.97 (m, 2H), 5.70-5.79 (m, 1H), 3.39-3.45 (m, 9H), 3.23,3.36 (m, 4H), 3.11-3.14 (m, 1H), 2.86 (s, 3H), 2.47 (s, 4H), 1.88-2.12 (m, 4H) | 573 |
| 166 | 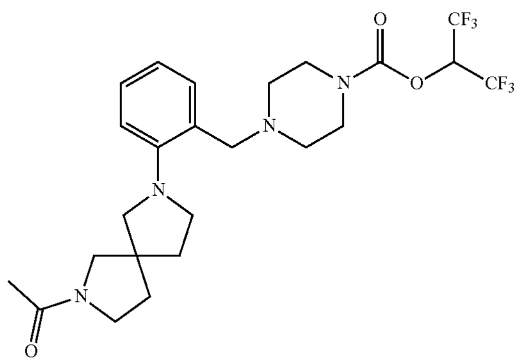 [SMILES: CC(=O)N1CCC2(CCN(c3ccccc3CN3CCN(C(=O)OC(C(F)(F)F)C(F)(F)F)CC3)C2)C1] | 1,1,1,3,3,3-Hexafluoropropan-2-yl 4-(2-(7-acetyl-2,7-diazaspiro[4.4]nonan-2-yl)benzyl)piperazine-1-carboxylate | (Chloroform-d) δ 7.34-7.37 (m, 1H), 7.20-7.21 (m, 1H), 6.92-6.97 (m, 2H), 5.71-5.79 (m, 1H), 3.46-3.64 (m, 9H), 3.27-3.44 (m, 3H), 3.11-3.23 (m, 2H), 2.46 (s, 4H), 1.87-2.08 (m, 7H) | 537 |

-continued

| Ex | Structure | Name | NMR (¹H NMR, 300 MHz or 400 MHz, Methanol-d4) | MS [M+ H]⁺ |
|---|---|---|---|---|
| 167 | 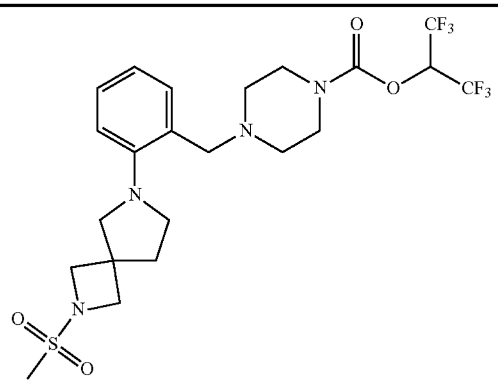 | 1,1,1,3,3,3-Hexafluoropropan-2-yl 4-(2-(2-(methylsulfonyl)-2,6-diazaspiro[3.4]octan-6-yl)benzyl)piperazine-1-carboxylate | (Chloroform-d) δ 7.38-7.40 (m, 1H), 7.19-7.24 (m, 1H), 6.92-6.99 (m, 2H), 5.71-5.79 (m, 1H), 3.92-3.94 (m, 4H), 3.53 (s, 6H), 3.40 (s, 2H), 3.21-3.26 (m, 2H), 2.88 (s, 3H), 2.46 (s, 4H), 2.16-2.20 (m, 2H) | 559 |
| 168 | 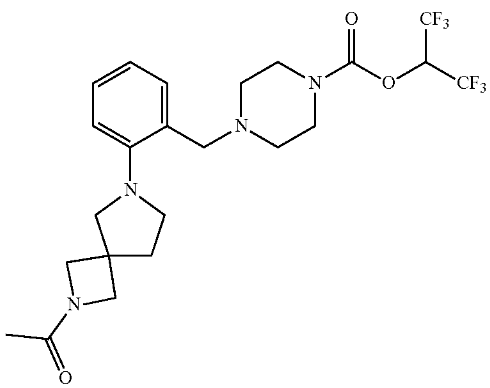 [SMILES: CC(=O)N1CC2(CCN(c3ccccc3CN3CCN(C(=O)OC(C(F)(F)F)C(F)(F)F)CC3)C2)C1] | 1,1,1,3,3,3-Hexafluoropropan-2-yl 4-(2-acetyl-2,6-diazaspiro[3.4]octan-6-yl)benzyl)piperazine-1-carboxylate | (Chloroform-d) δ 7.38-7.41 (m, 1H), 7.18-7.23 (m, 1H), 6.92-6.98 (m, 2H), 5.71-5.79 (m, 1H), 4.02-4.12 (m, 2H), 3.95-3.99 (m, 2H), 3.54 (s, 6H), 3.21-3.41 (m, 4H), 2.46 (s, 4H), 2.15-2.20 (m, 2H), 1.90 (s, 3H) | 523 |

| Ex | Structure | Name | NMR (¹H NMR, 300 MHz or 400 MHz, Methanol-d4) | MS [M+ H]⁺ |
|---|---|---|---|---|
| 169 | 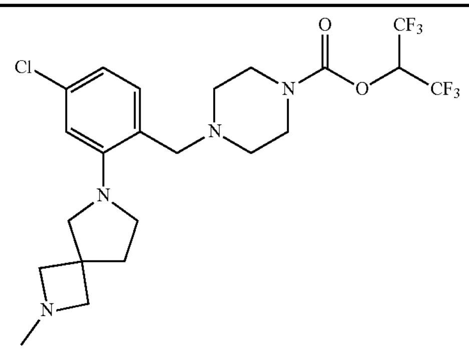 | 1,1,1,3,3,3-Hexafluoropropan-2-yl 4-(4-chloro-2-(2-methyl-2,6-diazaspiro[3.4]octan-6-yl)benzyl)piperazine-1-carboxylate | (Chloroform-d) δ 7.28 (d, J = 8.0 Hz, 1H), 6.81-6.85 (m, 2H), 5.72-5.79 (m, 1H), 3.53-3.54 (m, 4H), 3.48 (s, 2H), 3.36 (s, 2H), 3.20-3.27 (m, 6H), 2.38-2.46 (m, 7H), 2.12 (t, J = 6.8 Hz, 2H) | 529 |
| 170 | 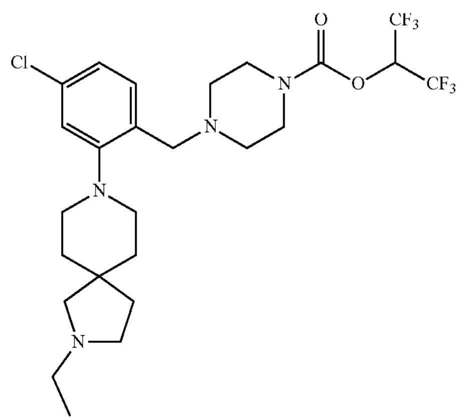 [SMILES: CCN1CCC2(CCN(c3cc(Cl)ccc3CN3CCN(C(=O)OC(C(F)(F)F)C(F)(F)F)CC3)CC2)C1] | 1,1,1,3,3,3-Hexafluoropropan-2-yl 4-(4-chloro-2-(2-ethyl-2,8-diazaspiro[4.5]decan-8-yl)benzyl)piperazine-1-carboxylate | (Chloroform-rf) δ 7.35 (d, J = 8.0 Hz, 1H), 7.00-7.04 (m, 2H), 5.72-5.78 (m, 1H), 3.52-3.53 (m, 6H), 2.83 (t, J = 5.2 Hz, 4H), 2.62 (s, 2H), 2.46-2.49 (m, 8H), 1.67-1.74 (m, 6H), 1.14 (t, J = 7.0 Hz, 3H) | 571 |
| 171 | 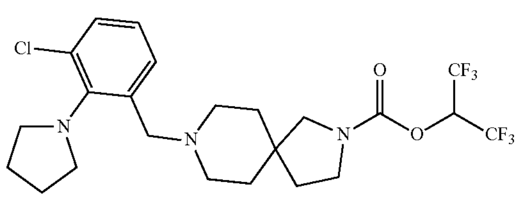 [SMILES: O=C(OC(C(F)(F)F)C(F)(F)F)N1CCC2(CCN(Cc3cccc(Cl)c3N3CCCC3)CC2)C1] | 1,1,1,3,3,3-Hexafluoropropan-2-yl 8-(3-chloro-2-(pyrrolidin-1-yl)benzyl)-2,8-diazaspiro[4.5]decane-2-carboxylate | (Chloroform-d) δ 7.34-7.37 (m, 1H), 7.25-7.27 (m, 1H), 7.05-7.10 (m, 1H), 5.69-5.78 (m, 1H), 3.49-3.56 (m, 4H), 3.28-3.32 (m, 2H), 3.19-3.23 (m, 4H), 2.50 (s, 2H), 2.32 (s, 2H), 1.95-2.03 (m, 4H), 1.76-1.83 (m, 2H), 1.59 (s, 4H) | 528 |

| Ex | Structure | Name | NMR (¹H NMR, 300 MHz or 400 MHz, Methanol-d4) | MS [M+ H]⁺ |
|---|---|---|---|---|
| 172 | 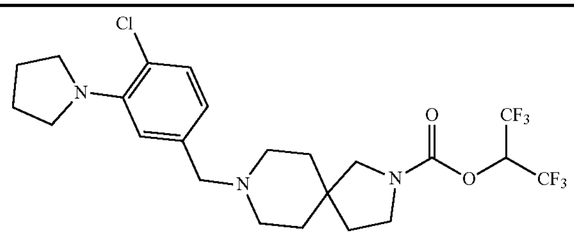 | 1,1,1,3,3,3-Hexafluoropropan-2-yl 8-(4-chloro-3-(pyrrolidin-1-yl)benzyl)-2,8-diazaspiro[4.5]decane-2-carboxylate | (Chloroform-d) δ 7.20-7.23 (m, 1H), 6.84 (s, 1H), 6.71-6.74 (m, 1H), 5.68-5.79 (m, 1H), 3.49-3.54 (m, 2H), 3.36-3.44 (m, 6H), 3.27-3.30 (m, 2H), 2.50 (s, 2H), 2.32 (s, 2H), 1.89-1.99 (m, 4H), 1.72-1.82 (nt, 2H), 1.60 (s, 4H) | 528 |
| 173 | 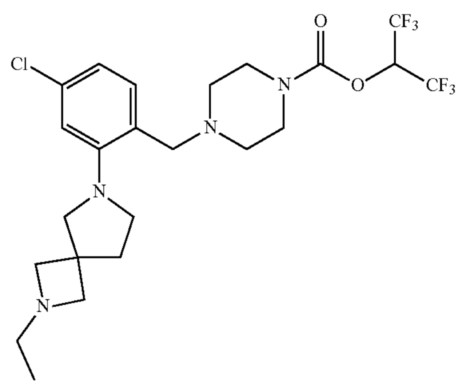 [SMILES: CCN1CC2(CCN(c3cc(Cl)ccc3CN3CCN(C(=O)OC(C(F)(F)F)C(F)(F)F)CC3)C2)C1] | 1,1,1,3,3,3-Hexafluoropropan-2-yl 4-(4-chloro-2-(2-ethyl-2,6-diazaspiro[3.4]octan-6-yl)benzyl)piperazine-1-carboxylate | (Chloroform-d) δ 7.28 (d, J = 8.4 Hz, 1H), 6.81-6.88 (m, 2H), 5.70-5.79 (m, 1H), 3.53 (s, 4H), 3.49 (s, 2H), 3.37 (s, 2H), 3.21-3.24 (m, 6H), 2.49-2.52 (m, 2H), 2.40-2.46 (m, 4H), 2.12 (t, J = 6.8 Hz, 2H), 1.00 (t, J = 6.8 Hz, 3H) | 543 |
| 174 | 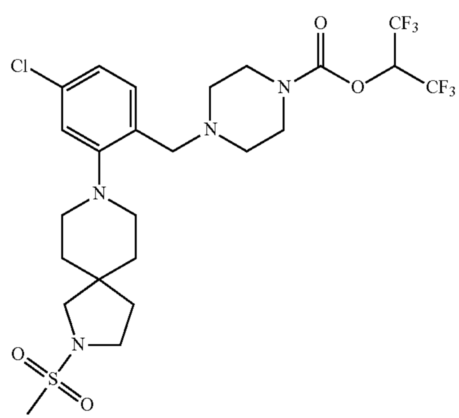 [SMILES: CS(=O)(=O)N1CCC2(CCN(c3cc(Cl)ccc3CN3CCN(C(=O)OC(C(F)(F)F)C(F)(F)F)CC3)CC2)C1] | 1,1,1,3,3,3-Hexafluoropropan-2-yl 4-(4-chloro-2-(2-(methylsulfonyl)-2,8-diazaspiro[4.5]decan-8-yl)benzyl)piperazine-1-carboxylate | (Chloroform-d) δ 7.35-7.37 (m, 1H), 7.04-7.05 (m, 2H), 5.72-5.78 (m, 1H), 3.52-3.54 (m, 6H), 3.44 (t, J = 7.0 Hz, 2H), 3.25 (s, 2H), 2.90-2.96 (m, 2H), 2.81-2.86 (m, 5H), 2.47 (s, 4H), 1.90 (t, J = 7.2 Hz, 2H), 1.69-1.80 (m, 4H) | 621 |

| Ex | Structure | Name | NMR (¹H NMR, 300 MHz or 400 MHz, Methanol-d4) | MS [M+ H]⁺ |
|---|---|---|---|---|
| 175 | 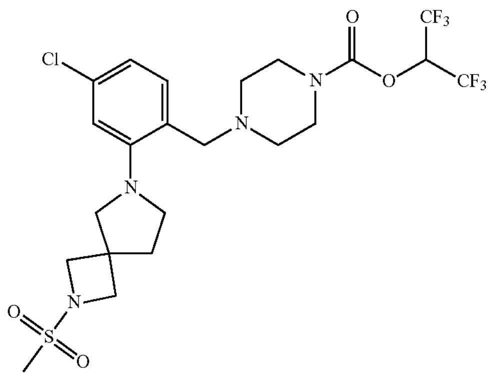 [SMILES: CS(=O)(=O)N1CC2(CCN(c3cc(Cl)ccc3CN3CCN(C(=O)OC(C(F)(F)F)C(F)(F)F)CC3)C2)C1] | 1,1,1,3,3,3-Hexafluoropropan-2-yl 4-(4-chloro-2-(2-(methylsulfonyl)-2,6-diazaspiro[3.4]octan-6-yl)benzyl)piperazine-1-carboxylate | (Chloroform-d) δ 7.29 (d, J = 8.0 Hz, 1H), 6.90 (d, J = 8.4 Hz, 1H), 6.84 (s, 1H), 5.72-5.78 (m, 1H), 3.92 (s, 4H), 3.55 (s, 4H), 3.48 (s, 2H), 3.43 (s, 2H), 3.26 (t, J = 7.0 Hz, 2H), 2.88 (s, 3H), 2.44 (s, 4H), 2.18 (t, J = 7.0 Hz, 2H) | 593 |
| 176 | 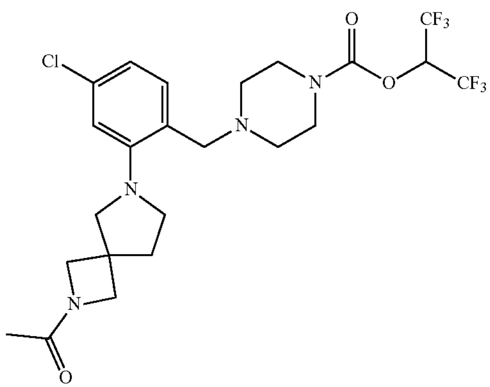 [SMILES: CC(=O)N1CC2(CCN(c3cc(Cl)ccc3CN3CCN(C(=O)OC(C(F)(F)F)C(F)(F)F)CC3)C2)C1] | 1,1,1,3,3,3-Hexafluoropropan-2-yl 4-(2-acetyl-2,6-diazaspiro[3.4]octan-6-yl)-4-chlorobenzyl)piperazine-1-carboxylate | (Chloroform-d) δ 7.30 (d, J = 8.4 Hz, 1H), 6.89 (d, J = 8.0 Hz, 1H), 6.85 (s, 1H), 5.72-5.78 (m, 1H), 4.06-4.11 (m, 2H), 3.95-4.00 (m, 2H), 3.43-3.55 (m, 6H), 3.35-3.40 (m, 2H), 3.26-3.33 (m, 2H), 2.46 (s, 4H), 2.18 (t, J = 6.8 Hz, 2H), 1.90 (s, 3H) | 557 |

| Ex | Structure | Name | NMR (¹H NMR, 300 MHz or 400 MHz, Methanol-d4) | MS [M+ H]⁺ |
|---|---|---|---|---|
| 177 | 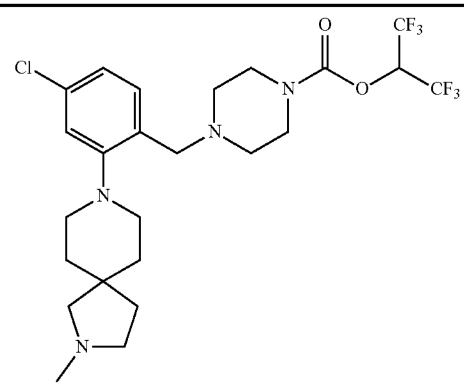 | 1,1,1,3,3,3-Hexafluoropropan-2-yl 4-(4-chloro-2-(2-methyl-2,8-diazaspiro[4.5]decan-8-yl)benzyl)piperazine-1-carboxylate | (Chloroform-d) δ 7.35 (d, J = 7.8 Hz, 1H), 7.00-7.03 (m, 2H), 5.71-5.79 (m, 1H), 3.52 (s, 6H), 2.83 (t, J = 5.2 Hz, 4H), 2.61 (t, J = 6.8 Hz, 2H), 2.46 (s, 6H), 2.37 (s, 3H), 1.65-1.78 (m, 6H) | 557 |
| 178 | 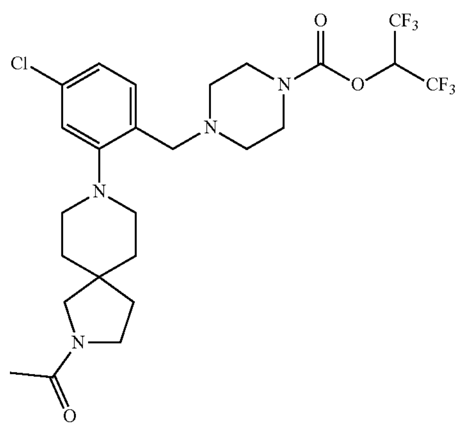 [SMILES: CC(=O)N1CCC2(CCN(c3cc(Cl)ccc3CN3CCN(C(=O)OC(C(F)(F)F)C(F)(F)F)CC3)CC2)C1] | 1,1,1,3,3,3-Hexafluoropropan-2-yl 4-(2-acetyl-2,8-diazaspiro[4.5]decan-8-yl)-4-chlorobenzyl)piperazine-1-carboxylate | (Chloroform-d) δ 7.36-7.40 (m, 1H), 7.06 (d, J = 7.6 Hz, 2H), 5.72-5.78 (m, 1H), 3.52-3.58 (m, 8H), 3.42 (m, 1H), 3.33 (m, 1H), 2.91-2.97 (m, 2H), 2.81-2.87 (m, 2H), 2.50 (s,4H), 2.06-2.07 (m, 3H), 1.81-1.92 (m, 2H), 1.69-1.74 (m, 4H) | 585 |

| Ex | Structure | Name | NMR (¹H NMR, 300 MHz or 400 MHz, Methanol-d4) | MS [M+ H]⁺ |
|---|---|---|---|---|
| 179 | 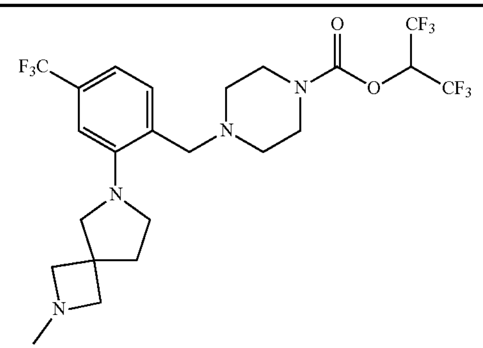 | 1,1,1,3,3,3-Hexafluoropropan-2-yl 4-(2-(2-methyl-2,6-diazaspiro[3.4]octan-6-yl)-4-(trifluoromethyl)benzyl)piperazine-1-carboxylate | (Chloroform-d) δ 7.51 (d, J = 8.1 Hz, 1H), 7.12 (d, J = 8.1 Hz, 1H), 7.05 (s, 1H), 5.71-5.79 (m, 1H), 3.56 (s,6H), 3.39 (s, 2H), 3.23,3.30 (m, 6H), 2.42-2.48 (m, 4H), 2.37 (s, 3H), 2.15 (t, J = 6.8 Hz, 2H) | 563 |
| 180 | 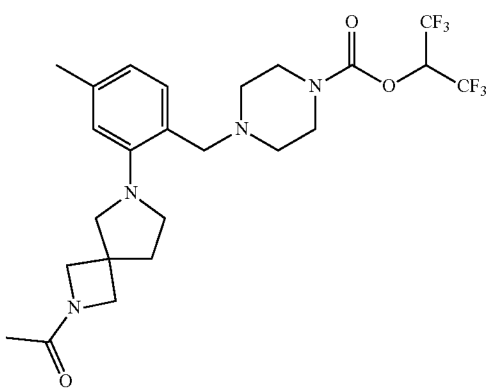 [SMILES: CC(=O)N1CC2(CCN(c3cc(C)ccc3CN3CCN(C(=O)OC(C(F)(F)F)C(F)(F)F)CC3)C2)C1] | 1,1,1,3,3,3-Hexafluoropropan-2-yl 4-(2-(2-acetyl-2,6-diazaspiro[3.4]octan-6-yl)-4-(trifluoromethyl)benzyl)piperazine-1-carboxylate | (Chloroform-rf) δ 7.53 (d, J = 7.8 Hz, 1H), 7.17 (d, J = 8.1 Hz, 1H), 7.08 (s, 1H), 5.71-5.79 (m, 1H), 4.10-4.13 (m, 2H), 3.96-4.07 (m, 2H), 3.55 (s, 6H), 3.28-3.50 (m, 4H), 2.46 (s, 4H), 2.20 (t, J = 6.9 Hz, 2H), 1.90 (s, 3H) | 591 |
| 181 | 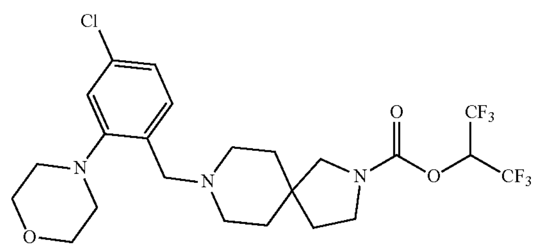 [SMILES: O=C(OC(C(F)(F)F)C(F)(F)F)N1CCC2(CCN(Cc3ccc(Cl)cc3N3CCOCC3)CC2)C1] | 1,1,1,3,3,3-Hexafluoropropan-2-yl 8-(4-chloro-2-morpholinobenzyl)-2,8-diazaspiro[4.5]decane-2-carboxylate | (Chloroform-d) δ 7.41-7.34 (m, 1H), 7.10-7.01 (m, 2H), 5.82-5.70 (m, 1H), 3.91-3.81 (m, 4H), 3.59-3.47 (m, 4H), 3.37-3.27 (m, 2H), 3.05-2.95 (m, 4H), 2.62-2.27 (m, 4H), 1.85-1.76 (m, 2H), 1.65-1.52 (m, 4H) | 544 |

| Ex | Structure | Name | NMR (¹H NMR, 300 MHz or 400 MHz, Methanol-d4) | MS [M+ H]⁺ |
|---|---|---|---|---|
| 182 | 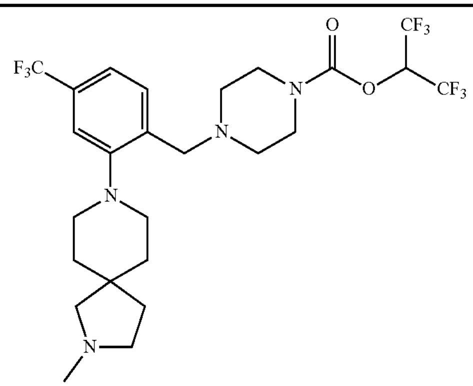 | 1,1,1,3,3,3-Hexafluoropropan-2-yl 4-(2-(2-methyl-2,8-diazaspiro[4.5]decan-8-yl)-4-(trifluoromethyl)benzyl)piperazine-1-carboxylate | (Chloroform-d) δ 7.58 (d, J = 8.1 Hz, 1H), 7.28-7.30 (m, 2H), 5.71-5.81 (m, 1H), 3.55-3.60 (m, 6H), 2.86 (t, J = 5.1 Hz, 4H), 2.60 (t, J = 6.6 Hz, 2H), 2.46-2.49 (m, 6H), 2.36 (s, 3H), 1.71-1.87 (m, 6H) | 591 |
| 183 | 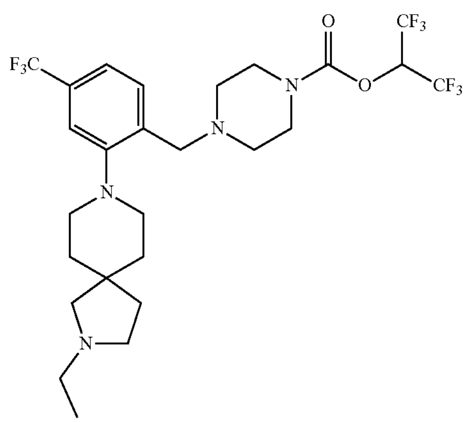 [SMILES: CCN1CCC2(CCN(c3cc(C(F)(F)F)ccc3CN3CCN(C(=O)OC(C(F)(F)F)C(F)(F)F)CC3)CC2)C1] | 1,1,1,3,3,3-Hexafluoropropan-2-yl 4-(2-(2-ethyl-2,8-diazaspiro[4.5]decan-8-yl)-4-(trifluoromethyl)benzyl)piperazine-1-carboxylate | (Chloroform-d) δ 7.59 (d, J = 7.8 Hz, 1H), 7.28-7.32 (m, 2H), 5.69-5.81 (m, 1H), 3.54-3.59 (m, 6H), 2.72-2.88 (m, 10H), 2.48-2.49 (m, 4H), 1.81-1.90 (m, 6H), 1.27 (t, 7 = 7.2 Hz, 3H) | 605 |

| Ex | Structure | Name | NMR (¹H NMR, 300 MHz or 400 MHz, Methanol-d4) | MS [M+ H]⁺ |
|---|---|---|---|---|
| 184 | 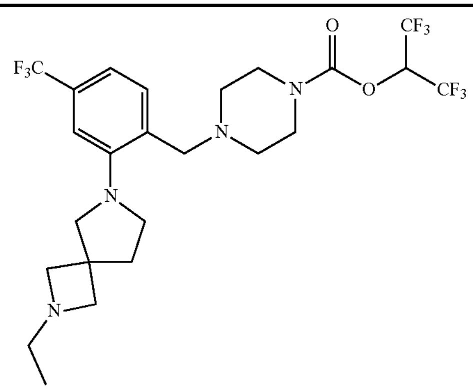 | 1,1,1,3,3,3-Hexafluoropropan-2-yl 4-(2-ethyl-2,6-diazaspiro[3.4]octan-6-yl)-4-(trifluoromethyl)benzyl)piperazine-1-carboxylate | (Chloroform-d) δ 7.52 (d, J = 7.8 Hz, 1H), 7.12 (d, J = 8.1 Hz, 1H), 7.05 (s, 1H), 5.70-5.79 (m, 1H), 3.56 (s,6H), 3.40 (s, 2H), 3.24-3.28 (m, 6H), 2.45-2.54 (m, 6H), 2.15 (t, J = 6.9 Hz, 2H), 1.00 (t, J = 7.0 Hz, 3H) | 577 |
| 185 | 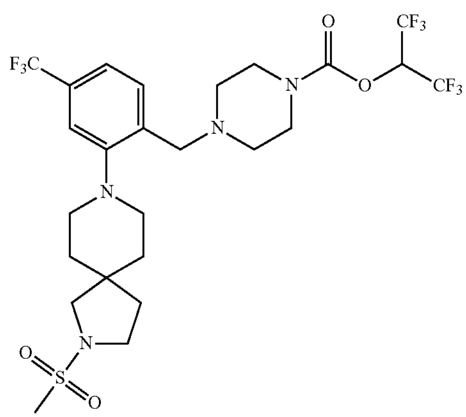 [SMILES: CS(=O)(=O)N1CCC2(CCN(c3cc(C(F)(F)F)ccc3CN3CCN(C(=O)OC(C(F)(F)F)C(F)(F)F)CC3)CC2)C1] | 1,1,1,3,3,3-Hexafluoropropan-2-yl 4-(2-(2-(methylsulfonyl)-2,8-diazaspiro[4.5]decan-8-yl)-4-(trifluoro methyl)benzyl)piperazine-1-carboxylate | (Chloroform-d) δ 7.59 (d, J = 7.8 Hz, 1H), 7.30-7.34 (m, 2H), 5.71-5.79 (m, 1H), 3.56-3.60 (m, 6H), 3.45 (t, J = 7.0 Hz, 2H), 3.27 (s, 2H), 2.87-2.98 (m, 7H), 2.48-2.50 (m, 4H), 1.91 (t, J = 7.2 Hz, 2H), 1.72-1.77 (m, 4H) | 655 |

-continued

| Ex | Structure | Name | NMR (¹H NMR, 300 MHz or 400 MHz, Methanol-d4) | MS [M+ H]⁺ |
|---|---|---|---|---|
| 186 | 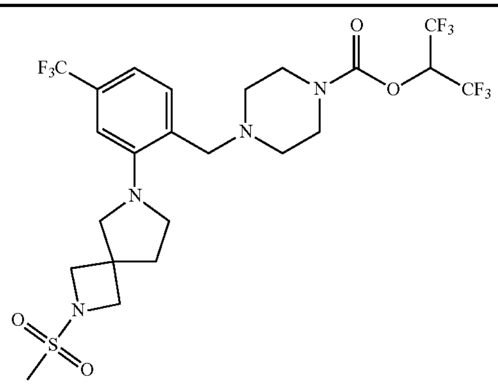 | 1,1,1,3,3,3-Hexafluoropropan-2-yl 4-(2-(2-(methylsulfonyl)-2,6-diazaspiro[3.4]octan-6-yl)-4-(trifluoromethyl)benzyl)piperazine-1-carboxylate | (Chloroform-0 δ 7.53 (d, J = 8.1 Hz, 1H), 7.17 (d, J = 8.1 Hz, 1H), 7.08 (s, 1H), 5.71-5.79 (m, 1H), 3.93 (s, 4H), 3.46-3.68 (m, 8H), 3.30 (t, J = 6.9 Hz, 2H), 2.88 (s, 3H), 2.46 (s, 4H), 2.21 (t, J = 6.9 Hz, 2H) | 627 |
| 187 | 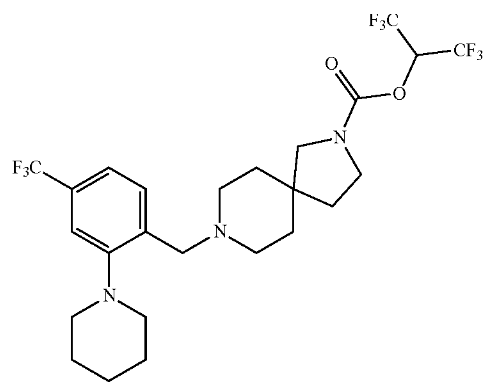 [SMILES: O=C(OC(C(F)(F)F)C(F)(F)F)N1CCC2(CCN(Cc3ccc(C(F)(F)F)cc3N3CCCCC3)CC2)C1] | 1,1,1,3,3,3-Hexafluoropropan-2-yl 8-(2-(piperidin-1-yl)-4-(trifluoromethyl)benzyl)-2,8-diazaspiro[4.5]decane-2-carboxylate | (Chloroform-d) δ 7.52 (d, J = 8.0 Hz, 1H), 7.21 (d, J = 6.3 Hz, 2H), 5.67 (m, 1H), 3.57-3.40 (m, 4H), 3.24 (d, J = 14.2 Hz, 2H), 2.85-2.72 (m, 4H), 2.37 (d, J = 70.6 Hz, 4H), 1.77-1.70 (m, 2H), 1.68-1.61 (m, 4H), 1.57-1.47 (m, 6H) | 576 |

| Ex | Structure | Name | NMR (¹H NMR, 300 MHz or 400 MHz, Methanol-d4) | MS [M+ H]⁺ |
|---|---|---|---|---|
| 188 | 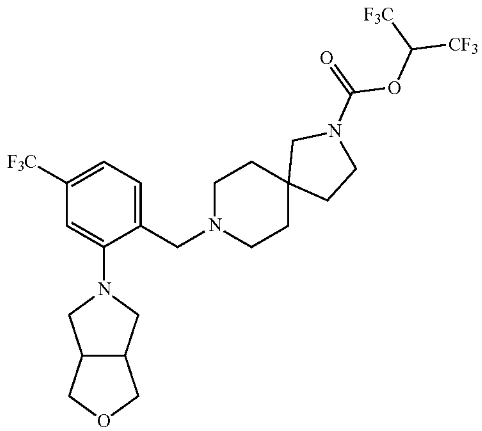 [SMILES: O=C(OC(C(F)(F)F)C(F)(F)F)N1CCC2(CCN(Cc3ccc(C(F)(F)F)cc3N3CC4COCC4C3)CC2)C1] | 1,1,1,3,3,3-Hexafluoropropan-2-yl 8-(2-(tetrahydro-1H-furo[3,4-c]pyrrol-5(3H)-yl)-4-(trifluoromethyl)benzyl)-2,8-diazaspiro[4.5]decane-2-carboxylate | (Chloroform-d) δ 7.52 (d, J = 7.5 Hz, 1H), 7.22-7.15 (m, 2H), 5.74-5.60 (m, 1H), 4.02-3.90 (m, 2H), 3.64-3.38 (m, 6H), 3.30-3.18 (m, 2H), 3.12-2.83 (m, 6H), 2.55-2.18 (m, 4H), 1.81-1.69 (m, 2H) | 604 |
| 189 | 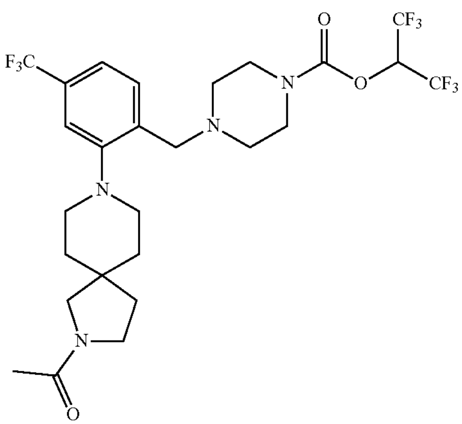 [SMILES: CC(=O)N1CCC2(CCN(c3cc(C(F)(F)F)ccc3CN3CCN(C(=O)OC(C(F)(F)F)C(F)(F)F)CC3)CC2)C1] | 1,1,1,3,3,3-Hexafluoropropan-2-yl 4-(2-acetyl-2,8-diazaspiro[4.5]decan-8-yl)-4-(trifluoromethyl)benzyl)piperazine-1-carboxylate | (Chloroform-d) δ 7.60 (s, 1H), 7.32 (s, 2H), 5.71-5.79 (m, 1H), 3.44-3.59 (m, 8H), 3.35 (s, 2H), 2.85-3.01 (m, 4H), 2.50 (s, 4H), 2.30-2.31 (m, 3H), 1.82-1.94 (m, 2H), 1.73-1.77 (m, 4H) | 619 |

| Ex | Structure | Name | NMR (¹H NMR, 300 MHz or 400 MHz, Methanol-d4) | MS [M+ H]⁺ |
|---|---|---|---|---|
| 190 | 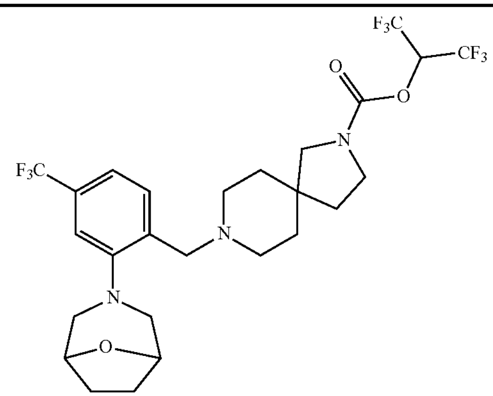 | 1,1,1,3,3,3-Hexafluoropropan-2-yl 8-(2-(8-oxa-3-azabicyclo[3.2.1]octan-3-yl)-4-(trifluoromethyl)benzyl)-2,8-diazaspiro[4.5]decane-2-carboxylate | (Chloroform-d) δ 7.57-7.45 (m, 1H), 7.32-7.22 (m, 2H), 5.74-5.60 (m, 1H), 4.42-4.30 (m, 2H), 3.58-3.50 (m, 2H), 3.51-3.40 (m, 2H), 3.25 (d, J = 16.1 Hz, 2H), 3.05-2.95 (m, 2H), 2.86-2.72 (m, 2H), 2.55-2.37 (m, 2H), 2.37-2.17 (m, 2H), 2.13-2.02(m, 2H), 1.99-1.87 (m, 2H), 1.80-1.70 (m, 2H), 1.59-1.46 (m, 4H) | 604 |
| 191 | 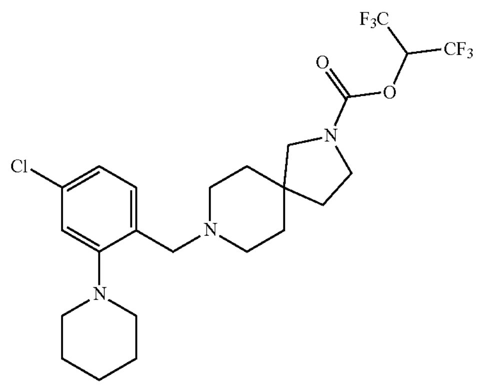 [SMILES: O=C(OC(C(F)(F)F)C(F)(F)F)N1CCC2(CCN(Cc3ccc(Cl)cc3N3CCCCC3)CC2)C1] | 1,1,1,3,3,3-Hexafluoropropan-2-yl 8-(4-chloro-2-(piperidin-1-yl)benzyl)-2,8-diazaspiro[4.5]decane-2-carboxylate | (Chloroform-d) δ 7.35-7.26 (m, 1H), 6.96-6.88 (m, 2H), 5.74-5.60 (m, 1H), 3.49-3.39 (m, 4H), 3.22 (d, J = 13.9 Hz, 2H), 2.84-2.69 (m, 4H), 2.53-2.17 (m, 4H), 1.77-1.68 (m, 2H), 1.67-1.56 (m, 4H), 1.56-1.43 (m, 6H) | 542 |

| Ex | Structure | Name | NMR (1H NMR, 300 MHz or 400 MHz, Methanol-d4) | MS [M+ H]+ |
|---|---|---|---|---|
| 192 | 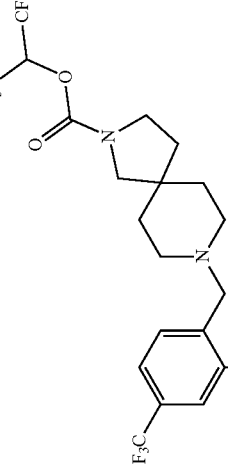 | 1,1,1,3,3,3-Hexafluoropropan-2-yl 8-(2-(4-fluoropiperidin-1-yl)-4-(trifluoromethyl)benzyl)-2,8-diazaspiro[4.5]decane-2-carboxylate | (Chloroform-d) δ 7.65-7.56 (m, 1H), 7.36-7.30 (m, 2H), 5.83-5.69 (m, 1H), 4.95-4.71 (m, 1H), 3.63,3.50(m, 4H), 3.33 (d, J = 13.8 Hz, 2H), 3.21-3.10 (m, 2H), 2.96-2.84 (m, 2H), 2.64-2.45 (m, 2H), 2.47-2.29 (m, 2H), 2.16-1.96 (m, 4H), 1.89-1.78 (m, 2H), 1.68-1.54 (m, 4H) | 594 |
| 193 | 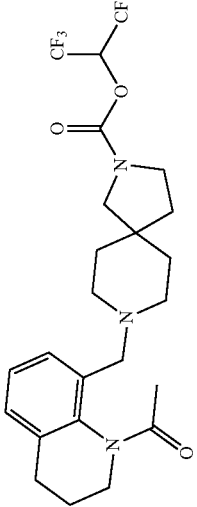 | 1,1,1,3,3,3-Hexafluoropropan-2-yl 8-((1-acetyl-1,2,3,4-tetrahydroquinolin-8-yl)methyl)-2,8-diazaspiro[4.5]decane-2-carboxylate | (DMSO-d6) δ 7.31 (s, 1H), 7.10 (s, 2H), 6.29-6.20 (m, 1H), 4.58-4.04 (m, 1H), 3.44-3.34 (m, 4H), 3.20 (s, 2H), 2.62 (s, 2H), 2.40-1.44 (m, 16H) | 522 |
| 194 | 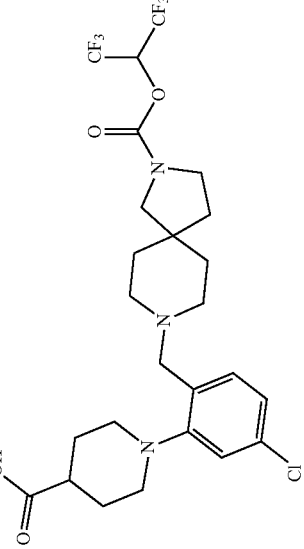 | 1-(5-Chloro-2-(((((1,1,1,3,3,3-hexafluoropropan-2-yl)oxy)carbonyl)-2,8-diazaspiro[4.5]decan-8-yl)methyl)phenyl)piperidine-4-carboxylic acid | (Chloroform-d) δ 7.48 - 7.29 (m, 1H), 7.14-6.99 (m, 2H), 5.76-5.69 (m, 1H), 3.81 (s, 2H), 3.64-3.35 (m, 4H), 3.17 -3.06 (m, 2H), 2.97-2.47 (m, 6H), 2.61-2.41 (m, 1H), 2.06 -2.03 (m, 2H), 1.94-1.86 (m, 2H), 1.73-1.60 (m, 2H), 1.60 -1.45 (m, 4H) | 586 |

-continued

| Ex | Structure | Name | NMR (¹H NMR, 300 MHz or 400 MHz, Methanol-d4) | MS [M+ H]⁺ |
|---|---|---|---|---|
| 195 | F₃C-[structure with piperidine-4-carboxylic acid, benzyl linker, 2,8-diazaspiro[4.5]decane, and CF₃-ethyl carbamate] | 1-(2-((2-(((1,1,1,3,3,3-Hexafluoropropan-2-yl)oxy)carbonyl)-2,8-diazaspiro[4.5]decan-8-yl)methyl)-5-(trifluoromethyl)phenyl)piperidine-4-carboxylic acid | (Chloroform-d) δ 7.66-7.60 (m, 1H), 7.29-7.26 (m, 2H), 5.75-5.68 (m, 1H), 3.78-3.45 (m, 4H), 3.39-3.26 (m, 2H), 3.19-3.07 (m, 2H), 2.78-2.71 (m, 2H), 2.66-2.24 (m, 5H), 2.16-2.00 (m, 2H), 1.99-1.88 (m, 2H), 1.82-1.78 (m, 2H), 1.78-1.46(m, 4H) | 620 |
| 196 | F₃C-[structure with methylsulfonyl-piperazine, benzyl linker, 2,8-diazaspiro[4.5]decane, and CF₃-ethyl carbamate] | 1,1,1,3,3,3-Hexafluoropropan-2-yl 4-(2-(8-(methylsulfonyl)-2,8-diazaspiro[4.5]decan-2-yl)-4-(trifluoromethyl)benzyl)piperazine-1-carboxylate | (Chloroform-d) δ 7.48-7.40 (m, 1H), 7.09-7.04 (m, 1H), 7.03 -6.98 (m, 1H), 5.73-5.62 (m, 1H), 3.55-3.41 (m, 6H), 3.30-3.13 (m, 6H), 3.05 (s, 2H), 2.74 (s, 3H), 2.43-2.32 (m, 4H), 1.82-1.67 (m, 6H) | 655 |

| Ex | Structure | Name | NMR (¹H NMR, 300 MHz or 400 MHz, Methanol-d4) | MS [M+ H]⁺ |
|---|---|---|---|---|
| 197 | 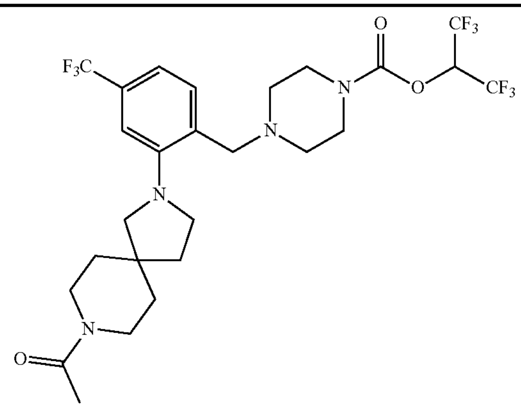 | 1,1,1,3,3,3-Hexafluoropropan-2-yl 4-(2-(8-acetyl-2,8-diazaspiro[4.5]decan-2-yl)-4-(trifluoromethyl)benzyl)piperazine-1-carboxylate | (Chlorofom-d) δ 7.53-7.48 (m, 1H), 7.17-7.11 (m, 1H), 7.11-7.06 (m, 1H), 5.83-5.71 (m, 1H), 3.69-3.60 (m, 2H), 3.61-3.52 (m, 6H), 3.52-3.44 (m, 2H), 3.39-3.31 (m, 2H), 3.21 -3.12 (m, 2H), 2.52-2.43 (m, 4H), 2.13 (s, 3H), 1.90-1.82 (m, 2H), 1.73-1.61 (m, 4H) | 618 |
| 198 | 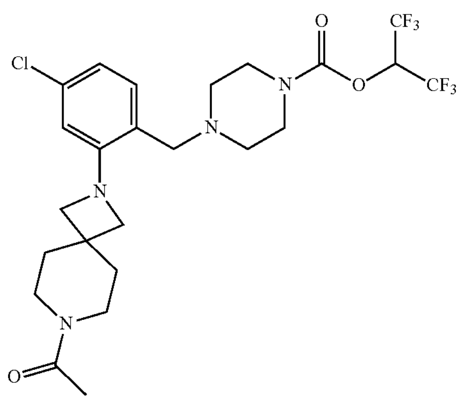 [SMILES: CC(=O)N1CCC2(CC1)CN(c1cc(Cl)ccc1CN1CCN(C(=O)OC(C(F)(F)F)C(F)(F)F)CC1)C2] | 1,1,1,3,3,3-Hexafluoropropan-2-yl 4-(2-(7-acetyl-2,7-diazaspiro[3.5] nonan-2-yl)-4-chlorobenzyl)piperazine-1-carboxylate | (Chlorofom-d) δ 7.17-7.07 (m, 1H), 6.76-6.70 (m, 1H), 6.43 (s, 1H), 5.82-5.70 (m, 1H), 3.77 (s, 4H), 3.63-3.52 (m, 6H), 3.48-3.35 (m, 4H), 2.51-2.39 (m, 4H), 2.13 (s, 3H), 1.89-1.76 (m, 4H) | 571 |

| Ex | Structure | Name | NMR (¹H NMR, 300 MHz or 400 MHz, Methanol-d4) | MS [M+ H]⁺ |
|---|---|---|---|---|
| 199 | 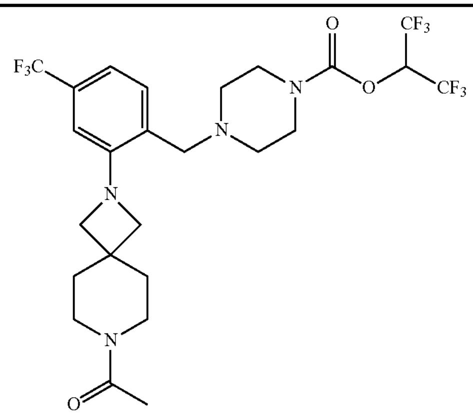 | 1,1,1,3,3,3-Hexafluoropropan-2-yl 4-(2-(7-acetyl-2,7-diazaspiro[3.5]nonan-2-yl)-4-(trifluoromethyl)benzyl)piperazine-1-carboxylate | (Chloroform-d) δ 7.40-7.32 (m, 1H), 7.05-6.99 (m, 1H), 6.66 (s, 1H), 5.82-5.72 (m, 1H), 3.80 (s, 4H), 3.65-3.53 (m, 6H), 3.52-3.43 (m, 4H), 2.56-2.38 (m, 4H), 2.14 (d, J = 1.2 Hz, 3H), 1.90-1.79 (m, 4H) | 605 |
| 200 | 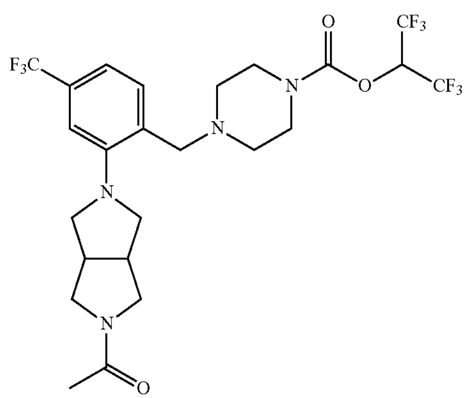 [SMILES: CC(=O)N1CC2CN(c3cc(C(F)(F)F)ccc3CN3CCN(C(=O)OC(C(F)(F)F)C(F)(F)F)CC3)CC2C1] | 1,1,1,3,3,3-Hexafluoropropan-2-yl 4-(2-(5-acetylhexahydropyrrolo[3,4-c]pyrrol-2(1H)-yl)-4-(trifluoromethyl)benzyl)piperazine-1-carboxylate | (Chloroform-d) δ 7.62-7.51 (s, 1H), 7.28-7.20 (m, 1H), 7.17 (s, 1H), 5.79-5.69 (m, 1H), 3.90-3.75 (m, 2H), 3.70-3.45 (m, 7H), 3.43-3.31 (m, 2H), 3.30-3.15 (m, 2H), 3.15-2.92 (m, 3H), 2.45 (s, 4H), 2.08 (s, 3H) | 591 |

| Ex | Structure | Name | NMR (¹H NMR, 300 MHz or 400 MHz, Methanol-d4) | MS [M+ H]⁺ |
|---|---|---|---|---|
| 201 | 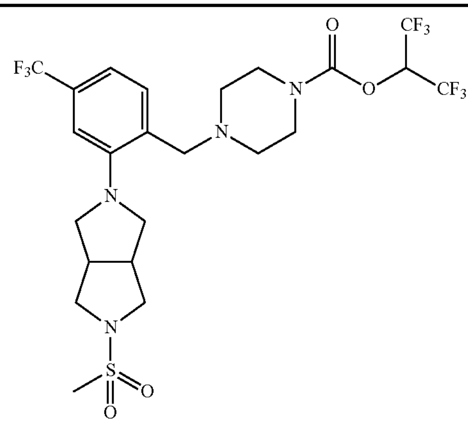 | 1,1,1,3,3,3-Hexafluoropropan-2-yl 4-(2-(5-(methylsulfonyl)hexahydropyrrolo[3,4-c]pyrrol-2(1H)-yl)-4-(trifluoromethyl)benzyl)piperazinc-1-carboxylate | (DMSO-d₆) δ 7.61 (d, J= 7.8 Hz, 1H), 7.29 (d, J = 8.1 Hz, 1H), 7.21 (s, 1H), 5.60-5.50 (m, 1H), 3.60 (s, 2H), 3.52 -3.40 (m, 6H), 3.25-3.15 (m, 2H), 3.14-3.04 (m, 4H), 3.02 -2.93 (s, 2H), 2.91 (s, 3H), 2.42 (s, 4H) | 627 |
| 202 | 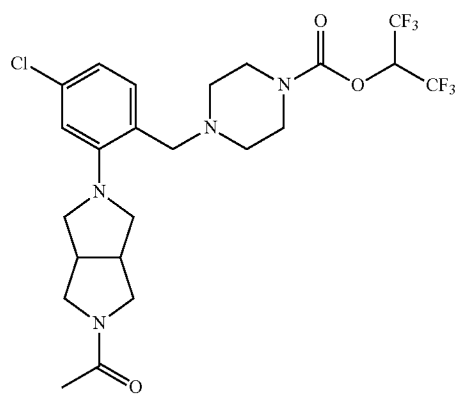 [SMILES: CC(=O)N1CC2CN(c3cc(Cl)ccc3CN3CCN(C(=O)OC(C(F)(F)F)C(F)(F)F)CC3)CC2C1] | 1,1,1,3,3,3-Hexafluoropropan-2-yl 4-(2-(5-acetylhexahydropyrrolo[3,4-c]pyrrol-2(1H)-yl)-4-chlorobenzyl)piperazine-1-carboxylate | (Chloroform-d) δ 7.45 (s, 1H), 7.05-6.95 (m, 2H), 5.79-5.69 (m, 1H), 3.90-3.40 (m, 10H), 3.35-3.30 (m, 2H), 3.30-2.85 (m, 5H), 2.52 (s, 3H), 2.09 (s, 3H) | 557 |

| Ex | Structure | Name | NMR (¹H NMR, 300 MHz or 400 MHz, Methanol-d4) | MS [M+ H]⁺ |
|---|---|---|---|---|
| 203 | 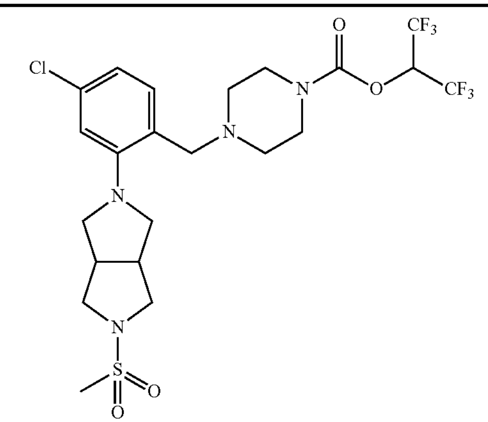 | 1,1,1,3,3,3-Hexafluoropropan-2-yl 4-(4-chloro-2-(5-(methylsulfonyl)hexahydropyrrolo[3,4-c]pyrrol-2(1H)-yl)benzyl)piperazine-1-carboxylate | (Chloroform-d) δ 5 7.37 (s, 1H), 7.05-6.95 (m, 2H), 5.79-5.69 (m, 1H), 3.75-3.40 (m, 8H), 3.35-2.95 (m, 9H), 2.83 (s, 3H), 2.45 (s, 3H) | 593 |
| 204 | 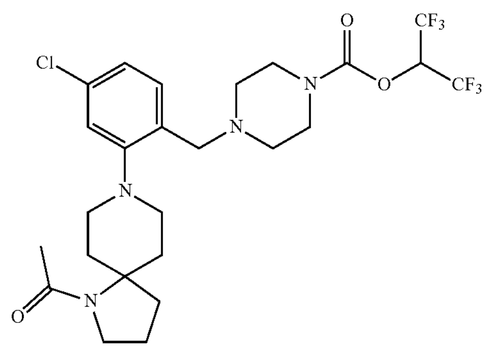 [SMILES: CC(=O)N1CCCC12CCN(c1cc(Cl)ccc1CN1CCN(C(=O)OC(C(F)(F)F)C(F)(F)F)CC1)CC2] | 1,1,1,3,3,3-Hexafluoropropan-2-yl 4-(2-(1-acetyl-1,8-diazaspiro[4.5]decan-8-yl)-4-chlorobenzyl)piperazine-1-carboxylate | (Chloroform-d) δ 7.31 (d, J = 7.9 Hz, 1H), 7.05-6.96 (m, 2H), 5.81-5.69 (m, 1H), 3.61 -3.42 (m, 8H), 3.31-3.09 (m, 4H), 2.69 (t, J = 11.9 Hz, 2H), 2.51 (s, 4H), 2.06 (s, 3H), 2.06 -1.94 (m, 2H), 1.92-1.83 (m, 2H), 1.32 (d, J = 11.9 Hz, 2H) | 585 |

-continued
| Ex | Structure | Name | NMR (¹H NMR, 300 MHz or 400 MHz, Methanol-d4) | MS [M+ H]⁺ |
|---|---|---|---|---|
| 205 | 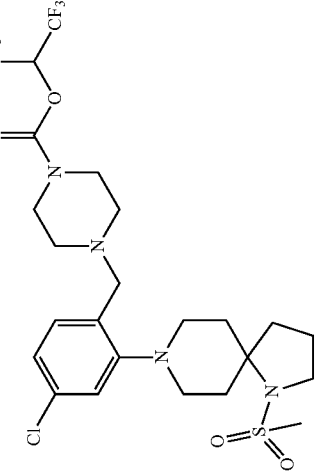 | 1,1,1,3,3,3-Hexafluoropropan-2-yl 4-(4-chloro-2-(1-(methylsulfonyl)-1,8-diazaspiro[4.5]decan-8-yl)benzyl)piperazine-1-carboxylate | (Chloroform-d) δ 7.31 (s, 1H), 7.02 (s, 2H), 5.81-5.69 (m, 1H), 3.61-3.39 (m, 8H), 3.21-3.09 (m, 2H), 2.90 (s, 3H), 2.82-2.40 (m, 8H), 2.10-2.00 (m, 2H), 1.97-1.85 (m, 2H), 1.66-1.55 (m, 2H) | 621 |
| 206 | 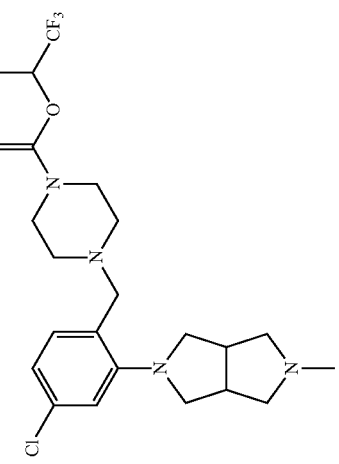 | 1,1,1,3,3,3-Hexafluoropropan-2-yl 4-(4-chloro-2-(5-methylhexahydropyrrolo[3,4-c]pyrrol-2(1H)-yl)benzyl)piperazine-1-carboxylate | (Chloroform-d) δ 7.35 (d, J = 8.0 Hz, 1H), 7.05-6.95 (m, 2H), 5.79-5.71 (m, 1H), 3.55-3.51 (m, 6H), 3.10-3.00 (m, 2H), 2.98-2.92 (m, 2H), 2.90-2.82 (m, 4H), 2.43 (s, 4H), 2.36 (s, 3H), 2.35-2.28 (d, J = 4.2 Hz, 2H) | 529 |

-continued

| Ex | Structure | Name | NMR (¹H NMR, 300 MHz or 400 MHz, Methanol-d4) | MS [M+ H]⁺ |
|---|---|---|---|---|
| 207 | 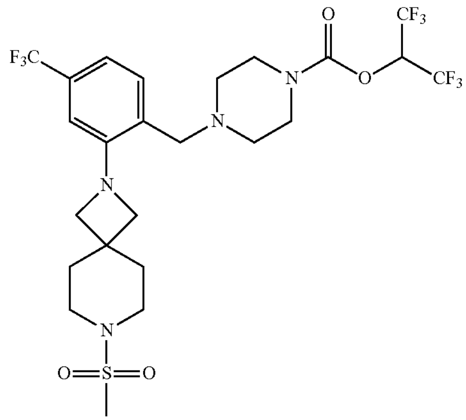 [SMILES: CS(=O)(=O)N1CCC2(CC1)CN(c1cc(C(F)(F)F)ccc1CN1CCN(C(=O)OC(C(F)(F)F)C(F)(F)F)CC1)C2] | 1,1,1,3,3,3-Hexafluoropropan-2-yl 4-(2-(7-(methylsulfonyl)-2,7-diazaspiro[3.5]nonan-2-yl)-4-(trifluoromethyl)benzyl)piperazine-1-carboxylate | (Chloroform-d) δ 7.39-7.32 (m, 1H), 7.07-7.00 (m, 1H), 6.67-6.63 (m, 1H), 5.82-5.72 (m, 1H), 3.80 (s,4H), 3.63-3.55 (m, 4H), 3.47(s, 2H), 3.31-3.23 (m, 4H), 2.82 (s, 3H), 2.53-2.42 (m, 4H), 2.03-1.94 (m, 4H) | 641 |
| 208 | 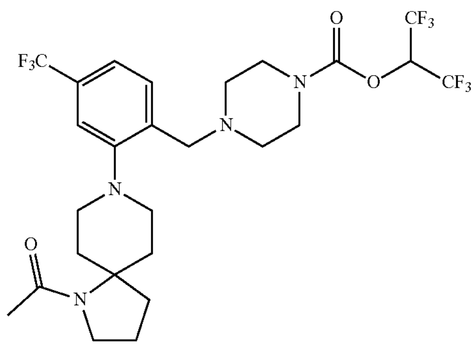 [SMILES: CC(=O)N1CCCC12CCN(c1cc(C(F)(F)F)ccc1CN1CCN(C(=O)OC(C(F)(F)F)C(F)(F)F)CC1)CC2] | 1,1,1,3,3,3-Hexafluoropropan-2-yl 4-(2-(1-acetyl-1,8-diazaspiro[4.5]decan-8-yl)-4-(trifluoromethyl)benzyl)piperazine-1-carboxylate | (Chloroform-d) δ 7.55 (s, 1H), 7.31 (s, 2H), 5.81-5.73 (m, 1H), 3.65 (s, 2H), 3.60-3.45 (m, 6H), 3.31-3.24 (m, 2H), 3.23-3.12 (m, 2H), 2.85-2.71 (m, 2H), 2.54 (s, 4H), 2.08 (s, 3H), 2.06-1.94 (m, 2H), 1.92-1.38 (m, 2H), 1.36 (d, J = 11.9 Hz, 2H) | 619 |

| Ex | Structure | Name | NMR (¹H NMR, 300 MHz or 400 MHz, Methanol-d4) | MS [M+ H]⁺ |
|---|---|---|---|---|
| 209 | 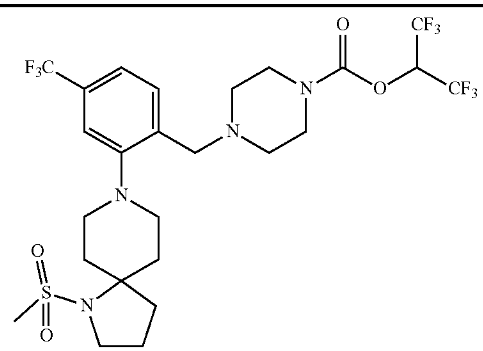 | 1,1,1,3,3,3-Hexafluoropropan-2-yl 4-(2-(1-(methylsulfonyl)-1,8-diazaspiro[4.5]decan-8-yl)-4-(trifluoromethyl)benzyl)piperazine-1-carboxylate | (Chloroform-d) δ 7.55 (s, 1H), 7.31 (s, 2H), 5.81-5.73 (m, 1H), 3.65-3.45 (m, 8H), 3.17 (s, 2H), 2.93 (s, 3H), 2.85-2.75 (m, 4H), 2.54 (s, 4H), 2.13-2.06 (m, 2H), 2.01-1.90 (m, 2H), 1.73-1.61 (m, 2H) | 655 |
| 210 | 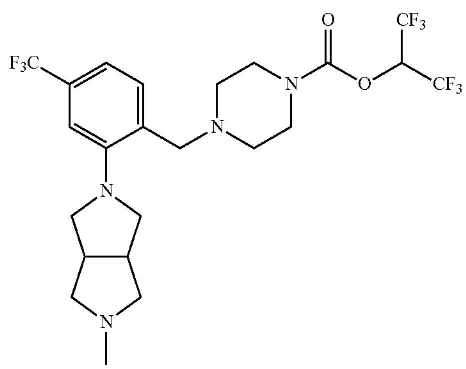 [SMILES: CN1CC2CN(c3cc(C(F)(F)F)ccc3CN3CCN(C(=O)OC(C(F)(F)F)C(F)(F)F)CC3)CC2C1] | 1,1,1,3,3,3-Hexafluoropropan-2-yl 4-(2-(5-methylhexahydropyrrolo[3,4-c]pyrrol-2(1H)-yl)-4-(trifluoromethyl)benzyl)piperazine-1-carboxylate | (Chloroform-d) δ 7.60 (d, J = 7.89 Hz, 1H), 7.30 (s, 1H), 7.29 (s, 1H), 5.80-5.70 (m, 1H), 3.64-3.55 (m, 6H), 3.15-3.05 (m, 2H), 3.02-2.88 (m, 6H), 3.52-3.44 (m, 4H), 2.41 (s, 5H) | 563 |

-continued

| Ex | Structure | Name | NMR (¹H NMR, 300 MHz or 400 MHz, Methanol-d4) | MS [M+ H]⁺ |
|---|---|---|---|---|
| 211 | 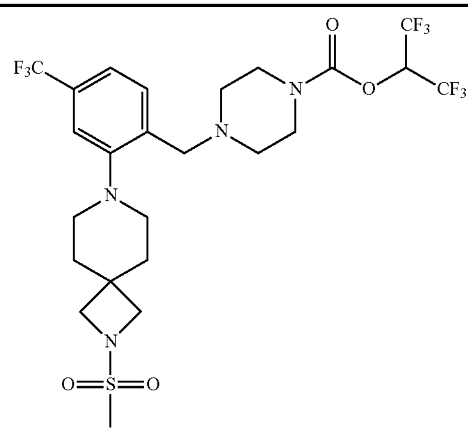 | 1,1,1,3,3,3-Hexafluoropropan-2-yl 4-(2-(2-(methylsulfonyl)-2,7-diazaspiro[3.5]nonan-7-yl)-4-(trifluoromethyl)benzyl)piperazine-1-carboxylate | (Chloroform-of) δ 7.67-7.54 (m, 1H), 7.43-7.30 (m, 1H), 7.28-7.22 (m, 1H), 5.83-5.70 (m, 1H), 3.81-3.72 (m, 4H), 3.70-3.34 (m, 6H), 2.97-2.79 (m, 7H), 2.58-2.40 (m, 4H), 2.05-1.91 (m, 4H) | 641 |
| 212 | 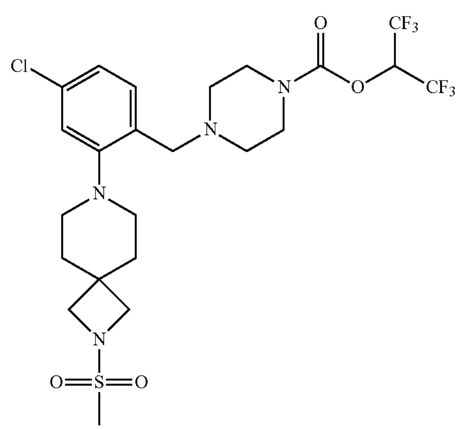 [SMILES: CS(=O)(=O)N1CC2(CCN(c3cc(Cl)ccc3CN3CCN(C(=O)OC(C(F)(F)F)C(F)(F)F)CC3)CC2)C1] | 1,1,1,3,3,3-Hexafluoropropan-2-yl 4-(4-chloro-2-(2-(methylsulfonyl)-2,7-diazaspiro[3.5]nonan-7-yl)benzyl)piperazine-1-carboxylate | (Chloroform-of) δ 7.43-7.35 (m, 1H), 7.12-6.99 (m, 2H), 5.82-5.72 (m, 1H), 3.78-3.72 (m, 4H), 3.61-3.49 (m, 6H), 2.93-2.89 (m, 3H), 2.89-2.80 (m, 4H), 2.55-2.42 (m, 4H), 2.02-1.91 (m, 4H) | 607 |

| Ex | Structure | Name | NMR (¹H NMR, 300 MHz or 400 MHz, Methanol-d4) | MS [M+ H]⁺ |
|---|---|---|---|---|
| 213 | 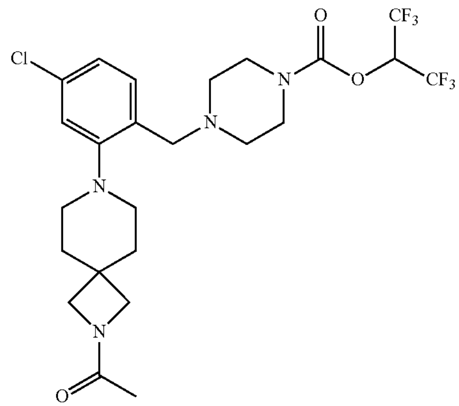 [SMILES: CC(=O)N1CC2(CCN(c3cc(Cl)ccc3CN3CCN(C(=O)OC(C(F)(F)F)C(F)(F)F)CC3)CC2)C1] | 1,1,1,3,3,3-Hexafluoropropan-2-yl 4-(2-acetyl-2,7-diazaspiro[3.5]nonan-7-yl)-4-chlorobenzyl)piperazine-1-carboxylate | (Chloroform-d) δ 7.35-7.25 (m, 1H), 7.02-6.90 (m, 2H), 5.73-5.61 (m, 1H), 3.83-3.76 (m, 2H), 3.73, 3.66 (m, 2H), 3.55-3.37 (m, 6H), 2.76 (s, 4H), 2.40 (s, 4H), 1.86-1.80 (m, 7H) | 571 |
| 214 | 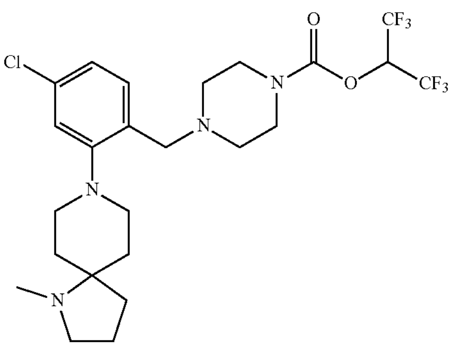 [SMILES: CN1CCCC12CCN(c1cc(Cl)ccc1CN1CCN(C(=O)OC(C(F)(F)F)C(F)(F)F)CC1)CC2] | 1,1,1,3,3,3-Hexafluoropropan-2-yl 4-(4-chloro-2-(1-methyl-1,8-diazaspiro[4.5]decan-8-yl)benzyl)piperazine-1-carboxylate | (Chloroform-d) δ 7.38 (d, J = 8.1 Hz, 1H), 7.08-7.02 (m, 2H), 5.81-5.69 (m, 1H), 3.61-3.49 (d, J = 11.8 Hz, 2H), 2.83 (t, J = 6.0 Hz, 2H), 2.71 (t, J = 10.7 Hz, 2H), 2.53-2.42 (m, 4H), 2.40 (s,3H), 1.92-1.76 (m, 6H), 1.35 (d, J = 11.8 Hz, 2H) | 557 |

| Ex | Structure | Name | NMR (¹H NMR, 300 MHz or 400 MHz, Methanol-d4) | MS [M+ H]⁺ |
|---|---|---|---|---|
| 215 | 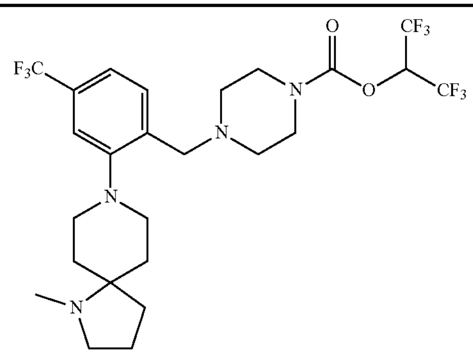 | 1,1,1,3,3,3-Hexafluoropropan-2-yl 4-(2-(1-methyl-1,8-diazaspiro[4.5]decan-8-yl)-4-(trifluoromethyl)benzyl)piperazine-1-carboxylate | (Chloroform-d) δ 7.61 (d, J = 8.2 Hz, 1H), 7.31 (s, 2H), 5.81-5.69(m, 1H), 3.65-3.51 (m, 6H), 3.13 (d, J = 11.8 Hz, 2H), 2.88 (s, 2H), 2.74 (t, J = 10.7 Hz, 2H), 2.52 (s, 4H), 2.42 (s, 3H), 1.95-1.80 (m, 6H), 1.42 (d, J = 11.8 Hz, 2H) | 591 |
| 216 | 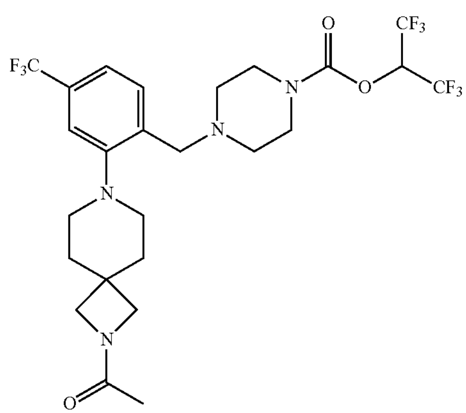 [SMILES: CC(=O)N1CC2(CCN(c3cc(C(F)(F)F)ccc3CN3CCN(C(=O)OC(C(F)(F)F)C(F)(F)F)CC3)CC2)C1] | 1,1,1,3,3,3-Hexafluoropropan-2-yl 4-(2-(2-acetyl-2,7-diazaspiro[3.5]nonan-7-yl)-4-(trifluoromethyl)benzyl)piperazine-1-carboxylate | (Chloroform-d) δ 7.65-7.57 (m, 1H), 7.36-7.31 (m, 1H), 7.28 (s, 1H), 5.82-5.70 (m, 1H), 3.94-3.85 (m, 2H), 3.82-3.73 (m, 2H), 3.64-3.50 (m, 6H), 2.98-2.79 (m, 4H), 2.53-2.44 (m, 4H), 2.01-1.87 (m, 7H) | 605 |

| Ex | Structure | Name | NMR (¹H NMR, 300 MHz or 400 MHz, Methanol-d4) | MS [M+ H]⁺ |
|---|---|---|---|---|
| 217 | 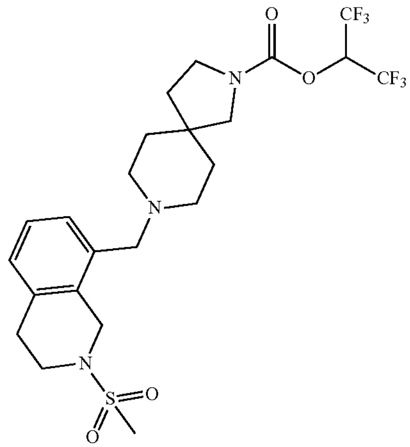 [SMILES: CS(=O)(=O)N1CCc2cccc(CN3CCC4(CC3)CCN(C(=O)OC(C(F)(F)F)C(F)(F)F)C4)c2C1] | 1,1,1,3,3,3-Hexafluoropropan-2-yl 8-((2-(methylsulfonyl)-1,2,3,4-tetrahydroisoquinolin-8-yl)methyl)-2,8-diazaspiro[4.5]decane-2-carboxylate | (Chloroform-d) δ 7.23-7.11 (m, 3H), 5.77-5.71 (m, 1H), 4.65 (s, 2H), 3.59 (t, J = 6.0 Hz, 2H), 3.68 (t, J = 6.0 Hz, 2H), 3.45 (d, J = 6.0 Hz, 2H), 3.32 (d, J = 14.8 Hz, 2H), 3.03 (t, J = 6.0 Hz, 2H), 2.85 (s, 3H), 2.50 (s, 2H), 2.33 (s, 2H), 1.81 (s, 2H), 1.58 (s, 4H) | 558 |
| 218 | 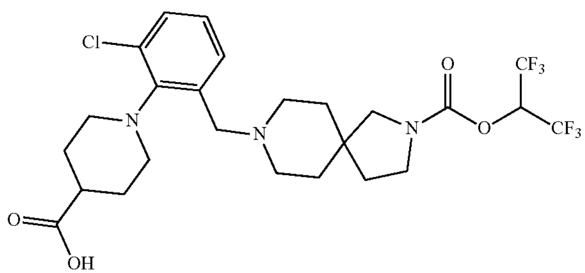 [SMILES: O=C(O)C1CCN(c2c(Cl)cccc2CN2CCC3(CC2)CCN(C(=O)OC(C(F)(F)F)C(F)(F)F)C3)CC1] | 1-(2-Chloro-6-{[(((1,1,1,3,3,3-hexafluoropropan-2-yl)oxy)carbonyl)-2,8-diazaspiro[4.5]decan-8-yl]methyl}phenyl)piperidine-4-carboxylic acid | (Chloroform-d) δ 7.29-7.33 (m, 1H), 7.22-7.24 (m, 1H), 7.05-7.10(m, 1H), 5.68-5.78 (m, 1H), 3.71 (s, 1H), 3.45-3.54 (m, 4H), 3.28-3.32 (m, 2H), 2.90-3.02 (m, 2H), 2.30-2.51 (m, 6H), 1.99-2.02 (m, 2H), 1.77-1.88 (m, 4H), 1.62 (s, 4H) | 586 |

| Ex | Structure | Name | NMR (¹H NMR, 300 MHz or 400 MHz, Methanol-d4) | MS [M+H]⁺ |
|---|---|---|---|---|
| 219 | 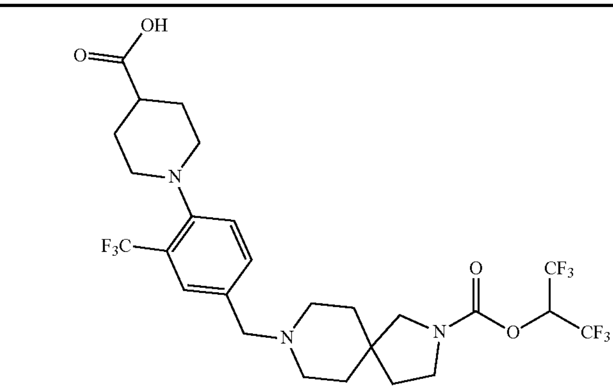 | 1-(4-((2-(((1,1,1,3,3,3-Hexafluoropropan-2-yl)oxy)carbonyl)-2,8-diazaspiro[4.5]decan-8-yl)methyl)-2-(trifluoromethyl)phenyl)piperidine-4-carboxylic acid | δ 7.67 (s, 1H), 7.57-7.60 (m, 1H), 7.44-7.47 (m, 1H), 6.04-6.14 (m, 1H), 3.75 (s, 2H), 3.49-3.56 (m, 2H), 3.32-3.33 (m, 2H), 3.02-3.06 (m, 2H), 2.71-2.82 (m, 4H), 2.62 (s, 2H), 2.32-2.39 (m, 1H), 1.83-1.99 (m, 6H), 1.67-1.78 (m, 4H) | 620 |
| 220 | 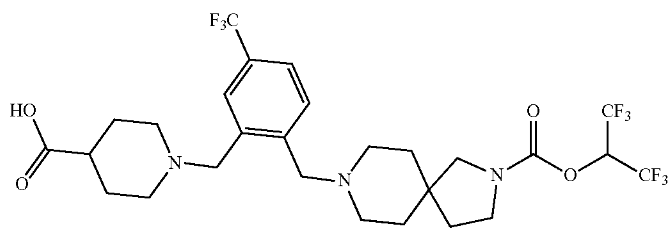 [SMILES: O=C(O)C1CCN(Cc2cc(C(F)(F)F)ccc2CN2CCC3(CC2)CCN(C(=O)OC(C(F)(F)F)C(F)(F)F)C3)CC1] | 1-(2-((2-(((1,1,1,3,3,3-Hexafluoropropan-2-yl)oxy)carbonyl)-2,8-diazaspiro[4.5]decan-8-yl)methyl)-5-(trifluoromethyl)benzyl)piperidine-4-carboxylic acid | δ 7.89 (s, 1H), 7.80 (d,J = 8.0 Hz, 1H), 7.71 (d, J = 8.0 Hz, 1H), 6.07-6.18 (m, 1H), 4.31 (S, 2H), 4.03 (s, 2H), 3.51-3.59 (m, 2H), 3.43 (s, 2H), 3.29 (s, 2H), 2.90 (s, 4H), 2.73 (s, 2H), 2.40 (s, 1H), 2.06-2.09 (m, 2H), 1.90-1.99 (m, 4H), 1.70-1.77 (m, 1H) | 634 |
| 221 | 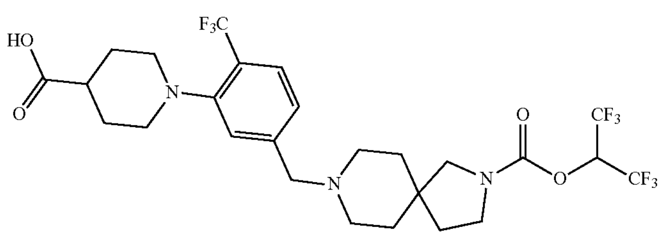 [SMILES: O=C(O)C1CCN(c2cc(CN3CCC4(CC3)CCN(C(=O)OC(C(F)(F)F)C(F)(F)F)C4)ccc2C(F)(F)F)CC1] | 1-(5-((2-(((1,1,1,3,3,3-Hexafluoropropan-2-yl)oxy)carbonyl)-2,8-diazaspiro[4.5]decan-8-yl)methyl)-2-(trifluoromethyl)phenyl)piperidine-4-carboxylic acid | δ 7.60 (d, J = 7.8 Hz, 1H), 7.47 (s, 1H), 7.26 (d, J = 7.8 Hz, 1H), 6.07-6.11 (m, 1H), 3.70 (s, 2H), 3.50-3.56 (m, 2H), 3.30-3.31 (m, 2H), 3.04-3.08 (m, 2H), 2.37-2.84 (m, 7H), 1.83-1.95 (1a 6H), 1.66-1.69 (m, 4H) | 620 |

| Ex | Structure | Name | NMR (¹H NMR, 300 MHz or 400 MHz, Methanol-d4) | MS [M+ H]⁺ |
|---|---|---|---|---|
| 222 | 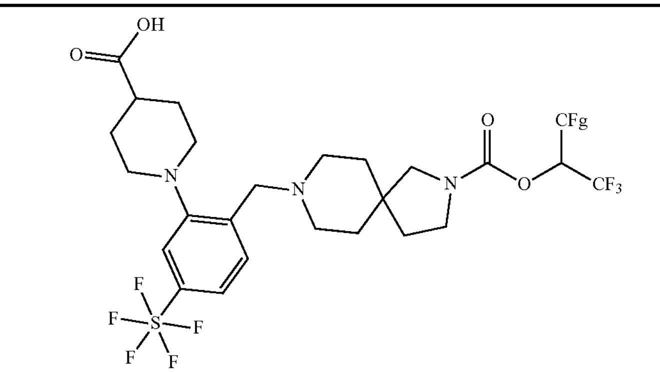 | 1-(2-((((1,1,1,3,3,3-Hexafluoropropan-2-yl)oxy)carbonyl)-2,8-diazaspiro[4.5]decan-8-yl)methyl)-5-(pentafluoro-16-sulfaneyl)phenyl)piperidine-4-carboxylic acid | δ 7.61-7.68 (m, 1H), 7.52-7.55 (m, 2H), 6.06-6.11 (m, 1H), 3.83 (s, 2H), 3.49-3.56 (m, 2H), 3.30-3.33 (m, 2H), 3.12-3.19 (m, 2H), 2.64-2.80 (m, 6H), 2.34-2.46 (m, 1H), 2.02-2.09 (m, 2H), 1.80-1.98 (m, 4H), 1.61-1.69 (m, 4H) | 678 |
| 223 | 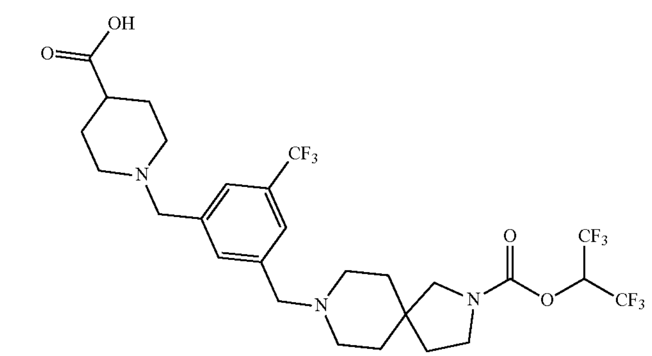 [SMILES: O=C(O)C1CCN(Cc2cc(CN3CCC4(CC3)CCN(C(=O)OC(C(F)(F)F)C(F)(F)F)C4)cc(C(F)(F)F)c2)CC1] | 1-(3-((2-((((1,1,1,3,3,3-Hexafluoropropan-2-yl)oxy)carbonyl)-2,8-diazaspiro[4.5]decan-8-yl)methyl)-5-(trifluoromethyl)benzyl)piperidine-4-carboxylic acid | δ 7.68 (s, 3H), 6.04-6.14 (m, 1H), 3.92 (s, 2H), 3.70 (s, 2H), 3.48-3.55 (m, 2H), 3.32 (s, 2H), 3.07-3.10 (m, 2H), 2.29-2.61 (m, 7H), 1.76-1.99 (m, 6H), 1.64-1.68 (m, 4H) | 634 |
| 224 | 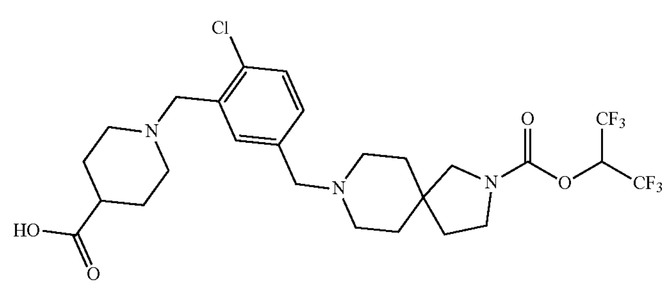 [SMILES: O=C(O)C1CCN(Cc2cc(CN3CCC4(CC3)CCN(C(=O)OC(C(F)(F)F)C(F)(F)F)C4)ccc2Cl)CC1] | 1-(2-Chloro-5-((2-((((1,1,1,3,3,3-hexafluoropropan-2-yl)oxy)carbonyl)-2,8-diazaspiro[4.5]decan-8-yl)methyl)benzyl)piperidine-4-carboxylic acid | δ 7.57 (s, 1H), 7.44 (d, J = 8.4 Hz, 1H), 7.35 (d, J = 8.4 Hz, 1H), 6.07-6.12 (m, 1H), 3.95 (s, 2H), 3.67 (s, 2H), 3.48-3.55 (m, 2H), 3.32 (s, 2H), 3.11-3.15 (m, 2H), 2.53-2.65 (m, 6H), 2.27-2.32 (m, 1H), 1.80-1.98 (m, 6H), 1.64-1.68 (m, 4H) | 600 |

| Ex | Structure | Name | NMR (¹H NMR, 300 MHz or 400 MHz, Methanol-d4) | MS [M+H]⁺ |
|---|---|---|---|---|
| 225 | 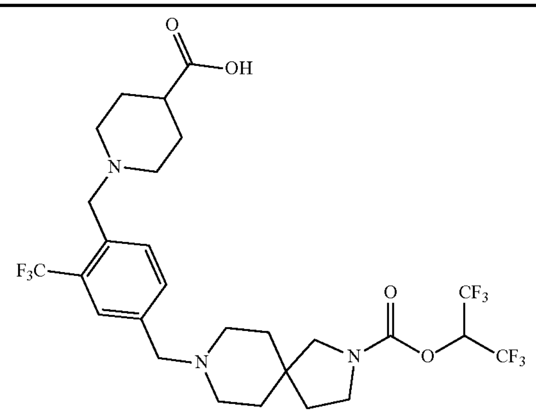 | 1-(4-((2-(((1,1,1,3,3,3-Hexafluoropropan-2-yl)oxy)carbonyl)-2,8-diazaspiro[4.5]decan-8-yl)methyl)-2-(trifluoromethyl)benzyl)piperidine-4-carboxylic acid | δ 7.81 (d, J = 8.1 Hz, 1H), 7.71 (s, 1H), 7.61 (d, J = 7.8 Hz, 1H), 6.12-6.07 (m, 1H), 3.74-3.72 (m, 4H), 3.56-3.49 (m, 2H), 3.32 (s, 2H), 2.94-2.90 (m, 2H), 2.66-2.55 (m, 4H), 2.29-2.22 (m, 3H), 1.92-1.65 (m, 10H) | 634 |
| 226 | 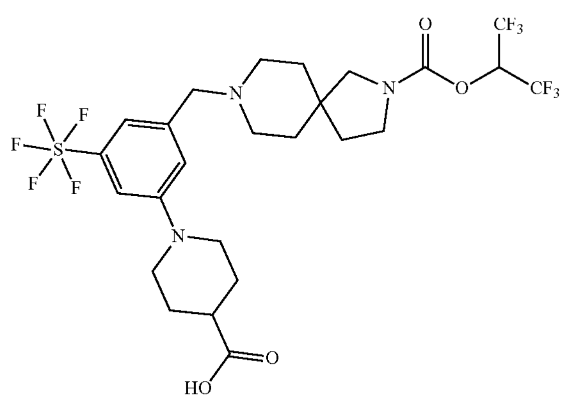 [SMILES: O=C(O)C1CCN(c2cc(CN3CCC4(CC3)CCN(C(=O)OC(C(F)(F)F)C(F)(F)F)C4)cc(S(F)(F)(F)(F)F)c2)CC1] | 1-(3-((2-(((1,1,1,3,3,3-Hexafluoropropan-2-yl)oxy)carbonyl)-2,8-diazaspiro[4.5]decan-8-yl)methyl)-5-(pentafluoro-16-sulfanyl)phenyl)piperidine-4-carboxylic acid | δ 7.24-7.20 (m, 3H), 6.13-6.04 (m, 1H), 3.73,3.70(m, 4H), 3.54-3.52 (m, 2H), 3.33 (s,2H), 2.91-2.82 (m, 2H), 2.78-2.35 (m, 5H), 2.02-1.99 (m, 2H), 1.88-1.69 (m, 8H) | 678 |

| Ex | Structure | Name | NMR (¹H NMR, 300 MHz or 400 MHz, Methanol-d4) | MS [M+ H]⁺ |
|---|---|---|---|---|
| 227 | 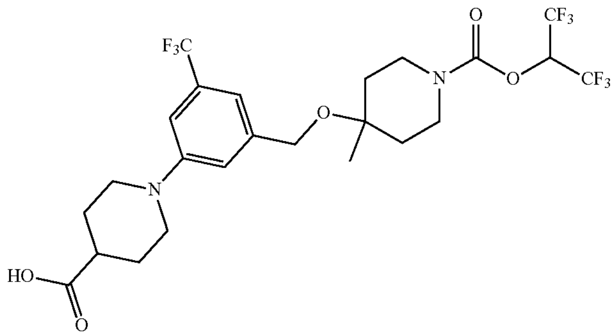 [SMILES: CC1(OCc2cc(N3CCC(C(=O)O)CC3)cc(C(F)(F)F)c2)CCN(C(=O)OC(C(F)(F)F)C(F)(F)F)CC1] | 1-(3-((1-(((1,1,1,3,3,3-Hexafluoropropan-2-yl)oxy)carbonyl)-4-methylpiperidin-4-yl)oxy)methyl)-5-(trifluoromethyl)phenyl)piperidine-4-carboxylic acid | δ 7.21 (s, 1H), 7.09 (s, 2H), 6.17-6.09 (m, 1H), 4.51 (s, 2H), 3.91-3.86 (m, 2H), 3.76-3.72 (m, 2H), 3.38-3.34 (m, 2H), 2.92-2.84 (m, 2H), 2.51-2.42 (m, 1H), 2.07-1.96 (m, 4H), 1.89-1.76 (m, 2H), 1.66-1.53 (m, 2H), 1.33 (s, 3H) | 595 |
| 228 | 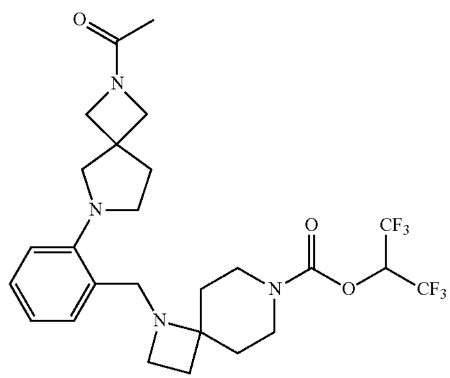 [SMILES: CC(=O)N1CC2(CCN(c3ccccc3CN3CCC34CCN(C(=O)OC(C(F)(F)F)C(F)(F)F)CC4)C2)C1] | 1,1,1,3,3,3-Hexafluoropropan-2-yl 1-(2-(2-acetyl-2,6-diazaspiro[3.4]octan-6-yl)benzyl)-1,7-diazaspiro[3.5]nonane-7-carboxylate | (Chloroform-d) δ 7.43 (d, J = 3.3 Hz, 1H), 7.14-7.16 (m, 1H), 6.87-6.93 (m, 2H), 5.68-5.86 (m, 1H), 3.95-4.13 (m, 6H), 3.61 (s, 2H), 3.22-3.36 (m, 6H), 2.82-2.96 (m, 2H), 2.15-2.20 (m, 2H), 1.90-2.11 (m, 7H), 1.61 (s, 2H) | 563 |

| Ex | Structure | Name | NMR (¹H NMR, 300 MHz or 400 MHz, Methanol-d4) | MS [M+ H]⁺ |
|---|---|---|---|---|
| 229 | 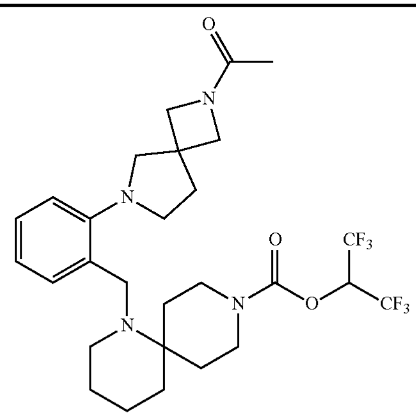 | 1,1,1,3,3,3-Hexafluoropropan-2-yl 1-(2-(2-acetyl-2,6-diazaspiro[3,4]octan-6-yl)benzyl)-1,9-diazaspiro[5.5]undecane-9-carboxylate | (Chloroform-d) δ 7.68 (d, J = 7.5 Hz, 1H), 7.14-7.19 (m, 1H), 6.94-7.04 (m, 2H), 5.72-5.80 (m, 1H), 3.95-4.12 (m, 4H), 3.80-3.84 (m, 2H), 3.60 (s, 2H), 3.10-3.32 (m, 6H), 2.51-2.55 (m, 2H), 2.16-2.20 (m, 2H), 1.89-2.10 (m, 5H), 1.50-1.69 (m, 8H) | 591 |
| 230 | 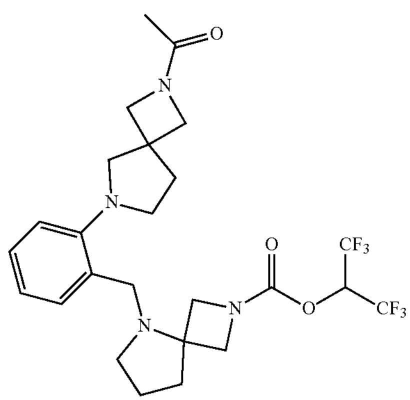 [SMILES: CC(=O)N1CC2(CCN(c3ccccc3CN3CCCC34CN(C(=O)OC(C(F)(F)F)C(F)(F)F)C4)C2)C1] | 1,1,1,3,3,3-Hexafluoropropan-2-yl 5-(2-(2-acetyl-2,6-diazaspiro[3,4]octan-6-yl)benzyl)-2,5-diazaspiro[3,4]octane-2-carboxylate | (Chloroform-d) δ 7.46 (d, J = 7.8 Hz, 1H), 7.18-7.23 (m, 1H), 6.98-7.04 (m, 2H), 5.62-5.70 (m, 1H), 4.24-4.31 (m, 2H), 4.02-4.13 (m, 2H), 3.77-3.99 (m, 6H), 3.10-3.32 (m, 4H), 2.62-2.67 (m, 2H), 2.10-2.21 (m, 4H), 1.89 (s, 3H), 1.70-1.81 (m, 2H) | 549 |

-continued

| Ex | Structure | Name | NMR (¹H NMR, 300 MHz or 400 MHz, Methanol-d4) | MS [M+ H]⁺ |
|---|---|---|---|---|
| 231 | 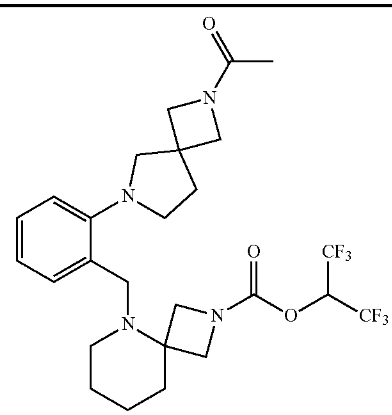 | 1,1,1,3,3,3-Hexafluoropropan-2-yl 5-(2-(2-acetyl-2,6-diazaspiro[3.4]octan-6-yl)benzyl)-2,5-diazaspiro[3.5]nonane-2-carboxylate | (Chloroform-d) δ 7.56-7.61 (m, 1H), 7.19-7.21 (m, 1H), 6.99-7.06 (m, 2H), 5.63-5.71 (m, 1H), 4.09-4.20 (m, 4H), 3.99 (s, 2H), 3.69-3.81 (m, 4H), 3.12-3.29 (m, 4H), 2.44 (s, 2H), 2.16-2.20 (m, 2H), 1.89 (s, 5H), 1.51-1.67 (m, 4H) | 563 |
| 232 | 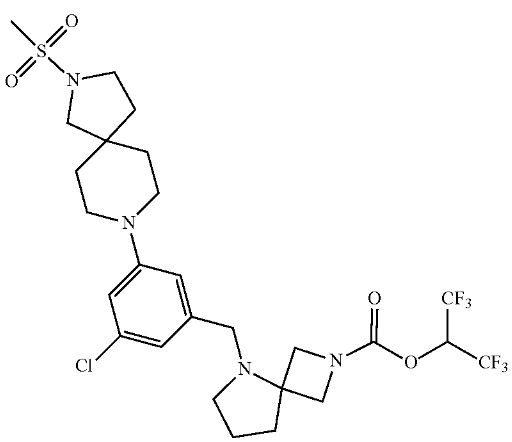 [SMILES: CS(=O)(=O)N1CCC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-((3-chloro-5-(2-(methylsulfonyl)-2,8-diazaspiro[4.5]decan-8-yl)cyclohexyl)methyl)-2,5-diazaspiro[3.4]octane-2-carboxylate | Chloroform-d) δ 6.76-6.81 (m, 3H), 5.61-570 (m, 1H), 4.24-4.25 (m, 2H), 3.94-3.97 (m, 2H), 3.73 (s, 2H), 3.44 (t, J = 7.2 Hz, 2H), 3.09-3.23 (m, 6H), 2.86 (s, 3H), 2.63-2.64 (m, 2H), 2.14-2.16 (m, 2H), 1.87 (t, J = 7.2 Hz, 2H), 1.69-1.76 (m, 6H) | 647 |

| Ex | Structure | Name | NMR (¹H NMR, 300 MHz or 400 MHz, Methanol-d4) | MS [M+ H]⁺ |
|---|---|---|---|---|
| 233 | 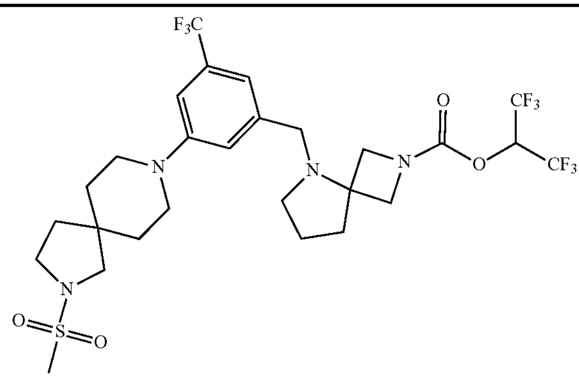 | 1,1,1,3,3,3-Hexafluoropropan-2-yl 5-(3-(2-(methylsulfonyl)-2,8-diazaspiro[4.5]decan-8-yl)-5-(trifluoromethyl)benzyl)-2,5-diazaspiro[3.4]octane-2-carboxylate | (Chloroform-d) δ 6.91-7.05 (m, 3H), 5.61-5.70 (m, 1H), 4.27-4.30 (m, 2H), 3.91-3.97 (m, 2H), 3.81 (s, 2H), 3.45 (t, J = 7.2 Hz, 2H), 3.20-3.36 (m, 4H), 3.09-3.29 (m, 2H), 2.86 (s, 3H), 2.63-2.64 (m, 2H), 2.16-2.18 (m, 2H), 1.89 (t, J = 7.2 Hz, 2H), 1.77-1.79 (d, 6H) | 681 |
| 234 | 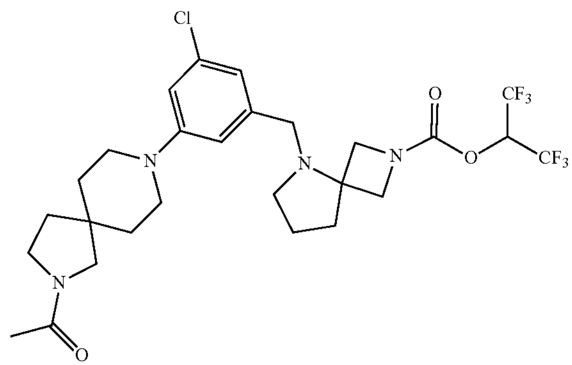 [SMILES: CC(=O)N1CCC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-(3-(2-acetyl-2,8-diazaspiro[4.5]decan-8-yl)-5-chlorobenzyl)-2,5-diazaspiro[3.4]octane-2-carboxylate | (Chloroform-d) δ 7.00-6.50 (m, 3H), 5.81-5.64 (m, 1H), 4.30-4.12 (m, 2H), 4.08-3.89 (m, 2H), 3.80 (s, 2H), 3.78-3.62 (m, 2H), 3.45 (s, 1H), 3.41-3.05 (m, 5H), 2.65 (s, 2H), 2.32-2.11 (m, 3H), 2.10-2.00 (m, 3H), 1.90-1.55 (m, 8H) | 611 |

| Ex | Structure | Name | NMR (¹H NMR, 300 MHz or 400 MHz, Methanol-d4) | MS [M+ H]⁺ |
|---|---|---|---|---|
| 235 | 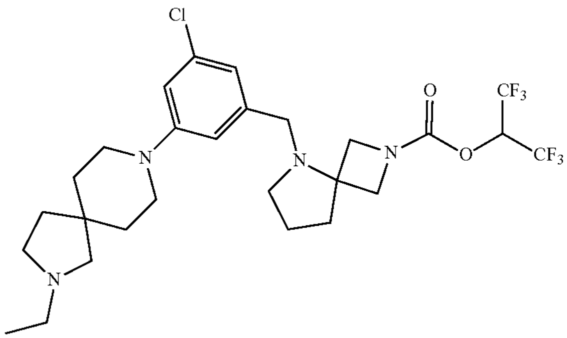 [SMILES: CCN1CCC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-(3-chloro-5-(2-ethyl-2,8-diazaspiro[4.5]decan-8-yl)benzyl)-2,5-diazaspiro[3.4]octane-2-carboxylate | (Chloroform-d) δ 6.90-6.50 (m, 3H), 5.81-5.50 (m, 1H), 4.40-4.19 (m, 2H), 4.12-3.89 (m, 2H), 3.75 (s, 2H), 3.31-2.95 (m, 4H), 2.71-2.55 (m, 4H), 2.52-2.35 (m, 4H), 2.31-2.08 (m, 2H), 1.90-1.63 (m, 8H), 1.27-1.01 (m, 3H) | 597 |
| 236 | 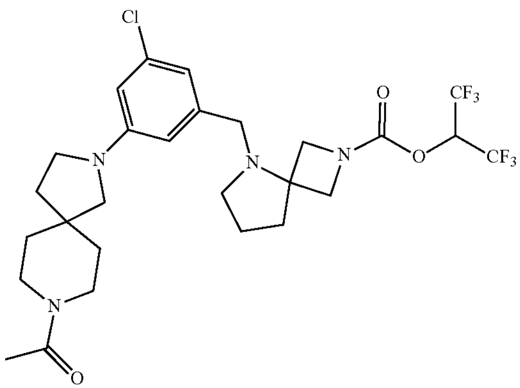 [SMILES: CC(=O)N1CCC2(CC1)CCN(c1cc(Cl)cc(CN3CCCC34CN(C(=O)OC(C(F)(F)F)C(F)(F)F)C4)c1)C2] | 1,1,1,3,3,3-Hexafluoropropan-2-yl 5-(3-(8-acetyl-2,8-diazaspiro[4.5]decan-2-yl)-5-chlorobenzyl)-2,5-diazaspiro[3.4]octane-2-carboxylate | (Chloroform-d) δ 6.65 (s, 1H), 6.51-6.35 (m, 2H), 5.89-5.44 (m, 1H), 4.50-4.22 (m, 2H), 4.08-3.89 (m, 2H), 3.78 (s,3H), 3.56-3.42 (m, 3H), 3.41-3.30 (m, 2H), 3.21-3.05 (m, 2H), 2.81-2.55 (m, 2H), 2.22-2.05 (m, 5H), 1.90-1.80 (m, 2H), 1.80-1.70 (m, 2H), 1.70-1.60 (m, 4H) | 611 |

| Ex | Structure | Name | NMR (¹H NMR, 300 MHz or 400 MHz, Methanol-d4) | MS [M+ H]⁺ |
|---|---|---|---|---|
| 237 | 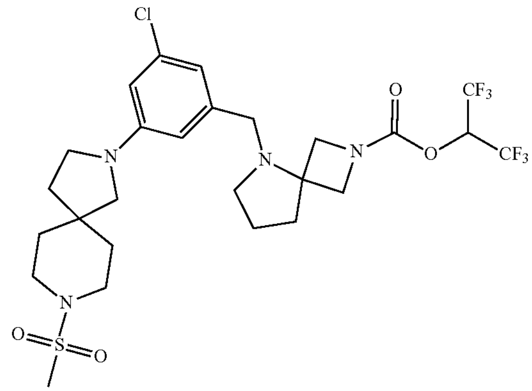 [SMILES: CS(=O)(=O)N1CCC2(CCN(c3cc(Cl)cc(CN4CCCC45CN(C(=O)OC(C(F)(F)F)C(F)(F)F)C5)c3)C2)CC1] | 1,1,1,3,3,3-Hexafluoropropan-2-yl 5-(3-chloro-5-(8-(methylsulfonyl)-2,8-diazaspiro[4.5]decan-2-yl)benzyl)-2,5-diazaspiro[3.4]octane-2-carboxylate | (Chloroform-d) δ 6.66 (s, 1H), 6.48-6.25 (m, 2H), 5.80-5.51 (m, 1H), 4.34-4.19 (m, 2H), 4.05-3.89 (m, 2H), 3.78 (s, 2H), 3.43-3.28 (m, 4H), 3.26-3.06 (m, 4H), 2.82 (s, 3H), 2.72-2.59 (m, 2H), 2.29-2.05 (m, 2H), 1.95-1.82 (m, 2H), 1.86-1.65 (m, 6H) | 647 |
| 238 | 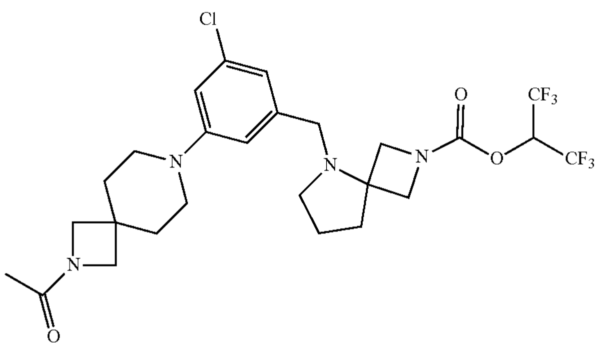 [SMILES: CC(=O)N1CC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-(3-(2-acetyl-2,7-diazaspiro[3.5]nonan-7-yl)-5-chlorobenzyl)-2,5-diazaspiro[3.4]octane-2-carboxylate | (Chloroform-d) δ 6.91-6.66 (m, 3H), 5.71-5.54 (m, 1H), 4.41-4.18 (m, 2H), 4.08-3.83 (m, 4H), 3.81-3.56 (m, 4H), 2.82-2.55 (m, 5H), 2.33-2.03 (m, 5H), 1.98 (s, 1H), 1.98-1.66 (m, 6H) | 597 |

| Ex | Structure | Name | NMR (¹H NMR, 300 MHz or 400 MHz, Methanol-d4) | MS [M+ H]⁺ |
|---|---|---|---|---|
| 239 | 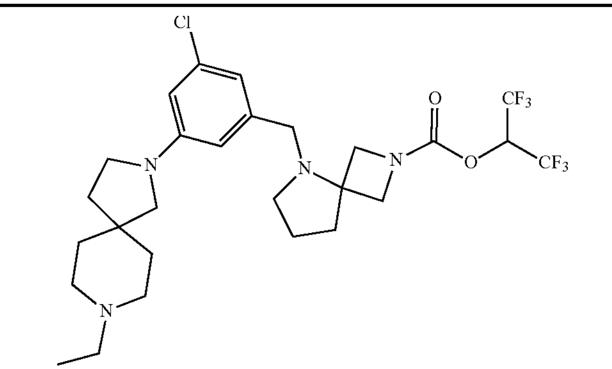 | 1,1,1,3,3,3-Hexafluoropropan-2-yl 5-(3-chloro-5-(8-ethyl-2,8-diazaspiro[4.5]decan-2-yl)benzyl)-2,5-diazaspiro[3.4]octane-2-carboxylate | (Chloroform-d) δ 6.75 (s, 1H), 6.42 (s, 1H), 6.33 (s, 1H), 5.78-5.55 (m, 1H), 4.34-4.19 (m, 2H), 4.02-3.89 (m, 2H), 3.71 (s, 2H), 3.32-3.22 (m, 2H), 3.16 (s, 2H), 2.71-2.55 (m, 4H), 2.55-2.35 (m, 4H), 2.24-2.13 (m, 2H), 1.92-1.81 (m, 2H), 1.81-1.61 (m, 6H), 1.22-1.10 (m, 3H) | 597 |
| 240 | 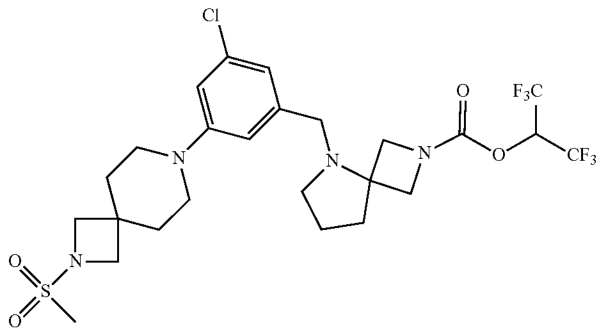 [SMILES: CS(=O)(=O)N1CC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-(3-chloro-5-(2-(methylsulfonyl)-2,7-diazaspiro[3.5]nonan-7-yl)benzyl)-2,5-diazaspiro[3.4]octane-2-carboxylate | (Chloroform-d) δ 6.91-6.56 (m, 3H), 5.76-5.58 (m, 1H), 4.39-4.10 (m, 2H), 4.03-3.83 (m, 4H), 3.81-3.56 (m, 4H), 2.88 (s, 3H), 2.82-2.55 (m, 4H), 2.51-2.31 (m, 2H), 2.29-2.01 (m, 5H), 1.91-1.63 (m, 2H) | 633 |
| 241 | 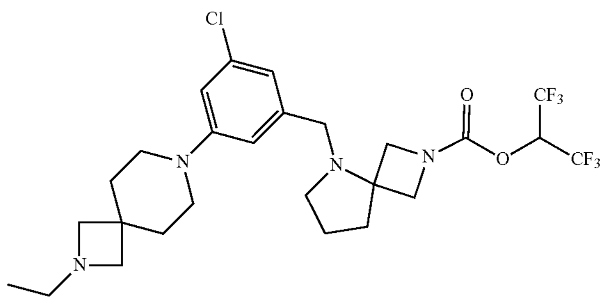 [SMILES: CCN1CC2(CCN(c3cc(Cl)cc(CN4CCCC45CN(C(=O)OC(C(F)(F)F)C(F)(F)F)C5)c3)CC2)C1] | 1,1,1,3,3,3-Hexafluoropropan-2-yl 5-(3-chloro-5-(2-ethyl-2,7-diazaspiro[3.5]nonan-7-yl)benzyl)-2,5-diazaspiro[3.4]octane-2-carboxylate | (Chloroform-d) δ 6.85 (s, 1H), 6.82-6.67 (m, 2H), 5.72-5.55 (m, 1H), 4.60-4.06 (m, 3H), 4.00-3.89 (m, 2H), 3.75 (s, 2H), 3.73, 3.31 (m, 3H), 3.13-2.71 (m, 4H), 2.73-2.57 (m, 2H), 2.54-2.22 (s, 3H), 2.21-1.86 (m, 5H), 1.85-1.65 (m, 2H), 1.40-1.15 (m, 3H) | 583 |

-continued
| Ex | Structure | Name | NMR (¹H NMR, 300 MHz or 400 MHz, Methanol-d4) | MS [M+ H]⁺ |
|---|---|---|---|---|
| 242 | 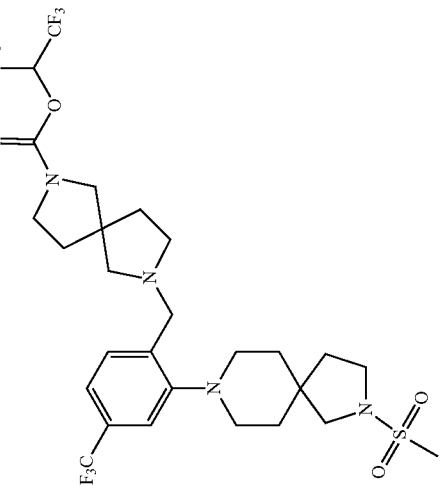 | 1,1,1,3,3,3-Hexafluoropropan-2-yl 7-(2-(2-(methylsulfonyl)-2,8-diazaspiro[4.5]decan-8-yl)-4-(trifluoromethyl)benzyl)-2,7-diazaspiro[4.4]nonane-2-carboxylate | (Chloroform-d) δ 7.54-7.56 (m, 1H), 7.26-7.32 (m, 2H), 5.68-5.76 (m, 1H), 3.69 (s, 2H), 3.40-3.58 (m, 5H), 3.26-3.37 (m, 1H), 3.23 (s, 2H), 2.87-2.97 (m, 4H), 2.86 (s, 3H), 2.43-2.73 (m, 4H), 1.91-1.93 (m, 4H), 1.69-1.88 (m, 6H) | 695 |

II. Biological Evaluation

Compounds are tested to assess their MAGL and serine hydrolase activity using the following in vitro and in vivo assays.

In Vitro Competitive Activity-Based Protein Profiling.

Proteomes (human prefrontal cortex or cell membrane fractions) (50 μL, 1.0 mg/mL total protein concentration) were preincubated with varying concentrations of inhibitors at 37° C. After 30 min, FP-Rh or HT-01 (1.0 μL, 50 μM in DMSO) was added and the mixture was incubated for another 30 min at room temperature. Reactions were quenched with SDS loading buffer (15 μL-4×) and run on SDS-PAGE. Following gel imaging, serine hydrolase activity was determined by measuring fluorescent intensity of gel bands corresponding to MAGL using ImageJ 1.49k software. $IC_{50}$ data from this assay is shown in Table 1.

Preparation of Mouse Brain Proteomes from Inhibitor Treated Mice.

Inhibitors were administered to wild-type C57B1/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | % Inh MGLL PC3 (Human, μM) | % Inh MGLL PFC (Human, μM) | % Inh MGLL Brain (Mouse, μM) | % Inh ABHD6 Brain (Mouse, μM) | $IC_{50}$ MGLL PC3 (Human, μM) | $IC_{50}$ MGLL PFC (Human, μM) | $IC_{50}$ MGLL Brain (Mouse, μM) | $IC_{50}$ ABHD6 (Mouse, μM) | % Inh 5 mg/kg MGLL (Mouse) |
|---|---|---|---|---|---|---|---|---|---|
| 1 | ### | ### | ### | # | *** | | | | ## |
| 2 | ### | ### | ### | # | *** | *** | | | |
| 3 | ### | ### | ### | # | *** | *** | *** | * | # |
| 4 | ### | ### | ### | # | *** | | | | ### |
| 5 | ### | | ### | # | *** | | | | ### |
| 6 | | ### | ### | # | *** | *** | | | # |
| 7 | | ### | ### | # | *** | | | | ### |
| 8 | | ### | ### | ## | *** | *** | *** | * | ### |
| 9 | ### | ### | ### | # | *** | | | | # |
| 10 | ### | ### | ### | # | | | | | ### |
| 11 | ### | ### | ### | # | | *** | | | |
| 12 | | ### | ### | ### | *** | | | | |
| 13 | | ### | ### | ### | | | *** | ** | |
| 14 | | ### | ### | ### | *** | | | | ### |
| 15 | | | ### | ### | | | *** | ** | |
| 16 | | | ### | ### | | | *** | ** | |
| 17 | | | ### | ### | | | | | |
| 18 | | | ## | ### | | | | | |
| 19 | | | ## | ### | | | | | |
| 20 | | ### | ### | ## | *** | *** | *** | * | ### |
| 21 | | ### | ### | ### | *** | | | | |
| 22 | | ### | ### | ### | *** | | | | |
| 23 | | ### | # | # | | | | | |
| 24 | | ### | ### | ## | *** | | | | |
| 25 | ### | ### | ### | ### | *** | | | | |
| 26 | ### | ### | ### | ### | *** | *** | | | |
| 27 | ### | | ### | ### | *** | *** | | | |
| 28 | | | ### | # | | | *** | * | ### |
| 29 | | | ### | # | | | *** | * | ### |
| 30 | | | ### | # | | | *** | * | # |
| 31 | | | ## | ### | | | * | ** | |
| 32 | | | ### | # | | | *** | * | ### |
| 33 | | | ### | ### | | | ** | ** | |
| 34 | | | ### | ### | | | *** | ** | |
| 35 | | | ### | ## | | | *** | ** | |
| 36 | | | ### | ### | | | *** | ** | |
| 37 | | | ### | ### | | | | | |
| 38 | | | ### | ## | | | ** | ** | |
| 39 | | | ### | ### | | | *** | ** | ### |
| 40 | | | ### | ### | | | *** | *** | |
| 41 | | | ### | ## | | | *** | ** | ### |
| 42 | | | ### | ### | | | *** | ** | |
| 43 | | | ### | ## | | | *** | ** | |
| 44 | | | ### | ### | | | *** | *** | ### |
| 45 | | | ### | ### | | | *** | *** | ### |
| 46 | | | ### | ### | | | *** | *** | ### |
| 47 | | | ### | ### | | | *** | *** | |
| 48 | | | ### | ### | | | *** | *** | |
| 49 | | | ### | ### | | | *** | *** | ### |
| 50 | | | ### | ### | | | *** | ** | # |
| 51 | | | ### | ### | | | *** | * | ### |
| 52 | | | ### | ### | | | *** | ** | ### |
| 53 | | | ### | ### | | | *** | ** | ### |
| 54 | | | ### | # | | | *** | * | # |
| 55 | | | ## | ### | | | | | |
| 56 | | | ## | ### | | | | | |

TABLE 1-continued

| Ex | % Inh MGLL PC3 (Human, μM) | % Inh MGLL PFC (Human, μM) | % Inh MGLL Brain (Mouse, μM) | % Inh ABHD6 Brain (Mouse, μM) | IC$_{50}$ MGLL PC3 (Human, μM) | IC$_{50}$ MGLL PFC (Human, μM) | IC$_{50}$ MGLL Brain (Mouse, μM) | IC$_{50}$ ABHD6 (Mouse, μM) | % Inh 5 mg/kg MGLL (Mouse) |
|---|---|---|---|---|---|---|---|---|---|
| 57 |  |  | ### | ### |  |  | *** | ** | ### |
| 58 |  |  | ### | ### |  |  | *** | ** | ### |
| 59 |  |  | ### | ### |  |  | *** | ** | ### |
| 60 |  |  | ### | ### |  |  | *** | * | ### |
| 61 |  |  | ### | ### |  |  | *** | ** | ## |
| 62 |  |  | ### | ### |  |  | *** | * | ## |
| 63 |  |  | ### | ### |  |  | *** | * | ### |
| 64 |  |  | ## | ### |  |  |  |  |  |
| 65 |  |  | ### | ### |  |  |  |  |  |
| 66 |  |  | ## | ### |  |  |  |  |  |
| 67 |  |  | ### | ### |  |  | *** | *** |  |
| 68 |  |  | ### | ### |  |  |  |  |  |
| 69 |  |  | ### | ### |  |  | *** | *** | ### |
| 70 |  |  | ### | ### |  |  |  |  |  |
| 71 |  |  | ### | ### |  |  |  |  |  |
| 72 |  |  | ### | # |  |  | *** | * | ### |
| 73 |  |  | ### | ### |  |  |  |  |  |
| 74 |  |  | # | ### |  |  |  |  |  |
| 75 |  |  | ### | ### |  |  |  |  |  |
| 76 |  |  | ### | # | *** | ** | * |  |  |
| 77 |  |  | ## | ### |  |  |  |  |  |
| 78 |  |  | ### | ### |  |  | *** | *** |  |
| 79 |  |  | ### | ### |  |  |  |  |  |
| 80 |  |  | ### | # |  |  | *** | * |  |
| 81 |  |  | ### | ### |  |  |  |  |  |
| 82 |  |  | ### | ### |  |  |  |  |  |
| 83 |  | ### | ### | ### |  |  | *** | ** |  |
| 84 |  |  | ### | ### |  |  |  |  |  |
| 85 |  |  | ### | ### |  |  |  |  |  |
| 86 |  |  | ### | ### |  |  | *** | *** |  |
| 87 |  |  | ### | ### |  |  |  |  |  |
| 88 |  |  | ### | ### |  |  |  |  |  |
| 89 |  |  | ### | ### |  |  | *** | *** |  |
| 90 |  |  | ### | ### |  |  |  |  |  |
| 91 |  |  | ### | ### |  |  |  |  |  |
| 92 |  |  | ### | ### |  |  |  |  |  |
| 93 |  |  | ### | ### |  |  |  |  |  |
| 94 |  |  | ### | ### |  |  |  |  |  |
| 95 |  |  | ### | ### |  |  |  |  |  |
| 96 |  |  | ### | ### |  |  |  |  |  |
| 97 |  |  | ### | ### |  |  |  |  |  |
| 98 |  |  | ### | ### |  |  |  |  |  |
| 99 | ### | ### | ### | *** | *** | *** | ** | ## |  |
| 100 | ### | ### | ### | *** |  |  |  |  |  |
| 101 | ### | ### | ### | *** |  |  |  |  |  |
| 102 | ### | ### | ### | *** |  |  |  |  |  |
| 103 | ### | ### | ## | *** |  |  |  |  |  |
| 104 | ### | ### | ### |  |  |  |  |  |  |
| 105 | ### | ### | ### |  |  |  |  |  |  |
| 106 | ### | ### | ### |  |  |  |  |  |  |
| 107 | ### | ### | # | *** |  |  |  |  |  |
| 108 | ### | ### | ## | *** |  |  | *** | ** | # |
| 109 | ### | ### | ### | *** |  |  |  |  |  |
| 110 | ### | ### | ### | *** |  |  |  |  |  |
| 111 | ### | ### | ### | *** |  |  |  |  |  |
| 112 | ### | ### | ## | *** |  |  |  |  | # |
| 113 | # | ## | # |  |  |  |  |  |  |
| 114 | ### | ### | # | *** | *** |  |  |  | ## |
| 115 | ### | ### | # | *** |  |  |  |  |  |
| 116 | ### | ### | ### |  |  |  |  |  |  |
| 117 | ### | ### | ## |  |  |  |  |  |  |
| 118 | ### | ### | ## | *** |  |  |  |  | ### |
| 119 | ### | ### | ### | *** |  |  |  |  |  |
| 120 | ### | ### | ### | *** |  |  |  |  |  |
| 121 | ### | ### | ### | *** |  |  |  |  |  |
| 122 | ### | ### | # | *** |  |  |  |  |  |
| 123 | ### | ### | # | ** |  |  |  |  |  |
| 124 | ### | ### | # | *** |  |  |  |  | ### |
| 125 | ### | ### | ### | *** |  |  |  |  | # |
| 126 | ### | ### | # | *** |  |  |  |  | # |
| 127 | ### | ### | ### | *** |  |  |  |  | # |
| 128 | ### | ### | # | *** |  |  |  |  | # |
| 129 | ## | ### | ### |  |  |  |  |  | # |
| 130 | ### | ### | # | *** |  |  |  |  | # |

TABLE 1-continued

| Ex | % Inh MGLL PC3 (Human, μM) | % Inh MGLL PFC (Human, μM) | % Inh MGLL Brain (Mouse, μM) | % Inh ABHD6 Brain (Mouse, μM) | $IC_{50}$ MGLL PC3 (Human, μM) | $IC_{50}$ MGLL PFC (Human, μM) | $IC_{50}$ MGLL Brain (Mouse, μM) | $IC_{50}$ ABHD6 (Mouse, μM) | % Inh 5 mg/kg MGLL (Mouse) |
|---|---|---|---|---|---|---|---|---|---|
| 131 | | ### | ## | ### | ** | | | | |
| 132 | ### | ### | ### | # | ** | | | | |
| 133 | ### | ### | ### | # | *** | | | | ### |
| 134 | ### | ### | ### | # | *** | | | | ### |
| 135 | ### | ### | ### | ### | | | | | |
| 136 | ### | ### | ### | # | *** | | | | |
| 137 | ### | ### | ### | # | *** | | | | ### |
| 138 | ### | ### | ### | ### | | *** | | | |
| 139 | | ### | ### | ## | *** | *** | | | # |
| 140 | ### | | ### | ### | *** | | | | |
| 141 | ### | ### | ### | # | *** | | | | ### |
| 142 | ### | ### | ### | # | *** | | | | ### |
| 143 | ### | ### | ### | # | *** | | | | ### |
| 144 | ### | ### | ### | # | *** | | | | |
| 145 | ### | ### | ### | # | ** | | | | |
| 146 | ### | ### | ### | ## | *** | | | | |
| 147 | ### | ### | ### | # | *** | | | | ### |
| 148 | | | ### | ### | | | ** | ** | |
| 149 | | | ### | ### | | | *** | ** | |
| 150 | | ## | # | ### | | | | | |
| 151 | | | ### | ### | | | *** | ** | ### |
| 152 | | | ### | ### | | | *** | *** | |
| 153 | | ### | ### | # | *** | | | | # |
| 154 | | ### | ### | # | *** | | | | # |
| 155 | | ### | ### | # | *** | | | | # |
| 156 | | ### | ### | # | *** | | | | # |
| 157 | | ### | ### | # | *** | | | | # |
| 158 | | ### | ### | # | *** | | | | # |
| 159 | ### | | ### | # | *** | | | | |
| 160 | ### | | ### | # | *** | | | | |
| 161 | ### | | ### | ### | *** | | | | |
| 162 | ### | | ### | # | *** | | | | |
| 163 | ### | | ### | # | *** | | | | |
| 164 | ### | | ### | # | *** | | | | |
| 165 | | | ### | # | | | *** | * | ### |
| 166 | | | ### | # | | | *** | * | # |
| 167 | | | ### | # | | | *** | * | ### |
| 168 | | | ### | # | *** | | *** | * | ### |
| 169 | | | ### | # | | | ** | * | |
| 170 | | | ### | # | | | ** | * | |
| 171 | | | ### | # | | | *** | * | ### |
| 172 | | | ### (at 10 uM) | ## (at 10 uM) | | | | | |
| 173 | | | ### | # | | | ** | * | |
| 174 | | | ### | # | *** | | *** | * | ### |
| 175 | | | ### | # | | | *** | * | ### |
| 176 | | | ### | # | | | *** | * | ### |
| 177 | | | ### | # | | | *** | * | ## |
| 178 | | | ### | # | | | *** | * | ### |
| 179 | | | ### | # | | | *** | * | ### |
| 180 | | | ### | # | *** | | *** | * | ### |
| 181 | | | ### | # | | | *** | * | ### |
| 182 | | | ### | # | | | * | * | # |
| 183 | | | ### | # | *** | | *** | * | # |
| 184 | | | ### | # | | | * | * | # |
| 185 | | | ### | # | *** | *** | *** | * | ### |
| 186 | | | ### | # | *** | | *** | * | ### |
| 187 | | | ### | # | | | *** | * | |
| 188 | | | ### | # | | | ** | * | |
| 189 | | | ### | # | *** | | *** | * | ### |
| 190 | | | ### | # | | | *** | * | ### |
| 191 | | | ### | # | | | *** | * | ### |
| 192 | | | ### | # | | | *** | * | ## |
| 193 | | | ## | # | | | * | * | |
| 194 | | | ### | # | *** | *** | ** | * | |
| 195 | | | ### | # | *** | ** | ** | * | |
| 196 | | | ### | # | | | *** | * | # |
| 197 | | | ### | # | | | *** | * | # |
| 198 | | | ### | # | | | *** | * | ### |
| 199 | | | ### | # | | | *** | * | ### |
| 200 | | | ### | # | | | *** | * | |
| 201 | | | ### | ## | | | *** | * | |
| 202 | | | ### | ## | | | ** | * | |
| 203 | | | ### | ### | | | ** | * | |

TABLE 1-continued

| Ex | % Inh MGLL PC3 (Human, μM) | % Inh MGLL PFC (Human, μM) | % Inh MGLL Brain (Mouse, μM) | % Inh ABHD6 Brain (Mouse, μM) | IC$_{50}$ MGLL PC3 (Human, μM) | IC$_{50}$ MGLL PFC (Human, μM) | IC$_{50}$ MGLL Brain (Mouse, μM) | IC$_{50}$ ABHD6 (Mouse, μM) | % Inh 5 mg/kg MGLL (Mouse) |
|---|---|---|---|---|---|---|---|---|---|
| 204 | | | ### | # | | | ** | * | |
| 205 | | | ### | ## | | | ** | * | |
| 206 | | | ### | # | | | ** | * | |
| 207 | | | ### | ## | | | *** | * | ### |
| 208 | | | ### | # | | | ** | * | |
| 209 | | | ### | # | | | *** | ** | |
| 210 | | | ### | # | *** | | ** | * | |
| 211 | | | ### | ### | | | *** | * | ### |
| 212 | | | ### | ## | | | *** | * | ### |
| 213 | | | ### | ## | | | *** | * | ### |
| 214 | | | ### | # | | | ** | * | |
| 215 | | | ### | # | | | ** | * | |
| 216 | | | ### | ## | *** | | *** | * | ### |
| 217 | | | ### | ### | | | *** | ** | |
| 218 | | ### | ### | # | *** | | | | ### |
| 219 | | ### | ## | ### | | | | | |
| 220 | | ## | ## | # | | | | | |
| 221 | | ### | ### | ### | *** | | | | |
| 222 | | ### | ### | ## | ** | | | | |
| 223 | | ## | # | # | | | | | |
| 224 | | # | ## | # | | | | | |
| 225 | | ## | # | ## | | | | | |
| 226 | | ### | ### | ## | *** | | | | |
| 227 | | ### | ### | ## | *** | | | | |
| 228 | | | ### | # | | | ** | * | |
| 229 | | | ## | # | | | | | |
| 230 | | | ## | # | | | | | |
| 231 | | | ## | ## | | | | | |
| 232 | | | ## (at 10 uM) | ### | | | * | ** | |
| 233 | | | ### | ## | | | *** | * | # |
| 234 | | | # | ### | | | | | |
| 235 | | | # | ### | | | | | |
| 236 | | | ### | ### | | | | | |
| 237 | | | ### | ## | | | | | |
| 238 | | | ### | ### | | | | | |
| 239 | | | ## | ## | | | | | |
| 240 | | | ### | ### | | | | | |
| 241 | | | # | # | | | | | |
| 242 | | | ### | ## | | | | | |

IC$_{50}$: *** is ≤ 100 nM,
** is between 100 nM and 1 μM,
* is > 1 μM
% Inhibition: ### is ≥75%;
## is between 25 and 75%;
is ≤25%

What is claimed is:

1. A compound having the structure of Formula (I'):

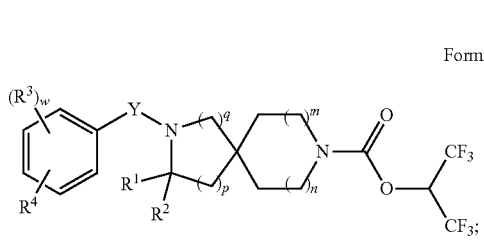

Formula (I')

wherein:

Y is —CH$_2$—;

R$^1$ is H or C$_{1-6}$alkyl;

R$^2$ is H or C$_{1-6}$alkyl;

each R$^3$ is independently selected from C$_{1-6}$alkyl, halogen, —CN, C$_{1-6}$haloalkyl, —SF$_5$, and —OR$^7$;

R$^4$ is selected from

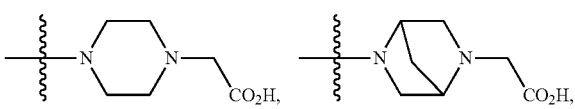

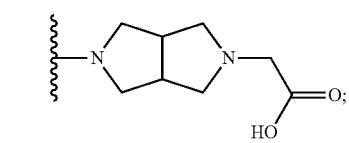

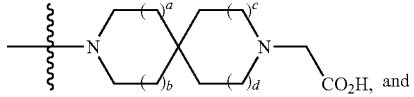

and

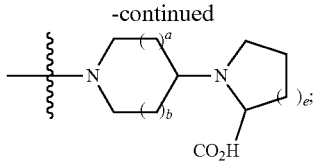

each R[7] is independently selected from H, $C_{1-6}$alkyl, $C_{1-6}$haloalkyl, $C_{3-8}$cycloalkyl, and $-C_{1-6}$alkyl-$C_{3-8}$cycloalkyl;
  a, b, c, and d are independently 0 or 1;
  e is 0, 1, or 2;
  w is 0, 1, 2, 3, or 4;
  n is 0 or 1;
  m is 0 or 1;
  p is 0, 1, or 2; and
  q is 0, 1, or 2; provided that when q is 0, then p is 2;
  or a solvate, hydrate, tautomer, N-oxide, stereoisomer, or pharmaceutically acceptable salt thereof.

2. The compound of claim 1, or a solvate, hydrate, tautomer, N-oxide, stereoisomer, or pharmaceutically acceptable salt thereof, wherein R[4] is

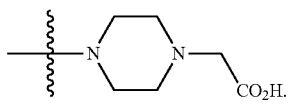

3. The compound of claim 1, or a solvate, hydrate, tautomer, N-oxide, stereoisomer, or pharmaceutically acceptable salt thereof, wherein R[4] is

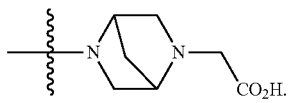

4. The compound of claim 1, or a solvate, hydrate, tautomer, N-oxide, stereoisomer, or pharmaceutically acceptable salt thereof, wherein R[1] is H.

5. The compound of claim 1, or a solvate, hydrate, tautomer, N-oxide, stereoisomer, or pharmaceutically acceptable salt thereof, wherein R[2] is H.

6. The compound of claim 1, or a solvate, hydrate, tautomer, N-oxide, stereoisomer, or pharmaceutically acceptable salt thereof, wherein R[1] and R[2] are both H.

7. The compound of claim 1, or a solvate, hydrate, tautomer, N-oxide, stereoisomer, or pharmaceutically acceptable salt thereof, wherein each R[3] is independently selected from halogen and $C_{1-6}$haloalkyl.

8. The compound of claim 1, or a solvate, hydrate, tautomer, N-oxide, stereoisomer, or pharmaceutically acceptable salt thereof, wherein each R[3] is independently selected from $C_{1-6}$haloalkyl.

9. The compound of claim 1, or a solvate, hydrate, tautomer, N-oxide, stereoisomer, or pharmaceutically acceptable salt thereof, wherein each R[3] is —$CF_3$.

10. The compound of claim 1, wherein w is 1.

11. The compound of claim 1, or a solvate, hydrate, tautomer, N-oxide, stereoisomer, or pharmaceutically acceptable salt thereof, wherein m is 1, n is 1, q is 1, and p is 1.

12. The compound of claim 1, or a solvate, hydrate, tautomer, N-oxide, stereoisomer, or pharmaceutically acceptable salt thereof, wherein m is 1, n is 1, q is 0, and p is 2.

13. The compound of claim 1 selected from:

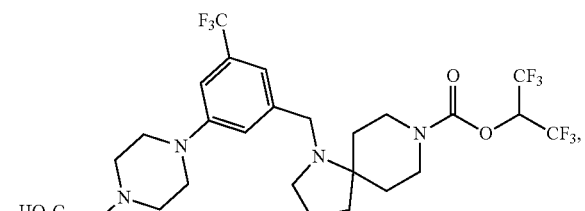

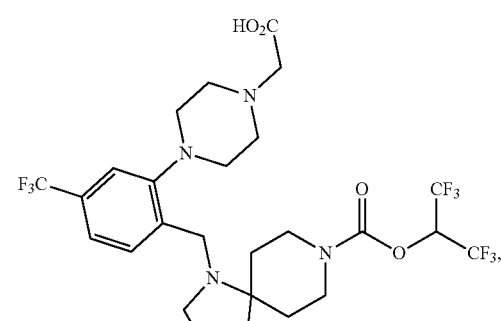

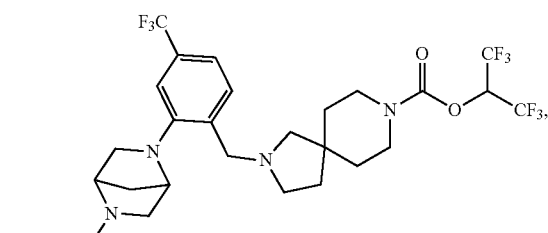

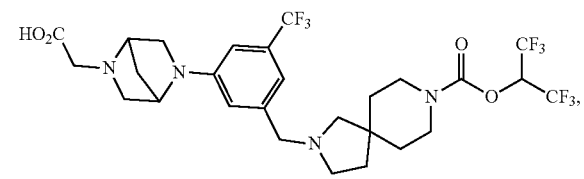

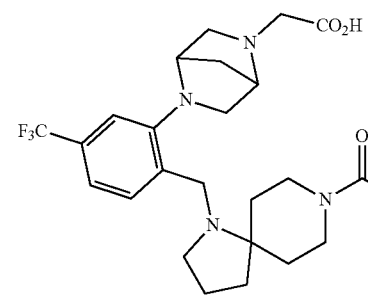

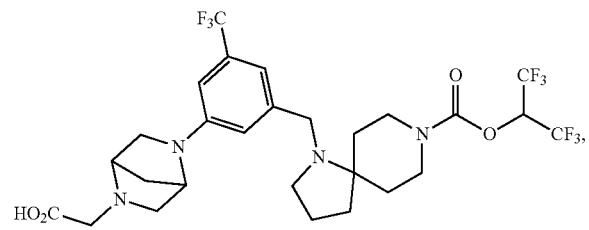

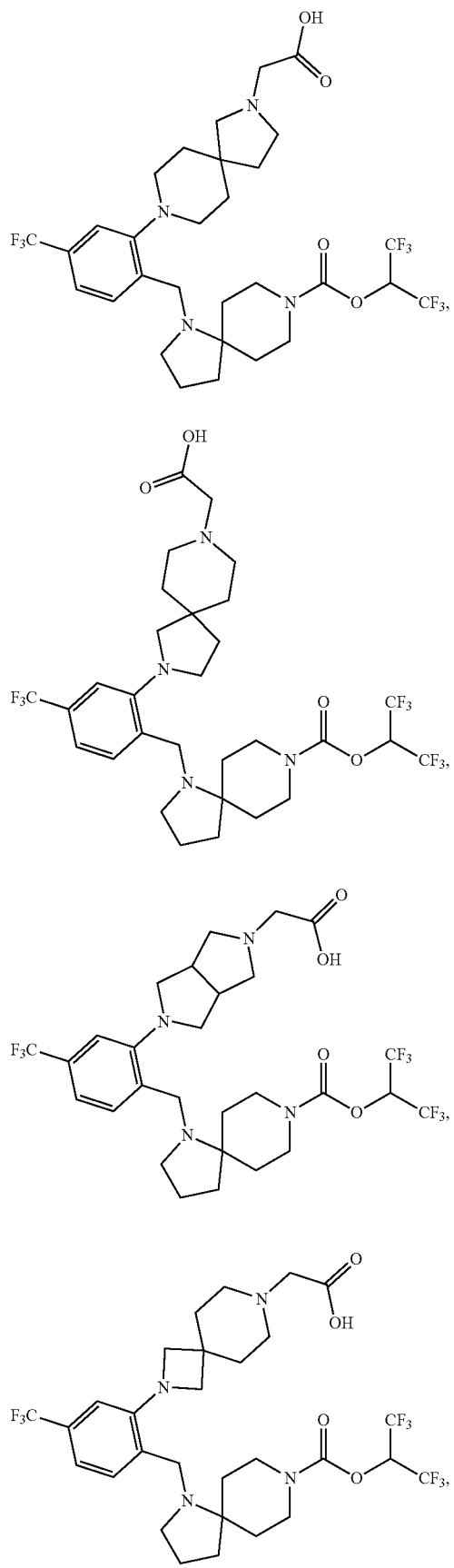
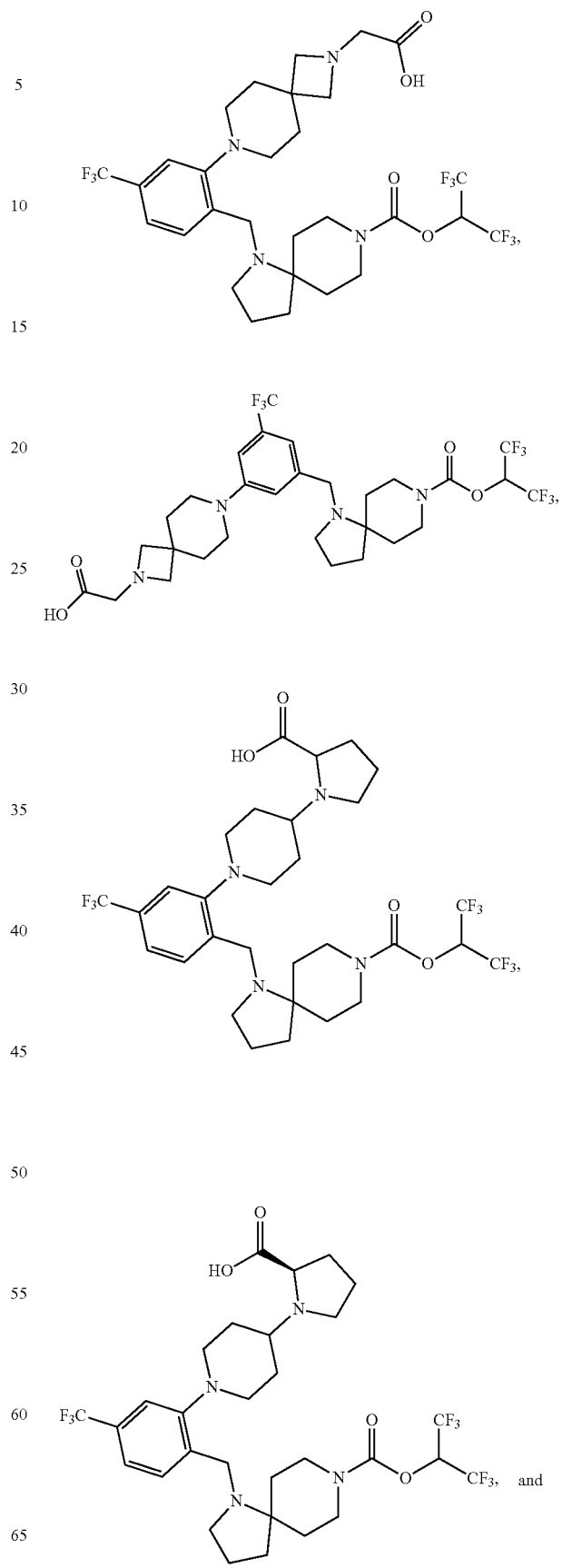

or a solvate, hydrate, tautomer, N-oxide, stereoisomer, or a pharmaceutically acceptable salt thereof.

14. A pharmaceutical composition comprising a compound of claim 1, or a solvate, hydrate, tautomer, N-oxide, stereoisomer, or a pharmaceutically acceptable salt thereof, and at least one pharmaceutically acceptable excipient.

15. A method of treating pain in a patient in need thereof, comprising administering to the patient a therapeutically effective amount of a compound of claim 1, or a solvate, hydrate, tautomer, N-oxide, stereoisomer, or a pharmaceutically acceptable salt thereof.

* * * * *

UNITED STATES PATENT AND TRADEMARK OFFICE
CERTIFICATE OF CORRECTION

PATENT NO. : 11,161,856 B2  
APPLICATION NO. : 16/642713  
DATED : November 2, 2021  
INVENTOR(S) : Cheryl A. Grice et al.

Page 1 of 1

It is certified that error appears in the above-identified patent and that said Letters Patent is hereby corrected as shown below:

On the Title Page

Left-hand column, the line reading:  
"(86) PCT No.: PCT/SU2018/048388"  
Should read:  
-- (86) PCT No.: PCT/US2018/048388 --

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*